United States Patent
Kelly et al.

(10) Patent No.: US 11,045,546 B1
(45) Date of Patent: Jun. 29, 2021

(54) METHODS OF TREATING CORONAVIRUS INFECTION

(71) Applicant: CytoDyn Inc., Vancouver, WA (US)

(72) Inventors: Scott Kelly, Vancouver, WA (US); Nader Pourhassan, Vancouver, WA (US); Bruce K. Patterson, Menlo Park, CA (US); Jacob B. Lalezari, Vancouver, WA (US)

(73) Assignee: CytoDyn Inc., Vancouver, WA (US)

( * ) Notice: Subject to any disclaimer, the term of this patent is extended or adjusted under 35 U.S.C. 154(b) by 0 days.

(21) Appl. No.: 16/902,212

(22) Filed: Jun. 15, 2020

Related U.S. Application Data

(60) Provisional application No. 63/019,256, filed on May 1, 2020, provisional application No. 63/018,506, filed on Apr. 30, 2020, provisional application No. 63/017,647, filed on Apr. 29, 2020, provisional application No. 63/016,285, filed on Apr. 27, 2020, provisional application No. 63/007,876, filed on Apr. 9, 2020, provisional application No. 63/006,693, filed on Apr. 7, 2020, provisional application No. 63/002,161, filed on Mar. 30, 2020.

(51) Int. Cl.
| | |
|---|---|
| A61K 39/395 | (2006.01) |
| A61P 31/14 | (2006.01) |
| A61K 45/06 | (2006.01) |
| A61K 39/00 | (2006.01) |
| A61K 31/351 | (2006.01) |
| A61K 31/215 | (2006.01) |
| A61K 31/196 | (2006.01) |
| A61K 31/685 | (2006.01) |

(52) U.S. Cl.
CPC ........ *A61K 39/3955* (2013.01); *A61K 31/196* (2013.01); *A61K 31/215* (2013.01); *A61K 31/351* (2013.01); *A61K 31/685* (2013.01); *A61K 45/06* (2013.01); *A61P 31/14* (2018.01); *A61K 2039/505* (2013.01); *A61K 2039/54* (2013.01); *A61K 2039/545* (2013.01); *C07K 2317/565* (2013.01)

(58) Field of Classification Search
CPC ................ A61K 39/3955; A61K 45/06; A61K 2039/54; A61K 2039/505; A61K 2039/545; A61P 31/14; C07K 2317/565
See application file for complete search history.

(56) References Cited

U.S. PATENT DOCUMENTS

| | | | |
|---|---|---|---|
| 4,704,362 A | 11/1987 | Itakura et al. | |
| 4,816,567 A | 3/1989 | Cabilly et al. | |
| 5,225,539 A | 7/1993 | Winter | |
| 5,283,173 A | 2/1994 | Fields et al. | |
| 5,468,614 A | 11/1995 | Fields et al. | |
| 5,585,089 A | 12/1996 | Queen et al. | |
| 5,693,761 A | 12/1997 | Queen et al. | |
| 6,165,793 A | 12/2000 | Stemmer | |
| 6,365,408 B1 | 4/2002 | Stemmer | |
| 6,413,774 B1 | 7/2002 | Stemmer et al. | |
| 6,458,355 B1 | 10/2002 | Hsei et al. | |
| 7,122,185 B2 | 10/2006 | Olson et al. | |
| 7,157,418 B1 | 1/2007 | McDonald et al. | |
| 7,175,988 B2 | 2/2007 | Roschke et al. | |
| 7,501,123 B2 | 3/2009 | Roschke et al. | |
| 7,862,818 B2 | 1/2011 | Roschke et al. | |
| 8,420,783 B2 | 4/2013 | Goldenberg et al. | |
| 8,623,416 B2 | 1/2014 | Zasloff | |
| 8,821,877 B2 | 9/2014 | Olson et al. | |
| 9,956,165 B2 | 5/2018 | Chen | |
| 10,265,291 B2 | 4/2019 | Zhao | |
| 10,328,157 B2 | 6/2019 | Zhao | |
| 2017/0049884 A1 | 2/2017 | Montgomery | |
| 2019/0002571 A1 | 1/2019 | Burger | |
| 2019/0016810 A1 | 1/2019 | Burger | |
| 2019/0112379 A1 | 4/2019 | Jensen et al. | |
| 2020/0024312 A1 | 1/2020 | Poma et al. | |
| 2020/0140547 A1 | 5/2020 | Bedi et al. | |

FOREIGN PATENT DOCUMENTS

| | | |
|---|---|---|
| WO | 2020/073345 A1 | 4/1920 |
| WO | 90/07861 A1 | 7/1990 |
| WO | 03/061659 A1 | 7/2003 |
| WO | 2004/011613 A2 | 2/2004 |
| WO | 2011/133658 A1 | 10/2011 |
| WO | 2012/016048 A1 | 2/2012 |
| WO | 2013/052844 A1 | 4/2013 |
| WO | 2015/151079 A2 | 10/2015 |
| WO | 2016/210130 A1 | 12/2016 |
| WO | 2017/025698 A1 | 2/2017 |
| WO | 2018/086139 A1 | 5/2018 |
| WO | 2019/127607 A1 | 7/2019 |

(Continued)

OTHER PUBLICATIONS

Agresti et al., Disruption of CCR5 signaling to treat COVID-19-associated cytokine storm: Case series of four critically ill patients treated with leronlimab. Journal of Translational Autoimmunity vol. 4, 2021, 100083.*

Yang et al., Clinical Characteristics and Outcomes of COVID-19 Patients Receiving Compassionate Use Leronlimab. Clin Infect Dis. Oct. 20, 2020, XX(XX):1-8.*

Patterson et al., CCR5 inhibition in critical COVID-19 patients decreases inflammatory cytokines, increases CD8 T-cells, and decreases SARS-CoV2 RNA in plasma by day 14. International Journal of Infectious Diseases 103: 25-32, Feb. 2021.*

Akalin et al., "Covid-19 and Kidney Transplantation," *The New England Journal of Medicine*, URL=https://www.nejm.org/doi/full/10.1056/NEJMc2011117, Apr. 24, 2020. (3 pages).

(Continued)

*Primary Examiner* — Ruixiang Li
(74) *Attorney, Agent, or Firm* — Seed IP Law Group LLP

(57) ABSTRACT

Provided herein are methods of preventing and treating viral infections (e.g., coronavirus infection) using a CCR5 binding agent.

19 Claims, 55 Drawing Sheets
(25 of 55 Drawing Sheet(s) Filed in Color)
Specification includes a Sequence Listing.

(56) References Cited

FOREIGN PATENT DOCUMENTS

| | | |
|---|---|---|
| WO | 2020/006722 A1 | 1/2020 |
| WO | 2020/155017 A1 | 8/2020 |

OTHER PUBLICATIONS

Altschul et al., "Gapped BLAST and PSI-BLAST: a new generation of protein database search programs," *Nucleic Acids Res.* 25(17):3389-3402, 1997.
Anft et al., "COVID-19 progression is potentially driven by T cell immunopathogenesis," URL=https://www.medrxiv.org/content/10.1101/2020.04.28.20083089v2, May 19, 2020. (15 pages).
Beigel et al., "Avian Influenza A (H5N1) Infection in Humans," *N. Engl. J. Med.* 353(13):1374-85, 2005.
Capon et al. "Designing CD4 immunoadhesins for AIDS therapy," *Nature* 337:525-531, 1989.
CBS Los Angeles, "Coronavirus Survivor Credits Artificial Antibody Experimental Treatment For Recovery," URL=https://losangeles.cbslocal.com/2020/04/10/coronavirus-survivor-leronlimab/, Apr. 10, 2020. (8 pages).
Channappanavar et al., "Pathogenic human coronavirus infections: causes and consequences of cytokine storm and immunopathology," *Semin. Immunopathol.* 39:529-539, 2017.
Chen et al., "Cellular Immune Responses to Severe Acute Respiratory Syndrome Coronavirus (SARS-CoV) Infection in Senescent BALB/c Mice: $CD4^+$ T Cells Are Important in Control of SARS-CoV Infection," *Journal of Virology* 84(3):1289-1301, 2010.
Chen et al., "Functional roles of CCL5/RANTES in liver disease," *Liver Research* 4:28-34, 2020.
Chen et al., "Response of Memory $CD8^+$ T Cells to Severe Acute Respiratory Syndrome (SARS) Coronavirus in Recovered SARS Patients and Healthy Individuals," *The Journal of Immunology* 175:591-598, 2005.
Chothia et al., "Canonical Structures for the Hypervariable Regions of Immunoglobulins," *J. Mol. Biol.* 196:901-917, 1987.
CytoDyn Inc., "Blood Samples at Day 0, 3 and 7 for Severely Ill COVID-19 Patients Clearly Indicate Leronlimab Has Significantly Reduced the Cytokine Storm in All (7) Patients and All Patients Demonstrated Immunological Benefit at Both Day 3 and Day 7," Press Release, Apr. 9, 2020. (4 pages).
CytoDyn Inc., "CytoDyn Collaborating with U.K.'s Department of Health to Provide Emergency Access to Leronlimab for Severe and Critically Ill COVID-19 Patients," Press Release, Apr. 7, 2020. (4 pages).
CytoDyn Inc., "CytoDyn Files a Clinical Trial Protocol with the FDA to Treat Severely Ill COVID-19 Patients with Leronlimab where the Primary Endpoint is Mortality Rate at Two Weeks," Press Release, Apr. 1, 2020. (4 pages).
CytoDyn Inc., "CytoDyn Files FDA-Suggested Modifications to IND and Protocol for Phase 2 Clinical Trial for COVID-19 Patients with Mild to Moderate Indications and a Second Randomized Protocol for All COVID-19 Patients in Severe Condition Will be Filed Next Week per FDA Recommendation," Press Release, Mar. 27, 2020. (4 pages).
CytoDyn Inc., "CytoDyn Files IND and Protocol for Phase 2 Clinical Trial for Treatment of Coronavirus Patients with Leronlimab (PRO 140)," Press Release, Mar. 9, 2020. (5 pages).
CytoDyn Inc., "CytoDyn Files IND and Protocol for Phase 2 Clinical Trial for Treatment of Patients with Coronavirus with Leronlimab (PRO 140)," Press Release, Mar. 8, 2020. (5 pages).
CytoDyn Inc., "CytoDyn Files Modified IND and Protocol for Phase 2 Clinical Trial for Treatment of Patients with Coronavirus with Leronlimab (PRO 140) and Advises Correction to Press Release Issued on Mar. 12, 2020," Press Release, Mar. 16, 2020. (4 pages).
CytoDyn Inc., "CytoDyn Reports Strong Results from eIND COVID-19 Patients Treated with Leronlimab; Majority of Patients Have Demonstrated Remarkable Recoveries," Press Release, Apr. 30, 2020. (4 pages).
CytoDyn Inc., "CytoDyn to Offer No-Cost Exploratory Laboratory Testing for Childhood Inflammatory Disease Associated with COVID-19," Press Release, May 15, 2020. (4 pages).
CytoDyn Inc., "CytoDyn to Prepare a Phase 3 Protocol to Submit to the FDA for a Three-arm Comparative and Combination Trial of Leronlimab and Remdesivir," Press Release, May 18, 2020. (4 pages).
CytoDyn Inc., "FDA Approves 54 Emergency INDs for Leronlimab Treatment of Coronavirus—CytoDyn Requests Compassionate Use from FDA for COVID-19 Patients Not Eligible for Participation in Two Ongoing Clinical Trials in U.S.—CytoDyn Targets Enrollment Completion for its 75 Patient, Phase 2 Trial by End of May," Press Release, May 4, 2020. (4 pages).
CytoDyn Inc., "FDA Clears CytoDyn's Phase 2 Randomized Trial to Treat Mild-to-Moderately Ill Coronavirus Patients with Leronlimab; Enrollment to Begin Immediately," Press Release, Mar. 31, 2020. (4 pages).
CytoDyn Inc., "First Patient Treated with Leronlimab in Phase 2b/3 Trial for COVID-19," Press Release, Apr. 15, 2020. (4 pages).
CytoDyn Inc., "First Two Patients Enrolled in Randomized Phase 2, COVID-19 Trial with Leronlimab; Five More Severely Ill COVID-19 Patients Treated Under Emergency IND and Two Patients Have Already Extubated," Press Release, Apr. 6, 2020. (4 pages).
CytoDyn Inc., "Leronlimab Used in Seven Patients with Severe COVID-19 Demonstrated Promise with Two Intubated Patients in ICU, Removed from ICU and Extubated with Reduced Pulmonary Inflammation," Press Release, Mar. 27, 2020. (4 pages).
CytoDyn Inc., "Manuscript Describes How CytoDyn's Leronlimab Disrupts CCL5/RANTES-CCR5 Pathway, Thereby Restoring Immune Homeostasis, Reducing Plasma Viral Load, Reversing Hyper Immune Activation and Inflammation in Critical COVID-19 Patients," Press Release, May 6, 2020. (5 pages).
CytoDyn Inc., "Novant Health Initiates Phase 2 COVID-19 Trial with CytoDyn's Leronlimab" Press Release, Apr. 7, 2020. (4 pages).
CytoDyn Inc., "Novant Health Initiates Phase 2b/3 Trial with CytoDyn's Leronlimab for Severely and Critically Ill COVID-19 Patients," Press Release, May 7, 2020. (4 pages).
CytoDyn Inc., "Severely Ill COVID-19 Patient at Leading Southern California Medical Center Extubated Three Days After Treatment with CytoDyn's Leronlimab; Two Moderate COVID-19 Patients Removed from External Oxygen Following One Day of Treatment with Leronlimab and Discharged from Hospital," Press Release, Apr. 9, 2020. (4 pages).
CytoDyn Inc., "Southern California Patients Treated with Leronlimab for COVID-19 under Emergency IND: 4 Patients with Moderate Indications Removed from Oxygen; 3 Patients Discharged from Hospital; 1 Patient Scheduled for Discharge Today; 1 Patient with Severe Indications Discharged, for Total of 5 Patients Discharged," Press Release, Apr. 13, 2020. (4 pages).
CytoDyn Inc., "Three Additional Patients with Severe COVID-19 Treated with Leronlimab in New York Medical Center Bringing the Total to 10 Patients," Press Release, Mar. 30, 2020. (4 pages).
CytoDyn Inc., "Treatment with CytoDyn's Leronlimab Indicates Significant Trend Toward Immunological Restoration in Severely Ill COVID-19 Patients," Press Release, Apr. 2, 2020. (4 pages).
CytoDyn Inc., "Two Additional Coronavirus Patients Treated at Leading New York Hospital with CytoDyn's Leronlimab, Bringing the Total to Four Patients," Press Release, Mar. 23, 2020. (4 pages).
CytoDyn Inc., "U.S. Food and Drug Administration (FDA) Grants Emergency IND for Two Coronavirus Patients Treated in New York with CytoDyn's Leronlimab," Press Release, Mar. 19, 2020. (4 pages).
Dhody et al., "PRO 140, a monoclonal antibody targeting CCR5, as a long-acting, single-agent maintenance therapy for HIV-1 infection," *HIV Clin. Trials* 19(3):85-93, 2018.
Dr. Yo, "Is LERONLIMAB A Game Changer? Coronavirus (COVID-19) Treatment | How does LERONLIMAB Work?," YouTube Video, May 1, 2020, URL=https://www.youtube.com/watch?v=OW6IxELNtj4&feature=youtu.be, 3 pages. (Screenshot).
Dunbar et al., "ANARCI: antigen receptor numbering and receptor classification," *Bioinformatics* 32(2):298-300, 2016.

(56) References Cited

OTHER PUBLICATIONS

Evaluate, "Human Genome Sciences Characterizes Panel of Novel Human Monoclonal Antibodies That Specifically Antagonize the CCR5 Receptor and Block HIV-1 Entry," Press Release, Nov. 2, 2004. (1 page).
Glass et al., "Functional analysis of the CC chemokine receptor 5 (CCR5) on virus-specific CD8+ T cells following coronavirus infection of the central nervous system," *Virology* 312:407-414, 2003.
Glass et al., "Reduced Macrophage Infiltration and Demyelination in Mice Lacking the Chemokine Receptor CCR5 Following Infection with a Neurotropic Coronavirus," *Virology* 288:8-17, 2001.
Grillet et al., "Acute Pulmonary Embolism Associated with COVID-19 Pneumonia Detected by Pulmonary CT Angiography," *Radiology*, URL=https://pubs.rsna.org/doi/10.1148/radiol.2020201544, Apr. 23, 2020. (8 pages).
Halama et al., "Tumoral immune cell exploitation in colorectal cancer metastases can be targeted effectively by anti-CCR5 therapy in cancer patients," *Cancer Cell* 29:587-601, 2016.
Honegger et al., "Yet Another Numbering Scheme for Immunoglobulin Variable Domains: An Automatic Modeling and Analysis Tool," *J. Mol. Bio.* 309:657-670 (2001).
Huang et al., "An Interferon-γ-Related Cytokine Storm in SARS Patients," *J. Med. Virol.* 75(2):185-194, 2005.
Huang et al., "Clinical features of patients infected with 2019 novel coronavirus in Wuhan, China," *Lancet* 395:497-506, 2020.
InvivoGen, "Engineered Fc Regions," URL=https://www.invivogen.com/sites/default/files/invivogen/resources/documents/reviews/review-Engineered-Fc-Regions-invivogen.pdf, 2011. (2 pages).
Jacobson et al., "Anti-HIV-1 activity of weekly or biweekly treatment with subcutaneous PRO 140, a CCR5 monoclonal antibody," *J. Infect. Dis.* 201(10):1481-1487, 2010.
Jacobson et al., "Antiviral activity of single-dose PRO 140, a CCR5 monoclonal antibody, in HIV-infected adults," *J. Infect. Dis.* 198:1345-1352, 2008.
Jacobson et al., "Phase 2a study of the CCR5 monoclonal antibody PRO 140 administered intravenously to HIV-infected adults," *Antimicrob. Agents Chemother.* 54(10):4137-4142, 2010.
Ji et al., "Novel CCR5 monoclonal antibodies with potent and broad-spectrum anti-HIV activities," *Antiviral Research* 74:125-137, 2007.
Kim et al., "High Cleavage Efficiency of a 2A Peptide Derived from Porcine Teschovirus-1 in Human Cell Lines, Zebrafish and Mice," *PLoS One* 6(4):e18556, 2011. (8 pages).
Kim et al., "Serum cytokine profiles in healthy young and elderly population assessed using multiplexed bead-based immunoassays," *J. Transl. Med.* 9(113):1-7, 2011.
Kohlmeier et al., "The Chemokine Receptor CCR5 Plays a Key Role in the Early Memory CD8+ T Cell Response to Respiratory Virus Infections," *Immunity* 29:101-103, 2008.
Kox et al., "Effects of the α7 nicotinic acetylcholine receptor agonist GTS-21 on the innate immune response in humans," *Shock* 36(1):5-11, 2011.
Lalezari et al., "Safety, Pharmacokinetics, and Antiviral Activity of HGS004, a Novel Fully Human IgG4 Monoclonal Antibody against CCR5, in HIV-1—Infected Patients," *The Journal of Infectious Diseases* 197:721-727, 2008.
Law et al., "Chemokine up-regulation in SARS-coronavirus-infected, monocyte-derived human dendritic cells," *Blood* 106(7):2366-2374, 2005.
Law et al., "Toll-like receptors, chemokine receptors and death receptor ligands responses in SARS coronavirus infected human monocyte derived dendritic cells," *BMC Immunology* 10:35, 2009. (12 pages).
Lefranc et al., "IMGT unique numbering for immunoglobulin and T cell receptor variable domains and Ig superfamily V-like domains," *Developmental and Comparative Immunology* 27:55-77, 2003.
Lescure et al., "Clinical and virological data of the first cases of COVID-19 in Europe: a case series," *Lancet Infect. Dis.* 20:697-706, 2020.
Li et al., "Association of RANTES with the replication of severe acute respiratory syndrome coronavirus in THP-1 cells," *Eur. J. Med. Res.* 10:117-120, 2005.
Machlus et al., "CCL5 derived from platelets increases megakaryocyte proplatelet formation," *Blood* 127(7):921-926, 2016.
Mehta et al., "COVID-19: consider cytokine storm syndromes and immunosuppression," *Lancet* 395:1033-1034, 2020.
Montefiore, "A Promising Drug for the Treatment of Severe Lung Inflammation in COVID-19 Patients: Montefiore-Einstein Scientists Lead Two Trials of Leronlimab," URL=https://www.montefiore.org/body.cfm?id=1738&action=detail&ref=1746, May 21, 2020. (1 page).
Navenot et al., "Molecular Anatomy of CCR5 Engagement by Physiologic and Viral Chemokines and HIV-1 Envelope Glycoproteins: Differences in Primary Structural Requirements for RANTES, MIP-1α, and vMIP-II Binding," *J. Mol. Biol.* 313:1181-1193, 2001.
Nicholls et al., "Lung pathology of fatal severe acute respiratory syndrome," *Lancet* 361:1773-1778, 2003.
Olson et al., "CCR5 Monoclonal Antibodies for HIV-1 Therapy," *Curr. Opin. HIV AIDS* 4(2):104-111, 2009.
Olson et al., "Differential inhibition of human immunodeficiency virus type 1 fusion, gp120 binding, and CC-chemokine activity by monoclonal antibodies to CCR5," *Journal of Virology* 73(5):4145-4155, 1999.
Patterson et al., "Disruption of the CCL5/RANTES-CCR5 Pathway Restores Immune Homeostasis and Reduces Plasma Viral Load in Critical COVID-19," URL=https://www.medrxiv.org/content/10.1101/2020.05.02.20084673v1, May 5, 2020. (24 pages).
Perricone et al., "The anti-viral facet of anti-rheumatic drugs: Lessons from COVID-19," *Journal of Autoimmunity* 11:102468, 2020 (19 pages).
Qin et al., "Dysregulation of immune response in patients with COVID-19 in Wuhan, China," *Clin. Infect. Dis.*, URL=https://academic.oup.com/cid/advance-article/doi/10.1093/cid/ciaa248/5803306, Mar. 12, 2020. (24 pages).
Ray-Saha et al., "Antibody Epitopes on G Protein-Coupled Receptors Mapped with Genetically Encoded Photoactivatable Cross-Linkers," *Biochemistry* 53:1302-1310, 2014.
Roschke et al., "Characterization of a Panel of Novel Human Monoclonal Antibodies that Specifically Antagonize CCR5 and Block HIV Entry," *44th Annual Interscience Conference on Antimicrobial Agents and Chemotherapy*, Washington, D.C., Oct. 30-Nov. 2, 2004. (Abstract) (1 page).
Richardson et al., "Presenting Characteristics, Comorbidities, and Outcomes Among 5700 Patients Hospitalized With COVID-19 in the New York City Area," *JAMA*, URL=https://www.ncbi.nlm.nih.gov/pmc/articles/PMC7177629/?report=printable, Apr. 22, 2020. (19 pages).
Scatchard, "The Attractions of Proteins for Small Molecules and Ions," *Ann. N.Y. Acad. Sci.* 51:660-672, 1949.
Stowe et al., "Plasma Cytokine Levels in a Population-Based Study: Relation to Age and Ethnicity," *J. Gerontol A Biol Sci. Med Sci* 65A(4):429-433, 2010.
Tamamis et al., "Elucidating a Key Anti-HIV-1 and Cancer-Associated Axis: The Structure of CCL5 (Rantes) in Complex with CCR5," *Scientific Reports* 4:5447, 2014. (9 pages).
Tisoncik et al., "Into the Eye of the Cytokine Storm," *Microbiol. Mol. Biol. Rev.* 76(1):16-32, 2012.
Trkola et al., "Potent, Broad-Spectrum Inhibition of Human Immunodeficiency Virus Type 1 by the CCR5 Monoclonal Antibody PRO 140," *J. Virol.* 75(2):579-588, 2001.
U.S. National Library of Medicine, "Study to Evaluate the Efficacy and Safety of Leronlimab for Mild to Moderate COVID-19," URL=https://clinicaltrials.gov/ct2/show/NCT04343651, first posted Apr. 13, 2020, downloaded May 21, 2020. (9 pages).
U.S. National Library of Medicine, "Study to Evaluate the Efficacy and Safety of Leronlimab for Patients With Severe or Critical Coronavirus Disease 2019 (COVID-19)," URL=https://clinicaltrials.gov/ct2/show/NCT04347239, first posted Apr. 15, 2020, downloaded May 21, 2020. (9 pages).

(56) References Cited

OTHER PUBLICATIONS

WallStreetReporter 1843, "CytoDyn (OTC: CYDY) Jun. 2, 2020—Livestream," YouTube Video, Jun. 2, 2020, URL=https://www.youtube.com/watch?v=Jbq1UDmHiCE&feature=youtu.be, 3 pages. (Screenshot).

Wang et al., "Characteristics of Peripheral Lymphocyte Subset Alteration in COVID-19 Pneumonia," *The Journal of Infectious Diseases 221*(11):1762-1769, 2020.

Wilson, "Analyzing Biomolecular Interactions," *Science 295*:2103-2105, 2002.

Wolff et al., "Monoclonal Antibody Homodimers. Enhanced Antitumor Activity in Nude Mice," *Cancer Research 53*:2560-2565, 1993.

Yen et al., "Modeling the early events of severe acute respiratory syndrome coronavirus infection in vitro," *Journal of Virology 80*(6):2684-2693, 2006.

Yu et al., "RANTES mediates kidney ischemia reperfusion injury through a possible role of HIF-1α and LncRNA PRINS," *Scientific Reports 6*:18424, 2016. (11 pages).

Zhang et al., "COVID-19 infection induces readily detectable morphological and inflammation-related phenotypic changes in peripheral blood monocytes, the severity of which correlate with patient outcome," *medRxiv*, URL=https://www.medrxiv.org/content/10.1101/2020.03.24.20042655v1, Mar. 26, 2020. (17 pages).

Zheng et al., "Elevated exhaustion levels and reduced functional diversity of T cells in peripheral blood may predict severe progression in COVID-19 patients," *Cellular & Molecular Immunology 17*:541-543, 2020.

\* cited by examiner

| Procedure/Assessments | Screening Visit | | Treatment Phase | | | | | Follow-Up | |
|---|---|---|---|---|---|---|---|---|---|
| Visit | V1 | V2 [16] | | V3 | V4 | V5 (EOT) | V6 | V7 |
| | | (Pre-Rx) | (Post-Rx) | | | | | |
| Day | Day | Day 0 | | Day 3 | Day 7 | Day 14 | Day 28 | Day 42 |
| Window Period | Within 7 days of the Screening Visit | 3(±1) days after V2 | 7(±1) days after V2 | 7(±1) days after V4 | 14(±3) days after EOT Visit | 28(±3) days after EOT Visit |
| Informed Consent [1] | X | | | | | | | |
| Eligibility Evaluation [2] | X | | | | | | | |
| Subject Demographics | X | | | | | | | |
| Medical History [3] | X | | | | | | | |
| Physical Examination | X | X | | X[4] | X[4] | X | X[4] | X[4] |
| Vital Signs [5] | X | X | X | X | X | X | X | X |
| Clinical Symptom Score Assessment [6] | X | X | | X | X | X | | |
| Pulse oxygen saturation (SpO2) | X | X | | X | X | X | | |
| National Early Warning Score 2 (NEWS2) Assessment [7] | X | X | | X | X | X | | |
| ECG | X | | | | | X | | |
| Laboratory tests: | | | | | | | | |
| Complete Blood Count [8] | X | | | X | X | X | X | X |
| Biochemistry [9] | X | | | X | X | X | X | X |
| Coagulation Indices [10] | X | | | X | X | X | X | X |
| Serum Pregnancy Test [11] | X | | | | | | | |
| Urinalysis [12] | X | | | X | X | X | | X |
| CD3+, CD4+ and CD8+ T cell count | | X | | | | | | |
| CCR5 receptor occupancy for Treg and macrophage | | X | | | | | | |

FIG. 3A

| Procedure/Assessments | Screening Visit | | Treatment Phase | | | | | Follow-Up | |
|---|---|---|---|---|---|---|---|---|---|
| Visit | V1 | V2 [16] (Pre-Rx) | V2 [16] (Post-Rx) | V3 | V4 | V5 (EOT) | V6 | V7 |
| Day | | Day 0 | Day 0 | Day 3 | Day 7 | Day 14 | Day 28 | Day 42 |
| Window Period | Within 7 days of the Screening Visit | | | 3(±1) days after V2 | 7(±1) days after V2 | 7(±1) days after V4 | 14(±3) days after EOT Visit | 28(±7) days after EOT Visit |
| Serum cytokine and chemokine levels | | X | | X | X | X | | |
| CCR5 Gene Polymorphisms [13] | | X | | X | X | X | | |
| Nasopharyngeal Swab Sample Collection [14] | X | X | | X | X | X | X | X |
| Chest radiograph or CT (if clinically indicated) [15] | X | | | | | X | | |
| Ordinal Scale Assessment | X | X | | X | X | X | | |
| Randomization [17] | | X | | | | | | |
| PRO 140 (700 mg) or Placebo Administration | | | X | | X | | | |
| Assessment for the requirement of: Mechanical Ventilation, Oxygen, and Hospital Stay | X | X | | X | X | X | | |
| Mortality Status | | | | | | X | X | X |
| Concomitant Medications | X | X | X | X | X | X | X | X |
| Adverse Events | | | X | X | X | X | X | X |

[1] Informed consent must be obtained prior to patient participation in any protocol-related activities that are not part of routine care.
[2] Initial evaluation of patient eligibility will be performed by Investigator.
[3] Medical history and current therapies (medications and non-medications).
[4] Symptom-directed physical examination
[5] Post treatment vital signs will be recorded at V2, V4, V5 (EOT) and will include blood pressure, heart rate, respiration rate, and temperature.
[6] Clinical Improvement will be assessed based on symptom score for fever, myalgia, dyspnea and cough. Each symptom is graded from 0 to 3. [0=none, 1=mild, 2=moderate, and 3=severe] The total score per patient ranges from 0 to 12 points. Clinical Improvement will be assessed daily while subject is hospitalized and will continue to be assessed on the scheduled treatment visits and at EOT after the subject is discharged from the hospital.
[7] National Early Warning Score 2 (NEWS2) Assessment is based on 7 clinical parameters (respiration rate, oxygen saturation, any supplemental oxygen, temperature, systolic blood pressure, heart rate, level of consciousness)
[8] Hemoglobin, Hematocrit (HCT), Red Blood Cells (RBC), White Blood Cells (WBC) with total and differential count, Absolute Neutrophil Count (ANC) and platelets.
[9] Biochemistry

*FIG. 3A (Continued)*

Schedule of Assessments

| Procedure/Assessments | Screening Visit | Treatment Phase | | | | | Follow-Up | |
|---|---|---|---|---|---|---|---|---|
| Visit | V1 | V [17] | V3 | V4 | V5 (EOT) | V6 | V7 | |
| | | (Pre-Rx) | (Post-Rx) | | | | | |
| Day | | Day 0 | | Day 3 | Day 7 | Day 14 | Day 28 | Day 42 |
| Window Period | | Within 7 days of the Screening Visit | | 3(±1) days after V2 | 7(±1) days after V2 | 7(±1) days after V4 | 14(±3) days after EOT Visit | 28(±3) days after EOT Visit |
| Informed Consent [1] | X | | | | | | | |
| Eligibility Evaluation [2] | X | | | | | | | |
| Subject Demographics | X | | | | | | | |
| Medical History [3] | X | | | | | | | |
| Physical Examination | X | X | | X[4] | X[4] | X | X[4] | X[4] |
| Vital Signs [5] | X | X | X | X | X | X | X | X |
| Clinical Status - Ordinal Scale | X | X | | X | X | X | | |
| PaO2/FiO2 | X | X | | X | X | X | | |
| Pulse oxygen saturation (SpO2) | X | X | | X | X | X | | |
| Positive End-Expiratory Pressure (PEEP), if intubated | | | | | | | | |
| Sequential Organ Failure Assessment (SOFA) score [6] | X | X | | X | X | X | | |
| National Early Warning Score 2 (NEWS2) Assessment[7] | X | X | | X | X | X | | |
| Assessment of clinical recovery [8] | | | | X | X | X | | |
| ECG | X | | | | | X | | |
| Laboratory tests: | | | | | | | | |
| Complete Blood Count [9] | X | | | X | X | X | | X |
| Biochemistry [10] | X | | | X | X | X | | X |
| Coagulation Indices [11] | X | | | X | X | X | | X |

*FIG. 3B*

| Procedure/Assessments | Screening Visit | Treatment Phase | | | | | Follow-Up | |
|---|---|---|---|---|---|---|---|---|
| Visit | V1 | V2 [17] | | V3 | V4 | V5 (EOT) | V6 | V7 |
| | | (Pre-Rx) | (Post-Rx) | | | | | |
| Day | Window Period | Day 0 | Within 7 days of the Screening Visit | Day 3 3(±1) days after V2 | Day 7 7(±1) days after V2 | Day 14 7(±1) days after V4 | Day 28 14(±3) days after EOT Visit | Day 42 28(±3) days after EOT Visit |
| Serum/Urine Pregnancy Test | X | | | | | X | | |
| Urinalysis [13] | X | | | | | X | | X |
| CD3+, CD4+ and CD8+ T | X | | | X | X | X | | |
| CCR5 receptor occupancy for | X | | | X | X | X | | |
| Serum cytokine and chemokine | X | | | X | X | X | | |
| CCR5 Gene Polymorphisms [14] | X | | | X | X | X | | |
| Nasopharyngeal Swab Sample | X | | | X | X | X | X | X |
| Chest radiograph or CT (if | X | | | | | X | | |
| Randomization [18] | | X | | | | | | |
| PRO 140 (700 mg) or Placebo | | X | | X | X | | | |
| Assessment for the requirement of Mechanical Ventilation, Non-Invasive Ventilation, Supplemental | X | | | X | X | X | | |
| Assessment for any new infections | | X | | X | X | X | | |
| Mortality Status | | | | | | X | X | X |
| Concomitant Medications | X | X | | X | X | X | X | X |
| Adverse Events | | X | | X | X | X | X | X |

[1] Informed consent must be obtained prior to patient participation in any protocol-related activities that are not part of routine care.
[2] Initial evaluation of patient eligibility will be performed by Investigator.
[3] Medical history and current therapies (medications and non-medications).
[4] Symptom-directed physical examination
[5] Post treatment vital signs will be recorded at V2, V4, V5 (EOT) and will include blood pressure, heart rate, respiration rate, and temperature.

FIG. 3B (Continued – 1)

[6] The SOFA score assessment will be based on PaO2/FiO2, platelets, Glasgow coma scale (GCS), bilirubin, Mean arterial pressure OR administration of vasoactive agents required, and creatine.
[7] National Early Warning Score 2 (NEWS2) Assessment is based on 7 clinical parameters (respiration rate, oxygen saturation, any supplemental oxygen, temperature, systolic blood pressure, heart rate, level of consciousness)
[8] Based on hospital discharge or normalization of fever, respiratory rate, alleviation of cough, and resolution of hypoxia.
[9] Hemoglobin, Hematocrit (HCT), Red Blood Cells (RBC), White Blood Cells (WBC) with total and differential count, Absolute Neutrophil Count (ANC) and platelets.
[10] Biochemistry
Hepatic function indicators: total bilirubin, alkaline phosphatase, aspartate aminotransferase (AST), alanine aminotransferase (ALT), total protein, albumin
Renal function indicators: Serum creatinine, creatinine clearance, or eGFR
Electrolytes: sodium, potassium, chloride, calcium and bicarbonate Lactate dehydrogenase (LDH)
Other: glucose (random), cholesterol (total), Creatine kinase, C-reactive protein
[11] Prothrombin time (PT) and International Normalized Ratio (INR)
[12] ONLY performed on women of childbearing potential.
[13] Urine samples will be tested for color, appearance, specific gravity, pH, protein, glucose, occult blood, ketones, leukocyte esterase, nitrite, bilirubin, urobilinogen, and microscopic examination of urine sediment.
[14] Blood samples collected for receptor occupancy testing will also be used for CCR5 gene polymorphism for PRO 140 susceptibility. [15] Swabs will be used for quantitative virologic testing. Samples are to be stored at -70°C.
[16] Chest radiograph or CT will be performed if clinically indicated by the treating physician.
[17] If Visit 2 (V2) takes place on the same day as the Screening Visit (V1), scheduled assessments performed under screening (V1) do not need to be repeated at V2. [18] Randomization via WebView CTMS system

*FIG. 3B (Continued – 2)*

```
                              30                              60
TCTAGACCACCATGAAGTTGCCTGTTAGGCTGTTGGTGCTGATGTTCTGGATTCCTGCTT
              M  K  L  P  V  R  L  L  V  L  M  F  W  I  P  A
                              90                             120
CCAGCAGTGATATTGTGATGACCCAATCTCCACTCTCCCTGCCTGTCACTCCTGGAGAGC
 S  S  S  D  I  V  M  T  Q  S  P  L  S  L  P  V  T  P  G  E
                             150                             180
CAGCCTCCATCTCTTGCAGATCTAGTCAGCGCCTTCTGAGCAGTTATGGACATACCTATT
 P  A  S  I  S  C  R  S  S  Q  R  L  L  S  S  Y  G  H  T  Y
                             210                             240
TACATTGGTACCTACAGAAGCCAGGCCAGTCTCCACAGCTCCTGATCTACGAAGTTTCCA
 L  H  W  Y  L  Q  K  P  G  Q  S  P  Q  L  L  I  Y  E  V  S
                             270                             300
ACCGATTTTCTGGGGTCCCAGACAGGTTCAGTGGCAGTGGGTCAGGGACAGATTTCACAC
 N  R  F  S  G  V  P  D  R  F  S  G  S  G  S  G  T  D  F  T
                             330                             360
TTAAGATCAGTAGAGTGGAGGCTGAGGATGTGGGAGTTTATTACTGCTCTCAAAGTACAC
 L  K  I  S  R  V  E  A  E  D  V  G  V  Y  Y  C  S  Q  S  T
                             390                             420
ATGTTCCTCTCACGTTCGGACAGGGGACCAAGGTGGAAATAAAACGTAAGTAGTCTTCTC
 H  V  P  L  T  F  G  Q  G  T  K  V  E  I  K  (SEQ. ID NO: 1)

429
AACTCTAGA (SEQ. ID NO: 2)
```

FIG. 4

```
                    30                                         59
ACGCGTCCACCATGGAATGGAGCGGAGTCTTTATCTTTCTCCTGTCAGTAACTGCAGGT
              M  E  W  S  G  V  F  I  F  L  L  S  V  T  A  G 89                                        118
GTCCACTCCGAGGTGCAGCTGGTGGAGTCTGGTGGAGGCTTGGTAAAGCCTGGAGGTTC
 V  H  S  E  V  Q  L  V  E  S  G  G  G  L  V  K  P  G  G  S

148
CCTTAGACTCTCCTGTGCAGCCTCTGGTTACACTTTCAGTAACTATTGGATCGGATGGG  177
 L  R  L  S  C  A  A  S  G  Y  T  F  S  N  Y  W  I  G  W 207                                       236
TCCGCCAGGCTCCAGGCAAAGGGCTGGAGTGGATTGGCGATATCTACCCTGGAGGGAAC
 V  R  Q  A  P  G  K  G  L  E  W  I  G  D  I  Y  P  G  G  N 266                                       295
TACATCAGGAACAATGAGAAGTTCAAGGACAAGACCACCCTGTCAGCAGATACTTCCAA
 Y  I  R  N  N  E  K  F  K  D  K  T  T  L  S  A  D  T  S  K 325                                       354
GAACACAGCCTATCTGCAAATGAACAGCCTGAAAACCGAGGACACAGCCGTGTATTACT
 N  T  A  Y  L  Q  M  N  S  L  K  T  E  D  T  A  V  Y  Y 384                                       413
GTGGAAGCAGCTTCGGTAGTAACTACGTGTTCGCCTGGTTTACTTACTGGGGCCAAGGG
 C  G  S  S  F  G  S  N  Y  V  F  A  W  F  T  Y  W  G  Q  G 443           457
ACTCTGGTCACAGTCTCCTCAGGTGAGTCCTTAAAACCTCTAGA  (SEQ. ID NO: 4)
 T  L  V  T  V  S  S     (SEQ. ID NO: 3)
```

FIG. 5

```
                            30                                    60
TCTAGACCACCATGGAATGGAGCGGGGTCTTTATCTTTCTCCTGTCAGTAACTGCAGGTG
         M  E  W  S  G  V  F  I  F  L  L  S  V  T  A  G
                            90                                   120
TCCACTCCCAGGTCCAACTGGTGCAGTCTGGACCTGATGTGAAAAAGCCTGGGACTTCAA
 V  H  S  Q  V  Q  L  V  Q  S  G  P  D  V  K  K  P  G  T  S
                           150                                   180
TGAAGATGTCCTGCAAGACGTCTGGATACACCTTCAGTAACTATTGGATCGGATGGGTA
 M  K  M  S  C  K  T  S  G  Y  T  F  S  N  Y  W  I  G  W  V
                           210                                   240
GGCAGGCGCCTGGACAAGGCCTTGAGTGGATTGGAGATATTTACCCTGGAGGGAACTATA
 R  Q  A  P  G  Q  G  L  E  W  I  G  D  I  Y  P  G  G  N  Y
                           270                                   300
TCAGGAACAATGAGAAGTTCAAGGACAAGACCACACTGACGGCAGACACATCGACCAGCA
 I  R  N  N  E  K  F  K  D  K  T  T  L  T  A  D  T  S  T  S
                           330                                   360
CGGCCTACATGCAACTTGGCAGCCTGAGATCTGAAGACACTGCCGTCTATTACTGTGGAA
 T  A  Y  M  Q  L  G  S  L  R  S  E  D  T  A  V  Y  Y  C  G
                           390                                   420
GCAGCTTCGGTAGTAACTACGTGTTCGCCTGGTTTACTTACTGGGGCCAAGGGACTCTGG
 S  S  F  G  S  N  Y  V  F  A  W  F  T  Y  W  G  Q  G  T  L
                     450      457
TCACAGTCTCCTCAGGTGAGTCCTTAAAACCTCTAGA (SEQ. ID NO: 6)
 V  T  V  S  S  (SEQ. ID NO: 5)
```

FIG. 6

| Cytokines (pg/ml) | Age < 45 | Age ≥ 65 | P-value[a] |
|---|---|---|---|
| G-CSF | 14.7 ± 13.2[b] (0.03-75.8) | 9.9 ± 8.8 (0.03-35.2) | 0.009 |
| GM-CSF | 40.9 ± 108.6 (0.5-728.1) | 20.3 ± 60.40 (0.50-415.1) | 0.021 |
| MCP1 | 213.5 ± 100.7 (27.9-667.8) | 168.0 ± 73.0 (39.34-355.9) | 0.027 |
| sCD40L | 2205.8 ± 4699.2 (268.6-27703.8) | 20370.6 ± 71662.0 (115.8-380396.7) | 0.016 |
| TGF-α | 3.2 ± 4.0 (0.93-26.8) | 4.9 ± 4.8 (0.86-20.8) | 0.026 |
| EGF | 31.3 ± 35.9 (3.2-210.5) | 61.0 ± 65.1 (3.20-251.6) | 0.073 |
| FGF-2 | 18.9 ± 11.3 (6.7-65.6) | 20.1 ± 13.9 (3.20-72.83) | 0.863 |
| Flt-3L | 10.2 ± 10.1 (0.84-59.3) | 13.2 ± 15.9 (0.03-78.42) | 0.759 |
| IFN-α2 | 21.3 ± 22.6 (2.42-102.2) | 33.3 ± 70.2 (2.42-449.2) | 0.822 |
| IFN-γ | 13.1 ± 22.7 (0.14-126.8) | 10.3 ± 18.4 (1.09-117.7) | 0.948 |
| IL-10 | 1.32 ± 3.06 (0.01-19.8) | 1.58 ± 6.17 (0.01-41.7) | 0.325 |
| IL-15 | 3.04 ± 2.17 (1.25-13.1) | 3.49 ± 4.31 (1.32-28.9) | 0.668 |
| IL-17 | 6.53 ± 7.42 (1.58-37.8) | 12.2 ± 37.9 (1.43-275.1) | 0.64 |
| IL-1β | 2.04 ± 4.93 (0.17-24.) | 2.52 ± 7.41 (0.17-39.0) | 0.645 |
| IL-2 | 5.13 ± 2.31 (2.88-18.3) | 5.58 ± 4.17 (3.06-32.1) | 0.601 |
| IL-6 | 2.91 ± 6.45 (0.16-37.7) | 2.57 ± 5.22 (0.16-31.5) | 0.75 |
| IL-8 | 23.9 ± 29.7 (4.2-132.6) | 27.6 ± 43.9 (4.76-217.0) | 0.995 |
| IP-10 | 462.2 ± 364.7 (145.3-2152.2) | 451.3 ± 256.4 (149.8-1394.8) | 0.673 |
| MIP-1β | 40.5 ± 38.8 (3.2-227.2) | 40.4 ± 33.6 (3.20-231.1) | 0.633 |
| PDGF-AA | 1528.3 ± 878.8 (140.6-3290.2) | 1615.3 ± 1125.0 (55.3-3421.7) | 0.485 |
| TNF-α | 3.21 ± 4.04 (0.93-26.8) | 4.94 ± 4.79 (0.86-20.8) | 0.916 |
| VEGF | 114.9 ± 147.1 (13.1-864.1) | 100.5 ± 75.4 (6.9-329.3) | 0.853 |

[a]Differences with P < 0.05 are considered significant.
[b]Average concentrations ± standard deviation in pg/mL.

*FIG. 7*

Immune Cell Frequencies

| Test | Patient 1† (KM) | | | | Patient 2† (IW) | | | | Patient 3 (Wsa) | | | | Patient 4† (WS) | | | | Patient 5† (AA) | | | |
|---|---|---|---|---|---|---|---|---|---|---|---|---|---|---|---|---|---|---|---|---|
| | Day 0 | Day 3 | Day 7 | Day 14 | Day 0 | Day 3 | Day 7 | Day 14 | Day 0 | Day 3 | Day 7 | Day 14 | Day 0 | Day 3 | Day 7 | Day 14 | Day 0 | Day 3 | Day 7 | Day 14 |
| CD4% | 23.58 | 18.96 | 19.4 | 23.4 | 28.0 | 30.2 | 29.3 | dec. | 32.1 | 38.9 | 37.4 | 45.6 | 52.1 | 30.3 | 37.3 | 35.4 | 23.2 | 20.5* | 25.6 | - |
| CD8% | 5.45 | 7.15 | 13.2 | 16.7 | 7.0 | 13.1 | 14.0 | dec. | 5 | 9.6 | 31.1 | 33.3 | 16.5 | 19.1 | 26.1 | 29.4 | 15.6 | 19.6* | 21.9 | - |
| CD4/CD8 | 4.33 | 2.65 | 1.48 | 1.4 | 4.0 | 2.3 | 2.1 | dec. | 6.42 | 4 | 1.2 | 1.4 | 3.15 | 1.6 | 1.43 | 1.2 | 1.5 | 1.1* | 1.2 | - |
| T-cell RO | 0% | 52% | 87% | 99% | 0% | 54% | 92% | dec. | 0% | 81.8% | 94.6% | 98% | 0% | 69% | 89.2% | 98% | 0% | 92%* | 99% | - |
| Macro RO | 0% | 55% | 74% | 94% | 0% | 63% | 98% | dec. | 0% | 72.3% | 87.5% | 95% | 0% | 83% | 94.5% | 97% | 0% | 84%* | 96% | - |
| T-reg RO | 0% | 87% | 92% | 99% | 0% | 94.8% | 99% | dec. | 0% | 89.2% | 97.8% | 99% | 0% | 61% | 98% | 99% | 0% | 99%* | 99% | - |

| Test | Patient 6† (AN) | | | | Patient 7† (PM) | | | | Patient 8† (MO) | | | | Patient 9 (JF) | | | | Patient 10 (AR) | | | |
|---|---|---|---|---|---|---|---|---|---|---|---|---|---|---|---|---|---|---|---|---|
| | Day 0 | Day 3 | Day 7 | Day 14 | Day 0 | Day 3 | Day 7 | Day 14 | Day 0 | Day 3 | Day 7 | Day 14 | Day 0 | Day 3 | Day 7 | Day 14 | Day 0 | Day 3 | Day 7 | Day 14 |
| CD4% | 43.1 | 44.8* | 46.9 | 35.2 | 22.9% | 28.8% | 33.7% | - | 31.4 | 30.3 | dec. | dec. | 27.3 | 24.4 | dec. | dec. | 48.3 | 42.1 | dec. | dec. |
| CD8% | 15.8 | 21.3* | 27.3 | 28.8 | 10.3% | 19.3%* | 24.9% | - | 23.9 | 25.6* | dec. | dec. | 8.1 | 13.1 | dec. | dec. | 9.4 | 17.5 | dec. | dec. |
| CD4/CD8 | 2.7 | 2.1 | 1.7 | 1.2 | 2.2 | 1.4* | 1.3 | - | 1.3 | 1.2 | dec. | dec. | 3.3 | 1.9 | dec. | dec. | 5.1 | 2.4 | dec. | dec. |
| T-cell RO | 0% | 97%* | 99% | 99% | 0% | 99%* | 99% | - | 0% | 88%* | dec. | dec. | 0 | 97% | dec. | dec. | 0 | 93% | dec. | dec. |
| Macro RO | 0% | 89%* | 97% | 98% | 0% | 91%* | 99% | - | 0% | 79%* | dec. | dec. | 0 | 91% | dec. | dec. | 0 | 68% | dec. | dec. |
| T-reg RO | 0% | 99%* | 99% | 99% | 0% | 99%* | 99% | - | 0% | 99%* | dec. | dec. | 0 | 99% | dec. | dec. | 0 | 99% | dec. | dec. |

RO = Receptor occupancy
"-" indicates data is unavailable
"dec." indicates patient is deceased.
*data differs from first reported results; samples were collected from the same patient at the same time and have been updated to reflect most recent data
† patient number identifiers differ from first reported identifiers, patient initial identifiers are the same

*FIG. 8*

| Patient 1† (KM) | | | | | |
|---|---|---|---|---|---|
| Cytokines | Day 0 | Day 3 | Day 7 | Day 14 | Day 21 |
| sCD40L | 1601 | 12023 | 3586 | 5553 | - |
| EGF | 122.2 | 922.8 | 100.2 | 69.1 | - |
| Eotaxin | 27 | 48.37 | 44.6 | 63.3 | - |
| FGF-2 | 180.3 | 90.7 | 201.5 | 193.8 | - |
| Flt-3 ligand | 31.73 | 61.5 | 60.5 | 41.5 | - |
| Fractalkine | 186 | 241.8 | 152.7 | 340.6 | - |
| G-CSF | 3.5 | 3 | 3 | 3 | - |
| GM-CSF | 1 | 5 | 5 | 6.37 | - |
| GROα | 15.8 | 81.4 | 1 | 10 | - |
| IFNα2 | 32.5 | 45.2 | 24.7 | 75.2 | - |
| IFNγ | <5.8 | <5.8 | 6.6 | 7.7 | - |
| IL-1α | 4.6 | 18 | 6.5 | 86.6 | - |
| IL-1β | 11.9 | 8.8 | 39.32 | 24.6 | - |
| IL-1ra | 287.7 | 227.9 | 3146 | 65.8 | - |
| IL-2 | <0.9 | <0.9 | <0.9 | 1.1 | - |
| IL-3 | 2.3 | 4.8 | 0.4 | 3.2 | - |
| IL-4 | <4.8 | <4.8 | <4.8 | 0.9 | - |
| IL-5 | <3.4 | 6.1 | 16.6 | 5.3 | - |
| IL-6 | 124.2 | 84.4 | 53.2 | 7.2 | - |
| IL-7 | 2.9 | 20.8 | 2.7 | 6.3 | - |
| IL-8 | 18.5 | 20.6 | 48.8 | 24.5 | - |
| IL-9 | <1.9* | 3.7* | 9.6 | 7.6 | - |
| IL-10 | <1.9 | 3.7 | 141.6 | 47.2 | - |
| IL-12 (p40) | 69.5 | 165.4 | 75.1 | 29.3 | - |

| Patient 1† (KM) | | | | | |
|---|---|---|---|---|---|
| Cytokines | Day 0 | Day 3 | Day 7 | Day 14 | Day 21 |
| IL-12 (p70) | 1.8 | 2.5 | 2 | 5.3 | - |
| IL-13 | <7.6 | <7.6 | <7.6 | 39.4 | - |
| IL-15 | 14 | 23.1 | 9.8 | 33.3 | - |
| IL-17A | <0.5 | <0.5 | <0.5 | 5.5 | - |
| IL-17E/IL-25 | 257.9 | 335.6 | 266.3 | 697.1 | - |
| IL-17F | <2.1 | <2.1 | 20.7 | 81.1 | - |
| IL-18 | 1005 | 153 | 1427 | 366.2 | - |
| IL-22 | <0.8 | 4.2 | 15 | 23.7 | - |
| IL-27 | 5357 | 7696 | 9374 | 7967 | - |
| IP-10 | 16351 | 10626 | 15029 | 3943 | - |
| MCP-1 | 209.7 | 180.4 | 45.7 | 49.7 | - |
| MCP-3 | 35.4 | 36.4 | 33.1 | 43.6 | - |
| M-CSF | 1012 | 696 | 868 | 250.8 | - |
| MDC (CCL22) | 654.3 | 944.5 | 695.1 | 580.4 | - |
| MIG | 18777 | 21200 | 34474 | 18802 | - |
| MIP-1α | 28 | 48.9 | 45.7 | 29.6 | - |
| MIP-1β | 52.8 | 107 | 166.6 | 150.6 | - |
| PDGF-AA | 2078 | 11820 | 5396 | 4802 | - |
| PDGF-AB/BB | 22072 | 30056 | 28969 | 30048 | - |
| RANTES | 102000 | 304300 | 218200 | 138300 | - |
| TGFα | 28.5 | 51.3 | 37.2 | 22.1 | - |
| TNFα | <8.2 | <8.2 | <8.2 | <8.2 | - |
| TNFβ | 4.2 | 8.3 | 3.5 | 4.1 | - |
| VEGF-A | 258.1 | 698.2 | 275 | 321.7 | - |

FIG. 9A

| Patient 2† (IW) | | | | | | Patient 2† (IW) | | | | |
|---|---|---|---|---|---|---|---|---|---|---|
| Cytokines | Day 0 | Day 3 | Day 7 | Day 14 | Day 21 | Cytokines | Day 0 | Day 3 | Day 7 | Day 14 | Day 21 |
| sCD40L | 168.2 | 783.8 | 661.2 | dec. | dec. | IL-12 (p70) | 1.1 | 1.8 | 2 | dec. | dec. |
| EGF | 4.1 | 14.6 | 3 | dec. | dec. | IL-13 | <7.6 | <7.6 | 7.7 | dec. | dec. |
| Eotaxin | 70.2 | 146.5 | 127.3 | dec. | dec. | IL-15 | 11.9 | 41.7 | 30.9 | dec. | dec. |
| FGF-2 | 45.6 | 66.8 | 90.8 | dec. | dec. | IL-17A | <0.5 | <0.5 | 2.1 | dec. | dec. |
| Flt-3 ligand | 18.8 | 42 | 17.9 | dec. | dec. | IL-17E/IL-25 | 60.9 | 184.3 | 180.8 | dec. | dec. |
| Fractalkine | 53.2 | 162.8 | 150.5 | dec. | dec. | IL-17F | <2.1 | <2.1 | 23.6 | dec. | dec. |
| G-CSF | 3.6 | 24.8 | 3 | dec. | dec. | IL-18 | 94.2 | 147.2 | 375.7 | dec. | dec. |
| GM-CSF | 1 | 1 | 5 | dec. | dec. | IL-22 | <0.8 | 10.9 | 8.7 | dec. | dec. |
| GROα | 1 | 11.2 | 5.9 | dec. | dec. | IL-27 | 2971 | 2778 | 6273 | dec. | dec. |
| IFNα2 | 42.1 | 31.4 | 15.8 | dec. | dec. | IP-10 | 10368 | 16351 | 4309 | dec. | dec. |
| IFNγ | <5.8 | 6.9 | 1.8 | dec. | dec. | MCP-1 | 359.2 | 2227 | 1327 | dec. | dec. |
| IL-1α | 4.2 | 4.9 | 6.5 | dec. | dec. | MCP-3 | 13.6 | 78.5 | 18.7 | dec. | dec. |
| IL-1β | 2 | 3.2 | 4 | dec. | dec. | M-CSF | 341 | 8335.9 | 380.8 | dec. | dec. |
| IL-1ra | 19.5 | 531.9 | 180.3 | dec. | dec. | MDC (CCL22) | 517.6 | 602.1 | 444.7 | dec. | dec. |
| IL-2 | <0.9 | <0.9 | <0.9 | dec. | dec. | MIG | 1513 | 6355 | 7331 | dec. | dec. |
| IL-3 | 0.4 | 0.65 | 0.7 | dec. | dec. | MIP-1α | 3.7 | 17.5 | 22.8 | dec. | dec. |
| IL-4 | <4.8 | <4.8 | <4.8 | dec. | dec. | MIP-1β | 9.6 | 46.2 | 62.9 | dec. | dec. |
| IL-5 | <3.4 | <3.4 | 5.6 | dec. | dec. | PDGF-AA | 225.2 | 596.9 | 1089 | dec. | dec. |
| IL-6 | 1000.1 | 344.2 | 26.5 | dec. | dec. | PDGF-AB/BB | 3935 | 14292 | 12439 | dec. | dec. |
| IL-7 | 0.2 | 1.2 | 1.1 | dec. | dec. | RANTES | 4094 | 22916 | 14032 | dec. | dec. |
| IL-8 | 1.6 | 11.4 | 5.5 | dec. | dec. | TGFα | 3.64 | 12.5 | 10.5 | dec. | dec. |
| IL-9 | <2.2 | <2.2 | 30.1 | dec. | dec. | TNFα | 19.5* | 8.5* | 119 | dec. | dec. |
| IL-10 | <1.9 | 7.7 | 20 | dec. | dec. | TNFβ | 0.5 | 8.9 | 1.4 | dec. | dec. |
| IL-12 (p40) | 16.7 | 49.3 | 25.1 | dec. | dec. | VEGF-A | 15.6 | 131.8 | 67.3 | dec. | dec. |

FIG. 9B

| Patient 3 (Wsa) | | | | |
|---|---|---|---|---|
| Cytokines | Day 0 | Day 3 | Day 7 | Day 14 | Day 21 |
| sCD40L | 2477 | 2010 | 926.8 | 1825 | - |
| EGF | 50.8 | 54.9 | 111 | 31.5 | - |
| Eotaxin | 39.1 | 49.5 | 30.7 | 79.8 | - |
| FGF-2 | 75.6 | 120.5 | 372.7 | 133.5 | - |
| Flt-3 ligand | 40.3 | 30.75 | 35.8 | 20.9 | - |
| Fractalkine | 262.9 | 378.7 | 140.3 | 110.3 | - |
| G-CSF | 21.7 | 5.8 | 3 | 3 | - |
| GM-CSF | 2.63 | 1.51 | 5 | 1 | - |
| GROα | 27.9 | 40.7 | 91.4 | 9.5 | - |
| IFNα2 | 23.1 | 15.2 | 23.4 | 17.2 | - |
| IFNγ | 10.6 | <5.8 | 7.4 | 3 | - |
| IL-1α | 3.3 | 6.6 | 6.1 | 6.4 | - |
| IL-1β | 4.2 | 4.9 | 4.7 | 17.5 | - |
| IL-1ra | 359.7 | 167.2 | 6126 | 61 | - |
| IL-2 | 15.1 | 1.9 | 13.8 | 0.8 | - |
| IL-3 | 0.6 | 1.2 | 0.4 | 0.8 | - |
| IL-4 | 7.3 | <4.8 | 1.9 | 1 | - |
| IL-5 | 9.9 | <3.4 | 43.6 | 22.4 | - |
| IL-6 | 351.7 | 242.2 | 138.1 | 19.3 | - |
| IL-7 | 24.2 | 7.1 | 13.4 | 0.6 | - |
| IL-8 | 13.8 | 12.8 | 222.5 | 52.2 | - |
| IL-9 | 8.3* | 15.3* | 20.9 | 10 | - |
| IL-10 | 35.8 | 14.8 | 56.9 | 132.9 | - |
| IL-12 (p40) | 63.5 | 80.7 | 137.9 | 104.7 | - |

| Patient 3 (Wsa) | | | | |
|---|---|---|---|---|
| Cytokines | Day 0 | Day 3 | Day 7 | Day 14 | Day 21 |
| IL-12 (p70) | 2.2 | 2.7 | 2.4 | 2.1 | - |
| IL-13 | 17.8 | 9.7 | 28.3 | 10.6 | - |
| IL-15 | 38.7 | 49.6 | 54.9 | 15.9 | - |
| IL-17A | 3.5 | <0.5 | 2.6 | 2 | - |
| IL-17E/IL-25 | 334 | 248.5 | 208.8 | 154.3 | - |
| IL-17F | 8.1 | 30.6 | 31.3 | 28 | - |
| IL-18 | 30.3 | 44.5 | 382.4 | 153.5 | - |
| IL-22 | 17.9 | <0.8 | 31 | 13 | - |
| IL-27 | 1746 | 1149 | 2812 | 1215 | - |
| IP-10 | 16351 | 16351 | 15029 | 53026 | - |
| MCP-1 | 804.1 | 1782 | 1328 | 374.4 | - |
| MCP-3 | 19.8 | 45.1 | 41.9 | 18.5 | - |
| M-CSF | 499.6 | 197 | 221.2 | 246.8 | - |
| MDC (CCL22) | 289.8 | 621.9 | 987.7 | 827 | - |
| MIG | 8456 | 12714 | 37112 | 46949 | - |
| MIP-1α | 22.5 | 28.6 | 42.3 | 25.3 | - |
| MIP-1β | 37.2 | 51.5 | 68.2 | 66 | - |
| PDGF-AA | 2544 | 1664 | 5212 | 1477 | - |
| PDGF-AB/BB | 25383 | 24101 | 24686 | 19542 | - |
| RANTES | 62264 | 7953 | 177500 | 18480 | - |
| TGFα | 17.7 | 18.8 | 17.3 | 11.5 | - |
| TNFα | 22.6 | <8.2 | 13.6 | 9.4 | - |
| TNFβ | 1.5 | 2.4 | 7.3 | 2.8 | - |
| VEGF-A | 65.6 | 128.2 | 675.8 | 347.5 | - |

FIG. 9C

| Patient 4† (WS) | | | | | | Patient 4† (WS) | | | | |
|---|---|---|---|---|---|---|---|---|---|---|
| Cytokines | Day 0 | Day 3 | Day 7 | Day 14 | Day 21 | Cytokines | Day 0 | Day 3 | Day 7 | Day 14 | Day 21 |
| sCD40L | 565.4 | 1485 | 1409 | 1220 | - | IL-12 (p70) | 1.3 | 1.4 | 2 | 2.7 | - |
| EGF | 8 | 22.2 | 40.2 | 20.2 | - | IL-13 | <7 | <7 | 16.3 | 30.6 | - |
| Eotaxin | 101.5 | 107.9 | 110.7 | 74.6 | - | IL-15 | 23.5 | 18.2 | 17.2 | 11.6 | - |
| FGF-2 | 61.1 | 163 | 187.4 | 97.4 | - | IL-17A | 0.8 | <0.5 | 1 | 2.1 | - |
| Flt-3 ligand | 9.8 | 15.7 | 12.3 | 38.1 | - | IL-17E/IL-25 | 300.5 | 391.9 | 266.3 | 319.4 | - |
| Fractalkine | 179.4 | 156.7 | 131.1 | 139.6 | - | IL-17F | 10.5 | 4.2 | 11 | 11 | - |
| G-CSF | 50 | 49.8 | 21.6 | 43.1 | - | IL-18 | 100.1 | 1299 | 924.1 | 247.4 | - |
| GM-CSF | 1 | 1 | 1 | 1 | - | IL-22 | 49.4 | 13.9 | 18.2 | 48.9 | - |
| GROα | 3.1 | 5.2 | 12.9 | 2.1 | - | IL-27 | 3366 | 3731 | 4635 | 2673 | - |
| IFNα2 | 15.2 | 21.1 | 18.3 | 24.8 | - | IP-10 | 255.2 | 197.5 | 214.8 | 13378 | - |
| IFNγ | <5.8 | <5.8 | 3 | 5.5 | - | MCP-1 | 647.7 | 643.1 | 596.9 | 375.8 | - |
| IL-1α | 6.3 | 9.1 | 5.5 | 6.8 | - | MCP-3 | 19.77 | 14.8 | 17.1 | 25 | - |
| IL-1β | 3.4 | 7.1 | 5.5 | 4.8 | - | M-CSF | 91.88 | 134.5 | 91.4 | 254.8 | - |
| IL-1ra | 164.3 | 292.5 | 741.4 | 70.3 | - | MDC (CCL22) | 365.7 | 609.2 | 504.6 | 705.5 | - |
| IL-2 | <0.8 | <0.8 | <0.8 | 0.8 | - | MIG | 9005 | 5763 | 6188 | 18370 | - |
| IL-3 | 0.94 | 0.64 | 0.5 | 0.8 | - | MIP-1α | 14.9 | 17.9 | 17.2 | 24.1 | - |
| IL-4 | <4.8 | <4.8 | <4.8 | 2.3 | - | MIP-1β | 32.9 | 45.3 | 49.9 | 60.7 | - |
| IL-5 | <3.4 | <3.4 | <3.4 | 4.1 | - | PDGF-AA | 727.5 | 1369 | 2092 | 1430 | - |
| IL-6 | 161 | 78 | 47 | 33.7 | - | PDGF-AB/BB | 10675 | 21384 | 22045 | 17558 | - |
| IL-7 | 0.14 | 0.21 | 0.5 | 0.5 | - | RANTES | 24663 | 53673 | 78670 | 38647 | - |
| IL-8 | 9.1 | 52 | 54.2 | 7.9 | - | TGFα | 6.2 | 26.7 | 21.5 | 8.4 | - |
| IL-9 | 6 | 5.6 | 15.6 | 15.2 | - | TNFα | 19.5 | 8.5 | 3.3 | 105.3 | - |
| IL-10 | 13.3 | 2.6 | 21.8 | 7.7 | - | TNFβ | 1.6 | 1.8 | 1.9 | 2.8 | - |
| IL-12 (p40) | 50.2 | 39.6 | 30 | 53.5 | - | VEGF-A | 80.3 | 153.5 | 154.8 | 95.6 | - |

FIG. 9D

| Patient 5† (AA) | | | | | | Patient 5† (AA) | | | | | |
|---|---|---|---|---|---|---|---|---|---|---|---|
| Cytokines | Day 0 | Day 3 | Day 7 | Day 14 | Day 21 | Cytokines | Day 0 | Day 3 | Day 7 | Day 14 | Day 21 |
| sCD40L | 1245 | 345.9 | 192.4 | - | - | IL-12 (p70) | 2 | 2.94 | 3.8 | - | - |
| EGF | 35.6 | 17 | 18.9 | - | - | IL-13 | 11.3* | 20* | 14.2 | - | - |
| Eotaxin | 219.75 | 100.6 | 114.1 | - | - | IL-15 | 50.3 | 55.8 | 30.8 | - | - |
| FGF-2 | 161.5 | 184.1 | 239.9 | - | - | IL-17A | 2.4* | 3.8* | 4.4 | - | - |
| Flt-3 ligand | 65.6 | 51.9 | 28.3 | - | - | IL-17E/IL-25 | 295.8 | 436.8 | 493.4 | - | - |
| Fractalkine | 290.5 | 184.8 | 289.8 | - | - | IL-17F | 24.5* | 38.4* | 36.9 | - | - |
| G-CSF | 42.7 | 946.8 | 4 | - | - | IL-18 | 1097 | 1217 | 2908 | - | - |
| GM-CSF | 20.3 | 5 | 9.9 | - | - | IL-22 | 31.4* | 44.3* | 30.8 | - | - |
| GROα | 18.3 | 10.3 | 19.3 | - | - | IL-27 | 7265 | 16235 | 7745 | - | - |
| IFNα2 | 42.5 | 39.7 | 47.5 | - | - | IP-10 | 15029 | 15029 | 10320 | - | - |
| IFNγ | 6.4* | 8.7* | 6.2 | - | - | MCP-1 | 3074 | 4144 | 2184 | - | - |
| IL-1α | 5 | 6.1 | 7.4 | - | - | MCP-3 | 130.2 | 122.2 | 59.7 | - | - |
| IL-1β | 24.4 | 13.9 | 13.4 | - | - | M-CSF | 981.9 | 767.9 | 988.7 | - | - |
| IL-1ra | 4063 | 3007 | 246.2 | - | - | MDC (CCL22) | 561.2 | 448.2 | 626.6 | - | - |
| IL-2 | 0.8* | 1.9* | 3 | - | - | MIG | 2621 | 3226 | 3127 | - | - |
| IL-3 | 0.4 | 0.5 | 1.2 | - | - | MIP-1α | 31.3 | 96.7 | 34.9 | - | - |
| IL-4 | 0.8* | 1* | 1.4 | - | - | MIP-1β | 51.7 | 127.9 | 92.5 | - | - |
| IL-5 | 2.7* | 4.2* | 3.4 | - | - | PDGF-AA | 1628 | 1704 | 1099 | - | - |
| IL-6 | 3900* | 742* | 168 | - | - | PDGF-AB/BB | 20080 | 19343 | 18014 | - | - |
| IL-7 | 6.1 | 15.4 | 3.1 | - | - | RANTES | 27646 | 20934 | 9374 | - | - |
| IL-8 | 7.7 | 19.9 | 18.4 | - | - | TGFα | 33.5 | 20.6 | 25.8 | - | - |
| IL-9 | 10.5* | 16.8* | 15.5 | - | - | TNFα | 215* | 379.8* | 195.4 | - | - |
| IL-10 | 349.9* | 530.9* | 73.7 | - | - | TNFβ | 3.5 | 12.4 | 3.3 | - | - |
| IL-12 (p40) | 139.7 | 81.6 | 53.5 | - | - | VEGF-A | 90.8 | 98.1 | 141.2 | - | - |

FIG. 9E

| Patient 6† (AN) | | | | | | Patient 6† (AN) | | | | |
| --- | --- | --- | --- | --- | --- | --- | --- | --- | --- | --- |
| Cytokines | Day 0 | Day 3 | Day 7 | Day 14 | Day 21 | Cytokines | Day 0 | Day 3 | Day 7 | Day 14 | Day 21 |
| sCD40L | 713.3 | 1528 | 3059 | 1568 | - | IL-12 (p70) | 2 | 2 | 2.6 | 1.4 | - |
| EGF | 24.8 | 34.7 | 71.6 | 43 | - | IL-13 | 9.9* | 14.8* | 18 | 8.7 | - |
| Eotaxin | 88.4 | 59.5 | 57 | 118.4 | - | IL-15 | 13.1 | 15.4 | 13.2 | 4.5 | - |
| FGF-2 | 138.3 | 68.1 | 121.5 | 126.5 | - | IL-17A | 1* | 1.7* | 2.4 | 1.4 | - |
| Flt-3 ligand | 35 | 33.1 | 26.1 | 23 | - | IL-17E/IL-25 | 119 | 190 | 209.4 | 279.5 | - |
| Fractalkine | 206.9 | 217.6 | 248.9 | 286.9 | - | IL-17F | 11* | 12.2* | 28 | 19 | - |
| G-CSF | 3 | 3 | 3 | 3 | - | IL-18 | 1217 | 827.5 | 495.3 | 330.1 | - |
| GM-CSF | 5 | 5 | 5 | 0.9 | - | IL-22 | 44.3* | 15* | 13 | 13 | - |
| GROα | 2.2 | 6.6 | 5.5 | 2.4 | - | IL-27 | 1265 | 1956 | 2504 | 3832 | - |
| IFNα2 | 52.1 | 30.1 | 26.1 | 10.7 | - | IP-10 | 11453 | 12107 | 30257 | 1057 | - |
| IFNγ | 3.5 | 2.5 | 5 | 13.2 | - | MCP-1 | 383.8 | 340.6 | 274 | 208.8 | - |
| IL-1α | 3 | 4.2 | 7.1 | 5 | - | MCP-3 | 27 | 32.7 | 24.1 | 16 | - |
| IL-1β | 13.2 | 2.7 | 7.3 | 6.6 | - | M-CSF | 1087 | 630.7 | 633.1 | 87.9 | - |
| IL-1ra | 831.6 | 75.1 | 119.1 | 227.5 | - | MDC (CCL22) | 590.7 | 717.1 | 857.9 | 664.7 | - |
| IL-2 | 0.5* | 0.5* | 0.6 | 0.3 | - | MIG | 1550 | 1493 | 5050 | 24296 | - |
| IL-3 | 0.4 | 0.4 | 0.8 | 0.5 | - | MIP-1α | 56.5 | 73.3 | 47.3 | 62.1 | - |
| IL-4 | 0.5* | 0.5* | 0.7 | 0.2 | - | MIP-1β | 11.6 | 24.2 | 35.3 | 44.8 | - |
| IL-5 | 1.9* | 2.7* | 4.5 | 2 | - | PDGF-AA | 1333 | 2775 | 2477 | 1638 | - |
| IL-6 | 44.1* | 14.9* | 13.2 | 4.5 | - | PDGF-AB/BB | 12875 | 19830 | 22813 | 145265 | - |
| IL-7 | 0.6 | 0.9 | 1.3 | 0.7 | - | RANTES | 41113 | 168000 | 105600 | 1027 | - |
| IL-8 | 5 | 5.6 | 3.3 | 2.1 | - | TGFα | 7.3 | 3.9 | 12.5 | 5.1 | - |
| IL-9 | 5.6* | 5.4* | 6.1 | 8.6 | - | TNFα | 90* | 83.7* | 71.5 | 50.7 | - |
| IL-10 | 29* | 29* | 39.7 | 12.5 | - | TNFβ | 0.9 | 0.9 | 1.5 | 0.8 | - |
| IL-12 (p40) | 99.6 | 71 | 82.8 | 124.1 | - | VEGF-A | 92 | 97.5 | 271.5 | 106 | - |

| Patient 7† (PM) | | | | | |
|---|---|---|---|---|---|
| Cytokines | Day 0 | Day 3 | Day 7 | Day 14 | Day 21 |
| sCD40L | 2578 | 611.6 | 990.6 | - | - |
| EGF | 93.3 | 10.37 | 15 | - | - |
| Eotaxin | 78.7 | 36.9 | 27.7 | - | - |
| FGF-2 | 285.7 | 86.76 | 134.4 | - | - |
| Flt-3 ligand | 56.5 | 2.8 | 3.4 | - | - |
| Fractalkine | 108.1 | 83.7 | 147.8 | - | - |
| G-CSF | 3 | 3 | 3 | - | - |
| GM-CSF | 5 | 5 | 5 | - | - |
| GROα | 33.8 | 1 | 1.9 | - | - |
| IFNα2 | 30.1 | 15.2 | 21 | - | - |
| IFNγ | 7* | 1.55* | 2 | - | - |
| IL-1α | 9.6 | 3 | 6.1 | - | - |
| IL-1β | 11.4 | 3.2 | 1.9 | - | - |
| IL-1ra | 1717 | 121.5 | 59 | - | - |
| IL-2 | 0.5* | 0.5* | 0.68 | - | - |
| IL-3 | 0.4 | 0.4 | 0.8 | - | - |
| IL-4 | 1.1* | 0.5* | 0.4 | - | - |
| IL-5 | 9.1* | 10.8* | 3.4 | - | - |
| IL-6 | 672* | 70.5* | 13.5 | - | - |
| IL-7 | 32.1 | 11.4 | 4.1 | - | - |
| IL-8 | 3.2 | 1.1 | 7.4 | - | - |
| IL-9 | 15.6* | 3.4* | 4.9 | - | - |
| IL-10 | 59.9* | 64.6* | 39.5 | - | - |
| IL-12 (p40) | 60 | 18.5 | 16.6 | - | - |

| Patient 7† (PM) | | | | | |
|---|---|---|---|---|---|
| Cytokines | Day 0 | Day 3 | Day 7 | Day 14 | Day 21 |
| IL-12 (p70) | 2 | 2 | 1.6 | - | - |
| IL-13 | 17.9* | 7.2* | 11.8 | - | - |
| IL-15 | 28.6 | 26.7 | 22.8 | - | - |
| IL-17A | 3* | 1* | 2.1 | - | - |
| IL-17E/IL-25 | 285.9 | 64 | 143.7 | - | - |
| IL-17F | 33.5* | 11* | 28 | - | - |
| IL-18 | 2671 | 100.7 | 293 | - | - |
| IL-22 | 15* | 15* | 13 | - | - |
| IL-27 | 9032 | 8369 | 4908 | - | - |
| IP-10 | 15029 | 686.3 | 696.2 | - | - |
| MCP-1 | 693.8 | 404.1 | 216.8 | - | - |
| MCP-3 | 35 | 25.1 | 17.6 | - | - |
| M-CSF | 1538 | 296.7 | 576.5 | - | - |
| MDC (CCL22) | 307.8 | 231.1 | 265 | - | - |
| MIG | 2631 | 1691 | 4959 | - | - |
| MIP-1α | 23.8 | 10.3 | 16.6 | - | - |
| MIP-1β | 21 | 32.3 | 40.9 | - | - |
| PDGF-AA | 3228 | 749.8 | 700.8 | - | - |
| PDGF-AB/BB | 10182 | 16850 | 11600 | - | - |
| RANTES | 95893 | 12488 | 7329 | - | - |
| TGFα | 36.1 | 6.4 | 2.8 | - | - |
| TNFα | 124.5 | 40.3 | 57 | - | - |
| TNFβ | 2.4 | 4.3 | 1.3 | - | - |
| VEGF-A | 306.3 | 81.1 | 28.8 | - | - |

| Cytokines | Patient 8+(MO) | | | | | Cytokines | Patient 8+(MO) | | | | |
|---|---|---|---|---|---|---|---|---|---|---|---|
| | Day 0 | Day 3 | Day 7 | Day 14 | Day 21 | | Day 0 | Day 3 | Day 7 | Day 14 | Day 21 |
| sCD40L | 2401 | 2231 | dec. | dec. | dec. | IL-12 (p70) | 5.5 | 3.1 | dec. | dec. | dec. |
| EGF | 110.5 | 99.6 | dec. | dec. | dec. | IL-13 | 20.5* | 10.4* | dec. | dec. | dec. |
| Eotaxin | 220.2 | 177.7 | dec. | dec. | dec. | IL-15 | 27.9 | 27 | dec. | dec. | dec. |
| FGF-2 | 140.3 | 172.4 | dec. | dec. | dec. | IL-17A | 2.4* | 1.4* | dec. | dec. | dec. |
| Flt-3 ligand | 40.3 | 40.9 | dec. | dec. | dec. | IL-17E/IL-25 | 218.2 | 162.7 | dec. | dec. | dec. |
| Fractalkine | 198 | 181.7 | dec. | dec. | dec. | IL-17F | 31.6* | 34.2* | dec. | dec. | dec. |
| G-CSF | 3 | 3 | dec. | dec. | dec. | IL-18 | 380.7 | 827.9 | dec. | dec. | dec. |
| GM-CSF | 5 | 5 | dec. | dec. | dec. | IL-22 | 21.1* | 15* | dec. | dec. | dec. |
| GROα | 12.3 | 8.1 | dec. | dec. | dec. | IL-27 | 1839 | 1776 | dec. | dec. | dec. |
| IFNα2 | 42.5 | 17 | dec. | dec. | dec. | IP-10 | 15029 | 15029 | dec. | dec. | dec. |
| IFNγ | 6.6* | 7.6* | dec. | dec. | dec. | MCP-1 | 395.1 | 949.8 | dec. | dec. | dec. |
| IL-1α | 10.6 | 7.2 | dec. | dec. | dec. | MCP-3 | 41.9 | 45.9 | dec. | dec. | dec. |
| IL-1β | 6.9 | 47.5 | dec. | dec. | dec. | M-CSF | 588.9 | 1342 | dec. | dec. | dec. |
| IL-1ra | 737.9 | 797.3 | dec. | dec. | dec. | MDC (CCL22) | 186 | 240 | dec. | dec. | dec. |
| IL-2 | 0.5* | 0.5* | dec. | dec. | dec. | MIG | 4802 | 9295 | dec. | dec. | dec. |
| IL-3 | 0.51 | 0.4 | dec. | dec. | dec. | MIP-1α | 24.2 | 29 | dec. | dec. | dec. |
| IL-4 | 2.1* | 0.8* | dec. | dec. | dec. | MIP-1β | 17.9 | 58.2 | dec. | dec. | dec. |
| IL-5 | 4.5* | 4.9* | dec. | dec. | dec. | PDGF-AA | 3788 | 3498 | dec. | dec. | dec. |
| IL-6 | 148.4* | 55.3* | dec. | dec. | dec. | PDGF-AB/BB | 19830 | 23800 | dec. | dec. | dec. |
| IL-7 | 2.5 | 1.1 | dec. | dec. | dec. | RANTES | 86466 | 62123 | dec. | dec. | dec. |
| IL-8 | 3.2 | 39.8 | dec. | dec. | dec. | TGFα | 27.8 | 18.9 | dec. | dec. | dec. |
| IL-9 | 15.1* | 12* | dec. | dec. | dec. | TNFα | 114.5 | 89.9 | dec. | dec. | dec. |
| IL-10 | 29.6* | 29.4* | dec. | dec. | dec. | TNFβ | 5.3 | 6.3 | dec. | dec. | dec. |
| IL-12 (p40) | 37.3 | 84.6 | dec. | dec. | dec. | VEGF-A | 518.5 | 563.5 | dec. | dec. | dec. |

FIG. 9H

| Patient 9 (JF) | | | | | | Patient 9 (JF) | | | | |
|---|---|---|---|---|---|---|---|---|---|---|
| Cytokines | Day 0 | Day 3 | Day 7 | Day 14 | Day 21 | Cytokines | Day 0 | Day 3 | Day 7 | Day 14 | Day 21 |
| sCD40L | 1124 | 1090 | dec. | dec. | dec. | IL-12 (p70) | 2 | 4.4 | dec. | dec. | dec. |
| EGF | 7.2 | 10.9 | dec. | dec. | dec. | IL-13 | 28.3 | 57.2 | dec. | dec. | dec. |
| Eotaxin | 27 | 39.4 | dec. | dec. | dec. | IL-15 | 12.7 | 19.7 | dec. | dec. | dec. |
| FGF-2 | 246.3 | 183.9 | dec. | dec. | dec. | IL-17A | 9.6 | 8.8 | dec. | dec. | dec. |
| Flt-3 ligand | 13 | 11.2 | dec. | dec. | dec. | IL-17E/IL-25 | 208.8 | 263.5 | dec. | dec. | dec. |
| Fractalkine | 160.5 | 255.1 | dec. | dec. | dec. | IL-17F | 47.6 | 31.8 | dec. | dec. | dec. |
| G-CSF | 3 | 3 | dec. | dec. | dec. | IL-18 | 2736 | 911.4 | dec. | dec. | dec. |
| GM-CSF | 5 | 5 | dec. | dec. | dec. | IL-22 | 15 | 31.31 | dec. | dec. | dec. |
| GROα | 6.5 | 2.3 | dec. | dec. | dec. | IL-27 | 1500 | 954.2 | dec. | dec. | dec. |
| IFNα2 | 12.2 | 19.8 | dec. | dec. | dec. | IP-10 | 1361 | 1778 | dec. | dec. | dec. |
| IFNγ | 6.5 | 10.6 | dec. | dec. | dec. | MCP-1 | 209.2 | 189.8 | dec. | dec. | dec. |
| IL-1α | 25.9 | 31.3 | dec. | dec. | dec. | MCP-3 | 23.2 | 38.9 | dec. | dec. | dec. |
| IL-1β | 28.3 | 19.3 | dec. | dec. | dec. | M-CSF | 391.1 | 226.8 | dec. | dec. | dec. |
| IL-1ra | 4516 | 2862 | dec. | dec. | dec. | MDC (CCL22) | 813.1 | 1141 | dec. | dec. | dec. |
| IL-2 | 0.8 | 2.3 | dec. | dec. | dec. | MIG | 14975 | 13914 | dec. | dec. | dec. |
| IL-3 | 0.4 | 1.5 | dec. | dec. | dec. | MIP-1α | 33.6 | 29.8 | dec. | dec. | dec. |
| IL-4 | 0.5 | 0.7 | dec. | dec. | dec. | MIP-1β | 71.5 | 89.6 | dec. | dec. | dec. |
| IL-5 | 9.2 | 14.5 | dec. | dec. | dec. | PDGF-AA | 2170 | 1045 | dec. | dec. | dec. |
| IL-6 | 75.6 | 33.9 | dec. | dec. | dec. | PDGF-AB/BB | 22420 | 12681 | dec. | dec. | dec. |
| IL-7 | 1 | 0.8 | dec. | dec. | dec. | RANTES | 78834 | 35603 | dec. | dec. | dec. |
| IL-8 | 18.1 | 7.9 | dec. | dec. | dec. | TGFα | 15.3 | 8.1 | dec. | dec. | dec. |
| IL-9 | 12.3 | 10.8 | dec. | dec. | dec. | TNFα | 125.9 | 43.23 | dec. | dec. | dec. |
| IL-10 | 40.9 | 50.4 | dec. | dec. | dec. | TNFβ | 5.3 | 10.6 | dec. | dec. | dec. |
| IL-12 (p40) | 169.1 | 362.2 | dec. | dec. | dec. | VEGF-A | 27.6 | 30.6 | dec. | dec. | dec. |

FIG. 9I

| Patient 10 (AR) | | | | | | Patient 10 (AR) | | | | |
|---|---|---|---|---|---|---|---|---|---|---|
| Cytokines | Day 0 | Day 3 | Day 7 | Day 14 | Day 21 | Cytokines | Day 0 | Day 3 | Day 7 | Day 14 | Day 21 |
| sCD40L | 1306 | 3672 | dec. | dec. | dec. | IL-12 (p70) | 2 | 4 | dec. | dec. | dec. |
| EGF | 7.2 | 15.9 | dec. | dec. | dec. | IL-13 | 6.8 | 21.1 | dec. | dec. | dec. |
| Eotaxin | 639.1 | 219.4 | dec. | dec. | dec. | IL-15 | 11.4 | 19.1 | dec. | dec. | dec. |
| FGF-2 | 64.9 | 154.5 | dec. | dec. | dec. | IL-17A | 1 | 2.5 | dec. | dec. | dec. |
| Flt-3 ligand | 51.5 | 38.7 | dec. | dec. | dec. | IL-17E/IL-25 | 281 | 476.5 | dec. | dec. | dec. |
| Fractalkine | 214.7 | 312.1 | dec. | dec. | dec. | IL-17F | 16.3 | 28.5 | dec. | dec. | dec. |
| G-CSF | 3 | 3 | dec. | dec. | dec. | IL-18 | 215.2 | 1169 | dec. | dec. | dec. |
| GM-CSF | 5 | 5 | dec. | dec. | dec. | IL-22 | 15 | 13 | dec. | dec. | dec. |
| GROα | 1 | 1.9 | dec. | dec. | dec. | IL-27 | 4379 | 6321 | dec. | dec. | dec. |
| IFNα2 | 15.8 | 37.5 | dec. | dec. | dec. | IP-10 | 10823 | 118762 | dec. | dec. | dec. |
| IFNγ | 6 | 5.23 | dec. | dec. | dec. | MCP-1 | 1852 | 2375 | dec. | dec. | dec. |
| IL-1α | 7.4 | 14.7 | dec. | dec. | dec. | MCP-3 | 28.3 | 41.1 | dec. | dec. | dec. |
| IL-1β | 4.2 | 8.5 | dec. | dec. | dec. | M-CSF | 204.3 | 484.9 | dec. | dec. | dec. |
| IL-1ra | 505.5 | 10915 | dec. | dec. | dec. | MDC (CCL22) | 619.9 | 923.7 | dec. | dec. | dec. |
| IL-2 | 0.5 | 1.3 | dec. | dec. | dec. | MIG | 19817 | 33256 | dec. | dec. | dec. |
| IL-3 | 0.4 | 0.8 | dec. | dec. | dec. | MIP-1α | 14.6 | 29.1 | dec. | dec. | dec. |
| IL-4 | 0.5 | 0.5 | dec. | dec. | dec. | MIP-1β | 53.9 | 59.9 | dec. | dec. | dec. |
| IL-5 | 3.1 | 5.2 | dec. | dec. | dec. | PDGF-AA | 1291 | 1747 | dec. | dec. | dec. |
| IL-6 | 753.6 | 57.9 | dec. | dec. | dec. | PDGF-AB/BB | 16850 | 22740 | dec. | dec. | dec. |
| IL-7 | 0.5 | 1.5 | dec. | dec. | dec. | RANTES | 19044 | 25895 | dec. | dec. | dec. |
| IL-8 | 5.3 | 12.7 | dec. | dec. | dec. | TGFα | 15.3 | 28.5 | dec. | dec. | dec. |
| IL-9 | 5.4 | 12.3 | dec. | dec. | dec. | TNFα | 105.1 | 36.8 | dec. | dec. | dec. |
| IL-10 | 45 | 60.8 | dec. | dec. | dec. | TNFβ | 0.9 | 3.7 | dec. | dec. | dec. |
| IL-12 (p40) | 47 | 54.8 | dec. | dec. | dec. | VEGF-A | 85.9 | 54.5 | dec. | dec. | dec. |

FIG. 9J

| Patient | Age/Gender | Pre-existing conditions | Renal transplant year | Dialysis in hospital | Vasopressors used | Baseline status | Leronlimab start date | Extubated |
|---|---|---|---|---|---|---|---|---|
| P1 | 74/M | AKI, HTHD, Prostate CA (s/p prostatectomy), DM, Gout | N/A | Yes | Yes | Intubated | 3/21/20 | No |
| P2 | 74/F | ESRD, HTHD, DM, HLD | 2018 | Yes | Yes | Intubated | 3/18/20 | No |
| P3 | 54/M | RF, HTHD, HLD | N/A | Yes | Yes | Venturi mask, same day intubated | 3/20/20 | No |
| P4 | 56/M | HTHD, Skin CA, Papillary thyroid CA (s/p thyroidectomy), DM | N/A | Yes | Yes | Intubated | 3/18/20 | 3/19/20 |
| P5 | 58/M | ESRD, CKD stage 3 in renal allograft, recurrent UTI with MDR E.coli, DM, DR, HTHD, HLD | 2016 | Yes | Yes | Intubated | 3/28/20 | 4/10/20 |
| P6 | 42/M | FSGS, CKD stage 3, DVT/PE, Gout | 2005, 2016 | No | No | On 2L NC | 3/28/20 | N/A |
| P7 | 68/M | ESRD, Hydronephrosis (s/p stent placement) HTHD, HLD, DM with retinopathy and neuropathy | 2018 | Yes | Yes | On NRB | 3/27/20 | 4/12/20 |
| P8 | 56/F | ESRD, lung CA (s/p bilateral upper lobectomy), COPD, Asthma, DM, HTHD, HLD, Hepatitis C | 2009 | No | No | 3-4 L NC* | 3/25/20 | No |
| P9 | 51/F | AKI, HTHD, OSA (on Bilevel Positive Airway Pressure) | 2006 | Yes | Yes | Intubated | 3/29/20 | No |
| P10 | 79/M | AKI, CAD, Prostate CA, GERD, HTHD, HLD | N/A | Yes | Yes | Intubated | 3/29/20 | No |

*FIG. 11*

|  | Patient 1[†] (KM) | | | | | Patient 2[†] (JW) | | | | | Patient 3 (Wsa) | | | | |
|---|---|---|---|---|---|---|---|---|---|---|---|---|---|---|---|
| | Day 0 | Day 3 | Day 7 | Day 14 | Day 21 | Day 0 | Day 3 | Day 7 | Day 14 | Day 21 | Day 0 | Day 3 | Day 7 | Day 14 | Day 21 |
| Parameter | 3/21/2020 | (Date) | 3/28/2020 | 4/4/2020 | 4/11/2020 | 3/18/2020 | (Date) | 3/25/2020 | 4/1/2020 | 4/8/2020 | 3/20/2020 | (Date) | 3/27/2020 | 4/3/2020 | 4/10/2020 |
| Ferritin (ng/mL) | 5653 | - | 5653 | 3668 | 2338 | No Result | - | No Result | dec. | dec. | 1865 | - | 1865 | 1783 | 3221 |
| CRP (mg/dL) | 13.3 | - | 19.4 | 8.1 | 18.7 | 15.6 | - | 23 | dec. | dec. | 58 | - | 58 | 12.1 | 15.2 |
| Procalcitonin (ng/mL) | 1.1 | - | 2.1 | 1.8 | 1.8 | 3.9 | - | 1.5 | dec. | dec. | 11.5 | - | 14.4 | 16.8 | >50.0 |
| D-dimer (μg/mL) | 5.48 | - | 5.48 | 7.67 | 6.76 | No Result | - | No Result | dec. | dec. | >20.0 | - | >20 | 14.12 | 7.44 |
| Platelets ($10^3/\mu L$) | 355 | - | 427 | 344 | 142 | 120 | - | 204 | dec. | dec. | 213 | - | 580 | 320 | 320 |
| Hb (g/dL) | 11 | - | 10.9 | 10.7 | 9 | 8.1 | - | 8.4 | dec. | dec. | 12.9 | - | 9.4 | 6.8 | 8.4 |
| WBC ($10^3/\mu L$) | 12.5 | - | 16.4 | 13.4 | 15.7 | 5.6 | - | 14.3 | dec. | dec. | 10.6 | - | 16.7 | 13.3 | 7.8 |
| Lymphocyte ($10^3/\mu L$) | 1.1 | - | 1.3 | 1.6 | 1 | 0.4 | - | 0.4 | dec. | dec. | 1.1 | - | 0.3 | 1.7 | 0.9 |
| BUN (mg/dL) | 54 | - | >112 | 156 | 91 | 25 | - | 112 | dec. | dec. | 91 | - | 55 | 100 | 98 |
| Creatinine (mg/dL) | 5.6 | - | 5.4 | 6.5 | 1.9 | 1.2 | - | 5.5 | dec. | dec. | 8.3 | - | 5.2 | 6 | 7.7 |
| Sodium (mmol/L) | 134 | - | 139 | 142 | 142 | 138 | - | 143 | dec. | dec. | 131 | - | 129 | 134 | 134 |
| AST (IU/L) | 52 | - | 45 | 33 | 52 | 78 | - | 35 | dec. | dec. | 265 | - | 45 | 96 | 144 |
| ALT (IU/L) | 128 | - | 79 | 46 | 71 | 51 | - | 60 | dec. | dec. | 172 | - | 24 | 97 | 261 |
| Total Bilirubin (mg/dL) | 2.5 | - | 1.1 | 4.4 | 0.8 | 0.3 | - | 0.3 | dec. | dec. | 0.7 | - | 1 | 0.6 | 0.8 |

"-" indicates data is unavailable.
"dec." indicates patient is deceased.
[†] patient number identifiers differ from first reported identifiers, patient initial identifiers are the same

*FIG. 16A*

| Parameter | Patient 4† (WS) | | | | Patient 5† (AA) | | | | | Patient 6† (AN) | | | | |
|---|---|---|---|---|---|---|---|---|---|---|---|---|---|---|
| | Day 0 | Day 3 | Day 7 | Day 14 | Day 21 | Day 0 | Day 3 | Day 7 | Day 14 | Day 21 | Day 0 | Day 3 | Day 7 | Day 14 | Day 21 |
| | 3/18/2020 | (Date) | 3/25/2020 | 4/1/2020 | 4/8/2020 | 3/28/2020 | (Date) | 4/4/2020 | 4/11/2020 | 4/18/2020 | 3/28/2020 | (Date) | 4/4/2020 | 4/11/2020 | 4/18/2020 |
| Ferritin (ng/mL) | 1750 | - | 1750 | 1750 | 1764 | 9259 | - | 9267 | 7151 | 4666 | 1261 | - | 1679 | 1592 | 786 |
| CRP (mg/dL) | 24.9 | - | 10 | 9.2 | 3.7 | 32.1 | - | 18.6 | 14.7 | 21 | 7.4 | - | 5.2 | 1.7 | 1 |
| Procalcitonin (ng/mL) | 2.4 | - | 0.8 | 0.8 | 0.8 | 1.6 | - | 9.4 | 10.6 | 1.5 | 0.2 | - | 0.4 | 0.4 | 0.4 |
| D-dimer (μg/mL) | 6.08 | - | 6.08 | 4.68 | 4.68 | 3.74 | - | 12.26 | 19.5 | >20 | 0.83 | - | 2.34 | 2.53 | 1.55 |
| Platelets (10³/μl) | 224 | - | 361 | 278 | 276 | 188 | - | 137 | 310 | 257 | 110 | - | 234 | 325 | 230 |
| Hb (g/dL) | 7.8 | - | 5.3 | 7.4 | 7.5 | 10.9 | - | 8.9 | 8.7 | 7.4 | 14.6 | - | 13.3 | 12.1 | 10.6 |
| WBC (10³/μl) | 9.7 | - | 13 | 10.1 | 8.9 | 9.5 | - | 17.6 | 12.9 | 11.1 | 2.7 | - | 6.5 | 6.5 | 4.9 |
| Lymphocyte (10³/μl) | 0.4 | - | 0.8 | 0.9 | 0.7 | 0.4 | - | 0.4 | 0.6 | 0.9 | 0.5 | - | 1.1 | 2.3 | 1.7 |
| BUN (mg/dL) | 63 | - | 132 | 96 | 76 | 38 | - | 42 | 46 | 43 | 33 | - | 36 | 33 | 15 |
| Creatinine (mg/dL) | 5.4 | - | 12.1 | 11.6 | 8.1 | 3.6 | - | 3.9 | 6.1 | 4.6 | 2.5 | - | 1.8 | 1.7 | 1.4 |
| Sodium (mmol/L) | 137 | - | 137 | 132 | 133 | 133 | - | 133 | 135 | 142 | 2 | - | 1.8 | 1.7 | 1.4 |
| AST (IU/L) | 29 | - | <20 | 25 | <20 | 38 | - | 128 | 74 | 29 | 55 | - | 40 | 90 | 30 |
| ALT (IU/L) | 41 | - | 33 | 30 | <10 | 13 | - | 70 | 54 | 17 | 32 | - | 43 | 116 | 55 |
| Total Bilirubin (mg/dL) | 0.3 | - | 0.3 | 0.3 | 0.2 | 0.2 | - | 0.6 | 0.5 | 0.4 | 0.5 | - | 0.6 | 0.3 | 0.6 |

"-" indicates data is unavailable.
"dec." indicates patient is deceased.
† patient number identifiers differ from first reported identifiers, patient initial identifiers are the same

*FIG. 16B*

| Parameter | Patient 7† (PM) | | | | | Patient 8† (MO) | | | | | Patient 9 (JF) | | | | |
|---|---|---|---|---|---|---|---|---|---|---|---|---|---|---|---|
| | Day 0 | Day 3 | Day 7 | Day 14 | Day 21 | Day 0 | Day 3 | Day 7 | Day 14 | Day 21 | Day 0 | Day 3 | Day 7 | Day 14 | Day 21 |
| | 3/27/2020 | (Date) | 4/3/2020 | 4/10/2020 | 4/17/2020 | 3/25/2020 | (Date) | 4/1/2020 | 4/8/2020 | 4/15/2020 | 3/29/2020 | (Date) | 4/5/2020 | 4/12/2020 | 4/19/2020 |
| Ferritin (ng/mL) | 3343 | - | 3361 | 4308 | 3462 | No result | - | dec. | dec. | dec. | No Result | - | dec. | dec. | dec. |
| CRP (mg/dL) | 16 | - | 13.3 | 22.8 | 21.2 | 4.5 | - | dec. | dec. | dec. | 44.1 | - | dec. | dec. | dec. |
| Procalcitonin (ng/mL) | 0.4 | - | 3.8 | 1.3 | 2.2 | 0.5 | - | dec. | dec. | dec. | 7 | - | dec. | dec. | dec. |
| D- dimer (µg/mL) | >20 | - | 5.07 | 1.89 | 1.51 | No Result | - | dec. | dec. | dec. | No Result | - | dec. | dec. | dec. |
| Platelets ($10^3$/µl) | 326 | - | 271 | 248 | 125 | 243 | - | dec. | dec. | dec. | 216 | - | dec. | dec. | dec. |
| Hb (g/dL) | 10.9 | - | 8.1 | 8 | 8.6 | 10.1 | - | dec. | dec. | dec. | 6.8 | - | dec. | dec. | dec. |
| WBC ($10^3$/µl) | 11.1 | - | 19.2 | 16.7 | 12.2 | 18.2 | - | dec. | dec. | dec. | 10.3 | - | dec. | dec. | dec. |
| Lymphocyte ($10^3$/µl) | 0.9 | - | 0.7 | 1.4 | 0.6 | 0.9 | - | dec. | dec. | dec. | 0.8 | - | dec. | dec. | dec. |
| BUN (mg/dL) | 28 | - | 59 | 88 | 53 | 65 | - | dec. | dec. | dec. | 27 | - | dec. | dec. | dec. |
| Creatinine (mg/dL) | 1.2 | - | 3.8 | 3.7 | 2.4 | 2.6 | - | dec. | dec. | dec. | 4.5 | - | dec. | dec. | dec. |
| Sodium (mmol/L) | 135 | - | 135 | 149 | 147 | 129 | - | dec. | dec. | dec. | 134 | - | dec. | dec. | dec. |
| AST (IU/L) | <20 | - | 23 | 25 | 27 | <20 | - | dec. | dec. | dec. | 20 | - | dec. | dec. | dec. |
| ALT (IU/L) | 13 | - | 25 | 17 | 36 | 13 | - | dec. | dec. | dec. | 16 | - | dec. | dec. | dec. |
| Total Bilirubin (mg/dL) | 0.6 | - | 0.4 | 0.2 | 0.4 | 0.1 | - | dec. | dec. | dec. | 0.3 | - | dec. | dec. | dec. |

"-" indicates data is unavailable.
"dec." indicates patient is deceased.
† patient number identifiers differ from first reported identifiers, patient initial identifiers are the same

*FIG. 16C*

|  | Patient 10 (AR) | | | | Patient 11 (JH) | | | | |
|---|---|---|---|---|---|---|---|---|---|
|  | Day 0 | Day 3 | Day 7 | Day 14 | Day 21 | Day 0 | Day 3 | Day 7 | Day 14 | Day 21 |
| Parameter | 3/29/2020 | (Date) | 4/5/2020 | 4/12/2020 | 4/19/2020 | 4/2/2020 | (Date) | 4/9/2020 | 4/16/2020 | 4/23/2020 |
| Ferritin (ng/mL) | 3898 | - | dec. | dec. | dec. | 2332 | - | dec. | dec. | dec. |
| CRP (mg/L) | 18.4 | - | dec. | dec. | dec. | 37.4 | - | dec. | dec. | dec. |
| Procalcitonin (ng/mL) | 0.6 | - | dec. | dec. | dec. | 0.7 | - | dec. | dec. | dec. |
| D-dimer (mg/L) | >20 | - | dec. | dec. | dec. | 2.32 | - | dec. | dec. | dec. |
| Platelets (cells/µl) | 136 | - | dec. | dec. | dec. | 265 | - | dec. | dec. | dec. |
| Hb (g/dL or mmol/L) | 11.3 | - | dec. | dec. | dec. | 8.1 | - | dec. | dec. | dec. |
| WBC (cells/µl) | 10.7 | - | dec. | dec. | dec. | 11.7 | - | dec. | dec. | dec. |
| Lymphocyte (cells/µl) | 0.9 | - | dec. | dec. | dec. | 0.1 | - | dec. | dec. | dec. |
| BUN (mg/dL or mmol/L) | 102 | - | dec. | dec. | dec. | 74 | - | dec. | dec. | dec. |
| creatinine (mg/dL) | 3.2 | - | dec. | dec. | dec. | 3.4 | - | dec. | dec. | dec. |
| Sodium (mEq/L) | 145 | - | dec. | dec. | dec. | 128 | - | dec. | dec. | dec. |
| AST (units/L) | 86 | - | dec. | dec. | dec. | 67 | - | dec. | dec. | dec. |
| ALT (units/L) | 63 | - | dec. | dec. | dec. | 56 | - | dec. | dec. | dec. |
| Total Bilirubin (mg/dL) | 0.5 | - | dec. | dec. | dec. | 0.2 | - | dec. | dec. | dec. |

"-" indicates data is unavailable.
"dec." indicates patient is deceased.
† patient number identifiers differ from first reported identifiers, patient initial identifiers are the same

FIG. 16D

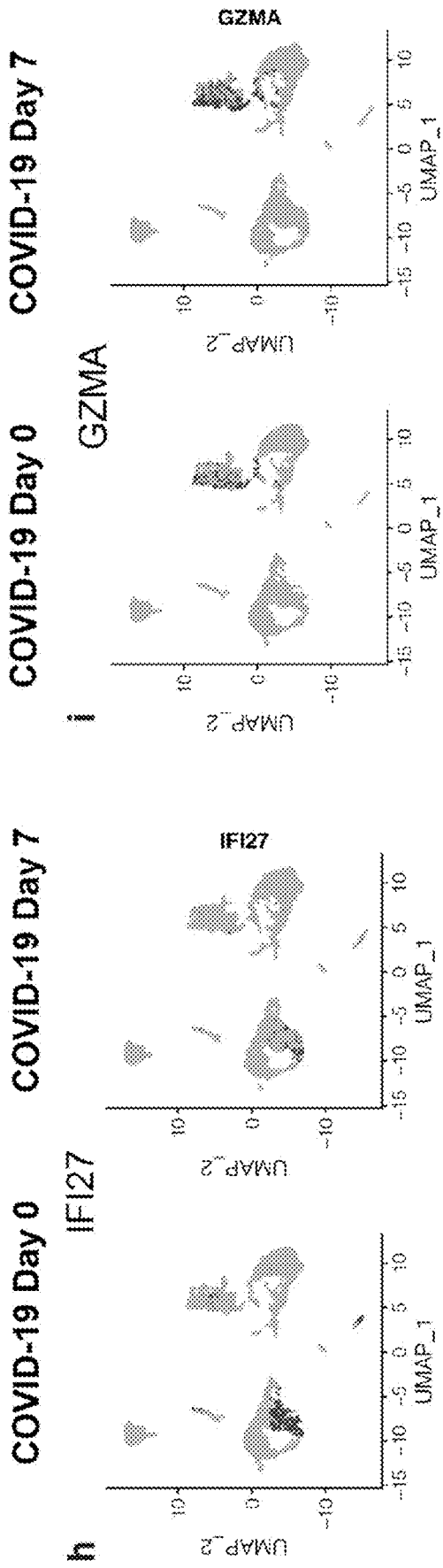

| Immune Profiling Markers | Fluorochrome | Clone | Vendor | μg per Test |
|---|---|---|---|---|
| CD8 | BUV496 | RPA-T8 | BD | 0.2 |
| CD4 | BUV661 | SK3 | BD | 0.08 |
| CD45 | BUV805 | HI30 | BD | 0.1 |
| CD103 | BV421 | Ber-ACT8 | BioLegend | 0.2 |
| TIM3 | BV605 | 7D3 | BD | 0.6 |
| CD56 | BV650 | HCD56 | BioLegend | 0.3 |
| LAG-3 | BV711 | 11C3C65 | BioLegend | 0.3 |
| CD14 | BV786 | M5E2 | BioLegend | 0.3 |
| PD-1 | BB700 | EH12.1 | BD | 0.6 |
| FoxP3 | PE | 259D/C7 | BD | 0.3 |
| CD19 | PE-Dazzle5 | HIB19 | BioLegend | 0.15 |
| CD3 | APC | UCHT1 | BioLegend | 0.05 |
| CTLA-4 | PE-Cy7 | BN13 | BioLegend | 0.3 |
| CD16 | AF700 | 3G8 | BioLegend | 0.75 |
| HLA-DR | APC/Fire750 | L243 | BioLegend | 0.6 |

| Receptor Occupancy Markers | Fluorochrome | Clone | Vendor | μg per Test |
|---|---|---|---|---|
| CD4 | FITC | SK3 | BioLegend | 0.1 |
| CD14 | PerCPCy5.5 | HCD14 | BioLegend | 0.6 |
| PRO140 | PE | PRO140 | IncellDx | 0.25 |
| CD16 | Alexa647 | 3G8 | BD | 0.5 |
| FoxP3 | Alexa647 | 206D | Biolegend | 0.12 |
| CD45RO | PE-Cy7 | UCHL1 | Beckman Coulter | 0.25 |

*FIG. 20*

METHODS OF TREATING CORONAVIRUS INFECTION

STATEMENT REGARDING SEQUENCE LISTING

The Sequence Listing associated with this application is provided in text format in lieu of a paper copy, and is hereby incorporated by reference into the specification. The name of the text file containing the Sequence Listing is 230042_432_SEQUENCE_LISTING.txt. The text file is 15.3 KB, was created on Jun. 4, 2020, and is being submitted electronically via EFS-Web.

BACKGROUND

COVID-19, influenza, and other infectious diseases can cause not only severe respiratory system distress and lung damage, but can be fatal due to an overreaction of the body's immune system, which is sometimes referred to as a cytokine storm. Such hyperinflammation a common complication not only of COVID-19 and influenza but of other respiratory diseases caused by coronaviruses such as SARS-CoV-1 (SARS) and MERS. Cytokine storms are also associated with non-infectious diseases including, but not limited to, multiple sclerosis and pancreatitis.

Cytokines are small proteins released by many different cells in the body, including those of the immune system where they coordinate the body's response against infection and trigger inflammation. Sometimes the body's response is one of overreaction over reacts to infection. For example, when SARS-CoV-2, the virus behind the COVID-19 pandemic, enters the lungs, it triggers an immune response, attracting immune cells to the region to attack the virus, resulting in localized inflammation. But in some patients, excessive or uncontrolled levels of cytokines are released which then activate more immune cells, resulting in hyperinflammation. This can seriously harm or even kill the patient.

The CCR5 receptor is a C-C chemokine G-coupled protein receptor expressed on lymphocytes (e.g., NK cells, B cells), monocytes, macrophages, dendritic cells, a subset of T cells, etc. Among other ligands, the CCR5 receptor binds to a chemokine known as CCL5 (C-C chemokine ligand 5), which is an inflammatory chemokine that plays an important role in immunologic mechanisms such as controlling cell recruitment and activation in basal and inflammatory circumstances. CCL5 acts as a key regulator of T cell migration to inflammatory sites, directing migration of T cells to damaged or infected sites. CCL5 also regulates T cell differentiation. Many biologic effects of chemokines are mediated by their interaction with chemokine receptors on cell surfaces.

Two coronaviruses that have recently emerged in the human population, SARS-CoV-1 (SARS) and SARS-CoV-2 (COVID-19). Coronavirus disease 2019 (COVID-19) is a viral respiratory illness that can spread from person to person. Patients with COVID-19 have had mild to severe respiratory illness with symptoms such as fever, cough, and shortness of breath along with non-specific symptoms including myalgia and fatigue.

The current standard of care for COVID-19 supportive treatment includes oxygen therapy. There is no specific antiviral treatment recommended for COVID-19 by Centers for Disease Control and Prevention (CDC). People with COVID-19 should receive supportive care to help relieve symptoms. For severe cases, treatment should include care to support vital organ functions.

Acute respiratory distress syndrome (ARDS) is the leading cause of mortality for COVID-19.

Secondary haemophagocytic lymphohistiocytosis (sHLH) is a hyperinflammatory syndrome characterized by a fulminant and fatal hypercytokinaemia with multi-organ failure. In adults, sHLH is most commonly triggered by viral infections and occurs in 3.7-4.3% of sepsis cases. Cardinal features of sHLH include unremitting fever, cytopenias, and hyperferritinaemia; pulmonary involvement (including ARDS) occurs in approximately 50% of patients.

A cytokine profile similar to sHLH is associated with COVID-19 disease severity, characterized by increased inflammatory cytokines such as interleukin (IL)-2, IL-7, granulocyte colony stimulating factor, interferon-γ inducible protein 10, monocyte chemoattractant protein 1, macrophage inflammatory protein 1-α, and tumor necrosis factor-α.

Predictors of fatality from a retrospective, multicenter study of 150 confirmed COVID-19 cases in Wuhan, China, included elevated ferritin suggesting that mortality might be due to virus-induced hyperinflammation. Mehta et al., *COVID-19: consider cytokine storm syndromes and immunosuppression*, THE LANCET, vol. 395, issue 10229, pp. 1033-1034 (2020). There is an urgent need for therapies that can treat coronavirus-induced respiratory illnesses such as acute respiratory distress syndrome.

Many efforts are underway to identify and develop suitable treatments for COVID-19, including several of which address problems associated with cytokine storm. For example, it is reported that at least the following products, none of which target CCR5, are currently being investigated for use in treating COVID-19: baricitinib (Eli Lilly) and ruxolitinib (InCyte) are each orally-dosed inhibitors of Janus kinases 1 and 2 (JAK1/2); tocilizumab (Hoffman La Roche and Chugai) is an IV-administered monoclonal antibody targeting both the soluble and transmembrane IL-6 receptor; siltuximab (EUSA Pharma) is an IV-administered chimeric monoclonal antibody targeting IL-6; sarilumab is an IV-administered fully human monoclonal antibody targeting both the soluble and transmembrane IL-6 receptor (Regeneron Pharmaceuticals and Sanofi); TZLS-501 (Tiziana Life Sciences) is a fully human monoclonal antibody targeting both the soluble and transmembrane IL-6 receptor while also depleting circulating levels of IL-6 in the blood; anakinra (Swedish Orphan Biovitrum) is a recombinant IL-1R antagonist protein; emapalumab (Novimmune and Swedish Orphan Biovitrum) is an IV-administered human IgG1 monoclonal antibody targeting IFN-γ; hydroxychloroquine is an orally-administered drug that a) enters antigen-presenting cells (APCs) and prevents antigen processing and MHC class II-mediated autoantigen presentation to T cells, preventing T cell activation and cytokine production and b) disrupts interaction of DNA/RNA with toll-like receptors (TLRs) and the nucleic acid sensor cGAS, ultimately inhibiting the transcription of pro-inflammatory genes; TJM2 (I-Mab Biopharma) is an IV-administered human monoclonal antibody targeting granulocyte-macrophage colony stimulating factor (GM-CSF); gimsilumab (Roivant Sciences) is an IV-administered human monoclonal antibody targeting GM-CSF; lenzilumab (Humanigen Inc.) is an IV-administered humanized monoclonal antibody targeting GM-CSF; fingolimod (Novartis) is a S1PR modulator that blocks the capacity of lymphocytes to egress from lymph nodes, reducing the number of circulating lymphocytes; and CD24-Fc (Oncoimmune) binds and sequesters DAMPs to prevent their interaction with TLR receptor.

The present disclosure provides CCR5 binding agents that are useful in treating or preventing hyperinflammation associated with, for example, viral infections, including the coronavirus that causes COVID-19.

BRIEF SUMMARY

In one aspect, the present disclosure provides a method of treating or preventing hyperinflammation, for example hyperinflammation associated with a viral infection, comprising administering to the subject an effective amount of a CCR5 binding agent.

In some embodiments, the viral infection is a coronavirus infection.

In some embodiments, the coronavirus infection is SARS-CoV-1 of SARS-CoV-2.

In some embodiments, the subject has a coronavirus-induced respiratory illness, such as COVID-19 or acute respiratory distress syndrome (ARDS).

In some embodiments, the CCR5 binding agent is an antibody or antigen binding fragment thereof. In some embodiments, the CCR5 binding agent is leronlimab or an antigen binding fragment thereof.

In another aspect, the present disclosure provides a method for normalizing the cytokine profile of a subject infected with coronavirus comprising administering a CCR5 binding agent.

In another aspect, the present disclosure provides a method for facilitating normalization of the CD4 T cell/CD8 T cell ratio in the subject infected with coronavirus, comprising administering a CCR5 binding agent.

In another aspect, the present disclosure provides a method for facilitating normalization of the cytokine profile of an immunocompromised subject infected with, or likely to be infected with, coronavirus, comprising administering a CCR5 binding agent.

In another aspect, the present disclosure provides a method of treating a subject for hyperinflammation in a subject infected with, or likely to be infected with, coronavirus, comprising administering to the subject an effective amount of a CCR5 binding agent.

In another aspect, the present disclosure provides a method of treating a subject with hyperinflammation, comprising administering to the subject an effective amount of a CCR5 binding agent.

In another aspect, the present disclosure provides a method of treating a subject for SARS-CoV-2 infection, comprising administering to the subject an effective amount of a CCR5 binding agent.

In another aspect, the present disclosure provides a method of reducing elevated plasma CCL5 level associated with a viral infection in a subject, comprising administering to the subject an effective amount of a CCR5 binding agent.

In another aspect, the present disclosure provides a method of increasing CD8+ T cell frequency in a subject infected with coronavirus, comprising administering an effective amount of a CCR5 binding agent.

In another aspect, the present disclosure provides a method for reducing migration of CCR5+ immune cells in a subject infected with coronavirus, comprising administering an effective amount of a CCR5 binding agent.

In another aspect, the present disclosure provides method for reducing T cell exhaustion in a subject infected with coronavirus, comprising administering an effective amount of a CCR5 binding agent.

In another aspect, the present disclosure provides a method for reducing plasma coronavirus viral load in a subject, comprising administering to the subject an effective amount of a CCR5 binding agent.

In another aspect, the present disclosure provides a method of reducing plasma levels of at least one inflammatory cytokine and/or chemokine in a subject infected with coronavirus, comprising administering to the subject an effective amount of a CCR5 binding agent.

In another aspect, the present disclosure provides a method of reducing occurrence or risk of liver toxicity or kidney failure in a subject infected with coronavirus, comprising administering an effective amount of a CCR5 binding agent.

In another aspect, the present disclosure provides a method of reducing occurrence or risk of a coagulation event in a subject infected with coronavirus, comprising administering an effective amount of a CCR5 binding agent.

In another aspect, the present disclosure provides a therapeutic composition comprising a CCR5 binding agent and at least one of an anti-viral therapeutic agent, an immune checkpoint molecule inhibitor, a non-CCR5 binding immunomodulatory agent, a non-CCL5 binding immunomodulatory agent, or any combination thereof.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

FIGS. 3A-3B provide schedules of assessments for the studies described in Examples 2 and 4, respectively.

FIG. 4 shows the amino acid sequence of the light chain variable region of the humanized version of mouse anti-CCR5 antibody PA14 (SEQ ID NO: 1) and the nucleic acid sequence encoding the same (SEQ ID NO: 2). The CDRs are underlined.

FIG. 5 shows the amino acid sequence of a first heavy chain variable region of a humanized version of mouse anti-CCR5 antibody PA14 (SEQ ID NO: 3), and the nucleic acid sequence encoding the same (SEQ ID NO: 4), in accordance with the invention. This heavy chain variable region is present in the antibody designated herein as PRO 140 #2. The CDRs are underlined.

FIG. 6 shows the amino acid sequence of a second heavy chain variable region of a humanized version of mouse humanized anti-CCR5 antibody PA14 (SEQ ID NO: 5) and the nucleic acid sequence encoding the same (SEQ ID NO: 6) in accordance with the invention. This heavy chain variable region is present in the antibody designated herein as PRO 140 #1. The CDRs are underlined.

FIG. 7 shows normal cytokine levels in serum by age group (<45 years and ≥65 years). Source: Kim H O, Kim H S, Youn J C, Shin E C, Park S. *Serum cytokine profiles in healthy young and elderly population assessed using multiplexed bead-based immunoassays.* J Transl Med. 2011; 9:113.

FIG. 8 shows the immunological status of the ten patients 3 to 7 days after leronlimab therapy.

FIGS. 9A-9J. shows plasma cytokine levels from ten patients of each measured cytokine following leronlimab therapy. All values are shown in pg/mL, and all samples are performed in duplicate. "-" indicates data is unavailable. "dec." indicates patient is deceased. "*" indicates that data differs from first reported results; samples were collected from the same patient at the same time and have been updated to reflect most recent data. "†" indicates that the patient number identifiers differ from first reported identifiers, patient initial identifiers are the same (FIG. 10A) and Day 7 post-leronlimab treatment (FIG. 10B). Frequencies of CD3+ and CD3+CD8+ populations in "Patient #3 WSa" are depicted.

FIG. 11 shows summaries for ten critical COVID-19 patients. N/A=not applicable, s/p=status post-, AKI=acute kidney injury, HTHD=hypertensive heart disease, DM=diabetes mellitus, HLD=hyperlipidemia, ESRD=end-stage renal disease, HD=hemodialysis, CA=cancer, COPD=chronic obstructive pulmonary disease, LUL=left upper lobe, RUL=right upper lobe, MDR=multi-drug resistant, CKD=chronic kidney disease, UTI=urinary tract infection, FSGS=Focal segmental glomerulosclerosis, DVT=deep vein thrombosis, PE=pulmonary embolism, OSA=obstructive sleep apnea, CAD=coronary artery disease, GERD=gastroesophageal reflux disease, RF=renal failure, DR=diabetic retinopathy, NC=nasal canula, NRB=non-rebreather mask, *Patient declined intubation due to poor baseline pulmonary status.

FIGS. 16A-16D show comprehensive blood panel for patients for Day 0 to Day 21 post-leronlimab treatment.

FIGS. 19A-19I show longitudinal single-cell transcriptomics of COVID-19 following leronlimab. UMAP feature plots of single-cell transcriptome profiles of CD3 (T cells) versus CD8 (CD8+ T cells) versus CD14 (monocyte/myeloid) versus CD79a (B cells) (FIG. 19A), IFI6 (FIG. 19B), IL-1β (FIG. 19C), CCL3 (FIG. 19D), KLRB1 (FIG. 19E), CCL4 (FIG. 19F), IFITM3 (FIG. 19G), IFI27 (FIG. 19H), and Granzyme A (FIG. 19I) before and 7 days post leronlimab treatment for severe COVID-19 patients P2 and P4.

FIG. 20 shows a list of antibodies used for immune profiling markers and receptor occupancy markers.

DETAILED DESCRIPTION

Figure 1:
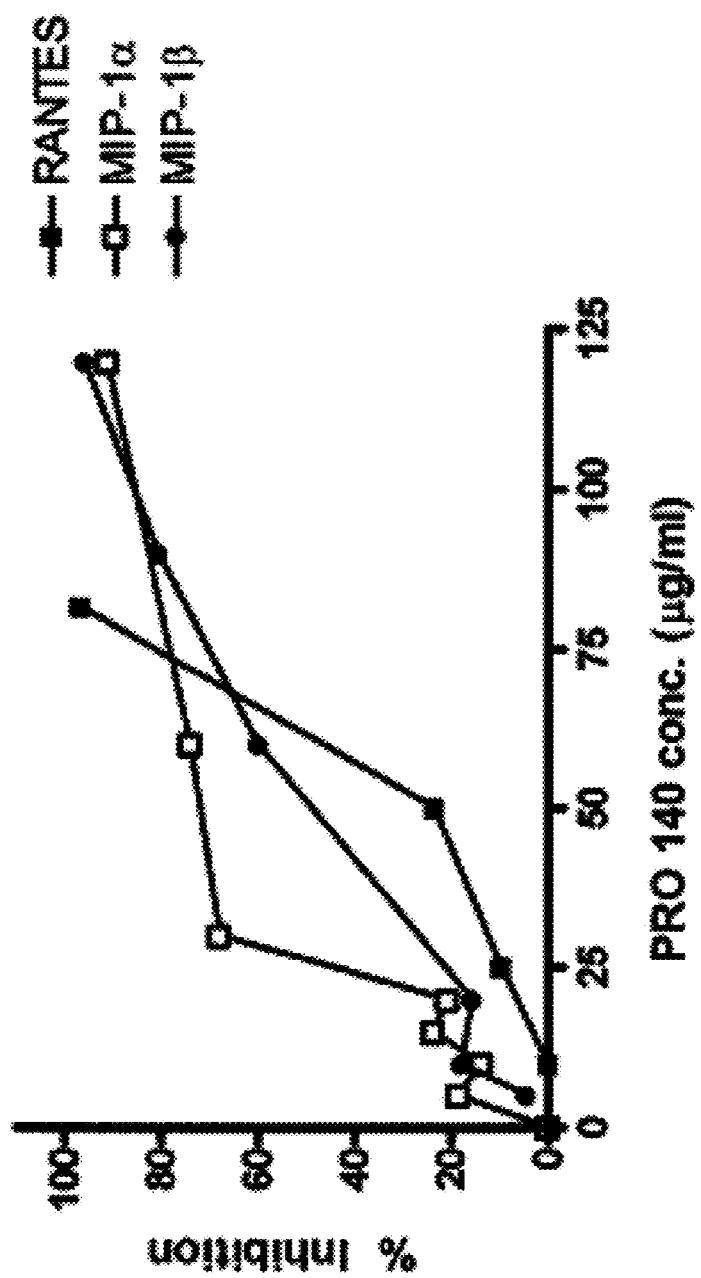
FIG. 1 depicts the dose response curve for inhibition of CC-chemokine-induced calcium mobilization by PRO 140.

The present disclosure provides CCR5 binding agents that are useful in treating viral infections (e.g., coronavirus infections), such as viral infections associated with elevated CCL5 (RANTES) expression. CCL5 is a chemotactic molecule able to amplify inflammatory responses towards immunopathology. CCL5-CCR5 axis induces chemotaxis of inflammatory CCR5+ expressing immune cells (e.g., macrophages and T cells). Elevated CCL5 may lead to disruption of immune homeostasis, e.g., elevated levels of inflammatory cytokines and/or chemokines (e.g., hyperinflammation), mass migration of CCR5+ expressing immune cells (e.g., macrophages and T cells), elevated CD4:CD8 T cell ratio, CD8 T cell depletion, T cell exhaustion, or any combination thereof. Thus, CCR5 binding agents of the present disclosure may be useful in treating hyperinflammation, reducing mass migration of CCR5+ expressing immune cells, restoring CD4:CD8 T cell ratio, improving CD8 T cell number, reducing or reversing T cell exhaustion, or any combination thereof, that is associated with viral infections, e.g., coronavirus infections, optionally in combination with other therapeutic agents, such as, for example anti-viral therapeutic agents, cytokine storm therapeutic agents, immune checkpoint molecule inhibitors, or any combination thereof. Furthermore, CCR5 binding agents of the present disclosure may be used to reduce plasma viral load in subjects infected with coronavirus. Moreover, CCR5 binding agents of the present disclosure may be useful in treating other indications beyond its immune-corrective effects, such as improving liver or kidney function or reducing complications associated with coagulation.

CCR5 binding agents as provided herein are capable of binding CCR5 expressing cells (e.g., lymphocytes, monocytes, macrophages, dendritic cells, a subset of T cells, etc.). CCR5 binding agents, such as, for example antibodies, can bind to CCR5 receptors on certain T cells, and slow the rate at which those cells produce inflammatory cytokines, the signaling molecules that promote inflammation in the body. One such anti-CCR5 binding agent is leronlimab (PRO 140), which may be used, for example, to modulate movement of macrophages and T cells (e.g., Tregs), production of inflammatory cytokines and/or chemokines, e.g., CCL5, TNF and IL-6; thus, potentially stopping, reducing, mitigating, or alleviating lung damage mediated by hyperinflammation. Accordingly, anti-CCR5 binding agents, such as, for example leronlimab, may provide or facilitate effective treatment or prevention for a subject suffering from hyperinflammation associated with a viral infection, e.g., in COVID-19 patients, by reducing inflammation associated with virally-induced respiratory illness including, for example, Acute Respiratory Distress Syndrome (ARDS). Moreover, anti-CCR5 binding agents may be used to prevent hyperinflammation associated with a viral infection.

Prior to setting forth this disclosure in more detail, it may be helpful to an understanding thereof to provide definitions of certain terms to be used herein. Unless defined otherwise, all technical and scientific terms used herein have the same meaning as is commonly understood by one of skill in the art to which this invention belongs. Additional definitions are set forth throughout this disclosure.

In the present description, the term "about" means±20% of the indicated range, value, or structure, unless otherwise indicated. The term "consisting essentially of" limits the scope of a claim to the specified materials or steps and those that do not materially affect the basic and novel characteristics of the claimed invention. It should be understood that the terms "a" and "an" as used herein refer to "one or more" of the enumerated components. The use of the alternative (e.g., "or") should be understood to mean either one, both, or any combination thereof of the alternatives. As used herein, the terms "include" and "have" are used synonymously, which terms and variants thereof are intended to be construed as non-limiting. The term "comprise" means the presence of the stated features, integers, steps, or components as referred to in the claims, but that it does not preclude the presence or addition of one or more other features, integers, steps, components, or groups thereof. Any ranges provided herein include all the values and narrower ranges in the ranges.

As used herein, "chemokine" refers to a low-molecular weight cytokine that can stimulate recruitment of leukocytes. Chemokines have cysteine residues in conserved locations that are key to forming their 3-dimensional shape. Chemokines may be classified into four main subfamilies: Cys-Cys (C-C), Cys-X-Cys (CXC), $CX_3C$, and XC depending on the spacing of their first two amino terminal cysteine residues. Chemokines may also be grouped according to their function, such as whether they are inflammatory or homeostatic. There are 47 known chemokines, including but not limited to CCL5 (also known as RANTES), MIP-1α, MIP-1β, or SDF-1, or another chemokine which has similar activity.

As used herein, "C-C chemokine receptor 5," also known as "CCR5" or "CD195" refers to a G protein-coupled receptor expressed on lymphocytes (e.g., NK cells, B cells, T cells), macrophages, dendritic cells, eosinophils, and microglia, which functions as a chemokine receptor for the C-C chemokine group. CCR5's cognate ligands include CCL3, CCL4, CCL3L1, and CCL5. In some embodiments, CCR5 refers to human CCR5. In some embodiments, CCR5 refers to a protein having an amino acid sequence provided in NCBI Reference Sequence: NP 000570.1 (SEQ ID NO:15).

As used herein, "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that functions in a manner similar to a naturally occurring amino acid.

As used herein, "mutation" refers to a change in the sequence of a nucleic acid molecule or polypeptide molecule as compared to a reference or wild-type nucleic acid molecule or polypeptide molecule, respectively. A mutation can result in several different types of change in sequence, including substitution, insertion or deletion of nucleotide(s) or amino acid(s).

As used herein, "protein" or "polypeptide" as used herein refers to a compound made up of amino acid residues that are covalently linked by peptide bonds. The term "protein" may be synonymous with the term "polypeptide" or may refer, in addition, to a complex of two or more polypeptides. A polypeptide may further contain other components (e.g., covalently bound), such as a tag, a label, a bioactive molecule, or any combination thereof. In certain embodiments, a polypeptide may be a fragment. As used herein, a "fragment" means a polypeptide that is lacking one or more amino acids that are found in a reference sequence. A fragment can comprise a binding domain, antigen, or epitope found in a reference sequence. A fragment of a reference polypeptide can have at least about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or more of amino acids of the amino acid sequence of the reference sequence.

As described herein, a "variant" polypeptide species has one or more non-natural amino acids, one or more amino acid substitutions, one or more amino acid insertions, one or more amino acid deletions, or any combination thereof at one or more sites relative to a reference polypeptide as presented herein. In certain embodiments, "variant" means a polypeptide having a substantially similar activity (e.g., enzymatic function, immunogenicity) or structure relative to a reference polypeptide). A variant of a reference polypeptide can have at least about 40%, 45%, 50%, 55%, 60%, 65%, 70%, 75%, 80%, 85%, 90%, 91%, 92%, 93%, 94%, 95%, 96%, 97%, 98%, 99%, or more sequence identity to the amino acid sequence for the reference polypeptide as determined by sequence alignment programs and parameters known in the art. The variant can result from, for example, a genetic polymorphism or human manipulation. Conservative substitutions of amino acids are well known and may occur naturally or may be introduced when a protein is recombinantly produced. Amino acid substitutions, deletions, and additions may be introduced into a protein using mutagenesis methods known in the art (see, e.g., Sambrook et al., *Molecular Cloning: A Laboratory Manual*, 3d ed., Cold Spring Harbor Laboratory Press, N Y, 2001). Oligonucleotide-directed site-specific (or segment specific) mutagenesis procedures may be employed to provide an altered polynucleotide that has particular codons altered according to the substitution, deletion, or insertion desired. Alternatively, random or saturation mutagenesis techniques, such as alanine scanning mutagenesis, error prone polymerase chain reaction mutagenesis, and oligonucleotide-directed mutagenesis may be used to prepare polypeptide variants (see, e.g., Sambrook et al., supra). A "conservative substitution" refers to amino acid substitutions that do not significantly affect or alter binding characteristics of a particular protein. Generally, conservative substitutions are ones in which a substituted amino acid residue is replaced with an amino acid residue having a similar side chain. Conservative substitutions include a substitution found in one of the following groups: Group 1: Alanine (Ala or A), Glycine (Gly or G), Serine (Ser or S), Threonine (Thr or T); Group 2: Aspartic acid (Asp or D), Glutamic acid (Glu or Z); Group 3: Asparagine (Asn or N), Glutamine (Gln or Q); Group 4: Arginine (Arg or R), Lysine (Lys or K), Histidine (His or H); Group 5: Isoleucine (Ile or I), Leucine (Leu or L), Methionine (Met or M), Valine (Val or V); and Group 6: Phenylalanine (Phe or F), Tyrosine (Tyr or Y), Tryptophan (Trp or W). Additionally or alternatively, amino acids can be grouped into conservative substitution groups by similar function, chemical structure, or composition (e.g., acidic, basic, aliphatic, aromatic, or sulfur-containing). For example, an aliphatic grouping may include, for purposes of substitution, Gly, Ala, Val, Leu, and Ile. Other conservative substitutions groups include: sulfur-containing: Met and Cysteine (Cys or C); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information can be found in Creighton (1984) Proteins, W.H. Freeman and Company.

The terms "identical" or "percent identity," in the context of two or more polypeptide or nucleic acid molecule sequences, means two or more sequences or subsequences that are the same or have a specified percentage of amino acid residues or nucleotides that are the same over a specified region (e.g., 60%, 65%, 70%, 75%, 80%, 85%, 90%, 91%, 92%, 93%, 94%, 95%, 96%, 97%, 98%, 99%, or 100% identity), when compared and aligned for maximum correspondence over a comparison window, or designated region, as measured using methods known in the art, such as a sequence comparison algorithm, by manual alignment, or by visual inspection. The algorithm used herein for determining percent sequence identity and sequence similarity is the BLAST 2.0 algorithm, as described in Altschul et al. "Gapped BLAST and PSI-BLAST: a new generation of protein database search programs," Nucleic Acids Res. 2007, 25, 3389-3402. Within the context of this disclosure, it will be understood that where sequence analysis software is used for analysis, the results of the analysis are based on the "default values" of the program referenced. "Default values" mean any set of values or parameters which originally load with the software when first initialized.

As used herein, a "fusion protein" comprises a single chain polypeptide having at least two distinct domains, wherein the domains are not naturally found together in a protein. A nucleic acid molecule encoding a fusion protein may be constructed using PCR, recombinantly engineered, or the like, or such fusion proteins can be made synthetically. A fusion protein may further contain other components (e.g., covalently bound), such as a tag, linker, transduction marker, or bioactive molecule.

A "nucleic acid molecule" or "polynucleotide" refers to a polymeric compound containing nucleotides that are covalently linked by 3'-5' phosphodiester bonds. Nucleic acid molecules include polyribonucleic acid (RNA), polydeoxyribonucleic acid (DNA), which includes genomic DNA, mitochondrial DNA, cDNA, or vector DNA. A nucleic acid molecule may be double stranded or single stranded, and if single stranded, may be the coding strand or non-coding (anti-sense strand). A nucleic acid molecule may contain natural subunits or non-natural subunits. A nucleic acid molecule encoding an amino acid sequence includes all nucleotide sequences that encode the same amino acid sequence. Some versions of the nucleotide sequences may also include intron(s) to the extent that the intron(s) would be removed through co- or post-transcriptional mechanisms. In other words, different nucleotide sequences may encode the same amino acid sequence as the result of the redundancy or degeneracy of the genetic code, or by splicing.

Variants of the polynucleotides of this disclosure are also contemplated. Variant polynucleotides are at least 80%, 85%, 90%, 95%, 99%, or 99.9% identical to a reference polynucleotide as described herein, or that hybridizes to a reference polynucleotide of defined sequence under stringent hybridization conditions of 0.015M sodium chloride, 0.0015M sodium citrate at about 65°–68° C. or 0.015M sodium chloride, 0.0015M sodium citrate, and 50% formamide at about 42° C. The polynucleotide variants retain the capacity to encode an immunoglobulin-like binding protein or antigen-binding fragment thereof having the functionality described herein.

The term "isolated" means that the material is removed from its original environment (e.g., the natural environment if it is naturally occurring). For example, a naturally occurring polynucleotide or polypeptide present in a living animal is not isolated, but the same polynucleotide or polypeptide, separated from some or all of the co-existing materials in the natural system, is isolated. Such polynucleotide could be part of a vector and/or such polynucleotide or polypeptide could be part of a composition (e.g., a cell lysate), and still be isolated in that such vector or composition is not part of the natural environment for the nucleic acid or polypeptide.

As used herein, the term "engineered," "recombinant," or "non-natural" refers to an organism, microorganism, cell, nucleic acid molecule, or vector that includes at least one genetic alteration or has been modified by introduction of an exogenous or heterologous nucleic acid molecule, wherein such alterations or modifications are introduced by genetic engineering (i.e., human intervention). Genetic alterations include, for example, modifications introducing expressible nucleic acid molecules encoding functional RNA, proteins, fusion proteins or enzymes, or other nucleic acid molecule additions, deletions, substitutions, or other functional disruption of a cell's genetic material. Additional modifications include, for example, non-coding regulatory regions in which the modifications alter expression of a polynucleotide, gene, or operon.

As used herein, "heterologous" or "exogenous" nucleic acid molecule, construct or sequence refers to a nucleic acid molecule or portion of a nucleic acid molecule that is not native to a host cell, but may be homologous to a nucleic acid molecule or portion of a nucleic acid molecule from the host cell. The source of the heterologous or exogenous nucleic acid molecule, construct or sequence may be from a different genus or species. In certain embodiments, a heterologous or exogenous nucleic acid molecule is added (i.e., not endogenous or native) to a host cell or host genome by, for example, conjugation, transformation, transfection, electroporation, or the like, wherein the added molecule may integrate into the host genome or exist as extra-chromosomal genetic material (e.g., as a plasmid or other form of self-replicating vector), and may be present in multiple copies. In addition, "heterologous" refers to a non-native enzyme, protein, or other activity encoded by an exogenous nucleic acid molecule introduced into the host cell, even if the host cell encodes a homologous protein or activity.

As used herein, the term "endogenous" or "native" refers to a gene, protein, or activity that is normally present in a host cell. Moreover, a gene, protein or activity that is mutated, overexpressed, shuffled, duplicated or otherwise altered as compared to a parent gene, protein or activity is still considered to be endogenous or native to that particular host cell. For example, an endogenous control sequence from a first gene (e.g., promoter, translational attenuation sequences) may be used to alter or regulate expression of a second native gene or nucleic acid molecule, wherein the expression or regulation of the second native gene or nucleic acid molecule differs from normal expression or regulation in a parent cell.

As used herein, the term "expression", refers to the process by which a polypeptide is produced based on the encoding sequence of a nucleic acid molecule, such as a gene. The process may include transcription, post-transcriptional control, post-transcriptional modification, translation, post-translational control, posttranslational modification, or any combination thereof. An expressed nucleic acid molecule is typically operably linked to an expression control sequence (e.g., a promoter).

As used herein, the term "operably linked" refers to the association of two or more nucleic acid molecules on a single nucleic acid fragment so that the function of one is affected by the other. For example, a promoter is operably linked with a coding sequence when it is capable of affecting the expression of that coding sequence (i.e., the coding sequence is under the transcriptional control of the promoter). "Unlinked" means that the associated genetic elements are not closely associated with one another and the function of one does not affect the other.

As used herein, "expression vector" refers to a DNA construct containing a nucleic acid molecule that is operably linked to a suitable control sequence capable of effecting the expression of the nucleic acid molecule in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, a virus, or simply a potential genomic insert. Once transformed into a suitable host, the vector may replicate and function independently of the host genome, or may, in some instances, integrate into the genome itself. In the present specification, "plasmid," "expression plasmid," "virus" and "vector" are often used interchangeably.

As used herein, the term "host" refers to a cell (e.g., T cell, Chinese Hamster Ovary (CHO) cell, HEK293 cell, B cell, or the like) or microorganism targeted for genetic modification with a heterologous nucleic acid molecule to produce a polypeptide of interest (e.g., a CCR5 antibody of the present disclosure). In certain embodiments, a host cell may optionally already possess or be modified to include other genetic modifications that confer desired properties related or unrelated to, e.g., biosynthesis of the heterologous protein (e.g., inclusion of a detectable marker; deleted, altered or truncated endogenous BCR).

As described herein, more than one heterologous nucleic acid molecule can be introduced into a host cell as separate nucleic acid molecules, as a plurality of individually controlled genes, as a polycistronic nucleic acid molecule (e.g., a heavy chain and a light chain of an antibody), as a single nucleic acid molecule encoding a protein (e.g., a heavy chain of an antibody), or any combination thereof. When two or more heterologous nucleic acid molecules are introduced into a host cell, it is understood that the two or more heterologous nucleic acid molecules can be introduced as a single nucleic acid molecule (e.g., on a single vector), on separate vectors, integrated into the host chromosome at a single site or multiple sites, or any combination thereof. The number of referenced heterologous nucleic acid molecules or protein activities refers to the number of encoding nucleic acid molecules or the number of protein activities, not the number of separate nucleic acid molecules introduced into a host cell.

As used herein, the term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid molecule may be incorporated into the genome of a cell (e.g., chromosome, plasmid, plastid, or mitochondrial DNA), converted into an autonomous replicon, or transiently expressed (e.g., transfected mRNA).

"Treat" or "treatment" or "ameliorate" refers to medical management of a disease, disorder, or condition of a subject (e.g., a human or non-human mammal, such as a primate, horse, cat, dog, goat, mouse, or rat). In general, an appropriate dose or treatment regimen comprising a CCR5 binding agent of the present disclosure is administered in an amount sufficient to elicit a therapeutic effect or therapeutic benefit. Therapeutic effect or therapeutic benefit includes improved clinical outcome; modulation of immune response to lessen, reduce, or dampen counterproductive inflammatory cytokine activity; modulation of immune response to normalize counterproductive inflammatory cytokine activity; lessening or alleviation of symptoms associated with a disease; decreased occurrence of symptoms; improved quality of life; longer disease-free status; diminishment of extent of disease, stabilization of disease state; delay of disease progression; remission; survival; prolonged survival; or any combination thereof.

A prophylactic treatment meant to "prevent" a disease or condition (e.g., coronavirus induced respiratory illness in a subject or patient) is a treatment administered to a subject who does not exhibit signs of a disease or exhibits only early signs, for the purpose of decreasing the risk of developing a pathology or further advancement of the early disease. For example, if an individual at risk of developing a coronavirus induced respiratory illness is treated with the methods of the present disclosure and does not later develop coronavirus induced respiratory illness, then the disease has been prevented, at least over a period of time, in that individual. A prophylactic treatment can mean preventing recurrence of a disease or condition in a patient that has previously been treated for the disease or condition, e.g., by preventing relapse or recurrence of coronavirus induced respiratory illness.

A "therapeutically effective amount" or "effective amount" of a CCR5 binding agent of this disclosure refers to an amount of CCR5 binding agent sufficient to result in a therapeutic effect, including improved clinical outcome; lessening or alleviation of symptoms associated with a disease; modulating immune response to lessen, reduce, or dampen counterproductive inflammatory cytokine activity; modulating immune response to normalize counterproductive inflammatory cytokine activity; decreased occurrence of symptoms; improved quality of life; longer disease-free status; diminishment of extent of disease, stabilization of disease state; delay of disease progression; remission; survival; or prolonged survival in a statistically significant manner. When referring to an individual active ingredient or a cell expressing a single active ingredient, administered alone, a therapeutically effective amount refers to the effects of that ingredient or cell expressing that ingredient alone. When referring to a combination, a therapeutically effective amount refers to the combined amounts of active ingredients or combined adjunctive active ingredient with a cell expressing an active ingredient that results in a therapeutic effect, whether administered serially or simultaneously.

The term "pharmaceutically acceptable excipient or carrier" or "physiologically acceptable excipient or carrier" refer to biologically compatible vehicles, e.g., physiological saline, which are described in greater detail herein, that are suitable for administration to a human or other non-human mammalian subject and generally recognized as safe or not causing a serious adverse event.

Additional definitions are provided in the sections below.

CCR5 Binding Agents

The present disclosure provides for use a CCR5 binding agent in treating viral infections (e.g., coronavirus), including viral infections associated with elevated CCL5 (RANTES) expression in a subject. In some embodiments, treating a viral infection associated with elevated CCL5 expression comprises treatment of hyperinflammation associated with a viral infection (e.g., coronavirus) in a subject. CCR5 binding agents for use in the present disclosure are inhibitors of CCR5 activity induced by CCL5 binding. The term "inhibit" or "inhibitor" refers to a diminishing, blunting, reduction, masking, interrupting, blocking, mitigation, or slowing directly or indirectly, in the expression, amount or activity of a target or signaling pathway relative to (1) a control, endogenous or reference target or pathway, or (2) the absence of a target or pathway, wherein the diminishing, blunting, reduction, masking, interrupting, blocking, mitigation, or slowing is statistically, biologically, or clinically significant. For example, an inhibitor of CCR5 may diminish, blunt, reduce, mask, interrupt, block, mitigate, or slow CCR5 signaling activity induced by CCL5 binding by about 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or more as compared to untreated CCR5. CCR5 activity induced by CCL5 binding may be measured by detecting, for example, a decrease in cAMP, cell migration, or both.

The CCR5 receptor is a C-C chemokine G-coupled protein receptor expressed on lymphocytes (e.g., NK cells, B cells), monocytes, macrophages, dendritic cells, a subset of T cells, etc. The extracellular portions represent potential targets for antibodies targeting CCR5, and comprise an amino-terminal domain (Nt) and three extracellular loops (ECL1, ECL2, and ECL3). The extracellular portions of CCR5 comprise just 90 amino acids distributed over four domains. The largest of these domains are at the Nt and ECL2 at approximately 30 amino acids each (Olson et al., Curr. Opin. HIV AIDS, March, 4(2): 104-111 (2009)).

The CCR5 receptor binds to a chemokine known as CCL5 (C-C chemokine ligand 5), which is an inflammatory chemokine that plays an important role in immunologic mechanisms such as controlling cell recruitment and activation in basal and inflammatory circumstances. CCL5 acts as a key regulator of CCR5+ cell (e.g., macrophage and T cell) migration to inflammatory sites, directing migration of macrophages and T cells to damaged or infected sites. CCR5 also plays a crucial role in differentiation and activation of CD8+ T cells. Many biologic effects of chemokines are mediated by their interaction with chemokine receptors on cell surfaces. The most relevant known receptor for CCL5 is the CCR5 receptor; however, CCR1 and CCR3 are also known CCL5 receptors and CCR4 and CD44 are auxiliary receptors. Tamamis et al., Elucidating a Key Anti-HIV-1 and Cancer-Associated Axis: The Structure of CCL5 (Rantes) in Complex with CCR5, SCIENTIFIC REPORTS, 4: 5447 (2014).

The formation of the CCRL ligand and CCR5 receptor complex causes a conformational change in the receptor that activates the subunits of the G-protein, inducing signaling and leading to changed levels of cyclic AMP (cAMP), inositol triphosphate, intracellular calcium and tyrosine kinase activation. These signaling events cause cell polarization and translocation of the transcription factor NF-kB, which results in the increase of phagocytic ability, cell survival, and transcription of proinflammatory genes.

CCR5 binding agents include, but are not limited to, small molecules, antibodies or antigen binding fragments thereof, proteins, peptides, nucleic acids, and aptamers.

In some embodiments, a CCR5 binding agent is an anti-CCR5 antibody or antigen-binding fragment thereof that specifically binds to CCR5, e.g., to an epitope on CCR5. The term "epitope" or "antigenic epitope" includes any molecule, structure, amino acid sequence, or protein determinant that is recognized and specifically bound by a cognate binding molecule, such as an immunoglobulin, T cell receptor (TCR), chimeric antigen receptor, or other binding molecule, domain or protein. Epitopic determinants generally contain chemically active surface groupings of molecules, such as amino acids or sugar side chains, and can have specific three dimensional structural characteristics, as well as specific charge characteristics.

As used herein, "specifically binds" or "specific for" may in some embodiments refer to an association or union of a binding protein (e.g., an anti-CCR5 antibody) or a binding domain (or fusion protein thereof) to a target molecule with an affinity or $K_a$ (i.e., an equilibrium association constant of a particular binding interaction with units of 1/M) equal to or greater than $10^5 M^{-1}$ (which equals the ratio of the on-rate

[k$_{on}$] to the off-rate [k$_{off}$] for this association reaction), while not significantly associating or uniting with any other molecules or components in a sample. Binding domains (or fusion proteins thereof) may be classified as "high affinity" binding domains (or fusion proteins thereof) and "low affinity" binding domains (or fusion proteins thereof). "High affinity" binding domains refer to those binding domains with a K$_a$ of at least $10^8 M^{-1}$, at least $10^9 M^{-1}$, at least $10^{10} M^{-1}$, at least $10^{11} M^{-1}$, at least $10^{12} M^{-1}$, or at least $10^{13} M^{-1}$, preferably at least $10^8 M^{-1}$ or at least $10^9 M^{-1}$. "Low affinity" binding domains refer to those binding domains with a K$_a$ of up to $10^8 M^{-1}$, up to $10^7 M^{-1}$, up to $10^6 M^{-1}$, up to $10^5 M^{-1}$. Alternatively, affinity may be defined as an equilibrium dissociation constant (K$_D$) of a particular binding interaction with units of M (e.g., $10^{-5}$ M to $10^{-13}$ M), (which equals the ratio of the off-rate [k$_{off}$] to the on-rate [k$_{on}$] for this association reaction).

A variety of assays are known for identifying binding domains of the present disclosure that specifically bind a particular target, as well as determining binding domain or fusion protein affinities, such as Western blot, ELISA, analytical ultracentrifugation, spectroscopy and surface plasmon resonance (Biacore®) analysis (see, e.g., Scatchard et al., *Ann. N.Y. Acad. Sci.* 51:660, 1949; Wilson, *Science* 295:2103, 2002; Wolff et al., *Cancer Res.* 53:2560, 1993; and U.S. Pat. Nos. 5,283,173, 5,468,614, or the equivalent).

Terms understood by those in the art of antibody technology are each given the meaning acquired in the art, unless expressly defined differently herein. The term "antibody" refers to an intact antibody comprising at least two heavy (H) chains and two light (L) chains inter-connected by disulfide bonds, as well as any antigen-binding portion or fragment of an intact antibody, such as an scFv, Fab, or Fab'2 fragment, that has or retains the ability to bind to the antigen target molecule recognized by the intact antibody. Thus, the term "antibody" herein is used in the broadest sense and includes polyclonal and monoclonal antibodies, including intact antibodies and functional (antigen-binding) antibody fragments thereof, including fragment antigen binding (Fab) fragments, F(ab')2 fragments, Fab' fragments, Fv fragments, recombinant IgG (rIgG) fragments, single chain antibody fragments, including single chain variable fragments (scFv), and single domain antibodies (e.g., sdAb, sdFv, nanobody). The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific antibodies, diabodies, triabodies, tetrabodies, tandem di-scFv, and tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof (IgG1, IgG2, IgG3, IgG4), IgM, IgE, IgA, and IgD.

An anti-CCR5 monoclonal antibody or antigen-binding portion thereof for use in the methods disclosed herein may be non-human (e.g., murine), chimeric, humanized, or human. Immunoglobulin structure and function are reviewed, for example, in Harlow et al., Eds., Antibodies: A Laboratory Manual, Chapter 14 (Cold Spring Harbor Laboratory, Cold Spring Harbor, 1988).

The terms "VL" and "VH" refer to the variable binding region from an antibody light chain and an antibody heavy chain, respectively. The variable binding regions comprise discrete, well-defined sub-regions known as "complementarity determining regions" (CDRs) and "framework regions" (FRs). The terms "complementarity determining region," and "CDR," are synonymous with "hypervariable region" or "HVR," and refer to sequences of amino acids within antibody variable regions, which, in general, together confer the antigen specificity and/or binding affinity of the antibody, wherein consecutive CDRs (i.e., CDR1 and CDR2, CDR2 and CDR3) are separated from one another in primary amino acid sequence by a framework region. There are three CDRs in each variable region (HCDR1, HCDR2, HCDR3; LCDR1, LCDR2, LCDR3; also referred to as CDRHs and CDRLs, respectively). In certain embodiments, an antibody VH comprises four FRs and three CDRs as follows: FR1-HCDR1-FR2-HCDR2-FR3-HCDR3-FR4; and an antibody VL comprises four FRs and three CDRs as follows: FR1-LCDR1-FR2-LCDR2-FR3-LCDR3-FR4. In general, the VH and the VL together form the antigen-binding site through their respective CDRs.

Numbering of CDR and framework regions may be determined according to any known method or scheme, such as the Kabat, Chothia, EU, IMGT, and AHo numbering schemes (see, e.g., Kabat et al., "Sequences of Proteins of Immunological Interest, US Dept. Health and Human Services, Public Health Service National Institutes of Health, 1991, 5$^{th}$ ed.; Chothia and Lesk, *J. Mol. Biol.* 196:901-917 (1987)); Lefranc et al., *Dev. Comp. Immunol.* 27:55, 2003; Honegger and Plückthun, *J. Mol. Mo.* 309:657-670 (2001)). Equivalent residue positions can be annotated and for different molecules to be compared using Antigen receptor Numbering And Receptor Classification (ANARCI) software tool (2016, Bioinformatics 15:298-300). Accordingly, identification of CDRs of an exemplary variable domain (VH or VL) sequence as provided herein according to one numbering scheme is not exclusive of an antibody comprising CDRs of the same variable domain as determined using a different numbering scheme.

In some embodiments, the present disclosure provides use of an anti-CCR5 antibody or antigen binding fragment thereof having a light chain variable region (VL) that is at least 70% identical to SEQ ID NO: 1, at least 75% identical to SEQ ID NO: 1, at least 80% identical to SEQ ID NO: 1, at least 85% identical to SEQ ID NO: 1, or at least 90% identical to SEQ ID NO: 1. In some embodiments, the present disclosure provides use of an anti-CCR5 antibody or antigen binding fragment thereof having a light chain variable antibody region that is 70%-100% identical to SEQ ID NO: 1, 75%-100% identical to SEQ ID NO: 1, 80%-100% identical to SEQ ID NO: 1, 85%-100% identical to SEQ ID NO: 1, 90%-100% identical to SEQ ID NO: for 91%-100% identical to SEQ ID NO: 1.

In some embodiments, the present disclosure provides use of an anti-CCR5 antibody or antigen binding fragment thereof having a light chain variable region (VL) that is at least 70% identical to amino acids 20-131 of SEQ ID NO: 1, at least 75% identical to amino acids 20-131 of SEQ ID NO: 1, at least 80% identical to amino acids 20-131 of SEQ ID NO: 1, at least 85% identical to amino acids 20-131 of SEQ ID NO: 1, or at least 90% identical to amino acids 20-131 of SEQ ID NO: 1. In some embodiments, the present disclosure provides use of an anti-CCR5 antibody or antigen binding fragment thereof having a light chain variable antibody region that is 70%-100% identical to amino acids 20-131 of SEQ ID NO: 1, 75%-100% identical to amino acids 20-131 of SEQ ID NO: 1, 80%-100% identical to amino acids 20-131 of SEQ ID NO: 1, 85%-100% identical to amino acids 20-131 of SEQ ID NO: 1, 90%-100% identical to amino acids 20-131 of SEQ ID NO: 1 or 91%-100% identical to amino acids 20-131 of SEQ ID NO: 1.

In some embodiments, the present disclosure provides use of an anti-CCR5 antibody or antigen binding fragment thereof having a heavy chain variable region (VH) that is at least 70% identical to SEQ ID NO:3, at least 75% identical to SEQ ID NO:3, at least 80% identical to SEQ ID NO:3, at least 85% identical to SEQ ID NO:3, or at least 90% identical to SEQ ID NO:3. In some embodiments the present disclosure provides use of an anti-CCR5 antibody or antigen binding fragment thereof having a heavy chain antibody variable region that is 70%-100% identical to SEQ ID NO: 3, 75%-100% identical to SEQ ID NO: 3, 80%-100% identical to SEQ ID NO: 3, 85%-100% identical to SEQ ID NO: 3, 90%-100% identical to SEQ ID NO: 3, or 91%-100% identical to SEQ ID NO:3.

In some embodiments, the present disclosure provides use of an anti-CCR5 antibody or antigen binding fragment thereof having a heavy chain variable region (VH) that is at least 70% identical to amino acids 20-141 of SEQ ID NO:3, at least 75% identical to amino acids 20-141 of SEQ ID NO:3, at least 80% identical to amino acids 20-141 of SEQ ID NO:3, at least 85% identical to amino acids 20-141 of SEQ ID NO:3, or at least 90% identical to amino acids 20-141 of SEQ ID NO:3. In some embodiments the present disclosure provides use of an anti-CCR5 antibody or antigen binding fragment thereof having a heavy chain antibody variable region that is 70%-100% identical to amino acids 20-141 of SEQ ID NO: 3, 75%-100% identical to amino acids 20-141 of SEQ ID NO: 3, 80%-100% identical to amino acids 20-141 of SEQ ID NO: 3, 85%-100% identical to amino acids 20-141 of SEQ ID NO: 3, 90%-100% identical to amino acids 20-141 of SEQ ID NO: 3, or 91%-100% identical to amino acids 20-141 of SEQ ID NO:3.

In some embodiments, the present disclosure provides use of an anti-CCR5 antibody having a heavy chain variable region (VH) that is at least 70% identical to SEQ ID NO:5, at least 75% identical to SEQ ID NO: 5, at least 80% identical to SEQ ID NO: 5, at least 85% identical to SEQ ID NO: 5, or at least 90% identical to SEQ ID NO: 5. In some embodiments the present disclosure provides use of an anti-CCR5 antibody having a heavy chain variable antibody region that is 70%-100% identical to SEQ ID NO: 5, 75%-100% identical to SEQ ID NO: 5, 80%-100% identical to SEQ ID NO: 5, 85%-100% identical to SEQ ID NO: 5, 90%-100% identical to SEQ ID NO: 5, or 91%-100% identical to SEQ ID NO: 5.

In some embodiments, the present disclosure provides use of an anti-CCR5 antibody having a heavy chain variable region (VH) that is at least 70% identical to amino acids 20-141 of SEQ ID NO:5, at least 75% identical to amino acids 20-141 of SEQ ID NO: 5, at least 80% identical to amino acids 20-141 of SEQ ID NO: 5, at least 85% identical to amino acids 20-141 of SEQ ID NO: 5, or at least 90% identical to amino acids 20-141 of SEQ ID NO: 5. In some embodiments the present disclosure provides use of an anti-CCR5 antibody having a heavy chain variable antibody region that is 70%-100% identical to amino acids 20-141 of SEQ ID NO: 5, 75%-100% identical to amino acids 20-141 of SEQ ID NO: 5, 80%-100% identical to amino acids 20-141 of SEQ ID NO: 5, 85%-100% identical to amino acids 20-141 of SEQ ID NO: 5, 90%-100% identical to amino acids 20-141 of SEQ ID NO: 5, or 91%-100% identical to amino acids 20-141 of SEQ ID NO: 5.

In some embodiments, the present disclosure provides use of an anti-CCR5 antibody or an antigen-binding fragment thereof comprising a heavy chain variable region (VH) and a light chain variable region (VL), wherein the VH comprises a heavy chain CDR1 (VH-CDR1) comprising the amino acid sequence of SEQ ID NO:12, a heavy chain CDR2 (VH-CDR2) comprising the amino acid sequence of SEQ ID NO:13, and a heavy chain CDR3 (VH-CDR3) comprising the amino acid sequence of SEQ ID NO:14; and the VL comprises a light chain CDR1 (VL-CDR1) comprising the amino acid sequence of SEQ ID NO:9, a light chain CDR2 (VL-CDR2) comprising the amino acid sequence of SEQ ID NO:10, and a light chain CDR3 (VL-CDR3) comprising the amino acid sequence of SEQ ID NO:11. In some such embodiments, the VH comprises an amino acid sequence that has at least 70%, 75%, 80%, 85%, 90%, 91%, 92%, 93%, 94%, 95%, 96%, 97%, 98%, or 99% identity with the amino acid sequence of SEQ ID NO:3 or amino acids 20-141 of SEQ ID NO:3, and a VL comprises an amino acid sequence that has at least 70%, 75%, 80%, 85%, 90%, 91%, 92%, 93%, 94%, 95%, 96%, 97%, 98%, or 99% identity with the amino acid sequence of SEQ ID NO:1 or amino acids 20-131 of SEQ ID NO:1, provided that the amino acid sequences of the VH-CDRs (SEQ ID NOS:12-14) and VL-CDRs (SEQ ID NOS:9-11) are unchanged; or the VH comprises an amino acid sequence that has at least 70%, 75%, 80%, 85%, 90%, 91%, 92%, 93%, 94%, 95%, 96%, 97%, 98%, or 99% identity with the amino acid sequence of SEQ ID NO:5 or amino acids 20-141 of SEQ ID NO:5, and a VL comprises an amino acid sequence that has at least 70%, 75%, 80%, 85%, 90%, 91%, 92%, 93%, 94%, 95%, 96%, 97%, 98%, or 99% identity with the amino acid sequence of SEQ ID NO:1 or amino acids 20-131 of SEQ ID NO:1, provided that the amino acid sequences of the VH-CDRs (SEQ ID NOS:12-14) and VL-CDRs (SEQ ID NOS:9-11) are unchanged.

In some embodiments, the present disclosure provides use of an anti-CCR5 antibody or an antigen-binding fragment thereof comprising: (a) a VH comprising an amino acid sequence of SEQ ID NO:3 or amino acids 20-141 of SEQ ID NO:3, and a VL comprising an amino acid sequence of SEQ ID NO:1 or amino acids 20-131 of SEQ ID NO:1; or (b) a VH comprising an amino acid sequence of SEQ ID NO:5 or amino acids 20-141 of SEQ ID NO:5, and a VL comprising an amino acid sequence of SEQ ID NO:1 or amino acids 20-131 of SEQ ID NO:1.

In some embodiments, the present disclosure provides use of an anti-CCR5 antibody comprising a heavy chain (HC) and a light chain (LC). The heavy chain typically comprises a VH and a heavy chain constant region (CH). Depending on the antibody isotype from which it derives, a heavy chain constant region may comprise CH1, CH2, and CH3 domains (IgA, IgD, IgG), or CH1, CH2, CH3, and CH4 domains (IgE, IgM). In some embodiments, the heavy chain constant region comprises a human IgG1, IgG2, IgG3, or IgG4 constant region. In some embodiments, the constant region of the anti-CCR5 antibody is an IgG4 constant region. The light chain typically comprises a VL and a light chain constant region (CL). In some embodiments, a CL comprises a C kappa ("CK") constant region. In some embodiments, a CL comprises a C lambda (Cλ) constant region. In some embodiments, an anti-CCR5 antibody of the present disclosure comprises two heavy chains and two light chains, held together covalently by disulfide bridges.

In some embodiments, the present disclosure provides use of an anti-CCR5 antibody comprising a Fc region portion. As used herein, "Fc region portion" refers to the heavy chain constant region segment of the Fc fragment (the "fragment crystallizable" region or Fc region) from an antibody, which can include one or more constant domains, such as CH2, CH3, CH4 or any combination thereof. In some embodiments, an Fc region portion includes the CH2 and CH3 domains of an IgG, IgA, or IgD antibody or any combination thereof, or the CH3 and CH4 domains of an IgM or IgE antibody, and any combination thereof. In some embodiments, a CH2CH3 or a CH3CH4 structure has sub-region domains from the same antibody isotype and are human, such as human IgG1, IgG2, IgG3, IgG4, IgA1, IgA2, IgD, IgE, or IgM (e.g., CH2CH3 from human IgG1). By way of background, an Fc region is responsible for the effector functions of an antibody, such as ADCC (antibody-dependent cell-mediated cytotoxicity), CDC (complement-dependent cytotoxicity) and complement fixation, binding to Fc receptors (e.g., CD16, CD32, FcRn), greater half-life in vivo relative to a polypeptide lacking an Fc region, protein A binding, and perhaps even placental transfer (see Capon et al. *Nature* 337: 525, 1989). In some embodiments, a Fc region portion in an antibody or antigen-binding fragment of the present disclosure is capable of mediating one or more of these effector functions. In some embodiments, a Fc region portion in an antibody or antigen-binding fragment of the present disclosure has normal effector function, meaning having less than 20%, 15%, 10%, 5%, 1% difference in effector function (e.g., ADCC, CDC, half-life or any combination thereof) as compared to a wild type IgG1 antibody.

In some embodiments, the present disclosure provides use of an anti-CCR5 antibody comprising a Fc region portion having an increase in one or more of these effector functions by way of, for example, one or more amino acid substitutions or deletions in the Fc region portion known in the art. An antibody or antigen-binding fragment having a mutated or variant Fc region portion having increased effector function means that the antibody exhibits an increase of at least 20%, 25%, 30%, 35%, 40%, 45%, 50%, 55%, 60%, 65%, 70%, 75%, 80%, 85%, 90%, 95%, or 99% in FcR binding, ADCC, CDC, or any combination thereof, as compared to an antibody having a wild type Fc region portion. In some embodiments, the mutated or variant Fc region portion exhibits increased binding to FcRn, FcγRI (CD64), FcγRIIA (CD32), FcγRIIIA (CD16a), FcγRIIIB (CD16b), or any combination thereof. In some embodiments, the Fc region portion in an antibody or antigen-binding fragment of the present disclosure is a variant Fc region portion having increased ADCC, CDC, half-life, or any combination thereof.

Amino acid modifications (e.g., substitutions) to modify (e.g., improve, reduce, or ablate) Fc functionalities include, for example, the T250Q/M428L, M252Y/S254T/T256E, H433K/N434F, M428L/N434S, E233P/L234V/L235A/ G236+A327G/A330S/P331S, E333A, S239D/A330L/ I332E, P257I/Q311, K326W/E333S, S239D/I332E/G236A, N297Q, K322A, S228P, L235E+E318A/K320A/K322A, L234A/L235A, and L234A/L235A/P329G mutations, which mutations are summarized and annotated in "Engineered Fc Regions", published by InvivoGen (2011) and available online at www. invivogen.com/PDF/review/review-Engineered-Fc-Regions-invivogen.pdf?utm_source= review&utm_medium=pdf&utm_campaign=review&utm_ content=Engineered-Fc-Regions, and are incorporated herein by reference.

In some embodiments, the present disclosure provides use of an anti-CCR5 antibody comprising a Fc region portion having a reduction in one or more of these effector functions or lack one or more effector functions by way of, for example, one or more amino acid substitutions or deletions in the Fc region portion known in the art. An antibody or antigen-binding fragment having a mutated or variant Fc region portion having reduced effector function means that the antibody exhibits a decrease of at least 20%, 25%, 30%, 35%, 40%, 45%, 50%, 55%, 60%, 65%, 70%, 75%, 80%, 85%, 90%, 95%, or 99% in FcR binding, ADCC, CDC, or any combination thereof, as compared to an antibody having a wild type Fc region portion. In some embodiments, the mutated or variant Fc region portion exhibits decreased binding to FcRn, FcγRI (CD64), FcγRIIA (CD32), FcγRIIIA (CD16a), FcγRIIIB (CD16b), or any combination thereof. In some embodiments, the Fc region portion in an antibody or antigen-binding fragment of the present disclosure is a variant Fc region portion having reduced ADCC, CDC, half-life, or any combination thereof. In some embodiments, the Fc region portion is a variant IgG1 Fc region portion comprising a mutation corresponding to amino acid E233P, L234V, L234A, L235A, L235E, AG236, G237A, E318A, K320A, K322A, A327G, P329G, A330S, P331S, or any combination thereof, as numbered according to the EU set forth in Kabat. For example, amino acid substitutions L234A, L235E, G237A introduced into an IgG1 Fc region portion reduces binding to FcγRI, FcγRIIa, and FcγRIII receptors, and A330S and P331S introduced into an IgG1 Fc region portion reduces C1q-mediated complement fixation.

In some embodiments, the present disclosure provides use of an anti-CCR5 antibody comprising a Fc region portion having an increase in one or more of these effector functions by way of, for example, one or more amino acid substitutions or deletions in the Fc region portion known in the art. An antibody or antigen-binding fragment having a mutated or variant Fc region portion having increased effector function means that the antibody exhibits an increase of at least 20%, 25%, 30%, 35%, 40%, 45%, 50%, 55%, 60%, 65%, 70%, 75%, 80%, 85%, 90%, 95%, or 99% in FcR binding, ADCC, CDC, or any combination thereof, as compared to an antibody having a wildtype Fc region portion. In some embodiments, the mutated or variant Fc region portion exhibits increased binding to FcRn, FcγRI (CD64), FcγRIIA (CD32), FcγRIIIA (CD16a), FcγRIIIB (CD16b), or any combination thereof. In some embodiments, the Fc region portion in an antibody or antigen-binding fragment of the present disclosure is a variant Fc region portion having increased ADCC, CDC, half-life, or any combination thereof.

In some embodiments, the present disclosure provides use of an anti-CCR5 antibody that is glycosylated. IgG subtype antibodies contain a conserved glycosylation site at amino acid N297 in the CH2 domain of the Fc region portion. In some such embodiments, the Fc region portion in an antibody or antigen-binding fragment of the present disclosure comprises a N297 as numbered according to EU set forth in Kabat. In some embodiments, the present disclosure provides use of an anti-CCR5 antibody that comprises a mutation that alters glycosylation at N297 in the Fc region portion, optionally wherein the mutation that alters glycosylation comprises N297A, N297Q, or N297G. In some embodiments, an antibody or antigen-binding fragment thereof comprising a N297A, N297Q, or N297G mutation exhibits reduced Fc interaction with one or more low affinity FcγR(s), reduced CDC, reduced ADCC, or any combination thereof.

In some embodiments, the present disclosure provides use of an anti-CCR5 antibody that comprises a heavy chain (HC) and a light chain (LC), wherein the HC comprises an amino acid sequence that has at least 90%, 91%, 92%, 93%, 94%, 95%, 96%, 97%, 98%, 99%, or 100% identity with the amino acid sequence of SEQ ID NO:7, and the LC comprises an amino acid sequence that has at least 90%, 91%, 92%, 93%, 94%, 95%, 96%, 97%, 98%, or 99% identity with the amino acid sequence of SEQ ID NO:8 In some embodiments, the present disclosure provides use of an anti-CCR5 antibody that comprises a HC comprising an amino acid sequence that has the amino acid sequence of SEQ ID NO:7, and a LC comprising an amino acid sequence that has the amino acid sequence of SEQ ID NO:8.

In some embodiments, the present disclosure provides use of an anti-CCR5 antibody that comprises a Fc region or a fragment thereof, including a CH2 (or a fragment thereof), a CH3 (or a fragment thereof), or a CH2 and a CH3, wherein the CH2, the CH3, or both can be of any isotype and may contain amino acid substitutions or other modifications as compared to a corresponding wild-type CH2 or CH3, respectively. In certain embodiments, a Fc region of the present disclosure comprises two CH2-CH3 polypeptides that associate to form a dimer.

As used herein, unless otherwise provided, a position of an amino acid residue in the constant region of human IgG1 heavy chain is numbered assuming that the variable region of human IgG1 is composed of 128 amino acid residues according to the Kabat numbering convention. The numbered constant region of human IgG1 heavy chain is then used as a reference for numbering amino acid residues in constant regions of other immunoglobulin heavy chains. A position of an amino acid residue of interest in a constant region of an immunoglobulin heavy chain other than human IgG1 heavy chain is the position of the amino acid residue in human IgG1 heavy chain with which the amino acid residue of interest aligns. Alignments between constant regions of human IgG1 heavy chain and other immunoglobulin heavy chains may be performed using software programs known in the art, such as the Megalign program (DNASTAR Inc.) using the Clustal W method with default parameters. According to the numbering system described herein, for example, although human IgG2 CH2 region may have an amino acid deletion near its amino-terminus compared with other CH2 regions, the position of the "N" located at 296 in human IgG2 CH2 is still considered position 297 because this residue aligns with "N" at position 297 in human IgG1 CH2.

In addition, the present disclosure provides use of an anti-CCR5 antibody that comprises a hinge sequence that is typically situated between the Fab and Fc region (but a lower section of the hinge may include an amino-terminal portion of the Fc region). By way of background, an immunoglobulin hinge acts as a flexible spacer to allow the Fab portion to move freely in space. In contrast to the constant regions, hinges are structurally diverse, varying in both sequence and length between immunoglobulin classes and even among subclasses. For example, a human IgG1 hinge region is freely flexible, which allows the Fab fragments to rotate about their axes of symmetry and move within a sphere centered at the first of two inter-heavy chain disulfide bridges. By comparison, a human IgG2 hinge is relatively short and contains a rigid poly-proline double helix stabilized by four inter-heavy chain disulfide bridges, which restricts the flexibility. A human IgG3 hinge differs from the other subclasses by its unique extended hinge region (about four times as long as the IgG1 hinge), containing 62 amino acids (including 21 prolines and 11 cysteines), forming an inflexible poly-proline double helix and providing greater flexibility because the Fab fragments are relatively far away from the Fc fragment. A human IgG4 hinge is shorter than IgG1 but has the same length as IgG2, and its flexibility is intermediate between that of IgG1 and IgG2. Immunoglobulin structure and function are reviewed, for example, in Harlow et al., Eds., Antibodies: A Laboratory Manual, Chapter 14 (Cold Spring Harbor Laboratory, Cold Spring Harbor, 1988).

In some embodiments, the present disclosure provides use of an anti-CCR5 antibody or antigen binding fragment thereof that is chimeric, humanized, or human. Chimeric and humanized forms of non-human (e.g., murine) antibodies can be intact (full length) chimeric immunoglobulins, immunoglobulin chains or antigen binding fragments thereof (such as Fv, Fab, Fab', F(ab')$_2$ or other target-binding subdomains of antibodies), which can contain sequences derived from non-human immunoglobulin. In general, in the humanized antibody or antigen binding fragment thereof most or all of the amino acids outside the CDR regions (e.g., the framework (FR) regions) are replaced with corresponding amino acids derived from human immunoglobulin molecules. In one embodiment of the humanized forms of the antibodies, some, most, or all of the amino acids outside the CDR regions have been replaced with amino acids from human immunoglobulin molecules but where some, most, or all amino acids within one or more CDR regions are unchanged. Small additions, deletions, insertions, substitutions, or modifications of amino acids are permissible as long as they would not abrogate the ability of the antibody to bind a given antigen. A humanized antibody can also comprise at least a portion of a human immunoglobulin constant region (Fc). Suitable human immunoglobulin molecules for use in humanizing a non-human antibody would include IgG1, IgG2, IgG3, IgG4, IgA, and IgM molecules. A "humanized" antibody would retain a similar antigenic specificity as the original antibody, e.g., in the present disclosure, the ability to bind CCR5.

"Human antibodies" can include antibodies having, for example, the amino acid sequence of a human immunoglobulin and include antibodies isolated from human immunoglobulin libraries or from animals transgenic for one or more human immunoglobulins and that typically do not express endogenous immunoglobulins. Human antibodies can be produced using transgenic mice incapable of expressing functional endogenous immunoglobulins, but capable of expressing human immunoglobulin genes. Completely human antibodies that recognize a selected epitope can be generated using guided selection. In this approach, a selected non-human monoclonal antibody, e.g., a mouse antibody, is used to guide the selection of a completely human antibody recognizing the same epitope.

In some embodiments, the present disclosure provides use of an anti-CCR5 antibody or antigen binding fragment thereof that is a part of a multispecific antibody, e.g., a bispecific antibody or a dual variable domain antibody (DVD). Bispecific and DVD antibodies are monoclonal, often human or humanized, antibodies that have binding specificities for at least two different antigens, one of which is CCR5.

In some embodiments, the present disclosure provides use of an anti-CCR5 antibody or antigen binding fragment thereof that are derivatized or otherwise modified. For example, derivatized antibodies can be modified by glycosylation, acetylation, pegylation, phosphorylation, amidation, derivatization by known protecting/blocking groups, proteolytic cleavage, or the like.

In any of the aforementioned embodiments, the anti-CCR5 antibody or antigen binding fragment thereof is conjugated to a small molecule drug to form an antibody drug conjugate.

In some embodiments, the present disclosure provides use of the monoclonal antibody PA14, produced by the hybridoma cell line designated PA14 (ATCC Accession No. HB-12610), or an antigen binding fragment thereof, or an antibody that competes with monoclonal antibody PA-14 in binding to CCR5.

In some embodiments, the present disclosure provides use of leronlimab (PRO14) antibody or antigen binding fragment thereof. Leronlimab (PRO140) is a humanized IgG4 monoclonal antibody that binds to CCR5 described in U.S. Pat. Nos. 7,122,185 and 8,821,877, which are incorporated herein by reference, in their entirety. Leronlimab (PRO 140) is a humanized version of the murine monoclonal antibody, PA14, which was generated against CD4$^+$ CCR5$^+$ cells. Olson et al., *Differential Inhibition of Human Immunodeficiency Virus Type* 1 *Fusion, gp* 120 *Binding and CC-Chemokine Activity of Monoclonal Antibodies to CCR5*, J. VIROL., 73: 4145-4155. (1999). PRO 140 binds to CCR5 expressed on the surface of a cell, and potently inhibits HIV-1 entry and replication at concentrations that do not affect CCR5 chemokine receptor activity in vitro and in the hu-PBL-SCID mouse model of HIV-1 infection. Olson et al., *Differential Inhibition of Human Immunodeficiency Virus Type* 1 *Fusion, gp* 120 *Binding and CC-Chemokine Activity of Monoclonal Antibodies to CCR5*, J. VIROL., 73: 4145-4155. (1999); Trkola et al., *Potent, Broad-Spectrum Inhibition of Human Immunodeficiency Virus Type* 1 *by the CCR5 Monoclonal Antibody PRO* 140, J. VIROL., 75: 579-588 (2001).

Leronlimab does not downregulate CCR5 surface expression or deplete CCR5-expressing cells, but does prevent CCL5-induced calcium mobilization in CCR5+ cells with an IC$_{50}$ of 45 μg/ml. In some embodiments, a CCR5 binding agent does not downregulate CCR5 surface expression, deplete CCR5-expressing cells, or both. In some embodiments, a CCR5 binding agent inhibits CCL5-induced calcium mobilization of CCR5+ cells with an IC$_{50}$ of 45 μg/ml. In some embodiments, the CCR5 binding agent is leronlimab.

Leronlimab (PRO 140) binds to CCR5 and blocks viral entry by interfering with the final phase of viral binding to the cell surface prior to fusion of the viral and cell membranes. Leronlimab (PRO 140) has been administered intravenously or subcutaneously to more than 750 healthy and HIV-1 infected individuals in Phase I/II/III studies. The drug has been well tolerated following intravenous administration of single doses of 0.5 to 10 mg/kg or up to 700 mg weekly doses as subcutaneous (SC) injection. Overall, 324 subjects have been exposed to leronlimab (PRO 140) 350 mg SC weekly dose with the longest duration of exposure lasting 4 years. Similarly, more than 250 and 150 subjects have been exposed to leronlimab (PRO 140) 525 mg and 700 mg SC weekly dose, respectively.

It is contemplated that leronlimab (PRO 140) inhibits migration of Tregs into areas of inflammation and inhibits the innate immune response against pathogens and most importantly, e.g., the migration of macrophages and release of pro-inflammatory cytokines in lungs. CCR5 engagement of macrophages by leronlimab changes them into effector cells rather than mediators of inflammation. In some embodiments, CCR5 binding agents may be used to treat emerging infections, as CCR5 binding agents may help regulate the innate immune response, which is critical for infections the body has not been introduced to before (e.g. COVID-19).

In some embodiments, the present disclosure provides use of an anti-CCR5 antibody that binds to the same epitope as that to which leronlimab binds or competes with leronlimab in binding to CCR5. Leronlimab binds to a discontinuous epitope spanning multiple extracellular domains on CCR5, which include the N-terminus and second extracellular loop (ECL2) of CCR5 (Trkola et al. J. Virol. 75:579-588, incorporated by reference in its entirety). Leronlimab directly blocks binding of HIV Env to the CCR5 co-receptor via a competitive mechanism. Leronlimab binding at least requires amino acid residues D2 in the N-terminus and R168 and Y176 in the ECL2; mutation of amino acids D95 and C101 in the ECL1, and C178 in ECL2 also affect leronlimab binding, e.g., by conformational perturbation (Olson et al. J. Virol. 73:4145-4155, incorporated by reference in its entirety). Targeted loss-of-function mutagenesis and subsequent photo-cross-linking using genetically encoded unnatural amino acids method was also used to map antibody-GPCR complexes and identified residues 174 and 175 at the amino-terminal end of ECL2 as forming the strongest links with leronlimab (Ray-Saha et al., Biochem. 53:1302-13010).

CCR5 amino acid residues that are involved in CCL5 (RANTES) binding include Kl, D2, D11, E18, K26 in the N-terminus, D95 in the ECL1, and K171, K191, and R274 in the ECL2 (Navenot et al. J. Mol. Biol. 313:1181-1193, incorporated by reference in its entirety).

Nucleic acids encoding heavy and light chains of the humanized PA14 antibodies have been deposited with the ATCC. Specifically, the plasmids designated pVK-HuPRO140, pVg4-HuPRO140 (mut B+D+I) and pVg4-HuPRO140 HG2, respectively, were deposited pursuant to, and in satisfaction of, the requirements of the Budapest Treaty with the ATCC, Manassas, Va., U.S.A. 20108, on Feb. 22, 2002, under ATCC Accession Nos. PTA 4097, PTA 4099, and PTA 4098, respectively. The American Type Culture Collection (ATCC) is now located at 10801 University Boulevard, Manassas, Va. 20110-2209. The plasmids designated pVK-HuPRO140 and pVg4-HuPRO140 HG2 encode the light chain and heavy chain, respectively, of leronlimab.

The HCDR1-3 and LCDR1-3 amino acid sequences of leronlimab are set forth in SEQ ID NOS:12-14 and 9-11, respectively. The VH and VL sequences of leronlimab are set forth in amino acids 20-141 of SEQ ID NO:3 and amino acids 20-131 of SEQ ID NO:1, respectively. The heavy chain and light chain sequences of leronlimab are set forth in SEQ ID NOS:7 and 8, respectively.

In some embodiments, the present disclosure provides use of an anti-CCR5 antibody comprising: (i) two light chains, each light chain comprising the expression product of the plasmid designated pVK:HuPRO140-VK (ATCC Deposit Designation PTA-4097), and (ii) two heavy chains, each heavy chain comprising the expression product of either the plasmid designated pVg4:HuPRO140 HG2-VH (ATCC Deposit Designation PTA-4098) or the plasmid designated pVg4:HuPRO140 (mut B+D+I)-VH (ATCC Deposit Designation PTA-4099).

In some embodiments, the present disclosure provides use of an anti-CCR5 antibody comprising: (i) two light chains, each light chain comprising the light chain variable (V$_L$) and constant (C$_L$) regions encoded by the plasmid designated pVK:HuPRO140-VK (ATCC Deposit Designation PTA-4097), and (ii) two heavy chains, each heavy chain comprising the heavy chain variable (V$_H$) and constant (C$_H$) regions encoded either by the plasmid designated pVg4:HuPRO140 HG2-VH (ATCC Deposit Designation PTA-4098) or by the plasmid designated pVg4:HuPRO140 (mut B+D+I)-VH (ATCC Deposit Designation PTA-4099).

Various CCR5 binding agents are known. In some embodiments, the present disclosure provides use of a CCR5 binding agent that is maraviroc. Maraviroc is a negative allosteric modulator of CCR5. Competitive binding studies involving the CCR5 receptor and various anti-CCR5 binding agents including its natural ligand CCL5, and PRO 140 and maraviroc demonstrate that each of these components has a different binding capacity, and each binds to one or more distinct portions of the CCR5 receptor. PRO 140 binds to extracellular portions of the CCR5 receptor and effectively diminishes the downstream immunomodulatory effects of CCL5 binding on the CCL5 receptor. Also, unlike maraviroc, PRO 140 is shown to have no CCL5 receptor agonist activity when bound to CCR5 with respect to cAMP levels or cell migration. Accordingly, PRO 140 is shown to provide an advantageous application and gives rise to new uses for this CCR5 receptor competitive inhibitor to inhibit, interrupt, block, mitigate, dampen, slow the progress of, and/or therapeutically treat conditions resulting, in whole or in part, from the downstream immunomodulatory effects induced by CCL5 ligand binding on the CCL5 receptor.

In some embodiments, the present disclosure provides use of a CCR5 binding agent that is vicriviroc, a non-competitive allosteric CCR5 antagonist.

In some embodiments, the present disclosure provides use of a CCR5 binding agent that is cenicriviroc.

In some embodiments, the present disclosure provides use of a CCR5 binding agent that is TAK-779.

In some embodiments, the present disclosure provides use of a CCR5 binding agent that is Met-CCL5 (Met-RANTES).

In some embodiments, the present disclosure provides use of a CCR5 binding agent that is anibamine.

In some embodiments, the present disclosure provides use of a CCR5 binding agent that is GSK706769.

In some embodiments, the present disclosure provides use of a CCR5 binding agent that is INCB009471.

In some embodiments, the present disclosure provides use of a CCR5 binding agent that is DT-13.

In some embodiments, the present disclosure provides use of a CCR5 binding agent that is aplaviroc.

In some embodiments, the present disclosure provides use of a CCR5 binding agent that is the CCR5mAb004 antibody or an antigen binding fragment thereof. CCR5mAb004 is a fully human monoclonal IgG4 antibody generated using the Abgenix XenoMouse® technology. See Yadavalli et al., J Infect Dis. 2008; 197:721-727; Roschke et al., *Characterization of a Panel of Novel Human Monoclonal Antibodies That Specifically Antagonize CCR5 and Block HIV Entry*, 44th Annual Interscience CONFERENCE ON ANTIMICROBIAL AGENTS AND CHEMOTHERAPY, Washington, D.C., Oct. 30-Nov. 2, 2004 (2004); HGS Press Release, *Human Genome Sciences Characterizes Panel of Novel Human Monoclonal Antibodies That Specifically Antagonize the CCR5 Receptor and Block HIV-1 Entry*, Nov. 2, 2004 (2004); HGS Press Release, *Human Genome Sciences Begins Dosing of Patients in a Phase* 1 *Clinical Trial of CCR5 mAb in Patients Infected With HIV-1*, Mar. 30, 2005 (2005).

In some embodiments, the present disclosure provides use of a CCR5 binding agent that is the RoAb13 antibody or an antigen binding fragment thereof. RoAb13 is a mouse, anti-human CCR5 monoclonal antibody that does not show agonist activity or cause internalization of CCR5 (Ji et al. Antiviral Res. 74:125-37).

In some embodiments, the present disclosure provides use of a CCR5 binding agent that is a competitive inhibitor to CCR5. The term "competitive inhibitor" as used herein refers to a molecule that competes with a reference molecule for binding to a target, and thereby blunts, inhibits, dampens, reduces, or blocks the effects of the reference molecule on the target. Thus a competitive inhibitor to CCR5 would compete with CCL5 for binding to CCR5. In some embodiments, a competitive inhibitor to CCR5 is an antibody or antigen binding fragment thereof that comprises:

(i) a heavy chain variable region (VH) and a light chain variable region (VL), wherein the VH comprises a heavy chain CDR1 (VH-CDR1) comprising the amino acid sequence of SEQ ID NO:12, a heavy chain CDR2 (VH-CDR2) comprising the amino acid sequence of SEQ ID NO:13, and a heavy chain CDR3 (VH-CDR3) comprising the amino acid sequence of SEQ ID NO:14; and the VL comprises a light chain CDR1 (VL-CDR1) comprising the amino acid sequence of SEQ ID NO:9, a light chain CDR2 (VL-CDR2) comprising the amino acid sequence of SEQ ID NO:10, and a light chain CDR3 (VL-CDR3) comprising the amino acid sequence of SEQ ID NO:11;

(ii) a VH comprising the amino acid sequence of SEQ ID NO:3 or amino acids 20-141 of SEQ ID NO:3, and a VL comprising the amino acid sequence of SEQ ID NO:1 or amino acids 20-131 of SEQ ID NO:1;

(iii) a VH comprises the amino acid sequence of SEQ ID NO:5 or amino acids 20-141 of SEQ ID NO:5, and a VL comprises the amino acid sequence of SEQ ID NO:1 or amino acids 20-131 of SEQ ID NO:1; or (iv) a heavy chain comprising the amino acid sequence of SEQ ID NO:7 and a light chain comprising the amino acid sequence of SEQ ID NO:8.

In some embodiments, the present disclosure provides use of an anti-CCR5 antibody or an antigen-binding fragment thereof comprising: (a) a VH comprising an amino acid sequence of SEQ ID NO:3 or amino acids 20-141 of SEQ ID NO:3, and a VL comprising an amino acid sequence of SEQ ID NO:1 or amino acids 20-131 of SEQ ID NO:1; or (b) a VH comprising an amino acid sequence of SEQ ID NO:5 or amino acids 20-141 of SEQ ID NO:5, and a VL comprising an amino acid sequence of SEQ ID NO:1 or amino acids 20-131 of SEQ ID NO:1.

In some embodiments, the present disclosure provides use of a CCR5 binding agent that is a competitive inhibitor to CCR5 and does not have CCL5 agonist activity upon binding to CCR5. CCL5 agonist activity may be detected by measuring a decrease in cAMP; induced cell migration; or both cAMP decrease and induced cell migration triggered in response to CCL5-CCR5 axis activity. Some CCR5 binding agents even while acting to inhibit, interrupt, block, mitigate, dampen, slow the progress of, or eliminate the triggering of the downstream effects of CCL5 on CCR5 receptor positive cells also gives rise to independent and separate CCL5 agonistic downstream CCL5/CCR5 axis signaling effects that may counteract or diminish the effectiveness of these CCR5 competitive inhibitors for the purposes of immunomodulatory regulation, alteration, or control for therapeutic purposes. In some embodiments, a competitive inhibitor to CCR5 that does not have CCL5 agonist activity is an antibody or antigen binding fragment thereof that comprises:

(i) a heavy chain variable region (VH) and a light chain variable region (VL), wherein the VH comprises a heavy chain CDR1 (VH-CDR1) comprising the amino acid sequence of SEQ ID NO:12, a heavy chain CDR2 (VH-CDR2) comprising the amino acid sequence of SEQ ID NO:13, and a heavy chain CDR3 (VH-CDR3) comprising the amino acid sequence of SEQ ID NO:14; and the VL comprises a light chain CDR1 (VL-CDR1) comprising the amino acid sequence of SEQ ID NO:9, a light chain CDR2 (VL-CDR2) comprising the amino acid sequence of SEQ ID NO:10, and a light chain CDR3 (VL-CDR3) comprising the amino acid sequence of SEQ ID NO:11;

(ii) a VH comprising the amino acid sequence of SEQ ID NO:3 or amino acids 20-141 of SEQ ID NO:3, and a VL comprising the amino acid sequence of SEQ ID NO:1 or amino acids 20-131 of SEQ ID NO:1;

(iii) a VH comprises the amino acid sequence of SEQ ID NO:5 or amino acids 20-141 of SEQ ID NO:5, and a VL comprises the amino acid sequence of SEQ ID NO:1 or amino acids 20-131 of SEQ ID NO:1; or (iv) a heavy chain comprising the amino acid sequence of SEQ ID NO:7 and a light chain comprising the amino acid sequence of SEQ ID NO:8.

Nucleic Acids, Vectors, and Host Cells

In another aspect, the present disclosure provides an isolated nucleic acid that encodes the anti-CCR5 antibody or antigen binding fragment thereof as described herein. In some embodiments, the isolated nucleic acid encodes the VH, the VL, or both the VH and VL of the antibody or antigen binding fragment thereof. In some embodiments, the isolated nucleic acid encodes the heavy chain, the light chain, or both the heavy and light chain of the antibody or antigen binding fragment thereof. In some embodiments, the nucleic acid encoding the anti-CCR5 antibody or antigen binding fragment thereof is codon optimized to enhance or maximize expression in certain types of cells (e.g., Scholten et al., *Clin. Immunol.* 119: 135-145, 2006). As used herein a "codon optimized" polynucleotide is a heterologous polypeptide having codons modified with silent mutations corresponding to the abundances of host cell tRNA levels.

In some embodiments, a nucleic acid molecule encoding an anti-CCR5 antibody or antigen binding fragment thereof of the present disclosure (e.g., an antibody heavy chain and light chain, or VH and VL regions) comprises a nucleic acid sequence for a heavy chain or VH region and a light chain or VL, respectively, wherein the heavy chain or VH region is separated from the light chain or VL region by a 2A self-cleaving peptide. In some embodiments, the 2A self-cleaving peptide is a porcine teschovirus-1 (P2A), equine rhinitis A virus (E2A), Thosea asigna virus (T2A), foot-and-mouth disease virus (F2A), or any combination thereof (see, e.g., Kim et al., *PLOS One* 6:e18556, 2011, which 2A nucleic acid and amino acid sequences are incorporated herein by reference in their entirety).

In another aspect, an expression construct comprising a nucleic acid encoding an anti-CCR5 antibody or antigen binding fragment thereof as described herein is provided. In some embodiments, a nucleic acid may be operably linked to an expression control sequence (e.g., expression construct). As used herein, "expression construct" refers to a DNA construct containing a nucleic acid molecule that is operably-linked to a suitable control sequence capable of effecting the expression of the nucleic acid molecule in a suitable host. An expression construct may be present in a vector (e.g., a bacterial vector, a viral vector) or may be integrated into a genome. The term "operably linked" refers to the association of two or more nucleic acids on a single polynucleotide fragment so that the function of one is affected by the other. For example, a promoter is operably-linked with a coding sequence when it is capable of affecting the expression of that coding sequence (i.e., the coding sequence is under the transcriptional control of the promoter). The term "expression control sequence" (also called a regulatory sequence) refers to nucleic acid sequences that effect the expression and processing of coding sequences to which they are operably linked. For example, expression control sequences may include transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; and possibly sequences that enhance protein secretion.

In some embodiments, a nucleic acid or an expression construct encoding an anti-CCR5 antibody or antigen binding fragment thereof is present in a vector. A "vector" is a nucleic acid molecule that is capable of transporting another nucleic acid. Vectors may be, for example, plasmids, cosmids, viruses, a RNA vector or a linear or circular DNA or RNA molecule that may include chromosomal, non-chromosomal, semi-synthetic or synthetic nucleic acids. Exemplary vectors are those capable of autonomous replication (episomal vector) or expression of nucleic acids to which they are linked (expression vectors). Exemplary viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields et al., Eds., Lippincott-Raven Publishers, Philadelphia, 1996). In some embodiments, a vector is a plasmid. In some other embodiments, a vector is a viral vector. In some such embodiments, the viral vector is a lentiviral vector or a γ-retroviral vector.

In a further aspect, the present disclosure also provides an isolated host cell comprising a nucleic acid, expression construct, or vector encoding an anti-CCR5 antibody or antigen binding fragment thereof as described herein. As used herein, the term "host" refers to a cell or microorganism targeted for genetic modification with a heterologous or exogenous nucleic acid molecule to produce a polypeptide of interest (e.g., an anti-CCR5 antibody or antigen-binding fragment thereof). In certain embodiments, a host cell may optionally already possess or be modified to include other genetic modifications that confer desired properties related or unrelated to biosynthesis of the heterologous or exogenous protein (e.g., inclusion of a selectable marker). More than one heterologous or exogenous nucleic acid molecule can be introduced into a host cell as separate nucleic acid molecules, as a plurality of individually controlled genes, as a polycistronic nucleic acid molecule, as a single nucleic acid molecule encoding a fusion protein, or any combination thereof. When two or more exogenous nucleic acid molecules are introduced into a host cell, it is understood that the two more exogenous nucleic acid molecules can be introduced as a single nucleic acid molecule (e.g., on a single vector), on separate vectors, integrated into the host chromosome at a single site or multiple sites. The number of referenced heterologous nucleic acid molecules or protein activities refers to the number of encoding nucleic acid molecules or the number of protein activities, not the number of separate nucleic acid molecules introduced into a host cell.

Examples of host cells include, but are not limited to, eukaryotic cells, e.g., yeast cells, animal cells, insect cells, plant cells; and prokaryotic cells, including E. coli. In some embodiments, the cells are mammalian cells. In some embodiments, the host cell is a human embryonic kidney (HEK293) cell, Y0 cell, Sp2/0 cell, NS0 murine myeloma cell, PER.C6® human cell, baby hamster kidney cell (BHK), COS cell, or Chinese hamster ovary (CHO) cell. In some embodiments, the host cell is a CHO-K1 cell. In some embodiments, the host cell is a CHOK1SV cell. Host cells are cultured using methods known in the art.

In yet another aspect, the present disclosure provides a process for making an anti-CCR5 antibody or antigen binding fragment thereof as described herein, comprising culturing a host cell of the present disclosure, under suitable conditions and for a sufficient time to express the anti-CCR5 antibody or antigen binding fragment thereof, and optionally isolating the anti-CCR5 antibody or antigen binding fragment thereof from the culture. Purification of soluble antibodies or antigen binding fragments thereof may be performed according to methods known in the art.

Pharmaceutical Compositions

In another aspect, the present disclosure provides use of pharmaceutical compositions comprising CCR5 binding agents described herein for administration to a subject in need thereof. Pharmaceutical compositions can comprise the CCR5 binding agents described herein and one or more pharmaceutically acceptable carrier, diluent, or excipient, suitable for administration by a selected route. A pharmaceutical composition can comprise any CCR5 binding agent described herein. Pharmaceutically acceptable carriers for diagnostic and therapeutic use are well known in the pharmaceutical art, and are described, for example, in *Remington's Pharmaceutical Sciences*, Mack Publishing Co. (A. R. Gennaro (Ed.), 18$^{th}$ Edition, 1990) and in *CRC Handbook of Food, Drug, and Cosmetic Excipients*, CRC Press LLC (S. C. Smolinski, ed., 1992). Exemplary pharmaceutically acceptable carriers include any adjuvant, carrier, excipient, glidant, diluent, preservative, dye/colorant, surfactant, wetting agent, dispersing agent, suspending agent, stabilizer, isotonic agent, solvent, emulsifier, or any combination thereof. For example, sterile saline and phosphate buffered saline at physiological pH can be suitable pharmaceutically acceptable carriers. Preservatives, stabilizers, dyes or the like may also be provided in the pharmaceutical composition. In addition, antioxidants and suspending agents may also be used. Pharmaceutical compositions may also contain diluents such as water, buffers, antioxidants such as ascorbic acid, low molecular weight polypeptides (less than about 10 residues), proteins, amino acids, carbohydrates (e.g., glucose, sucrose, dextrins), chelating agents (e.g., EDTA), glutathione, and other stabilizers and excipients. Neutral buffered saline or saline mixed with nonspecific serum albumin are exemplary diluents.

Pharmaceutical compositions comprising a CCR5 binding agent can be manufactured, for example, by lyophilizing the CCR5 binding agent, mixing, dissolving, emulsifying, encapsulating or entrapping the CCR5 binding agent. The pharmaceutical compositions can also include the CCR5 binding agents described herein in a free-base form or pharmaceutically-acceptable salt form.

A pharmaceutical composition may be formulated in the form of a solid, semi-solid or liquid composition. Solid compositions may include powders and tablets. In some embodiments, the pharmaceutical compositions described here are lyophilized or in powder form for re-constitution with a suitable vehicle, e.g., sterile water, before use. In some embodiments, the pharmaceutical compositions described herein is a suspension, solution, or emulsion. The pharmaceutical compositions and formulations can be sterilized. Sterilization can be accomplished by filtration through sterile filtration.

The pharmaceutical compositions described herein can be formulated for oral, topical, transdermal, inhalation, parenteral, sublingual, buccal, rectal, vaginal, and intranasal administration. The term "parenteral", as used herein, includes subcutaneous, intravenous, intramuscular, intrasternal, and intratumoral injection or infusion techniques. In some embodiments, the pharmaceutical compositions described herein are formulated for administration as an injection, e.g., an intravenous or subcutaneous injection. Non-limiting examples of formulations for injection can include a sterile suspension, solution or emulsion in oily or aqueous vehicles. Suitable oily vehicles can include, but are not limited to, lipophilic solvents or vehicles such as fatty oils or synthetic fatty acid esters, or liposomes. Aqueous injection suspensions can contain substances which increase the viscosity of the suspension. The suspension can also contain suitable stabilizers. Alternatively, the pharmaceutical compositions described herein can be lyophilized or in powder form for reconstitution with a suitable vehicle, e.g., sterile pyrogen-free water, before use.

The CCR5 binding agents can be formulated for administration in a unit dosage form in association with a pharmaceutically acceptable vehicle. Such vehicles can be inherently nontoxic, and non-therapeutic. A vehicle can be water, saline, Ringer's solution, dextrose solution, and 5% human serum albumin. Non-aqueous vehicles such as fixed oils and ethyl oleate can also be used. The vehicle can contain minor amounts of additives such as substances that enhance isotonicity and chemical stability (e.g., buffers and preservatives).

In some embodiments, an aqueous formulation of a CCR5 binding agent provided herein, such as for subcutaneous administration, has a pH from 4-5.7. The aqueous formulation may comprise one or more excipients, such as, for example, one or more buffering agents, one or more lyoprotectants, and the like. In some embodiments, the pH of the formulation is from 4.0-6.0, 4.1-5.1, 4.2-5.1, 4.3-5.1, 4.4-5.1, 4.5-5.1, 4-5, 4.1-5, 4.2-5, 4.3-5, 4.4-5, 4.5-5, or about 4.5-5.5, about 5.3, about 5.4, about 5.5, about 5.6, or about 5.7. In some embodiments, the formulation comprises at least one buffer. In various embodiments, the buffer may be selected from histidine, citrate, aspartate, acetate, phosphate, lactate, tromethamine, gluconate, glutamate, tartrate, succinate, malic acid, fumarate, α-ketoglutarate, and combinations thereof. In some embodiments, the buffer is at least one buffer selected from histidine, citrate, aspartate, acetate, and combinations thereof. In some embodiments, the buffer is a combination of histidine and aspartate. In some embodiments, the total concentration of the buffer in the aqueous formulation is 10 mM to 40 mM, such as 15 mM-30 mM, 15 mM-25 mM, or 20 mM.

In some embodiments, the aqueous formulation comprises at least one lyoprotectant. In some such embodiments, the at least one lyoprotectant is selected from sucrose, arginine, glycine, sorbitol, glycerol, trehalose, dextrose, alpha-cyclodextrin, hydroxypropyl beta-cyclodextrin, hydroxypropyl gamma-cyclodextrin, proline, methionine, albumin, mannitol, maltose, dextran, and combinations thereof. In some embodiments, the lyoprotectant is sucrose.

In some embodiments, the total concentration of lyoprotectant in the aqueous formulation is 3-12%, such as 5-12%, 6-10%, 5-9%, 7-9%, or 8%.

In some embodiments, the aqueous formulation comprises at least one surfactant. Exemplary surfactants include polysorbate 80, polysorbate 20, poloxamer 88, and combinations thereof. In some embodiments, the aqueous formulation comprises polysorbate 80. In some embodiments, the total concentration of the at least one surfactant is 0.01%-0.1%, such as 0.01%-0.05%, 0.01%-0.08%, or 0.01%-0.06%, 0.01%-0.04%, 0.01%-0.03%, or 0.02%.

In some embodiments, pharmaceutical compositions of the present invention are formulated in a single dose unit or in a form comprising a plurality of dosage units. Methods of preparing such dosage forms are known, or will be apparent, to those skilled in this art; for example, see Remington: The Science and Practice of Pharmacy, 20th Edition (Philadelphia College of Pharmacy and Science, 2000).

In some embodiments, the concentration of the CCR5 binding agent in the aqueous formulation is 1 mg/mL-250 mg/mL, such as 10 mg/mL-220 mg/mL, 10 mg/mL-200 mg/mL 10 mg/mL-175 mg/mL, 10 mg/mL-150 mg/mL, 10 mg/mL-100 mg/mL, 20 mg/mL-200 mg/mL, 20 mg/mL-175 mg/mL, 20 mg/mL-150 mg/mL, 20 mg/mL-125 mg/mL, 20 mg/mL-100 mg/mL, 30 mg/mL-200 mg/mL, 30 mg/mL-175 mg/mL, 30 mg/mL-150 mg/mL, 30 mg/mL-125 mg/mL, 30 mg/mL-100 mg/mL, 40 mg/mL-200 mg/mL 40 mg/mL-175 mg/mL, 40 mg/mL-150 mg/mL, 40 mg/mL-125 mg/mL, 40 mg/mL-100 mg/mL, 50 mg/mL-200 mg/mL 50 mg/mL-175 mg/mL, 50 mg/mL-150 mg/mL, 50 mg/mL-125 mg/mL, 50 mg/mL-100 mg/mL, 60 mg/mL-200 mg/mL, 60 mg/mL-175 mg/mL, 60 mg/mL-150 mg/mL, 60 mg/mL-125 mg/mL, 60 mg/mL-100 mg/mL, 70 mg/mL-200 mg/mL, 70 mg/mL-175 mg/mL, 70 mg/mL-150 mg/mL, 70 mg/mL-125 mg/mL, 80 mg/mL-200 mg/mL, 80 mg/mL-175 mg/mL, 80 mg/mL-150 mg/mL, 80 mg/mL-125 mg/mL, 100 mg/mL-200 mg/mL, 125 mg/mL-200 mg/mL, 150 mg/mL-200 mg/mL, or 160 mg/mL-190 mg/mL, 170 mg/mL-180 mg/mL, or 175 mg/mL. In some embodiments, the concentration of the CCR5 binding agent in the aqueous formulation is 100 mg/mL-200 mg/mL. In some embodiments, the concentration of the CCR5 binding agent in the aqueous formulation is 175 mg/mL.

In some embodiments, the CCR5 binding agent is an anti-CCR5 antibody or antigen binding fragment thereof formulated in a high protein concentration. High protein concentration formulations containing an exemplary anti-CCR5 antibody are described in U.S. Pat. No. 9,956,165 (incorporated by reference in its entirety).

In some embodiments, the anti-CCR5 antibody or antigen binding fragment is in a formulation comprising concentrated anti-CCR5 antibody or antigen binding fragment thereof in an amount greater than about 100 mg/mL and less than about 200 mg/mL; a tonicifier consisting essentially of a sodium salt and a histidine and glycine buffer present in a combined amount of from about 110 mM to about 120 mM and wherein the buffer is present in an amount of about 10 mM to about 25 mM; and a surfactant, wherein the formulation is hypotonic and has a total salt concentration of less than 100 mM.

In some embodiments, the anti-CCR5 antibody or antigen binding fragment is in a formulation comprising: concentrated anti-CCR5 antibody or antigen binding fragment in an amount greater than about 100 mg/mL and less than about 200 mg/mL; a sodium salt in an amount greater than about 90 mM and less than 100 mM; a histidine and glycine buffer in an amount greater than about 5 mM and less than about 25 mM; a surfactant in an amount greater than about 0.001% w/v and less than about 0.2% w/v; and, optionally, a stabilizing agent or non-salt tonicifier in an amount of about 0.05% w/v to about 1.8% w/v; wherein the formulation has an osmolality of about 250 to about 280 mOsm and has a total salt concentration of less than 100 mM.

In some embodiments, the anti-CCR5 antibody or antigen binding fragment is formulated in a low viscosity, hypotonic formulation, comprising: (a) concentrated anti-CCR5 antibody or antigen binding fragment in an amount greater than about 100 mg/mL and less than about 200 mg/mL; (b) a sodium salt in an amount selected from about 90 mM or about 95 mM; (c) a histidine and glycine buffer in an amount of about 20 mM; (d) a surfactant in an amount of 0.005% to 0.2% w/v; and optionally (e) a stabilizing agent or non-salt tonicifier in an amount sufficient to provide an osmolality of the formulation of about 260-280 mOs/kg; wherein the formulation has a total salt concentration of less than 100 mM.

In some embodiments, the anti-CCR5 antibody or antigen binding fragment is in a low viscosity hypotonic formulation, comprising: (a) concentrated anti-CCR5 antibody or antigen binding fragment in an amount greater than about 100 mg/mL and less than about 200 mg/mL; (b) a salt in an amount selected from about 90 mM or about 95 mM, wherein the salt is selected from sodium chloride, sodium gluconate, or sodium lactate; (c) a histidine and glycine buffer in an amount of about 20 mM; (d) a surfactant in an amount of about 0.005% to about 0.2% w/v, wherein the surfactant is a polysorbate, a poloxamer, or a pluronic; and (e) a stabilizing agent or non-salt tonicifier present in an amount sufficient to provide an osmolality of the formulation of about 230 mOs/kg to about 280 mOs/kg, wherein the stabilizing agent or non-salt tonicifier is selected from a sugar alcohol, a monosaccharide, a disaccharide, or a combination thereof; wherein the formulation has a total salt concentration of less than 100 mM.

In some embodiments, anti-CCR5 antibody or antigen binding fragment is formulated in a composition comprising anti-CCR5 antibody or antigen binding fragment in an amount greater than about 100 mg/mL and less than about 200 mg/mL, a tonicifier comprising a sodium salt present in a concentration of greater than about 90 mM and a histidine and glycine buffer present in a combined amount of from 110 mM to 120 mM and a surfactant present in an amount of from about 0.001% to about 0.2% w/v, wherein the composition has an osmolality of about 230 to about 290 mOs/kg and a total salt concentration of less than 100 mM.

In some embodiments, anti-CCR5 antibody or antigen binding fragment is provided as an article of manufacture comprising a container and a formulation comprising anti-CCR5 antibody or antigen binding fragment in a concentration of greater than 100 mg/mL and less than 200 mg/mL, a tonicifier of a sodium salt present in a concentration of greater than about 90 mM and a histidine and glycine buffer present in a combined amount of from about 110 mM to about 120 mM and the formulation has a total salt concentration of less than 100 mM, a surfactant in an amount of from about 0.005% to about 0.2%, and instructions for use.

In some embodiments, anti-CCR5 antibody or antigen binding fragment is administered in a dose of 700 mg of anti-CCR5 antibody or antigen binding fragment (175 mg/mL) delivered as two injections of 2 mL each and administered subcutaneously on opposite sides of the abdomen. Each vial of the anti-CCR5 antibody or antigen binding fragment product may contain ~1.4 mL antibody at a concentration of 175 mg/mL.

In any of the aforementioned pharmaceutical compositions, the CCR5 binding agent may be leronlimab.

Methods of Use

The CCR5 receptor binds to a chemokine known as CCL5 (C-C chemokine ligand 5), which is an inflammatory chemokine that plays an important role in immunologic mechanisms such as controlling cell recruitment and activation in basal and inflammatory circumstances. CCL5 acts as a key regulator of CCR5+ cell (e.g., macrophage and T cell) migration to inflammatory sites, directing migration of macrophages and T cells to damaged or infected sites. CCR5 also plays a crucial role in differentiation and activation of CD8+ T cells. CCL5 directly promotes M1 polarization and impedes M2 polarization in macrophages. The M1 macrophage phenotype is characterized by the production of high levels of pro-inflammatory cytokines, an ability to mediate resistance to pathogens, strong microbicidal properties, high production of reactive nitrogen and oxygen intermediates, and promotion of TH1 responses. In contrast, M2 macrophages are characterized by their involvement in parasite control, tissue remodeling, immune regulation, tumor promotion and efficient phagocytic activity. The formation of the CCL ligand and CCR5 receptor complex causes a conformational change in the receptor that activates the subunits of the G-protein, inducing signaling and leading to changed levels of cyclic AMP (cAMP), inositol triphosphate, intracellular calcium and tyrosine kinase activation. These signaling events cause cell polarization and translocation of the transcription factor NF-kB, which results in the increase of phagocytic ability, cell survival, and transcription of proinflammatory genes. Elevated CCL5 may lead to immune dysfunction or dysregulation, e.g., elevated levels of inflammatory cytokines and/or chemokines (e.g., hyperinflammation), excessive migration of CCR5+ expressing immune cells (e.g., macrophages and T cells), elevated CD4:CD8 T cell ratio, CD8 T cell depletion, T cell exhaustion, or any combination thereof.

CCR5 binding agents of the present disclosure bind to the CCR5 receptor and reduces, inhibits, blocks the downstream immunomodulatory effects of CCL5 binding on the CCL5 receptor. Thus, CCR5 binding agents of the present disclosure may be used to treat subjects with pathologies involving the CCL5-CCR5 pathway. In some embodiments, the present disclosure provides methods of treating hyperinflammation, including cytokine release syndrome, reducing excessive CCR5+ immune cell migration (e.g., T cells and macrophages) to infected sites (e.g., lungs), normalizing CD4:CD8 T cell ratio, increasing CD8 T cell frequency, reducing or reversing T cell exhaustion, or any combination thereof in a subject infected with coronavirus comprising administering to the subject an effective amount of a CCR5 binding agent. In another embodiment, the present disclosure provides methods of treating hyperinflammation in a subject comprising administering to the subject an effective amount of a CCR5 binding agent.

Furthermore, study of ten critically ill patients with COVID-19 showed signatures of cytokine release syndrome, significantly elevated plasma levels of inflammatory cytokines IL-1β, IL-6, and IL-8 compared to healthy controls. Notably, CCL5 levels were markedly elevated in severe COVID-19 patients over healthy controls and mild or moderate COVID-19 patients. Patients with mild or moderate COVID-19 also had elevated CCL5 levels over healthy controls. High levels of CCL5 can cause kidney failure and liver toxicity, common findings in severe COVID-19 infection. Furthermore, CCL5 can trigger platelet activation, which leads to the initiation of the coagulation cascade.

Recent studies have shown that COVID-19 patents experience increased risk of strokes, blood clots, pulmonary embolism, and other thromboembolic events. Thus, CCL5 may be a predominant component of cytokine release syndrome and other pathologies associated with coronavirus infection. In some embodiments, the present disclosure provides methods of reducing the occurrence or risk of developing liver toxicity, kidney failure, or a coagulation event (e.g., stroke, blood clot, pulmonary embolism) in a subject infected with coronavirus comprising administering to the subject an effective amount of a CCR5 binding agent.

In some embodiments, the present disclosure provides methods of reducing elevated CCL5 level associated with a viral (e.g., coronavirus such as SARS-CoV-2) infection in a subject comprising administering to the subject an effective amount of a CCR5 binding agent. In some embodiments, the CCL5 level is at least 5-fold, 10-fold, 20-fold, 30-fold, 40-fold, 50-fold, 60-fold, 70-fold, 80-fold, 90-fold or 100-fold higher than normal levels. In some embodiments the viral infection is an emerging viral infection. In some embodiments, the viral infection is a coronavirus infection, such as SARS-CoV-2. The level of inflammatory chemokine CCL5 was found to be elevated at least 100-fold in subjects with severe COVID-19 compared to a normal control. Without wishing to be bound by theory, CCL5 may be a key regulator of the pathologies associated with COVID-19, e.g., hyperinflammation, CD8 T cell deficiency, abnormal CD4: CD8 T cell ratio, T cell exhaustion, and other comorbidities (e.g., kidney failure, liver toxicity, coagulation events). Inhibition of CCR5 activation by CCL5 may restore or normalize the immune system, decrease viral load indirectly by enhancing the immune response, reduce the occurrence or likelihood of developing comorbidities, or any combination thereof. The level of inflammatory chemokine CCL5 was found to be elevated at least 5-fold in a subject with mild-to-moderate COVID-19 compared to a normal control. CCR5 binding agents may also be beneficial for mild-to-moderate COVID-19 patients who do not yet exhibit symptoms of severe disease, but may transition to severe disease of CCL5 levels or CCR5 activation are not reduced, blocked, inhibited.

Patients or subjects that can be treated by CCR5 binding agents of the present disclosure include, but are not limited to, a mammal, such as human or non-human primates (e.g., monkeys and apes). In some embodiments, the subject is human. The subject can be male or female and can be any suitable age, including infant, juvenile, adolescent, adult, and geriatric.

In one aspect, the present disclosure provides a method of treating a subject for hyperinflammation comprising administering to the subject an effective amount of a CCR5 binding agent. Following viral infection and proliferation, macrophages migrate to the infection site to kill infected cells, leading to the release of inflammatory cytokines and chemokines. The response to this stimuli is local inflammation and increased blood flow, enabling plasma and leukocytes to travel to the infection site. However, severe viral infections are characterized by hyper-induction of this immune response, termed "hyper-inflammation." Hyperinflammation is characterized by severe, systemic, and uncontrolled immune cell activation and inflammatory cytokine/chemokine production in response to a persistent trigger (e.g., viral infection). Clinical presentation of hyperinflammation may include unremitting fever, splenomegaly, coagulopathy, hepatitis, cytopenia and, if unrestrained, multi-organ failure and death. In some embodiments, hyperinflammation is associated with a viral infection and is cytokine storm, hemophagocytic lymphohistiocytosis (HLH), Acute respiratory distress syndrome (ARDS), or macrophage activation syndrome.

"Cytokine storm," also known as "cytokine release syndrome," refers to an acute systemic inflammatory response that can be induced by a variety of factors such as infection by a virus, therapeutic antibodies, or cellular immunotherapy. Symptoms include fever, nausea, fatigue and headache. Potentially life-threatening complications of cytokine storm include, renal failure, hepatic failure, respiratory distress, and cardiac dysfunction. Soluble mediators of inflammation, including cytokines and chemokines, contribute to the pathophysiology of cytokine storm. These inflammatory cytokines/chemokines include IL-6, TNFα, IFNγ, IL-1β, IL-2, IL-6, IL-8, and IL-10. Elevated levels of inflammatory cytokines have been identified in patients with viral infections, including *Orthomyxoviridae influenza* A infections [Beigel, 2005]. As described in Example 3, CCL5 (RANTES) is an inflammatory chemokine that was found to be elevated in ten critically ill COVID-19 patients with plasma signatures of cytokine storm (IL-1β, IL-6, and IL-8). Plasma CCL5 levels were found to be >100-fold increased in critically ill COVID-19 patients compared to normal controls. CCL5 may also be a marker and mediator of cytokine storm. Cytokine storms are associated with a number of other viral infections, including Epstein-Barr virus of the Herpesviridae family, group A *Streptococcus pyogenes*, and *Orthopoxvirus variola* [Tisoncik, 2012]. Betacoronavirus infection, including infection by the SARS-CoV-1, which causes severe acute respiratory syndrome (SARS) is also associated with a cytokine storm characterized by elevated levels of inflammatory cytokines and immunopathological damage [Huang, 2005]. In some embodiments, a virus associated with cytokine storm for treatment according the methods described herein is Epstein-Barr virus, *Orthopoxvirus variola, Orthomyxoviridae influenza* (A, B, or C), or a coronavirus (e.g., SARS-CoV-1, SARS-CoV-2). In some embodiments, a virus associated with cytokine storm does not include respiratory syncytial virus (RSV), hepatitis C virus (HCV), cytomegalovirus (CMV), West Nile virus (WNV).

In some embodiments, a virus associated with hyperinflammation is "SARS-CoV-1". Used herein, the term "SARS-CoV-1" refers to the strain of Betacoronavirus that emerged in 2003 and causes severe acute respiratory syndrome (SARS).

In some embodiments, a virus associated with hyperinflammation is "SARS-CoV-2". Used herein, the term "SARS-CoV-2" refers to the strain of Betacoronavirus that emerged in 2019 and causes the respiratory illness Coronavirus disease 2019 (COVID-19).

In another aspect, the present disclosure provides methods of treating a subject having a coronavirus infection comprising administering to the subject an effective amount of a CCR5 binding agent. In some embodiments, the coronavirus is SARS-CoV-1 or SARS-CoV-2.

In some embodiments, subject infected with a coronavirus has a coronavirus-induced respiratory illness. "Coronavirus-induced respiratory illness" refers to pathology directly resulting from SARS-CoV-1 or SARS-CoV-2 viral infection as well as immunopathology resulting from induction of a pro-inflammatory immune response. This includes secondary infections, bacterial and viral, that arise from SARS-CoV-1 and SARS-CoV-2-related immunodeficiency during the anti-viral response. In some embodiments, the coronavirus-induced respiratory illness comprises COVID-19. As used herein, "COVID-19" refers to the infectious disease caused by SARS-CoV-2 and characterized by, for example, fever, cough, respiratory symptoms, rhinorrhea, sore throat, malaise, headache, chills, repeated shaking with chills, diarrhea, new loss of smell or taste, muscle pain, or a combination thereof.

In some embodiments, the subject with a coronavirus exhibits one or more symptoms associated with mild COVID-19, moderate COVID-19, mild-to-moderate COVID-19, severe COVID-19 (e.g., critical COVID-19), or exhibits no symptoms associated with COVID-19 (asymptomatic). It should be understood that in reference to the treatment of patients with different COVID-19 disease severity, "asymptomatic" infection refers to patients diagnosed with COVID-19 by a standardized RT-PCR assay that do not present with fever, cough, respiratory symptoms, rhinorrhea, sore throat, malaise, headache, or muscle pain.

As used herein, "mild" infection refers to patients diagnosed with COVID-19 by a standardized RT-PCR assay exhibiting fever, rhinorrhea, mild cough, sore throat, malaise, headache, muscle pain, malaise, or any combination thereof, but with no shortness of breath. Patients with "mild" infection present no signs of a more serious lower airway disease and have a respiratory rate of less than 20 breaths per minute, a heart rate of less than 90 beats per minute, and oxygen saturation (pulse oximetry) greater than 93% on room air.

As used herein, "moderate" infection refers to patients diagnosed with COVID-19 by a standardized RT-PCR assay exhibiting symptoms in the mild category and additional symptoms. These include more significant lower respiratory symptoms, including shortness of breath (at rest or with exertion) or signs of moderate pneumonia, including a respiratory rate of ≥20 but <30 breaths per minute, a heart rate of ≥90 but <125 beats per minute and oxygen saturation (pulse oximetry) greater than 93% on room air. If some embodiments, subjects with moderate infection further exhibit lung infiltrates based on X-ray or CT scan that are <50% present.

As used herein "mild-to-moderate" infection collectively refers to mild and moderate infections, as defined herein.

As used herein, "severe" infection refers to patients diagnosed with COVID-19 by a standardized RT-PCR assay having significant lower respiratory symptoms, including difficulty in breathing or shortness of breath at rest or one or more of the following signs of severe pneumonia: a respiratory rate ≥30 breaths per minute, oxygen saturation (pulse oximetry) ≤93% on room air, partial pressure of oxygen/fraction of inspired oxygen (PaO2/FiO2) ≤300 mmHg (1 mmHg=0.133 kPa). Additionally, clinical assessment shows evidence of rales/crackles on exam or if available, radiographic evidence of pulmonary infiltrates (chest x-ray, CT scan, etc.).

As used herein "critical" infection refers to a severe infection in which the patient has at least one of the following: (1) respiratory failure requiring at least one of the following: Endotracheal intubation and mechanical ventilation, oxygen delivered by high-flow nasal cannula, noninvasive positive pressure ventilation, or ECMO; (2) a clinical diagnosis of respiratory failure (in setting of resource limitation); (3) Septic shock (defined by SBP <90 mm Hg, or Diastolic BP<60 mm Hg); and (4) Multiple organ dysfunction/failure.

In some embodiments, the subject exhibits no symptoms associated with COVID-19 but has been exposed to another subject known or suspected of having COVID-19.

In some embodiments, the subject with a coronavirus exhibits one or more symptoms selected from dry cough, shortness of breath, and fever.

In some embodiments, the corona-virus induced respiratory illness comprises Acute respiratory distress syndrome (ARDS). ARDS refers to a respiratory condition characterized by severe hypoxemia and may be induced by viral infection. ARDS is characterized by severe impairment in gas exchange and lung mechanics. The innate immune response plays a fundamental role in the pathophysiology of ARDS. Virally-induced inflammation promotes pulmonary epithelial and endothelial cellular damage leading to increased capillary permeability. The migration of macrophages and neutrophils and release of pro-inflammatory cytokines (cytokine storm) leads to acute respiratory distress syndrome (ARDS). Multiple immunologic processes involving neutrophils, macrophages, and dendritic cells participate in mediating tissue injury. Inflammatory injury, either locally from the lungs or systemically from extrapulmonary sites, affect bronchial epithelium, alveolar macrophages, and vascular endothelium, causing accumulation of protein-rich edema fluid into the alveoli and, subsequently, hypoxemia due to impaired gas exchange. Alveolar macrophages play a central role in orchestrating inflammation as well as the resolution of ARDS. Once alveolar macrophages are stimulated, they recruit neutrophils and circulating macrophages to the pulmonary sites of injury. These cells produce diverse array of bioactive mediators including proteases, reactive oxygen species, eicosanoids, phospholipids, and cytokines that perpetuate inflammatory responses. Consequently, these mediators damage or induce distal cell death, specifically alveolar type 2 epithelial cells. These cells serve vital functions by synthesizing and secreting pulmonary surfactant, which is an indispensable material that lines the inner lung surface to lower alveolar surface tension. Type 2 cells also actively partake in ion transport to control lung fluid. Together, these inflammatory events lead to histological changes typical of an acute exudative phase that results in significant impairment in lung mechanics and gas exchange. During the initial inflammatory and/or resolution phases of ARDS, alveolar macrophages signal in a paracrine manner with other cells including epithelial cells, lymphocytes, and mesenchymal stem cells that can result in augmentation of the inflammatory response or accentuation of tissue injury. Patients with ARDS may exhibit buildup of fluid in the lung and have reduced oxygen levels in the blood.

In some embodiments, the corona-virus induced respiratory illness comprises Hemophagocytic lymphohistiocytosis (HLH). HLH refers to a severe systemic hyperinflammatory syndrome characterized by a fulminant and fatal hypercytokinaemia with multiorgan failure. Herein, HLH is characterized by unremitting fever, cytopenias, hyperferritinaemia and optionally, pulmonary involvement. In some embodiments, the treatment of a subject according to the methods described herein reduces the likelihood of the subject developing secondary HLH. A subject can be evaluated for symptoms consistent with HLH by scoring clinical parameters using the HScore for secondary HLH scoring system. A score of greater than 169 can indicate that the subject has secondary HLH. Mehta et al., *COVID-19: consider cytokine storm syndromes and immunosuppression*, THE LANCET, vol. 395, issue 10229, pp. 1033-1034 (2020).

The present disclosure also provides prophylactic treatment of a subject prior to receipt of a positive test result confirming viral infection (e.g., SARS-CoV-2) with an effective amount of a CCR5 binding agent. The subject may be at risk of contracting the virus. Prophylactic treatment would be administered to individuals at high risk of exposure to infected patients, for example, immunocompromised individuals, medical personnel, people with known exposure, and essential workers.

In one embodiment, the present disclosure provides for the use of an anti-CCR5 antibody or antigen binding fragment thereof, e.g., leronlimab or antigen binding fragment thereof, in treating or preventing a coronavirus-induced disease or disorder, such as COVID-19. As used herein, "mechanism of action" refers to the biochemical interaction of leronlimab with components of the immune system by which leronlimab attenuates COVID19 morbidity and mortality. Leronlimab binds to CCR5 expressed on the surface of a cell, and potently inhibits HIV-1 entry and replication at concentrations that do not affect CCR5 chemokine receptor activity in vitro and in the hu-PBL-SCID mouse model of HIV-1 infection. Olson et al., *Differential Inhibition of Human Immunodeficiency Virus Type 1 Fusion, gp 120 Binding and CC-Chemokine Activity of Monoclonal Antibodies to CCR5*, J. VIROL., 73: 4145-4155. (1999); Trkola et al., *Potent, Broad-Spectrum Inhibition of Human Immunodeficiency Virus Type 1 by the CCR5 Monoclonal Antibody PRO 140*, J. VIROL., 75: 579-588 (2001).

In the setting of HIV/AIDS, leronlimab is a viral-entry inhibitor; it masks CCR5, thus protecting healthy T cells from viral infection by blocking the predominant HIV (R5) subtype from entering those cells. Leronlimab has been the subject of nine clinical trials, each of which demonstrated that leronlimab could significantly reduce or control HIV viral load in humans. The leronlimab antibody appears to be a powerful antiviral agent leading to potentially fewer side effects and less frequent dosing requirements compared with daily drug therapies currently in use.

In the setting of cancer, research has shown that CCR5 may play a role in tumor invasion, metastases, and tumor microenvironment control. Increased CCR5 expression is an indicator of disease status in several cancers. Published studies have shown that blocking CCR5 can reduce tumor metastases in laboratory and animal models of aggressive breast and prostate cancer. Leronlimab reduced human breast cancer metastasis by more than 98% in a murine xenograft model.

Also, the CCR5 receptor appears to play a central role in modulating immune cell trafficking to sites of inflammation. It may be crucial in the development of acute graft-versus-host disease (GvHD) and other inflammatory conditions. Clinical studies by others further support the concept that blocking CCR5 using a chemical inhibitor can reduce the clinical impact of acute GvHD without significantly affecting the engraftment of transplanted bone marrow stem cells. Additional studies with leronlimab are underway to further assess whether the CCR5 receptor on engrafted cells is critical for the development of acute GvHD, and that blocking the CCR5 receptor from recognizing specific immune signaling molecules is a viable approach to mitigating acute GvHD.

In some embodiments, treatment of a subject that does not have respiratory symptoms associated with either COVID-19 or ARDS reduces the likelihood of the subject developing one or more of mild, moderate, or severe respiratory symptoms.

In some embodiments, treatment of a subject according to the methods described herein results in reduction of the severity or duration of the severe respiratory symptoms. Severe respiratory symptoms may include, for example, shortness of breath, difficulty breathing, reduced respiratory rate, and wheezing. In some embodiments, severe respiratory symptoms comprises difficulty in breathing or shortness of breath at rest, severe pneumonia, a respiratory rate ≥30 breaths per minute, oxygen saturation (pulse oximetry) ≤93% on room air, partial pressure of oxygen/fraction of inspired oxygen (PaO2/FiO2) ≤300 mmHg (1 mmHg=0.133 kPa), evidence of rales/crackles, radiographic evidence of pulmonary infiltrates (chest x-ray, CT scan, etc.), or any combination thereof.

Figure 18:
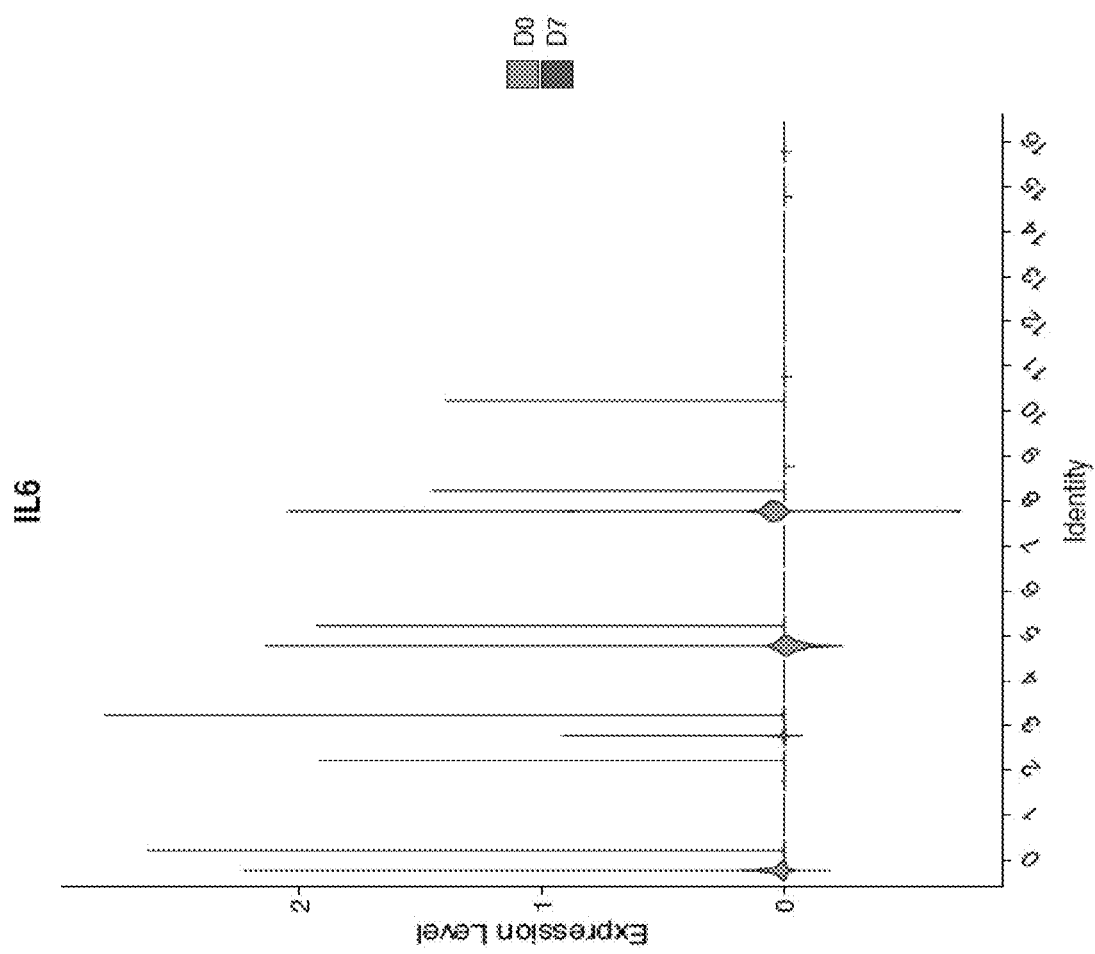
FIG. 18 shows a violin plot of IL-6 gene transcripts in single cell transcriptome clusters of COVID-19 participants before and 7 days following leronlimab. Low levels of IL-6 transcription are observed across multiple cell clusters at day 7 post leronlimab (D7) compared to baseline (D0). Of note, IL-6 gene expression significantly reduced in myeloid cluster 8 comparing baseline and 7 days post leronlimab.
Figure 19A:
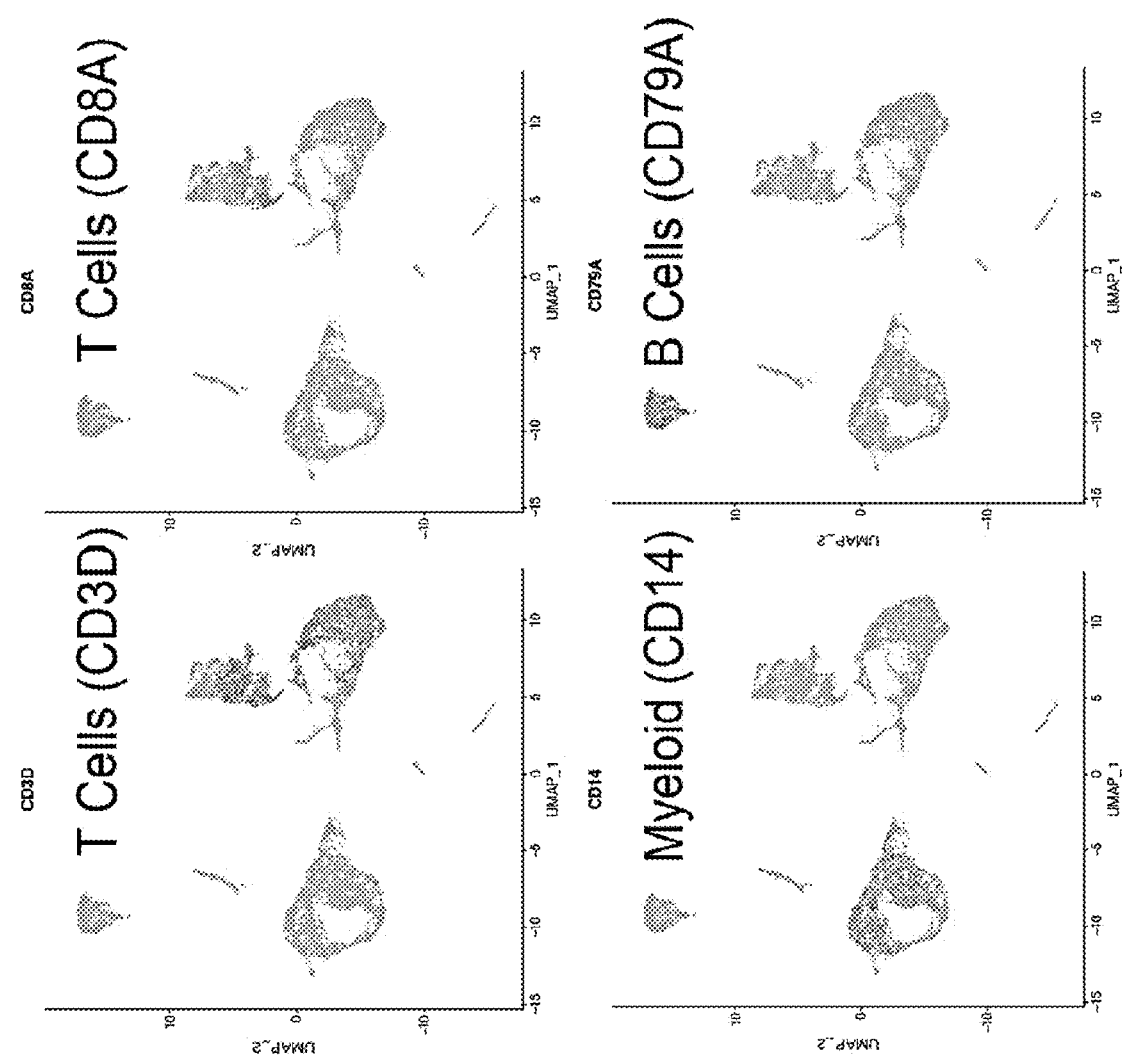
Figures 19B, 19C:
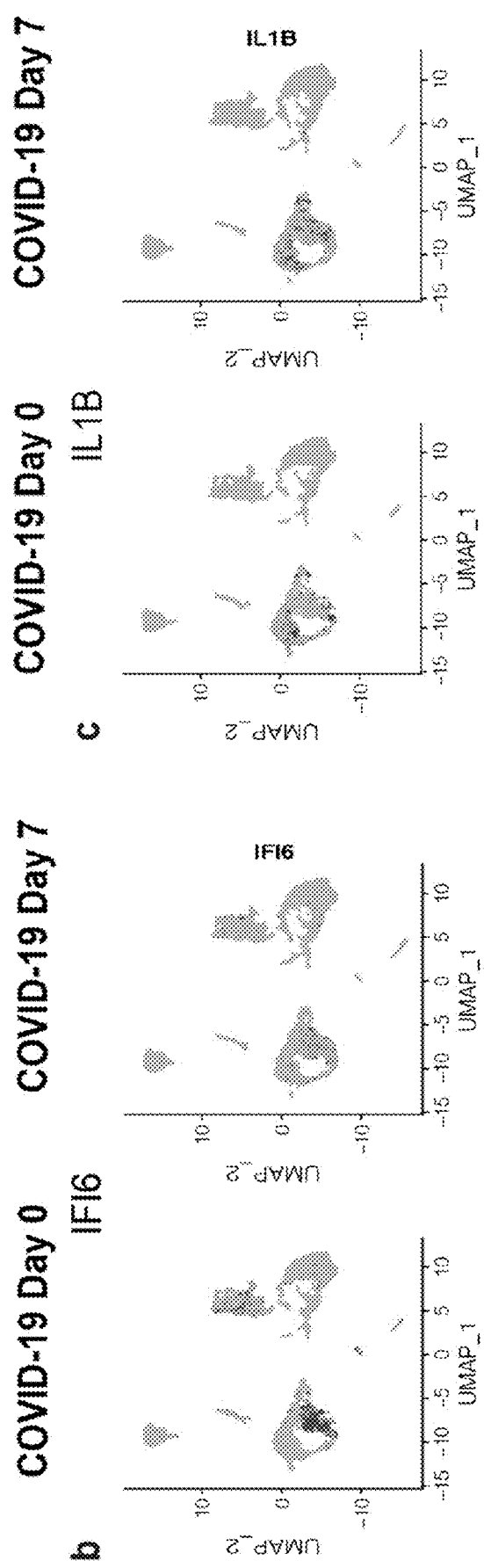
Figures 19D, 19E:
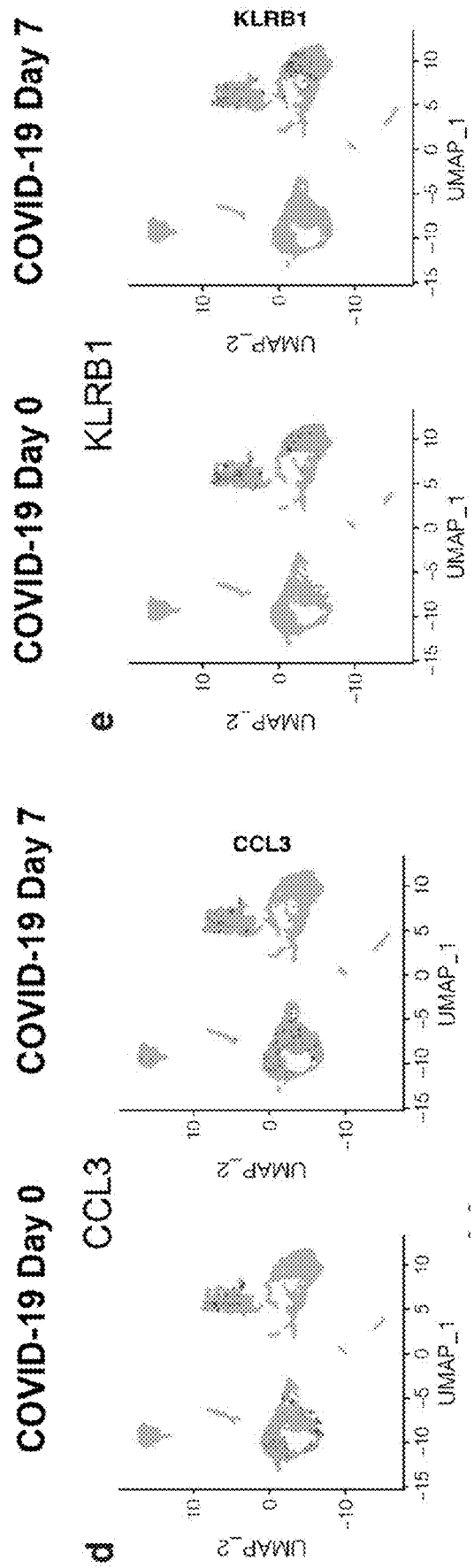
Figures 19F, 19G:
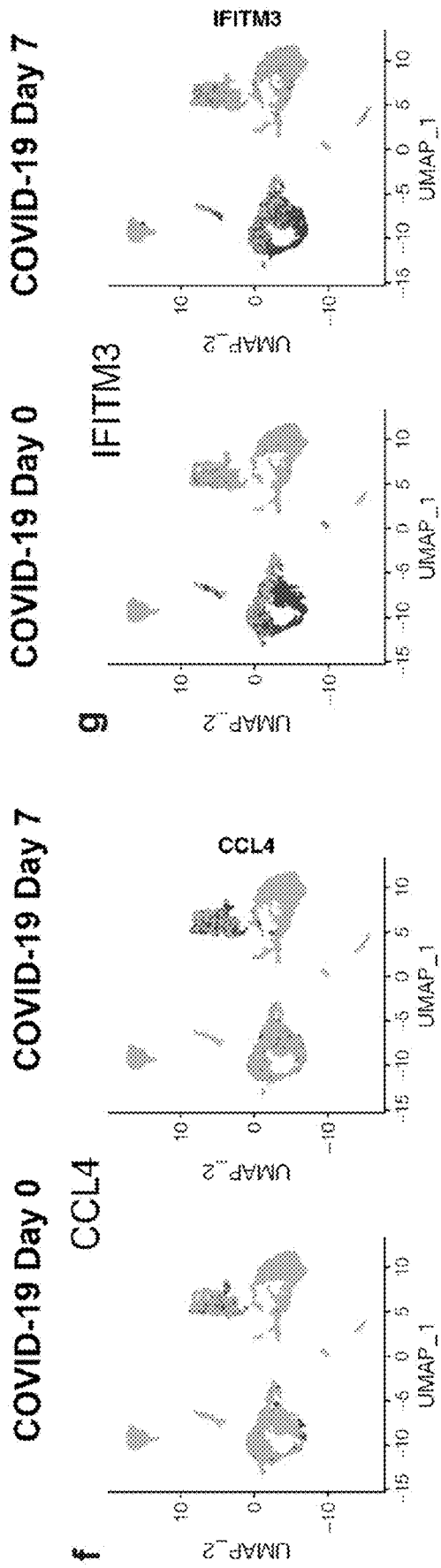

In some embodiments, treatment of a subject according to the methods described herein results in reduction of one or more inflammatory cytokines and/or chemokines. In some embodiments, the inflammatory cytokine or chemokine is a cytokine or chemokine listed in FIGS. 9A-9J (e.g., sCD40L, EGF, Eotaxin (CCL11), FGF-2, Flt-3 ligand, Fractalkine, G-CSF, GM-CSF, GROα (CXCL1), IFN-α2, IFN-γ, IL-1α, IL-1β, IL-1RA, IL-2, IL-3, IL-4, IL-5, IL-6, IL-7, IL-8 (CXCL8), IL-9, IL-10, IL-12 (p40), IL-12 (p70), IL-13, IL-15, IL-17A, IL-17E/IL-25, IL-17F, IL-18, IL-22, IL-27, IP-10 (CXCL10), MCP-1 (CCL2), MCP-3, M-CSF, MDC (CCL22), MIG (CXCL9), MIP-1α (CCL3), MIP-1β (CCL4), PDGF-AA, PDGF-AB/BB, RANTES (CCL5), TGF-α, TNF-α, TNF-β, TNF-r1, or VEGF-A), in FIG. 12A-D (CCL5, IL-6, IL-8, IL-1β), in FIGS. 17-19, CCL5, IL-5, IL-13, IL-2, IL-6, IL-10, IL-9, IFN-γ, TNF-α. IL-17A, IL-17F, IL-4, IL-21, IL-22, or any combination thereof. In some embodiments, the inflammatory cytokine and/or chemokine may comprise a cytokine or chemokine selected from one of CCL5, sCD40L, EGF, Eotaxin, FGF-2, Flt-3 ligand, Fractalkine, G-CSF, GM-CSF, GROα, IFN-α2, IFN-γ, IL-1α, IL-1β, IL-1ra, IL-2, IL-3, IL-4, IL-5, IL-6, IL-7, IL-8, IL-9, IL-10, IL-12 (p40), IL-12 (p70), IL-13, IL-15, IL-17A, IL-17E/IL-25, IL-17F, IL-18, IL-21, IL-22, IL-27, IP-10, MCP-1, MCP-3, M-CSF, MDC (CCL22), MIG, MIP-1α, MIP-1β, PDGF-AA, PDGF-AB/BB, RANTES, TGF-α, TNF-α, TNF-β, TNF-r1, C reactive protein (CRP), VEGF-A or any combination thereof. In some embodiments, the one or more inflammatory cytokines and/or chemokines comprises CCL5, IL-6, IL-8, IL-1β, IL-10, TNF-α, or any combination thereof. In some embodiments, the one or more inflammatory cytokines and/or chemokines comprises CCL5, IL-6, TNF-α, or a combination thereof. In some embodiments, the one or more inflammatory cytokines and/or chemokines comprises CCL5, IL-6, IL-1β, IL-8, or any combination thereof. In some embodiments, the inflammatory cytokine and/or chemokine is reduced by 0.1 to 200-fold on day 3, 7, or 14 days post-treatment compared to day 0. In some embodiments, the reduction of levels of the at least one inflammatory cytokine and/or chemokine occurs by Day 3, Day 4, Day 5, Day 6, Day 7, Day 8, Day 9, Day 10, Day 11, Day 12, Day 13, or Day 14 of treatment. In some embodiments, the reduction of IL-6 is normalized in the subject by Day 3, Day 7, or Day 14 of treatment. The level of the inflammatory cytokine and/or chemokines may be measured in blood plasma, e.g., by enzyme-linked immunosorbent assays (ELISA), bead-based immunoassays and other immunoassays. The transcriptional level of inflammatory cytokines and/or chemokines may also be measured by RNA sequencing.

In some embodiments, the levels for an inflammatory cytokine selected from G-CSF, GM-CSF, MCP-1, sCD40L, TGF-α, EGF, FGF-2, Flt-3L, IFN-α2, IFN-γ, IL-10, IL-15, IL-17, IL-1β, IL-2, IL-6, IL-8, IP-10, MIP-1β, PDGF-AA, TNF-α, VEGF, or any combination thereof from a subject younger than 45 years old, or 65 years old or older are compared to normal (non-elevated) cytokine levels shown in (FIG. 7 showing normal cytokine levels stratified by age group from Kim, H. O., et al. Journal of Translational Medicine. 2011, 9:113). In some embodiments, the levels for an inflammatory cytokine selected from IL-6, IL-10, TNF-α, or any combination thereof is from a subject younger than 45 years old, or 65 years old or older and are compared to normal (non-elevated) cytokine levels shown in FIG. 7. In some embodiments, the levels for an inflammatory cytokine selected from IL-6, TNF-α, or both is from a subject younger than 45 years old, or 65 years old or older and are compared to normal (non-elevated) cytokine levels shown in FIG. 7.

In some embodiments, the levels for an inflammatory cytokine selected from IL-1ra, IL-6, IL-10, TNF-r1, C-reactive protein (CRP), or any combination thereof is from a subject in one of the following age groups 25-29 years, 30-39 years, 40-49 years, 50-59 years, 60-69 years, 70-79 years, or 80 years or older and compared to normal (non-elevated) cytokine levels as described in Stowe et al., J. Gerontol A Biol Sci. Med Sci (2010) 65A:429-433 and shown in Table 2 below.

TABLE 2

Normal Cytokine Levels Stratified By Age Group

| Age Group (years) | n | IL-1ra | IL-6 | IL-10 | TNF-r1 | CRP (mg/dL) |
|---|---|---|---|---|---|---|
| 25-29 | 103 | 182 ± 38 | 1.4 ± 0.5 | 4.6 ± 1.6 | 1461 ± 140 | 12.4 ± 1.6 |
| 30-39 | 262 | 122 ± 24 | 1.7 ± 0.3 | 5.0 ± 1.0 | 1529 ± 88 | 14.2 ± 1.0 |
| 40-49 | 289 | 180 ± 23 | 1.5 ± 0.3 | 6.7 ± 0.9 | 1466 ± 84 | 12.4 ± 1.0 |
| 50-59 | 269 | 213 ± 24 | 2.1 ± 0.3 | 4.3 ± 1.0 | 1819 ± 87 | 14.3 ± 1.0 |
| 60-69 | 234 | 145 ± 25 | 1.8 ± 0.3 | 3.9 ± 1.0 | 1947 ± 93 | 14.0 ± 1.1 |
| 70-79 | 193 | 184 ± 28 | 2.8 ± 0.3 | 4.0 ± 1.1 | 2494 ± 103 | 13.1 ± 1.2 |
| 80+ | 61 | 95 ± 49 | 3.3 ± 0.6 | 5.9 ± 2.0 | 2946 ± 182 | 15.7 ± 2.1 |
| p Value for ANOVA | | 0.084 | 0.025 | 0.433 | <.001 | 0.624 |
| p Value for linear age trend | | 0.391 | 0.002 | 0.911 | <.001 | 0.306 |

Note:
All data are expressed as means ± SE. ANOVA = analysis of variance; CRP = C-reactive protein; IL = interleukin; IL-1ra = interleukin-1 receptor antagonist; TNF-r1 = tumor necrosis factor-receptor 1.

In some embodiments, the level of inflammatory chemokine CCL5 is elevated at least 5-fold, 6-fold, 7-fold, 8-fold, 9-fold, 10-fold, 20-fold, 30-fold, 40-fold, 50-fold, 60-fold, 70-fold, 80-fold, 90-fold, or 100-fold in the subject infected with a virus (e.g., coronavirus, SARS-CoV-2) compared to a normal control. In some embodiments, the level of inflammatory chemokine CCL5 is compared to normal CCL5 level shown in FIG. 12D. In some embodiments, the level of inflammatory chemokine CCL5 is elevated at least 5-fold in a subject with mild-to-moderate COVID-19 compared to a normal control. In some embodiments, the level of inflammatory chemokine CCL5 is elevated at least 100-fold in a subject with severe COVID-19 compared to a normal control.

In some embodiments, prophylactic treatment with a CCR5 binding agent reduces the likelihood of a subject developing elevated levels of one or more inflammatory cytokine or chemokine. In some embodiments, the inflammatory cytokine or chemokine may comprise a cytokine or chemokine selected from one of CCL5, 40L, EGF, Eotaxin, FGF-2, Flt-3 ligand, Fractalkine, G-CSF, GM-CSF, GROα, IFN-α2, IFN-γ, IL-1α, IL-1β, IL-1ra, IL-2, IL-3, IL-4, IL-5, IL-6, IL-7, IL-8, IL-9, IL-10, IL-12 (p40), IL-12 (p70), IL-13, IL-15, IL-17A, IL-17E/IL-25, IL-17F, IL-18, IL-21, IL-22, IL-27, IP-10, MCP-1, MCP-3, M-CSF, MDC (CCL22), MIG, MIP-1α, MIP-1β, PDGF-AA, PDGF-AB/

BB, RANTES, TGF-α, TNF-α, TNF-β, TNF-r1, C reactive protein (CRP), VEGF-A or any combination thereof. In some embodiments, the one or more inflammatory cytokines or chemokines comprises CCL5, IL-6, IL-10, TNF-α, or any combination thereof. In some embodiments, the one or more inflammatory cytokine or chemokines comprises CCL5, IL-6, TNF-α, or both. Elevated cytokine levels may be an increase of at least 10%, 20%, 30%, 40%, 50%, 60%, 70%, 80%, 90%, 100%, 125%, 150%, 175%, 200%, 250%, 300%, 350%, 400%, 450%, 500%, 550%, 600%, 650%, 700%, 750%, 800%, 850%, 900%, 950%, 1000% or more over normal cytokine levels, for example the normal ranges provided in FIG. 7 and Table 2. In some embodiments, the elevated level of CCL5 is at least 5-fold, 6-fold, 7-fold, 8-fold, 9-fold, 10-fold, 20-fold, 30-fold, 40-fold, 50-fold, 60-fold, 70-fold, 80-fold, 90-fold, or 100-fold higher than normal CCL5 levels. In some embodiments, normal CCL5 levels is provided in FIG. 12D.

In some embodiments, treatment of a subject according to the methods described herein results in reduction or normalization of levels of one or more inflammatory cytokines and/or chemokines. In some embodiments, the one or more cytokines or chemokines may comprise a cytokine or chemokine selected from one of CCL5 (RANTES), 40L, EGF, Eotaxin, FGF-2, Flt-3 ligand, Fractalkine, G-CSF, GM-CSF, GROα, IFN-α2, IFN-γ, IL-1α, IL-1β, IL-1ra, IL-2, IL-3, IL-4, IL-5, IL-6, IL-7, IL-8, IL-9, IL-10, IL-12 (p40), IL-12 (p70), IL-13, IL-15, IL-17A, IL-17E/IL-25, IL-17F, IL-18, IL-21, IL-22, IL-27, IP-10, MCP-1, MCP-3, M-CSF, MDC (CCL22), MIG, MIP-1α, MIP-1β, PDGF-AA, PDGF-AB/BB, RANTES, TGF-α, TNF-α, TNF-β, TNF-r1, C reactive protein (CRP), VEGF-A, a cytokine or chemokine listed in FIG. 9, or any combination thereof. In some embodiments, the one or more inflammatory cytokine or chemokine comprises CCL5, IL-6, TNF-α, or any combination thereof. In some embodiments, reduction or normalization of one or more cytokines or chemokines occurs within 3, 4, 5, 6, 7, 8, 9, 10, 11, 12, 13, or 14 days of administration of the CCR5 binding agent. Normalization refers to bringing of the level(s) (e.g., one or more cytokine or chemokine levels, cell number, cell ratio, protein level, enzyme level, liver function marker, kidney function marker, etc.) from a dysregulated level (over- or under-normal ranges) in the direction towards the normal range (e.g., for the one or more cytokines or chemokines, cell number, cell ratio, protein level, enzyme level, liver function marker, kidney function marker, etc.). Normalization may result in return of the level to the normal range, or the level may still be outside of the normal range but reflect movement towards the normal range. Normal ranges of cytokines or chemokines for the assays as described herein are described in FIG. 8, FIGS. 12A-D, Table 2, and FIGS. 17-19; however, it is understood that the normal ranges may vary from assay to assay. The level of the inflammatory cytokine may be measured in blood plasma by enzyme-linked immunosorbent assays (ELISA), bead-based immunoassays and other immunoassays, and RNA sequencing.

In some embodiments, treatment of a subject according to the methods described herein results in reduction of a symptom associated hyperinflammation. In some embodiments, hyperinflammation is cytokine release syndrome, hemophagocytic lymphohistiocytosis (HLH), macrophage activation syndrome, or acute respiratory distress syndrome (ARDS).

In some embodiments, treatment of a subject according to the methods described herein reduces migration of CCR5+ immune cells. In some embodiments, the CCR5+ immune cells comprise macrophages, T cells, or both.

In some embodiments, treatment of a subject according to the methods described herein improves at least one respiratory parameter in the subject. In some embodiments, treatment of a subject according to the methods described herein increases oxygen saturation in the subject.

In some embodiments, treatment of a subject according to the methods described herein results in the CCR5+ immune cells of the subject exhibiting at least 50%, 55%, 60%, 65%, 70%, 75%, 80%, 85%, 90%, or 95% receptor occupancy by Day 3 of treatment or at least 75%, 80%, 85%, 90%, 95%, 97%, or 99% receptor occupancy by Day 7 of treatment. In some embodiments, the CCR5+ immune cells of the subject exhibit at least 90%, 95%, 96%, 97%, 98% or 99% receptor occupancy by Day 14 of treatment. In some embodiments, the CCR5+ immune cells of the subject exhibit receptor occupancy for at least 7 days, 10 days, or 14 days post-treatment. In some embodiments, the CCR5+ immune cells comprise T cells, macrophages, or both. In some embodiments, the T cells comprise regulatory T cells (Tregs).

Figures 13A, 13B, 13C:
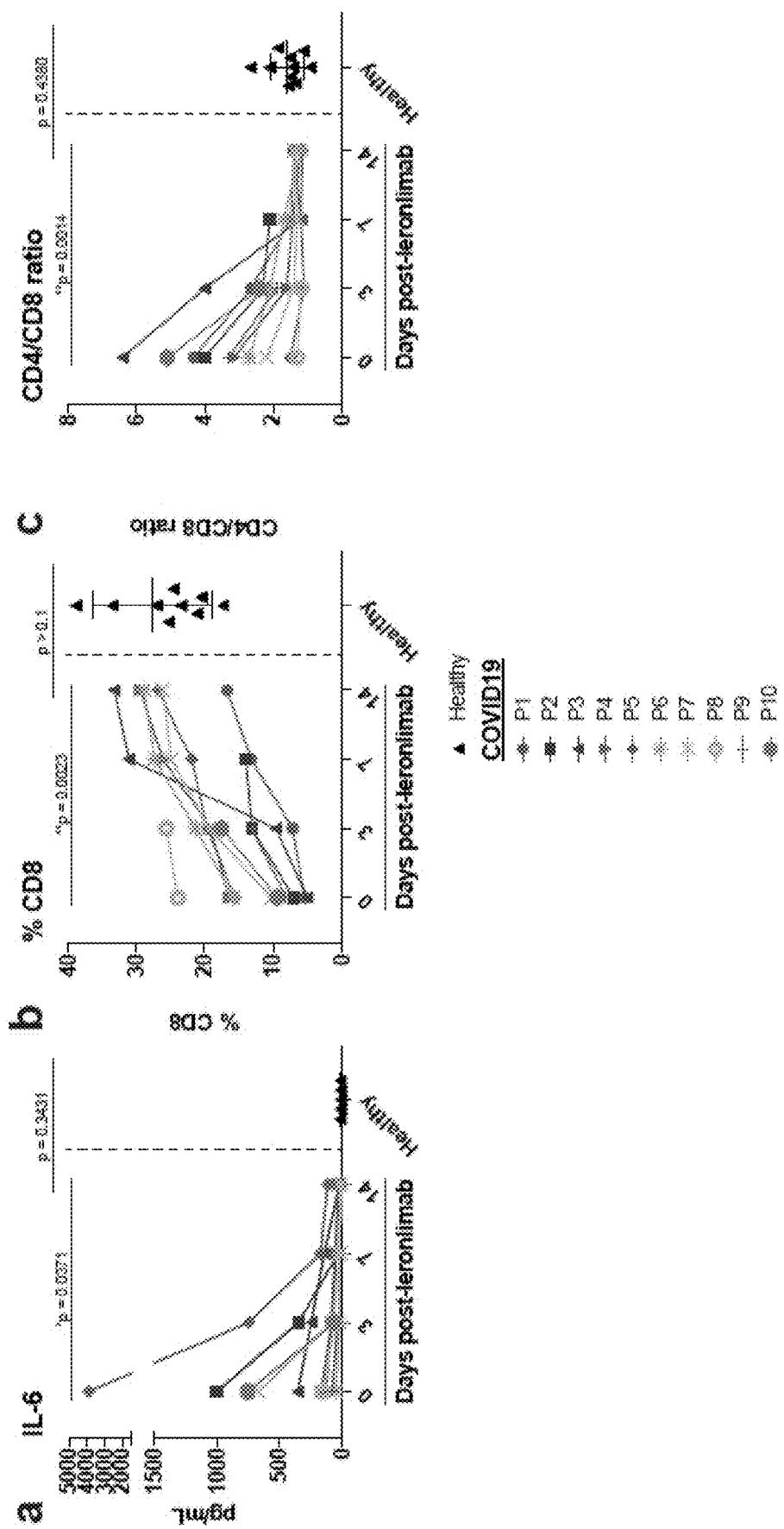
FIGS. 13A-13F show reversal of immune dysfunction and CCR5 receptor occupancy in critically ill COVID-19 patients after leronlimab administration. Plasma levels of IL-6 (FIG. 13A), and peripheral blood CD8+ T cell percentages of CD3+ cells (FIG. 13B) and CD4/CD8 T cell ratio (FIG. 13C) at days 0 (n=10), 3 (n=10), 7 (n=7), and 14 (n=6) post-leronlimab administration. Healthy controls (n=10) shown in black triangles. Graphs display p-values calculated by Dunn's Kruskal-Wallis test: not significant p>0.05, *p≤0.05, p≤0.01, *p≤0.001, ****p≤0.0001. CCR5 receptor occupancy on peripheral blood bulk T cells (FIG. 13D), and monocytes (FIG. 13E). SARS-CoV-2 plasma viral load at days 0 and 7 post-leronlimab (n=7) (FIG. 13F). Graph displays p-value calculated by Mann-Whitney test: *p≤0.05, p≤0.01, *p≤0.001, ****p≤0.0001.

In some embodiments, treatment of a subject according to the methods described herein results in normalization of CD4 T cell frequency, CD8 T cell frequency, and/or CD4/CD8 T cell ratio. Healthy (or normal) ranges for CD8 T cell frequency are shown in FIG. 13B. Healthy (or normal) ranges for CD4 T cell frequency range from about 30% to about 40%, healthy ranges for CD4 T cell frequency range from about 30% to about 35%, and healthy CD4/CD8 ratios are range from about 0.9 to about 1.9 for the assays described herein. In some embodiments CD4:CD8 ratios are more normalized by Day 3, Day 4, Day 5, Day 6, Day 7, Day 8, Day 9, Day 10, Day 11, Day 12, Day 13, or Day 14 of treatment. It is understood that the normal ranges may vary from assay to assay. CD4 T cell frequency, CD8 T cell frequency, and CD4/CD8 T cell ratio are determined by using flow cytometry-based measurements of whole blood or peripheral blood mononuclear cells isolated from patient blood samples.

In some embodiments, treatment of a subject according to the methods described herein results in increased CD8 T cell frequency in the subject. In some embodiments, the CD8 T cell frequency in the subject is more normalized by Day 3, Day 4, Day 5, Day 6, Day 7, Day 8, Day 9, Day 10, Day 11, Day 12, Day 13, or Day 14 of treatment.

In some embodiments, treatment of a subject according to the methods described herein results in restoration of CD8 effector levels/function.

In some embodiments, treatment of a subject according to the methods described herein results in reduction or reversal of T cell exhaustion. T cell exhaustion may be detecting by measuring expression of immune checkpoint molecules on T cells, including for example, TIM-3, PD-1, LAG-3, or any combination thereof. In some embodiments, reduction of expression of immune checkpoint molecules is observed by day 7 or day 14 post-treatment. Exhaustion markers, such as PD-1 and LAG3, may be associated with decreased liver transaminases.

In some embodiments, treatment of a subject according to the methods described herein results in reduced occurrence or risk of developing liver toxicity, kidney failure or a coagulation event. In some embodiments, the coagulation event comprises a blood clot, stroke, or pulmonary embolism. In some embodiments, treatment results in more normalization of kidney function. Kidney function may be measured by measuring blood levels of creatine, BUN, sodium, or any combination thereof in the subject blood. In some embodiments, treating results in more normalization of liver function. Liver function may be measured by measuring blood levels of bilirubin, alanine transaminase (ALT), aspartate aminotransferase (AST), or any combination thereof.

In some embodiments, treatment of a subject according to the methods described herein results in reduction of SARS-CoV-2 viral load in the subject. In some embodiments, the reduction in plasma SARS-CoV-2 viral load occurs by day 7 of treatment. In some embodiments, the plasma SARS-CoV-2 viral load is measured by droplet digital PCR. In some embodiments, the plasma SARS-CoV-2 viral load is measured by detecting the nucleocapsid (N) gene. Without wishing to be bound by theory, COVID-19 patients exhibit elevated CCL5 levels, which results in disruption of immune homeostasis (reduction of CD8 T cell frequency, elevated CD4:CD8 T cell ratio, increased T cell exhaustion, excessive CCR5+ immune cell migration, excessive inflammation). By inhibiting the CCL5-CCR5 axis, CCR5 binding agents of the present disclosure (e.g., leronlimab) are able to restore immune homeostasis and enhance the body's own immune response to eliminate virally infected cells. CCR5 binding agents of the present disclosure may provide certain advantages over virus-specific binding agents, e.g., SARS-CoV-2 specific antibodies, which can only bind and neutralize free virus but are not effective against virally infected cells.

In some embodiments, treatment of a subject according to the methods described herein results in reduced duration or occurrence of hospitalization, ventilation or dialysis of the subject.

In some embodiments, treatment of a subject according to the methods described herein results in reduced lung damage to the subject.

In some embodiments, treatment of a subject according to the methods described herein results in the subject having a faster and/or more extensive recovery than a subject with similar symptoms who has not been treatment with the CCR5 binding agent.

In some embodiments, treatment of a subject according to the methods described herein is not accompanied by any serious, adverse side effects.

The present disclosure also provides for treatment of a subject with mild, moderate, or severe COVID-19 (e.g., critical COVID-19) in subject comprising administering to the subject an effective amount of a CCR5 binding agent, e.g., leronlimab. In some embodiments, the subject has severe COVID-19. In particular embodiments, the subject has critical COVID-19. In other embodiments, the subject has severe COVID-19, but the infection does not meet the definition of critical provided herein. As described in the examples, elevated CCL5 (RANTES) levels was observed in patients with severe as well as mild and moderate COVID-19 compared to healthy controls. Excessive signaling via the CCL5-CCR5 is a driver of hyperinflammation and immune dysfunction, and interruption of this access allows for rebalancing of immune cells (e.g., normalization of cytokine or chemokine levels, restoration of CD8 T cell levels, normalization of CD4:CD8 T cell ratio, reduction of T cell exhaustion). In some embodiments, administration of a CCR5 binding agent results in reduction or normalization of IL-6 levels by Day 7, 8, 9, 10, 11, 12, 13, or 14 post-treatment. In some embodiments, administration of a CCR5 binding agent results in restoration of CD8 T cell levels, normalization of CD4:CD8 T cell ratio, or both by Day 14 post treatment.

Furthermore, elevated CCL5 is involved in other comorbidities, such as kidney failure, liver toxicity, and coagulation. Thus, in some embodiments, the present disclosure provides for treatment of a subject with elevated CCL5 levels (e.g., a subject with mild, moderate, or severe COVID-19 (e.g., critical COVID-19, severe, but not critical COVID-19, or both)) comprising administering to the subject an effective amount of a CCR5 binding agent, e.g., leronlimab, wherein administration of the CCR5 binding agent reduces, reverses, or inhibits the risk of development of, occurrence of, or progression of kidney injury, liver injury, or coagulation events (e.g., strokes, blood clots, pulmonary embolism, and other thromboembolic events).

In some embodiments, the present disclosure provides methods of treating a subject with mild, moderate, or severe COVID-19 (e.g., critical COVID-19, severe, but not critical COVID-19, or both), wherein administration of an effective amount of a CCR5 binding agent, e.g., leronlimab, results in reduction of SARS-CoV-2 plasma viremia. In some embodiments, the reduction of SARS-CoV-2 plasma viremia may be detected by Day 7 post-treatment. SARS-CoV-2 plasma viremia may be measured by detecting N1, N2, RP, or a combination thereof, using droplet digital polymerase chain reaction as described in the Examples. Thus, CCR5 binding agents of the present disclosure, e.g., leronlimab may act as both an immune modulator to restore immune balance (reducing hyperinflammation and restoring immune homeostasis) and indirectly, as an antiviral agent by enhancing the immune response against the virus.

An appropriate dose, suitable duration, and frequency of administration of the CCR5 binding agents will be determined by such factors as the condition of the patient, size, weight, body surface area, age, sex, type and severity of the disease, particular therapy to be administered, particular form of the active ingredient, time and the method of administration, and other drugs being administered concurrently, which can readily be determined by a person skilled in the art.

Dosages can range from 0.1 to 100,000 µg/kg. Based upon the composition, the dose can be delivered continuously, such as by continuous pump, or at periodic intervals, e.g., on one or more separate occasions. Desired time intervals of multiple doses of a particular composition can be determined without undue experimentation by one skilled in the art.

In some embodiments, the CCR5 binding agent is administered to the subject a plurality of times and each administration delivers from 0.01 mg per kg body weight to 50 mg per kg body weight of the antibody or binding fragment thereof to the subject. In another embodiment, each administration delivers from 0.05 mg per kg body weight to 25 mg per kg body weight of the CCR5 binding agent to the subject. In a further embodiment, each administration delivers from 0.1 mg per kg body weight to 10 mg per kg body weight of the CCR5 binding agent to the subject. In a still further embodiment, each administration delivers from 0.5 mg per kg body weight to 5 mg per kg body weight of the CCR5 binding agent to the subject. In another embodiment, each administration delivers from 1 mg per kg body weight to 3 mg per kg body weight of the CCR5 binding agent to the subject. In another embodiment, each administration delivers about 2 mg per kg body weight of the CCR5 binding agent to the subject.

In one embodiment, the CCR5 binding agent is administered once.

In one embodiment, the CCR5 binding agent is administered twice.

In one embodiment, the CCR5 binding agent is administered a plurality of times, and a first administration is separated from the subsequent administration by an interval of less than one week. In another embodiment, the first administration is separated from the subsequent administration by an interval of at least one week. In a further embodiment, the first administration is separated from the subsequent administration by an interval of one week. In another embodiment, the first administration is separated from the subsequent administration by an interval of two to four weeks. In another embodiment, the first administration is separated from the subsequent administration by an interval of two weeks. In a further embodiment, the first administration is separated from the subsequent administration by an interval of four weeks. In yet another embodiment, the CCR5 binding agent is administered a plurality of times, and a first administration is separated from the subsequent administration by an interval of at least one month. In yet another embodiment, the CCR5 binding agent is administered once a week for two weeks. In yet another embodiment, the CCR5 binding agent is administered once per week as long as needed.

In a further embodiment, the CCR5 binding agent is administered to the subject via intravenous infusion. In another embodiment, the CCR5 binding agent is administered to the subject via subcutaneous injection. In another embodiment, the CCR5 binding agent is administered to the subject via intramuscular injection.

In some embodiments, the CCR5 binding agent is administered at a once weekly dose of 350 mg to 1400 mg, or about 525 mg or about 700 mg or about 1050 mg. In some embodiments, the CCR5 binding agent is administered at a twice weekly dose of 350 mg to 1400 mg, or about 525 mg or about 700 mg or about 1050 mg. In some embodiments, the CCR5 binding agent is administered at a dose of about 700 mg, once weekly.

In some embodiments, the CCR5 binding agent used in the methods described herein is leronlimab. Leronlimab (PRO 140) is currently under development for the indication of HIV, Graft versus host disease (GVHD), metastatic triple negative breast cancer (mTNBC), and metastatic colorectal cancer (mCRC). The safety profile of leronlimab (PRO 140) has been extensively evaluated in clinical trials. Leronlimab (PRO 140) has been administered intravenously or subcutaneously to more than 750 healthy and HIV-1 infected individuals in Phase I/II/III studies. The drug has been well tolerated following intravenous administration of single doses of 0.5 to 10 mg/kg or up to 700 mg weekly doses as subcutaneous (SC) injection. Overall, 324 subjects have been exposed to leronlimab (PRO 140) 350 mg SC weekly dose with the longest duration of exposure lasting 4 years. Similarly, more than 250 and 150 subjects have been exposed to leronlimab (PRO 140) 525 mg and 700 mg SC weekly dose, respectively.

Available safety data from 131 subjects that received 700 mg dose in previous studies shows that less than 10% of subjects reported adverse events (AEs) considered definitely related to study treatment. All of these AEs were injection site reactions and considered to be mild or moderate in severity.

By severity, three subjects (2.3%, 3/131) reported AEs that were considered severe and two subjects (1.5%, 2/131) reported events that were deemed to be life-threatening. No events were considered related to the study treatment.

Serious adverse events (SAEs) were reported for six subjects (4.6%, 6/131). None of SAEs were considered related to the study treatment. Additionally, there have been 49 patients with severe COVID-19 infection treated with 700 mg leronlimab (PRO 140) under individual patient, emergency use INDs.

Given the safety profile of leronlimab, one advantage to using leronlimab for treating COVID-19 is that the drug may be used in patients having underlying issues, e.g. organ failure/kidney failure, whereas other drugs that might be used to modulate immune response are contraindicated. In some embodiments, leronlimab may provide an effective treatment for certain patient sub-populations with COVID-19 where no other immune modulating therapy is reasonably or practicably available.

In some embodiments, leronlimab (PRO 140) 700 mg is administered once weekly for two weeks in a subject with mild to moderate COVID-19 disease. Most patients with mild to moderate COVID-19 disease fully recover within 2 weeks of developing initial symptoms.

In some embodiments, leronlimab is administered in a dose of 700 mg (175 mg/mL) delivered as two subcutaneous injections of 2 mL each on opposite sides of the abdomen.

While leronlimab has shown weak activity relative to the positive control (2D7, an anti-CCR5 antibody) in a study, the IC50 values were: 59.1 µg/mL for RANTES (CCL5), 21.2 µg/mL for MIP-1α and 39.6 µg/mL for MIP-1β. The modeled Cmax* for the proposed 700 mg weekly dose is 267.2 µg/mL which is 4.5-12.6-fold higher than the IC50 values for these cytokines. In addition, at leronlimab concentrations greater than 75 µg/ml for RANTES (CCL5) and greater than 100 µh/ml for MIP-1α and MIP-1β, inhibition of 80% or more was seen for these cytokines (FIG. 1). Therefore, leronlimab is expected to inhibit these cytokines following the 700 mg once weekly dose regimen.

It is also contemplated that treatment of a subject according to the methods described herein may use a CCL5 binding agent in addition to, or in lieu of a CCR5 binding agent. CCL5 binding agents include, but are not limited to, small molecules, antibodies or antigen binding fragments thereof, proteins, peptides, nucleic acids, and aptamers. Any subject who would benefit from diminishing, blunting, reduction, masking, interrupting, blocking, mitigation, or slowing directly or indirectly in the expression, amount, or activity of the CCR5 signaling pathway induced by CCL5 as described in the present disclosure, e.g., a subject infected with coronavirus, such as SARS-CoV-2, could also be treated by administering an effective amount of a CCL5 binding agent. CCL5 binding agents inhibit activity induced by CCL5 binding to one or more of its cognate receptors, e.g., CCR5, CCR3, and CCR1. In some embodiments, a CCL5 binding agent inhibits activity induced by CCL5 binding to CCR5. CCR5 activity induced by CCL5 binding may be measured by detecting, for example, a decrease in cAMP, cell migration, or both.

In some embodiments, a CCL5 binding agent is a soluble CCR5-Ig fusion protein.

In some embodiments, a CCL5 binding agent is OTR4120 or OTR4131.

In certain embodiments, the methods of the present disclosure include administration of a CCR5 binding agent provided herein to a subject in combination with one or more additional therapeutic agents. In some embodiments, the one or more additional therapeutic agents comprises an antiviral agent, a non-CCR5 immunomodulatory agent, a CCL5 binding agent, an immune checkpoint molecule inhibitor, or any combination thereof. In some embodiments, the one or more additional therapeutic agents is administered simultaneously, separately, or sequentially with the CCR5 binding agent.

As used herein, the term "immune checkpoint molecule" refers to one or more proteins, molecules, compounds or complexes providing inhibitory signals to assist in controlling or suppressing an immune response. For example, immune checkpoint molecules include those molecules that partially or totally block immune stimulation; decrease, prevent or delay immune activation; or increase, activate, or up regulate immune suppression. Exemplary immune checkpoint molecules are described in further detail herein and include PD-1, PD-L1, PD-L2, CD80, CD86, B7-H3, B7-H4, HVEM, adenosine, GALS, VISTA, CEACAM-1, PVRL2, CTLA-4, BTLA, KIR, LAG3, TIM3, A2aR, CD244/2B4, CD160, TIGIT, LAIR-1, PVRIG/CD112R, and certain metabolic enzymes, such as arginase, indoleamine 2,3-dioxygenase (IDO).

An immune checkpoint molecule inhibitor may be a compound, an antibody, an antibody fragment or fusion polypeptide (e.g., Fc fusion, such as CTLA4-Fc or LAG3-Fc), an antisense molecule, a ribozyme or RNAi molecule, or a low molecular weight organic molecule. In some embodiments, a CCR5 binding agent is administered in combination with a PD-1 inhibitor, for example a PD-1-specific antibody or binding fragment thereof, such as pidilizumab, nivolumab (Keytruda, formerly MDX-1106), pembrolizumab (Opdivo, formerly MK-3475), MEDI0680 (formerly AMP-514), AMP-224, BMS-936558 or any combination thereof. In some embodiments, a CCR5 binding agent is administered in combination with a PD-L1 specific antibody or binding fragment thereof, such as BMS-936559, durvalumab (MEDI4736), atezolizumab (RG7446), avelumab (MSB0010718C), MPDL3280A, or any combination thereof. In some embodiments, a CCR5 binding agent is administered in combination with an inhibitor of CTLA4, such as ipilimumab, tremelimumab, CTLA4-Ig fusion proteins (e.g., abatacept, belatacept), or any combination thereof.

As used herein, the term "antiviral agents" refers to a class of drugs for treating viral infections. An antiviral agent may be, for example, a small molecule, peptide, protein, antibody, nucleic acid, or aptamer that targets one or more components in the viral life cycle: attachment to host cell; release of viral genes and possibly enzymes into the host cell; replication of viral components using host cell machinery; assembly of viral components into viral particles; and release of viral particles to infect new host cells. Targets of antiviral agents include critical viral proteins such as neuraminidase, M2 ion channel protein, hemagglutinin, viral RNA polymerase, NTPase/helicase, spike (S) glycoprotein (S1 domain), and 3C-like cysteine protease. Examples of anti-viral agents include seltamivir, zanamivir, laninamivir, laninamivir, peramivir, and remdesivir. Other compounds with antiviral properties include chloroquine and hydroxychloroquine. As used herein, the term "non-CCR5 immunomodulatory agent" refers to a classes of drugs, including but not limited to a small molecule, peptide, protein, antibody, nucleic acid, or aptamer, that prevents, reduces, or counteracts elevation of pro-inflammatory cytokines and/or hyperimmune responses, e.g., cytokine storm, but does not bind to CCR5 or inhibit CCR5 receptor signaling. Non-limiting examples of drugs that currently being investigated for use in treating cytokine storm associated with COVID-19 include: baricitinib (Eli Lilly) and ruxolitinib (InCyte) are each orally-dosed inhibitors of Janus kinases 1 and 2 (JAK1/2); tocilizumab (Hoffman La Roche and Chugai) is an IV-administered monoclonal antibody targeting both the soluble and transmembrane IL-6 receptor; siltuximab (EUSA Pharma) is an IV-administered chimeric monoclonal antibody targeting IL-6; sarilumab is an IV-administered fully human monoclonal antibody targeting both the soluble and transmembrane IL-6 receptor (Regeneron Pharmaceuticals and Sanofi); TZLS-501 (Tiziana Life Sciences) is a fully human monoclonal antibody targeting both the soluble and transmembrane IL-6 receptor while also depleting circulating levels of IL-6 in the blood; anakinra (Swedish Orphan Biovitrum) is a recombinant IL-1R antagonist protein; emapalumab (Novimmune and Swedish Orphan Biovitrum) is an IV-administered human IgG1 monoclonal antibody targeting IFN-γ; hydroxychloroquine is an orally-administered drug that a) enters antigen-presenting cells (APCs) and prevents antigen processing and MHC class II-mediated autoantigen presentation to T cells, preventing T cell activation and cytokine production and b) disrupts interaction of DNA/RNA with toll-like receptors (TLRs) and the nucleic acid sensor cGAS, ultimately inhibiting the transcription of pro-inflammatory genes; TJM2 (I-Mab Biopharma) is an IV-administered human monoclonal antibody targeting granulocyte-macrophage colony stimulating factor (GM-CSF); gimsilumab (Roivant Sciences) is an IV-administered human monoclonal antibody targeting GM-CSF; lenzilumab (Humanigen Inc.) is an IV-administered humanized monoclonal antibody targeting GM-CSF; fingolimod (Novartis) is a S1PR modulator that blocks the capacity of lymphocytes to egress from lymph nodes, reducing the number of circulating lymphocytes; and CD24-Fc (Oncoimmune) binds and sequesters DAMPs to prevent their interaction with TLR receptor.

The present disclosure also provides a therapeutic composition comprising a CCR5 binding agent and at least one of an anti-viral therapeutic agent, an immune checkpoint molecule inhibitor, a non-CCR5 binding immunomodulatory agent, or any combination thereof.

REFERENCES

Beigel J H, Farrar J, Han A M, et al. Avian influenza A (H5N1) infection in humans. N Engl J Med. 2005; 353 (13):1374-85.

Tisoncik J R, Korth M J, Simmons C P, Farrar J, Martin T R, Katze M G. Into the eye of the cytokine storm. Microbiol Mol Biol Rev. 2012; 76(1):16-32.

Huang K J, Su I J, Theron M, et al. An interferon-gamma-related cytokine storm in SARS patients. J Med Virol. 2005; 75(2):185-94.

Kox M, Pompe J C, Gordinou de gouberville M C, Van der hoeven J G, Hoedemaekers C W, Pickkers P. Effects of the α7 nicotinic acetylcholine receptor agonist GTS-21 on the innate immune response in humans. Shock. 2011; 36(1): 5-11.

World Health Organization. Coronavirus disease (COVID-2019) situation reports. https://www.who.int/emergencies/diseases/novel-coronavirus-2019/situation-reports.

Huang, C. et al. Clinical features of patients infected with 2019 novel coronavirus in Wuhan, China. *Lancet* 395, 497-506 (2020).

Zhang, D. et al. COVID-19 infection induces readily detectable morphological and inflammation-related phenotypic changes in peripheral blood monocytes, the severity of which correlate with patient outcome. *medRxiv* 2020.03.24.20042655 (2020). doi:10.1101/2020.03.24.20042655

Mehta, P. et al. COVID-19: consider cytokine storm syndromes and immunosuppression. *Lancet* 395, 1033-1034 (2020).

Qin, C. et al. Dysregulation of immune response in patients with COVID-19 in Wuhan, China. *Clin. Infect. Dis.* (2020). doi:10.1093/cid/ciaa248

Channappanavar, R. & Perlman, S. Pathogenic human coronavirus infections: causes and consequences of cytokine storm and immunopathology. *Semin Immunopathol* 39, 529-539 (2017).

Nicholls, J. M. et al. Lung pathology of fatal severe acute respiratory syndrome. *Lancet* 361, 1773-1778 (2003).

Law, H. K. W. et al. Chemokine up-regulation in SARS-coronavirus-infected, monocyte-derived human dendritic cells. *Blood* 106, 2366-2374 (2005).

Yen, Y.-T. et al. Modeling the early events of severe acute respiratory syndrome coronavirus infection in vitro. *Journal of Virology* 80, 2684-2693 (2006).

Jacobson, J. M. et al. Antiviral activity of single-dose PRO 140, a CCR5 monoclonal antibody, in HIV-infected adults. *J. Infect. Dis.* 198, 1345-1352 (2008).

Jacobson, J. M. et al. Anti-HIV-1 activity of weekly or biweekly treatment with subcutaneous PRO 140, a CCR5 monoclonal antibody. *J. Infect. Dis.* 201, 1481-1487 (2010).

Jacobson, J. M. et al. Phase 2a study of the CCR5 monoclonal antibody PRO 140 administered intravenously to HIV-infected adults. *Antimicrob. Agents Chemother.* 54, 4137-4142 (2010).

Dhody, K. et al. PRO 140, a monoclonal antibody targeting CCR5, as a long-acting, single-agent maintenance therapy for HIV-1 infection. *HIV Clin Trials* 19, 85-93 (2018).

Olson, W. C. et al. Differential inhibition of human immunodeficiency virus type 1 fusion, gp120 binding, and CC-chemokine activity by monoclonal antibodies to CCR5. *Journal of Virology* 73, 4145-4155 (1999).

Akalin, E. et al. Covid-19 and Kidney Transplantation. *N Engl J Med* NEJMc2011117 (2020). doi:10.1056/NEJMc2011117.

Richardson, S. et al. Presenting Characteristics, Comorbidities, and Outcomes Among 5700 Patients Hospitalized With COVID-19 in the New York City Area. *JAMA* (2020). doi:10.1001/jama.2020.6775

Yu, T-M et al. RANTES mediates kidney ischemia reperfusion injury through a possible role of HIF-1α and LncRNA PRINS. *Scientific Reports* (2016) 10.1038/srep18424

Chen, L. Functional roles of CCL5/RANTES in liver disease. Liver Research (2020) 28e34 Lescure, F.-X. et al. Clinical and virological data of the first cases of COVID-19 in Europe: a case series. *Lancet Infect Dis* (2020). doi:10.1016/S1473-3099(20)30200-0

Halama, N., et al. Tumoral immune cell exploitation in colorectal cancer metastases can be targeted effectively by anti-CCR5 therapy in cancer patients. *Cancer Cell* (2016) 29, 587-601, 2016.

Grillet, F., Behr, J., Calame, P., Aubry, S. & Delabrousse, E. Acute Pulmonary Embolism Associated with COVID-19 Pneumonia Detected by Pulmonary CT Angiography. *Radiology* 201544 (2020). doi:10.1148/radiol.2020201544

Machlus, K. R. et al. CCL5 derived from platelets increases megakaryocyte proplatelet formation. *Blood* 127, 921-926 (2016).

Coronavirus survivor credits artificial antibody experimental treatment for recovery. *Los Angeles CBS Local* (2020). https://losangeles.cbslocal.com/2020/04/10/coronavirus-survivor-leronlimab/

US National Library of Medicine. Study to Evaluate the Efficacy and Safety of Leronlimab for Mild to Moderate COVID-19. ClinicalTrials.gov. https://clinicaltrials.gov/ct2/show/NCT04343651 (2020).

US National Library of Medicine. Study to Evaluate the Efficacy and Safety of Leronlimab for Patients With Severe or Critical Coronavirus Disease 2019 (COVID-19). *ClinicalTrials.gov.* https://clinicaltrials.gov/ct2/show/NCT04347239 (2020).

EXAMPLES

Example 1

Preclinical Study of IV and SC Administration

Acute toxicity of leronlimab (PRO 140) was evaluated in New Zealand rabbits, following IV administration of 5 or 15 mg/kg. Chronic toxicity was evaluated in cynomolgus monkeys following biweekly administration of IV doses up to 10 mg/kg for six months and biweekly administration of various SC doses up to 50 mg/kg for 24 weeks. The drug was generally well tolerated. Biweekly administration of IV doses up to 10 mg/kg for six months resulted in minimum to mild lymphoid hyperplasia in assorted lymph nodes and spleen, which was considered an expected immune response to a foreign protein. Biweekly administration of SC doses up to 50 mg/kg for 24 weeks resulted in minimum injection-site reactions (minimal, multifocal, mononuclear cell infiltrates in the subcutis), which were considered due to an inflammatory response to the injected antigen. Monkeys tolerated treatment with leronlimab (PRO 140) for 24 weeks without evidence of local or systemic toxicity. Leronlimab (PRO 140) caused no mortality, cageside observations, in-life injection-site observations, or gross pathologic findings. Chronic treatment with leronlimab (PRO 140) did not affect body weight, food consumption, hematology, clinical chemistry or coagulation parameters.

Both IV and SC administration resulted in elimination half-lives of approximately 200 hours, and overall exposure increased with increasing doses. Following SC administration of leronlimab (PRO 140) in monkeys, the maximal concentration (Cmax) was achieved within 56 hours and bioavailability for leronlimab (PRO 140) after SC dosing was approximately 70%.

Example 2

Study Protocol for Use of Leronlimab to Treat Mild-to-Moderate COVID-19

The purpose of this Phase 2 study is to assess the safety and efficacy of Leronlimab administered as weekly subcutaneous injection in subjects with Coronavirus 2019 (COVID-2019) disease.

Figure 2:
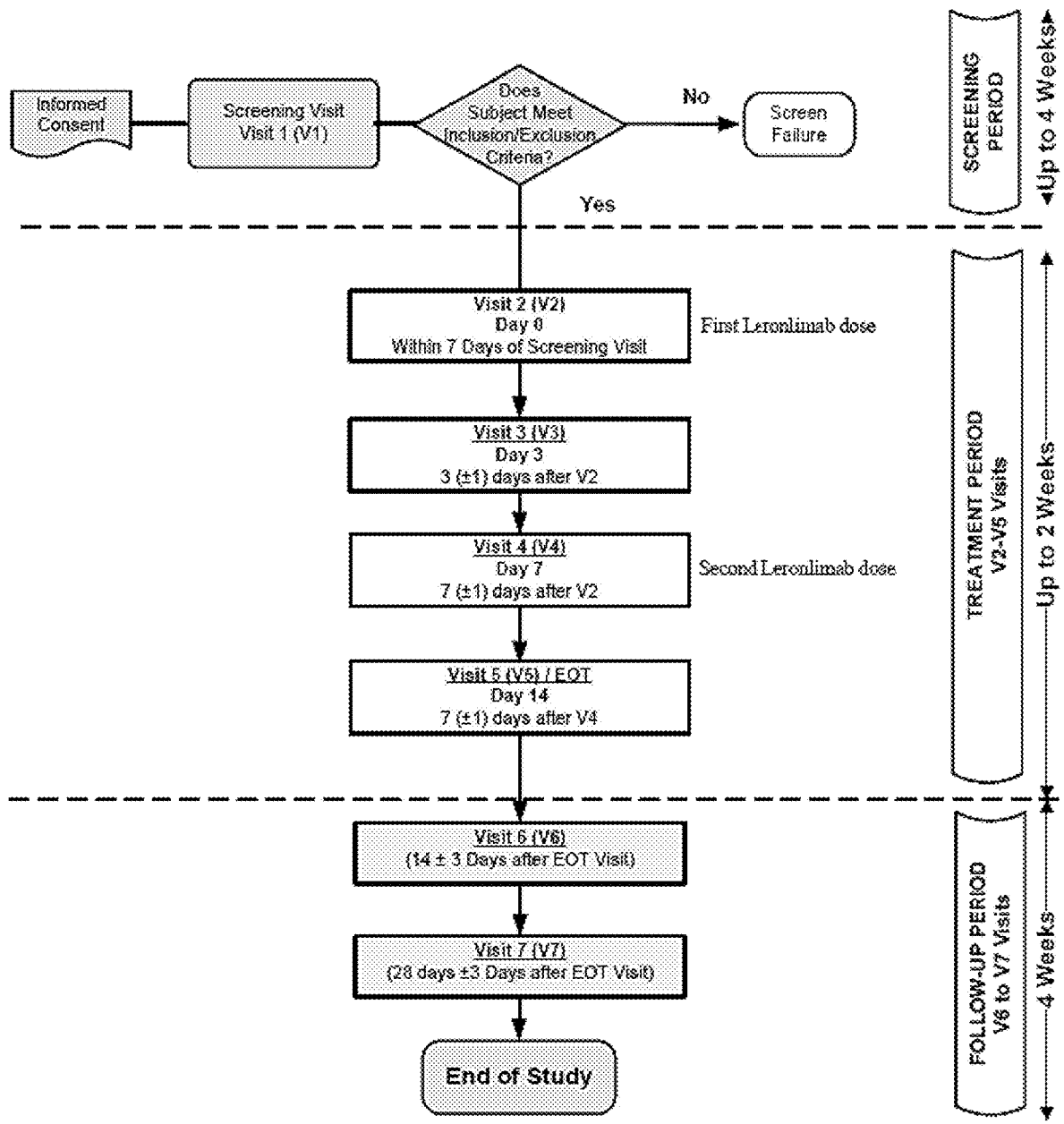
FIG. 2 shows a schematic of the study described in Example 2 and Example 4.

This study is a Phase 2, two arm, randomized, double-blind, placebo-controlled study to evaluate the safety and efficacy of leronlimab (PRO 140) in patients with mild-to-moderate symptoms of respiratory illness caused by Coronavirus disease 2019 (COVID-19). Patients will be randomized 2:1 to receive leronlimab (PRO 140) or placebo. Subjects will receive weekly 700 mg leronlimab (PRO 140) or placebo via subcutaneous injection for two weeks. The study will enroll 30 subjects. The study flow diagram is presented in FIG. 2.

The target population for this study is adult subjects with mild-to-moderate symptoms of respiratory illness caused by coronavirus disease 2019 (COVID-19).

Inclusion Criteria.

1. Male or female adults ≥18 years of age at time of enrollment;

2. Subjects with mild-to-moderate symptoms of respiratory illness caused by coronavirus 2019 infection;

Mild (uncomplicated) Illness, defined as:

Diagnosed with COVID-19 by a standardized RT-PCR assay AND

Mild symptoms, such as fever, rhinorrhea, mild cough, sore throat, malaise, headache, muscle pain, or malaise, but with no shortness of breath AND No signs of a more serious lower airway disease AND RR<20, HR<90, oxygen saturation (pulse oximetry) >93% on room air Moderate Illness, defined as:

Diagnosed with COVID-19 by a standardized RT-PCR assay AND

In addition to symptoms above, more significant lower respiratory symptoms, including shortness of breath (at rest or with exertion) OR Signs of moderate pneumonia, including RR ≥20 but <30, HR ≥90 but less than 125, oxygen saturation (pulse oximetry) >93% on room air AND If available, lung infiltrates based on X-ray or CT scan <50% present 3. Clinically normal resting 12-lead ECG at Screening Visit or, if abnormal, considered not clinically significant by the Principal Investigator;

4. Subject (or legally authorized representative) provides written informed consent prior to initiation of any study procedures;

5. Understands and agrees to comply with planned study procedures; and

6. Women of childbearing potential must agree to use at least one primary form of contraception for the duration of the study (acceptable methods will be determined by the site).

Exclusion Criteria.

Potential subjects meeting any of the following criteria will be excluded from enrollment:

1. Subjects showing signs of acute respiratory distress syndrome (ARDS) or respiratory failure necessitating mechanical ventilation at the time of screening;

2. History of severe chronic respiratory disease and requirement for long-term oxygen therapy;

3. Subjects showing signs of clinical jaundice at the time of screening;

4. History of moderate and severe liver disease (Child-Pugh score >12);

5. Subjects requiring Renal Replacement Therapy (RRT) at the time of screening;

6. History of severe chronic kidney disease or requiring dialysis;

7. Pregnancy or breast feeding;

8. Any active infection or malignancy requiring acute therapy

Note: Subjects infected with chronic hepatitis B virus or hepatitis C virus will be eligible for the study if they have no signs of hepatic decompensation.

Note: Subjects infected with HIV-1 will be eligible for the study with undetectable viral load and are on a stable ART regimen 9. Patients with malignant tumor, or other serious systemic diseases;

10. Patients who are participating in other clinical trials;

11. Patients who have a history of allergic reactions attributed to compounds of similar chemical or biologic composition to leronlimab (PRO 140) are not eligible; and 12. Inability to provide informed consent or to comply with test requirements.

The study will have three phases: Screening Period, Treatment Period, and Follow-Up Period. The study Schedule of Assessments in presented in FIG. 3.

All subjects who fail to meet eligibility criteria are considered screen failures, and are exited from the study without further evaluation.

Screening Period (up to 1 week). Screening assessments will commence at Visit 1 (V1) after obtaining signed informed consent, and will include review of medical and medication history, eligibility evaluation, physical examination, vital signs, Clinical Symptom Score assessment, pulse oxygen saturation, National Early Warning Score 2 (NEWS2) assessment, electrocardiogram (ECG), nasopharyngeal swab sample collection, chest radiograph or CT (if clinically indicated), ordinal scale assessment, and laboratory sample collection for routine serum biochemical, hematologic, coagulation, urinalysis, and serum pregnancy (if applicable). These assessments must be conducted within 7 days of the First Treatment Visit (V2).

Treatment Period (2 weeks±allowed windows). The schedule of visits during Treatment Period is as follows:

Visit 2 (V2) [first treatment]: Within 1 week of the Screening Visit

Visit 3 (V3): 3 (±1) day after V2

Visit 4 (V4) [second treatment]: 7 (±1) days after V2

Visit 5 (V5)/End of Treatment (EOT) Visit: 7 (±1) days after V4.

Subjects who meet the eligibility criteria will have completed the following evaluations and assessments at V2 prior to treatment: review of any changes in medical and medication history, physical examination, vital signs, Clinical Symptom Score assessment, pulse oxygen saturation, National Early Warning Score 2 (NEWS2) assessment, nasopharyngeal swab sample collection, health status assessment on an ordinal scale, baseline assessment for the requirement of: mechanical ventilation, oxygen, and hospital stay, and blood sample collection for CD3+, CD4+ and CD8+ T cell count, CCR5 receptor occupancy for Treg and macrophages, serum cytokine and chemokine levels, and CCR5 gene polymorphisms. If Visit 2 (V2) takes place on the same day as the Screening Visit (V1), scheduled assessments performed under screening (V1) do not need to be repeated at V2.

The treatment groups are shown below in Table 3.

TABLE 3

| Study Drug | Dosage Form | IP Concentration | Dosing Frequency & Amount | Route of Administration |
|---|---|---|---|---|
| Leronlimab (700 mg) | Parenteral solution | 175 mg/ml | 2 injections of PRO 140 (2 X 2 mL/inj.) per week on opposite sides of abdomen | SC injection |
| Placebo | Parenteral solution | 0 mg/ml | 2 injections of placebo (2 X 2 mL/inj.) per week on opposite sides of abdomen | SC injection |

At V2, subjects will be randomized to receive leronlimab (PRO 140) or placebo which will be administered subcutaneously weekly at Visit 2 (Day 0) and Visit 4 (Day 7) by a qualified medical professional at clinic or at subject's home.

The following assessments will be performed at V3, V4, and V5/EOT: physical examination, vital signs, Clinical Symptom Score assessment, pulse oxygen saturation, NEWS2 assessment, nasopharyngeal swab sample collection, health status assessment on an ordinal scale, assessment for the requirement of: mechanical ventilation, oxygen, and hospital stay, and laboratory sample collection for routine serum biochemical, hematologic, coagulation, urinalysis, CD3+, CD4+ and CD8+ T cell count, CCR5 receptor occupancy for Treg and macrophage, serum cytokine and chemokine levels, and CCR5 gene polymorphisms.

Additionally, a chest radiograph or CT (if clinically indicated), mortality assessment, and ECG will be performed at V7/EOT visit. Adverse events and medications will be monitored throughout the study.

Follow Up Period (2 and 4 weeks after EOT±allowed windows)

Follow-up visits will be performed at 2 weeks (V6) and 4 weeks (V7) after the End of Treatment (EOT) visit. The following assessments will be performed at V6 and V7 visit: review of adverse events and concomitant medications, physical examination, vital signs, mortality status, and blood collection for routine serum biochemical, hematologic, coagulation and urine laboratory assessments (V7 only).

Note: During visits conducted at the study clinic, subjects and site personnel will use appropriate protective gear (e.g., masks, gloves) to prevent the spread of the infection. If possible, scheduled study visits can be conducted by a visiting nurse (or trained site staff) at the subject's home to mitigate the risk of spreading COVID-19.

During visits conducted at the subject's home, the visiting nurse (or trained site staff) will administer study drug (if applicable), monitor subjects for safety, perform blood draw, and all other assessments related to study outcomes measures. All procedures (except chest radiograph or CT scan) listed under the schedule of assessments can be performed by visiting nurse at visits taking place in the subject's home.

Screening Phase. The subject (or Legally Acceptable Representative (LAR)) will sign and date the informed consent form (ICF) and Health Insurance Portability Accountability Act (HIPAA) authorization (according to site policy and practices) prior to any study-related procedures. All study centers will be instructed to maintain the study-specific screening and enrollment logs at their sites. If a subject initially fails to meet inclusion/exclusion criteria and is later reconsidered for participation, the subject will be re-consented and assigned a new unique identification number at the time of re-screening. Subjects who fail their first screening attempt may be re-screened a maximum of once and may be enrolled if they are found to meet all inclusion and no exclusion criteria when re-screened.

Screening Visit (V1). After the ICF has been signed, screening procedures and information will be obtained to confirm subject eligibility, including:

Demographic information;
A detailed medical history;
Physical examination;
Vital signs;
Clinical symptom score assessment;
Pulse oxygen saturation (SpO2);
National Early Warning Score 2 (NEWS2) assessment;
12-lead electrocardiogram;
Collection of blood specimens for Complete blood count; Biochemistry; Coagulation indices; Serum pregnancy test, for female subjects of childbearing potential; and Urine sample for urinalysis parameters.

Nasopharyngeal Swab Sample Collection
Chest radiograph or computer tomography (CT) scan (if clinically indicated);
Ordinal scale assessment;
Assessment for the requirement of mechanical ventilation, oxygen, and hospital stay; and
Prior medications assessment.

All screening information will be fully documented in the subject's medical records (i.e., source documents).

For consented subjects who do not meet eligibility criteria, a Screen Failure Case Report Form (CRF) will be completed. The Screen Failure CRF will contain the following details: the subject identification number, the date of ICF signature, demographic information, and the reason for screen failure. No additional information will be required for subjects who fail screening.

For consented subjects who meet eligibility criteria, all required screening information will be transcribed onto the appropriate page of the CRF.

Treatment Phase. Subjects who meet all eligibility criteria, as per data gathered from Screening Period are to be treated. All subjects who fail to meet eligibility criteria will be considered screen failure and will exit the study without further evaluation Visit 2 (V2). The following assessments will be performed at the first treatment visit prior to the first treatment administration. If Visit 2 (V2) takes place on the same day as the Screening Visit (V1), scheduled assessments performed under screening (V1) do not need to be repeated at V2.

Physical examination;
Vital Signs;
Clinical symptom score assessment;
Pulse oxygen saturation (SpO2);
National Early Warning Score 2 (NEWS2) Assessment;
Collection of blood specimen for CD3+, CD4+ and CD8+ T cell count; CCR5 receptor occupancy for Treg and macrophage; Serum cytokine and chemokine levels; and CCR5 Gene Polymorphisms.
Nasopharyngeal Swab Sample Collection;
Ordinal scale assessment;
Assessment for the requirement of mechanical ventilation, oxygen, and hospital stay; and
Prior medications assessment.

Subjects will be randomized 2:1 via WebView CTMS system to Leronlimab (PRO 140, 700 mg) or Placebo.

Leronlimab (PRO 140) or placebo will be administered subcutaneously to all subjects at a weekly dose of 700 mg. After receiving the first leronlimab (PRO 140) dose, the following assessments will be performed: Vital signs, Concomitant medications assessment, and Review of adverse events.

Visits 3 and 4, (V3 and V4). The following assessments will be performed during the remaining visits during the treatment period:

Physical examination;
Vital Signs;
Clinical symptom score assessment;
Pulse oxygen saturation (SpO2);
National Early Warning Score 2 (NEWS2) Assessment;
Collection of blood specimens for Complete blood count; Biochemistry; Coagulation indices; Urine sample for urinalysis parameters; CD3+, CD4+ and CD8+ T cell count; CCR5 receptor occupancy for Treg and macrophage; Serum cytokine and chemokine levels; and CCR5 Gene Polymorphisms.
Nasopharyngeal Swab Sample Collection;
Ordinal scale assessment;

Leronlimab (PRO 140) or Placebo Administration—V4 only;

Assessment for the requirement of mechanical ventilation, oxygen, and hospital stay;

Prior medications assessment; and

Review of adverse events.

End of Treatment—EOT (V5). The last visit during the treatment phase will be considered at the End of Treatment (EOT) visit. The assessments performed at this visit will include:

Physical examination;

Vital Signs;

Clinical symptom score assessment;

Pulse oxygen saturation (SpO2);

National Early Warning Score 2 (NEWS2) Assessment;

12-lead electrocardiogram;

Collection of blood specimens for Complete blood count; Biochemistry; Coagulation indices; Urine sample for urinalysis parameters; CD3+, CD4+ and CD8+T cell count; CCR5 receptor occupancy for Treg and macrophage; Serum cytokine and chemokine levels; and CCR5 Gene Polymorphisms.

Nasopharyngeal Swab Sample Collection;

Chest radiograph or computer tomography (CT) scan (if clinically indicated);

Ordinal scale assessment;

Assessment for the requirement of mechanical ventilation, oxygen, and hospital stay;

Review of mortality status;

Prior medications assessment; and

Review of adverse events.

FOLLOW-UP PHASE. The first visit of the follow-up phase is scheduled 14(±3) days after EOT Visit. Two follow-up visits are included in the follow-up phase: Visit 6 (V6) and Visit 7 (V7).

The assessments performed at these visits will include:

Physical examination;

Vital Signs;

Collection of blood specimens at Visit 9 only for Complete blood count; Biochemistry; Coagulation indices; and Urine sample for urinalysis parameters.

Nasopharyngeal Swab Sample Collection

Review of mortality status;

Prior medications assessment; and

Review of adverse events.

UNSCHEDULED VISITS. In the event that the subject will return to clinic at a time other than a regularly scheduled study visit, the visit will be regarded as an unscheduled visit. Assessments at unscheduled visits are at the discretion of the Investigator. All pertinent findings, including adverse events or changes in medications, will be noted in the eCRF.

Subject Completion, Withdrawal and Criteria for Stopping the Study.

SUBJECT COMPLETION. A subject is considered to have completed the study once all follow-up visit assessments have been completed.

EARLY STOPPING RULES. Upon occurrence of any of the following events, data will be reviewed by the Medical Monitor and the Lead Principal Investigator.

1. Death in any subject in which the cause of death is judged to be probably or definitely related to the study drug by the treating investigator;

2. The occurrence in any subject of a life-threatening SAE whose causal relationship to study drug is judged to be probable or definite by the treating investigator;

3. Two (2) occurrences of Grade 4 toxicities that are assessed to be probably or definitely related to the study drug by the treating investigator;

4. Two (2) occurrences of a Grade 2 or higher allergic/hypersensitivity reaction directly related to the study drug that lead to permanent discontinuation of study drug.

In case the above listed event(s) occurred, patient accrual will be suspended pending further review and the FDA will be notified. The study will be stopped if any of these stopping criteria are met unless, after reviewing the safety events of interest, the medical monitor and Sponsor, agree to allow the study to proceed.

REMOVAL OF SUBJECTS FROM STUDY TREATMENT AND/OR STUDY AS A WHOLE. Subjects can be taken off the study treatment and/or study as a whole at any time at their own request, or they may be withdrawn at the discretion of the investigator for safety, behavioral or administrative reasons. In the case that a subject is removed from the study due to safety reasons, the FDA will be notified. The reason(s) for discontinuation must be clearly documented on the appropriate eCRF and may include:

Subject voluntarily withdraws from treatment (follow-up permitted);

Subject withdraws consent (no follow-up permitted);

Subject is unable to comply with protocol requirements;

Subject experiences unacceptable toxicity;

Treating physician determines that continuation on the study would not be in the subject's best interest;

Subject becomes pregnant;

Subject becomes lost to follow-up (LTF);

Subject will be withdrawn from the study if 2 consecutive injections of study drug are missed;

Subject manifesting Grade 4 toxicity attributable to the Leronlimab (PRO 140).

If a subject fails to return for the scheduled study visit or is discontinued from the study, an attempt will be made to determine the reason(s). If the subject is unreachable by telephone, a registered letter will be sent to the subject requesting that he/she contact the clinic.

All patients with an ongoing SAE at the Post-Study (Follow-up) Visit (scheduled or premature) must be followed until the event is resolved (with or without sequelae) or deemed stable.

DATA COLLECTED FROM WITHDRAWN SUBJECTS. Every attempt should be made to collect follow-up information. The reason for withdrawal from the study will be recorded in the source documents and on the appropriate page of the CRF.

Before a subject is identified as lost-to-follow up, the site should make all reasonable efforts to contact the subject. These attempts must be documented and should include at a minimum one phone call and one certified letter.

In the event that a subject is withdrawn from the study at any time due to an adverse event or SAE, the procedures stated in "Adverse Events (Definitions and Reporting)" must be followed.

SCREEN FAILURES. A subject who signed a consent form, but did not meet the inclusion/exclusion criteria is classified as a screen failure. Subject number, demographics and reason for screen failure will be recorded.

In the event that a subject initially fails to meet inclusion/exclusion criteria and is later reconsidered for participation, the subject will be re-consented and assigned a new screening number at the time of re-screening. Subjects who fail their first screening attempt may be re-screened again (i.e., up to two screenings) and may be enrolled if they are found to meet all inclusion and no exclusion criteria at the subsequent screening visit.

Study Treatment.

Leronlimab (PRO 140) or placebo will be administered subcutaneously (SC) at a weekly as follows in Table 4.

TABLE 4

| Study Drug | Dose | Route | Schedule |
|---|---|---|---|
| Leronlimab (PRO 140) | 700 mg | SC | Weekly (2 doses) |
| Placebo | 0 mg | SC | Weekly (2 doses) |

Leronlimab (PRO 140). Leronlimab (PRO 140) is a humanized IgG4,κ monoclonal antibody (mAb) to the chemokine receptor CCR5. Leronlimab (PRO 140) is provided at a concentration of 175 mg/mL and is intended for SC route of administration.

One study injection kit will be assigned per subject per treatment visit. Kits will be labeled with a unique identification number. Each kit used during the Treatment Period will contain four vials of leronlimab (PRO 140) or placebo for SC injection.

A dose of 700 mg of Leronlimab (PRO 140) (175 mg/mL) or placebo will be delivered as two injections of 2 mL each and administered subcutaneously on opposite sides of the abdomen.

Each vial of the Leronlimab (PRO 140) product contains ~1.4 mL antibody at 175 mg/mL in a buffer containing 5 mM L-histidine, 15.0 mM glycine, 95 mM sodium chloride, 0.3% (w/v) sorbitol, 0.005% (w/v) polysorbate 20 (Tween 20®), and sterile water for injection, at pH of 5.5.

Each vial of the Placebo product contains 5 mM Histidine, 15 mM Glycine, 95 mM Sodium Chloride, 0.3% (w/v) Sorbitol, 0.005% (w/v) Polysorbate 20 at a pH of 5.5.

Note: 1 mL will be drawn from 1.4 mL solution filled vial. Remaining 0.4 mL medication will be discarded appropriately from each vial. The contents from 2 vials (2 mL) will be drawn into a syringe and administered as subcutaneous injection.

Leronlimab information is provided in Table 5.

TABLE 5

| IP Dosage | Dosage Form | IP Concentration | Dosing Frequency & Amount | Route of Administration |
|---|---|---|---|---|
| PRO 140 (700 mg) | Parenteral solution | 175 mg/ml | 2 inj. of PRO 140 (2 ml/inj.) per week on opposite sides of abdomen for 2 weeks | SC injection |
| Placebo | Parenteral solution | 0 mg/ml | 2 inj. of placebo (2X2 ml/inj..) per week on opposite sides of abdomen for 2 weeks | SC injection |

Note: Patients with low body fat percentages may find subcutaneous injections uncomfortable. In such cases, leronlimab (PRO 140) 700 mg can be injected as four 175 mg/ml injections and/or subcutaneous injections can be placed at different areas other than abdomen as per discretion of the Investigator.

Leronlimab (PRO 140)—Packaging and Labeling. The contents of each vial are described in the "Study Treatment" section. Leronlimab (PRO 140) kits will be labeled with information such as: study protocol #; fill volume; concentration; storage condition; a "use as per study protocol" statement; a cautionary statement; sponsor's name and address; and the kit number.

Leronlimab (PRO 140)—Storage and Handling. Study drug will be shipped at 2° C. to 8° C. (refrigerated [36° F. to 46° F.]) to the investigator's site. Upon receipt at the site, the responsible site staff or pharmacist should verify the integrity of the vials. Study drug should be stored at 2° C. to 8° C. (refrigerated [36° F. to 46° F.]). The contents of the vial should appear as a clear to opalescent, colorless to yellow solution; fine translucent particles may be present. This is normal.

The investigator must maintain an accurate record of the shipment, storage, and dispensing of the study drug in a drug accountability log. An accurate record including the date and amount of study drug dispensed to each subject must be available for inspection at any time. A study CRA assigned to monitor the investigational site will review these documents once study drug has been received by the investigational site. Study drug will be accounted for on an ongoing basis during the study.

Leronlimab (PRO 140)—Administration. Guidelines for dose preparation can be found in the pharmacy manual.

Leronlimab (PRO 140) or placebo will be provided to the administering personnel in single-use syringes prepared from vials of study drug stored at 2-8° C. at the site pharmacy prior to use. Each of two syringes is filled to deliver 2 mL of study drug.

Equivalent volumes of PRO 140 will be administered subcutaneously on opposite sides of the abdomen.

A 20-gauge needle should be used to remove PRO 140 from vial and a 25-gauge needle is used for administration to subjects.

IP should be administered slowly over 15 seconds per mL. Leronlimab (PRO 140) should not be kept in syringe for longer than 60 minutes.

Following each SC delivery of drug, careful examination will be made to assess the appearance of any study drug Injection Site Reactions (ISRs) as per CTCAE v5.0.

Leronlimab (PRO 140) will be administered as SC injection by a qualified medical professional at the study clinic or at the subject's home.

Note: It is preferred that the same injection site be used throughout the study. At the same time, it is not recommended to inject the study drug into areas where skin shows signs of a previous injection site reaction. It is advised to change the injection site if any previous injection site reaction remains unresolved.

Leronlimab (PRO 140)—Post Injection Monitoring. Subject will be observed at approximately 30 minutes post-injection or longer if necessary for injection site reaction as per CTCAE v5.0.

Leronlimab (PRO 140)—Dose Modifications. The dose interruption, reduction, and permanent discontinuation for any toxicity are described below.

Dose interruption: Refer to Tables 6 and 7 below. Recovery to acceptable levels must occur to allow leronlimab (PRO 140) continuation.

TABLE 6

Leronlimab (PRO 140) Dose Modification and
Management for Injection Site Reactions

| CTCAE Grade | Treatment Modification |
|---|---|
| Grade 1 | No dose adjustment is required |
| Grade 2 | First Occurrence: No dose adjustment is required. Second Occurrence of the same event: Closely follow-up for resolution of the AE to Grade ≤ 1 |
| Grade 3 | Withhold treatment until symptoms resolve to: Grade 1 or less |
| Grade 4 | Study treatment will be permanently discontinued |

TABLE 7

Leronlimab (PRO 140) Dose Management for all Other
Potential Toxicities (Attributable to Leronlimab).

| CTCAE Grade (attributable to leronlimab) | Treatment Modification |
|---|---|
| Grade 1 | No dose adjustment is required |
| Grade 2 | Withhold treatment until symptoms resolve to: Grade 1 or less |
| Grade 3 | Withhold treatment until symptoms resolve to: Grade 1 or less |
| Grade 4 | Study treatment will be permanently discontinued |

Description of Protocol Assessments and Procedures.

Demographic information and medical history will be collected. For COVID-19 diagnosis, the number of days between the onset of symptoms and the initiation of treatment for each subject will be documented.

PHYSICAL EXAMINATION. The physical examination will include routine examinations for the following:
Constitutional/General Appearance
Head, Ears, Eyes, Nose, Throat (HEENT)
Neurologic
Cardiovascular
Musculoskeletal and Extremities
Dermatologic
Respiratory
Gastrointestinal
Genitourinary
Lymphatic
Psychiatric Each abnormality will be recorded and the Investigator will record an assessment of its clinical significance.

VITAL SIGNS, HEIGHT AND WEIGHT. The following will be collected: Systolic Blood Pressure, Diastolic Blood Pressure, Heart Rate, Temperature, Respiratory Rate, Height, Weight, and Body Mass Index.

CONCOMITANT MEDICATIONS. All medications and therapies administered or taken by the subject beginning 30 days prior to Screening Visit and throughout the study will be recorded in the source documents and on the appropriate page of the Case Report Form (CRF). Additionally, all other investigational and off-label therapies for COVID-19 will be recorded. Subjects must be questioned at each study visit concerning any new medications or changes in current medications including over-the-counter medication and topical medication.

For each medication and non-study treatment, the following will be documented:

Medication/treatment name (generic name may be used if trade name is unknown)

Dose, unit, and frequency of dosing (individual dosages, not total daily dose).

Note: Each new dose of medication should be recorded as a separate entry, with the exception of medications that are given on a sliding scale. For these, it is acceptable to enter the range of the dosage, including the start and stop dates for which the specified dosage range was used.

Route of dosing

Indication for use

The start date

The stop date (if medication/therapy is not ongoing).

Excluded Medications. The following medications are prohibited:

The use of immunosuppressive medications are prohibited with the following exceptions:

Intranasal, inhaled, topical steroids, or local steroid injections;

Systemic corticosteroids at physiologic doses not to exceed 10 mg/day of prednisone or its equivalent. Note: Organ transplant patients will be allowed to continue baseline immunosuppressive therapy during the course of study;

Other CCR5 antagonists;

Other investigational products for indications other than COVID-19.

Allowable Medications and Therapies. Patients with underlying chronic viral illnesses will be allowed to receive antiviral therapy.

CLINICAL LABORATORY ASSESSMENTS. Blood samples will be collected for analysis of the following parameters described in Tables 8-12.

Biochemistry and Complete Blood Count (CBC): At Screening (V1), V3, V4, V5 (EOT), and V7.

Serum pregnancy test (for female subjects of childbearing potential): At Screening (V1)

All laboratory reports will be reviewed by the Investigator. Abnormal results that are considered by the Investigator to be clinically significant will be recorded as adverse events. If in the Investigator judgment, in order to make the determination of clinical significance the testing may be needed to be repeated. Validated, quality-controlled laboratory data will be transferred to the main database for analyses.

TABLE 8

| CBC Parameters |
|---|
| Hemoglobin (g/dL) |
| Hematocrit (%) |
| RBC/Erythrocytes ($10^{12}$/L) |
| WBC/Leukocytes ($10^{6}$/L) |
| Absolute Neutrophil Count ($10^{6}$/L) |
| Platelets ($10^{9}$/L) |
| Differential WBC: |
| Neutrophils (%) |
| Lymphocytes (%) |
| Monocytes (%) |
| Eosinophils (%) |
| Basophils (%) |

TABLE 9

| Biochemistry Parameters |
| --- |
| Liver Function Tests |
| Total bilirubin (mg/dL) |
| Alkaline Phosphatase (ALP) (U/L) |
| Aspartate Aminotransferase (AST) (or SGOT) (U/L) |
| Alanine Aminotransferase (ALT) (or SGPT) (U/L) |
| Total Protein (g/dL) |
| Albumin (g/dL) |
| Lactate Dehydrogenase (U/L) |
| Renal Function Tests |
| Creatinine clearance, |
| eGFR |
| Electrolytes |
| Sodium (mEq/L) |
| Potassium (mEq/L) |
| Chloride (mEq/L) |
| Calcium (mg/dL) |
| Bicarbonate (mEq/L) |
| Other: |
| Glucose, Random (mg/dL) |
| Cholesterol, Total (mg/dL) |
| Creatine kinase, |
| C-reactive protein |
| Coagulation Parameters |
| Prothrombin time (PT) |
| International Normalized Ratio (INR) |

TABLE 10

| Urinalysis |
| --- |
| pH |
| Specimen Appearance |
| Color |
| Specific Gravity |
| Ketones |
| Bilirubin |
| Occult Blood |
| Glucose |
| Protein |
| Nitrite |
| Urobilinogen (mg/dL) |
| Leukocyte Esterase |
| Leukocytes (/HPF) |

TABLE 11

| Cytokine and Chemokine Panel |
| --- |
| sCD40L, EGF, Eotaxin (CCL11), FGF-2, Flt-3 ligand, Fractalkine, G-CSF, GM-CSF, GRO alpha (CXCL1), IFN-alpha2, IFN-gamma, IL-1 alpha, IL-1 beta, IL-1RA, IL-2, IL-2R, IL-3, IL-4, IL-5, IL-6, IL-7, IL-8 (CXCL8), IL-9, IL-10, IL-12 (p40/p70) IL-13, IL-15, IL-17A, IL-17E/IL-25, IL-17F, IL-18, IL-22, IL-27, IP-10 (CXCL10), MCP-1 (CCL2), MCP-3, M-CSF, MDC (CCL22), MIG (CXCL9), MIP-1 alpha (CCL3), MIP-1 beta (CCL4), PDGF-AA, PDGF-AB/BB, RANTES(CCL5), TGF-alpha, TNF-alpha, TNF-beta, VEGF-A. |

TABLE 12

| Miscellaneous |
| --- |
| Serum pregnancy test |
| Urine pregnancy test (for female subjects of childbearing potential) |
| CD3+, CD4+ and CD8+ T cell count |
| CCR5 receptor occupancy for Treg and macrophage |
| CCR5 Gene Polymorphisms |

CLINICAL SYMPTOM SCORE ASSESSMENT. Clinical Improvement will be assessed based on symptom score for fever, myalgia, dyspnea and cough. Each symptom is graded from 0 to 3. [0=none, 1=mild, 2=moderate, and 3=severe].

The total score per patient ranges from 0 to 12 points. Clinical Improvement will be assessed daily while subject is hospitalized and will continue to be assessed on the scheduled treatment visits and at EOT after the subject is discharged from the hospital.

PULSE OXYGEN SATURATION (SPO2). Pulse Oxygen Saturation (SPO2) will be measured at Screening and at V2 (pre-dose), V3, V4, and V5 (EOT).

NATIONAL EARLY WARNING SCORE 2 ASSESSMENT. The National Early Warning Score 2 (NEWS2) Assessment is based on 7 clinical parameters (respiration rate, oxygen saturation, any supplemental oxygen, temperature, systolic blood pressure, heart rate, level of consciousness).

12-LEAD ELECTROCARDIOGRAM. A resting supine 12-lead ECG will be conducted at the Screening Visit (V1) and Visit 5 (End of Treatment). A 12-lead ECG will be repeated during the study only if clinically indicated and at the discretion of the treating physician. The results will be evaluated by the Investigator. The following parameters will be recorded: ventricular rate (beats per minute), PR interval (msec), QRS interval (msec), QT interval (msec), and QTc interval (msec). Additionally, the Investigator will record the overall results of the ECG reading as either normal or abnormal, and as either not clinically significant or clinically significant. If abnormalities are observed, each will be recorded.

NASOPHARYNGEAL SWAB SAMPLE COLLECTION. Nasopharyngeal swabs will be used for quantitative virologic testing. The subject will be followed and samples will be collected for the entire duration of the study. Samples are to be stored at −70° C.

CHEST RADIOGRAPH OR COMPUTED TOMOGRAPHY SCAN. If clinically indicated by the treating physician, a chest radiograph or CT scan will be performed at Screening Visit (V1) and V5 (EOT)

ORDINAL SCALE ASSESSMENT. Subject clinical status will be assessed using a 7-category ordinal scale. The scale ranges from:

(1) Death;
(2) Hospitalized, on invasive mechanical ventilation or extracorporeal membrane oxygenation (ECMO);
(3) Hospitalized, on non-invasive ventilation or high flow oxygen devices;
(4) Hospitalized, requiring supplemental oxygen;
(5) Hospitalized, not requiring supplemental oxygen;
(6) Not hospitalized, limitation on activities;
(7) Not hospitalized, no limitations on activities.

REQUIREMENT OF MECHANICAL VENTILATION, OXYGEN, AND HOSPITAL STAY. The incidence and duration, in days, of mechanical ventilation, oxygen, and hospital stay will be assessed at Screening (V1) and V3, V4, and V5 (EOT).

RANDOMIZATION. Subjects who are eligible to participate in the trial will be randomized to one of the treatment groups via IWRS (Interactive Web Based Randomization System) at Visit 2 prior to IP administration. The randomization will be central and will use mixed block size of 3 and 6 with a 2:1 ratio of Active Treatment to Control Treatment to ensure even distribution of Active and Control subjects.

STATISTICAL ANALYSIS. This section presents general information about statistical considerations and concepts and a brief discussion on analysis methodology, as well as some data conventions. Detailed descriptions of the statistical analysis methods and data conventions that will be used in this study will be in a separate document; i.e., the Statistical Analysis Plan (SAP).

TREATMENT GROUPS. There will be two treatment groups in the study:

700 mg Leronlimab (PRO 140); Placebo

Description of Study Outcomes (Endpoints).

Primary Outcome (Endpoints) Measures. The primary outcome (endpoint) measure is: Clinical Improvement as assessed by change in total symptom score (for fever, myalgia, dyspnea and cough). Note: The total score per patient ranges from 0 to 12 points. Each symptom is graded from 0 to 3. [0=none, 1=mild, 2=moderate, and 3=severe].

Secondary Outcome (Endpoints) Measures. The secondary outcome (endpoints) measures for the study are:

1. Time to clinical resolution (TTCR). Time to clinical resolution (TTCR), defined as the time from initiation of study treatment until resolution of clinical symptoms (fever, myalgia, dyspnea and cough).

2. Change from baseline in National Early Warning Score 2 (NEWS2) at Days 3, 7, and 14. This score is based on 7 clinical parameters (respiration rate, oxygen saturation, any supplemental oxygen, temperature, systolic blood pressure, heart rate, level of consciousness).

3. Change from baseline in pulse oxygen saturation (SpO2) at Days 3, 7, and 14

4. Change from baseline in the patient's health status on a 7-category ordinal scale at Days 3, 7, and 14. A 7-category ordinal scale of patient health status ranges from: 1) Death; 2) Hospitalized, on invasive mechanical ventilation or extracorporeal membrane oxygenation (ECMO); 3). Hospitalized, on non-invasive ventilation or high flow oxygen devices; 4) Hospitalized, requiring supplemental oxygen; 5) Hospitalized, not requiring supplemental oxygen; 6) Not hospitalized, limitation on activities; 7) Not hospitalized, no limitations on activities.

5. Incidence and duration (days) of hospitalization

6. Incidence and duration (days) of mechanical ventilation supply

7. Incidence and duration (days) of oxygen use

8. Mortality rate at Day 14

9. Time to return to normal activity

Exploratory Outcome (Endpoints) Measures.

1. Change in size of lesion area by chest radiograph or CT

2. Change from baseline in serum cytokine and chemokine levels at Days 3, 7, and 14

3. Change from baseline in CCR5 receptor occupancy levels for Tregs and macrophages at Days 3, 7, and 14

4. Change from baseline in CD3+, CD4+ and CD8+ T cell count at Days 3, 7, and 14

Safety Measures. Safety will be assessed using:

Incidence of treatment-related adverse events (TEAEs) Incidence and severity of treatment-emergent adverse events (TEAEs);

Incidence of serious adverse events (SAEs);

Incidence of TEAEs and SAEs leading to discontinuation of study medication;

Changes in blood chemistry, hematology and coagulation parameter results;

Changes in vital signs including temperature, pulse, respiratory rate, systolic and diastolic blood pressure;

Changes in physical examination results;

Changes in electrocardiogram (ECG) results.

SAMPLE SIZE DETERMINATION AND RATIONALE.

A total of 75 subjects will be enrolled in this study. The sample size is based on clinical judgment. No statistical power calculation is used to establish the sample size for this proof-of-concept study.

Randomization

An individual, independent of the clinical trial team, will develop the randomization schedules. The actual randomization assignment will be made through an Interactive Web Based Response System (IWRS) called WebView®. Subjects who have provided written informed consent and have met all the inclusion criteria and none of the exclusion criteria will be randomized to one of the treatment groups.

Blinding

All subjects, Investigators and their staff, and all Sponsor/CRO personnel involved in the management of the study will be blinded to treatment assignments.

The contract research organization Information Technology department will be unblinded to treatment. As noted above, the contract research organization Technology department is not otherwise involved with the study.

Treatment unblinding for the study will occur after all clinical data have been received, data inconsistencies have been resolved, and the database is locked, except for safety reasons on a case-by-case basis (i.e., emergency unblinding).

STRATIFICATION. Randomization will be stratified by baseline total symptom score (i.e., using categories ≤4, >4)), and also by age (i.e., using categories <60, ≥60).

INTERIM ANALYSIS. No Interim Analysis (IA) will be performed for efficacy

General Statistical Considerations.

All collected study data will be presented in subject data listings. Statistical analyses will be performed using SAS® for Windows, version 9.4 or later. Descriptive statistics (n, mean, standard deviation, median, minimum and maximum) will be presented for continuous variables. Frequencies and percentages will be presented for categorical variables.

Analysis Populations.

Intent-to-Treat Population. The Modified Intent-to-Treat (mITT) population is defined as the set of subjects who have received at least one dose of leronlimab (PRO 140) or placebo. This population will be used for the analysis of efficacy parameters or measurements.

PP Population. The Per Protocol (PP) population is defined as the set of subjects who meet the Evaluable Population requirements and were not associated with any major protocol violations. This population will be identified before the database lock.

Safety Population. The Safety Population will include all subjects who have received one dose of leronlimab (PRO 140) or placebo. This population will be used for the analysis of safety parameters or measurements.

Covariates. There is no planned inferential statistics and there will be no covariates for this study. Stratification factors will be included in the analysis model.

Missing Data. Every effort will be made to obtain required data at each scheduled evaluation from all subjects who have been randomized to minimize missing data. However, in the event when there is missing data the following imputation methods will be used.

For efficacy evaluations, multiple imputation methods will be used to handle missing data. This imputation method is a robust method to impute missing measurements. The imputation will be carried out in SAS version 9.4 or later using PROC MI. Each imputation model will include the stratification factor as a covariate in the model. The details of multiple imputation will be included in the statistical analysis plan.

Analysis Methods

A SAP will be developed and approved before the database is locked. The SAP will present the detailed statistical methodology to be used in analyzing the data from this trial.

Subject Disposition. The disposition of all subjects who signed an ICF will be provided. The number of subjects screened, screen failed, received at least one treatment, completed, and discontinued during the study, as well as the reasons for all discontinuations will be summarized. Disposition and reason for study discontinuation will also be provided as a by-subject listing.

Demographic and Baseline Characteristics. Demographics and baseline characteristics including medical history, prior and concomitant medications/therapies will be summarized using appropriate descriptive statistics.

Study Outcome Assessment.

Efficacy Summaries. The evaluable population will be the primary analysis population for the analysis of the efficacy outcome measures of the study. All the primary and secondary outcome measures will be analyzed according to the variable type. Continuous data summaries will include:

Number of observations, mean, standard deviation, median, and minimum and maximum values;

Analysis of Covariance (ANCOVA) adjusted for the stratification factors for inferential statistics.

Categorical data summaries will include: Frequency counts and percentages, and Logit model will be used for inferential statistics using the stratification factors.

Safety Summaries.

Adverse Events. Adverse events will be coded using the most recent version of Medical Dictionary for Regulatory Activities (MedDRA). Treatment Emergent AE's (TEAE) are defined as events with an onset on or after the first treatment. TEAEs will be summarized by System Organ Class and preferred term by treatment group. The following TEAE summaries will be provided:

Overall (i.e., regardless of severity or relationship to treatment);

By intensity (mild, moderate, severe, life threatening or death);

By causality (definitely, probably, possibly, remotely or unrelated);

By impact on study treatment (dose increased, dose not changed, dose rate reduced, dose reduced, drug interrupted, drug withdrawn, not applicable, or unknown).

In addition, separate summaries of serious adverse events, and adverse events resulting in discontinuation of study treatment will be presented.

Clinical Laboratory Data. All laboratory values will be listed. Laboratory measurements will also be summarized by treatment group and presented by time point.

ECG. All ECG values will be listed. ECG measurements will also be summarized by treatment group and presented by time point.

Vital Signs. All vital sign findings will be listed and/or summarized by treatment group.

Physical Examination. All physical examination findings will be listed and/or summarized by treatment group.

Adverse Events (Definitions and Reporting)

The Investigator is responsible for the detection and documentation of events meeting the criteria and definition of an AE or SAE, as provided in this protocol. During the study when there is a safety evaluation, the Investigator or site staff will be responsible for detecting, documenting and reporting AEs and SAEs as detailed in this section of the protocol.

ADVERSE EVENT (AE). An adverse event (AE) is defined as any unfavorable or unintended sign, symptom, or disease that occurs or is reported by the patient to have occurred, or a worsening of a pre-existing condition. An adverse event may or may not be related to the study treatment.

AEs will be elicited through direct questioning and subject reports. Any abnormality in physical examination findings or laboratory results that the investigator believes is clinically significant (CS) to the research subject and that occurred after initiation of the first study treatment will be reported as AEs. Abnormal findings that are NOT clinically significant should not be recorded as an AE.

REPORTING OF ADVERSE EVENTS. Report initiation for all AEs and SAEs will begin at the time of the first treatment visit and continue until the end of final study visit. All events will be followed to resolution or until the subject completes the study. A final assessment of outcome will be made at that time.

All AEs must be recorded in the subject's medical records and on the CRF. AEs will be reported using customary medical terminology along with the following information: the onset and end dates, whether the event is considered to be a SAE, the impact the event had on study treatment, the Common Terminology Criteria for Adverse Events (CTCAE) grade (intensity) of the event, the causality of the event, whether treatment was given as a result of the event, and the outcome of the event.

Impact on Study Treatment. The impact the event had on the study treatment will be assessed as either: dose increased, dose not changed, dose rate reduced, dose reduced, drug interrupted, drug withdrawn, not applicable, or unknown. The "not applicable" assessment will be used only when the subject is no longer in the Treatment Phase of the protocol.

CTCAE Grade (Intensity) Assessment. The guidelines outlined in CTCAE v5.0 will be used for assessing the intensity of the event. The general guidelines for assessing the AE grade appear below in Table 13.

TABLE 13

| Grade | Description |
| --- | --- |
| Grade 1 | Mild; asymptomatic or mild symptoms; clinical or diagnostic observations only; intervention not indicated. |
| Grade 2 | Moderate; minimal, local or noninvasive intervention indicated; limiting age-appropriate instrumental activities of daily living (ADL)*. |
| Grade 3 | Severe or medically significant but not immediately life-threatening; hospitalization or prolongation of hospitalization indicated; disabling; limiting self-care ADL†. |
| Grade 4 | Life-threatening consequences; urgent intervention indicated. |

*Instrumental ADL refer to preparing meals, shopping for groceries or clothes, using the telephone, managing money, ect.
†Self-care ADL refers to bathing, dressing and undressing, feeding self, using the toilet, taking medications, and not bedridden.

*Instrumental ADL refers to preparing meals, shopping for groceries or clothes, using the telephone, managing money, etc.

†Self-care ADL refers to bathing, dressing and undressing, feeding self, using the toilet, taking medications, and not bedridden.

Causality Assessment. AEs will be assigned a relationship (causality) to the study treatment. The Investigator will be responsible for determining the relationship between an AE and the study treatment. The type of event, organ system affected, and timing of onset of the event will be factors in assessing the likelihood that an AE is related to the study treatment. Relationship of AEs to study treatment will be classified as follows:

1. Definitely related: This category applies to those AEs that the Investigator feels are incontrovertibly related to the study treatment. An AE may be assigned an attribution of definitely related if or when it meets all of the following criteria: (1) it follows a reasonable temporal sequence from administration of the study treatment; (2) it could not be reasonably explained by the known characteristics of the subject's clinical state, environmental or toxic factors, or other modes of therapy administered to the subject; (3) it follows a known response pattern to treatment with the study treatment.

2. Probably related: This category applies to those AEs which, after careful medical consideration at the time they are evaluated, are felt with a high degree of certainty to be related to the study treatment. An AE may be considered probable if or when (must have three): (1) it follows a reasonable temporal sequence from administration of the study treatment. (2) It could not readily have been produced by subject's clinical state, environmental or toxic factors, or other therapies administered to the subject. (3) Disappears or is decreased upon discontinuation of the study treatment. (4) It follows a known response pattern to treatment with the study treatment.

Possibly related: This category applies to those AEs which, after careful medical consideration at the time they are evaluated, are judged unlikely but cannot be ruled out with certainty to the study treatment. An AE may be considered possible if or when (must have two): (1) it follows a reasonable temporal sequence from administration of the study treatment. (2) It could not readily have been produced by subject's clinical state, environmental or toxic factors, or other therapies administered to the subject. (3) Disappears or is decreased upon discontinuation of the study treatment. (4) It follows a known response pattern to treatment with the study treatment.

4. Remotely related: In general this category can be considered applicable to those AEs which, after careful medical consideration at the time they are evaluated, are judged likely to be unrelated to the study treatment. An AE may be considered unlikely if or when (must have two): (1) it does not follow a reasonable temporal sequence from administration of the study treatment. (2) It could not readily have been produced by subject's clinical state, environmental or toxic factors, or other therapies administered to the subject. (3) Disappears or is decreased upon discontinuation of the study treatment. (4) It does not follow a known response pattern to treatment with the study treatment.

5. Unrelated: This category applies to those AEs which, after careful consideration at the time they are evaluated, are clearly and incontrovertibly due to extraneous causes (disease, environment, etc.) and determined with certainty to have no relationship to the study treatment.

Treatment Given as a Result of the Event. The event impact in terms of treatment provided will be as either: none, medication administered, non-drug therapy administered, surgery performed, hospitalization, or other (with a specification).

Outcome Assessment. The outcome of the event will be assessed as either: fatal, not recovered/not resolved, recovered/resolved, recovered/resolved with sequelae, recovering/resolving, or unknown. Only one AE per subject is allowed to have an outcome assessment as "death." If there are multiple causes of death for a given subject, only the primary cause of death will have an outcome of death.

Serious Adverse Events

A SAE is defined as any AE that:

Results in death;

Is life threatening (the subject is at immediate risk of dying from the adverse experience);

Requires subject's hospitalization or prolongs existing hospitalization;

Results in persistent or significant disability/incapacity;

Is a congenital anomaly/birth defect;

Important medical events that may not result in death, be life-threatening, or require hospitalization may be considered a serious adverse effect when, based upon appropriate medical judgment, they may jeopardize the subject or subject and may require medical or surgical intervention to prevent one of the outcomes listed in this definition.

SAE FOLLOW-UP. All subjects experiencing an SAE, including the discontinued subjects, must be closely followed until sufficient information is obtained to indicate a return to normal status or until the event stabilizes at a level acceptable to the investigator (i.e., recovery, return to baseline status, no further improvement expected, or death).

For each SAE indicated as an unresolved event on the initial report, regardless of whether the subject completed the study or withdrew, the site should submit a follow-up report with updated information.

Results

While not under this phase 2 protocol, two patients with moderate COVID-19, were treated with leronlimab under an Emergency Investigational New Drug (EIND) and subsequently revealed clinical improvement. These patients were removed from external oxygen support one day following leronlimab treatment, and subsequently discharged from the hospital. Based on these results, an additional four patients with moderate COVID-19 have been administered leronlimab and results are pending.

Example 2A

Study to Evaluate the Efficacy and Safety of Leronlimab for Mild to Moderate COVID-19

Brief Summary:

This is a Phase 2, two-arm, randomized, double blind, placebo controlled multicenter study to evaluate the safety and efficacy of leronlimab (PRO 140) in patients with mild-to-moderate symptoms of respiratory illness caused by coronavirus 2019 infection.

Detailed Description:

This is a Phase 2, two-arm, randomized, double blind, placebo controlled multicenter study to evaluate the safety and efficacy of leronlimab (PRO 140) in patients with mild-to-moderate symptoms of respiratory illness caused by coronavirus 2019 infection. Patients will be randomized to receive weekly doses of 700 mg leronlimab (PRO 140), or placebo. Leronlimab (PRO 140) and placebo will be administered via subcutaneous injection.

The study will have three phases: Screening Period, Treatment Period, and Follow-Up Period.

A total of 75 subjects will be randomized 2:1 in this study.

Arms and Interventions

Drug: Leronlimab (700 mg). Leronlimab (PRO) 140 is a humanized IgG4, monoclonal antibody (mAb) to the C-C chemokine receptor type 5 (CCR5). Other Name: PRO 140.

Placebo Comparator: Placebo.

Outcome Measures:
Primary Outcome Measures:
1. Clinical Improvement as assessed by change in total symptom score (for fever, myalgia, dyspnea and cough) [Time Frame: Day 14]
Note: The total score per patient ranges from 0 to 12 points. Each symptom is graded from 0 to 3. [0=none, 1=mild, 2=moderate, and 3=severe]. Higher scores mean a worse outcome.

Secondary Outcome Measures:
1. Time to clinical resolution (TTCR) [Time Frame: Day 14]
2. Change from baseline in National Early Warning Score 2 (NEWS2) [Time Frame: Days 3, 7, and 14]
This score is based on 7 clinical parameters (respiration rate, oxygen saturation, any supplemental oxygen, temperature, systolic blood pressure, heart rate, level of consciousness). Higher scores mean a worse outcome.
3. Change from baseline in pulse oxygen saturation (SpO2) [Time Frame: Days 3, 7, and 14]
4. Change from baseline in the patient's health status on a 7-category ordinal scale [Time Frame: Days 3, 7, and 14]
A 7-category ordinal scale of patient health status ranges from: 1) Death; 2) Hospitalized, on invasive mechanical ventilation or extracorporeal membrane oxygenation (ECMO); 3) Hospitalized, on non-invasive ventilation or high flow oxygen devices; 4) Hospitalized, requiring supplemental oxygen; 5) Hospitalized, not requiring supplemental oxygen; 6) Not hospitalized, limitation on activities; 7) Not hospitalized, no limitations on activities.
Lower scores mean a worse outcome.
5. Incidence of hospitalization [Time Frame: Day 14]
6. Duration (days) of hospitalization [Time Frame: Day 14]
7. Incidence of mechanical ventilation supply [Time Frame: Day 14]
8. Duration (days) of mechanical ventilation supply [Time Frame: Day 14]
9. Incidence of oxygen use [Time Frame: Day 14]
10. Duration (days) of oxygen use [Time Frame: Day 14]
11. Mortality rate [Time Frame: Day 14]
12. Time to return to normal activity [Time Frame: Day 14]

Other Outcome Measures:
1. Change in size of lesion area by chest radiograph or CT [Time Frame: Day 14]
2. Change from baseline in serum cytokine and chemokine levels [Time Frame: Days 3, 7, and 14]
3. Change from baseline in CCR5 receptor occupancy levels for Tregs and macrophages [Time Frame: Days 3, 7, and 14]
4. Change from baseline in CD3+, CD4+ and CD8+ T cell count [Time Frame: Days 3, 7, and 14]

Eligibility Criteria
Inclusion Criteria:
1. Male or female adult ≥18 years of age at time of enrollment.
2. Subjects with mild-to-moderate symptoms of respiratory illness caused by coronavirus 2019 infection as defined below:
   Mild (uncomplicated) Illness:
      Diagnosed with COVID-19 by a standardized RT-PCR assay AND
      Mild symptoms, such as fever, rhinorrhea, mild cough, sore throat, malaise, headache, muscle pain, or malaise, but with no shortness of breath AND
      No signs of a more serious lower airway disease AND
      RR<20, HR<90, oxygen saturation (pulse oximetry) >93% on room air
   Moderate Illness:
      Diagnosed with COVID-19 by a standardized RT-PCR assay AND
      In addition to symptoms above, more significant lower respiratory symptoms, including shortness of breath (at rest or with exertion) OR
      Signs of moderate pneumonia, including RR ≥20 but <30, HR ≥90 but less than 125, oxygen saturation (pulse oximetry) >93% on room air AND
      If available, lung infiltrates based on X-ray or CT scan <50% present
3. Clinically normal resting 12-lead ECG at Screening Visit or, if abnormal, considered not clinically significant by the Principal Investigator.
4. Subject (or legally authorized representative) provides written informed consent prior to initiation of any study procedures.
5. Understands and agrees to comply with planned study procedures.
6. Women of childbearing potential must agree to use at least one medically accepted method of contraception (e.g., barrier contraceptives [condom, or diaphragm with a spermicidal gel], hormonal contraceptives [implants, injectables, combination oral contraceptives, transdermal patches, or contraceptive rings], or intrauterine devices) for the duration of the study.

Exclusion Criteria:
1. Subjects showing signs of acute respiratory distress syndrome (ARDS) or respiratory failure necessitating mechanical ventilation at the time of screening;
2. History of severe chronic respiratory disease and requirement for long-term oxygen therapy;
3. Subjects showing signs of clinical jaundice at the time of screening;
4. History of moderate and severe liver disease (Child-Pugh score >12);
5. Subjects requiring Renal Replacement Therapy (RRT) at the time of screening;
6. History of severe chronic kidney disease or requiring dialysis;
7. Any uncontrolled active systemic infection requiring admission to an intensive care unit (ICU); Note: Subjects infected with chronic hepatitis B virus or hepatitis C virus will be eligible for the study if they have no signs of hepatic decompensation.
Note: Subjects infected with HIV-1 will be eligible for the study with undetectable viral load and are on a stable ART regimen. Investigators are required to review the subjects' medical records to confirm HIV-1 RNA suppression within the previous 3 months.
Note: Empirical antibiotic treatment for secondary bacterial infections is allowed during the course of study.
8. Patients with malignant tumor, or other serious systemic diseases;
9. Patients who are participating in other clinical trials;
10. Patients who have a history of allergic reactions attributed to compounds of similar chemical or biologic composition to leronlimab (PRO 140) are not eligible; and Inability to provide informed consent or to comply with test requirements

Example 3

Study Protocol for Use of Leronlimab to Treat Severe COVID-19

Assessment of Plasma Cytokine and Chemokine Levels.

Fresh plasma was used for cytokine quantification using a customized 13-plex bead-based flow cytometric assay (LegendPlex, Biolegend, Inc) on a CytoFlex flow cytometer. For each patient sample 25 µL of plasma was used in each well of a 96-well plate. Raw data was analyzed using LegendPlex software (Biolegend, Inc., San Diego, Calif.). Samples were run in duplicate. In addition, split sample confirmation testing was performed by ELISA (MDBiosciences, Minneapolis, Minn.). A 48-plex cytokine/chemokine/growth factor panel and RANTES-CCL5 (Millipore Sigma) assay were performed following manufacturer's protocol on a Luminex MAGPIX instrument. Confirmation testing was also performed in duplicate. Samples falling outside the linear range of the appropriate standard curves were diluted and repeated incorporating the dilution factor into the final average. Cytokine, chemokines, and growth factors assessed included: sCD40L, EGF, Eotaxin, FGF-2, Flt-3, Fractalkine, G-CSF, GM-CSF, GRO-α, IFNα2, IFNγ, IL-1α, IL-1β, IL-1ra, IL-2, IL-3, IL-4, IL-5, IL-5, IL-6, IL-7, IL-8, IL-9, IL-10, IL-12 (p40), IL-12 (p70), IL-13, IL-15, IL-17A, IL-17E/IL-25, IL-17F, IL-18, IL-22, IL-27, IP-10, MCP-1, MCP-3, M-CSF, MDC, MIG, MIP-1α, MIP-1β, PDGF-AA, PDGF-AB/BB, RANTES, TGF-α, TNF-α, TNF-β, and VEGF.

Flow Cytometry.

Figure 21A:
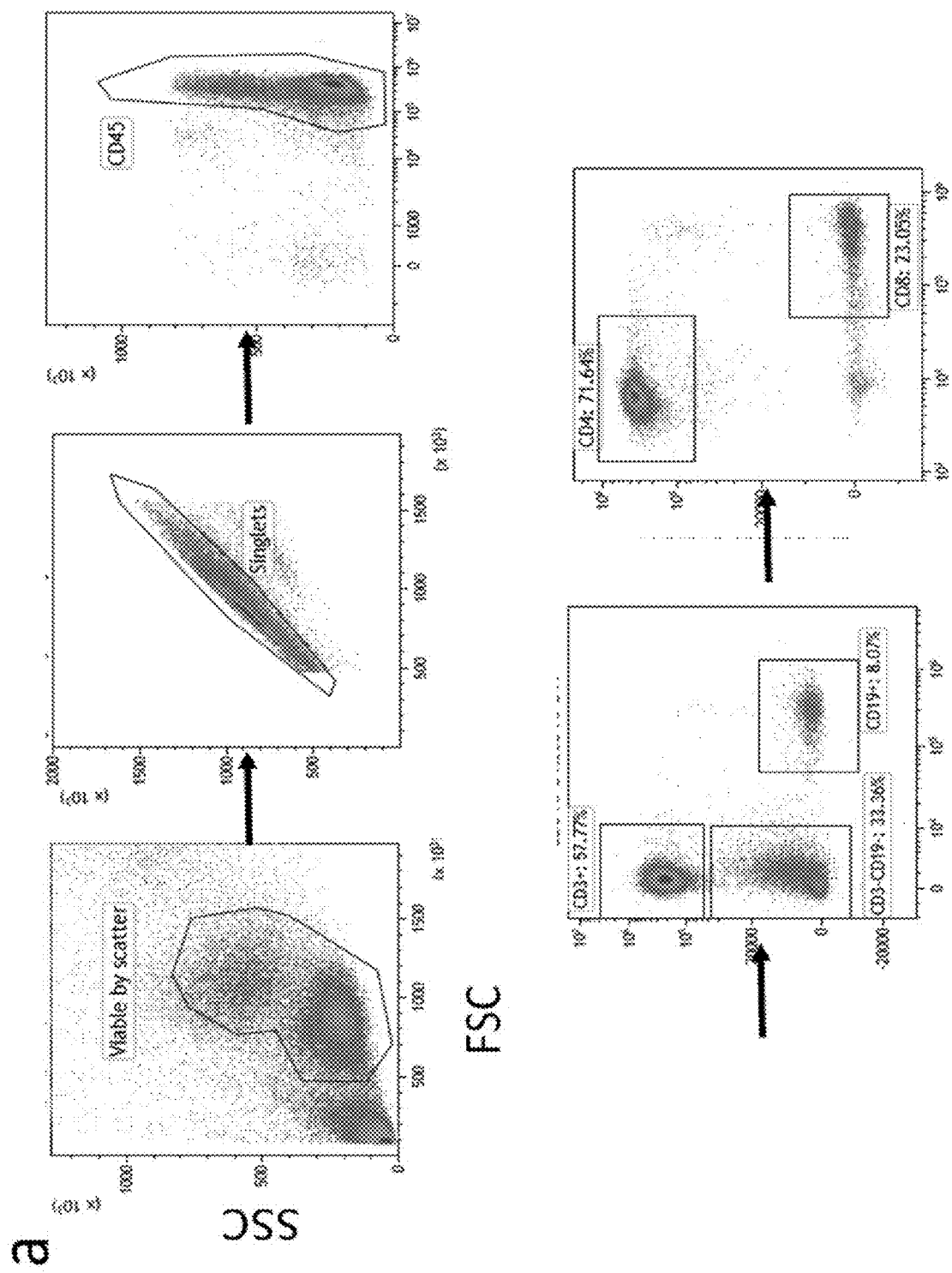
FIGS. 21A and 21B show example gating strategy for flow cytometry. Gating hierarchy for determination of peripheral blood CD4+ an CD8+ T cells: viable/singlets/CD45+/CD3+CD19-/CD4+ or CD8+(FIG. 21A), and for peripheral blood monocytes: viable/singlets/CD45+/CD3-CD19-/CD14+CD16+ according to methods (FIG. 21B).
Figure 21B:
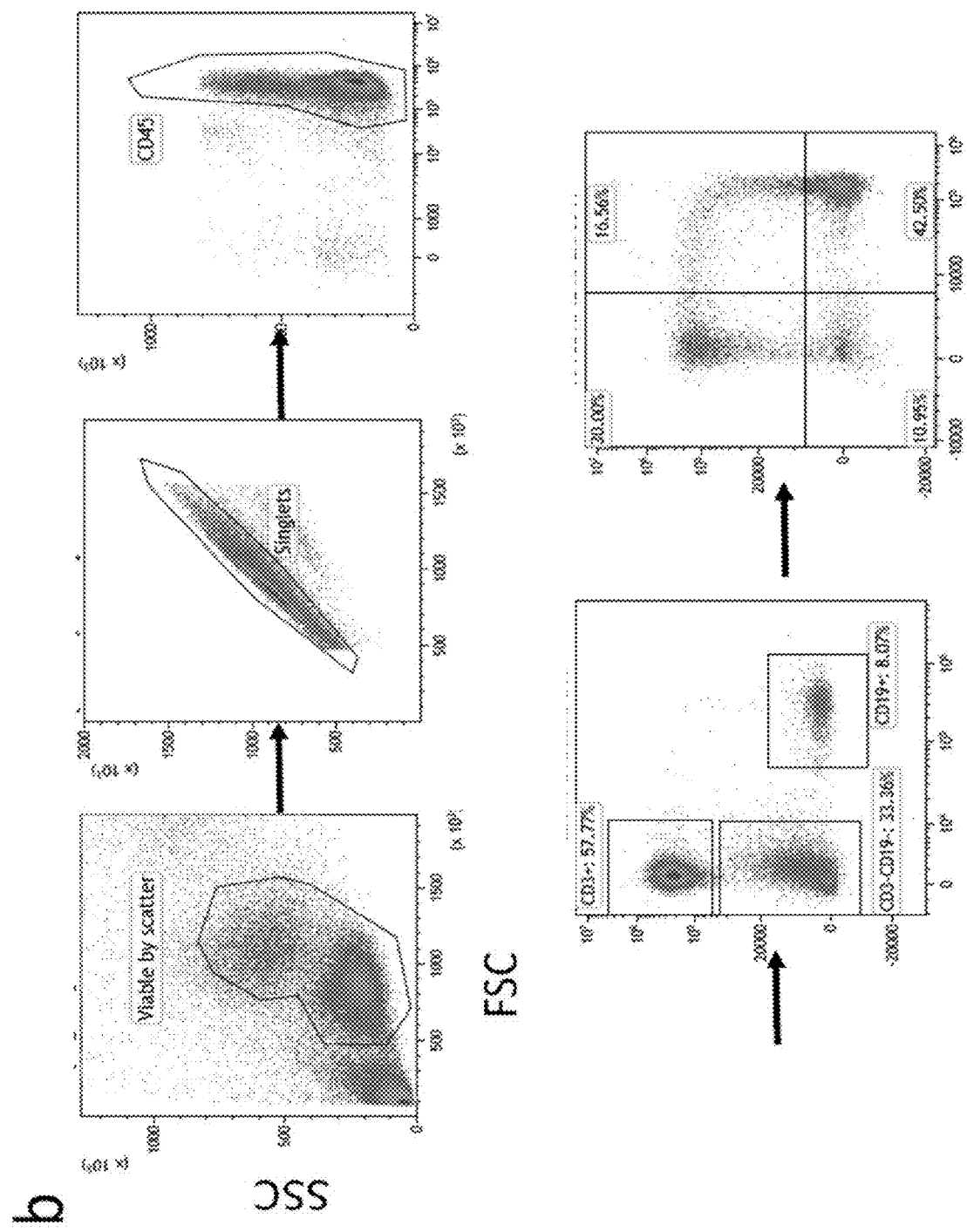

Peripheral blood mononuclear cells were isolated from peripheral blood using Lymphoprep density gradient (STEMCELL Technologies, Vancouver, Canada). Aliquots of cells were frozen in media that contained 90% fetal bovine serum (HyClone, Logan, Utah) and 10% dimethyl sulfoxide (Sigma-Aldrich, St. Louis, Mo.) and stored at −70 C. Cells were quick thawed, washed, and incubated with 2% solution of bovine serum albumin (Blocker BSA, ThermoFisher, Waltham, Mass.) diluted in D-PBS (HyClone) for 5 min. Each sample received a cocktail containing 10 µL Brilliant Stain Buffer (BD Biosciences, Franklin Lakes, N.J.), 5 µL True-Stain Monocyte Blocker (BioLegend, San Diego, Calif.), and the following surface marker antibodies: anti-CD19 (PE-Dazzle594), anti-CD3 (APC), anti-CD16 (Alexa700), HLA-DR (APC/Fire750), and anti-CTLA-4 (PE-Cy7). The following antibodies were then added to each tube individually: anti-CD8 (BUV496), anti-CD4 (BUV661), anti-CD45 (BUV805), anti-CD103 (BV421), anti-TIM3 (BV605), anti-CD56 (BV650), anti-LAG-3 (BV711), anti-CD14 (BB785), and anti-PD-1 (BB700), followed by a 30 min. incubation in the dark at room temperature. Cells were washed once with 2% BSA solution before fixation and permeabilization. Cells were fixed and permeabilized in a one-step reaction with 1×incellMAX (IncellDx, Inc. San Carlos, Calif.) at a concentration of 1 million cells per mL and incubated for 60 min. in the dark at room temperature. Cells were washed once with 2% BSA solution and analyzed on a Cytoflex LX with 355 nm (20 mW), 405 nm (80 mW), 488 nm (50 mW), 561 nm (30 mW), 638 nm (50 mW), and 808 nm (60 mW) lasers (Beckman Coulter Life Sciences, Indianapolis, Ind.). Analysis was performed with Kaluza version 2.1 software. The panel used is shown in FIG. 20 and examples of the gating strategy is shown in FIG. 21A and FIG. 21B.

CCR5 Receptor Occupancy.

Figure 22:
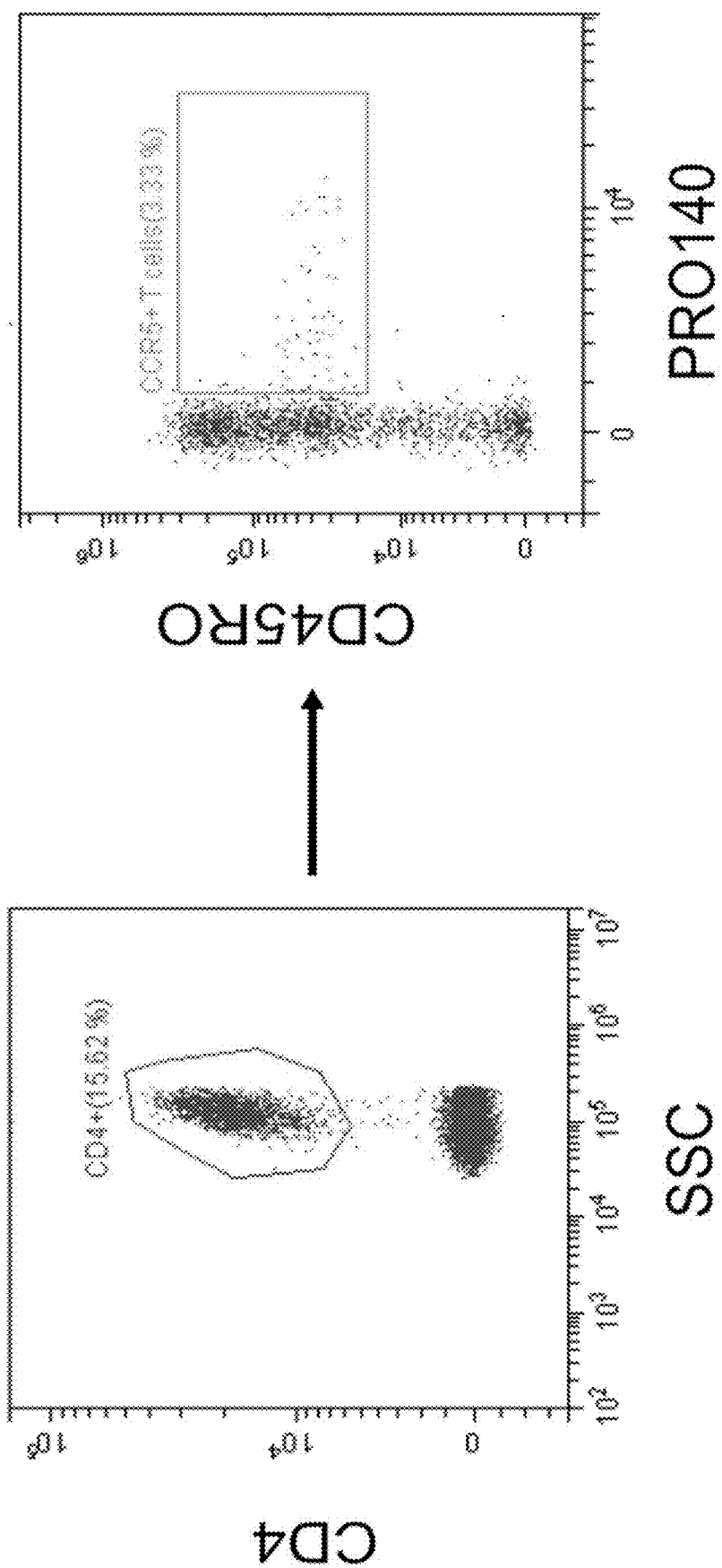
FIG. 22 shows an example gating strategy of CCR5 receptor occupancy for flow cytometry. Leronlimab-PE was used to stain the peripheral blood of a COVID-19 patient that had received 700 mg subcutaneous Leronlimab.

CCR5 receptor occupancy by leronlimab was determined using phycoerythrin-labeled leronlimab (IncellDx, Inc.) in a competitive flow cytometry assay. CCR5-expressing immune cells including CD4+, CD45RO+T-lymphocytes, CD4+, FoxP3+T-regulatory cells, and CD14+, CD16+ monocytes/macrophages were included in the panel using the appropriate immunophenotypic markers for each population in addition to PE-labeled leronlimab. Cells were incubated for 30 min. in the dark at room temperature and washed twice with 2% BSA solution before flow acquisition on a 3-laser CytoFLEX fitted with 405 nm (80 mW), 488 nm (50 mW), and 638 nm (50 mW) lasers (Beckman Coulter Life Sciences, Indianapolis, Ind. Life Sciences, Indianapolis, Ind.). Receptor occupancy was determined by the loss of CCR5 detection over time (FIG. 22) and calculated with the following equation: $1-AB \times 100$ where A is Day 0 and B is Day 7.

Measurement of Plasma SARS-CoV-2 Viral Loads.

The QIAamp Viral Mini Kit (Qiagen, Catalog #52906) was used to extract nucleic acids from 300-400 µL from plasma samples according to instructions from the manufacturer and eluted in 50 µL of AVE buffer (RNase-free water with 0.04% sodium azide). The purified nucleic acids were used immediately with the Bio-Rad SARS-CoV-2 ddPCR Kit (Bio-Rad, Hercules, Calif.). Each batch of samples extracted comprised positive and extraction controls which are included in the kit, as well as a no template control (nuclease free water). The Bio-Rad SARS-CoV-2 ddPCR Test is a reverse transcription (RT) droplet digital polymerase chain reaction (ddPCR) test designed to detect RNA from SARS-CoV-2. The oligonucleotide primers and probes for detection of SARS-CoV-2 are the same as those reported by CDC and were selected from regions of the viral nucleocapsid (N) gene. The panel is designed for specific detection of the 2019-nCoV (two primer/probe sets). An additional primer/probe set to detect the human RNase P gene (RP) in control samples and clinical specimens is also included in the panel as an internal control. The Bio-Rad SARS-CoV-2 ddPCR Kit includes these three sets of primers/probes into a single assay multiplex to enable a one-well reaction. RNA isolated and purified from the plasma samples (5.5 µL) were added to the mastermix comprised of 1.1 µL of 2019-nCoV triplex assay, 2.2 µL of reverse transcriptase, 5.5 µL of supermix, 1.1 µL of Dithiothreitol (DTT) and 6.6 µL of nuclease-free water. Twenty-two microliters (22 µl) from these sample and mastermix RT-ddPCR mixtures were loaded into the wells of a 96-well PCR plate. The mixtures were then fractionated into up to 20,000 nanoliter-sized droplets in the form of a water-in-oil emulsion in the QX200 Automated Droplet Generator (Bio-Rad, Hercules Calif.). The 96-well RT-ddPCR ready plate containing droplets was sealed with foil using a plate sealer and thermocycled to achieve reverse transcription of RNA followed by PCR amplification of cDNA in a C1000 Touch thermocycler (Bio-Rad, Hercules Calif.). Subsequent to PCR, the plate was loaded into the QX200 Droplet Reader (Bio-Rad, Hercules Calif.) and the fluorescence intensity of each droplet was measured in two channels (FAM and HEX). The Droplet Reader singulates the droplets and flows them past a two-color fluorescence detector. The detector reads the droplets to determine which contain target (positive) and which do not (negative) for each of the targets identified with the Bio-Rad SARS-CoV-2 ddPCR Test: N1, N2, and RP. The fluorescence data is then analyzed by the QuantaSoft 1.7 and QuantaSoft Analysis Pro 1.0 Software to determine the presence of SARS-CoV-2 N1 and N2 in the specimen.

| Bio-Rad SARS-CoV-2 RT-ddPCR Thermal Cycling Protocol | | | |
|---|---|---|---|
| Cycling Step | Temperature (° C.) | Time | Number of Cycles |
| Reverse Transcription | 50 | 60 minutes | 1 |
| PCR enzyme activation | 95 | 10 minutes | 1 |
| Template Denaturation | 94 | 30 seconds | 40 |
| Annealing/Extension | 55 | 60 seconds | |
| Droplet Stabilization | 4 | 30 minutes | 1 |
| Hold (optional) | 4 | Overnight | 1 |

Patient Samples and IRB.

All patients were enrolled in this study under an FDA emergency use authorization (EUA). Informed consent was obtained from patients following approval by the institutional review board (IRB). One 8 mL EDTA tube and one 4 mL plasma preparation (PPT) tube were drawn by venipuncture at Day 0 (pre-treatment), Day 3, Day 7, and Day 14 (post-treatment). Blood was shipped overnight to IncellDX for processing and analysis. Peripheral blood mononuclear cells (PBMC) were isolated from peripheral blood using Lymphoprep density gradient (STEMCELL Technologies, Vancouver, Canada). Aliquots of cells were frozen in media that contained 90% fetal bovine serum (HyClone, Logan, Utah) and 10% dimethyl sulfoxide (Sigma-Aldrich, St. Louis, Mo.) and stored at −70 C.

Statistical Analysis.

The inflammatory cytokines IL-1β, IL-6, IL-8, and CCL5 levels between groups were compared using non-parametric Kruskal-Wallis test followed by Dunn's multiple comparison correction to control the experimental wise error rate. To assess reversal of immune dysfunction and CCR5 receptor occupancy as well as cytokine and chemokine levels in severe COVID-19 patients after Leronlimab, Kruskal-Wallis test with Dunn's multiple comparison correction was used. Changes in SARS-CoV-2 plasma viral loads were assessed using the Mann-Whitney test.

10× Genomics 5' Single-Cell RNA-Sequencing

Cryopreserved PBMC cells were thawed in RMPI 1640 complete medium, washed in PBS BSA 0.5%, and cell number and viability measured using a Countess II automated cell counter (Thermo Fisher Scientific). Cells were then diluted to a concentration of 1 million cells per mL for loading into the 10× chip. Single-cell RNA-Sequencing library preparation occurred with the Chromium Next GEM Single Cell Immune Profiling (v.1.1 Chemistry) according to manufacturer's protocols on a Chromium Controller instrument. The library was sequenced using a High Output Flowcell and Illumina NextSeq 500 instrument. For data processing, Cellranger (v.3.0.2) mkfastq was applied to the Illumina BCL output to produce FASTQ files. Cellranger count was then applied to each FASTQ file to produce a feature barcoding and gene expression matrix. Cellranger aggr was used to combine samples for merged analysis. For quality control, the Seurat package for cell clustering and differential expression analyses was applied.

Treatment and Preliminary Outcomes Under Study Protocol for Use of Leronlimab to Treat Severe COVID-19

Treatment with leronlimab is being administered under an EIND recently granted by the U.S. Food and Drug Administration (FDA). Leronlimab treatment is intended to serve as a therapy for patients who experience respiratory complications as a result of contracting SARS-CoV-2 causing the Coronavirus Disease 2019 (COVID-19).

So far at least 54 patients have been approved for treatment and 49 patients have been treated under this emergency IND, with results still pending.

Eleven patients were treated in a New York hospital. All treated patients were in Intensive Care Units (ICU) because of acute respiratory failure, eight of whom were intubated (placed on mechanical ventilation). One patient was not intubated because of poor baseline pulmonary status (history of lung cancer and had undergone bilateral upper lobectomy). Seven patients were organ-transplant recipients (six patients were renal-transplant recipients and one patient had a history of heart transplant) and were on immunosuppressive regimen. Ten patients were on dialysis and nine were on vasopressors during hospitalization. Despite their pre-existing and severe conditions, the lives of four patients were saved. All patient blood samples were evaluated and important powerful results from the effect of leronlimab were demonstrated in almost all of these patients. Interim study data for at least ten of the eleven patients ("Patient 1" through "Patient 10") treated for severe COVID-19 in New York are available and described herein. Limited data is available for Patient 11.

One patient was treated with leronlimab in another New York hospital. This patient was taken off oxygen and discharged from the hospital after leronlimab treatment.

Twenty-three patients in a Southern California hospital were treated with leronlimab. Six patients were in critical condition (intubated) and 17 patients were severely-ill, needing oxygen support. No death was reported. Out of the six critical patients, three were extubated (taken off ventilator), two patients remain relatively stable and still breathing with the assistance of a ventilator, and one patient had shown deterioration in respiratory parameters. Of 17 patients in severe condition (but not critical), 11 patients demonstrated improvement in respiratory parameters (eight patients were discharged from hospital), two patients remain relatively stable, two patients have shown deterioration in respiratory parameters, and information is pending for two recently treated patients.

Three patients were treated in a Georgia hospital. All three patients were ICU patients and were intubated. Two of the three patients had renal failure at the start of leronlimab treatment. Of these three patients, two were extubated (taken off ventilator) and one patient remains on a ventilator but is improving.

One patient was treated in a Northern California hospital. This patient is now weaning from ventilator and has been transferred to rehabilitation hospital.

Patient characteristics, pre-existing conditions and clinical status prior to start of Leronlimab treatment for Patient 1 through Patient 10 are shown in FIG. 11.

Figures 15A, 15B, 15C, 15D:
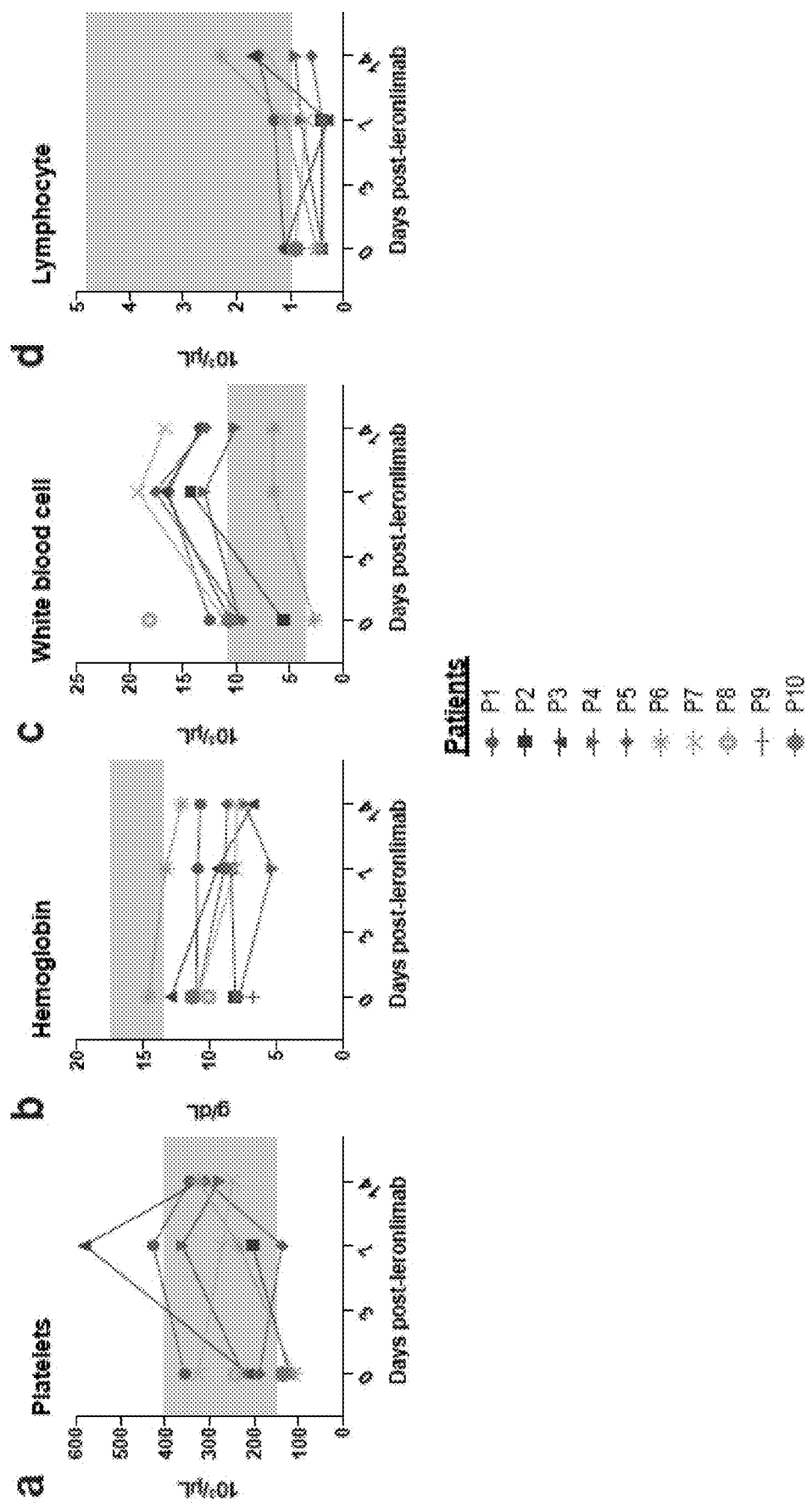
FIGS. 15A-15N show complete blood count and serum chemistry values in critically ill COVID-19 patients after leronlimab administration. Peripheral blood levels of platelets (FIG. 15A), hemoglobin (FIG. 15B), white blood cells (FIG. 15C), and lymphocytes (FIG. 15D). Serum levels of ferritin (FIG. 15E), C-reactive protein (FIG. 15F), Procalcitonin (FIG. 15G), D-dimer, values >20 graphed as 20 (FIG. 15H), aspartate aminotransferases (AST), values <20 graphed as 0 (FIG. 15I), alanine aminotransferase (ALT), values <10 graphed as 0 (FIG. 15J), blood urea nitrogen (BUN) (FIG. 15K), creatinine (CREA) (FIG. 15L), sodium (FIG. 15M), and total bilirubin (FIG. 15N). Gray boxes indicate standard reference ranges for each parameter.
Figures 15E, 15F, 15G, 15H:
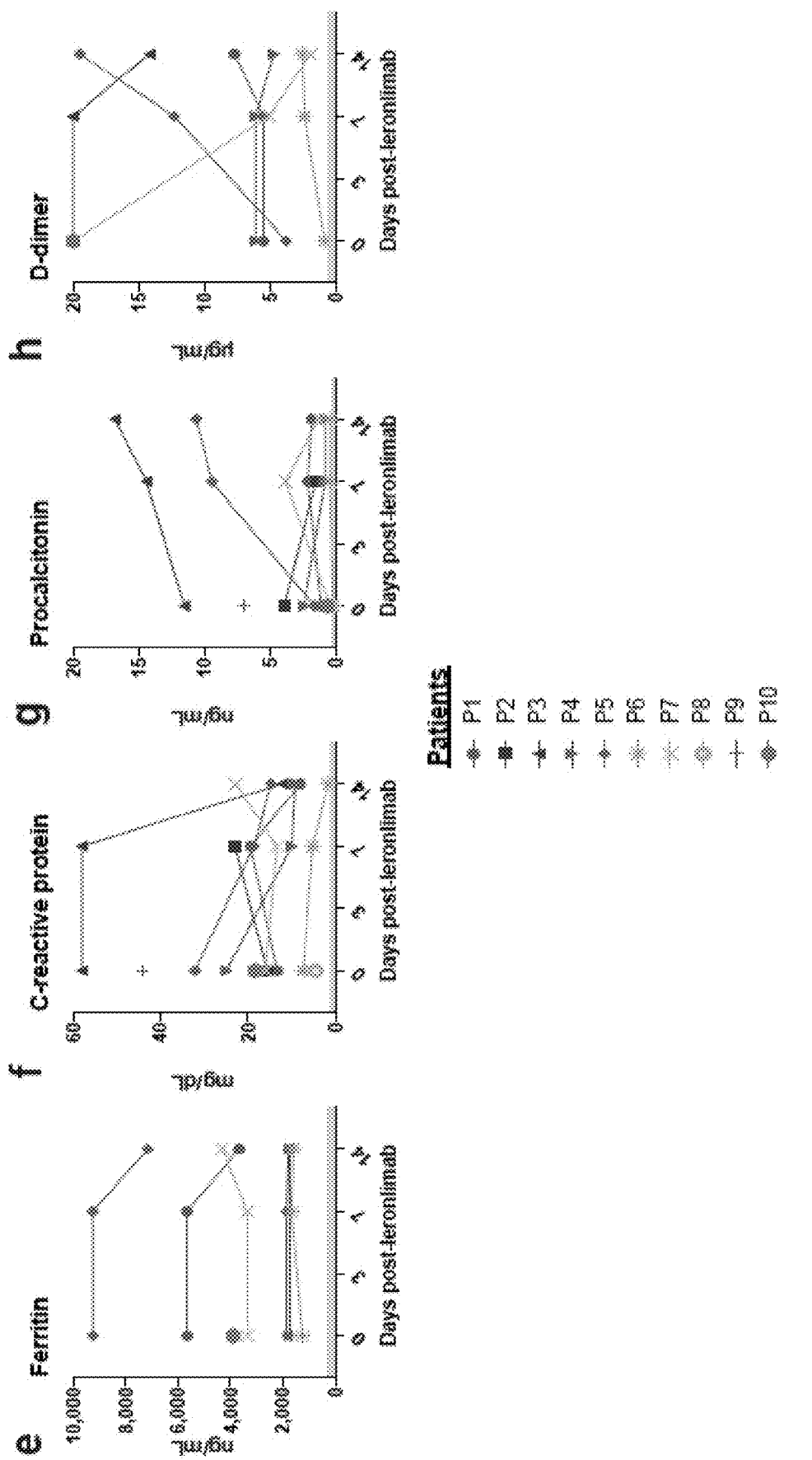
Figures 15I, 15J, 15K, 15L:
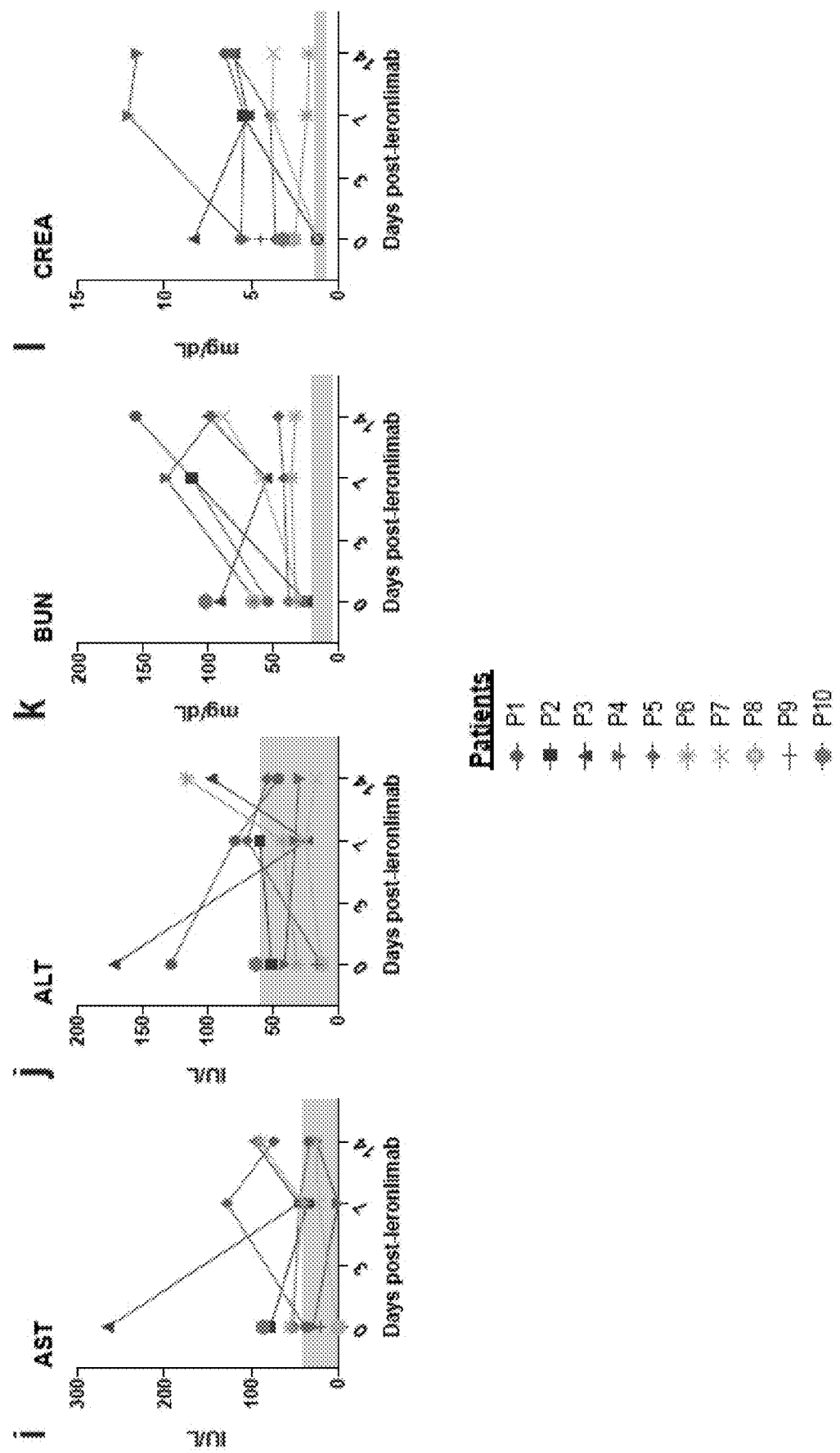
Figures 15M, 15N:
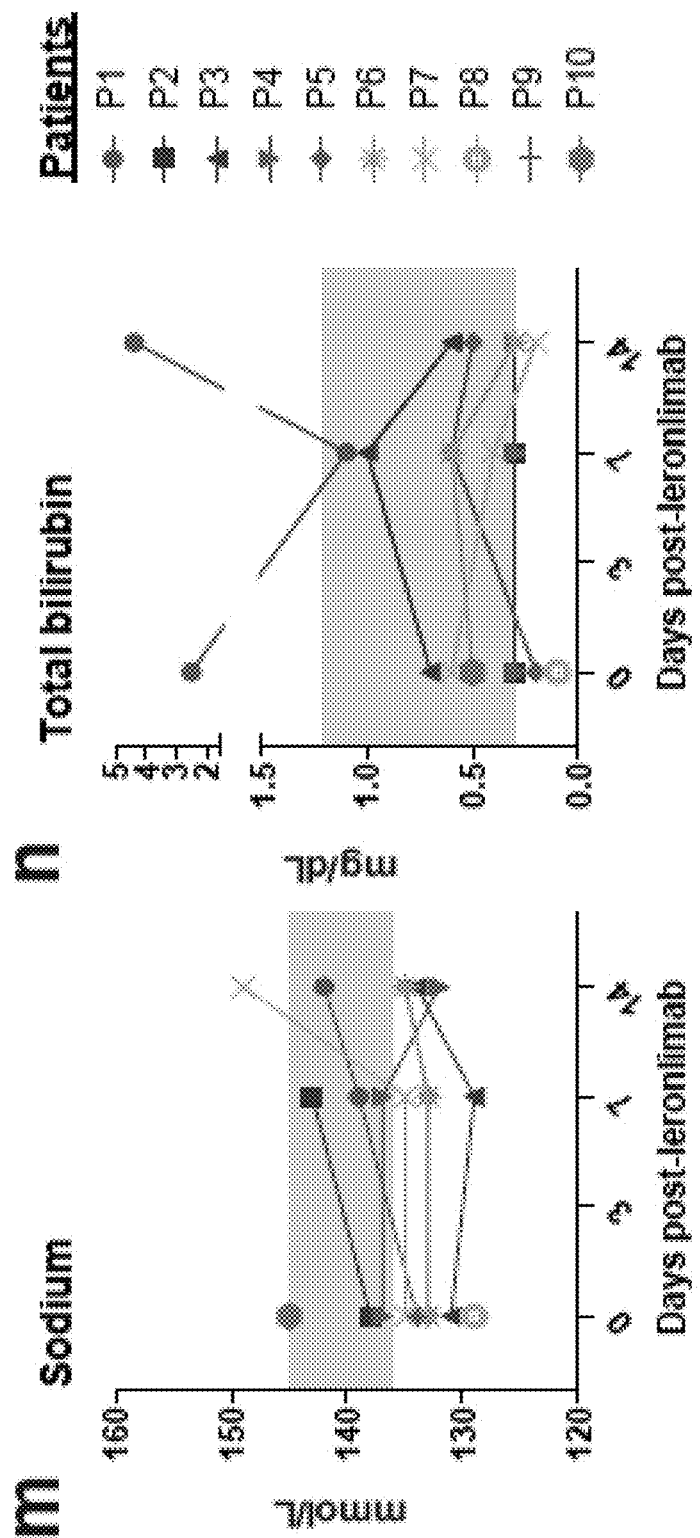
Figure 17A:
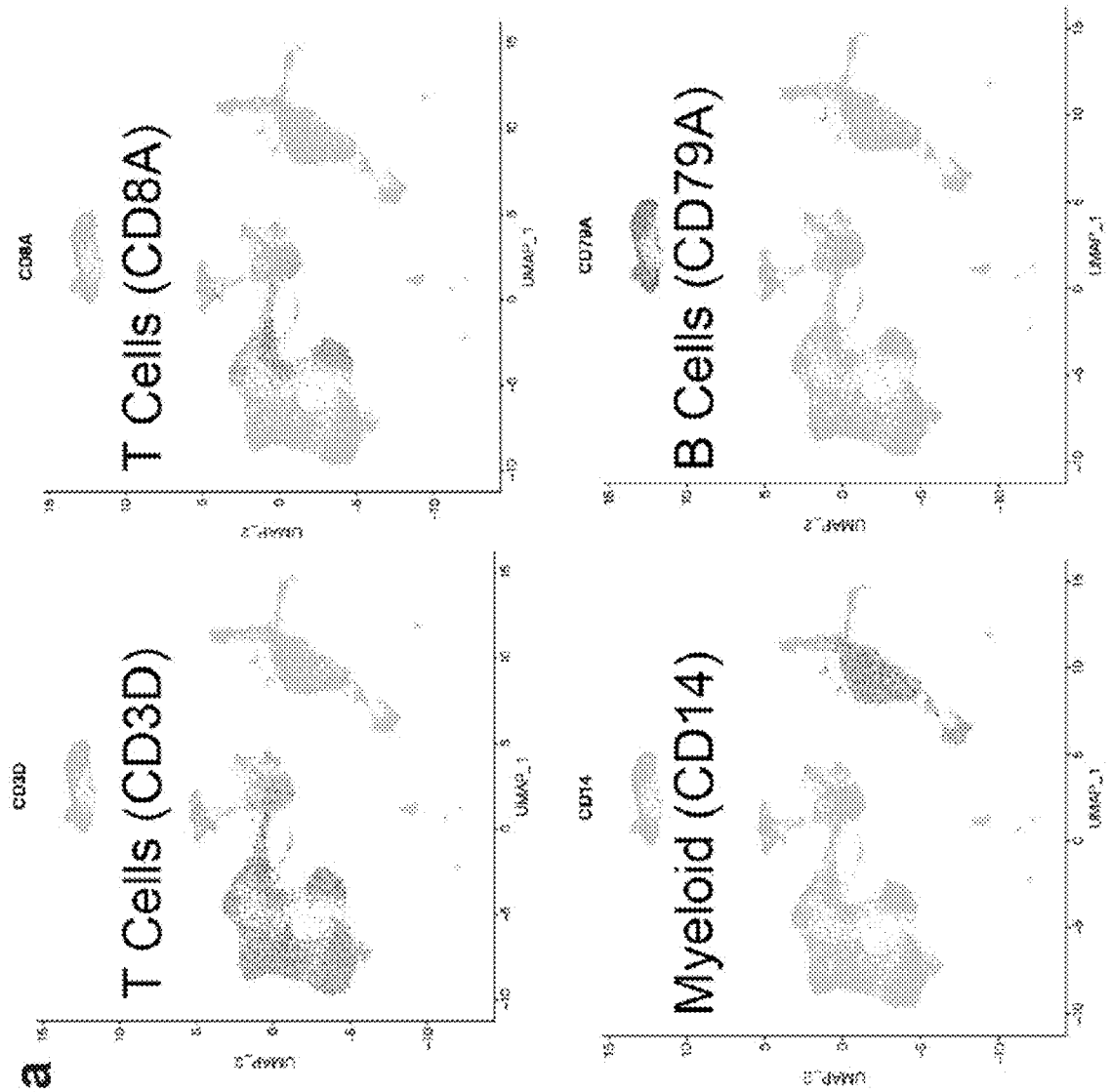
FIGS. 17A-17K show single-cell transcriptomics associated with COVID-19. UMAP feature plots of single-cell transcriptome profiles of CD3+ T cells versus CD8+ T cells versus CD14+ myeloid cells versus CD79a B cells (FIG. 17A), CXCL8 (FIG. 17B), IL-1β (FIG. 17C), CCL3 (FIG. 17D), KLRB1 (FIG. 17E), CCL4 (FIG. 17F), CD69 (FIG. 17G), CCL5 (FIG. 17H), IFITM3 (FIG. 17I), IFI27 (FIG. 17J), and Granzyme A (FIG. 17K) in a donor uninfected SARS-CoV-2 participant and severe COVID-19 participants.
Figures 17B, 17C:
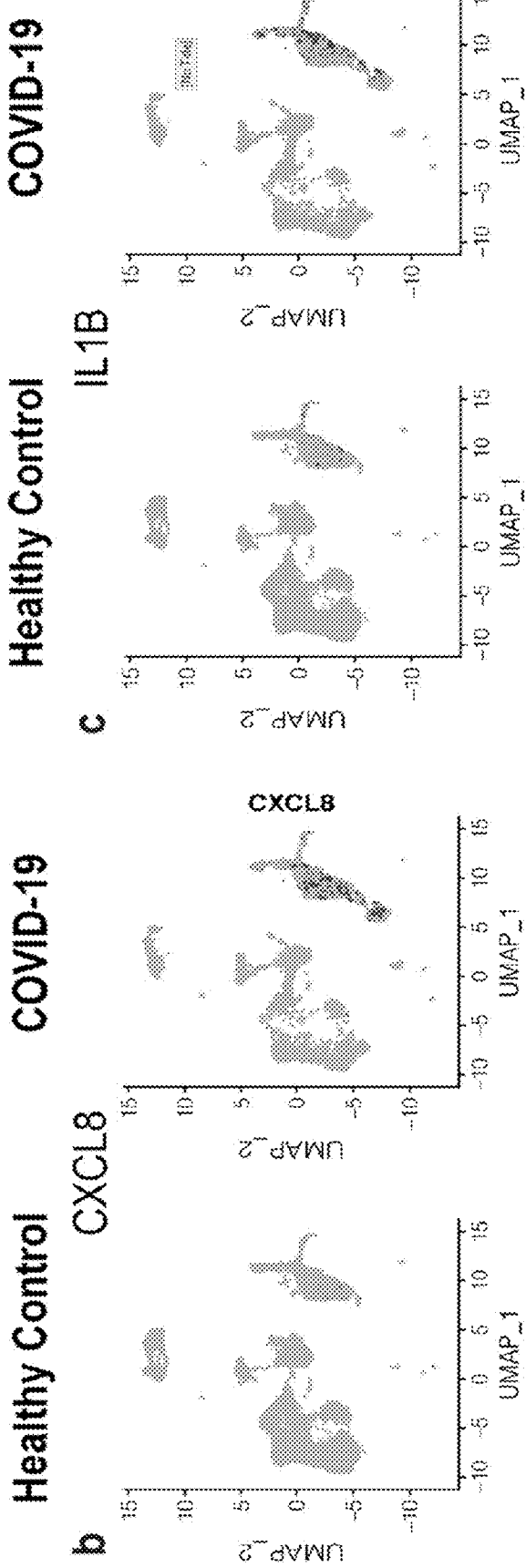
Figures 17D, 17E:
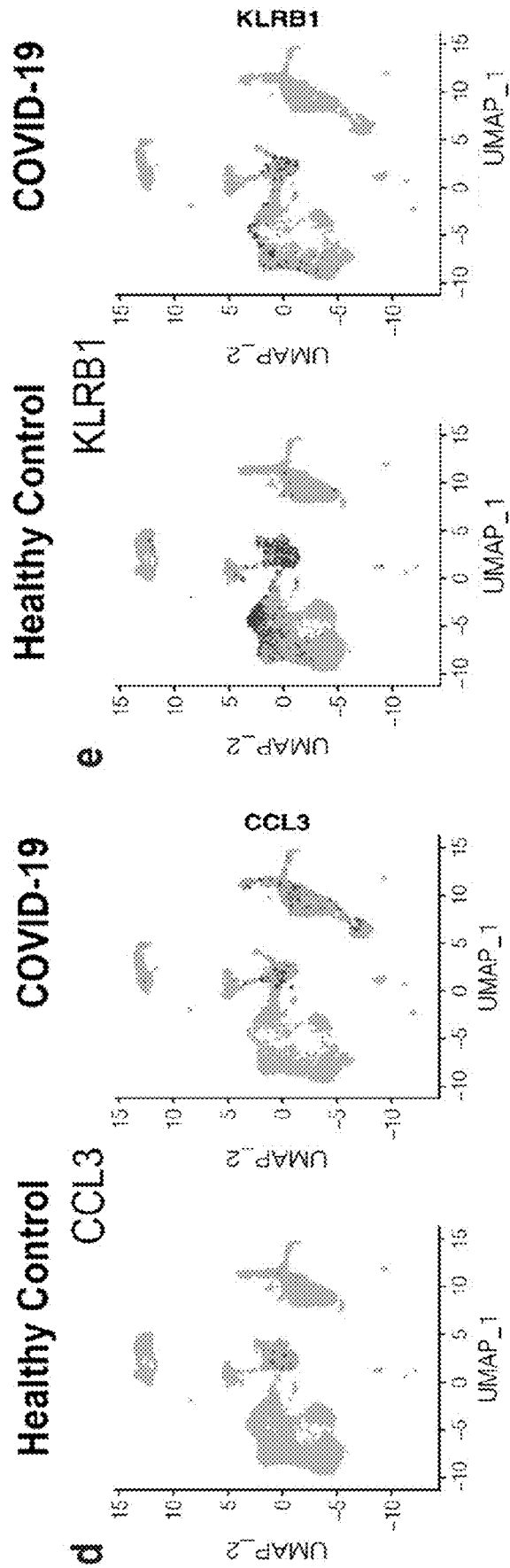
Figures 17F, 17G:
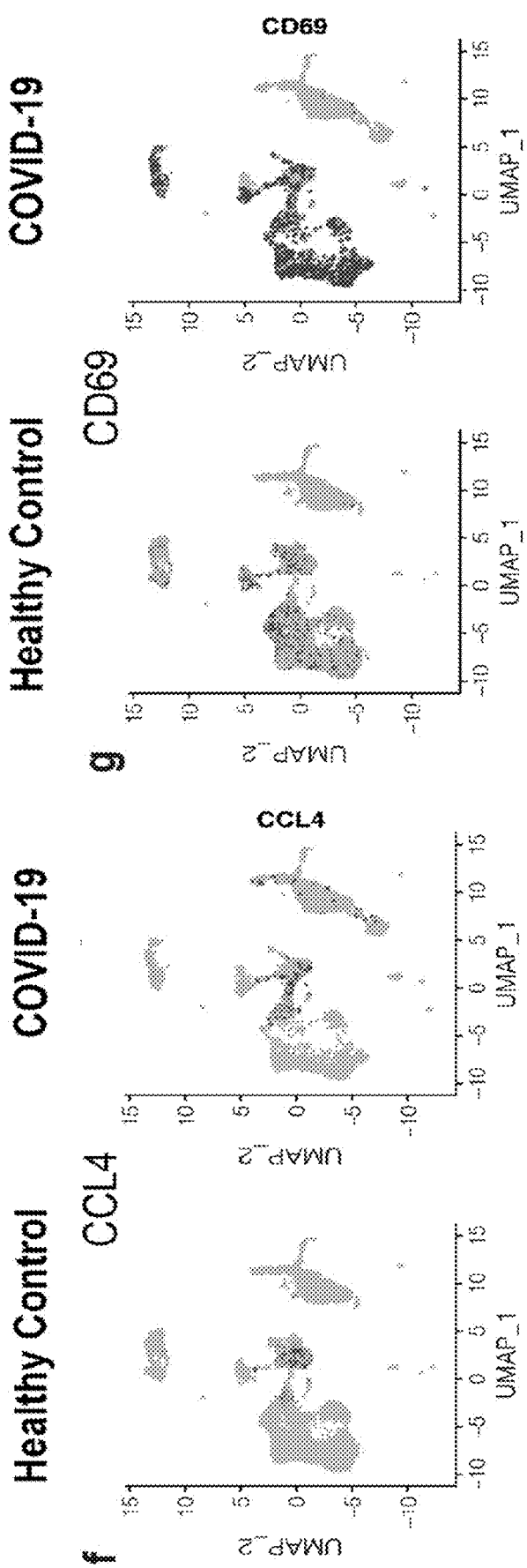
Figures 17H, 17I:
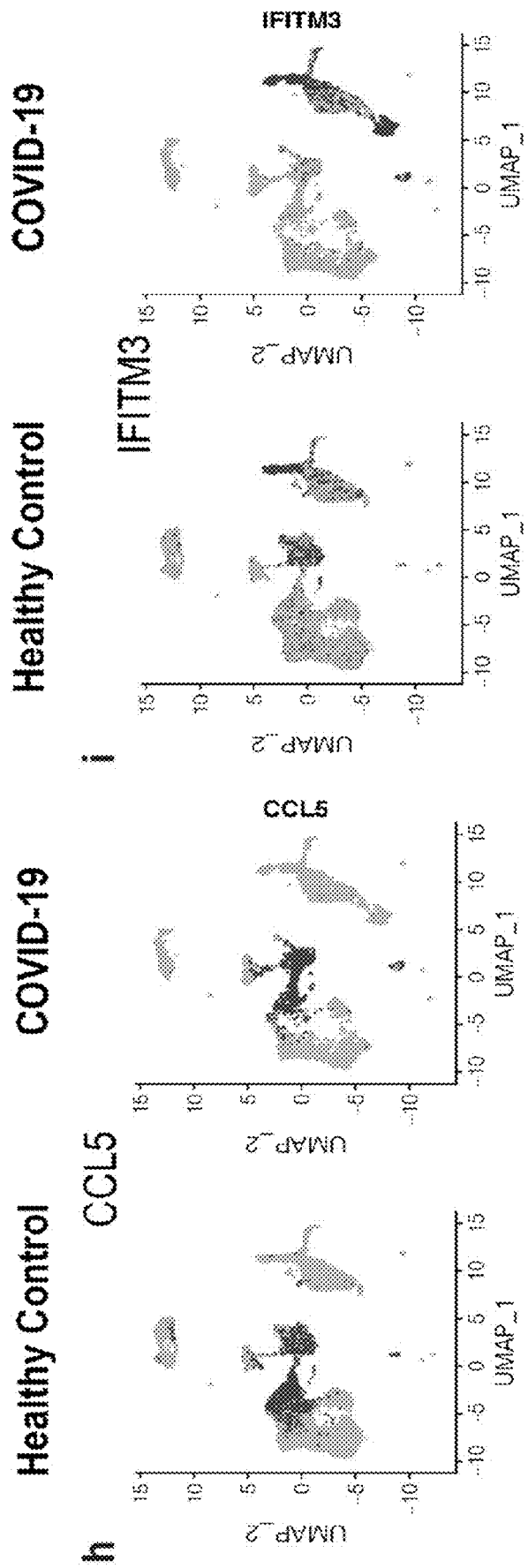
Figures 17J, 17K:
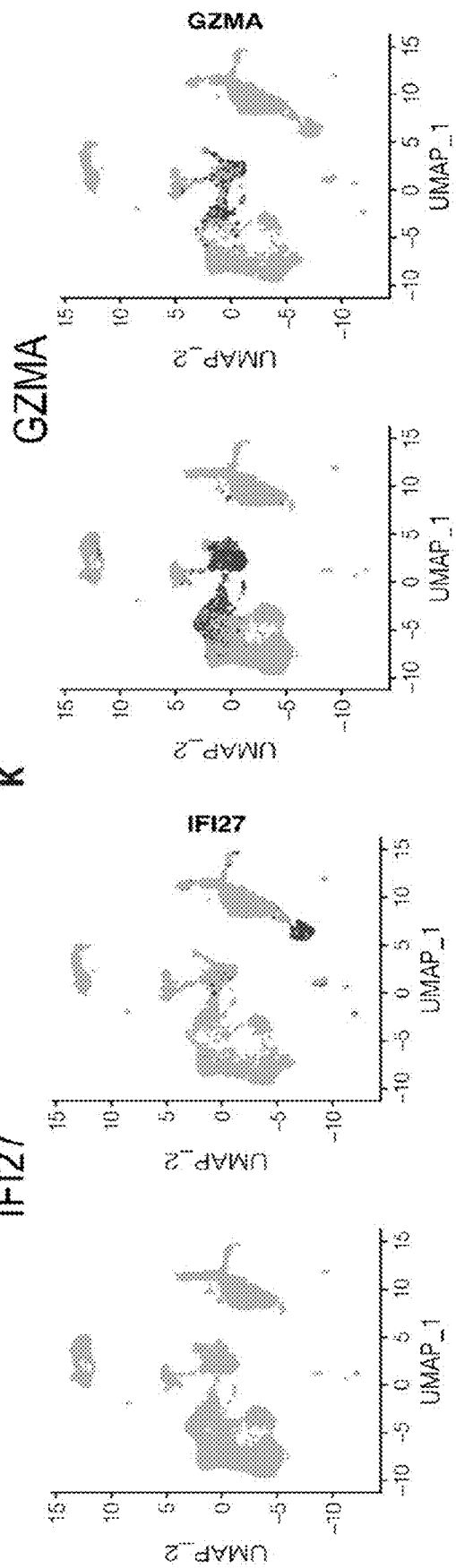

At the time of treatment, Patients 1 through 10 were hospitalized with a new onset respiratory illness and confirmed to be currently infected by coronavirus disease 2019 using polymerase chain reaction (PCR) or other commercial or public health assay. These confirmed SARS-CoV-2 positive patients had significant pre-existing co-morbidities, including previous kidney transplants, and were receiving intensive care treatment including mechanical ventilation or supplemental oxygen for ARDS. They further showed evidence of lymphopenia with liver and kidney damage and elevated liver and kidney enzymes (FIGS. 15A-15N and 16A-16D). At leronlimab treatment baseline, CCL5/RANTES was >100-fold increased compared to normal controls. Further, signatures of CRS were present in the plasma of all ten patients in the form of significantly elevated levels of the inflammatory cytokines IL-6, and IL-8 compared with healthy controls (FIG. 12). In comparison to patients with mild or moderate COVID-19, only IL-6 was present at significantly higher levels in critically-ill patients. Further, plasma CCL5 levels in the ten critically ill patients were markedly elevated over those in both healthy controls and mild or moderate COVID-19 patients (FIG. 12). High levels of CCL5 can cause acute renal failure and liver toxicity, both common findings in COVID-19 infection. Indeed, the critically ill patients presented with varying degrees of kidney and liver injury, although several had also previously received kidney transplants (FIG. 11 and FIGS. 15A-15N). Four of the patients died during the fourteen-day study period due to a combination of disease complications and severe constraints on medical equipment culminating in medical triage. As there is no placebo control group for comparison, it is noted that a recent study of other critically-ill COVID-19 patients in the New York City area indicates mortality rates as high as 88%.

At day 0, a single 700 mg dose of leronlimab was administered subcutaneously following baseline blood collection and patients were monitored at regular intervals two weeks post-injection by physical examination, clinical score assessment, pulse oxygen saturation (SpO$_2$), National Early Warning Score 2 (NEWS2) Assessment, ratio of percentage of inspired oxygen to partial pressure of arterial oxygen (PaO2/FiO2 ratio), electrocardiogram, chest radiograph or CT scan, and Ordinal Scale Assessment (OSA). Laboratory tests were performed at routine intervals, including Complete Blood Count (CBC), Biochemistry, Coagulation Indices, Serum Pregnancy Test, urinalysis, Arterial Blood Gas (ABG), T cell count (CD3+, CD4+ and CD8+), and CCR5 receptor occupancy for regulatory T cells and macrophages.

Per the protocol, leronlimab (PRO 140) 700 mg is to be administered subcutaneously weekly for up to 2 weeks. A weekly 700 mg dose of leronlimab (PRO 140) (175 mg/mL) is delivered as two injections of 2 mL each and administered subcutaneously on opposite sides of the abdomen. A 20-gauge needle should be used to remove PRO 140 from vial and a 25-gauge needle should be used for administration to subjects. Two vials of leronlimab will be used per treatment (per week). Each vial of the PRO 140 product contains ~2.4 mL antibody at 175 mg/mL in a buffer. Note: 2 mL injection will be drawn from 2.4 mL solution in a vial. Remaining 0.4 mL medication will be discarded appropriately from each vial. Leronlimab (PRO 140) will be stored in refrigerator at 2° C. to 8° C. (36° F. to 46° F.).

Accordingly, evaluation of initial test results from the first ten patients following a first 700 mg dose of leronlimab showed immunological benefits as early as three days post-treatment. These effects included normalization of previously dysregulated CD4/CD8 T cell ratio and reduction in levels of IL-6, a cytokine associated with COVID-19-induced cytokine storm (FIG. 13). Restoration of T cell homeostasis and a reduction in pro-inflammatory IL-6 following treatment demonstrates leronlimab may help hospitalized patients with COVID-19 avoid or recover from pulmonary inflammation. A reduction in pulmonary inflammation following leronlimab treatment may ameliorate symptoms of ARDS while reducing mortality and need for mechanical ventilation.

The immunological status of the ten patients 3 to 14 days after leronlimab therapy are shown in FIG. 8.

Figure 10A:
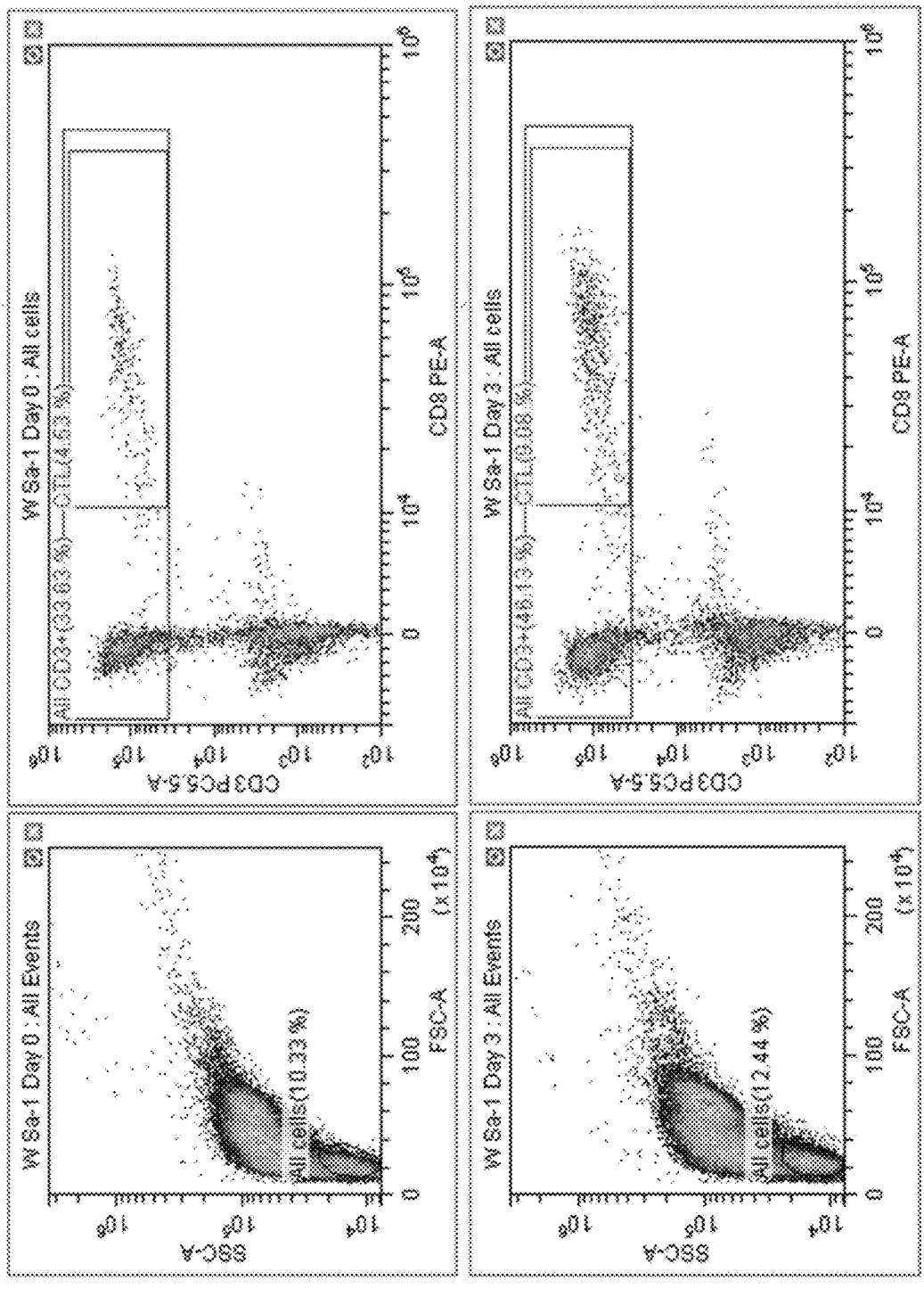
FIGS. 10A-10B shows representative flow cytometry data for Day 0 and Day 3 post-leronlimab treatment.
Figure 10B:
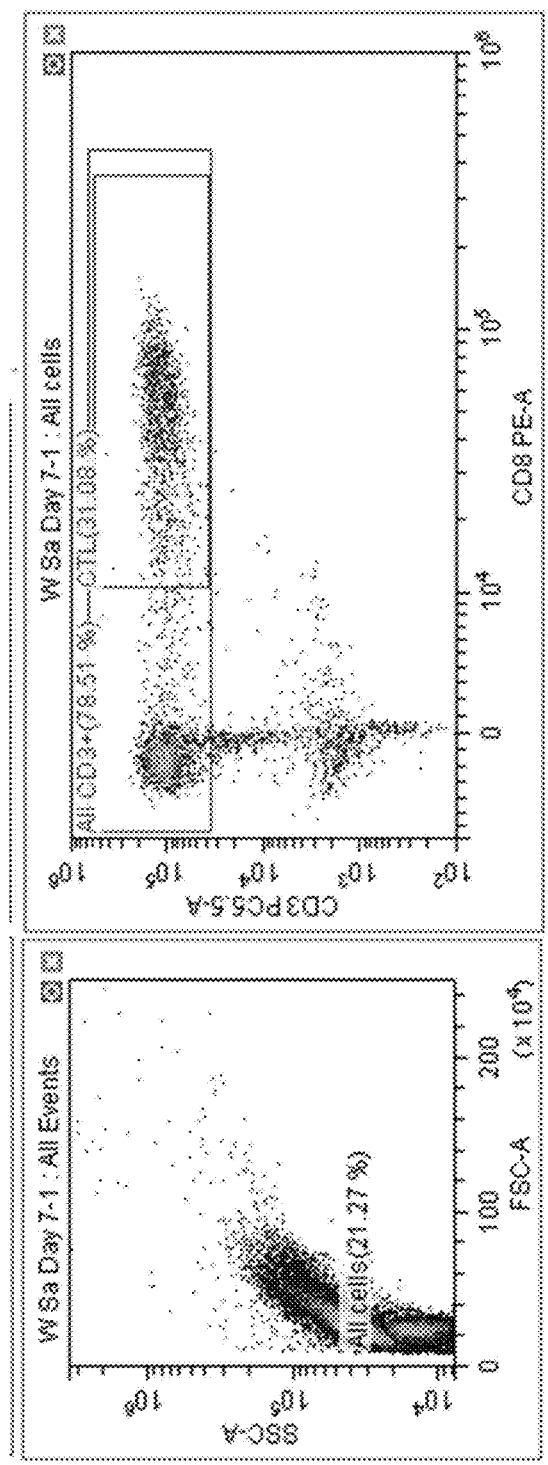
Figures 12A, 12B:
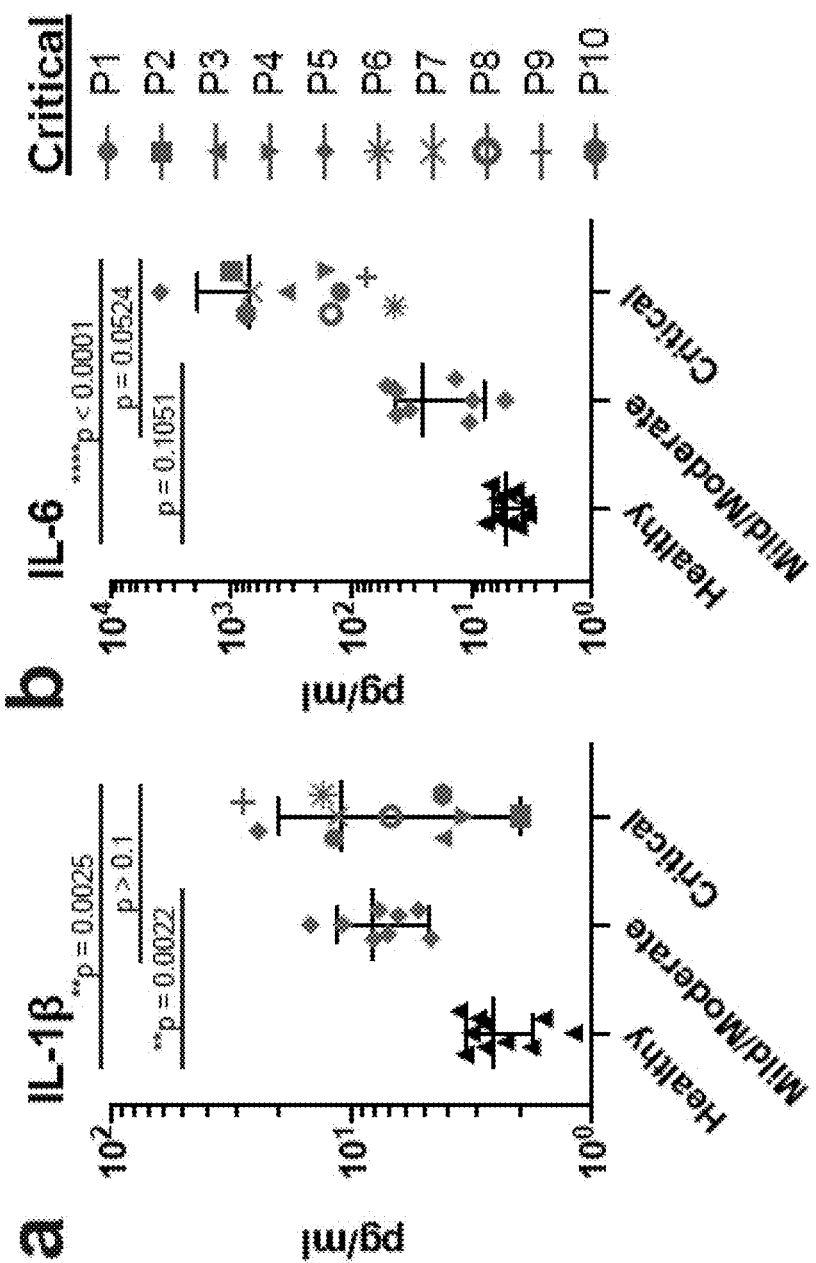
FIGS. 12A-12D show elevated cytokine and chemokine levels in critically ill COVID-19 patients. Plasma levels of IL-1β (FIG. 12A), IL-6 (FIG. 12B), IL-8 (FIG. 12C), and CCL5 (FIG. 12D) in patients with mild/moderate (n=8, purple symbols) and critical (n=10, red symbols) COVID-19 disease, compared to healthy controls (n=10, black symbols). Graphs display p-values calculated by Dunn's Kruskal-Wallis test: *p≤0.05, p≤0.01, *p≤0.001, ****p≤0.0001.
Figures 12C, 12D:
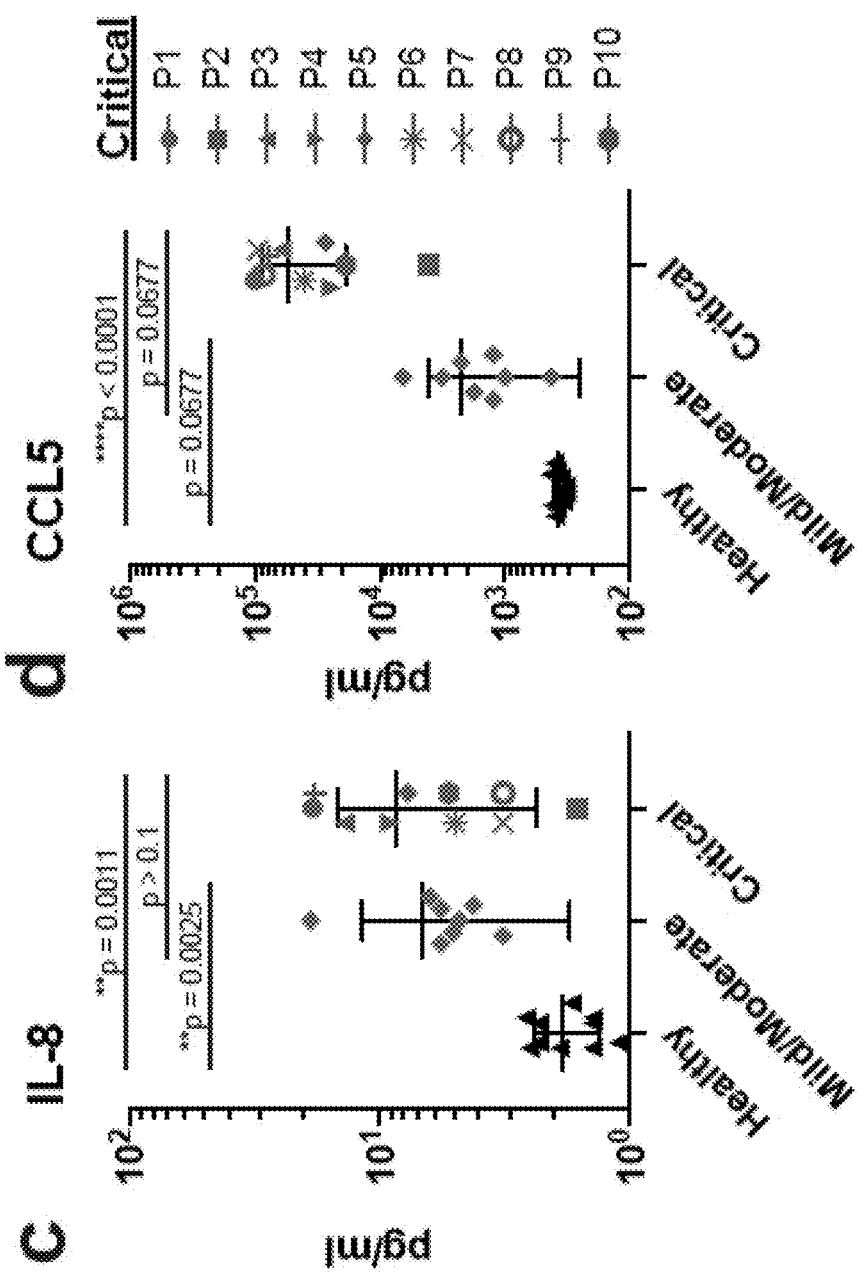

These data show increases in CD8% and lowered CD4/CD8 ratio (closer to, or within, approximate normal range) both of which are improved by Day 3 after a single dose of leronlimab (PRO 140) 700 mg in patients with severe COVID-19 infection treated under individual patient, EINDs. Representative flow cytometry data for Day 0, Day 3 (FIG. 10A) and Day 7 (FIG. 10B) post-leronlimab treatment show increased frequencies of CD3+ and CD3+CD8+ T cell populations in "Patient #3 WSa" by Day 3 and continued improvement by Day 7. Healthy (or normal) ranges for CD4% are between 30% and 40%, healthy ranges for CD8% are between 30% and 35%, and healthy CD4/CD8 ratios are between 0.9 and 1.9. For receptor occupancy (RO) assays, receptors are 0% occupied in the absence of drug. From previous HIV studies, leronlimab occupies close to 100% of CCR5 sites on T cell, macrophage, and T-reg populations by seven days of treatment. In severely ill COVID-19 patients treated with Leronlimab, CCR5 occupancy ranged from 87%-99% on T cell, macrophage, and T-reg populations by Day 7, as determined by available data from seven patients (FIG. 8). The plasma cytokine levels of each measured cytokine 3 to 14 days following leronlimab therapy are shown in FIG. 9A-FIG. 9J.

As seen in FIG. 9, IL-6, a pro-inflammatory cytokine associated with COVID-19-induced cytokine storm may be significantly reduced as early as three days and up to fourteen days following treatment with leronlimab.

Figures 13D, 13E, 13F:
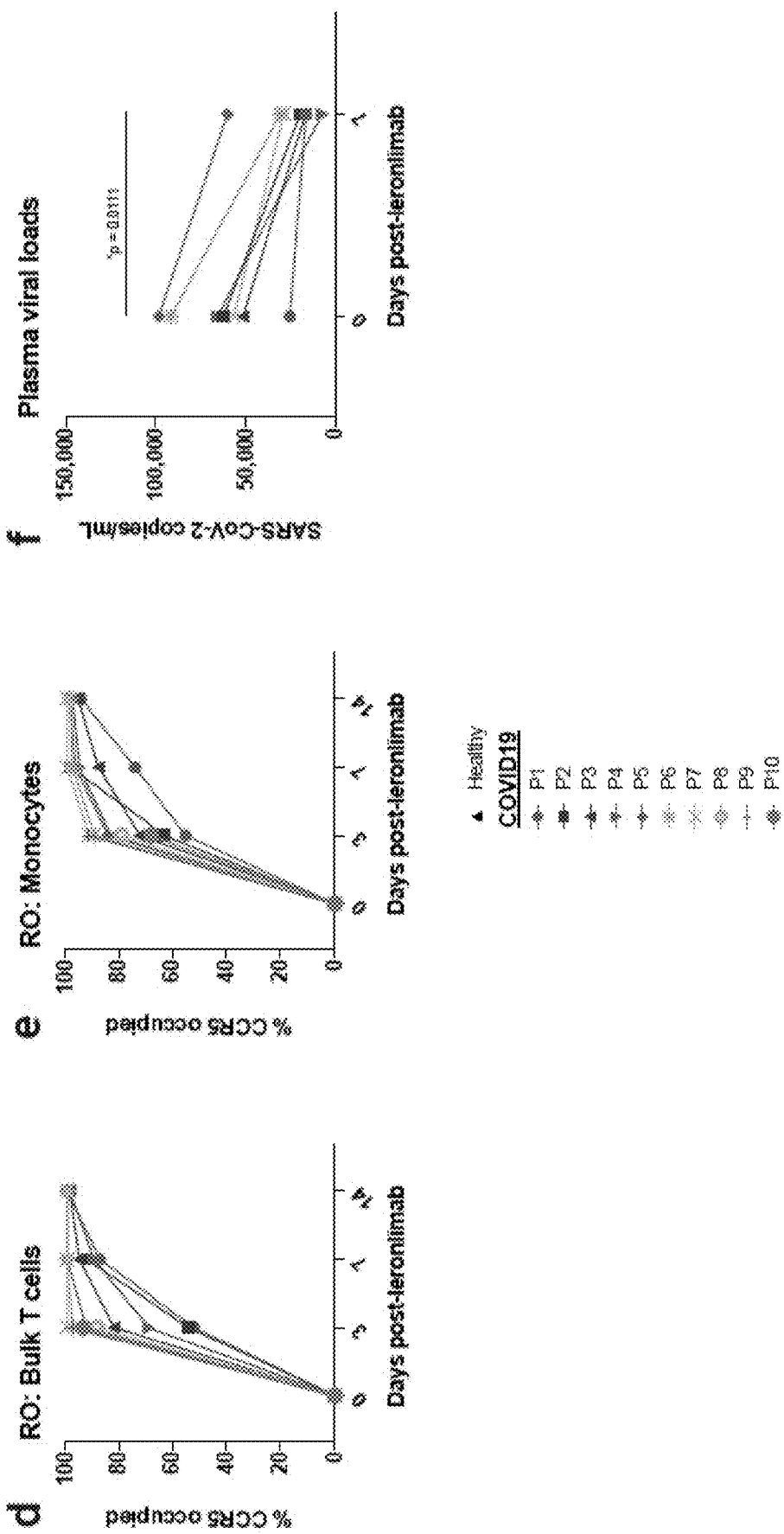
Figures 14A, 14B:
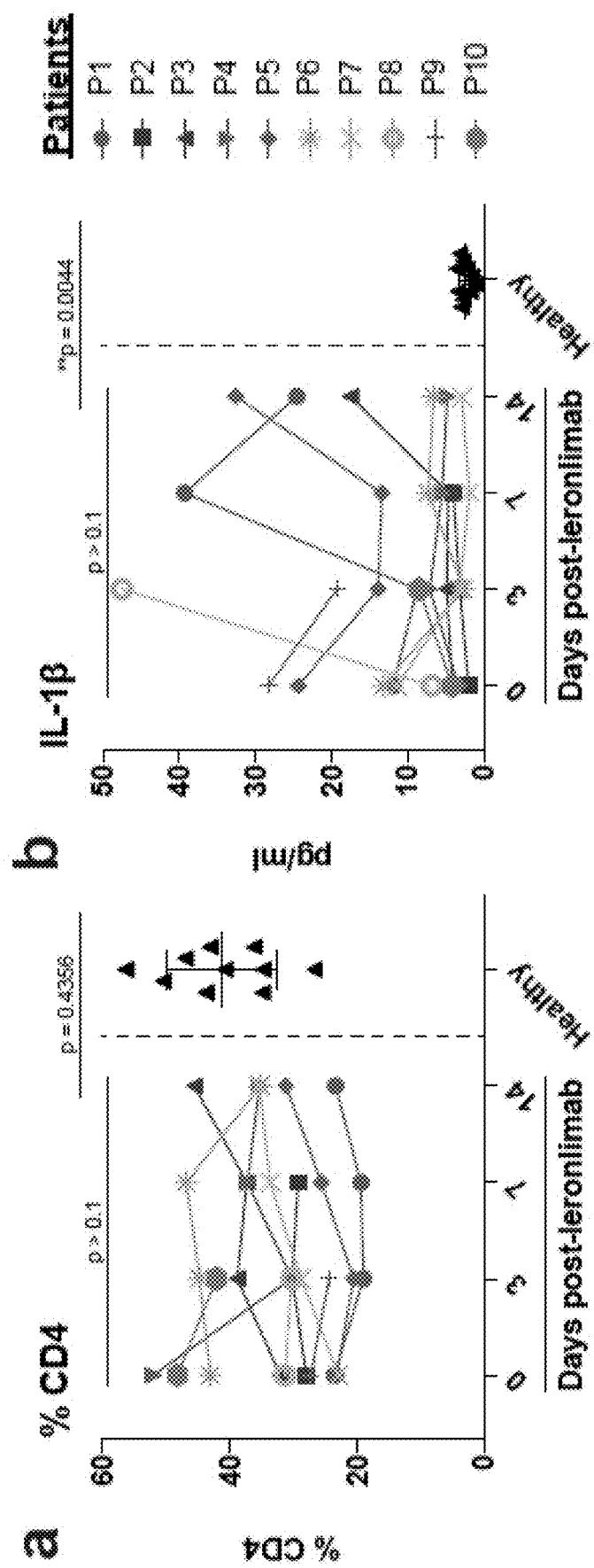
FIGS. 14A-14D show immunological parameters in critically ill COVID-19 patients after leronlimab administration. Peripheral blood CD4+ T cell percentages (FIG. 14A) of CD3+ cells, and plasma levels of IL-1b (FIG. 14B), IL-8 (FIG. 14C), and CCL5 (FIG. 14D) at days 0 (n=10), 3 (n=10), 7 (n=7), and 14 (n=6) post-leronlimab administration. Healthy controls (n=10) shown in black triangles. Graphs display p-values calculated by Dunn's Kruskal-Wallis test: not significant p>0.05, *p≤0.05, p≤0.01, *p≤0.001, ****p≤0.0001.
Figures 14C, 14D:
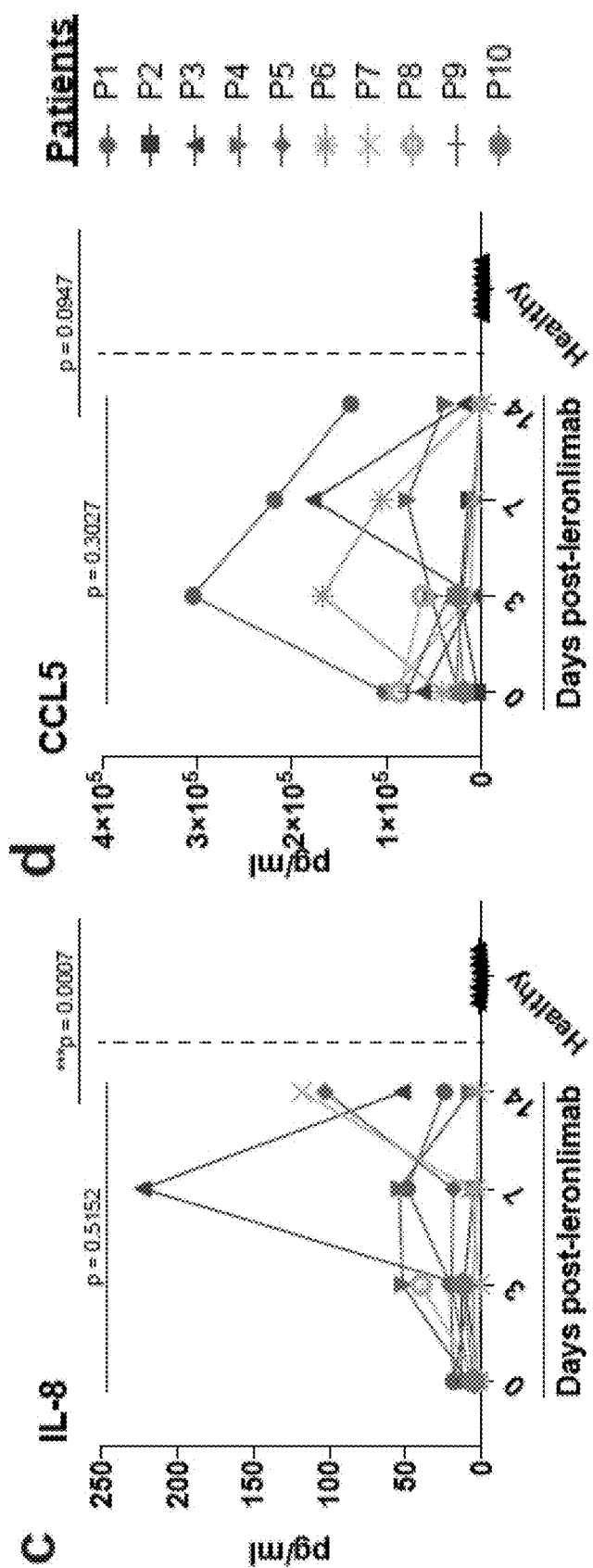

A reduction of plasma IL-6 was observed as early as three days following leronlimab, with full resolution achieved by day 14 (FIG. 13A). In contrast, more variable levels were observed with IL-1β, IL-8, and CCL5 after leronlimab treatment (FIG. 14B, FIG. 14C, FIG. 14D). Following leronlimab, a marked restoration of CD8+ T cell numbers (FIG. 13B) and a normalization of the CD4+ and CD8+ T cell ratio in blood was observed (FIG. 13C). These immunological changes occurred concomitant with full leronlimab CCR5 receptor occupancy on the surface of CCR5+ T cells and macrophages (FIG. 13D, FIG. 13E). Low levels of SARS-CoV-2 have been detected, but not yet quantified in the plasma of COVID-19 patients. SARS-CoV-2 viremia was measured by high sensitivity, digital droplet PCR to at baseline (FIG. 13F). Viremia also concurrently declined following leronlimab administration. SARS-CoV-2 plasma viremia decreased in all patients at day seven suggesting more effective anti-viral immunity following leronlimab-mediated CCR5 blockade.

UMAP feature plots of single-cell transcriptome profiles of CXCL8, CCL3, KLRB1, CCL4, CD69, CCL5, IFITM3, IFI27 and Granzyme A from a representative healthy individual and two severe COVID-19 patients are shown in FIG. 17.

To establish an unbiased gene repertoire for COVID-19 infection, 10× Genomics 5' single cell RNA-sequencing of peripheral blood mononuclear cells was used to evaluate transcriptional changes between an uninfected healthy donor and the two severe COVID-19 patients (P2 and P4) for which sufficient baseline, pre-leronlimab treatment COVID-19 samples were available for this analysis. Between the two groups, 2,890 differentially expressed transcripts were identified. The two severe COVID-19 patients had a greater abundance of myeloid cells upregulating inflammatory-, interferon (IFN)-, and chemokine-related genes compared to a healthy control (FDR <0.05) (Table 14). Notable genes overexpressed in COVID-19 patient samples included chemokines (CXCL8, CCL4, CCL3), inflammatory and immune activation genes (IL-1b, CD69), and the IFN-related genes (IFI27, IFITM3) (FIG. 17). A downregulation in cell clusters for the chemokine CCL5 gene, effector molecules granzyme A and the immunoregulatory gene KLRB1 as compared to a healthy control were also observed.

To identify markers that would inform effective leronlimab treatment, differential expression analysis was conducted for the same two severe COVID-19 participants (P2 and P4) for which baseline and day seven post leronlimab samples were available. The longitudinal COVID-19 single cell dataset profiled an estimated 4,105 cells at baseline and 4,888 cells at the 7-day post leronlimab time point. 2,037 differentially expressed transcripts (FDR <0.05) were identified (Table 14). IL-6 was downregulated between day 0 and day 7 in monocytes, in line with the decrease of IL-6 protein levels observed in plasma (FIG. 18) and consistent with repolarization of monocytes/macrophages following CCR5 blockade. Myeloid cells expressing chemokine and interferon-related genes such as CCL3 and CCL4 (FIG. 19) and CCL5, ADAR, APOBEC3A, IFI44L, ISG15, and MX1 were downregulated at 7 days post leronlimab compared to baseline (FIG. 19A-FIG. 19I and Table 15). Within the T cell population, we observed increased expression of granzyme A, suggesting improved antiviral function. These transcriptomic results further underscore the potential impact of leronlimab-mediated CCR5 blockade on the inflammatory state in COVID-19.

Interim data for ten critically ill COVID-19 patients treated with leronlimab under an EIND granted by the U.S. Food and Drug Administration (FDA) is described here. Treatment with leronlimab is a therapy for patients who experience respiratory complications as a result of contracting SARS-CoV-2 causing the Coronavirus Disease 2019 (COVID-19). Leronlimab is believed to provide therapeutic benefit by enhancing the immune response through normalizing cell type distribution in circulating T cells while mitigating the cytokine storm that leads to morbidity and mortality in these patients. Initial laboratory evaluation of the first ten patients treated with leronlimab revealed that the distribution of circulating immune cells in these patients approached or reached normal frequencies and that cytokines elevated during cytokine storm (including IL-6) were reduced following one dose of leronlimab. It is believed that disrupting the CCL5-CCR5 axis via leronlimab-mediated CCR5 blockade prevents pulmonary trafficking of pro-inflammatory leukocytes and reverses cytokine storm in the COVID-19 patients.

The initial results observed in ten patients who were severely ill with COVID-19 and treated with leronlimab are encouraging. A fairly rapid and positive laboratory response was seen in all ten patients treated. The most pronounced immune restoration is observed by day 7 in these patients, especially in the CD8 T-lymphocyte population, the major immune cell responsible for eliminating virally infected cells. In newly received day 14 data, CD8 T-lymphocyte populations are increased or maintained in these patients. In addition, there is a continued dramatic reduction in the critical cytokine storm cytokine, IL-6, from day 7 to day 14.

Patient 1 through Patient 10 treated with Leronlimab, all were receiving intensive care treatment including mechanical ventilation or supplemental oxygen for ARDS and six had prior renal transplant. Six out of 10 critically ill patients with COVID-19 survived by Day 14 with four patients extubated and released. Further, all patients exhibited immune restoration including T-cell numbers and improvement in exhaustion markers. Importantly, all patients showed significantly decreased IL-6 by Day 7, while RANTES levels remained high yet blocked by close to 100% CCR5 receptor occupancy at Day 7. In patients where Day 14 data was available, RANTES levels dropped as plasma IL-6 levels decreased. These data demonstrate a reduction of inflammation, restoration of T cell lymphocytopenia, and reduced SARS-CoV-2 plasma viremia following leronlimab-mediated CCR5 blockade. Further, platelet activation, which leads to the initiation of the coagulation cascade, can be triggered by chemokines including CCL5, suggesting that leronlimab treatment may be beneficial beyond its immunomodulatory effects on inflammation and hemostasis in COVID-19 patients.

In summary, complete CCR5 receptor occupancy on macrophage and T cells, rapid reduction of plasma IL-6, restoration of the CD4/CD8 ratio, and a significant decrease in SARS-CoV-2 plasma viremia were observed after leronlimab treatment. Consistent with reduction of plasma IL-6, single-cell RNA-sequencing revealed declines in transcriptomic myeloid cell clusters expressing IL-6 and interferon-related genes. These results demonstrate a novel approach to resolving unchecked inflammation, restoring immunologic deficiencies, and reducing SARS-CoV-2 plasma viral load via disruption of the CCL5-CCR5 axis. Further, these results present evidence that inhibition of CCL5 activity via CCR5 blockade represents a novel therapeutic strategy for COVID-19 with both immunologic and virologic implications.

Collectively, these results are correlating with patients' recovery. Some patients have been removed from ventilators, including one patient who was taken off of a heart/lung bypass machine. To date, three critically ill patients are experiencing the benefit of extubating following treatment with leronlimab.

Example 4

Study Protocol for Use of Leronlimab to Treat Severe COVID-19

An additional protocol to evaluate the safety and efficacy of leronlimab (PRO 140) in patients with severe symptoms of respiratory illness caused by COVID-19 is detailed in this section.

The purpose of this study is to assess the safety and efficacy of leronlimab administered as weekly subcutaneous injection to treat subjects with severe Coronavirus 2019 (COVID-2019) disease.

This study is a Phase 2b/3, randomized, double-blind, placebo-controlled, adaptive design multicenter study to evaluate the safety and efficacy of leronlimab (PRO 140) in patients with severe symptoms of respiratory illness caused by Coronavirus disease 2019 (COVID-19). 390 patients will be randomized 2:1 to receive leronlimab (PRO 140) or placebo. Subjects will receive weekly 700 mg leronlimab (PRO 140) or placebo via subcutaneous injection for two weeks. The study will enroll 390 subjects. The study flow diagram is presented in FIG. 2.

The target population for this study is adult subjects with severe symptoms of respiratory illness caused by coronavirus disease 2019 (COVID-19).

Inclusion Criteria.

1. Male or female adults ≥18 and <65 years of age at time of screening;

2. Subjects hospitalized with severe symptoms of respiratory illness caused by coronavirus 2019 infection as defined below;

Diagnosed with COVID-19 by a standardized RT-PCR assay within 5 days of screening AND Significant lower respiratory symptoms, including difficulty in breathing or shortness of breath at rest OR one of the following signs of severe pneumonia: RR ≥30, oxygen saturation (pulse oximetry) ≤93% on room air, partial pressure of oxygen/fraction of inspired oxygen (PaO2/FiO2) ≤300 mmHg (1 mmHg=0.133 kPa) AND Clinical assessment shows evidence of rales/crackles on exam OR radiographic evidence of pulmonary infiltrates (chest x-ray, CT scan, etc.), if available.

3. Subject is not intubated (or intubated within 72 hours of the screening). If intubated, positive end-expiratory pressure (PEEP) <15 cmH2O with PaO2/FiO2 >150 mmHg.

4. Clinically normal resting 12-lead ECG at Screening Visit or, if abnormal, considered not clinically significant by the Principal Investigator.

5. Subject (or legally authorized representative) provides written informed consent prior to initiation of any study procedures.

6. Understands and agrees to comply with planned study procedures.

7. Women of childbearing potential must agree to use at least one medically accepted method of contraception (e.g., barrier contraceptives [condom, or diaphragm with a spermicidal gel], hormonal contraceptives [implants, injectables, combination oral contraceptives, transdermal patches, or contraceptive rings], or intrauterine devices) for the duration of the study.

Exclusion Criteria

Potential subjects meeting any of the following criteria will be excluded from enrollment:

1. Subject exhibits signs of multi-organ failure.
2. Subject on vasopressors for >24 hours at time of screening.
3. Subject is lying in the prone position.
4. Subjects showing signs of clinical jaundice or alanine aminotransferase (ALT) and aspartate aminotransferase (AST) >5 times the upper limit of normal within last 24 hours prior to the screening.
5. Subject has end stage renal disease and requires chronic dialysis.
6. Subjects who have a history of allergic reactions attributed to compounds of similar chemical or biologic composition to leronlimab (PRO 140) are not eligible.
7. Inability to provide informed consent or to comply with test requirements.
8. Consideration by the investigator, for any reason, that the subject is an unsuitable candidate to receive study treatment.

Note: Subjects infected with chronic hepatitis B virus or hepatitis C virus will be eligible for the study if they have no signs of hepatic decompensation.

Note: Subjects infected with HIV-1 will be eligible for the study with undetectable viral load and are on a stable ART regimen. Investigators are required to review the subjects' medical records to confirm HIV-1 RNA suppression within the previous 3 months.

The study will have three phases: Screening Period, Treatment Period, and Follow-Up Period. The study Schedule of Assessments in presented in FIG. 4-2.

All subjects who fail to meet eligibility criteria are considered screen failures, and are exited from the study without further evaluation.

Screening assessments will commence at Visit 1 (V1) after obtaining signed informed consent, and will include review of medical and medication history, eligibility evaluation, physical examination, vital signs, clinical status—ordinal scale assessment, PaO2/FiO2 measurement, pulse oxygen saturation (SpO2), positive end-expiratory pressure (PEEP) (for intubated subjects), National Early Warning Score 2 (NEWS2) assessment, electrocardiogram (ECG), nasopharyngeal swab sample collection, chest radiograph or CT (if clinically indicated), assessment for the requirement of: mechanical ventilation, non-invasive ventilation, supplemental oxygen, vasopressors use, renal replacement therapy, ICU admission and hospital stay and laboratory sample collection for routine serum biochemical, hematologic, coagulation, urinalysis, and serum/urine pregnancy (if applicable). These assessments must be conducted within 7 days of the First Treatment Visit (V2).

Treatment Period (2 weeks±allowed windows). The schedule of visits during Treatment Period is as follows:

Visit 2 (V2) [first treatment]: Within 1 week of the Screening Visit

Visit 3 (V3): 3 (±1) day after V2

Visit 4 (V4) [second treatment]: 7 (±1) days after V2

Visit 5 (V5)/End of Treatment (EOT) Visit: 7 (±1) days after V4.

Subjects who meet the eligibility criteria will have completed the following evaluations and assessments at V2 prior to treatment: review of any changes in medical and medication history, physical examination, vital signs, clinical status—ordinal scale assessment, PaO2/FiO2 measurement, pulse oxygen saturation (SpO2), positive end-expiratory pressure (PEEP) (for intubated subjects), sequential Organ Failure Assessment (SOFA) score, National Early Warning Score 2 (NEWS2) assessment, nasopharyngeal swab sample collection, baseline assessment for the requirement of: mechanical ventilation, non-invasive ventilation, supplemental oxygen, vasopressors use, renal replacement therapy, ICU admission and hospital stay, and blood sample collection for CD3+, CD4+ and CD8+ T cell count, CCR5 receptor occupancy for Treg and macrophages, serum cytokine and chemokine levels, and CCR5 gene polymorphisms. If Visit 2 (V2) takes place on the same day as the Screening Visit (V1), scheduled assessments performed under screening (V1) do not need to be repeated at V2.

The treatment groups are shown below in Table 16.

TABLE 16

| Study Drug | Dosage Form | IP Concentration | Dosing Frequency & Amount | Route of Administration |
|---|---|---|---|---|
| Leronlimab (PRO 14) (700 mg) | Parenteral solution | 175 mg/ml | 2 injections of PRO 140 (2 × 2 mL/inj.) per week on opposite sides of abdomen | SC injection |
| Placebo | Parenteral solution | 0 mg/ml | 2 injections of placebo (2 × 2 mL/inj.) per week on opposite sides of abdomen | SC injection |

At V2, subjects will be randomized to receive leronlimab (PRO 140) or placebo which will be administered subcutaneously weekly at Visit 2 (Day 0) and Visit 4 (Day 7) by a qualified medical professional at clinic or at subject's home. If the subject is discharged from the hospital prior to Visit 7 (Day 42), the visit can be completed at the subject's home.

The following assessments will be performed at V3, V4, and V5/EOT: physical examination, vital signs, clinical status—ordinal scale assessment, PaO2/FiO2 measurement, pulse oxygen saturation (SpO2), positive end-expiratory pressure (PEEP) (for intubated subjects), sequential Organ Failure Assessment (SOFA) score, NEWS2 assessment, nasopharyngeal swab sample collection, health status assessment on an ordinal scale, assessment for the requirement of: mechanical ventilation, non-invasive ventilation, supplemental oxygen, vasopressors use, renal replacement therapy, ICU admission and hospital stay, and laboratory sample collection for routine serum biochemical, hematologic, coagulation, serum/urine pregnancy test (V5/EOT), urinalysis, CD3+, CD4+ and CD8+ T cell count, CCR5 receptor occupancy for Treg and macrophage, serum cytokine and chemokine levels, and CCR5 gene polymorphisms.

Additionally, a chest radiograph or CT (if clinically indicated), mortality assessment, and ECG will be performed at V5/EOT visit. Adverse events and medications will be monitored throughout the study.

Follow Up Period (2 and 4 weeks after EOT±allowed windows)

Follow-up visits will be performed at 2 weeks (V6) and 4 weeks (V7) after the End of Treatment (EOT) visit. The following assessments will be performed at V6 and V7 visit: review of adverse events and concomitant medications, physical examination, vital signs, mortality status, and blood collection for routine serum biochemical, hematologic, coagulation and urine laboratory assessments (V7 only).

Note: During visits conducted at the study clinic, subjects and site personnel will use appropriate protective gear (e.g., masks, gloves) to prevent the spread of the infection. If possible, scheduled study visits can be conducted by a visiting nurse (or trained site staff) at the subject's home to mitigate the risk of spreading COVID-19.

During visits conducted at the subject's home, the visiting nurse (or trained site staff) will administer study drug (if applicable), monitor subjects for safety, perform blood draw, and all other assessments related to study outcomes measures. All procedures (except chest radiograph or CT scan) listed under the schedule of assessments can be performed by visiting nurse at visits taking place in the subject's home.

Screening Phase. The subject (or Legally Acceptable Representative (LAR)) will sign and date the informed consent form (ICF) and Health Insurance Portability Accountability Act (HIPAA) authorization (according to site policy and practices) prior to any study-related procedures. All study centers will be instructed to maintain the study-specific screening and enrollment logs at their sites. If a subject initially fails to meet inclusion/exclusion criteria and is later reconsidered for participation, the subject will be re-consented and assigned a new unique identification number at the time of re-screening. Subjects who fail their first screening attempt may be re-screened a maximum of once and may be enrolled if they are found to meet all inclusion and no exclusion criteria when re-screened.

Screening Visit (V1). After the ICF has been signed, screening procedures and information will be obtained to confirm subject eligibility, including:
Demographic information;
A detailed medical history;
Physical examination;
Vital signs;
Clinical Status—Ordinal scale assessment;
PaO2/FiO2;
Pulse oxygen saturation (SpO2);
Positive End-Expiratory Pressure (PEEP), if intubated;
National Early Warning Score 2 (NEWS2) assessment;
12-lead electrocardiogram;
Collection of blood specimens for Complete blood count; Biochemistry; Coagulation indices; Serum/urine pregnancy test, for female subjects of childbearing potential; and Urine sample for urinalysis parameters.
Nasopharyngeal Swab Sample Collection;
Chest radiograph or computer tomography (CT) scan (if clinically indicated);
Ordinal scale assessment;
Assessment for the requirement of mechanical ventilation, Non-Invasive Ventilation, Supplemental Oxygen, Vasopressors Use, Renal Replacement Therapy, ICU Admission, and hospital stay; and
Prior medications assessment.

All screening information will be fully documented in the subject's medical records (i.e., source documents).

For consented subjects who do not meet eligibility criteria, a Screen Failure Case Report Form (CRF) will be completed. The Screen Failure CRF will contain the following details: the subject identification number, the date of ICF signature, demographic information, and the reason for screen failure. No additional information will be required for subjects who fail screening.

For consented subjects who meet eligibility criteria, all required screening information will be transcribed onto the appropriate page of the CRF.

Treatment Phase. Subjects who meet all eligibility criteria, as per data gathered from Screening Period are to be treated. All subjects who fail to meet eligibility criteria will be considered screen failure and will exit the study without further evaluation.

Visit 2 (V2). The following assessments will be performed at the first treatment visit prior to the first treatment administration. If Visit 2 (V2) takes place on the same day as the Screening Visit (V1), scheduled assessments performed under screening (V1) do not need to be repeated at V2.
Physical examination;
Vital Signs;
Clinical Status—Ordinal scale assessment;
PaO2/FiO2;
Pulse oxygen saturation (SpO2);
Positive End-Expiratory Pressure (PEEP), if intubated;
Sequential Organ Failure Assessment (SOFA) score;
National Early Warning Score 2 (NEWS2) Assessment;
Collection of blood specimens for CD3+, CD4+ and CD8+ T cell count; CCR5 receptor occupancy for Treg and macrophage; Serum cytokine and chemokine levels; and CCR5 Gene Polymorphisms.
Nasopharyngeal Swab Sample Collection;
Assessment for the requirement of mechanical ventilation, Non-Invasive Ventilation, Supplemental Oxygen, Vasopressors Use, Renal Replacement Therapy, ICU Admission, and hospital stay;
Assessment for any new infections; and
Prior medications assessment;
Subjects will be randomized 2:1 via WebView CTMS system to Leronlimab (PRO 140, 700 mg) or Placebo.
Leronlimab (PRO 140) or placebo will be administered subcutaneously to all subjects at a weekly dose of 700 mg.

After receiving the first leronlimab (PRO 140) dose, the following assessments will be performed: Vital signs, Concomitant medications assessment, and Review of adverse events.

Visits 3 and 4, (V3 and V4). The following assessments will be performed during the remaining visits during the treatment period:
Physical examination;
Vital Signs;
Clinical Status—Ordinal scale assessment;
PaO2/FiO2;
Pulse oxygen saturation (SpO2);
Positive End-Expiratory Pressure (PEEP), if intubated;
Sequential Organ Failure Assessment (SOFA) score;
National Early Warning Score 2 (NEWS2) Assessment;
Assessment of Clinical Recovery;
Collection of blood specimens for Complete blood count; Biochemistry; Coagulation indices; Urine sample for urinalysis parameters; CD3+, CD4+ and CD8+T cell count; CCR5 receptor occupancy for Treg and macrophage; Serum cytokine and chemokine levels; and CCR5 Gene Polymorphisms.
Nasopharyngeal Swab Sample Collection;
Leronlimab (PRO 140) or Placebo Administration—V4 only;
Assessment for the requirement of mechanical ventilation, Non-Invasive Ventilation, Supplemental Oxygen, Vasopressors Use, Renal Replacement Therapy, ICU Admission, and hospital stay;
Assessment for any new infections;
Prior medications assessment; and
Review of adverse events.
End of Treatment—EOT (V5). The last visit during the treatment phase will be considered at the End of Treatment (EOT) visit. The assessments performed at this visit will include:
Physical examination;
Vital Signs;
Clinical Status—Ordinal scale assessment;
PaO2/FiO2;
Pulse oxygen saturation (SpO2);
Positive End-Expiratory Pressure (PEEP), if intubated;
Sequential Organ Failure Assessment (SOFA) score;
National Early Warning Score 2 (NEWS2) Assessment;
Assessment of Clinical Recovery;
12-lead electrocardiogram;
Collection of blood specimens for Complete blood count; Biochemistry; Coagulation indices; Serum/urine pregnancy test, for female subjects of childbearing potential; Urine sample for urinalysis parameters; CD3+, CD4+ and CD8+ T cell count; CCR5 receptor occupancy for Treg and macrophage; Serum cytokine and chemokine levels; and CCR5 Gene Polymorphisms.
Nasopharyngeal Swab Sample Collection;
Chest radiograph or computer tomography (CT) scan (if clinically indicated);
Assessment for the requirement of mechanical ventilation, Non-Invasive Ventilation, Supplemental Oxygen, Vasopressors Use, Renal Replacement Therapy, ICU Admission, and hospital stay.
Assessment for any new infections;
Review of mortality status;
Prior medications assessment; and
Review of adverse events.

FOLLOW-UP PHASE. The first visit of the follow-up phase is scheduled 14(±3) days after EOT Visit. Two follow-up visits are included in the follow-up phase: Visit 6 (V6) and Visit 7 (V7).
The assessments performed at these visits will include:
Physical examination;
Vital Signs;
Collection of blood specimens at Visit 9 only for Complete blood count; Biochemistry; Coagulation indices; and Urine sample for urinalysis parameters.
Nasopharyngeal Swab Sample Collection
Review of mortality status;
Prior medications assessment; and
Review of adverse events.
UNSCHEDULED VISITS. In the event that the subject will return to clinic at a time other than a regularly scheduled study visit, the visit will be regarded as an unscheduled visit. Assessments at unscheduled visits are at the discretion of the Investigator. All pertinent findings, including adverse events or changes in medications, will be noted in the eCRF.
Subject Completion, Withdrawal and Criteria for Stopping the Study.
SUBJECT COMPLETION. A subject is considered to have completed the study once all follow-up visit assessments have been completed.
EARLY STOPPING RULES. Upon occurrence of any of the following events, data will be reviewed by the Medical Monitor and the Lead Principal Investigator.
1. Death in any subject in which the cause of death is judged to be probably or definitely related to the study drug by the treating investigator;
2. The occurrence in any subject of a life-threatening SAE whose causal relationship to study drug is judged to be probable or definite by the treating investigator;
3. Two (2) occurrences of Grade 4 toxicities that are assessed to be probably or definitely related to the study drug by the treating investigator;
4. Two (2) occurrences of a Grade 2 or higher allergic/hypersensitivity reaction directly related to the study drug that lead to permanent discontinuation of study drug.
In case the above listed event(s) occurred, patient accrual will be suspended pending further review and the FDA will be notified. The study will be stopped if any of these stopping criteria are met unless, after reviewing the safety events of interest, the medical monitor and Sponsor, agree to allow the study to proceed.
REMOVAL OF SUBJECTS FROM STUDY TREATMENT AND/OR STUDY AS A WHOLE. Subjects can be taken off the study treatment and/or study as a whole at any time at their own request, or they may be withdrawn at the discretion of the investigator for safety, behavioral or administrative reasons. In the case that a subject is removed from the study due to safety reasons, the FDA will be notified. The reason(s) for discontinuation must be clearly documented on the appropriate eCRF and may include:
Subject voluntarily withdraws from treatment (follow-up permitted);
Subject withdraws consent (no follow-up permitted);
Subject is unable to comply with protocol requirements;
Subject experiences unacceptable toxicity;
Treating physician determines that continuation on the study would not be in the subject's best interest;
Subject becomes pregnant;
Subject becomes lost to follow-up (LTF);
Subject will be withdrawn from the study if 2 consecutive injections of study drug are missed;

Subject manifesting Grade 4 toxicity attributable to the Leronlimab (PRO 140).

If a subject fails to return for the scheduled study visit or is discontinued from the study, an attempt will be made to determine the reason(s). If the subject is unreachable by telephone, a registered letter will be sent to the subject requesting that he/she contact the clinic.

All patients with an ongoing SAE or AE attributable (definitely, probably, or possibly related) to the study treatment at the Post-Study (Follow-up) Visit (scheduled or premature) must be followed until the event is resolved (with or without sequelae) or deemed stable.

DATA COLLECTED FROM WITHDRAWN SUBJECTS. Every attempt should be made to collect follow-up information. The reason for withdrawal from the study will be recorded in the source documents and on the appropriate page of the CRF. Before a subject is identified as lost-to-follow up, the site should make all reasonable efforts to contact the subject. These attempts must be documented and should include at a minimum one phone call and one certified letter.

In the event that a subject is withdrawn from the study at any time due to an adverse event or SAE, the procedures stated in "Adverse Events (Definitions and Reporting)" must be followed.

SCREEN FAILURES. A subject who signed a consent form, but did not meet the inclusion/exclusion criteria is classified as a screen failure. Subject number, demographics and reason for screen failure will be recorded.

In the event that a subject initially fails to meet inclusion/exclusion criteria and is later reconsidered for participation, the subject will be re-consented and assigned a new screening number at the time of re-screening. Subjects who fail their first screening attempt may be re-screened again (i.e., up to two screenings) and may be enrolled if they are found to meet all inclusion and no exclusion criteria at the subsequent screening visit.

Study Treatment

Leronlimab (PRO 140) or placebo will be administered subcutaneously (SC) at a weekly as follows in Table 17.

TABLE 17

| Study Drug | Dose | Route | Schedule |
| --- | --- | --- | --- |
| Leronlimab (PRO 140) | 700 mg | SC | Weekly (2 doses) |
| Placebo | 0 mg | SC | Weekly (2 doses) |

Leronlimab (PRO 140). Leronlimab (PRO 140) is a humanized IgG4,κ monoclonal antibody (mAb) to the chemokine receptor CCR5. Leronlimab (PRO 140) is provided at a concentration of 175 mg/mL and is intended for SC route of administration.

Leronlimab (PRO 140) kit will contain two vials. Each vial of the Leronlimab (PRO 140) product contains ~2.4 mL antibody at 175 mg/mL in a buffer containing 5 mM L-histidine, 15.0 mM glycine, 95 mM sodium chloride, 0.3% (w/v) sorbitol, 0.005% (w/v) polysorbate 20 (Tween 20®), and sterile water for injection, at pH of 5.5. For subjects assigned to Leronlimab (PRO 140) arm, one kit will be assigned per treatment visit.

A dose of 700 mg of Leronlimab (PRO 140) (175 mg/mL) or placebo will be delivered as two injections of 2 mL each and administered subcutaneously on opposite sides of the abdomen.

Isotonic 0.9% Sodium Chloride Injection, USP will be used as Placebo.

Note: 2 mL will be drawn from 2.4 mL solution filled vial. Remaining 0.4 mL medication will be discarded appropriately from each via and administered as subcutaneous injection.

Leronlimab information is provided in Table 18.

TABLE 18

| IP Dosage | Dosage Form | IP Concentration | Dosing Frequency & Amount | Route of Administration |
| --- | --- | --- | --- | --- |
| PRO 140 (700 mg) | Parenteral solution | 175 mg/ml | 2 inj. of PRO 140 (2 ml/inj.) per week on opposite sides of abdomen for 2 weeks | SC injection |
| Placebo | Parenteral solution | 0 mg/ml | 2 inj. of placebo (2 × 2 ml/inj..) per week on opposite sides of abdomen for 2 weeks | SC injection |

Note: Patients with low body fat percentages may find subcutaneous injections uncomfortable. In such cases, leronlimab (PRO 140) 700 mg can be injected as four 175 mg/ml injections and/or subcutaneous injections can be placed at different areas other than abdomen as per discretion of the Investigator.

Leronlimab (PRO 140)—Packaging and Labeling. The contents of each vial are described in the "Study Treatment" section. Leronlimab (PRO 140) kits will be labeled with information such as: study protocol #; fill volume; concentration; storage condition; a "use as per study protocol" statement; a cautionary statement; sponsor's name and address; and the kit number.

Leronlimab (PRO 140)—Storage and Handling. Study drug will be shipped at 2° C. to 8° C. (refrigerated [36° F. to 46° F.]) to the investigator's site. Upon receipt at the site, the responsible site staff or pharmacist should verify the integrity of the vials. Study drug should be stored at 2° C. to 8° C. (refrigerated [36° F. to 46° F.]). The contents of the vial should appear as a clear to opalescent, colorless to yellow solution; fine translucent particles may be present. This is normal.

The investigator must maintain an accurate record of the shipment, storage, and dispensing of the study drug in a drug accountability log. An accurate record including the date and amount of study drug dispensed to each subject must be available for inspection at any time. A study CRA assigned to monitor the investigational site will review these documents once study drug has been received by the investigational site. Study drug will be accounted for on an ongoing basis during the study.

Leronlimab (PRO 140)—Administration. Guidelines for dose preparation can be found in the pharmacy manual.

Leronlimab (PRO 140) or placebo will be provided to the administering personnel in single-use syringes prepared from vials of study drug stored at 2-8° C. at the site pharmacy prior to use. Syringes will be prepared by an unblinded pharmacist or designated site staff. Each of two syringes is filled to deliver 2 mL of study drug.

Equivalent volumes of PRO 140 will be administered subcutaneously on opposite sides of the abdomen.

A 20-gauge needle should be used to remove PRO 140 from vial and a 25-gauge needle is used for administration to subjects.

IP should be administered slowly over 15 seconds per mL. Leronlimab (PRO 140) should not be kept in syringe for longer than 60 minutes unless otherwise stated in the Pharmacy Manual.

Following each SC delivery of drug, careful examination will be made to assess the appearance of any study drug Injection Site Reactions (ISRs) as per CTCAE v5.0.

Leronlimab (PRO 140) will be administered as SC injection by a qualified medical professional at the study clinic. If the subject is discharged from the hospital prior to Visit 7 (Day 42), the visit can be completed or at the subject's home.

Note: It is preferred that the same injection site be used throughout the study. At the same time, it is not recommended to inject the study drug into areas where skin shows signs of a previous injection site reaction. It is advised to change the injection site if any previous injection site reaction remains unresolved.

Leronlimab (PRO 140)—Post Injection Monitoring. Subject will be observed at approximately 30 minutes post-injection or longer if necessary for injection site reaction as per CTCAE v5.0.

Leronlimab (PRO 140)—Toxicity Management. Refer to Tables 19 and 20 below. Recovery to acceptable levels must occur to allow leronlimab (PRO 140) continuation.

TABLE 19

Leronlimab (PRO 140) Dose Modification and Management for Injection Site Reactions

| CTCAE Grade | Treatment Management |
| --- | --- |
| Grade 1 | No dose adjustment is required |
| Grade 2 | First Occurrence: No dose adjustment is required. Second Occurrence of the same event: Closely follow-up for resolution of the AE to Grade ≤1 |
| Grade 3 | Withhold treatment until symptoms resolve to: Grade 1 or less |
| Grade 4 | Study treatment will be permanently discontinued |

TABLE 20

Leronlimab (PRO 140) Management for all Other Potential Toxicities (Attributable to Leronlimab).

| CTCAE Grade (attributable to leronlimab) | Treatment Management |
| --- | --- |
| Grade 1 | No dose adjustment is required |
| Grade 2 | Withhold treatment until symptoms resolve to: Grade 1 or less or baseline |
| Grade 3 | Study treatment will be permanently discontinued |
| Grade 4 | Study treatment will be permanently discontinued |

Description of Protocol Assessments and Procedures.

Demographic information and medical history will be collected. For COVID-19 diagnosis, the number of days between the onset of symptoms and the initiation of treatment for each subject will be documented.

PHYSICAL EXAMINATION. The physical examination will include routine examinations for the following:
Constitutional/General Appearance
Head, Ears, Eyes, Nose, Throat (HEENT)
Neurologic
Cardiovascular
Musculoskeletal and Extremities
Dermatologic
Respiratory
Gastrointestinal
Genitourinary
Lymphatic
Psychiatric Each abnormality will be recorded and the Investigator will record an assessment of its clinical significance.

VITAL SIGNS, HEIGHT AND WEIGHT. The following will be collected: Systolic Blood Pressure, Diastolic Blood Pressure, Heart Rate, Temperature, Respiratory Rate, Height, Weight, and Body Mass Index.

CONCOMITANT MEDICATIONS. All medications and therapies administered or taken by the subject beginning 30 days prior to Screening Visit and throughout the study will be recorded in the source documents and on the appropriate page of the Case Report Form (CRF). Additionally, all other investigational and off-label therapies for COVID-19 will be recorded. Subjects must be questioned at each study visit concerning any new medications or changes in current medications including over-the-counter medication and topical medication.

For each medication and non-study treatment, the following will be documented:

Medication/treatment name (generic name may be used if trade name is unknown)

Dose, unit, and frequency of dosing (individual dosages, not total daily dose).

Note: Each new dose of medication should be recorded as a separate entry, with the exception of medications that are given on a sliding scale. For these, it is acceptable to enter the range of the dosage, including the start and stop dates for which the specified dosage range was used.

Route of dosing;
Indication for use;
The start date;
The stop date (if medication/therapy is not ongoing).

Excluded Medications. The following medications are prohibited:
Other CCR5 antagonists;
Other investigational products.

Allowable Medications and Therapies. The following medications and therapies are allowed:

Patients with underlying chronic viral illnesses will be allowed to receive antiviral therapy.

Organ transplant patients will be allowed to continue baseline immunosuppressive therapy during the course of study.

Empirical antibiotic treatment for secondary bacterial infections is allowed during the course of study.

Intravenous immunoglobulin (IVIG)

Treatment for COVID-19 in accordance with standards of care and/or institutional policy Note: Subjects infected with chronic hepatitis B virus or hepatitis C virus will be eligible for the study if they have no signs of hepatic decompensation.

Note: Subjects infected with HIV-1 will be eligible for the study with undetectable viral load and are on a stable ART regimen. Investigators are required to review the subjects' medical records to confirm HIV-1 RNA suppression within the previous 3 months.

CLINICAL LABORATORY ASSESSMENTS. Blood samples will be collected for analysis of the following parameters described in Tables 21-25.

Biochemistry and Complete Blood Count (CBC): At Screening (V1), V3, V4, V5 (EOT), and V7.

Serum/urine pregnancy test (for female subjects of childbearing potential): At Screening (V1)

All laboratory reports will be reviewed by the Investigator. Abnormal results that are considered by the Investigator to be clinically significant will be recorded as adverse events. If in the Investigator judgment, in order to make the determination of clinical significance the testing may be needed to be repeated. Validated, quality-controlled laboratory data will be transferred to the main database for analyses.

TABLE 21

CBC Parameters

Hemoglobin (g/dL)
Hematocrit (%)
RBC/Erythrocytes (10 ∧ 12/L)
WBC/Leukocytes (10 ∧ 6/L)
Absolute Neutrophil Count (10 ∧ 6/L)
Platelets (10 ∧ 9/L)
Differential WBC:
- Neutrophils (%)
- Lymphocytes (%)
- Monocytes (%)
- Eosinophils (%)
- Basophils (%)

TABLE 22

Biochemistry Parameters

Liver Function Tests
Total bilirubin (mg/dL)
Alkaline Phosphatase (ALP) (U/L)
Aspartate Aminotransferase (AST) (or SGOT) (U/L)
Alanine Aminotransferase (ALT) (or SGPT) (U/L)
Total Protein (g/dL)
Albumin (g/dL)
Lactate Dehydrogenase (U/L)
Renal Function Tests
Serum Creatine
Creatinine clearance
eGFR
Electrolytes
Sodium (mEq/L)
    Potassium (mEq/L)
  Chloride (mEq/L)
  Calcium (mg/dL)
Bicarbonate (mEq/L)
Other:
Glucose, Random (mg/dL)
Cholesterol, Total (mg/dL)
Creatine kinase,
C-reactive protein
Coagulation Parameters
Prothrombin time (PT)
    International Normalized Ratio (INR)

TABLE 23

Urinalysis pH
Specimen Appearance
Color
Specific Gravity
Ketones
Bilirubin
Occult Blood
Glucose
Protein
Nitrite
Urobilinogen (mg/dL)
Leukocyte Esterase
Leukocytes(/HPF)

TABLE 24

Cytokine and Chemokine Panel sCD40L, EGF, Eotaxin (CCL11), FGF-2, Flt-3 ligand, Fractalkine, G-CSF, GM-CSF, GRO alpha (CXCL1), IFN-alpha2, IFN-gamma, IL-1 alpha, IL-1 beta, IL-1RA, IL-2, IL-2R, IL-3, IL-4, IL-5, IL-6, IL-7, IL-8 (CXCL8), IL-9, IL-10, IL-12 (p40/p70) IL-13, IL-15, IL-17A, IL-17E/IL-25, IL-17F, IL-18, IL-22, IL-27, IP-10 (CXCL10), MCP-1 (CCL2), MCP-3, M-CSF, MDC (CCL22), MIG (CXCL9), MIP-1 alpha (CCL3), MIP-1 beta (CCL4), PDGF-AA, PDGF- AB/BB, RANTES(CCL5), TGF-alpha, TNF-alpha, TNF-beta, VEGF-A.

TABLE 25

Miscellaneous

Serum pregnancy test (for female subjects of childbearing potential)
Urine pregnancy test (for female subjects of childbearing potential)
CD3+, CD4+ and CD8+ T cell count
CCR5 receptor occupancy for Treg and macrophage
CCR5 Gene Polymorphisms CLINICAL STATUS—ORDINAL SCALE ASSESSMENT. Subject clinical status will be assessed using a 7-category ordinal scale. The scale ranges from:

(1) Death;

(2) Hospitalized, on invasive mechanical ventilation or extracorporeal membrane oxygenation (ECMO);

(3) Hospitalized, on non-invasive ventilation or high flow oxygen devices;

(4) Hospitalized, requiring supplemental oxygen;

(5) Hospitalized, not requiring supplemental oxygen;

(6) Not hospitalized, limitation on activities;

(7) Not hospitalized, no limitations on activities.

PAO2/FIO2MEASUREMENT. PaO2/FiO2 will be measured at Screening and at V2 (pre-dose), V3, V4, and V5 (EOT).

PULSE OXYGEN SATURATION (SPO2). Pulse Oxygen Saturation (SPO2) will be measured at Screening and at V2 (pre-dose), V3, V4, and V5 (EOT).

POSITIVE END-EXPIRATORY PRESSURE (PEEP), IF INTUBATED. If the subject is intubated, positive end-expiratory pressure (PEEP) will be measured at Screening and at V2 (pre-dose), V3, V4, and V5 (EOT).

Sequential Organ Failure Assessment (Sofa) Score

The SOFA score assessment will be based on PaO2/FiO2, platelets, Glasgow coma scale (GCS), bilirubin, Mean arterial pressure OR administration of vasoactive agents required, and creatine.

NATIONAL EARLY WARNING SCORE 2 ASSESSMENT. The National Early Warning Score 2 (NEWS2) Assessment is based on 7 clinical parameters (respiration rate, oxygen saturation, any supplemental oxygen, temperature, systolic blood pressure, heart rate, level of consciousness).

ASSESSMENT OF CLINICAL RECOVERY. The assessment of clinical recovery is based on hospital discharge or normalization of fever, respiratory rate, alleviation of cough and resolution of hypoxia.

12-LEAD ELECTROCARDIOGRAM. A resting supine 12-lead ECG will be conducted at the Screening Visit (V1) and Visit 5 (End of Treatment). A 12-lead ECG will be repeated during the study only if clinically indicated and at the discretion of the treating physician. The results will be evaluated by the Investigator. The following parameters will be recorded: ventricular rate (beats per minute), PR interval (msec), QRS interval (msec), QT interval (msec), and QTc interval (msec). Additionally, the Investigator will record the overall results of the ECG reading as either normal or abnormal, and as either not clinically significant or clinically significant. If abnormalities are observed, each will be recorded.

NASOPHARYNGEAL SWAB SAMPLE COLLECTION. Nasopharyngeal swabs will be used for quantitative virologic testing. The subject will be followed and samples will be collected for the entire duration of the study. Samples are to be stored at −70° C.

CHEST RADIOGRAPH OR COMPUTED TOMOGRAPHY SCAN. If clinically indicated by the treating physician, a chest radiograph or CT scan will be performed at Screening Visit (V1) and V5 (EOT)

REQUIREMENT OF MECHANICAL VENTILATION, NON-INVASIVE VENTILATION, SUPPLEMENTAL OXYGEN, VASOPRESSORS USE, RENAL REPLACEMENT THERAPY, ICU ADMISSION, AND HOSPITAL STAY. The incidence and duration, in days, of mechanical ventilation, non-invasive ventilation, supplemental oxygen, vasopressors use, renal replacement therapy, ICU admission and hospital stay will be assessed at Screening (V1) and V3, V4, and V5 (EOT).

RANDOMIZATION. Subjects who are eligible to participate in the trial will be randomized to one of the treatment groups via IWRS (Interactive Web Based Randomization System) at Visit 2 prior to IP administration. The randomization will be central with a 2:1 ratio of Active Treatment to Control Treatment to ensure even distribution of Active and Control subjects.

STATISTICAL ANALYSIS. This section presents general information about statistical considerations and concepts and a brief discussion on analysis methodology, as well as some data conventions. Detailed descriptions of the statistical analysis methods and data conventions that will be used in this study will be in a separate document; i.e., the Statistical Analysis Plan (SAP).

TREATMENT GROUPS. There will be two treatment groups in the study:

700 mg Leronlimab (PRO 140); Placebo

Description of Study Outcomes (Endpoints).

Primary Endpoint. The primary endpoint for the study is: Mortality rate at Day 14.

Secondary Endpoint. The secondary efficacy endpoints for the study are:

Change in clinical status of subject at Days 3, 7, and 14 (on a 7 point ordinal scale): a 7-category ordinal scale of patient health status ranges from: 1) Death; 2) Hospitalized, on invasive mechanical ventilation or extracorporeal membrane oxygenation (ECMO); 3) Hospitalized, on non-invasive ventilation or high flow oxygen devices; 4) Hospitalized, requiring supplemental oxygen; 5) Hospitalized, not requiring supplemental oxygen; 6) Not hospitalized, limitation on activities; 7) Not hospitalized, no limitations on activities.

Proportion of subjects extubated within 14 days of start of study treatment. Note: This applies only for subjects who were intubated at the time of randomization Proportion of subjects admitted into an intensive care unit (ICU) after randomization. Note: This applies only for subjects who were hospitalized but not in an intensive care unit (ICU) at the time of randomization.

Proportion of subjects requiring non-invasive ventilation after randomization. Note: This applies only for subjects who does not require non-invasive ventilation at the time of randomization.

Proportion of subjects requiring the use of high flow nasal cannula after randomization. Note: This applies only for subjects who does not require oxygenation at the time of randomization Length of hospital stay (days)

Length of ICU stay (days)

Duration (days) of supplemental oxygenation (if applicable)

Duration (days) of mechanical ventilation (if applicable)

Time to clinical recovery. Time from initiation of the study to discharge or to normalization of fever (defined as <36.6° C. from axillary site, or <37.2° C. from oral site or <37.8° C. from rectal or tympanic site), respiratory rate (<24 bpm while breathing room air), alleviation of cough (defined as mild or absent in a patient reported scale of 0=absent, 1=mild, 2=moderate, and 3=severe) and resolution of hypoxia (defined as SpO2≥93% in room air or P/F≥300 mmHg). All these improvements must be sustained for at least 24 hours.

Change from baseline in pulse oxygen saturation (SpO2) at Days 3, 7, and 14

Change from baseline in Sequential Organ Failure Assessment (SOFA) score at Days 3, 7, and 14.

Change from baseline in National Early Warning Score 2 (NEWS2) at Days 3, 7, and 14. This score is based on 7 clinical parameters (respiration rate, oxygen saturation, any supplemental oxygen, temperature, systolic blood pressure, heart rate, level of consciousness).

Incidence of transaminitis, defined as an increase in alanine aminotransferase (ALT) and/or aspartate aminotransferase (AST) to >5 times the upper limit of normal.

Incidence of subjects requiring Renal Replacement Therapy (RRT) after randomization Incidence of new bacterial, invasive fungal, or opportunistic infection Exploratory Outcome (Endpoints) Measures.

Change in size of lesion area by chest radiograph or CT

Change from baseline in serum cytokine and chemokine levels at Days 3, 7, and 14

Change from baseline in CCR5 receptor occupancy levels for Tregs and macrophages at Days 3, 7, and 14

Change from baseline in CD3+, CD4+ and CD8+ T cell count at Days 3, 7, and 14

Safety Measures. Safety will be assessed using:

Incidence of treatment-related adverse events (TEAEs)

Incidence and severity of treatment-emergent adverse events (TEAEs)

Incidence of serious adverse events (SAEs)

Incidence of TEAEs and SAEs leading to discontinuation of study medication.

Changes in blood chemistry, hematology and coagulation parameter results

Changes in vital signs including temperature, pulse, respiratory rate, systolic and diastolic blood pressure Changes in physical examination results Changes in electrocardiogram (ECG) results SAMPLE SIZE DETERMINATION AND RATIONALE. This is a randomized study with two treatment groups. The subjects will be randomized to the treatment groups (leronlimab or placebo) in a 2:1 ratio.

A total of three hundred ninety (390) subjects will be randomized in a 2:1 ratio to leronlimab or placebo groups with the goal of having 324 subjects (216 subjects in the leronlimab and 108 in the placebo group) complete the study. The sample size is obtained based on the assumption that there will be a clinically meaningful difference in the rate of Day 14 mortality (i.e., 15% which is 35% Day 14 mortality rate for the placebo group versus 20% Day 14 mortality rate in the leronlimab group). This sample size is based on using a 2-sided Z-test test with 80% power and an overall significance level of 0.05. The expected dropout rate is 5%. To accommodate subject attritions due to the potential discontinuations, it is recommended randomizing an estimated 390 subjects (2/3 in the leronlimab group and 1/3 placebo group). Sample size is estimated using PASS sample size software, tests for two proportions.

Randomization.

This is a multi-center randomized clinical trial. The randomization will use block size of 3 with a 2:1 ratio of leronlimab group and placebo group to ensure balanced distribution of leronlimab group and placebo subjects. An individual, independent of the clinical trial team, will develop the randomization schedules. The actual randomization assignment will be made through an Interactive Web Based Response System (IWRS) called WebView®. Subjects who have provided written informed consent and have met all the inclusion criteria and none of the exclusion criteria will be randomized to one of the treatment groups.

Stratification.

Randomization will be stratified into one of the three categories based on clinical status of the study at baseline:

Hospitalized, not in intensive care unit (ICU)

Hospitalized, in ICU, on mechanical ventilation, not on vasopressors

Hospitalized, in ICU, on mechanical ventilation, on vasopressors

For the purpose of stratification, on vasoporessors dose is defined as: norepinephrine >10 µg/min and/or vasopressin 0.4 units/min.

Blinding.

All subjects, Investigators and their staff (except unblinded pharmacist or designated site staff), and all Sponsor/CRO personnel involved in the management of the study will be blinded to treatment assignments.

The Amarex Information Technology department will be unblinded to treatment. As noted above, the Amarex Technology department is not otherwise involved with the study.

Treatment unblinding for the study will occur after all clinical data have been received, data inconsistencies have been resolved, and the database is locked, except for safety reasons on a case-by-case basis (i.e., emergency unblinding).

The process for emergency unblinding will be outlined in details in the Randomization Plan. In addition, any subject that is unblinded for any reason will be identified and discussed in the final clinical study report.

INTERIM ANALYSIS. Unblinded treatment assignments for the interim analysis will only be given to an independent statistician who will conduct the analysis. For this analysis there will be no subject specific unblinding to any other personnel in the study.

EMERGENCY UNBINDING. Breaking the blind prematurely will be allowed only if the subject's well-being requires knowledge of the subject's treatment allocation. Every attempt will be made to maintain the blind throughout the study.

In the event of an urgent safety issue where the randomized treatment of a subject is necessary to manage and treat the affected study subject (e.g., unblinding subjects because of SAEs that meet "expedited criteria" and requires reporting to FDA), the Investigator will contact the Medical Monitor. The Medical Monitor, in consultation with sponsor, will make a decision to unblind. If the decision has been made to unblind, a prompt written notification will be provided to the Investigator. The reason for unblinding must be recorded; however the investigator must not record the subject's treatment assignment in study documentation and must not reveal the subject's treatment assignment to the clinical monitor.

If reporting of an adverse event is to be performed unblinded as per regulatory authority guidelines, study-unrelated personnel will unblind the individual subject's treatment group and will perform the unblinded reporting. No treatment group information would be shared with study personnel.

FINAL ANALYSIS. Treatment unblinding and release of the randomization codes of the investigational product assignments for the study will occur immediately following database lock when all randomized subjects have completed the study or discontinued from the study and after all clinical data have been received and data inconsistencies have been resolved.

INTERIM ANALYSIS. An Interim Analysis (IA) will be conducted when approximately 50% (~171 subjects) have been randomized and completed 2 weeks of randomized treatment or are withdrawn from the study, whichever occurs first.

The main objectives of the IA are safety and sample size re-assessment.

The IA will have prospectively assigned rules and a method to protect the type I error rate and the integrity of the trial, due to the unblinded look. The IA will be conducted under the auspices of an independent Data Safety Monitoring Committee (DSMC) according to a written Charter. The procedures for this IA will be based on a standard operating procedure (SOP) that has a well-established a firewall to protect the integrity of the trial. The IA will be performed by an independent un-blinded statistician, who is not otherwise associated with the conduct of this trial. The timing, purpose, and procedures for this interim analysis will be detailed in the SAP.

The details of the interim analysis will be included in the Interim Analysis Plan.

General Statistical Considerations.

All collected study data will be presented in subject data listings. Statistical analyses will be performed using SAS® for Windows, version 9.4 or later. Descriptive statistics (n, mean, standard deviation, median, minimum and maximum) will be presented for continuous variables. Frequencies and percentages will be presented for categorical variables.

Analysis populations: Intent-to-Treat Population. The Intent-to-Treat (ITT) population is defined as all randomized subjects. This population will be used as the primary analysis population for analysis of the primary and secondary efficacy endpoints.

Analysis populations: PP Population. The Per Protocol (PP) population is defined as the set of subjects who meet the ITT Population requirements and are not associated with any major protocol violations. This population will be identified before the database lock. This population will be used as the supportive analysis population for analysis of the primary and secondary efficacy endpoints.

Analysis populations: Safety Population. The Safety Population will include all subjects who have received one dose of leronlimab (PRO 140) or placebo. This population will be used for the analysis of safety parameters or measurements.

Covariates. For efficacy analyses important prognostic factors that need adjustment will be specified in the Statistical Analysis Plan (SAP) for the study.

Missing Data. Every effort will be made to obtain required data at each scheduled evaluation from all subjects who have been randomized to minimize missing data. However, in the event when there is missing data the following imputation methods will be used.

For efficacy evaluations, multiple imputation methods will be used to handle missing data. This imputation method is a robust method to impute missing measurements. The imputation will be carried out in SAS version 9.4 or later using PROC MI. Each imputation model will include the stratification factor as a covariate in the model. The details of multiple imputation will be included in the statistical analysis plan.

Analysis Methods.

A Statistical Analysis Plan (SAP) will be developed and approved before the database is locked. The SAP will present the detailed statistical methodology to be used in analyzing the data from this trial.

Subject Disposition. The disposition of all subjects who signed an ICF will be provided. The number of subjects screened, screen failed, randomized, received at least one treatment, completed, and discontinued during the study, as well as the reasons for all discontinuations will be summarized by treatment group. Disposition and reason for study discontinuation will also be provided as a by-subject listing.

Demographic and Baseline Characteristics. Demographics and baseline characteristics including medical history, will be summarized by treatment group using appropriate descriptive statistics.

Concomitant Medications/Therapies. Concomitant medications/therapies will be summarized separately for the Safety population. All prior and concomitant medications recorded in the case report form will be coded to matching Anatomic Therapeutic Classification codes using the most recent version of the WHO Drug Dictionary. Descriptive summaries by treatment group will be prepared using the coded term. All concomitant medications/therapies recorded in the case report form will be listed.

Efficacy Analyses.

Primary Analysis: The ITT population will be the primary population for the analysis of the efficacy endpoints of the study.

Primary Endpoint: The primary endpoint for this study is the proportion of subjects with Mortality at Day 14 between leronlimab and placebo. The difference in the Day 14 mortality between the leronlimab and placebo treatment groups will be compared using Logistic regression model.

Secondary Endpoints: To maintain the trial-wise Type I error rate at 0.05, a closed test procedure will be used for the secondary endpoints. The order of the secondary endpoints will prospectively specified in the SAP.

Analysis of the secondary and exploratory endpoints will be summarized according to the variable type.

Continuous data summaries will include: If the Normality assumption is met, Analysis of Covariance (ANCOVA) would be used; If the Normality assumption is not met, a non-parametric method or a rank—ANCOVA analysis i.e., an ANCOVA analysis on rank-transformed data will be used.

Categorical data summaries will be based on Logit model will be used.

Time-dependent data: Cox proportional hazards model will be used to analyze time dependent data and to depict the time to event data.

Supportive Analysis. To assess the consistency of the Primary Analysis results, supportive analysis will be conducted using the Intent to Treat (ITT) and Per Protocol (PP) populations. Statistical methodology for the supportive analyses will be the same as that of the primary analysis, with the exception of the analysis population used.

Subgroup Analysis. Subgroup analyses will be conducted for the predefined stratification factors for the study. Additional exploratory subgroup analysis will be conducted using the baseline clinical characteristics and laboratory parameters such as, CD4/CD8 ratio and IL-6. The details will be prospectively specified in the SAP.

Safety Summaries.

Adverse Events. Adverse events will be coded using the most recent version of Medical Dictionary for Regulatory Activities (MedDRA). Treatment Emergent AE's (TEAE) are defined as events with an onset on or after the first treatment. TEAEs will be summarized by System Organ Class and preferred term by treatment group. The following TEAE summaries will be provided:

Overall (i.e., regardless of severity or relationship to treatment);

By intensity (mild, moderate, severe, life threatening or death);

By causality (definitely, probably, possibly, remotely or unrelated);

By impact on study treatment (dose increased, dose not changed, dose rate reduced, dose reduced, drug interrupted, drug withdrawn, not applicable, or unknown).

In addition, separate summaries of serious adverse events, and adverse events resulting in discontinuation of study treatment will be presented.

Clinical Laboratory Data. All laboratory values will be listed. Laboratory measurements will also be summarized by treatment group and presented by time point.

ECG. All ECG values will be listed. ECG measurements will also be summarized by treatment group and presented by time point.

Vital Signs. All vital sign findings will be listed and/or summarized by treatment group.

Physical Examination. All physical examination findings will be listed and/or summarized by treatment group.

Adverse Events (Definitions and Reporting).

The Investigator is responsible for the detection and documentation of events meeting the criteria and definition of an AE or SAE, as provided in this protocol. During the study when there is a safety evaluation, the Investigator or site staff will be responsible for detecting, documenting and reporting AEs and SAEs as detailed in this section of the protocol.

ADVERSE EVENT (AE). An adverse event (AE) is defined as any unfavorable or unintended sign, symptom, or disease that occurs or is reported by the patient to have occurred, or a worsening of a pre-existing condition. An adverse event may or may not be related to the study treatment.

AEs will be elicited through direct questioning and subject reports. Any abnormality in physical examination findings or laboratory results that the investigator believes is clinically significant (CS) to the research subject and that occurred after initiation of the first study treatment will be reported as AEs. Abnormal findings that are NOT clinically significant should not be recorded as an AE.

REPORTING OF ADVERSE EVENTS. Report initiation for all AEs and SAEs will begin at the time of the first treatment visit and continue until the end of final study visit. All events will be followed to resolution or until the subject completes the study. A final assessment of outcome will be made at that time.

All AEs must be recorded in the subject's medical records and on the CRF. AEs will be reported using customary medical terminology along with the following information: the onset and end dates, whether the event is considered to be a SAE, the impact the event had on study treatment, the Common Terminology Criteria for Adverse Events (CTCAE) grade (intensity) of the event, the causality of the event, whether treatment was given as a result of the event, and the outcome of the event.

Impact on Study Treatment. The impact the event had on the study treatment will be assessed as either: dose increased, dose not changed, dose rate reduced, dose reduced, drug interrupted, drug withdrawn, not applicable, or unknown. The "not applicable" assessment will be used only when the subject is no longer in the Treatment Phase of the protocol.

CTCAE Grade (Intensity) Assessment. The guidelines outlined in CTCAE v5.0 will be used for assessing the intensity of the event. The general guidelines for assessing the AE grade appear below in Table 26.

TABLE 26

| Grade | Description |
| --- | --- |
| Grade 1 | Mild; asymptomatic or mild symptoms; clinical or diagnostic observations only; intervention not indicated. |
| Grade 2 | Moderate; minimal, local or noninvasive intervention indicated; limiting age-appropriate instrumental activities of daily living (ADL)*. |
| Grade 3 | Severe or medically significant but not immediately life-threatening; hospitalization or prolongation of hospitalization indicated; disabling; limiting self care ADL†. |
| Grade 4 | Life-threatening consequences; urgent intervention indicated. |
| Grade 5 | Death related to AE. |

*Instrumental ADL refer to preparing meals, shopping for groceries or clothes, using the telephone, managing money, ect.
†Self care ADL refer to bathing, dressing and undressing, feeding self, using the toilet, taking medications, and not bedridden.

*Instrumental ADL refer to preparing meals, shopping for groceries or clothes, using the telephone, managing money, etc.

†Self care ADL refer to bathing, dressing and undressing, feeding self, using the toilet, taking medications, and not bedridden.

Causality Assessment. AEs will be assigned a relationship (causality) to the study treatment. The Investigator will be responsible for determining the relationship between an AE and the study treatment. The type of event, organ system affected, and timing of onset of the event will be factors in assessing the likelihood that an AE is related to the study treatment. Relationship of AEs to study treatment will be classified as follows:

1. Definitely related: This category applies to those AEs that the Investigator feels are incontrovertibly related to the study treatment. An AE may be assigned an attribution of definitely related if or when it meets all of the following criteria: (1) it follows a reasonable temporal sequence from administration of the study treatment; (2) it could not be reasonably explained by the known characteristics of the subject's clinical state, environmental or toxic factors, or other modes of therapy administered to the subject; (3) it follows a known response pattern to treatment with the study treatment.

2. Probably related: This category applies to those AEs which, after careful medical consideration at the time they are evaluated, are felt with a high degree of certainty to be related to the study treatment. An AE may be considered probable if or when (must have three): (1) it follows a reasonable temporal sequence from administration of the study treatment. (2) It could not readily have been produced by subject's clinical state, environmental or toxic factors, or other therapies administered to the subject. (3) Disappears or is decreased upon discontinuation of the study treatment. (4) It follows a known response pattern to treatment with the study treatment.

Possibly related: This category applies to those AEs which, after careful medical consideration at the time they are evaluated, are judged unlikely but cannot be ruled out with certainty to the study treatment. An AE may be considered possible if or when (must have two): (1) it follows a reasonable temporal sequence from administration of the study treatment. (2) It could not readily have been produced by subject's clinical state, environmental or toxic factors, or other therapies administered to the subject. (3) Disappears or is decreased upon discontinuation of the study treatment. (4) It follows a known response pattern to treatment with the study treatment.

4. Remotely related: In general this category can be considered applicable to those AEs which, after careful medical consideration at the time they are evaluated, are judged likely to be unrelated to the study treatment. An AE may be considered unlikely if or when (must have two): (1) it does not follow a reasonable temporal sequence from administration of the study treatment. (2) It could not readily have been produced by subject's clinical state, environmental or toxic factors, or other therapies administered to the subject. (3) Disappears or is decreased upon discontinuation of the study treatment. (4) It does not follow a known response pattern to treatment with the study treatment.

5. Unrelated: This category applies to those AEs which, after careful consideration at the time they are evaluated, are clearly and incontrovertibly due to extraneous causes (disease, environment, etc.) and determined with certainty to have no relationship to the study treatment.

Treatment Given as a Result of the Event. The event impact in terms of treatment provided will be as either: none, medication administered, non-drug therapy administered, surgery performed, hospitalization, or other (with a specification).

Outcome Assessment. The outcome of the event will be assessed as either: fatal, not recovered/not resolved, recovered/resolved, recovered/resolved with sequelae, recovering/resolving, or unknown. Only one AE per subject is allowed to have an outcome assessment as "death." If there are multiple causes of death for a given subject, only the primary cause of death will have an outcome of death.

Serious Adverse Events.

A SAE is defined as any AE that:

Results in death

Is life threatening (the subject is at immediate risk of dying from the adverse experience)

Requires subject's hospitalization or prolongs existing hospitalization

Results in persistent or significant disability/incapacity

Is a congenital anomaly/birth defect

Important medical events that may not result in death, be life-threatening, or require hospitalization may be considered a serious adverse effect when, based upon appropriate medical judgment, they may jeopardize the subject or subject and may require medical or surgical intervention to prevent one of the outcomes listed in this definition.

SAE FOLLOW-UP. All subjects experiencing an SAE, including the discontinued subjects, must be closely followed until sufficient information is obtained to indicate a return to normal status or until the event stabilizes at a level acceptable to the investigator (i.e., recovery, return to baseline status, no further improvement expected, or death).

For each SAE indicated as an unresolved event on the initial report, regardless of whether the subject completed the study or withdrew, the site should submit a follow-up report with updated information.

Study participants should be instructed to notify the investigator and discontinue investigational product immediately if they become pregnant at any time during the study or if they become pregnant within 30 days of last investigational product dose. A participant whose partner has become pregnant or suspects she is pregnant during the study must report the information to the investigator. The Investigator is required to report any notification of pregnancy to CytoDyn, Inc/designated CRO promptly. The participants should receive appropriate monitoring and care until the conclusion of the pregnancy. Any complication experienced through the end of the pregnancy should be considered as an adverse event (AE), and should be recorded, and if it meets the seriousness criteria, it must be reported to CytoDyn Inc/designated CRO promptly. Pregnancy outcomes will be reported in the clinical study report.

Results

Initial results are available for a subset of patients as follows. A patient with severe COVID-19 was treated under the Phase 2b/3 study to evaluate the safety and efficacy of leronlimab (PRO 140) in patients with severe symptoms of respiratory illness caused by Coronavirus disease 2019 (COVID-19). The patient was intubated and in critical condition in the ICU, and had received an IL-6 blocking agent four days earlier without apparent benefit. Concomitantly, the patient also received either an antiretroviral agent or placebo as part of an unrelated clinical trial. With no clinical improvement observed over the ensuing four days, the patient then received leronlimab under an emergency IND granted by the U.S. Food and Drug Administration (FDA). Within twenty-four hours of receiving an injection of leronlimab, the patient showed significant clinical improvement and was removed from external ventilation three days later.

Example 4A

Study to Evaluate the Efficacy and Safety of Leronlimab for Patients with Severe or Critical Coronavirus Disease 2019 (COVID-19)

Brief Summary:

The purpose of this study is to assess the safety and efficacy of leronlimab (PRO 140) administered as weekly subcutaneous injection in subjects with severe or critical COVID-19 disease.

Detailed Description:

This is a Phase 2b/3, two-arm, randomized, double blind, placebo controlled, adaptive design multicenter study to evaluate the safety and efficacy of leronlimab (PRO 140) in patients with severe or critical symptoms of respiratory illness caused by coronavirus 2019 infection. Patients will be randomized to receive weekly doses of 700 mg leronlimab (PRO 140), or placebo. Leronlimab (PRO 140) and placebo will be administered via subcutaneous injection.

The study will have three phases: Screening Period, Treatment Period, and Follow-Up Period.

Arms and Interventions:

Drug: Leronlimab (700 mg). Leronlimab (PRO) 140 is a humanized IgG4, monoclonal antibody (mAb) to the C-C chemokine receptor type 5 (CCR5).

Placebo Comparator: Placebo

Outcome Measures:

Primary Outcome Measures:
1. All-cause mortality at Day 28 [Time Frame: Day 28]
   Day 0 refers to the data of randomization/first treatment.

Secondary Outcome Measures:
1. All-cause mortality at Day 14 [Time Frame: Day 14]
   Day 0 refers to the data of randomization/first treatment.
2. Change in clinical status of subject at Day 14 (on a 7 point ordinal scale) [Time Frame: Day 14]
   A 7-category ordinal scale of patient health status ranges from: 1) Death; 2) Hospitalized, on invasive mechanical ventilation or extracorporeal membrane oxygenation (ECMO); 3) Hospitalized, on non-invasive ventilation or high flow oxygen devices; 4) Hospitalized, requiring supplemental oxygen; 5) Hospitalized, not requiring supplemental oxygen; 6) Not hospitalized, limitation on activities; 7) Not hospitalized, no limitations on activities.
3. Change in clinical status of subject at Day 28 (on a 7 point ordinal scale) [Time Frame: Day 28]
   A 7-category ordinal scale of patient health status ranges from: 1) Death; 2) Hospitalized, on invasive mechanical ventilation or extracorporeal membrane oxygenation (ECMO); 3) Hospitalized, on non-invasive ventilation or high flow oxygen devices; 4) Hospitalized, requiring supplemental oxygen; 5) Hospitalized, not requiring supplemental oxygen; 6) Not hospitalized, limitation on activities; 7) Not hospitalized, no limitations on activities.
4. Change from baseline in Sequential Organ Failure Assessment (SOFA) score at Day 14. [Time Frame: Day 14]
   The SOFA score assessment will be based on PaO2/FiO2, platelets, Glasgow coma scale (GCS), bilirubin, Mean arterial pressure OR administration of vasoactive agents required, and Serum creatinine Eligibility Criteria:

Inclusion Criteria:
1. Male or female adult ≥18 and <65 years of age at time of screening.
2. Subjects hospitalized with severe or critical illness caused by coronavirus 2019 infection as defined below:

Severe Illness:
Diagnosed with COVID-19 by standard RT-PCR assay or equivalent testing within 5 days of screening
AND
Symptoms of severe systemic illness/infection with COVID-19:
At least 1 of the following: fever, cough, sore throat, malaise, headache, muscle pain, shortness of breath at rest or with exertion, confusion, or symptoms of severe lower respiratory symptoms including dyspnea at rest or respiratory distress
AND
Clinical signs indicative of severe systemic illness/infection with COVID-19, with at least 1 of the following:
RR ≥30, HR ≥125, SaO2<93% on room air or requires >2L oxygen by NC in order maintain SaO2 ≥93%, PaO2/FiO2<300
AND
No criteria for Critical Illness:
None of the following: Respiratory failure (defined by endotracheal intubation and mechanical ventilation, oxygen delivered by high-flow nasal cannula, noninvasive positive pressure ventilation, or clinical diagnosis of respiratory failure in setting of resource limitations), Septic shock (defined by SBP <90 mm Hg, or Diastolic BP<60 mm Hg), Multiple organ dysfunction/failure
Critical Illness:
Diagnosed with COVID-19 by standard RT-PCR assay or equivalent testing within 5 days of screening
AND
Evidence of critical illness, defined by at least 1 of the following:
Respiratory failure defined based on resource utilization requiring at least 1 of the following: Endotracheal intubation and mechanical ventilation, oxygen delivered by high-flow nasal cannula, noninvasive positive pressure ventilation, ECMO, or clinical diagnosis of respiratory failure (in setting of resource limitation)
OR
Shock (defined by SBP <90 mm Hg, or Diastolic BP<60 mm Hg or requiring vasopressors)
OR
Multiple organ dysfunction/failure
3. Subject is not intubated (or intubated within 72 hours of the screening). If intubated, positive endexpiratory pressure (PEEP) <15 cmH2O with PaO2/FiO2 >150 mmHg.
4. Clinically normal resting 12-lead ECG at Screening Visit or, if abnormal, considered not clinically significant by the Principal Investigator.
5. Subject (or legally authorized representative) provides written informed consent prior to initiation of any study procedures.
6. Understands and agrees to comply with planned study procedures.
7. Women of childbearing potential must agree to use at least one medically accepted method of contraception (e.g., barrier contraceptives [condom, or diaphragm with a spermicidal gel], hormonal contraceptives [implants, injectables, combination oral contraceptives, transdermal patches, or contraceptive rings], or intrauterine devices) for the duration of the study.
Exclusion Criteria:
1. Subjects with do-not-resuscitate (DNR) and/or do-not-intubate (DNI) orders
2. Subject on vasopressors for >24 hours at time of screening.
3. Subjects showing signs of clinical jaundice or alanine aminotransferase (ALT) and aspartate aminotransferase (AST) >5 times the upper limit of normal within last 24 hours prior to the screening.
4. Subject has end stage renal disease and requires chronic dialysis.
5. Subjects who have a history of allergic reactions attributed to compounds of similar chemical or biologic composition to leronlimab (PRO 140) are not eligible.
6. Inability to provide informed consent or to comply with test requirements
7. Consideration by the investigator, for safety reasons, that the subject is an unsuitable candidate to receive study treatment
8. Subject participating in another study with for an investigational treatment for COVID-19.
Note: Subject who were prescribed hydroxychloroquine or chloroquine with or without azithromycin for the off-label treatment of COVID-19 prior to study enrollment may be included and may continue to receive these agents.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

EMBODIMENTS

1. A method of treating a subject for a coronavirus-induced respiratory illness, comprising administering to the subject an effective amount of a CCR5 binding agent.
2. The method of claim 1, wherein the subject is infected with SARS-CoV-1 or SARS-CoV-2.
3. The method of claim 1, wherein the coronavirus-induced respiratory illness comprises COVID-19.
4. The method of claim 1, wherein the coronavirus-induced respiratory illness comprises acute respiratory distress syndrome (ARDS).
5. The method of one of claims 3 and 4, wherein the subject with a coronavirus-induced respiratory illness exhibits one or more symptoms associated with mild-to-moderate COVID-19.
6. The method of claim 3, wherein the subject with a coronavirus-induced respiratory illness exhibits one or more symptoms associated with severe COVID-19.
6a. The method of claim 6, wherein the coronavirus-induced respiratory illness exhibits one or more symptoms associated with critical COVID-19.
6b. The method of claim 6, wherein the coronavirus-induced respiratory illness exhibits one or more symptoms associated with critical COVID-19.
7. The method of one of claims 3 and 4, wherein the subject exhibits no symptoms associated with COVID-19.
8. The method of one of claims 3 and 4, wherein the subject exhibits no symptoms associated with COVID-19 but has been exposed to another subject known or suspected of having COVID-19.
9. The method of claim 1, wherein the subject with a coronavirus-induced respiratory illness exhibits one or more symptoms selected from dry cough, shortness of breath, and fever.
10. The method of claim 1, wherein the CCR5 binding agent comprises an antibody or a fragment thereof.
11. The method of claim 10, wherein the CCR5 binding agent is leronlimab or a fragment thereof.

12. The method of claim 11, wherein the leronlimab or fragment thereof is administered together with at least one additional immunomodulatory agent or antiviral agent, wherein said administration is one of simultaneous or sequential.
13. The method of claim 1, wherein the subject does not have respiratory symptoms associated with either COVID-19 or ARDS, and the treating reduces the likelihood of the subject developing one or more of mild, moderate, or severe respiratory symptoms.
14. The method of any one of claims 6, 6a, or 6b, wherein the subject has severe respiratory symptoms and the treating reduces the severity or duration of the severe respiratory symptoms.
15. The method of claim 1, wherein the treating results in reduction of plasma levels of at least one inflammatory cytokine and/or chemokine in the subject.
16. The method of claim 10, wherein the at least one cytokine or chemokine comprises Chemokine (C-C motif) ligand 5 (CCL5), interleukin-6 (IL-6) or TNF-alpha (TNFα) in the subject.
17. The method of claim 16, wherein the at least one of interleukin-6 (IL-6) or TNF-alpha (TNFα) is more normalized in the subject.
18. The method of claim 1, wherein the treating results in a more normalized CD4 T cell/CD8 T cell ratio in the subject.
19. The method of claim 18, wherein the more normalized CD4 T cell/CD8 T cell ratio in the subject is between 0.9-1.9.
20. The method of claim 11, wherein the leronlimab is administered in a dose of 700 mg and wherein the dose formulation has a protein concentration of 175 mg/mL.
21. The method of claim 20, wherein the dose is administered once weekly for two weeks.
22. A method for normalizing the cytokine and/or chemokine profile of a subject infected with coronavirus comprising administering a CCR5 binding agent.
23. The method of claim 22, wherein the CCR5 binding agent comprises an antibody or a fragment thereof.
24. The method of claim 23, wherein the CCR5 binding agent is leronlimab or a fragment thereof.
25. The method of claim 22, wherein the therapeutically effective dose is administered only once or twice.
26. The method claim 22, wherein the coronavirus is one of SARS-CoV-1 or SARS-CoV-2.
27. A method for facilitating normalization of the CD4 T cell/CD8 T cell ratio in a subject infected with coronavirus, comprising administering a CCR5 binding agent.
28. The method of claim 27, wherein the CCR5 binding agent comprises an antibody or a fragment thereof.
29. The method of claim 28, wherein the CCR5 binding agent is leronlimab or a fragment thereof.
30. The method of claim 27, wherein the therapeutically effective dose is administered only once or twice.
31. The method claim 27, wherein the coronavirus is one of SARS-CoV-1 or SARS-CoV-2.
32. A method for facilitating normalization of the cytokine and/or chemokine profile of an immunocompromised subject infected with, or likely to be infected with, coronavirus, comprising administering a CCR5 binding agent.
33. The method of claim 32, wherein the therapeutically effective dose is administered once per week for as long as needed.
34. The method claim 32, wherein the coronavirus is one of SARS-CoV-1 or SARS-CoV-2.
35. A method of treating a subject for hyperinflammation in a subject infected with, or likely to be infected with, coronavirus, comprising administering to the subject an effective amount of a CCR5 binding agent.
36. The method of claim 35, wherein the CCR5 binding agent comprises an antibody or a fragment thereof.
37. The method of claim 36, wherein the CCR5 binding agent is leronlimab or a fragment thereof.
38. A method of treating a subject with hyperinflammation, comprising administering to the subject an effective amount of a CCR5 binding agent.
39. The method of claim 38, wherein the CCR5 binding agent comprises an antibody or a fragment thereof.
40. The method of claim 39, wherein the CCR5 binding agent is leronlimab or a fragment thereof.
41. A therapeutic composition comprising a CCR5 binding agent and at least one of an anti-viral therapeutic agent, an immune checkpoint molecule inhibitor, a non-CCR5 binding immunomodulatory agent, or any combination thereof
42. The method of claim 41, wherein the CCR5 binding agent comprises an antibody or a fragment thereof.
43. The method of claim 42, wherein the CCR5 binding agent is leronlimab or a fragment thereof.
44. The method of any one of claims 10, 22, 28, 36, 39, and 42, wherein said antibody comprises: (a) a heavy chain variable region (VH) comprising an amino acid sequence of SEQ ID NO:3 or amino acids 20-141 of SEQ ID NO:3, and a VL comprising an amino acid sequence of SEQ ID NO:1 or amino acids 20-131 of SEQ ID NO:1; or (b) a VH comprising an amino acid sequence of SEQ ID NO:5 or amino acids 20-141 of SEQ ID NO:5, and a VL comprising an amino acid sequence of SEQ ID NO:1 or amino acids 20-131 of SEQ ID NO:1.
45. The method of any one of claims 10, 22, 28, 36, 39, and 42, wherein said antibody is modified to extend circulating half-life.
46. A method of treating a subject for SARS-CoV-2 infection, comprising administering to the subject an effective amount of a CCR5 binding agent.
47. The method of claim 46, wherein the subject has mild, moderate, or severe COVID-19.
47a. The method of claim 47, wherein the subject has critical COVID-19.
47b. The method of claim 47, wherein the subject has severe COVID-19, but not critical COVID-19.
48. The method of any one of claims 46, 47, 47a, 47b, wherein the subject exhibits no symptoms associated with COVID-19.
49. The method of claim 48, wherein the subject has been exposed to another subject known or suspected of having COVID-19.
50. The method of claim 46 or 49, wherein the subject exhibits one or more symptoms selected from dry cough, shortness of breath, and fever.
48. The method of claim 46 or 47, wherein the treating results in the reduction of plasma levels of at least one inflammatory cytokine and/or chemokine.
49. The method of claim 48, wherein the at least one inflammatory cytokine and/or chemokine comprises CCL5, IL-6, IL-1β, IL-8, or any combination thereof.
50. The method of claim 48 or 49, wherein the reduction of plasma levels of the at least one inflammatory cytokine and/or chemokine occurs by Day 3, Day 4, Day 5, Day 6, Day 7, Day 8, Day 9, Day 10, Day 11, Day 12, Day 13, or Day 14 of treatment.

51. The method of claim 49, wherein the plasma level of IL-6 is more normalized in the subject.

52. The method of claim 51, wherein the plasma level of IL-6 is normalized in the subject by Day 14 of treatment.

53. The method of any one of claims 46-52, wherein the subject has hyperinflammation and the treating reduces a symptom associated with hyperinflammation.

54. The method of claim 53, wherein the hyperinflammation is cytokine release syndrome, hemophagocytic lymphohistiocytosis (HLH), macrophage activation syndrome, or acute respiratory distress syndrome (ARDS).

55. The method of any one of claims 46-54, wherein the treating reduces migration of CCR5+ expressing immune cells.

56. The method of claim 55, wherein the CCR5+ immune cells comprise macrophages, T cells, or both.

57. The method of any one of claims 46-56, wherein the treating increases oxygen blood saturation in the subject.

49. The method of any one of claims 46-48, wherein the CCR5+ immune cells of the subject exhibit at least 50%, 55%, 60%, 65%, 70%, 75%, 80%, 85%, 90%, or 95% receptor occupancy by Day 3 of treatment or at least 75%, 80%, 85%, 90%, 95%, 97%, or 99% receptor occupancy by Day 7 of treatment.

50. The method of any one of claims 46-49, wherein the CCR5+ immune cells of the subject exhibit receptor occupancy for at least 7 days, 10 days, or 14 days post-treatment.

51. The method of claim 49 or 50, wherein the CCR5+ immune cells comprise T cells, macrophages, or both.

52. The method of claim 51, wherein the T cells comprise regulatory T cells (Tregs).

53. The method of any one of claims 46-52, wherein the treating results in a more normalized CD4:CD8 T cell ratio in the subject.

54. The method of claim 53, wherein the more normalized CD4:CD8 T cell ratio in the subject is between 0.9-1.9.

55. The method of any one of claims 46-54, wherein the treating results in increased CD8 T cell frequency in the subject.

56. The method of claim 55, wherein the CD8 T cell frequency in the subject is more normalized by Day 7, Day 8, Day 9, Day 10, Day 11, Day 12, Day 13, or Day 14 of treatment.

57. The method of any one of claims 46-56, wherein the treating reduces T cell exhaustion in the subject.

58. The method of claim 57, wherein T cell exhaustion is measured by measuring PD-1, LAG-3, TIM-3, or any combination thereof.

59. The method of any one of claims 46-58, wherein the treating results in reduced occurrence or risk of liver toxicity, kidney failure, or a coagulation event.

60. The method of claim 59, wherein the coagulation event comprises a blood clot, stroke, or pulmonary embolism.

61. The method of claim 59, wherein the treating results in more normalization of kidney function.

62. The method of claim 61, wherein kidney function is measured by measuring blood levels of creatine, BUN, sodium, or any combination thereof in the subject blood.

63. The method of claim 59, wherein the treating results in more normalization of liver function.

64. The method of claim 63, wherein liver function is measured by measuring blood levels of bilirubin, alanine transaminase (ALT), aspartate aminotransferase (AST), or any combination thereof.

65. The method of any one of claims 46-64, wherein the treating reduces plasma SARS-CoV-2 viral load in the subject.

66. The method of claim 65, wherein the reduction in plasma SARS-CoV-2 viral load occurs by day 7 of treatment.

67. The method of claim 65 or 66, wherein the plasma SARS-CoV-2 viral load is measured by droplet digital PCR.

68. The method of any one of claims 65-67, wherein the plasma SARS-CoV-2 viral load is measured by detecting the nucleocapsid (N) gene.

69. The method of any one of claims 46-68, wherein the treating results in reduced duration or occurrence of hospitalization, ventilation or dialysis of the subject.

70. The method of any one of claims 46-69, wherein the treating results in reduced lung damage to the subject.

71. The method of any one of claims 46-70, wherein the subject has a faster and/or more extensive recovery than a subject with similar symptoms who has not been treatment with the CCR5 binding agent.

72. The method of any one of claims 46-71, wherein the treating is not accompanied by any serious, adverse side effects.

73. The method of claim one of claims 46-72, wherein the CCR5 binding agent is leronlimab or antigen binding fragment thereof.

74. The method of claim 73, wherein leronlimab is administered at a dose of about 700 mg, once a week.

75. The method of any one of claims 46-74, wherein the CCR5 binding agent is administered by subcutaneous injection.

76. A method of reducing elevated plasma CCL5 level associated with a viral infection in a subject, comprising administering to the subject an effective amount of a CCR5 binding agent.

77. The method of claim 76, wherein the elevated plasma CCL5 is at least 10-fold or 100-fold higher than normal levels.

78. The method of claim 76 or 77, wherein the viral infection is an emerging viral infection.

79. The method of any one of claims 76-78, wherein the viral infection is a coronavirus infection.

80. The method of any one of claims 76-79, wherein the viral infection is a SARS-CoV-2 infection.

81. The method of claim 80, wherein the subject has mild, moderate or severe COVID-19.

81a. The method of claim 81, wherein the subject has critical COVID-19.

81b. The method of claim 81, wherein the subject has severe COVID-19, but not critical COVID-19.

82. The method of claim 80, wherein the subject exhibits no symptoms associated with COVID-19.

83. The method of claim 82, wherein the subject has been exposed to another subject known or suspected of having COVID-19.

84. The method of any one of claim 80, 81, or 83, wherein the subject exhibits one or more symptoms selected from dry cough, shortness of breath, and fever.

85. The method of any one of claims 76-84, wherein the treating results in the reduction of plasma levels of at least one inflammatory cytokine and/or chemokine.
86. The method of claim 85, wherein the at least one inflammatory cytokine and/or chemokine comprises CCL5, IL-6, IL-1β, IL-8, or any combination thereof.
87. The method of claim 85 or 86, wherein the reduction of plasma levels of the at least one inflammatory cytokine and/or chemokine occurs by Day 3, Day 4, Day 5, Day 6, Day 7, Day 8, Day 9, Day 10, Day 11, Day 12, Day 13, or Day 14 of treatment.
88. The method of claim 86, wherein the plasma level of IL-6 is more normalized in the subject.
89. The method of claim 88, wherein the plasma level of IL-6 is normalized in the subject by Day 14 of treatment.
90. The method of any one of claims 76-89, wherein the subject has hyperinflammation and the treating reduces a symptom associated with hyperinflammation.
91. The method of claim 90, wherein the hyperinflammation is cytokine release syndrome, hemophagocytic lymphohistiocytosis (HLH), macrophage activation syndrome, or acute respiratory distress syndrome (ARDS).
92. The method of any one of claims 76-91, wherein the treating reduces migration of CCR5+ expressing immune cells.
93. The method of claim 92, wherein the CCR5+ immune cells comprise macrophages, T cells, or both.
94. The method of any one of claims 76-93, wherein the treating increases oxygen blood saturation in the subject.
95. The method of any one of claims 76-94, wherein the CCR5+ immune cells of the subject exhibit at least 50%, 55%, 60%, 65%, 70%, 75%, 80%, 85%, 90%, or 95% receptor occupancy by Day 3 of treatment or at least 75%, 80%, 85%, 90%, 95%, 97%, or 99% receptor occupancy by Day 7 of treatment.
96. The method of claim 95, wherein the CCR5+ immune cells of the subject exhibit receptor occupancy for at least 7 days, 10 days, or 14 days post-treatment.
97. The method of claim 95 or 96, wherein the CCR5+ immune cells comprise T cells, macrophages, or both.
98. The method of claim 97, wherein the T cells comprise regulatory T cells (Tregs).
99. The method of any one of claims 76-98, wherein the treating results in a more normalized CD4:CD8 T cell ratio in the subject.
100. The method of claim 99, wherein the more normalized CD4:CD8 T cell ratio in the subject is between 0.9-1.9.
101. The method of any one of claims 76-100, wherein the treating results in increased CD8 T cell frequency in the subject.
102. The method of claim 101, wherein the CD8 T cell frequency in the subject is more normalized by Day 7, Day 8, Day 9, Day 10, Day 11, Day 12, Day 13, or Day 14 of treatment.
103. The method of any one of claims 76-102, wherein the treating reduces T cell exhaustion in the subject.
104. The method of claim 103, wherein T cell exhaustion is measured by measuring PD-1, LAG-3, TIM-3, or any combination thereof 105. The method of any one of claims 76-104, wherein the treating results in reduced occurrence or risk of liver toxicity, kidney failure, or a coagulation event.
106. The method of claim 105, wherein the coagulation event comprises a blood clot, stroke, or pulmonary embolism.
107. The method of claim 105, wherein the treating results in more normalization of kidney function.
108. The method of claim 107, wherein kidney function is measured by measuring blood levels of creatine, BUN, sodium, or any combination thereof in the subject blood.
109. The method of claim 105, wherein the treating results in more normalization of liver function.
110. The method of claim 109, wherein liver function is measured by measuring blood levels of bilirubin, alanine transaminase (ALT), aspartate aminotransferase (AST), or any combination thereof.
111. The method of any one of claims 80-110, wherein the treating reduces plasma SARS-CoV-2 viral load in the subject.
112. The method of claim 111, wherein the reduction in plasma SARS-CoV-2 viral load occurs by day 7 of treatment.
113. The method of claim 111 or 112, wherein the plasma SARS-CoV-2 viral load is measured by droplet digital PCR.
114. The method of any one of claims 111-113, wherein the plasma SARS-CoV-2 viral load is measured by detecting the nucleocapsid (N) gene.
115. The method of any one of claims 76-114, wherein the treating results in reduced duration or occurrence of hospitalization, ventilation or dialysis of the subject.
116. The method of any one of claims 76-115, wherein the treating results in reduced lung damage to the subject.
117. The method of any one of claims 76-116, wherein the subject has a faster and/or more extensive recovery than a subject with similar symptoms who has not been treatment with the CCR5 binding agent.
118. The method of any one of claims 76-117, wherein the treating is not accompanied by any serious, adverse side effects.
119. The method of claim one of claims 76-118, wherein the CCR5 binding agent is leronlimab or an antigen binding fragment thereof.
120. The method of claim 119, wherein leronlimab is administered at a dose of about 700 mg, once a week.
121. The method of any one of claims 76-120, wherein the CCR5 binding agent is administered by subcutaneous injection.
122. A method for increasing CD8+ T cell frequency in a subject infected with coronavirus, comprising administering an effective amount of a CCR5 binding agent.
123. The method of claim 122, wherein the CD8 T cell frequency in the subject is more normalized by Day 7, Day 8, Day 9, Day 10, Day 11, Day 12, Day 13, or Day 14 of treatment.
124. A method for normalizing CD4:CD8 T cell ratio in a subject infected with coronavirus, comprising administering an effective amount of a CCR5 binding agent.
125. The method of claim 124, wherein the more normalized CD4:CD8 T cell ratio in the subject is between 0.9-1.9.
126. A method for reducing migration of CCR5+ immune cells in a subject infected with coronavirus, comprising administering an effective amount of a CCR5 binding agent.
127. The method of claim 126, wherein the CCR5+ immune cells comprise macrophages, T cells, or both.

128. A method for reducing T cell exhaustion in a subject infected with coronavirus, comprising administering an effective amount of a CCR5 binding agent.

129. The method of claim 127, wherein T cell exhaustion is measured by measuring PD-1, LAG-3, TIM-3, or any combination thereof 130. A method for reducing plasma coronavirus viral load in a subject, comprising administering to the subject an effective amount of a CCR5 binding agent.

131. The method of claim 130, wherein the coronavirus is SARS-CoV-2.

132. The method of claim 131, wherein the reduction in plasma SARS-CoV-2 viral load occurs by day 7 of treatment.

133. The method of claim 130 or 131, wherein the plasma SARS-CoV-2 viral load is measured by droplet digital PCR.

134. The method of any one of claims 130-133, wherein the plasma SARS-CoV-2 viral load is measured by detecting the nucleocapsid (N) gene.

135. A method of reducing plasma levels of at least one inflammatory cytokine and/or chemokine in a subject infected with coronavirus, comprising administering to the subject an effective amount of a CCR5 binding agent.

136. The method of claim 135, wherein the coronavirus is SARS-CoV-2.

137. The method of claim 135 or 136, wherein the at least one inflammatory cytokine and/or chemokine comprises CCL5, IL-6, IL-1β, IL-8, or any combination thereof.

138. The method of any one of claims 135-137, wherein the reduction of plasma levels of the at least one inflammatory cytokine and/or chemokine occurs by Day 3, Day 4, Day 5, Day 6, Day 7, Day 8, Day 9, Day 10, Day 11, Day 12, Day 13, or Day 14 of treatment.

139. The method of claim 137, wherein the plasma level of IL-6 is more normalized in the subject.

140. The method of claim 139, wherein the plasma level of IL-6 is normalized in the subject by Day 14 of treatment.

141. A method of treating hyperinflammation in a subject infected with a coronavirus comprising administering to the subject an effective amount of a CCR5 binding agent, wherein the treating reduces a symptom associated with hyperinflammation.

142. The method of claim 141, wherein the coronavirus is SARS-CoV-2.

142. The method of claim 141 or 142, wherein the hyperinflammation is cytokine release syndrome, hemophagocytic lymphohistiocytosis (HLH), macrophage activation syndrome, or acute respiratory distress syndrome (ARDS).

143. A method of reducing occurrence or risk of liver toxicity or kidney failure in a subject infected with coronavirus, comprising administering an effective amount of a CCR5 binding agent.

144. The method of claim 143, wherein the coronavirus is SARS-CoV-2.

145. The method of claim 143 or 144, wherein the administration results in more normalization of kidney function.

146. The method of claim 144, wherein kidney function is measured by measuring blood levels of creatine, BUN, sodium, or any combination thereof in the subject blood.

147. The method of claim 143 or 144, wherein the administration results in more normalization of liver function.

148. The method of claim 147, wherein liver function is measured by measuring blood levels of bilirubin, alanine transaminase (ALT), aspartate aminotransferase (AST), or any combination thereof.

149. A method of reducing occurrence or risk of a coagulation event in a subject infected with coronavirus, comprising administering an effective amount of a CCR5 binding agent.

150. The method of claim 149, wherein the coronavirus is SARS-CoV-2.

151. The method of claim 150, wherein the coagulation event comprises a blood clot, stroke, or pulmonary embolism.

152. The method of any one of claims 122-151, wherein the CCR5 binding agent is leronlimab or an antigen binding fragment thereof.

153. The method of claim 152, wherein leronlimab is administered at a dose of about 700 mg, once a week.

154. The method of any one of claims 122-153, wherein the CCR5 binding agent is administered by subcutaneous injection.

TABLE 14

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| | | | | | | Seurat Cluster 0 | | | | | |
| TRBV12-4 | 0 | 0.290313365 | 0.033 | 0.96 | 0 | TMEM156 | 1.05E-72 | -0.269889862 | 0.068 | 0.321 | 2.10E-69 |
| TRAV21 | 1.96E-245 | 0.327062624 | 0.053 | 0.895 | 3.92E-242 | TIPARP | 1.97E-43 | -0.271249991 | 0.091 | 0.372 | 3.94E-40 |
| AC103591.3 | 9.02E-219 | -0.264102961 | 0.025 | 0.185 | 1.80E-215 | STAT1 | 1.55E-26 | 0.282833828 | 0.381 | 0.998 | 3.10E-23 |
| TRAV13-1 | 9.08E-176 | 0.251365921 | 0.084 | 0.882 | 1.82E-172 | TOB1 | 1.69E-20 | -0.278569358 | 0.198 | 0.441 | 3.39E-17 |
| TRBV6-2 | 1.54E-175 | 0.275705286 | 0.053 | 0.832 | 3.08E-172 | MT2A | 6.06E-18 | -0.528748442 | 0.327 | 0.817 | 1.21E-14 |
| TRBV7-2 | 9.46E-160 | 0.489628702 | 0.106 | 0.895 | 1.89E-156 | ZFP36 | 2.16E-10 | -0.370828441 | 0.624 | 0.847 | 4.33E-07 |
| TRBV6-6 | 6.20E-157 | 0.281732796 | 0.018 | 0.632 | 1.24E-153 | TRBV9 | 0.000211251 | 0.26115631 | 0.032 | 0.523 | 0.422501212 |
| TRAV29DV5 | 1.41E-150 | 0.32643269 | 0.071 | 0.84 | 2.81E-147 | ZFP36L2 | 0.002513927 | -0.30975941 | 0.943 | 0.998 | 1 |
| RGS1 | 1.81E-137 | -0.314768302 | 0.04 | 0.248 | 3.63E-134 | JUND | 0.039710195 | -0.293453673 | 0.155 | 0.536 | 1 |
| TRBV7-9 | 4.18E-129 | 0.356671141 | 0.064 | 0.809 | 8.36E-126 | TRBV12-3 | 0.081851578 | 0.295122039 | 0.036 | 0.534 | 1 |
| TRBV6-5 | 1.98E-113 | 0.280555007 | 0.045 | 0.765 | 3.96E-110 | KLRB1 | 0.47393198 | 0.250326551 | 0.432 | 0.784 | 1 |
| GZMA | 3.07E-110 | 0.344773147 | 0.214 | 0.981 | 6.15E-107 | TRBV3-1 | 0.840181846 | 0.410313913 | 0.045 | 0.5 | 1 |
| CCL5 | 2.37E-84 | 0.367943256 | 0.253 | 0.983 | 4.74E-81 | IFI44L | 0.993544463 | -0.441424979 | 0.048 | 0.456 | 1 |
| TRAV38-2DV8 | 2.33E-81 | 0.282026119 | 0.039 | 0.721 | 4.65E-78 | | | | | | |
| | | | | | | Seurat Cluster 1 | | | | | |
| PPBP | 1.97E-157 | -0.490971132 | 0.007 | 0.212 | 3.94E-154 | AL138963.3 | 1.97E-19 | 0.341376137 | 0.456 | 0.999 | 3.94E-16 |
| NR4A1 | 1.38E-90 | 0.260000965 | 0.253 | 0.975 | 2.76E-87 | AC015912.3 | 4.80E-14 | -0.277039216 | 0.074 | 0.44 | 9.60E-11 |
| CXCL2 | 3.93E-74 | -0.298191772 | 0.012 | 0.306 | 7.85E-71 | RHOB | 1.68E-09 | 0.277850267 | 0.469 | 1 | 3.35E-06 |
| CCL3 | 1.54E-57 | -0.376107215 | 0.055 | 0.335 | 3.07E-54 | TAGLN2 | 2.13E-07 | 0.316613955 | 0.7 | 0.825 | 0.000425946 |
| Z93241.1 | 1.95E-53 | 0.358815767 | 0.325 | 1 | 3.90E-50 | MNDA | 5.99E-07 | -0.261134407 | 0.855 | 1 | 0.001197441 |
| ADM | 1.46E-47 | -0.256557505 | 0.064 | 0.356 | 2.93E-44 | CXCL8 | 5.81E-05 | -0.449194726 | 0.034 | 0.469 | 0.116125545 |
| EREG | 3.99E-43 | -0.36616555 | 0.034 | 0.359 | 7.98E-40 | ISG15 | 8.31E-05 | 0.260291828 | 0.232 | 0.693 | 0.166201197 |
| TNFSF10 | 1.02E-37 | 0.297904417 | 0.372 | 0.996 | 2.04E-34 | NFKBIA | 0.010505475 | 0.259793925 | 0.713 | 0.91 | 1 |
| XIST | 1.68E-30 | 0.313989139 | 0.362 | 1 | 3.36E-27 | CLU | 0.034494675 | -0.385484131 | 0.003 | 0.524 | 1 |
| G0S2 | 1.40E-24 | -0.386125135 | 0.138 | 0.422 | 2.80E-21 | TNFAIP3 | 0.05847586 | -0.290285781 | 0.11 | 0.571 | 1 |
| EGR1 | 3.14E-20 | -0.501687758 | 0.033 | 0.408 | 6.28E-17 | | | | | | |
| | | | | | | Seurat Cluster 2 | | | | | |
| TRBV10-3 | 2.54E-241 | 0.287283756 | 0.026 | 0.968 | 5.08E-238 | IFIT2 | 2.10E-23 | -0.419138439 | 0.017 | 0.308 | 4.20E-20 |
| TRAV13-11 | 4.00E-196 | 0.263970255 | 0.084 | 0.968 | 8.00E-193 | TOB11 | 2.15E-20 | -0.298935835 | 0.148 | 0.431 | 4.30E-17 |
| TRAV8-4 | 6.69E-190 | 0.273286054 | 0.045 | 0.869 | 1.34E-186 | TRBV12-31 | 5.32E-18 | 0.653461099 | 0.037 | 0.416 | 1.06E-14 |
| TRBV18 | 1.81E-186 | 0.331134726 | 0.05 | 0.871 | 3.62E-186 | TRBV3-11 | 7.01E-17 | 0.298613572 | 0.037 | 0.41 | 1.40E-13 |
| S100A8 | 8.97E-186 | -0.349766869 | 0.019 | 0.183 | 1.79E-182 | TRBV4-1 | 5.27E-15 | 0.385108981 | 0.025 | 0.26 | 1.05E-11 |
| TUBB2A | 1.14E-183 | -0.310499869 | 0.014 | 0.187 | 2.28E-180 | HIST1H1C | 3.55E-14 | -0.306308266 | 0.28 | 0.759 | 7.11E-11 |
| TRBV12-41 | 1.80E-167 | 0.311171132 | 0.034 | 0.847 | 3.59E-164 | TRBV5-4 | 3.64E-14 | 0.3599121 | 0.039 | 0.606 | 7.29E-11 |
| TRBV19 | 1.82E-142 | 0.263509184 | 0.061 | 0.865 | 3.65E-139 | TRBV7-91 | 6.86E-08 | 0.441426861 | 0.059 | 0.596 | 0.00013729 |
| AC103591.31 | 4.99E-138 | -0.572462597 | 0.029 | 0.219 | 9.98E-135 | FOS | 1.05E-07 | -0.416376722 | 0.643 | 0.835 | 0.000210734 |
| TRAV38-2DV81 | 9.98E-111 | 0.313578255 | 0.046 | 0.791 | 2.00E-107 | JUND1 | 1.25E-07 | -0.383823049 | 0.093 | 0.469 | 0.000249478 |
| SGK1 | 2.95E-103 | -0.30037631 | 0.025 | 0.26 | 5.89E-100 | AL138963.31 | 5.73E-06 | 0.275906532 | 0.537 | 0.994 | 0.01146664 |
| PMAIP1 | 1.41E-86 | -0.371365134 | 0.21 | 0.922 | 2.83E-83 | SUB1 | 1.30E-05 | -0.2576887 | 0.62 | 0.845 | 0.026084297 |
| AC245014.3 | 3.61E-79 | -0.388930367 | 0.067 | 0.767 | 7.23E-76 | IFIT3 | 2.02E-05 | -0.34018572 | 0.008 | 0.314 | 0.040481881 |
| TRBV7-21 | 8.54E-78 | 0.461478708 | 0.052 | 0.746 | 1.71E-74 | ZFP36L21 | 0.000320428 | -0.351393053 | 0.937 | 0.996 | 0.640856318 |
| TRBV6-21 | 3.42E-66 | 0.416106429 | 0.047 | 0.32 | 6.84E-63 | TRBV20-1 | 0.05741925 | 0.670209009 | 0.104 | 0.531 | 1 |
| TRBV28 | 1.59E-54 | 0.319999864 | 0.309 | 1 | 3.17E-51 | NFKBIZ | 0.063411388 | -0.352219239 | 0.232 | 0.622 | 1 |
| STAT11 | | 0.250714807 | | | | IFI44L1 | 0.10069594 | -0.572018963 | 0.022 | 0.419 | 1 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| TMEM1561 | 3.03E-51 | -0.346873459 | 0.039 | 0.342 | 6.07E-48 | HSPA5 | 0.145732716 | -0.324926402 | 0.336 | 0.674 | 1 |
| NFKBIA1 | 8.94E-46 | -0.613367961 | 0.287 | 0.829 | 1.79E-42 | DUSP2 | 0.45267549 | -0.338075256 | 0.139 | 0.547 | 1 |
| MT2A1 | 1.94E-32 | -0.321909558 | 0.266 | 0.853 | 3.88E-29 | DDIT4 | 0.749157856 | -0.427598643 | 0.188 | 0.567 | 1 |
| TRBV6-51 | 6.25E-31 | 0.351276032 | 0.061 | 0.672 | 1.25E-27 | TNFAIP31 | 0.804359999 | -0.604513567 | 0.22 | 0.577 | 1 |
| H1FX | 6.77E-27 | -0.430906022 | 0.295 | 0.815 | 1.35E-23 | TRBV5-1 | 0.81953052 | 0.284053997 | 0.066 | 0.531 | 1 |
| AREG | 3.55E-26 | -0.314672728 | 0.055 | 0.396 | 7.10E-23 | HIST1H1D | 0.897333935 | -0.257756297 | 0.463 | 0.688 | 1 |
| | | | | | | Seurat Cluster 3 | | | | | |
| MYOM2 | 5.92E-241 | -0.302553484 | 0.03 | 0.941 | 1.18E-237 | TNF | 4.71E-13 | -0.349439263 | 0.128 | 0.688 | 9.42E-10 |
| FCER1G | 4.49E-218 | -0.326768578 | 0.032 | 0.954 | 8.99E-215 | MATK | 6.34E-12 | -0.290319405 | 0.41 | 0.918 | 1.27E-08 |
| CX3CR1 | 1.90E-193 | -0.280513027 | 0.035 | 0.839 | 3.80E-190 | AQP3 | 1.91E-11 | 0.480139816 | 0.396 | 1 | 3.81E-08 |
| FCGR3A | 5.65E-191 | -0.431727072 | 0.046 | 0.934 | 1.13E-187 | GPI | 3.10E-11 | -0.2637345 | 0.453 | 0.947 | 6.21E-08 |
| TRAV38-2DV82 | 3.60E-156 | 0.320543923 | 0.08 | 0.961 | 7.20E-153 | TLN1 | 4.60E-11 | -0.270689414 | 0.29 | 0.789 | 9.20E-08 |
| TRBV4-11 | 2.68E-150 | -0.358081946 | 0.03 | 0.868 | 5.36E-147 | SH3BGRL3 | 1.47E-10 | -0.264966355 | 0.986 | 1 | 2.94E-07 |
| FGR | 2.36E-147 | -0.301416512 | 0.074 | 0.931 | 4.73E-144 | TRBV20-11 | 1.47E-09 | 0.363717759 | 0.088 | 0.641 | 2.95E-06 |
| TRDV2 | 1.64E-137 | 0.392826931 | 0.122 | 0.99 | 3.28E-134 | GZMM | 3.30E-09 | -0.381016356 | 0.724 | 0.984 | 6.60E-06 |
| TRAV14DV4 | 1.80E-130 | 0.279423285 | 0.052 | 0.826 | 3.59E-127 | STAT12 | 1.02E-08 | 0.358972791 | 0.355 | 0.885 | 2.04E-05 |
| XCL1 | 9.09E-124 | -0.448022569 | 0.113 | 0.947 | 1.82E-120 | CD8A | 1.38E-08 | -0.431870631 | 0.613 | 0.961 | 2.77E-05 |
| XCL2 | 2.19E-123 | -0.39119526 | 0.144 | 0.993 | 4.37E-120 | CD74 | 1.79E-08 | -0.452961549 | 0.923 | 0.997 | 3.58E-05 |
| TRBV6-4 | 9.56E-99 | 0.314047606 | 0.057 | 0.664 | 1.91E-95 | ZEB2 | 2.92E-08 | -0.421691227 | 0.085 | 0.438 | 5.84E-05 |
| TRBV4-2 | 1.25E-82 | 0.754995408 | 0.085 | 0.822 | 2.50E-79 | CCL31 | 4.13E-08 | -0.295265328 | 0.015 | 0.401 | 8.26E-05 |
| HLA-DRB5 | 2.08E-79 | -0.300011535 | 0.16 | 0.921 | 4.15E-76 | CCL4 | 4.59E-08 | -1.070761349 | 0.153 | 0.635 | 9.18E-05 |
| TRBV12-42 | 6.10E-75 | 0.294989398 | 0.029 | 0.737 | 1.22E-71 | GZMA1 | 1.35E-07 | -0.378852374 | 0.737 | 0.997 | 0.000269887 |
| TRGV4 | 4.70E-74 | 0.267482851 | 0.151 | 0.911 | 9.41E-71 | PPIA | 1.70E-07 | -0.324420101 | 0.947 | 0.997 | 0.000340009 |
| S100B | 1.41E-72 | -0.401355009 | 0.003 | 0.115 | 2.82E-69 | HLA-DPA1 | 3.78E-07 | -0.366890849 | 0.358 | 0.74 | 0.000075563 |
| CLIC3 | 3.57E-70 | -0.523518146 | 0.147 | 0.888 | 7.13E-67 | GSTP1 | 3.87E-07 | -0.361488188 | 0.554 | 0.901 | 0.000773471 |
| IF127 | 3.17E-69 | -0.277599637 | 0.007 | 0.112 | 6.34E-66 | LGALS9 | 5.64E-07 | -0.317550087 | 0.023 | 0.441 | 0.001127599 |
| TRBV191 | 3.98E-69 | 0.360613143 | 0.052 | 0.783 | 7.96E-66 | IFITM2 | 1.40E-06 | -0.378079606 | 0.856 | 0.977 | 0.002809118 |
| SLC4A10 | 1.02E-65 | 0.342939487 | 0.181 | 0.868 | 2.03E-62 | HLA-DPB1 | 2.16E-06 | -0.338650895 | 0.387 | 0.75 | 0.004325005 |
| AC103591.32 | 6.72E-60 | -0.32274049 | 0.033 | 0.283 | 1.34E-56 | C12orf75 | 2.51E-06 | -0.259668141 | 0.429 | 0.842 | 0.005020991 |
| JAML | 9.04E-55 | 0.29447958 | 0.228 | 0.974 | 1.81E-51 | CD69 | 4.77E-06 | 0.251664227 | 0.716 | 0.799 | 0.009532324 |
| ATF3 | 3.33E-50 | -0.301688777 | 0.014 | 0.286 | 6.66E-47 | S100A4 | 5.15E-06 | -0.339486675 | 0.96 | 0.993 | 0.010298418 |
| HLA-DRA | 8.00E-48 | -0.557564077 | 0.083 | 0.763 | 1.60E-44 | IFNG | 9.49E-06 | -0.424524427 | 0.042 | 0.438 | 0.019986267 |
| TRBV6-22 | 8.55E-45 | 0.429951457 | 0.063 | 0.717 | 1.71E-41 | TRAV29-DV51 | 5.11E-05 | 0.30785626 | 0.043 | 0.562 | 0.102173357 |
| GNIY | 7.42E-43 | -0.967442527 | 0.141 | 0.799 | 1.48E-39 | MT2A2 | 0.000125568 | -0.273890653 | 0.462 | 0.806 | 0.251135614 |
| LTB | 1.59E-41 | 0.855272646 | 0.884 | 1 | 3.18E-38 | AHNAK | 0.000128706 | -0.344639553 | 0.693 | 0.993 | 0.2574111594 |
| RGS11 | 1.76E-38 | -0.314263353 | 0.05 | 0.329 | 3.53E-35 | NOSIP | 0.000221966 | 0.469918416 | 0.658 | 0.993 | 0.443932359 |
| MYC | 3.41E-35 | 0.412444141 | 0.252 | 0.934 | 6.82E-32 | HSP90B1 | 0.000336774 | -0.429469906 | 0.765 | 1 | 0.67354808 |
| IFIT21 | 4.00E-33 | -0.653260513 | 0.022 | 0.339 | 8.00E-30 | ISGI51 | 0.000360592 | -0.343961932 | 0.308 | 0.704 | 0.721184962 |
| NKG7 | 1.26E-32 | -0.745459463 | 0.819 | 0.99 | 2.53E-29 | ACTG1 | 0.000365946 | -0.419420654 | 0.969 | 1 | 0.73189297 |
| PLEK | 3.16E-32 | -0.274785618 | 0.344 | 1 | 6.32E-29 | SELL | 0.000371385 | 0.278640451 | 0.489 | 1 | 0.742770895 |
| OASL | 1.25E-30 | -0.321858459 | 0.046 | 0.349 | 2.50E-27 | CALR | 0.00039052 | -0.354508341 | 0.637 | 0.974 | 0.781040551 |
| PDE4D | 2.18E-30 | -0.303843413 | 0.124 | 0.355 | 4.37E-27 | CTSW | 0.000580184 | -0.495304384 | 0.803 | 0.951 | 1 |
| ADGRG1 | 9.23E-27 | -0.383654626 | 0.044 | 0.664 | 1.85E-23 | IFIT31 | 0.000874441 | -0.472669793 | 0.007 | 0.408 | 1 |
| IL7R | 1.65E-26 | 0.400020252 | 0.931 | 1 | 3.30E-23 | CORO1A | 0.000902923 | -0.272108303 | 0.957 | 0.997 | 1 |
| SAMD3 | 4.22E-25 | -0.347749252 | 0.41 | 0.98 | 8.44E-22 | ATP5F1B | 0.000915847 | -0.323137861 | 0.633 | 0.964 | 1 |
| KLRD1 | 8.58E-25 | -0.535137965 | 0.242 | 0.809 | 1.72E-21 | HSPA51 | 0.001162996 | -0.2802588 | 0.615 | 0.862 | 1 |
| LEF1 | 2.10E-24 | 0.283700275 | 0.217 | 0.839 | 4.19E-21 | C1orf21 | 0.003791981 | -0.343961932 | 0.054 | 0.464 | 1 |
| PRF1 | 2.28E-23 | -0.387689544 | 0.411 | 1 | 4.57E-20 | HNRNPA2B1 | 0.00520904 | -0.261065892 | 0.903 | 0.993 | 1 |
| APOBEC3G | 8.00E-23 | -0.359540569 | 0.396 | 0.984 | 1.60E-19 | ENC1 | 0.005597871 | -0.2621701 | 0.017 | 0.444 | 1 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| FCRL6 | 2.69E-22 | -0.383772058 | 0.109 | 0.707 | 5.38E-19 | PPIB | 0.00599809 | -0.279523431 | 0.872 | 0.997 | 1 |
| IFI44L2 | 3.20E-22 | -0.272063609 | 0.039 | 0.352 | 6.39E-19 | OAZ1 | 0.010061217 | -0.331946196 | 0.916 | 1 | 1 |
| CCL4L2 | 2.99E-21 | -0.299100294 | 0.04 | 0.638 | 5.97E-18 | IFITM3 | 0.012112277 | -0.257790928 | 0.571 | 1 | 1 |
| HOPX | 1.66E-20 | -0.379356681 | 0.414 | 0.984 | 3.31E-17 | KLRB11 | 0.013150695 | 0.704377752 | 0.498 | 0.993 | 1 |
| TGFBR3 | 1.75E-20 | -0.261386979 | 0.159 | 0.747 | 3.51E-17 | SPON2 | 0.013553115 | -0.47959563 | 0.074 | 0.569 | 1 |
| GZMH | 4.14E-20 | -0.747173606 | 0.079 | 0.632 | 8.28E-17 | GZMB | 0.0338446 | -0.756157579 | 0.025 | 0.47 | 1 |
| IDH2 | 9.67E-20 | -0.356183325 | 0.331 | 0.875 | 1.93E-16 | NCL | 0.054056293 | -0.308546859 | 0.773 | 0.997 | 1 |
| NELL2 | 4.68E-18 | 0.291850931 | 0.362 | 0.98 | 9.35E-15 | SLC9A3R1 | 0.079635492 | -0.339280695 | 0.702 | 1 | 1 |
| RPLP0 | 1.36E-17 | 0.255353081 | 0.998 | 1 | 2.72E-14 | PSMB9 | 0.083826179 | -0.327435609 | 0.817 | 1 | 1 |
| FGFBP2 | 1.23E-16 | -0.923877212 | 0.047 | 0.618 | 2.46E-13 | ANXA6 | 0.093864626 | -0.293644432 | 0.692 | 1 | 1 |
| TRAV1-2 | 1.29E-16 | 0.649731734 | 0.238 | 0.829 | 2.58E-13 | TUBA4A | 0.169732893 | -0.3200912 | 0.361 | 0.671 | 1 |
| CD63 | 1.52E-16 | -0.273537544 | 0.311 | 0.849 | 3.03E-13 | ANXA1 | 0.192443633 | -0.264968591 | 0.76 | 0.997 | 1 |
| MIR4435-2HG | 4.08E-16 | -0.329577736 | 0.056 | 0.401 | 8.15E-13 | CD7 | 0.211237839 | -0.297114927 | 0.747 | 0.98 | 1 |
| RHOB1 | 6.18E-16 | -0.296210998 | 0.063 | 0.401 | 1.24E-12 | NCR3 | 0.220722825 | 0.269099705 | 0.375 | 0.786 | 1 |
| CST7 | 1.89E-15 | -0.39732351 | 0.747 | 0.984 | 3.78E-12 | NFKBIZ1 | 0.281089606 | -0.288739192 | 0.231 | 0.622 | 1 |
| H1FX1 | 2.89E-15 | -0.314922296 | 0.285 | 0.438 | 5.77E-12 | MAP3K8 | 0.301277825 | -0.363206775 | 0.161 | 0.546 | 1 |
| ZBP1 | 4.02E-15 | -0.338017516 | 0.107 | 0.411 | 8.04E-12 | NEAT1 | 0.310099907 | -0.297147812 | 0.437 | 0.641 | 1 |
| ACTB | 4.02E-14 | -0.281098807 | 1 | 1 | 8.04E-11 | LCK | 0.394724681 | -0.284784018 | 0.839 | 1 | 1 |
| CTSC | 4.33E-14 | -0.261031676 | 0.469 | 0.974 | 8.67E-11 | HLA-DRB1 | 0.465479825 | -0.588148296 | 0.194 | 0.576 | 1 |
| TRAV2l1 | 6.85E-14 | 0.264869889 | 0.041 | 0.546 | 1.37E-10 | HERPUD1 | 0.494866952 | -0.316568296 | 0.287 | 0.592 | 1 |
| EFHD1 | 1.56E-13 | -0.481813422 | 0.136 | 0.684 | 3.11E-10 | TCF7 | 0.77788546 | 0.37350117 | 0.542 | 0.951 | 1 |
| LGALS1 | 1.57E-13 | -0.592669896 | 0.236 | 0.743 | 3.14E-10 | | | | | | |

Seurat Cluster 4

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| ATF31 | 3.07E-181 | -0.315361931 | 0.014 | 0.11 | 6.13E-178 | HBB | 1.36E-24 | -0.862077092 | 0.003 | 0.221 | 2.73E-21 |
| TRDV21 | 1.25E-176 | -0.354066379 | 0.009 | 0.751 | 2.50E-173 | CD3G | 3.10E-24 | -0.504188923 | 0.032 | 0.367 | 6.20E-21 |
| LILRB1 | 7.25E-157 | -0.305242261 | 0.024 | 0.137 | 1.45E-153 | FOSB | 1.12E-23 | -0.333159148 | 0.171 | 0.763 | 2.24E-20 |
| MT1E | 1.14E-150 | -0.277542215 | 0.003 | 0.127 | 2.28E-147 | XIST1 | 1.53E-23 | -0.418563648 | 0.151 | 0.386 | 3.06E-20 |
| LMNA | 2.29E-149 | -0.422604546 | 0.009 | 0.134 | 4.57E-146 | ZBP11 | 2.17E-23 | -0.440096927 | 0.202 | 0.388 | 4.34E-20 |
| AC10591.33 | 4.68E-130 | -0.404580574 | 0.021 | 0.173 | 9.36E-127 | CXXC5 | 2.60E-20 | 0.326143417 | 0.363 | 1 | 5.20E-17 |
| CD8B | 2.29E-129 | -0.253672158 | 0.023 | 0.801 | 4.59E-126 | PMAIP11 | 7.95E-20 | -0.496205737 | 0.166 | 0.398 | 1.59E-16 |
| LINC02446 | 5.84E-116 | -0.438680211 | 0.002 | 0.141 | 1.17E-112 | GSN | 8.50E-20 | 0.29926034 | 0.369 | 1 | 1.70E-16 |
| GRASP | 4.63E-115 | -0.412102333 | 0.011 | 0.173 | 9.26E-112 | GNLY1 | 2.03E-19 | 0.302032902 | 0.984 | 0.988 | 4.06E-16 |
| TRGV9 | 4.84E-112 | -0.341892854 | 0.16 | 0.976 | 9.69E-109 | TNF1 | 2.69E-19 | -0.417087447 | 0.027 | 0.379 | 5.39E-16 |
| ENC11 | 3.51E-109 | -0.465065568 | 0.024 | 0.199 | 7.01E-106 | RGS12 | 1.30E-18 | -0.276514913 | 0.013 | 0.367 | 2.60E-15 |
| IFI44L3 | 1.65E-103 | -0.425426104 | 0.006 | 0.211 | 3.30E-100 | IL32 | 1.94E-17 | 0.582231475 | 0.737 | 0.866 | 3.87E-14 |
| S100B1 | 3.83E-102 | -0.398010174 | 0.002 | 0.213 | 7.66E-99 | NR4A2 | 1.48E-14 | -0.337294692 | 0.157 | 0.429 | 2.97E-11 |
| RPS4Y1 | 1 35E-101 | -0.333419485 | 0 | 0.127 | 2.70E-98 | HLA-DPA11 | 1.09E-13 | -0.252149305 | 0.25 | 0.451 | 2.19E-10 |
| GZMK | 5.49E-99 | 0.375413545 | 0.109 | 0.894 | 1.10E-95 | ITGAX | 1.13E-13 | -0.3616746 | 0.103 | 0.664 | 2.27E-10 |
| PTMS | 7.35E-89 | -0.471744804 | 0.01 | 0.225 | 1.47E-85 | JUND2 | 3.33E-13 | -0.255941674 | 0.107 | 1 | 6.66E-10 |
| RGCC | 6.14E-87 | -0.396280044 | 0.031 | 0.791 | 1.23E-83 | GBP5 | 1.33E-12 | -0.402184522 | 0.027 | 0.429 | 2.65E-09 |
| MIDN | 3.66E-82 | -0.267643933 | 0.17 | 0.923 | 7.31E-79 | XCL11 | 1.44E-11 | 0.556388644 | 0.495 | 0.986 | 2.87E-08 |
| ERLEC1 | 6.24E-82 | -0.425426104 | 0.143 | 0.897 | 1.25E-78 | ISG1 52 | 1.42E-08 | -0.34610182 | 0.4 | 1 | 2.83E-05 |
| OASL1 | 1.62E-79 | -0.250758009 | 0.032 | 0.237 | 3.25E-76 | ABRACL | 5.17E-08 | 0.285546909 | 0.292 | 0.484 | 0.00010339 |
| EPST11 | 4.77E-75 | -0.558037848 | 0.073 | 0.254 | 9.54E-72 | LAT2 | 8.62E-07 | 0.304068618 | 0.428 | 1 | 0.00172439 |
| LAG3 | 2.55E-73 | -0.33181361 | 0.004 | 0.235 | 5.11E-70 | ELL2 | 9.83E-07 | -0.330237798 | 0.027 | 0.436 | 0.001965603 |
| S100A81 | 3.56E-70 | -0.387880696 | 0.014 | 0.182 | 7.11E-67 | HSP90B11 | 1.32E-06 | -0.391000402 | 0.669 | 0.99 | 0.002635406 |
| TRDV1 | 1.05E-66 | -0.260400102 | 0.004 | 0.23 | 2.11E-63 | TYMP | 3.39E-06 | -0.356514571 | 0.069 | 0.46 | 0.006778934 |
| CCL3L1 | 5.83E-61 | -0.322893863 | 0.011 | 0.281 | 1.17E-57 | MX1 | 0.000216947 | -0.349929346 | 0.057 | 0.47 | 0.421620834 |
| AREG1 | 8.30E-61 | -0.40889866 | 0.04 | 0.281 | 1.66E-57 | CCL41 | 0.000216947 | -0.429191165 | 0.61 | 0.978 | 0.43389379 |
| PDE4D1 | 1.76E-53 | -0.361004935 | 0.102 | 0.295 | 3.51E-50 | CTSW1 | 0.000250045 | -0.26461595 | 0.977 | 0998 | 0.500090263 |

TABLE 14-continued

|   | p_val | avg_logFC | pct.1 | pct.2 | p_val_adj |   | p_val | avg_logFC | pct1 | pct.2 | p_val_adj |
|---|---|---|---|---|---|---|---|---|---|---|---|
| IFIT22 | 8.48E-51 | -0.960226257 | 0.043 | 0.297 | 1.70E-47 | CCL51 | 0.000611888 | 0.259677345 | 0.811 | 0.954 | 1 |
| TRGV5 | 1.80E-50 | -0.291233352 | 0.001 | 0.209 | 3.60E-47 | BANF1 | 0.000771232 | 0.25859003 | 0.482 | 1 | 1 |
| NFKBIZ2 | 1.08E-46 | -0.571435993 | 0.081 | 0.309 | 2.16E-43 | ODC1 | 0.001404293 | -0.259277781 | 0.091 | 0.492 | 1 |
| IFIT32 | 3.13E-46 | -1.06279377 | 0.028 | 0.305 | 6.25E-43 | CCL32 | 0.001512817 | -0.446307489 | 0.213 | 0.659 | 1 |
| TIPARP1 | 1.90E-45 | -0.388615153 | 0.082 | 0.314 | 3.80E-42 | GLIPR1 | 0.002124906 | 0.336103619 | 0.344 | 0.796 | 1 |
| PTGDS | 4.56E-45 | -0.558063378 | 0.055 | 0.317 | 9.11E-42 | ZEB21 | 0.00383698 | -0.414775042 | 0.41 | 0.724 | 1 |
| CFAP20 | 4.68E-44 | -0.332921323 | 0.082 | 0.319 | 9.36E-41 | H1FX2 | 0.0049816 | -0.767864305 | 0.119 | 0.494 | 1 |
| KIR2DLI | 1.80E-43 | 0.365215647 | 0.219 | 0.902 | 3.60E-40 | CD3D | 0.005001565 | -0.905592197 | 0.047 | 0.554 | 1 |
| MYADM | 2.08E-43 | -0.392624581 | 0.094 | 0.321 | 4.16E-40 | HSPA52 | 0.06585.1836 | -0.2579733 | 0.595 | 0.823 | 1 |
| KLRC1 | 5.18E-42 | 0.352664039 | 0.299 | 1 | 1.04E-38 | FOS1 | 0.078103102 | -0.377918681 | 0.585 | 0.779 | 1 |
| HLA-DRB11 | 4.00E-39 | -0.566068979 | 0.08 | 0.329 | 8.00E-36 | LTA | 0.129412787 | -0.312600286 | 0.027 | 0.46 | 1 |
| KLRC3 | 1.38E-38 | -0.316437433 | 0.062 | 0.333 | 2.76E-35 | HNRNPA2-B11 | 0.217167231 | -0.392103753 | 0.871 | 0.995 | 1 |
| LGALS91 | 2.20E-38 | -0.305393331 | 0.052 | 0.333 | 4.39E-35 | TNFAIP32 | 0.2509555 | -0.633663443 | 0.115 | 0.52 | 1 |
| PTPRE | 3.87E-32 | -0.25216443 | 0.225 | 0.837 | 7.75E-29 | NEAT11 | 0.268476515 | -0.358823683 | 0.554 | 0.727 | 1 |
| EOMES | 4.33E-32 | 0.305691501 | 0.24 | 0.887 | 8.66E-29 | HERPUD11 | 0.352970264 | -0.272292118 | 0.231 | 0.58 | 1 |
| SIGLEC7 | 3.84E-31 | 0.308815833 | 0.321 | 1 | 7.68E-28 | TRGC2 | 0.470045005 | -0.367996139 | 0.064 | 0.54 | 1 |
| LYST | 7.91E-31 | -0.281911348 | 0.159 | 0.367 | 1.58E-27 | XCL21 | 0.498462907 | 0.447499826 | 0.535 | 1 | 1 |
| SDHC | 2.78E-28 | 0.300023083 | 0.313 | 0.966 | 5.56E-25 | PPIB1 | 0.502307283 | -0.257182907 | 0.845 | 1 | 1 |
| TIMP1 | 2.75E-27 | 0.310115035 | 0.341 | 0.988 | 5.51E-24 | ANXA11 | 0.660311834 | -0.355440558 | 0.726 | 0.998 | 1 |
| PRDM1 | 3.07E-27 | -0.371331186 | 0.122 | 0.369 | 6.14E-24 | MT2A3 | 0.874594274 | -0.343688783 | 0.353 | 0.633 | 1 |
| HERC5 | 5.33E-26 | -0.57215302 | 0.06 | 0.367 | 1.07E-22 | ACTG11 | 0.978978822 | -0.312955504 | 0.988 | 1 | 1 |
| PSMB2 | 3.04E-25 | v0.261627454 | 0.296 | 0.916 | 6.09E-22 |   |   |   |   |   |   |
|   |   |   |   |   |   | Seurat Cluster 5 |   |   |   |   |   |
| IGLV2-11 | 1.05E-220 | 1.155094172 | 0.033 | 0.945 | 2.09E-217 | IFI44L4 | 9.98E-22 | -0.489744739 | 0.036 | 0.346 | 2.00E-18 |
| IGHV1-24 | 5.57E-213 | 0.534267662 | 0.022 | 0.856 | 1.11E-209 | IGLV8-61 | 1.10E-21 | 0.36734382 | 0.018 | 0.527 | 2.19E-18 |
| IGKV1D-39 | 1.21E-201 | 0.284551642 | 0.046 | 0.966 | 2.42E-198 | EFHD21 | 8.56E-21 | -0.34618872 | 0.087 | 0.384 | 1.71E-17 |
| IGHV3-11 | 5.67E-178 | 0.420089427 | 0.029 | 0.873 | 1.13E-174 | BACH2 | 7.00E-19 | -0.575311555 | 0.402 | 0.925 | 1.40E-15 |
| IGHV4-34 | 1.25E-173 | 0.36518679 | 0.061 | 0.966 | 2.50E-170 | NR4A21 | 8.59E-18 | -0.604150402 | 0.137 | 0.394 | 1.72E-14 |
| IGHA2 | 2.26E-168 | -0.279804223 | 0.051 | 0.914 | 4.52E-165 | IGLV2-14 | 1.64E-17 | 1.093539556 | 0.085 | 0.682 | 3.29E-14 |
| IGHV3-74 | 3.60E-165 | 0.883164901 | 0.039 | 0.784 | 7.20E-162 | WARS | 9.64E-17 | -0.352610524 | 0.075 | 0.664 | 1.93E-13 |
| IGKV1-9 | 6.22E-159 | 0.660139597 | 0.021 | 0.822 | 1.24E-155 | IGHD | 9.38E-14 | 0.445223766 | 0.022 | 0.616 | 1.88E-10 |
| IGHV1-3 | 1.59E-145 | 0.332155202 | 0.032 | 0.866 | 3.18E-142 | ADAM28 | 3.33E-13 | -0.290892506 | 0.449 | 0.959 | 6.66E-10 |
| GNIY2 | 2.95E-145 | 0.917453719 | 0.069 | 0.928 | 5.91E-142 | AC245014.31 | 1.53E-11 | -0.31507883 | 0.492 | 0.993 | 3.06E-08 |
| KLF4 | 9.59E-136 | -0.382132493 | 0.016 | 0.161 | 1.92E-132 | FOSB1 | 1.93E-11 | -0.497058649 | 0.248 | 0.452 | 3.87E-08 |
| IGKV2D-29 | 2.26E-133 | 0.2670.2771 | 0.051 | 0.897 | 4.52E-130 | YWHAQ | 3.52E-11 | -0.345554043 | 0.229 | 0449 | 7.05E-08 |
| GZMA2 | 2.46E-132 | 0.272843376 | 0.06 | 0.76 | 4.92E-129 | CD22 | 1.98E-10 | -0.272343595 | 0.45 | 0.973 | 3.96E-07 |
| IGLV3-1 | 2.23E-129 | 0.6456187 | 0.043 | 0.86 | 4.45E-126 | TUBB4B | 2.75E-10 | -0.269197304 | 0.481 | 0.949 | 5.49E-07 |
| UTY | 9.58E-119 | -0.387526853 | 0 | 0.188 | 1.92E-115 | AC007952.4 | 4.23E-10 | -0.40243283 | 0.13 | 0.442 | 8.46E-07 |
| IGHV2-5 | 5.51E-116 | 0.574062951 | 0.025 | 0.788 | 1.10E-112 | MAP3K81 | 8.86E-10 | -0.502826182 | 0.416 | 0.877 | 1.77E-06 |
| IGHV2-8 | 1.59E-114 | 1.006148279 | 0.028 | 0.836 | 3.18E-111 | IGKV1-16 | 1.46E-09 | -0.408817914 | 0.256 | 0.455 | 2.92E-06 |
| IGKV4-1 | 9.77E-114 | 0.93568023 | 0.1 | 0.935 | 1.95E-110 | IGHV3-72 | 2.35E-09 | 0.309207753 | 0.006 | 0.401 | 4.70E-06 |
| NKG71 | 5.63E-112 | 0.56789674 | 0.07 | 0.726 | 1.13E-108 | HLA-DRB12 | 2.03E-08 | 0.350715937 | 0.012 | 0.479 | 4.05E-05 |
| CTSW2 | 9.26E-112 | 0.265468301 | 0.075 | 0.74 | 1.85E-108 | FCER2 | 2.13E-08 | -0.278042075 | 0.995 | 1 | 4.25E-05 |
| IGLV4-39 | 4.93E-104 | 1.171865881 | 0.081 | 0.89 | 9.86E-101 | HLA-DRA1 | 2.22E-08 | -0.339934777 | 0.566 | 0993 | 4.43E-05 |
| IGLV1-47 | 1.35E-102 | 1.028012779 | 0.088 | 0.897 | 2.70E-99 | HERPUD12 | 2.91E-08 | -0.266259335 | 0.991 | 1 | 5.82E-05 |
| IGL6-57 | 3.58E-99 | 0.526144389 | 0.026 | 0.671 | 7.16E-96 | BLK | 7.00E-08 | -0.37031016 | 0.364 | 0.795 | 0.000140025 |
| IGHV1-46 | 5.84E-92 | 0.581473382 | 0.02 | 0.185 | 1.17E-88 | HLA-DQB1 | 1.24E-07 | -0.372597726 | 0.56 | 0.99 | 0.000248652 |
| IGLV5-51 | 1.45E-90 | -0.734104524 | 0.06 | 0.842 | 2.89E-87 | HLA-DQA1 | 1.06E-06 | -0.447555863 | 0.947 | 1 | 0.002111594 |
| IGLV1-51 | 6.79E-89 | 1.11732593 | 0.051 | 0.825 | 1.36E-85 | IGKC | 1.10E-06 | -0.38491118 | 0.896 | 1 | 0.002191305 |
| IGLV2-23 | 1.23E-87 | 0.701191825 | 0.034 | 0.74 | 2.45E-84 |   | 5.85E-06 | -0.339188207 | 0.514 | 0.942 | 0.011704907 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| ELL21 | 3.31E-85 | -0.26169945 | 0.046 | 0.226 | 6.62E-82 | IGKV1-8 | 6.74E-06 | 0.445997002 | 0.012 | 0.421 | 0.013482593 |
| IGLV1-40 | 3.87E-83 | 1.344258843 | 0.057 | 0.825 | 7.74E-80 | MTSS1 | 1.64E-05 | -0.299548781 | 0409 | 0.805 | 0.032750843 |
| IGKV2-30 | 3.20E-82 | 0.688422243 | 0.034 | 0.733 | 6.39E-79 | RHOB2 | 2.04E-05 | -0.314318314 | 0.253 | 0.709 | 0.040844284 |
| IGKV3-20 | 1.14E-80 | 1.398847101 | 0.142 | 0.928 | 2.29E-77 | JUND3 | 2.05E-05 | -0.59062684 | 0.188 | 0.647 | 0.040989599 |
| IL321 | 1.52E-74 | 0.848906268 | 0.173 | 0.959 | 3.04E-71 | AL138963.32 | 4.71E-05 | 0.290299222 | 0.438 | 0.914 | 0.094170454 |
| IGHV3-15 | 1.64E-74 | 0.460127372 | 0.038 | 0.788 | 3.27E-71 | PRDX2 | 5.95E-05 | 0.263723832 | 0.284 | 0.774 | 0.118901695 |
| IGHV3-30 | 8.00E-72 | 0.683719346 | 0.084 | 0.836 | 1.60E-68 | MY ADM 1 | 8.62E-05 | -0.725747544 | 0.088 | 0.462 | 0.172454736 |
| GRASP 1 | 1.02E-70 | -0.334533223 | 0.03 | 0.253 | 2.04E-67 | SAT1 | 0.000116005 | -0.323248142 | 0.623 | 0.938 | 0.232009496 |
| TCF71 | 1.08E-66 | 0.251112369 | 0.126 | 0.863 | 2.17E-63 | IGKV1-5 | 0.000211677 | 0.894423346 | 0.058 | 0.442 | 0.423353915 |
| SOX4 | 2.36E-58 | -0.414816843 | 0.06 | 0.774 | 4.72E-55 | AHNAK1 | 0.000287385 | -0.446412712 | 0476 | 0.822 | 0.574769209 |
| IGLV3-25 | 1.04E-56 | 0.707552882 | 0.021 | 0.685 | 2.07E-53 | IGKV3-15 | 0.000412076 | 0.5363749 | 0.066 | 0.589 | 0.824152886 |
| IL7R1 | 1.04E-53 | 0.499098753 | 0.138 | 0.853 | 2.09E-50 | HSP90AB1 | 0.000761542 | -0.279663465 | 0.862 | 0.932 | 1 |
| CD3D1 | 1.54E-51 | 0.315280897 | 0.121 | 0.695 | 3.07E-48 | MEF2C | 0.006396117 | -0.336194182 | 0.665 | 0.976 | 1 |
| IGHV3-23 | 3.37E-50 | 0.722652538 | 0.162 | 0.873 | 6.75E-47 | S100A10 | 0.006428273 | 0.338462104 | 0.425 | 0.87 | 1 |
| LINC01781 | 2.17E-43 | 0.25459903 | 0.24 | 0.949 | 4.34E-40 | IGHV7-4-1 | 0.006913599 | 0.384547714 | 0.016 | 0.445 | 1 |
| CCL52 | 3.01E-43 | 0.450409688 | 0.094 | 0.774 | 6.01E-40 | IGLV3-21 | 0.007026764 | 0.74889379 | 0.043 | 0.548 | 1 |
| IGHV3-33 | 2.44E-41 | 0.326952701 | 0.03 | 0.705 | 4.88E-38 | AFF3 | 0.00914317 | -0.268874686 | 0.493 | 0.805 | 1 |
| IGHV6-1 | 6.91E-41 | 0.296448107 | 0.012 | 0.654 | 1.38E-37 | HNRNPA2B12 | 0.00966174 | -0.371799931 | 0.926 | 1 | 1 |
| IGHV1-2 | 1.27E-40 | 0.557558745 | 0.07 | 0.747 | 2.53E-37 | CD79A | 0.012253218 | -0.266070855 | 0.977 | 1 | 1 |
| IGHV3-21 | 1.15E-39 | 0.449128988 | 0.08 | 0.753 | 2.30E-36 | LYN | 0.036434942 | -0.267939408 | 0.617 | 0.866 | 1 |
| CEAP201 | 8.34E-39 | -0.67122265 | 0.057 | 0.318 | 1.67E-35 | IGHV4-31 | 0.038466823 | 0.411755496 | 0.032 | 0.466 | 1 |
| IGHV3-53 | 7.04E-38 | 0.349636911 | 0.013 | 0.503 | 1.41E-34 | NPM1 | 0.054393278 | -0.28626921 | 0.901 | 1 | 1 |
| LMNA1 | 2.64E-37 | -0.342508894 | 0.017 | 0.277 | 5.28E-34 | FOS2 | 0.075326876 | -0.368061169 | 0.505 | 0743 | 1 |
| YBX3 | 1.95E-36 | -0.397374069 | 0.133 | 0.325 | 3.91E-33 | OAZ11 | 0.094714993 | -0.270363436 | 0.952 | 1 | 1 |
| CD71 | 3.07E-36 | 0.438897782 | 0.13 | 0.647 | 6.14E-33 | HSPA53 | 0.258947561 | -0.505816993 | 0.334 | 0.654 | 1 |
| IGHV1-18 | 4.88E-36 | 0.910087666 | 0.046 | 0.705 | 9.76E-33 | CST71 | 0.326803072 | 0.267846532 | 0.065 | 0.144 | 1 |
| SLC9A3R11 | 2.92E-34 | 0.278185637 | 0.27 | 0.962 | 5.85E-31 | IGKV3-11 | 0.366045182 | 1.280284511 | 0.063 | 0.517 | 1 |
| NFKBIZ3 | 6.87E-32 | -0.254337447 | 0.169 | 0.342 | 1.37E-28 | VIM | 0.367138805 | -0.281666991 | 0.827 | 1 | 1 |
| IGLVI-44 | 3.89E-30 | 1.061898805 | 0.077 | 0.719 | 7.79E-27 | LINC00926 | 0.428458505 | -0.258847686 | 0.815 | 0.973 | 1 |
| AC103591.34 | 5.46E-29 | -0.843740701 | 0.048 | 0.346 | 1.09E-25 | TNF2 | 0.4608347 | -0.334851418 | 0.04 | 0.476 | 1 |
| PHACTR1 | 7.93E-29 | -0.376498032 | 0.199 | 0.818 | 1.59E-25 | HMGB1 | 0.480077205 | -0.289388188 | 0.856 | 0.962 | 1 |
| RAB11FIP1 | 4.16E-28 | -0.415329705 | 0.112 | 0.356 | 8.32E-25 | HLA-DRB51 | 0.619746498 | -0.262157207 | 0.979 | 1 | 1 |
| IGLV4-59 | 4.56E-28 | 0.670688524 | 0.089 | 0.726 | 9.12E-25 | GADD45B | 0.788956489 | -0.400704378 | 0.234 | 0.596 | 1 |
| NFKBID | 1.67E-27 | -0.36473843 | 0.118 | 0.36 | 3.34E-24 | CD83 | 0.833567752 | -0.504354016 | 0.373 | 0.616 | 1 |
| ITGB1 | 8.70E-24 | 0.325333538 | 0.225 | 0.846 | 1.74E-20 | S100A41 | 0.837005254 | 0.537833312 | 0.75 | 0.75 | 1 |
| IGHV3-7 | 2.24E-22 | 0.789603063 | 0.076 | 0.695 | 4.48E-19 | ATF32 | 0.855546489 | -0.254260497 | 0.01 | 0.469 | 1 |
| | | | | | | Seurat Cluster 6 | | | | | |
| TRBV10-31 | 2.37E-202 | 0.2661192108 | 0.014 | 0.731 | 4.74E-99 | TRBV20-12 | 1.50E-13 | 0.457774427 | 0.055 | 0.677 | 3.00E-10 |
| TRAV212 | 3.76E-77 | 0.313219153 | 0.065 | 0.925 | 7.52E-74 | NFKBIA2 | 1.75E-12 | -0.475744314 | 0.289 | 0.849 | 3.51E-09 |
| TRBV7-22 | 2.58E-75 | 0.412945804 | 0.051 | 0.892 | 5.16E-72 | IFI44L5 | 3.24E-12 | -0.268449118 | 0.009 | 0.226 | 6.48E-09 |
| TRBV7-6 | 1.28E-73 | 0.299095903 | 0.053 | 0.892 | 2.56E-70 | TRBV27 | 2.99E-11 | 0.385017476 | 0.079 | 0.688 | 5.97E-08 |
| TRBV91 | 6.60E-66 | 0.252859335 | 0.045 | 0.849 | 1.32E-62 | STAT13 | 4.34E-10 | 0.308779143 | 0.337 | 1 | 8.67E-07 |
| AC103591.35 | 4.02E-60 | -0.709925888 | 0.041 | 0.204 | 8.04E-57 | MT2A4 | 5.25E-09 | -0.361980414 | 0.395 | 0.978 | 1.05E-05 |
| TRBV7-92 | 1.73E-56 | 0.410368055 | 0.074 | 0.882 | 3.46E-53 | TRBV12-43 | 0.000312865 | 0.363184313 | 0.056 | 0.602 | 0.625729168 |
| S100A82 | 1.12E-55 | -0.397791074 | 0.017 | 0.237 | 2.24E-52 | SNRPD3 | 0.00115234 | 0.266463034 | 0.419 | 1 | 1 |
| TRBV4-21 | 2.43E-55 | 0.537852527 | 0.07 | 0.871 | 4.87E-52 | TRBV6-52 | 0.001765573 | 0.526812563 | 0.068 | 0.602 | 1 |
| PCSK1N | 1.29E-52 | -0.331761392 | 0.107 | 0.914 | 2.57E-49 | MT-ATP8 | 0.020697225 | 0.268437209 | 0.802 | 0.968 | 1 |
| TRBV4-12 | 1.40E-47 | 0.528529343 | 0.038 | 0.215 | 2.80E-44 | TRBC1 | 0.101460742 | 0.254487944 | 0.521 | 1 | 1 |
| TRBV5-6 | 8.54E-43 | 0.278143047 | 0.037 | 0.72 | 1.71E-39 | ZFP36L22 | 0.325722519 | -0.339149597 | 0.935 | 1 | 1 |
| BACH21 | 8.24E-19 | -0.296405109 | 0.237 | 0.892 | 1.65E-15 | AL138963.33 | 0.501929388 | 0.435757875 | 0.571 | 0.957 | 1 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| TRBV281 | 2.04E-15 | 0.296552998 | 0.041 | 0.656 | 4.07E-12 | AIF1 | 0.819010041 | 0.268127404 | 0.571 | 0.968 | 1 |
| | | | | | | Seurat Cluster 7 | | | | | |
| MRPL3 | 1.11E-121 | -0.025083287 | 0.008 | 0.986 | 2.22E-118 | TRBV4-22 | 2.20E-34 | 0.328126771 | 0.027 | 0.546 | 4.40E-31 |
| JAML1 | 4.08E-101 | 0.297906695 | 0.051 | 0.993 | 8.17E-98 | LAT | 3.30E-34 | 0.417315222 | 0.221 | 0.969 | 6.59E-31 |
| PTGDR | 3.45E-98 | 0.41601604 | 0.061 | 0.997 | 6.89E-95 | HIST1H4C | 2.49E-33 | 0.608091893 | 0.245 | 0.997 | 4.97E-30 |
| IGKV2D-291 | 4.46E-98 | 0.655816686 | 0.061 | 0.997 | 8.93E-95 | SPON21 | 3.13E-33 | -0.384925432 | 0.029 | 0.759 | 6.27E-30 |
| SIRPG | 4.24E-97 | 0.310556677 | 0.056 | 0.99 | 8.49E-94 | LDHB | 5.07E-33 | 0.343573689 | 0.237 | 0.979 | 1.01E-29 |
| FKBP2 | 7.55E-96 | 0.329400817 | 0.059 | 0.99 | 1.51E-92 | TCF72 | 1.87E-31 | 0.634677737 | 0.255 | 1 | 3.73E-28 |
| CD8B1 | 6.05E-95 | 0.33062605 | 0.066 | 0.997 | 1.21E-91 | ITGB11 | 1.37E-30 | 0.387184187 | 0.16 | 0.876 | 2.74E-27 |
| IFNG-AS1 | 7.61E-95 | 0.283315165 | 0.069 | 1 | 1.52E-91 | ID2 | 7.58E-30 | 0.322253644 | 0.109 | 0.289 | 1.52E-26 |
| CST3 | 3.64E-93 | -0.260623896 | 0.024 | 0.942 | 7.28E-90 | NOSIP1 | 2.52E-28 | 0.5611738 | 0.269 | 1 | 5.03E-25 |
| ACTN1 | 3.66E-93 | 0.437189027 | 0.064 | 0.99 | 7.33E-90 | S100A83 | 3.28E-28 | -0.848384551 | 0.027 | 0.278 | 6.57E-25 |
| KLRBI2 | 5.75E-90 | 0.275783817 | 0.077 | 0.997 | 1.15E-86 | GNLY3 | 2.11E-27 | -0.325465353 | 0.104 | 0.804 | 4.21E-24 |
| MRPL13 | 7.73E-90 | -0.293587408 | 0.019 | 0.928 | 1.55E-86 | DENND2D | 3.28E-27 | 0.604763426 | 0.125 | 0.832 | 6.57E-24 |
| CSTB | 1.06E-89 | 0.276041963 | 0.074 | 0.993 | 2.08E-86 | SAMHD1 | 2.08E-25 | 0.434774261 | 0.239 | 0.34 | 4.17E-22 |
| NUCB2 | 6.08E-89 | 0.275539032 | 0.08 | 0.997 | 1.22E-85 | ARMH1 | 1.02E-24 | 0.323929423 | 0.069 | 0.766 | 2.04E-21 |
| IGHV3-71 | 6.48E-86 | 0.47971952 | 0.032 | 0.838 | 1.30E-82 | FOSB2 | 4.51E-23 | 0.258249562 | 0.306 | 0.997 | 9.01E-20 |
| NAAA | 2.66E-85 | 0.259268531 | 0.088 | 0.997 | 5.32E-82 | LYST1 | 8.46E-23 | 0.271583426 | 0.088 | 0.32 | 1.69E-19 |
| CD82 | 1.28E-84 | 0.382029725 | 0.066 | 0.962 | 2.56E-81 | IFI44L6 | 7.81E-22 | -0.640606385 | 0.011 | 0.179 | 1.56E-18 |
| AL138963.34 | 2.37E-83 | 0.53929897 | 0.093 | 0.997 | 4.74E-80 | PPM1G | 3.66E-21 | 0.27673661 | 0.064 | 0.323 | 7.33E-18 |
| GPR183 | 1.38E-80 | -0.396454882 | 0.085 | 0.973 | 2.76E-77 | TNF3 | 6.72E-20 | -0.329043096 | 0.048 | 0.203 | 1.34E-16 |
| HIST1H2BC | 4.59E-79 | 0.524517205 | 0.101 | 0.997 | 9.17E-76 | MTRNR2L8 | 5.12E-19 | -0.70434539 | 0.12 | 0.763 | 1.02E-15 |
| PARP1 | 2.27E-77 | 0.375501028 | 0.109 | 1 | 4.55E-74 | KLRD11 | 1.88E-18 | -0.418161931 | 0.059 | 0.698 | 3.76E-15 |
| HIST1H2BJ | 2.73E-77 | 0.323198768 | 0.051 | 0.931 | 5.46E-74 | EPRS | 1.09E-17 | 0.257170096 | 0.061 | 0.722 | 2 19E-14 |
| IL4R | 3.94E-77 | -0.250659755 | 0.048 | 0.928 | 7.87E-74 | PLEC | 2.40E-17 | 0.514657531 | 0.168 | 0.811 | 4.79E-14 |
| NCF1 | 4.92E-77 | 0.362419643 | 0.037 | 0.12 | 9.84E-74 | LDHA | 8.13E-16 | 0.402893095 | 0.165 | 0.797 | 1.63E-12 |
| HIST1H2AG | 1.08E-76 | 0.352805774 | 0.109 | 0.997 | 2.16E-73 | Z93241.11 | 1.17E-15 | 0.636944933 | 0.093 | 0.735 | 2.35E-12 |
| CD27 | 5.39E-73 | 0.285708184 | 0.114 | 0.993 | 1.08E-69 | ENO1 | 1.50E-15 | 0.321673836 | 0.12 | 0.756 | 3.00E-12 |
| FGFBP2 | 5.47E-73 | -0.316394917 | 0.019 | 0.704 | 1.09E-69 | EPSTI11 | 2.08E-15 | -0.38924326 | 0.021 | 0.677 | 4.16E-12 |
| GZMK1 | 7.50E-73 | 0.742931029 | 0.12 | 1 | 1.50E-69 | ADGRG11 | 6.53E-14 | -0.250184049 | 0.016 | 0.502 | 1.31E-10 |
| CDC25B | 3.19E-72 | 0.369465831 | 0.122 | 0.997 | 6.37E-69 | H2AFY | 6.18E-11 | -0.28366471 | 0.064 | 0.677 | 1.24E-07 |
| UTY1 | 1.11E-71 | -0.482391992 | 0 | 0.127 | 2.21E-68 | PMAIP12 | 1.53E-10 | -0.417872159 | 0.072 | 0.677 | 3.07E-07 |
| POU2F2 | 3.30E-71 | 0.255063712 | 0.098 | 0.966 | 6.60E-68 | IFIT23 | 3.19E-10 | -0.855155786 | 0.008 | 0.186 | 6.38E-07 |
| CD38 | 7.06E-70 | -0.317597858 | 0.019 | 0.708 | 1.41E-66 | CST72 | 5.97E-10 | 0.539646385 | 0.098 | 0.409 | 1.19E-06 |
| CRIP2 | 8.88E-68 | 0.260081705 | 0.035 | 0.835 | 1.78E-64 | TGFBR31 | 2.65E-09 | 0.36118892 | 0.098 | 0.691 | 5.29E-06 |
| LYZ | 4.97E-67 | -0.447783023 | 0.024 | 0.876 | 9.95E-64 | DUSP21 | 5.43E-09 | 0.631236849 | 0.301 | 0.866 | 1.09E-05 |
| ILK | 1.17E-65 | 0.254604833 | 0.051 | 0.9 | 2.34E-62 | NFKBIZ4 | 1.82E-08 | -0.5711555 | 0.191 | 0.725 | 3.64E-05 |
| NUDT5 | 4.04E-64 | 0.343163313 | 0.056 | 0.893 | 8.08E-61 | MIF | 4.48E-08 | 0.307417372 | 0.149 | 0.718 | 8.96E-05 |
| NELL21 | 8.47E-64 | 0.266837562 | 0.146 | 1 | 1.69E-60 | CYB5D2 | 7.30E-08 | 0.31785975 | 0.024 | 0.399 | 0.000146024 |
| HIST1H2AC | 1.19E-63 | 0.503245142 | 0.128 | 0.979 | 2.37E-60 | CD3G1 | 3.66E-07 | 0.272497116 | 0.117 | 0.684 | 0.000731598 |
| CNN2 | 2.86E-60 | 0.324753786 | 0.133 | 0.973 | 5.73E-57 | TKT | 3.74E-07 | -0.278813781 | 0.021 | 0.612 | 0.000748019 |
| KLRG1 | 5.83E-60 | 0.379476354 | 0.152 | 0.993 | 1.17E-56 | OASL2 | 1.03E-06 | -0.745937983 | 0.005 | 0.237 | 0.002057444 |
| CUX1 | 6.56E-58 | 0.370485126 | 0.066 | 0.893 | 1.31E-54 | CPNE3 | 1.13E-06 | 0.273691411 | 0.045 | 0.629 | 0.002260924 |
| CCR7 | 1.14E-57 | 0.263998429 | 0.117 | 0.945 | 2.29E-54 | SLC25A39 | 3.76E-06 | 0.270919512 | 0.048 | 0.625 | 0.007513188 |
| EGR11 | 1.26E-57 | 0.53163752 | 0.16 | 0.997 | 2.52E-54 | CD28 | 2.17E-05 | 0.355365777 | 0.09 | 0.45 | 0.043321989 |
| FCRL3 | 3.84E-57 | 0.304470541 | 0.043 | 0.667 | 7.68E-54 | GADD45B1 | 2.54E-05 | 0.253054579 | 0.194 | 0.718 | 0.050845468 |
| ANXA61 | 2.28E-55 | 0.372393648 | 0.17 | 1 | 4.56E-52 | IFI6 | 4.38E-05 | -0.38821962 | 0.019 | 0.433 | 0.087505003 |
| CCL42 | 3.56E-54 | -0.327225254 | 0.019 | 0.612 | 7.13E-51 | TRGV3 | 0.00012477 | 0.28967059 | 0.04 | 0.392 | 0.249539598 |
| ATP2B1-AS1 | 6.06E-54 | 0.43523112 | 0.112 | 0.928 | 1.21E-50 | IL322 | 0.000280217 | 0.528417596 | 0.404 | 0.904 | 0.56043322 |
| PASK | 1.19E-52 | 0.409562939 | 0.066 | 0.876 | 2.38E-49 | MX11 | 0.000772732 | -0.277521404 | 0.061 | 0.584 | 1 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| FCGR3A1 | 3.55E-52 | -0.363248108 | 0.019 | 0.656 | 7.10E-49 | LTB1 | 0.000814078 | 0.604351586 | 0.468 | 0.997 | 1 |
| GART | 6.50E-52 | 0.253794634 | 0.088 | 0.746 | 1.30E-48 | TOB12 | 0.001306886 | -0.325325463 | 0.045 | 0.591 | 1 |
| ITGB7 | 7.56E-52 | 0.305215087 | 0.181 | 0.997 | 1.51E-48 | HSPA54 | 0.002260577 | -0.317412453 | 0.184 | 0.667 | 1 |
| SNRPG | 7.57E-52 | 0.298715324 | 0.061 | 0.196 | 1.51E-48 | HERC51 | 0.006377373 | -0.845980805 | 0.024 | 0.433 | 1 |
| FCMR | 1.49E-48 | 0.586566977 | 0.189 | 1 | 2.98E-45 | ZEB22 | 0.00725408 | -0.433513938 | 0.061 | 0.467 | 1 |
| LIMS1 | 8.90E-48 | 0.562549158 | 0.093 | 0.887 | 1.78E-44 | STAT14 | 0.007952197 | 0.27040986 | 0.098 | 0.612 | 1 |
| TRBC2 | 1.06E-47 | 0.590383871 | 0.191 | 0.997 | 2.11E-44 | SAT11 | 0.008545926 | 0.683576084 | 0.415 | 0.68 | 1 |
| TUBA1B | 3.26E-47 | 0.547089242 | 0.191 | 1 | 6.51E-44 | IL7R2 | 0.021522376 | 0.253920882 | 0.537 | 1 | 1 |
| HSP90B12 | 2.69E-46 | -0.283417208 | 0.215 | 1 | 5.39E-43 | CD691 | 0.032430846 | 0.396808686 | 0.322 | 0.773 | 1 |
| TSHZ2 | 4.79E-44 | -0.258004233 | 0.04 | 0.216 | 9.59E-41 | DUSP1 | 0.055520819 | 0.306955379 | 0.335 | 0.753 | 1 |
| ITGAX1 | 7.86E-44 | -0.361205122 | 0.003 | 0.134 | 1.57E-40 | TRBC11 | 0.064297712 | 0.487953902 | 0.154 | 0.632 | 1 |
| GBP51 | 3.00E-42 | -0.374335842 | 0.229 | 0.997 | 5.99E-39 | FOS3 | 0.120316398 | 0.265435429 | 0.394 | 0.784 | 1 |
| DAAMI | 7.56E-42 | 0.270649044 | 0.037 | 0.533 | 1.51E-38 | ACTB1 | 0.144790401 | -0.303263519 | 0.694 | 1 | 1 |
| CD3D2 | 1.16E-41 | 0.441444218 | 0.165 | 0.938 | 2.33E-38 | PRDX21 | 0.190913657 | 0.265454923 | 0.045 | 0.495 | 1 |
| TRBV6-53 | 2.98E-41 | 0.280288932 | 0.019 | 0.495 | 5.95E-38 | S100A42 | 0.257119509 | 0.334855889 | 0.181 | 0.625 | 1 |
| TXNDC11 | 3.43E-41 | -0.270816962 | 0.051 | 0.23 | 6.85E-38 | PRDM11 | 0.410617138 | -0.674302469 | 0.064 | 0.546 | 1 |
| PSMB91 | 7.19E-41 | 0.534783214 | 0.218 | 1 | 1.44E-37 | IFIT33 | 0.713267589 | -0.808330298 | 0.005 | 0.127 | 1 |
| S100A9 | 1.32E-40 | -0.629473284 | 0.037 | 0.23 | 2.63E-37 | JUN | 0.923271237 | 0.307252061 | 0.617 | 0.945 | 1 |
| GRAP2 | 1.22E-37 | 0.251421904 | 0.104 | 0.856 | 2.44E-34 | GZMH1 | 0.97939321 | -0.253278108 | 0.024 | 0.488 | 1 |
| TRAC | 3.18E-35 | 0.309098234 | 0.106 | 0.849 | 6.36E-32 | ZFP36L23 | 0.989143449 | -0.334145665 | 0.699 | 0.997 | 1 |
| | | | | | | Seurat Cluster 8 | | | | | |
| PPBP1 | 4.39E-52 | -0.453779957 | 0.006 | 0.142 | 8.78E-49 | LILRA5 | 0.000383136 | 0.298858669 | 0.741 | 0.787 | 0.766272535 |
| IGLV3-191 | 2.94E-45 | -0.294075575 | 0.003 | 0.52 | 5.87E-42 | H2AFY1 | 0.000439275 | -0.297845586 | 0.711 | 0.89 | 0.8785497 |
| CD3D3 | 1.68E-43 | 0.286411658 | 0.128 | 0.961 | 3.36E-40 | IFITM31 | 0.000905535 | 0.250080988 | 0.985 | 0.992 | 1 |
| IL7R3 | 1.54E-39 | 0.584900614 | 0.155 | 1 | 3.07E-36 | IGSF6 | 0.001161835 | -0.343451358 | 0.755 | 0984 | 1 |
| IL323 | 3.35E-35 | 0.610698634 | 0.172 | 1 | 6.71E-32 | PSME2 | 0.001410248 | -0.271986636 | 0.854 | 1 | 1 |
| IFI271 | 3.22E-30 | -0.724890408 | 0.003 | 0.181 | 6.43E-27 | CD36 | 0.001575745 | -0.33630283 | 0.16 | 0.465 | 1 |
| AC02916.1 | 3.68E-28 | -0.274779084 | 0.055 | 0.236 | 7.36E-25 | SHTN1 | 0.001827118 | -0.362006088 | 0.07 | 0.441 | 1 |
| LYPD2 | 3.63E-26 | 0.389967141 | 0.187 | 0.913 | 7.27E-23 | HLA-DPB11 | 0.004863695 | -0.347349902 | 0.956 | 1 | 1 |
| KCNMA1 | 3.54E-22 | -0.298215222 | 0.032 | 0.756 | 7.09E-19 | CDKN1C | 0.004884759 | 0.288753397 | 0.711 | 0.976 | 1 |
| CXCL81 | 1.79E-21 | -0.412013315 | 0.015 | 0.276 | 3.57E-18 | TNFSF101 | 0.005105431 | 0.312929209 | 0.662 | 1 | 1 |
| GNIY4 | 1.17E-20 | 0.354685354 | 0.044 | 0.756 | 2.35E-17 | HLA-DPA12 | 0.008403812 | -0.290242777 | 0.991 | 1 | 1 |
| PHACTR11 | 5.07E-20 | -0.282739957 | 0.073 | 0.283 | 1.01E-16 | C1QA | 0.009627667 | -0.843083646 | 0.175 | 0.646 | 1 |
| CCL43 | 9.12E-19 | -0.590784248 | 0.02 | 0.291 | 1.82E-15 | MNDA1 | 0.011345435 | -0.280401743 | 0.659 | 1 | 1 |
| CD163 | 7.99E-18 | -0.277643626 | 0.023 | 0.299 | 1.60E-14 | C1QC | 0.012015915 | -0.751988031 | 0.035 | 0.535 | 1 |
| CLEC10A | 1.30E-17 | -0.267020402 | 0.058 | 0.732 | 2.60E-14 | BIVRB | 0.018962322 | -0.279187321 | 0.478 | 0.772 | 1 |
| TCN2 | 3.27E-14 | -0.33586736 | 0.05 | 0.323 | 6.54E-11 | PTPREI | 0.028577634 | -0.361463007 | 0.332 | 0.709 | 1 |
| VMO1 | 1.16E-13 | 0.400549032 | 0.297 | 0.969 | 2.31E-10 | CRTAP | 0.031351088 | -0.361152174 | 0.274 | 0.669 | 1 |
| IER3 | 4.59E-13 | -0.304625003 | 0.017 | 0.331 | 9.18E-10 | AL138963.35 | 0.041132002 | 0.29276228 | 0.522 | 1 | 1 |
| CCL4L21 | 5.27E-13 | -0.439982129 | 0.003 | 0.331 | 1.05E-09 | MS4A6A | 0.04301 | -0.510887627 | 0.283 | 0.646 | 1 |
| EGR12 | 5.75E-13 | -0.352894603 | 0.058 | 0.331 | 1.15E-09 | ATP2B1-AS11 | 0.072513315 | -0.278735213 | 0.665 | 0.85 | 1 |
| RNASE6 | 1.57E-12 | -0.271730307 | 0.047 | 0.339 | 3.13E-09 | ODF3B | 0.141805579 | -0.252551059 | 0.335 | 0.709 | 1 |
| HES1 | 2.67E-12 | -0.255267638 | 0.035 | 0.339 | 5.35E-09 | MT-ND6 | 0.176339556 | 0.30899563 | 0.665 | 1 | 1 |
| RGCC1 | 1.29E-10 | -0.277029128 | 0.058 | 0.354 | 2.58E-07 | MSLN | 0.179503736 | 0.591799752 | 0.551 | 1 | 1 |
| LMNA2 | 9.58E-09 | -0.366751129 | 0.044 | 0.37 | 1.92E-05 | LY86 | 0.221249083 | -0.341520609 | 0.306 | 0.654 | 1 |
| IFITM21 | 2.90E-08 | 0.408235318 | 0.983 | 0.969 | 5.79E-05 | TNFAIP33 | 0.236087023 | -0.251653855 | 0.128 | 0.512 | 1 |
| CCL53 | 3.05E-07 | 0.293195133 | 0.07 | 1 | 0.000061098 | MARCO | 0.236130434 | -0.262467462 | 0.155 | 0.528 | 1 |
| CD741 | 5.85E-07 | -0.354240731 | 1 | 0.394 | 0.001169135 | CD14 | 0.237857898 | -0.411929908 | 0.248 | 0.551 | 1 |
| ADM1 | 1.27E-06 | -0.311312143 | 0.05 | 0.394 | 0.002547453 | RETN | 0.24850318 | 0.253909232 | 0.539 | 1 | 1 |
| CCL33 | 3.08E-06 | -0.661228958 | 0.041 | 0.394 | 0.006152162 | NKG72 | 0.26257825 | 0.251092298 | 0.236 | 0.591 | 1 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| PECAM1 | 4.31E-06 | 0.355529395 | 0.892 | 0.992 | 0.008619235 | SGK11 | 0.46678066 | -0.498147993 | 0.152 | 0.575 | 1 |
| LDHA1 | 2.01E-05 | 0.284850462 | 0.723 | 0.677 | 0.040223451 | LINC02432 | 0.497855804 | 0.275933386 | 0.455 | 0.89 | 1 |
| CKB | 2.21E-05 | 0.250315031 | 0.426 | 1 | 0.044249707 | G0S21 | 0.508959119 | -0.567688933 | 0.041 | 0.496 | 1 |
| HLA-DRA2 | 5.37E-05 | -0.354000299 | 0.988 | 1 | 0.107471169 | CD79B | 0.587300331 | 0.2958162 | 0.507 | 0.937 | 1 |
| LGALS2 | 7.20E-05 | -0.456811108 | 0.111 | 0.425 | 0.144066162 | LDHB1 | 0.613590774 | 0.289791782 | 0.437 | 0.764 | 1 |
| IL1B | 7.91E-05 | -0.439730716 | 0.07 | 0.417 | 0.158144187 | DDIT41 | 0.629503574 | -0.266320896 | 0.149 | 0.567 | 1 |
| HLA-DRB13 | 0.000285545 | -0.392565757 | 0.991 | 0.992 | 0.571089754 | C1QB | 0.688083775 | -1.112013278 | 0.047 | 0.504 | 1 |
| LYZ1 | 0.000297615 | -0.430160756 | 0.985 | 0.992 | 0.595229036 | MT2A5 | 0.731825345 | -0.658809534 | 0.767 | 0.803 | 1 |
| HLA-DMA | 0.000321395 | -0.357461562 | 0.598 | 0.89 | 0.642789676 | PLBD1 | 0.996660331 | -0.273808084 | 0.248 | 0.591 | 1 |
| | | | | | | Seurat Cluster 10 | | | | | |
| MAP7 | 1.57E-53 | -0.361775917 | 0.008 | 0.952 | 3.14E-50 | RNF130 | 0.004133348 | -0.325457734 | 0.168 | 0.381 | 1 |
| HIST1H2AM | 2.81E-33 | -0.265832814 | 0.034 | 0.952 | 5.61E-30 | VIM1 | 0.004536752 | 0.645467027 | 0.882 | 0.905 | 1 |
| TRBV6-23 | 9.94E-27 | 0.283138259 | 0.053 | 0.952 | 1.99E-23 | PASK1 | 0.004640887 | 0.336464284 | 0.172 | 0.571 | 1 |
| GPR82 | 6.53E-26 | -0.350389152 | 0.05 | 0.905 | 1.31E-22 | Z93241.12 | 0.005231323 | 0.256695287 | 0.332 | 0.952 | 1 |
| IER31 | 4.02E-23 | -0.325334157 | 0.027 | 0.857 | 8.05E-20 | CD3G2 | 0.005355597 | 0.789964799 | 0.469 | 0.619 | 1 |
| MAP1A | 3.72E-21 | -0.325933948 | 0 | 0.333 | 7.45E-18 | ITGB12 | 0.005557134 | 0.287696873 | 0.523 | 0.524 | 1 |
| S100A91 | 7.98E-21 | 0.273949509 | 0.065 | 0.143 | 1.60E-17 | NBPF14 | 0.009495928 | -0.629580817 | 0.16 | 0.714 | 1 |
| TRBV20-13 | 1.87E-20 | 0.444133122 | 0.08 | 0.952 | 3.74E-17 | IL2RB | 0.009644527 | -0.631794586 | 0.74 | 1 | 1 |
| S100A84 | 3.01E-20 | 0.669725068 | 0.027 | 0.19 | 6.01E-17 | KLRF1 | 0.009911971 | -0.693331794 | 0.664 | 1 | 1 |
| TRBV7-93 | 5.13E-20 | 0.346202541 | 0.031 | 0.667 | 1.03E-16 | NNJ1 | 0.010196712 | 0.289445064 | 0.29 | 0.476 | 1 |
| TRGC21 | 3.52E-19 | -0.464572666 | 0.069 | 0.905 | 7.04E-16 | S1PR4 | 0.010378329 | 0.44991666 | 0.351 | 1 | 1 |
| TRBV192 | 4.91E-19 | 0.599675939 | 0.088 | 0.952 | 9.83E-16 | ANXA2 | 0.015373363 | 0.396859045 | 0.363 | 0.524 | 1 |
| LYZ2 | 4.91E-19 | 0.262344726 | 0.088 | 0.952 | 9.83E-16 | AHNAK2 | 0.015966587 | -0.603310638 | 0.683 | 0.952 | 1 |
| HERC52 | 1.72E-18 | -0.278145358 | 0.084 | 0.143 | 3.44E-15 | FAM30A | 0.016012546 | -0.563032568 | 0.027 | 0.571 | 1 |
| TCF4 | 2.21E-16 | -0.397043349 | 0.023 | 0.762 | 4.42E-13 | TRDC | 0.017219461 | -0.420539279 | 0.702 | 1 | 1 |
| RBBP8 | 2.19E-15 | -0.483899018 | 0.023 | 0.238 | 4.38E-12 | CALR1 | 0.018887861 | 0.380737006 | 0.76 | 0.667 | 1 |
| ID3 | 6.32E-15 | -0.647598206 | 0.107 | 0.905 | 1.26E-11 | NUCB21 | 0.01939026 | -0.279165274 | 0.55 | 1 | 1 |
| TYMPI | 9.29E-15 | -0.258328661 | 0.069 | 0.857 | 1.86E-11 | LAT1 | 0.020147335 | 0.746377684 | 0.592 | 0.81 | 1 |
| GRASP2 | 2.31E-14 | -0.381080442 | 0.031 | 0.238 | 4.61E-11 | NCL1 | 0.02033344 | -0.41206978 | 0.87 | 1 | 1 |
| TRBV4-23 | 1.07E-13 | 0.257702259 | 0.027 | 0.429 | 2.13E-10 | COTL1 | 0.022972044 | -0.488376928 | 0.687 | 0.952 | 1 |
| GLUL | 1.24E-13 | -0.267706669 | 0.099 | 0.19 | 2.49E-10 | IL4R1 | 0.023087109 | -0.25956324 | 0.218 | 0.429 | 1 |
| KIR2DL4 | 6.89E-12 | -0.704754301 | 0.156 | 0.952 | 1.38E-08 | CD37 | 0.023777273 | -0.349447546 | 0.905 | 1 | 1 |
| CHMP1B | 1.93E-12 | -0.367426277 | 0.145 | 0.952 | 3.87E-09 | ANXA2R | 0.024659083 | 0.371452825 | 0.351 | 0.952 | 1 |
| SOX41 | 2.29E-12 | -0.308029425 | 0.141 | 0.952 | 4.58E-09 | CCL44 | 0.026306835 | 0.506799701 | 0.351 | 0.952 | 1 |
| IGFBP2 | 4.47E-12 | -0.263034263 | 0.008 | 0.19 | 8.94E-09 | HLA-DPB12 | 0.026594809 | -0.258067252 | 0.321 | 0.429 | 1 |
| CD8B2 | 6.44E-12 | 0.570991058 | 0.168 | 1 | 1.29E-08 | PLAC8 | 0.028483694 | -0.54177577 | 0.767 | 1 | 1 |
| IFIT24 | 1.14E-11 | -0.701694636 | 0.065 | 0.238 | 2.28E-08 | DST | 0.029192048 | -0.333375976 | 0.038 | 0.571 | 1 |
| FES | 1.25E-11 | -0.579117631 | 0.187 | 1 | 2.50E-08 | FCRL61 | 0.034484799 | 0.40579769 | 0.218 | 0.476 | 1 |
| SYK | 2.09E-11 | -0.310286657 | 0.191 | 1 | 4.19E-08 | CD631 | 0.03747749 | -0.400243654 | 0.615 | 1 | 1 |
| EBNA1BP2 | 4.12E-11 | -0.289739778 | 0.164 | 0.952 | 8.24E-08 | LGALS11 | 0.041840888 | 0.278462938 | 0.355 | 0.905 | 1 |
| SIRPG1 | 5.61E-11 | 0.337546607 | 0.233 | 0.19 | 1.12E-07 | VDAC3 | 0.045501862 | 0.298219358 | 0.382 | 1 | 1 |
| TRGV91 | 3.00E-10 | 0.251046126 | 0.187 | 1 | 6.00E-07 | TSPO | 0.047363226 | -0.330516271 | 0.683 | 1 | 1 |
| KIR3DL2 | 3.78E-10 | 0.325197549 | 0.164 | 0.238 | 7.55E-07 | RANBP1 | 0.048439813 | 0.297968425 | 0.378 | 0.952 | 1 |
| SPTSSB | 6.09E-10 | -0.566894587 | 0.24 | 1 | 1.22E-06 | IL7R4 | 0.049547528 | 0.396318303 | 0.84 | 0.952 | 1 |
| PPBP2 | 8.69E-10 | -0.426604337 | 0 | 0.143 | 1.74E-06 | HIST1H1D1 | 0.053427915 | -0.844768476 | 0.5 | 0.857 | 1 |
| LIPA | 1.98E-09 | -0.424443379 | 0.225 | 1 | 3.97E-06 | CALM2 | 0.053846754 | -0.401083752 | 0.718 | 1 | 1 |
| SIT1 | 2.84E-09 | 0.263723784 | 0.187 | 0.952 | 5.68E-06 | UBE2JI | 0.061434382 | -0.315843519 | 0.302 | 0.762 | 1 |
| OASL3 | 4.71E-09 | -0.436304518 | 0.05 | 0.286 | 9.41E-06 | ESYT1 | 0.062461769 | 0.331511648 | 0.389 | 1 | 1 |
| ELL22 | 4.73E-09 | -0.294721776 | 0.053 | 0.286 | 9.47E-06 | ANXA12 | 0.06842675 | 0.37127705 | 0.763 | 0.905 | 1 |
| MAL | 6.20E-09 | 0.519556192 | 0.328 | 0.238 | 1.24E-05 | TRBC21 | 0.069578836 | 0.328754156 | 0.828 | 0.952 | 1 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| BID | 7.22E-09 | 0.312581472 | 0.233 | 0.238 | 1.44E-05 | AIF1l | 0.074129358 | 0.271256109 | 0.183 | 0.714 | 1 |
| STMN1 | 1.45E-08 | 0.28121152 | 0.21 | 1 | 2.90E-05 | DNMT1 | 0.077480952 | 0.372433395 | 0.412 | 1 | 1 |
| S1PR5 | 4.05E-08 | 0.436025981 | 0.347 | 0.238 | 8.10E-05 | GATA3 | 0.077657452 | -0.309038068 | 0.477 | 1 | 1 |
| TNFRSF18 | 1.23E-07 | -0.568903051 | 0.271 | 0.952 | 0.000245151 | SNRPD31 | 0.080542826 | 0.320532981 | 0.527 | 0.667 | 1 |
| IGFBP4 | 1.32E-07 | -0.511076547 | 0.24 | 0.952 | 0.000264886 | ILK1 | 0.089871989 | 0.321228172 | 0.408 | 1 | 1 |
| PLEC1 | 1.90E-07 | -0.262857864 | 0.134 | 0.286 | 0.00038044 | CD72 | 0.090678142 | -0.482855353 | 0.989 | 1 | 1 |
| GZMH2 | 2.30E-07 | 0.265805809 | 0.324 | 0.238 | 0.000459545 | TRBC12 | 0.096422831 | 0.624622103 | 0.649 | 0.905 | 1 |
| IFIT34 | 2.90E-07 | -0.665424042 | 0.019 | 0.333 | 0.000580691 | TAGLN21 | 0.096499171 | -0.451981513 | 0.897 | 1 | 1 |
| NOP56 | 6.03E-07 | 0.25044677 | 0.237 | 1 | 0.0012059 | IDH21 | 0.096561292 | 0.310563651 | 0.363 | 1 | 1 |
| SPINT2 | 6.72E-07 | 0.251650663 | 0.168 | 0.762 | 0.001343862 | NOSIP2 | 0.098435888 | 0.507735772 | 0.71 | 1 | 1 |
| ARMH1 | 7.89E-07 | 0.266181777 | 0.137 | 0.714 | 0.001577709 | HOPX1 | 0.10045307 | -0.410536107 | 0.897 | 1 | 1 |
| MCM3 | 8.14E-07 | 0.253282227 | 0.21 | 0.952 | 0.001627434 | MYOM21 | 0.106344456 | 1.032110042 | 0.492 | 1 | 1 |
| ATP2B1-AS12 | 1.56E-06 | -0.645346811 | 0.275 | 1 | 0.003118904 | PRMT1 | 0.10901418 | -0.28708701 | 0.607 | 1 | 1 |
| MARCKSL1 | 2.07E-06 | 0.321153404 | 0.218 | 0.952 | 0.004142096 | TPST2 | 0.111164571 | -0.517633122 | 0.634 | 1 | 1 |
| GRAP21 | 2 07E-06 | 0.289751043 | 0.218 | 0.952 | 0.004142096 | S100A11 | 0.113806777 | 0.527802093 | 0.615 | 0.952 | 1 |
| GNLY5 | 2.25E-06 | -0.71416257 | 0.954 | 1 | 0.004506623 | PTGDR1 | 0.121558122 | -0.290453221 | 0.584 | 1 | 1 |
| LIME1 | 2.41E-06 | 0.35588775 | 0.431 | 0.286 | 0.004824721 | PIM2 | 0.136286928 | 0.303631788 | 0.405 | 0.952 | 1 |
| MIR22HG | 4.59E-06 | -0.34262567 | 0.019 | 0.333 | 0.009180367 | ATIC | 0.140131757 | 0.309719435 | 0.29 | 1 | 1 |
| IL324 | 8.12E-06 | 1.108052722 | 0.84 | 0.762 | 0.016237144 | CCL54 | 0.147869168 | 0.612384615 | 0.718 | 1 | 1 |
| GZMK2 | 1.04E-05 | -0.704411582 | 0.416 | 1 | 0.02088368 | CLIC31 | 0.149720465 | 0.768771318 | 0.611 | 1 | 1 |
| LTB2 | 1.25E-05 | 1.060966756 | 0.847 | 1 | 0.024911164 | YWHAQ1 | 0.150651552 | -0.360323655 | 0.66 | 1 | 1 |
| PRDX1 | 1.35E-05 | 0.323445162 | 0.427 | 0.333 | 0.027090241 | IFI44L7 | 0.157203474 | -0.80420138 | 0.057 | 0.571 | 1 |
| KLF10 | 1.95E-05 | -0.403363074 | 0.084 | 0.333 | 0.038979737 | SNRPE | 0.157317186 | 0.254383048 | 0408 | 0.619 | 1 |
| TMSB10 | 19.6E-05 | 0.452061609 | 0.989 | 1 | 0.03925825 | CD3D4 | 0.174909828 | 1.079748692 | 0.542 | 0.905 | 1 |
| MX12 | 2.20E-05 | -0.26113306 | 0.099 | 0.333 | 0.043981842 | FBL | 0.178601705 | -0.339669208 | 0.63 | 1 | 1 |
| RHOC | 4.80E-05 | -0.379668843 | 0.267 | 0.905 | 0.096005184 | NDUFB3 | 0.184203641 | 0.491379678 | 0.42 | 1 | 1 |
| HSH2D | 5.23E-05 | -0.35275577 | 0.439 | 1 | 0.104653249 | CPNE31 | 0.192181684 | 0.288992162 | 0.355 | 0.857 | 1 |
| BHLHE40 | 5.55E-05 | -0.446491398 | 0.336 | 0.905 | 0.11091668 | HLA-DRB14 | 0.193473315 | -0.595184041 | 0.187 | 0.476 | 1 |
| PPIB2 | 5.64E-05 | -0.50539468 | 0.885 | 1 | 0.11270057 | LDHA2 | 0.207678578 | -0.304015288 | 0.695 | 1 | 1 |
| AC''TN1l | 6.5 1E-05 | 0.371006962 | 0.252 | 0.905 | 0.130258136 | MDH1 | 0.210631696 | 0.266790103 | 0.466 | 1 | 1 |
| ITGAX2 | 9.64E-05 | -0.485758896 | 0.248 | 0.857 | 0.192759936 | TRBV7-23 | 0.211269625 | 0.358805404 | 0.031 | 0.19 | 1 |
| HLA-DMA1 | 9.70E-05 | -0.363619246 | 0.134 | 0.762 | 0.193963396 | FCER1G1 | 0.218964178 | -0.642545849 | 0.92 | 1 | 1 |
| KLRD12 | 9.76E-05 | -0.742969493 | 0.859 | 1 | 0.195158836 | CARD16 | 0.221042743 | 0.300418863 | 0.489 | 0.714 | 1 |
| FKBP11 | 0.000131149 | 0.322130769 | 0.37 | 1 | 0.262980361 | LRRN3 | 0.228622598 | 0.261583085 | 0.118 | 0.238 | 1 |
| PNP | 0.000141724 | 0.286971432 | 0.26 | 0.381 | 0.283448801 | 1-Sep | 0.241471064 | 0.410418498 | 0.687 | 1 | 1 |
| S100B2 | 0.000144829 | -1.021142332 | 0.011 | 0.381 | 0.289658401 | TUBA1B1 | 0.24373312 | 0.335257299 | 0.687 | 1 | 1 |
| RPA3 | 0.000145629 | 0.259284242 | 0.26 | 0.952 | 0.291257479 | FCMRI | 0.249935117 | 0.264163537 | 0.676 | 1 | 1 |
| PMAIP13 | 0.000148826 | -0.785820474 | 0.168 | 0.333 | 0.297652288 | SNX3 | 0.281212314 | -0.321139059 | 0.595 | 1 | 1 |
| MYC1 | 0.000166953 | 0.280264453 | 0.267 | 0.952 | 0.333906243 | KLRB13 | 0.282020109 | 0.284419745 | 0.74 | 1 | 1 |
| KLRG11 | 0.000213933 | 0.295890277 | 0.305 | 1 | 0.427866902 | CTSC1 | 0.294245153 | -0.25058934 | 0.679 | 1 | 1 |
| IFITM22 | 0.000239481 | -0.495062453 | 0.992 | 1 | 0.478962614 | PA2G4 | 0.317010175 | -0.301392609 | 0.626 | 0.952 | 1 |
| TPM4 | 0.00034075 | -0.296481638 | 0.359 | 1 | 0.681499498 | CD5 | 0.325589803 | 0.387093016 | 0.252 | 0.667 | 1 |
| S100A6 | 0.000380002 | 1.018529238 | 0.775 | 0.81 | 0.760004605 | CASP1 | 0.34812509 | 0.266135674 | 0.29 | 0.762 | 1 |
| CMC1 | 0.000389586 | -0.771535361 | 0.653 | 0.905 | 0.779172457 | CD271 | 0.349378695 | -0.274675895 | 0.5 | 1 | 1 |
| IFITM32 | 0.000566977 | -0.632669141 | 0.912 | 1 | 1 | ID21 | 0.361330801 | -0.456564045 | 0.645 | 1 | 1 |
| SELL1 | 0.000572559 | -0.60524215 | 0.908 | 1 | 1 | RGS2 | 0.371260361 | 0.303030415 | 0.076 | 0.571 | 1 |
| AQP31 | 0.000712702 | 0.609594634 | 0.309 | 1 | 1 | ABRACL1 | 0.37813247 | 0.25600129 | 0.611 | 1 | 1 |
| GSN1 | 0.00071273 | -0.46388518 | 0.389 | 0.952 | 1 | CRIP21 | 0.386891341 | 0.25601296 | 0.13 | 0.571 | 1 |
| CYB5D21 | 0.000753219 | -0.740118123 | 0.073 | 0.381 | 1 | NFKBIZ5 | 0.420953504 | -0.291051658 | 0.206 | 0.619 | 1 |
| CD742 | 0.00077867 | -0.713623754 | 0.95 | 1 | 1 | FOS4 | 0.42228888 | -0.662289226 | 0.916 | 0.952 | 1 |
| KLRC11 | 0.000936095 | -0.621859482 | 0.511 | 1 | 1 | KLRC31 | 0.445533768 | -0.632310765 | 0.107 | 0.571 | 1 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| TYROBP | 0.001038834 | -0.466278951 | 0.966 | 1 | 1 | SAT 12 | 0.451067679 | -0.448641225 | 0.592 | 0.714 | 1 |
| PLSCR1 | 0.001157811 | -0.276378703 | 0.103 | 0.381 | 1 | 1-Jun | 0.45509986 | -0.667752245 | 0.931 | 0.952 | 1 |
| ACTB2 | 0.001238517 | 0.308581692 | 1 | 1 | 1 | TTC38 | 0.466044297 | 0.361920958 | 0.435 | 0.905 | 1 |
| GZMB1 | 0.001617486 | 0.734677389 | 0.592 | 0.571 | 1 | FCGR3A2 | 0.48200542 | 0.659085054 | 0.569 | 1 | 1 |
| NDUFB6 | 0.00162094 | 0.41121067 | 0.424 | 0.476 | 1 | C12orf751 | 0.483247629 | 0.263444817 | 0.492 | 1 | 1 |
| XCL22 | 0.001747964 | -0.715010275 | 0.63 | 1 | 1 | NDUFAB1 | 0.539163449 | 0.312854331 | 0.489 | 1 | 1 |
| TIPARP2 | 0.001749622 | -1.046389272 | 0.095 | 0.381 | 1 | OSTC | 0.588544772 | 0.277905343 | 0.504 | 1 | 1 |
| XCL12 | 0.001772675 | -0.600884148 | 0.527 | 0.952 | 1 | TIMP11 | 0.61441725 | 0.297097672 | 0.412 | 0.714 | 1 |
| STAT15 | 0.001185324 | 0.274754164 | 0.336 | 1 | 1 | EPRS1 | 0.72014678 | 0.307847807 | 0.366 | 0.714 | 1 |
| CAPG | 0.001997297 | -0.34585769 | 0.305 | 0.905 | 1 | PYCARD | 0.724794053 | 0.252254124 | 0.366 | 0.762 | 1 |
| FGFBP22 | 0.002273346 | 1.029414565 | 0.473 | 0.571 | 1 | NUDT1 | 0.744010756 | -0.268457882 | 0.206 | 0.619 | 1 |
| SRGN | 0.002501268 | -0.520632843 | 0.901 | 1 | 1 | CSTB1 | 0.764913723 | 0.281747975 | 0.618 | 1 | 1 |
| RAMP1 | 0.00257517 | -0.329157706 | 0.183 | 0.762 | 1 | NEAT12 | 0.782123913 | -0.354249401 | 0.615 | 0.667 | 1 |
| PDE4D2 | 0.002649881 | -0.254489413 | 0.134 | 0.381 | 1 | CCR71 | 0.793026052 | 0.423887873 | 0.431 | 0.905 | 1 |
| SPON22 | 0.002737074 | 0.701812108 | 0.466 | 0.524 | 1 | ZFHX3 | 0.828025173 | -0.312236866 | 0.038 | 0.524 | 1 |
| CDK6 | 0.002801424 | -0.481068273 | 0.126 | 0.381 | 1 | C1QBP | 0.858961354 | 0.441110743 | 0.534 | 1 | 1 |
| TRBV5-11 | 0.002952081 | 0.376697286 | 0.034 | 0.524 | 1 | LEF11 | 0.865037539 | 0.31630874 | 0.466 | 0.81 | 1 |
| NAAA1 | 0.002986907 | 0.265218965 | 0.344 | 1 | 1 | CCT2 | 0.876675018 | 0.496853494 | 0.466 | 0.905 | 1 |
| EGR13 | 0.003241279 | -0.419622459 | 0.107 | 0.667 | 1 | SLC1A5 | 0.877813448 | -0.799348125 | 0.061 | 0.524 | 1 |
| GADD45B2 | 0.003500575 | -0.393646259 | 0.531 | 1 | 1 | CX3CR11 | 0.878388194 | 0.495915773 | 0.344 | 0.714 | 1 |
| CEAP202 | 0.003514797 | -0.289396411 | 0.153 | 0.381 | 1 | ALOX5AP | 0.918529831 | 0.556969172 | 0.458 | 0.905 | 1 |
| LDHB2 | 0.003566399 | 0.524424968 | 0.863 | 0.952 | 1 | AL138963.36 | 0.932847806 | 0.63977883 | 0.58 | 1 | 1 |
| CTSW3 | 0.003697699 | -0.344088794 | 0.981 | 1 | 1 | MTRNR2L12 | 0.934844698 | 0.257682892 | 1 | 1 | 1 |
| PLPP5 | 0.00384342 | -0.261135977 | 0.084 | 0.667 | 1 | RPS27L | 0.936668518 | 0.278303371 | 0.534 | 1 | 1 |
| ZMAT4 | 0.003847388 | -0.335481226 | 0.073 | 0.381 | 1 | MYDGF | 0.942401698 | -0.283043201 | 0.382 | 0.667 | 1 |
| S100A43 | 0.003888031 | 0.625937067 | 0.908 | 0.952 | 1 | HSPA8 | 0.967946762 | -0.264339624 | 0.962 | 1 | 1 |
| KIR2DL11 | 0.004101672 | 0.291337585 | 0.145 | 0.667 | 1 | CCL.34 | 0.972390132 | 0.274540297 | 0.122 | 0.571 | 1 |
| | | | | | | Seurat Cluster 11 | | | | | |
| IGKV3-111 | 6.39E-31 | 0.850435661 | 0.011 | 0.75 | 1.28E-27 | FERMT3 | 0.124733881 | 0.254619604 | 0.478 | 0.5 | 1 |
| RNASE1 | 1.12E-25 | -0.394522662 | 0.004 | 0.125 | 2.24E-22 | CFD | 0.124992098 | -0.373440415 | 0.664 | 0.875 | 1 |
| TUBB1 | 5.77E-22 | -0.320367307 | 0 | 0.125 | 1.15E-18 | PLAC81 | 0.125296697 | -0.584096925 | 0.387 | 0.5 | 1 |
| IRF4 | 1.63E-21 | -0.370931564 | 0.036 | 0.875 | 3.25E-18 | ATP2B1-AS13 | 0.12634956 | 0.714296193 | 0.591 | 0.75 | 1 |
| TSC22D1 | 4.85E-20 | -0.256017099 | 0.022 | 0.875 | 9.71E-17 | CTSD | 0.127017011 | 0.490717305 | 0.544 | 0.625 | 1 |
| IGKV3-201 | 3.55E-19 | 0.400353421 | 0.018 | 0.625 | 7.10E-16 | GZMA3 | 0.133743835 | 0.544501186 | 0.19 | 0.5 | 1 |
| TRBV5-61 | 3.55E-19 | 0.301543165 | 0.018 | 0.625 | 7.10E-16 | H1FX3 | 0.135344711 | 0.62968554 | 0.555 | 0.625 | 1 |
| IGLV2-141 | 3.71E-19 | 0.69698903 | 0.029 | 0.75 | 7.43E-16 | FGFBP23 | 0.137301694 | 0.250036721 | 0.08 | 0.25 | 1 |
| RHOC1 | 2.48E-18 | -0.586263504 | 0.066 | 1 | 4.97E-15 | MYADM2 | 0.138530922 | -0.371874811 | 0.46 | 0.875 | 1 |
| TPM1 | 2.08E-16 | -0.450242098 | 0.073 | 1 | 4.17E-13 | MT2A6 | 0.138879787 | -0.597357411 | 0.507 | 0.5 | 1 |
| TNF4 | 7.41E-16 | 0.272920441 | 0.047 | 0.125 | 1.48E-12 | DUT | 0.141925489 | -0.275133108 | 0.511 | 0.875 | 1 |
| CLU1 | 2.07E-15 | 0.345108177 | 0.004 | 0.25 | 4.14E-12 | RBP7 | 0.148939161 | -0.262459663 | 0.427 | 0.875 | 1 |
| TRBV7-61 | 7.87E-15 | -0.499104467 | 0.044 | 0.75 | 1.57E-11 | SOX42 | 0.152477739 | 0.44473162 | 0.237 | 0.5 | 1 |
| IGHV3-231 | 2.57E-13 | 0.299656539 | 0.033 | 0.625 | 5.14E-10 | ATP5F1A | 0.154813852 | 0.556272329 | 0.624 | 0.875 | 1 |
| TRBV92 | 8.64E-13 | 0.286539563 | 0.051 | 0.75 | 1.73E-09 | MPP1 | 0.155705188 | 0.369479062 | 0.223 | 0.5 | 1 |
| ASGR2 | 9.21E-13 | 0.418704009 | 0.117 | 0 | 1.84E-09 | NCF2 | 0.163175446 | 0.6366318 | 0.624 | 0.75 | 1 |
| BANKI | 1.60E-12 | -0.290845409 | 0.095 | 1 | 3.21E-09 | C19orf38 | 0.163799158 | 0.386776792 | 0.412 | 0.5 | 1 |
| UBE2S | 3.76E-12 | -0.340959084 | 0.099 | 1 | 7.53E-09 | CSTA | 0.166160366 | 0.478478195 | 0.682 | 0.75 | 1 |
| GZMK3 | 5.13E-12 | 0.323842166 | 0.095 | 1 | 1.03E-08 | KLRD13 | 0.167320607 | -0.757481411 | 0.099 | 0.25 | 1 |
| ZSCAN22 | 2.55E-11 | -0.42844096 | 0.004 | 0.25 | 5.10E-08 | FOSB3 | 0.169684531 | 0.321494873 | 0.704 | 0.625 | 1 |
| CCDC50 | 1.43E-10 | -0.286630635 | 0.117 | 1 | 2.86E-07 | IFITM33 | 0.171358465 | -0.283459593 | 0.781 | 0.625 | 1 |
| RACGAP1 | 3.33E-10 | -0.255002643 | 0.026 | 0.25 | 6.66E-07 | CSF3R | 0.172150416 | -0.549585498 | 0.504 | 0.875 | 1 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| CALHM6 | 1.00E-09 | 0.407544664 | 0.12 | 0.125 | | GZMM1 | 0.175530171 | 0.557126816 | 0.376 | 1 | 1 |
| SIGLEC1 | 1.18E-09 | -0.917172367 | 0.033 | 0.5 | | IFNGR2 | 0.178935281 | 0.331785695 | 0.409 | 0.5 | 1 |
| MANF | 2.25E-09 | -0.34246789 | 0.131 | 1 | | AHR | 0.185352932 | -0.767442856 | 0.19 | 0.625 | 1 |
| ITGB5 | 4.28E-09 | -0.335209341 | 0 | 0.375 | | LAG31 | 0.186662689 | -0.255845915 | 0.033 | 0.25 | 1 |
| HES11 | 4.28E-09 | -0.400090845 | 0 | 0.125 | | TNFRSF13C | 0.195194817 | -0.256253004 | 0.033 | 0.25 | 1 |
| MGST1 | 5.67E-09 | 0.822154069 | 0.219 | 0 | | VCL | 0.196489212 | 0.388873409 | 0.193 | 0.5 | 1 |
| KPNA2 | 8.56E-09 | -0.287523649 | 0.08 | 0.875 | | TRAV12-1 | 0.199566609 | -0.268815523 | 0.033 | 0.25 | 1 |
| MIR22HG1 | 1.21E-08 | 0.502334055 | 0.153 | 0.125 | | PRDX11 | 0.201451936 | 0.721169581 | 0.522 | 0.75 | 1 |
| TRBV282 | 1.22E-08 | 0.277254516 | 0.036 | 0.5 | | DUSP6 | 0.201568525 | -0.820062487 | 0.347 | 0.75 | 1 |
| TRDC1 | 2.34E-08 | -0.329654 | 0.088 | 0.75 | | SEC61B | 0.203670894 | -0.314172617 | 0.734 | 0.75 | 1 |
| BASP1 | 2.42E-08 | 0.298019667 | 0.102 | 0.125 | | HLA-DPB13 | 0.203670955 | 0.659955112 | 0.734 | 0.875 | 1 |
| MX13 | 3.50E-08 | 0.259269779 | 0.164 | 0.125 | | HSP90AB11 | 0.211782804 | -0.528445689 | 0.854 | 1 | 1 |
| TRBV20-14 | 3.57E-08 | 0.271522857 | 0.084 | 0.75 | | SNAP23 | 0.217709226 | 0.439504193 | 0.307 | 0.875 | 1 |
| TXNDC17 | 4.97E-08 | 0.880855148 | 0.38 | 0 | | NPC2 | 0.21849151 | 0.389482936 | 0.679 | 0.75 | 1 |
| SMIM3 | 1.09E-07 | -0.410117948 | 0.051 | 0.25 | | CD361 | 0.220035868 | 0.580509161 | 0.5 | 0.625 | 1 |
| ID31 | 1.64E-07 | 0.253977723 | 0.091 | 0.75 | | NKG73 | 0.222553462 | -0.286219409 | 0.266 | 0.5 | 1 |
| IF16I | 4.65E-07 | 0.291318926 | 0.208 | 0.125 | | FPR1 | 0.2263319 | 0.279252432 | 0.354 | 0.5 | 1 |
| COMTD1 | 8.79E-07 | -0.40936956 | 0.109 | 0.875 | | HSP90B13 | 0.22791383 | -0.399432006 | 0.668 | 0.875 | 1 |
| CD300LF | 1.06E-06 | -0.537636054 | 0.153 | 0.875 | | YWHAQ2 | 0.22953566 | -0.261007707 | 0.42 | 0.875 | 1 |
| CMC11 | 1.17E-06 | -0.352529148 | 0.172 | 1 | | LTB3 | 0.240422916 | 0.511388359 | 0.85 | 1 | 1 |
| MCM7 | 1.87E-06 | -0.297389554 | 0.113 | 0.875 | | DUSP11 | 0.242475662 | 0.368303578 | 0.449 | 0.625 | 1 |
| HPGD | 3.13E-06 | -0.286625244 | 0.033 | 0.25 | | PSME21 | 0.242804699 | 0.31724453 | 0.92 | 0.75 | 1 |
| TBX21 | 4.03E-06 | -0.587335733 | 0.088 | 0.625 | | CSTB2 | 0.243232704 | 0.303998599 | 0.712 | 0.75 | 1 |
| HSPB11 | 4.71E-06 | -0.314766113 | 0.193 | 1 | | LGALS12 | 0.248074171 | 0.518365731 | 0.715 | 1 | 1 |
| TRBV7-24 | 8.11E-06 | 0.755817008 | 0.058 | 0.5 | | B1'K | 0.250320611 | 0.28404802 | 0.901 | 1 | 1 |
| LMNA3 | 9.00E-06 | -0.265417363 | 0.091 | 0.25 | | STAB1 | 0.251065418 | 0.264531318 | 0.157 | 0.625 | 1 |
| CD8A1 | 1.03E-05 | 0.457732866 | 0.179 | 1 | | TMEM1562 | 0.256166781 | -0.965674717 | 0.172 | 0.625 | 1 |
| CDCA7L | 1.12E-05 | -0.299465634 | 0.058 | 0.625 | | HLA-DQB11 | 0.256701879 | -0.418410392 | 0.044 | 0.375 | 1 |
| EPSTI2 | 1.21E-05 | -0.549855774 | 0.102 | 0.25 | | IF130 | 0.258958853 | 0.463837938 | 0.434 | 1 | 1 |
| SAMD31 | 1.37E-05 | -0.300425857 | 0.172 | 0.875 | | IL325 | 0.258991072 | 0.531150464 | 0.504 | 0.625 | 1 |
| CD692 | 1.59E-05 | -1.44038262 | 0.405 | 1 | | LDHB3 | 0.25953391 | 0.667528577 | 0.737 | 1 | 1 |
| MCM31 | 1.82E-05 | -0.272065506 | 0.128 | 0.875 | | SYK1 | 0.262108817 | 0.339177288 | 0.807 | 1 | 1 |
| GBP52 | 1.87E-05 | -0.286825135 | 0.201 | 1 | | RAB32 | 0.265006 | 0.282044504 | 0.434 | 0.625 | 1 |
| EPHB6 | 2.21E-05 | -0.305399302 | 0.095 | 0.75 | | PA2G41 | 0.268265451 | 0.315880254 | 0.347 | 0.5 | 1 |
| MS4A1 | 2.29E-05 | 0.476529642 | 0.157 | 0.875 | | CCT7 | 0.276905017 | 0.566203227 | 0.496 | 0.75 | 1 |
| RPS4Y11 | 2.88E-05 | -0.645054544 | 0 | 0.625 | | PDCD5 | 0.27923503 | 0.408058077 | 0.416 | 1 | 1 |
| SWAP70 | 3.02E-05 | 0.424542221 | 0.058 | 0.25 | | AP2S1 | 0.280146292 | 0.528718591 | 0.044 | 0.625 | 1 |
| CISD1 | 3.04E-05 | -0.356068616 | 0.102 | 0.25 | | HP | 0.283932923 | 0.372288741 | 0.737 | 1 | 1 |
| GPR35 | 4.22E-05 | -0.255046304 | 0.142 | 0.875 | | SGK12 | 0.285243171 | -0.260981443 | 0.036 | 0.5 | 1 |
| IL2RB1 | 4.45E-05 | -0.462831387 | 0.055 | 0.25 | | UQCC2 | 0.289968904 | -0.69592224 | 0.303 | 0.625 | 1 |
| P2RY13 | 4.63E-05 | -0.305654768 | 0.106 | 0.75 | | SERPINA1 | 0.298081744 | 0.319999279 | 0.223 | 0.75 | 1 |
| HPRT1 | 5.18E-05 | 0.325252295 | 0.179 | 0.25 | | FGR1 | 0.30476537 | 0.438893568 | 0.788 | 0.875 | 1 |
| PIK3AP1 | 6.58E-05 | 0.412617272 | 0.193 | 0.25 | | CYTOR | 0.307819813 | 0.366601645 | 0.602 | 0.75 | 1 |
| MT1X | 7.62E-05 | 0.309201959 | 0.186 | 0.25 | | HLA-DRB15 | 0.317719262 | -0.368993872 | 0.142 | 0.625 | 1 |
| PTTGI | 8.31E-05 | -0.396364641 | 0.062 | 0.25 | | TRAV8-41 | 0.317719262 | -0.333423103 | 0.814 | 0.875 | 1 |
| CD79A1 | 0.000103759 | 0.829069861 | 0.172 | 0.875 | | PPP1CA | 0.320310946 | 0.384060861 | 0.044 | 0.125 | 1 |
| 1-Mar | 0.000104627 | -0.299502728 | 0.263 | 1 | | RAB31 | 0.320978803 | 0.555237847 | 0.679 | 1 | 1 |
| CD40 | 0.000113962 | 0.260553999 | 0.102 | 0.75 | | CTSC2 | 0.327391807 | 0.344072522 | 0.31 | 0.5 | 1 |
| GLIPR11 | 0.000121085 | 0.996753726 | 0.504 | 0.25 | | STXBP2 | 0.331576299 | -0.548422158 | 0.445 | 0.625 | 1 |
| SELENOS | 0.000127766 | 0.442828997 | 0.252 | 0.25 | | ADGRG12 | 0.333559584 | 0.389042791 | 0.719 | 0.75 | 1 |
| RPN1 | 0.000240063 | 0.671102114 | 0.42 | 0.25 | | | | -0.300998778 | 0.051 | 0.125 | 1 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| ASGR1 | 0.000374391 | −0.739060384 | 0.365 | 1 | 0.748781832 | SAT13 | 0.349868688 | 0.319912925 | 0.92 | 1 | 1 |
| DDIT42 | 0.000550103 | 0.356847682 | 0.307 | 0.25 | 1 | TRBV6-1 | 0.350799233 | 0.331732321 | 0.044 | 0.25 | 1 |
| PSMD8 | 0.000676413 | 0.375882552 | 0.394 | 0.25 | 1 | TIMM10 | 0.352076001 | 0.270171609 | 0.245 | 0.75 | 1 |
| PRF11 | 0.000678736 | −0.284329158 | 0.175 | 0.75 | 1 | Z93241.13 | 0.361682934 | 0.392104148 | 0.416 | 1 | 1 |
| CD40LG | 0.000849348 | 0.272725365 | 0.124 | 0.625 | 1 | DYNLL1 | 0.363973571 | 0.372259052 | 0.566 | 0.75 | 1 |
| AREG2 | 0.000865864 | −0.532884336 | 0.022 | 0.375 | 1 | CCT5 | 0.364087323 | 0.288192702 | 0.365 | 0.875 | 1 |
| PYGL | 0.00111709 | −0.418816903 | 0.259 | 0.875 | 1 | AL138963.37 | 0.379028503 | 1.18361385 | 0.635 | 1 | 1 |
| NELL22 | 0.001172758 | −0.258736237 | 0.142 | 0.625 | 1 | C1orf162 | 0.379591995 | −0.430649755 | 0.672 | 1 | 1 |
| RALGPS2 | 0.001213823 | 0.33724054 | 0.128 | 0.75 | 1 | CTSA | 0.381933747 | −0.269035266 | 0.347 | 0.5 | 1 |
| CEBPB | 0.001286425 | 1.124520403 | 0.599 | 1 | 1 | EMILIN2 | 0.392393338 | −0.299723175 | 0.321 | 0.625 | 1 |
| SNX22 | 0.001574577 | −0.53351614 | 0.026 | 0.375 | 1 | RAB11FIP11 | 0.393196422 | −0.260895072 | 0.339 | 0.75 | 1 |
| HIST1H1D2 | 0.002271379 | −0.552479725 | 0.405 | 1 | 1 | TBXAS1 | 0.394051279 | 0.336999647 | 0.365 | 0.625 | 1 |
| CTSW4 | 0.003144963 | 0.471786745 | 0.259 | 1 | 1 | MIF1 | 0.405223026 | 0.256965152 | 0.796 | 0.875 | 1 |
| CREB5 | 0.00361148 | −0.372702623 | 0.172 | 0.75 | 1 | 11-Sep | 0.40970899 | 0.523208038 | 0.438 | 1 | 1 |
| TREML1 | 0.002608136 | −0.323679079 | 0.004 | 0.125 | 1 | NBPF141 | 0.417984889 | −0.929023672 | 0.321 | 0.5 | 1 |
| CST73 | 0.00283788 | −0.26805637 | 0.208 | 0.875 | 1 | HISTH1E | 0.447887075 | 0.488625352 | 0.704 | 0.875 | 1 |
| AC10591.36 | 0.002961767 | −0.739457134 | 0.036 | 0.375 | 1 | TCL1A | 0.449081858 | 0.330147774 | 0.055 | 0.125 | 1 |
| ETFA | 0.003611748 | −0.329703395 | 0.237 | 0.875 | 1 | SLC9A3R12 | 0.45577828 | 0.348246266 | 0.478 | 1 | 1 |
| TRAV13-12 | 0.003802756 | 0.279111326 | 0.069 | 0.375 | 1 | CLEC12A | 0.465885281 | 0.341167774 | 0.325 | 0.75 | 1 |
| ACTG12 | 0.004163667 | 0.656878643 | 0.967 | 1 | 1 | SUPT16H | 0.468887263 | −0.2726557 | 0.208 | 0.5 | 1 |
| EPRS2 | 0.004607422 | 0.261188763 | 0.266 | 1 | 1 | ITGB71 | 0.476861762 | 0.391037556 | 0.255 | 0.75 | 1 |
| OSTC1 | 0.005053044 | 0.413961102 | 0.35 | 0.375 | 1 | PLEK1 | 0.484540957 | 0.331566798 | 0.536 | 0.75 | 1 |
| GZMB2 | 0.005307487 | 0.448849195 | 0.109 | 0.625 | 1 | DNMT11 | 0.490969168 | −0.337263967 | 0.332 | 0.75 | 1 |
| HLA-DQA11 | 0.00549148 | 0.368089009 | 0.277 | 1 | 1 | MT-ND61 | 0.494587994 | 1.021421787 | 0.569 | 0.75 | 1 |
| LINC00261 | 0.005503095 | 0.296727617 | 0.113 | 0.5 | 1 | CRTAP1 | 0.500559944 | 0.322609277 | 0.547 | 0.75 | 1 |
| ITGB13 | 0.00657206 | 0.608536612 | 0.365 | 0.875 | 1 | LTA4H | 0.50392923 | 0.68902917 | 0.602 | 1 | 1 |
| SULT1A1 | 0.006921291 | 0.519901695 | 0.321 | 0.375 | 1 | MTHFD2 | 0.505048185 | −0.313968811 | 0.139 | 0.5 | 1 |
| IDH22 | 0.008142054 | 0.314174534 | 0.303 | 0.375 | 1 | CD51 | 0.506842297 | 0.400275747 | 0.201 | 0.5 | 1 |
| GGCT | 0.008143096 | 0.283686991 | 0.142 | 0.375 | 1 | SSR4 | 0.515987622 | 0.276802059 | 0.741 | 1 | 1 |
| IGHV5-511 | 0.008261225 | 0.392482585 | 0.011 | 0.125 | 1 | MNDA2 | 0.525154944 | −0.285721714 | 0.755 | 1 | 1 |
| ERLEC11 | 0.008376856 | 0.37960566 | 0.179 | 0.375 | 1 | HLA-DQA2 | 0.532024299 | 0.275507477 | 0.496 | 1 | 1 |
| LYL1 | 0.008389862 | 0.332558571 | 0.175 | 0.375 | 1 | TRBV3-12 | 0.542624963 | 0.33608906 | 0.051 | 0.125 | 1 |
| ICAM1 | 0.00864583 | 0.285543985 | 0.142 | 0.375 | 1 | BHLHE401 | 0.546531262 | −0.334777439 | 0.175 | 0.5 | 1 |
| BCL2A1 | 0.008831632 | 0.599278745 | 0.27 | 0.375 | 1 | NUDT11 | 0.549410368 | 0.460759513 | 0.281 | 0.625 | 1 |
| PRDM12 | 0.008898682 | −0.409434926 | 0.066 | 0.125 | 1 | NDUFAB11 | 0.550753984 | 0.363316646 | 0.478 | 1 | 1 |
| VPREB3 | 0.009806668 | 0.251275555 | 0.08 | 0.375 | 1 | RGS21 | 0.560625316 | 0.27243667 | 0.522 | 1 | 1 |
| RXRA | 0.009868034 | 0.385980255 | 0.255 | 0.375 | 1 | VDAC31 | 0.566081397 | 0.442683703 | 0.277 | 0.625 | 1 |
| LDHA3 | 0.009868444 | 0.748885791 | 0.562 | 0.5 | 1 | LIMS11 | 0.566081477 | 0.449895884 | 0.277 | 0.625 | 1 |
| DMTN | 0.011285128 | −0.34394953 | 0.011 | 0.125 | 1 | CD821 | 0.57275278 | −0.349266568 | 0.201 | 0.5 | 1 |
| ACSL1 | 0.011498794 | −0.370582506 | 0.08 | 0.375 | 1 | MS4A6A1 | 0.581773208 | −0.315506072 | 0.726 | 0.875 | 1 |
| SLC31A2 | 0.012180253 | −0.254196024 | 0.157 | 0.75 | 1 | PTGTR4 | 0.585543942 | −0.342026713 | 0.164 | 0.5 | 1 |
| MZT1 | 0.012396313 | −0.54215531 | 0.164 | 0.75 | 1 | TUBB | 0.5910091 | 0.63043581 | 0.566 | 1 | 1 |
| IGLV1-401 | 0.012715437 | −1.077640904 | 0.007 | 0.25 | 1 | FCMR2 | 0.594130228 | 0.370878247 | 0.489 | 1 | 1 |
| HVCN1 | 0.013787503 | 0.33978598 | 0.212 | 0.875 | 1 | SLC7A7 | 0.606004061 | 0.630704612 | 0.445 | 0.75 | 1 |
| SLC25A37 | 0.017823548 | −0.592363311 | 0.19 | 0.75 | 1 | PSMA4 | 0.616658836 | 0.52579788 | 0.376 | 0.875 | 1 |
| ADGRE2 | 0.018674242 | −0.267458708 | 0.095 | 0.625 | 1 | JPT1 | 0.620721276 | 0.388946491 | 0.412 | 0.875 | 1 |
| INSIG1 | 0.01953729 | −0.286580172 | 0.106 | 0.375 | 1 | DMXL2 | 0.639189601 | −0.535998494 | 0.303 | 0.625 | 1 |
| CALR2 | 0.021227296 | 0.544992552 | 0.544 | 0.5 | 1 | CDK61 | 0.65757433 | −0.408177749 | 0.088 | 0.5 | 1 |
| AQP32 | 0.022260815 | 0.609258458 | 0.303 | 1 | 1 | HMGB2 | 0.659955662 | −0.559988619 | 0.365 | 0.625 | 1 |
| IGHV3-531 | 0.022607919 | 0.273573383 | 0.015 | 0.125 | 1 | CD73 | 0.66085159 | 0.41730244 | 0.518 | 1 | 1 |
| SELL2 | 0.023333818 | 0.770043889 | 0.704 | 0.625 | 1 | HIST3H2A | 0.663503184 | −0.306556602 | 0.069 | 0.5 | 1 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| FKBP21 | 0.02420394 | -0.608226208 | 0.328 | 0.375 | 1 | NLRP3 | 0.673083502 | -0.496975316 | 0.234 | 0.625 | 1 |
| SPN | 0.025374801 | 0.312957037 | 0.307 | 1 | 1 | IL7R5 | 0.693786204 | 0.291895667 | 0.635 | 1 | 1 |
| HIST1H1C | 0.025626165 | -0.35905968 | 0.343 | 0.875 | 1 | ID1 | 0.698033015 | -0.482073106 | 0.077 | 0.125 | 1 |
| RPA31 | 0.025822991 | -0.521277177 | 0.201 | 0.75 | 1 | FCRL1 | 0.701029084 | -0.269521871 | 0.036 | 0.5 | 1 |
| MT-ND4L | 0.02619526 | 0.455765097 | 0.989 | 1 | 1 | HSH2D1 | 0.711399723 | -0.352439736 | 0.157 | 0.5 | 1 |
| TRAC1 | 0.029521347 | 0.427329324 | 0.318 | 1 | 1 | RETN1 | 0.719922593 | 0.258766304 | 0.606 | 0.875 | 1 |
| CDKN1A | 0.032118492 | -0.543773256 | 0.226 | 0.75 | 1 | IGLC3 | 0.718413862 | -0.494763579 | 0.033 | 0.125 | 1 |
| IL1R2 | 0.03227604 | -0.388654218 | 0.004 | 0.375 | 1 | UCHL5 | 0.727914737 | -0.250066865 | 0.161 | 0.625 | 1 |
| HYOU1 | 0.03404984 | -0.283641437 | 0.113 | 0.625 | 1 | IGLC2 | 0.728240161 | -0.50224286 | 0.033 | 0.125 | 1 |
| ACTB3 | 0.034196746 | 0.327143805 | 1 | 1 | 1 | ALDH2 | 0.736030282 | 0.426213892 | 0.358 | 0.75 | 1 |
| HIST1H4C1 | 0.034808279 | -0.451979509 | 0.544 | 1 | 1 | ADA2 | 0.73655376 | 0.292125005 | 0.453 | 0.875 | 1 |
| NRGN | 0.034847958 | 0.326737743 | 0.255 | 0.375 | 1 | IGHA1 | 0.736630494 | -0.676268075 | 0.029 | 0.125 | 1 |
| CYB561A3 | 0.036312026 | 0.404947786 | 0.237 | 0.875 | 1 | RNASE2 | 0.737782448 | -0.498475677 | 0.073 | 0.5 | 1 |
| TLR2 | 0.036651693 | 0.319639906 | 0.193 | 0.75 | 1 | EFHD22 | 0.748222149 | -0.520613623 | 0.46 | 0.75 | 1 |
| SH3BGRL31 | 0.036891988 | 0.417473546 | 0.993 | 1 | 1 | SLC40A1 | 0.752204829 | 0.268440096 | 0.15 | 0.5 | 1 |
| HOPX2 | 0.038010754 | -0.351188475 | 0.164 | 0.75 | 1 | NPM11 | 0.756141175 | -0.278691651 | 0.85 | 1 | 1 |
| LAT3 | 0.038117196 | -0.373163946 | 0.405 | 1 | 1 | ANP32E | 0.766020531 | 0.317511492 | 0.328 | 0.75 | 1 |
| COTL11 | 0.038908445 | 0.419548342 | 0.942 | 1 | 1 | CD302 | 0.767806596 | 0.281139816 | 0.318 | 0.75 | 1 |
| RASSF4 | 0.043396801 | -0.34174408 | 0.332 | 0.875 | 1 | LILRA2 | 0.770668075 | 0.269199955 | 0.332 | 0.75 | 1 |
| IGKV1-51 | 0.044869018 | 0.666165155 | 0.018 | 0.125 | 1 | JAKMIP1 | 0.77724232 | -0.352699195 | 0.022 | 0.125 | 1 |
| GAPDH | 0.050581875 | 0.365271114 | 0.996 | 1 | 1 | PPIB3 | 0.782156789 | -0.413699355 | 0.766 | 1 | 1 |
| PRMT11 | 0.053339421 | 0.372411161 | 0.332 | 1 | 1 | ANKRD28 | 0.787509294 | -0.486057851 | 0.051 | 0.5 | 1 |
| HSPD1 | 0.053817138 | -0.381478162 | 0.369 | 0.875 | 1 | HCK | 0.787715592 | 0.537314663 | 0.522 | 0.875 | 1 |
| AHNAK3 | 0.05514013 | 0.780058356 | 0.803 | 0.875 | 1 | C5AR1 | 0.791184475 | -0.455367691 | 0.328 | 0.5 | 1 |
| ACTN12 | 0.056766644 | 0.60600167 | 0.339 | 0.5 | 1 | LCK1 | 0.804626594 | 0.286876943 | 0.595 | 1 | 1 |
| CD1631 | 0.057609772 | -0.374776562 | 0.208 | 0.75 | 1 | FCRL5 | 0.812943457 | -0.310198358 | 0.018 | 0.125 | 1 |
| LRRK2 | 0.063816932 | -0.260418382 | 0.193 | 0.75 | 1 | SPCS2 | 0.813087286 | 0.334587556 | 0.412 | 0.75 | 1 |
| PPM1G1 | 0.06432803 | -0.388253256 | 0.387 | 0.875 | 1 | IGKV4-11 | 0.831503945 | 0.391893988 | 0.015 | 0.375 | 1 |
| CACYBP | 0.064939521 | 0.530899863 | 0.325 | 0.5 | 1 | C12orf752 | 0.832490505 | 0.303918613 | 0.175 | 0.625 | 1 |
| GAS6 | 0.066335991 | -0.506029432 | 0.018 | 0.375 | 1 | MCTP1 | 0.832490505 | 0.275746352 | 0.175 | 0.625 | 1 |
| NDUFB31 | 0.069727095 | 0.412700802 | 0.376 | 0.5 | 1 | MARCKS | 0.833069773 | -0.253665002 | 0.299 | 0.5 | 1 |
| CTSS | 0.070285533 | 0.475786563 | 0.938 | 1 | 1 | ATP5MC1 | 0.844126305 | 0.28473284 | 0.42 | 0.75 | 1 |
| PYCARD1 | 0.072110899 | -0.328582292 | 0.766 | 0.75 | 1 | PCSK1N1 | 0.845398481 | -0.46947296 | 0.018 | 0.25 | 1 |
| IGHV3-211 | 0.07394262 | 0.37083932 | 0.022 | 0.125 | 1 | ABRACL2 | 0.853054401 | 0.450695016 | 0.566 | 1 | 1 |
| CD632 | 0.080592892 | -0.894466652 | 0.449 | 0.875 | 1 | TOR3A | 0.858179567 | 0.282493382 | 0.179 | 0.625 | 1 |
| CPPED1 | 0.080645093 | 0.375523367 | 0.361 | 0.5 | 1 | ZFHX31 | 0.870359474 | -0.495609535 | 0.153 | 0.5 | 1 |
| TAGLN22 | 0.082537291 | 0.61360985 | 0.81 | 0.875 | 1 | HMGA1 | 0.873023661 | -0.334276103 | 0.281 | 0.625 | 1 |
| CFP | 0.084723998 | 0.345495505 | 0.547 | 0.5 | 1 | XIST2 | 0.876752349 | 0.40185158 | 0.453 | 0.875 | 1 |
| ARHGAP24 | 0.087520731 | -0.333507795 | 0.153 | 0.625 | 1 | CCT8 | 0877123574 | 0.262404897 | 0.354 | 0.75 | 1 |
| S100A101 | 0.09080509 | 0.411086197 | 0.96 | 1 | 1 | DPYSL2 | 0.883650353 | 0.33722107 | 0.182 | 0.625 | 1 |
| SIRPG2 | 0.091360493 | 0.351909698 | 0.172 | 0.75 | 1 | CD3D5 | 0.889702175 | 0.531327361 | 0.588 | 1 | 1 |
| PGD | 0.093701568 | -0.339799947 | 0.522 | 0.875 | 1 | PRAM1 | 0.895822753 | -0.40887405 | 0.391 | 0.75 | 1 |
| SUB11 | 0.093843856 | 0.532143827 | 0.686 | 0.75 | 1 | HLA-DMB | 0.898634653 | 0.388680234 | 0.438 | 0.875 | 1 |
| KLF101 | 0.097437587 | 0.331926048 | 0.405 | 0.5 | 1 | IFI272 | 0.905986392 | -1.045154402 | 0.007 | 0.125 | 1 |
| NAIP | 0.098705367 | -0.250486039 | 0.361 | 0.875 | 1 | LILRB4 | 0.906819866 | -0.483028895 | 0.164 | 0.5 | 1 |
| H2AFY2 | 0.099797213 | 0.438152984 | 0.562 | 0.625 | 1 | NAAA2 | 0.907408609 | 0.299469991 | 0.464 | 0.875 | 1 |
| MRPL131 | 0.101337942 | 0.262466935 | 0.175 | 0.75 | 1 | NOSIP3 | 0.916064508 | 0.260506856 | 0.653 | 1 | 1 |
| ATP5F1B1 | 0.101916119 | 0.355694025 | 0.635 | 0.625 | 1 | TGFBI | 0.919717994 | 0.294957535 | 0.493 | 0.875 | 1 |
| CD93 | 0.106038347 | -0.265213821 | 0.27 | 0.75 | 1 | IGHV3-741 | 0.930966805 | -0.407981645 | 0.004 | 0.125 | 1 |
| PSMB8 | 0.106664204 | -0.448557645 | 0.584 | 0.875 | 1 | TRBV7-3 | 0.930966805 | -0.470544587 | 0.004 | 0.125 | 1 |
| NFKBIZ6 | 0.108472001 | -0.435176728 | 0.38 | 0.75 | 1 | LINC024461 | 0.932224651 | 0.357498308 | 0.102 | 0.25 | 1 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| MT-ATP81 | 0.108522638 | -0.327504465 | 0.664 | 1 | 1 | CD831 | 0.93387514 | 0.312722883 | 0.19 | 0.625 | 1 |
| CYP1B1 | 0.108833225 | 0.272144429 | 0.124 | 0.625 | 1 | CITED2 | 0.93517271 | -0.270152865 | 0.394 | 0.625 | 1 |
| SDHC1 | 0.110396355 | 0.349112162 | 0.318 | 0.5 | 1 | H2AFZ | 0.940550542 | 0.275945883 | 0.613 | 1 | 1 |
| ENO11 | 0.111072.564 | 0.448611889 | 0.745 | 0.75 | 1 | ALDH3B1 | 0.940840845 | -0.516306766 | 0.168 | 0.5 | 1 |
| P2RX1 | 0.111080199 | -0.501507566 | 0.088 | 0.625 | 1 | AC007952.41 | 0.965545493 | -0.250005609 | 0.588 | 1 | 1 |
| CPVL | 0.11291892 | 0.395487242 | 0.449 | 0.5 | 1 | PECAM11 | 0.967345384 | 0.619767345 | 0.434 | 0.875 | 1 |
| TRGV92 | 0.117076033 | -1.077562321 | 0029 | 0.125 | 1 | MIDN1 | 0.977693993 | -0.365538244 | 0.35 | 0.625 | 1 |
| TLN11 | 0.117251653 | 0.407113612 | 0.588 | 0.625 | 1 | PDIA6 | 0.977756509 | 0.288925549 | 0.354 | 0.75 | 1 |
| VIM2 | 0.117917317 | 0.334274515 | 0.978 | 1 | 1 | MRPL51 | 0.981643446 | -0.414509458 | 0.343 | 0.625 | 1 |
| CORO1A1 | 0.119900214 | 0.297217689 | 0.916 | 1 | 1 | MITCH2 | 0.983052983 | 0.303920172 | 0.197 | 0.625 | 1 |
| CALM21 | 0.123119419 | 0.268932646 | 0.734 | 0.625 | 1 | NDUFB61 | 0.985636864 | 0.482753918 | 0.336 | 0.75 | 1 |
| MTRNR2L121 | 0.124245367 | 0.488624409 | 0.971 | 1 | 1 | ITGAM | 0.997915298 | -0.563156446 | 0.318 | 0.625 | 1 |
| | | | | | | Seurat Cluster 12 | | | | | |
| IL326 | 2.20E-22 | 0.334012936 | 0.142 | 1 | 4.41E-19 | TAGLN23 | 0.061267648 | 0.252628206 | 0.962 | 1 | 1 |
| CXCL82 | 2.01E-15 | -0.301165921 | 0.009 | 0.25 | 4.03E-12 | RGS13 | 0.111065455 | -0.259847557 | 0.133 | 0.481 | 1 |
| C1QA1 | 4.28E-12 | -0.529993843 | 0.033 | 0.269 | 8.56E-09 | IF144L8 | 0.114401712 | -0.322771609 | 0.028 | 0.346 | 1 |
| APOBEC3A | 3.09E-11 | -0.25306851 | 0.038 | 0.288 | 6.17E-08 | TLN12 | 0.213475284 | -0.250005609 | 0.834 | 0.962 | 1 |
| PPBP3 | 7.83E-10 | -0.463897639 | 0.005 | 0.308 | 1.57E-06 | IFI62 | 0.349715378 | -0.312431714 | 0.299 | 0.558 | 1 |
| C1QB1 | 1.99E-07 | -0.533560964 | 0.005 | 0.231 | 0.000397132 | CD832 | 0.354468038 | -0.277969062 | 0.455 | 0.769 | 1 |
| RGS22 | 0.000463694 | 0.593374629 | 0.583 | 0.904 | 0.927387274 | MAFF | 0.429708887 | -0.251050603 | 0.028 | 0.481 | 1 |
| NR4A22 | 0.000791663 | -0.289697558 | 0.474 | 0.885 | 1 | CFD1 | 0.539356095 | -0.262052005 | 0.427 | 0.673 | 1 |
| EREG1 | 0.001792754 | -0.315558006 | 0.071 | 0.635 | 1 | TNF5 | 0.594131153 | -0.32006477 | 0.076 | 0.558 | 1 |
| TNFAIP34 | 0.008932992 | -0.389223669 | 0.18 | 0.673 | 1 | IFI273 | 0.626329062 | -0.911723344 | 0.005 | 0.212 | 1 |
| IFITM34 | 0.011040103 | -0.450128236 | 0.848 | 0.981 | 1 | ENHO | 0.652062713 | 0.319553694 | 0.483 | 0.846 | 1 |
| FCER1A | 0.023872131 | 0.390948115 | 0.815 | 1 | 1 | MTRNR2L122 | 0.743910924 | 0.287431966 | 1 | 1 | 1 |
| IGLV2-142 | 0.025919477 | 0.297387659 | 0.019 | 0.346 | 1 | MT2A7 | 0.778661195 | -0.631864421 | 0.464 | 0.615 | 1 |
| NEAT13 | 0.045551408 | -0.266598105 | 0.848 | 0.962 | 1 | TIPARP3 | 0.945199866 | -0.297663676 | 0.133 | 0.538 | 1 |
| MAP3K82 | 0.045929046 | -0.266025549 | 0.521 | 0.788 | 1 | AREG3 | 0.94834175 | -0.338274396 | 0.076 | 0.519 | 1 |
| | | | | | | Seurat Cluster 13 | | | | | |
| MINDY4 | 6.30E-14 | -0.267255744 | 0 | 0.982 | 1.26E-10 | LCN2 | 0.000280865 | -0.280100175 | 0.208 | 0.281 | 0.561729452 |
| PLXNB2 | 1.60E-13 | -0.313032909 | 0 | 0.956 | 3.19E-10 | NEAT14 | 0.000284346 | -0.411614336 | 0.25 | 0.947 | 0.566920578 |
| TCF41 | 1.68E-13 | -0.31192415 | 0 | 0.965 | 3.36E-10 | HIST1H2AM1 | 0.000305335 | -0.640189861 | 0 | 0.202 | 0.610670057 |
| NKG74 | 2.13E-13 | 1.689996716 | 0.125 | 0.026 | 4.25E-10 | KLHDC8B | 0.000330475 | -1.24105366 | 0 | 0.237 | 0.66094929 |
| FGR2 | 1.44E-12 | -0.394497788 | 0.042 | 1 | 2.88E-09 | FSTL1 | 0.00033771 | -0.31010105 | 0.083 | 0.246 | 0.67542075 |
| CD8B3 | 1.69E-12 | 0.362871396 | 0.042 | 0.991 | 3.39E-09 | CD3D6 | 0.000366639 | 0.55649477 | 0.208 | 0.921 | 0.732779386 |
| TRBV4-24 | 2.65E-12 | 0.593374629 | 0.042 | 0.991 | 5.30E-09 | FHL1 | 0.0003793 | 0.318294723 | 0.5 | 0.351 | 0.758599438 |
| CKS2 | 4.27E-12 | 0.322772145 | 0.042 | 0.965 | 8.53E-09 | AC123912 4 | 0.00038827 | -0.865921449 | 0.292 | 0.965 | 0.776540989 |
| DYTN | 9.13E-12 | -0.252250431 | 0.042 | 0.965 | 1.83E-08 | VDAC1 | 0.000584373 | 0.463024788 | 0.25 | 0.965 | 1 |
| AR | 9.13E-12 | -0.352897055 | 0.042 | 0.965 | 1.83E-08 | UBE2J11 | 0.000609124 | 0.344827315 | 0.25 | 0.316 | 1 |
| LINC024321 | 9.49E-12 | -0.289956986 | 0.042 | 0.965 | 1.90E-08 | DAB2 | 0.000798527 | -1.24231443 | 0.417 | 0.982 | 1 |
| CD833 | 1.06E-11 | 0.309187966 | 0.042 | 0.982 | 2.11E-08 | ALOX5AP1 | 0.000828282 | 0.501550793 | 0.25 | 0.956 | 1 |
| SULT1A11 | 1.42E-11 | -0.400412504 | 0 | 0.939 | 2.84E-08 | MAP1A1 | 0.000921365 | -0.728227808 | 0.375 | 0.991 | 1 |
| P2RY1 | 1.91E-11 | -0.635304363 | 0.042 | 0.965 | 3.82E-08 | MMD | 0.000946469 | -1.463597617 | 0.708 | 0.982 | 1 |
| IDH23 | 5.92E-11 | 0.339885795 | 0.167 | 0.088 | 1.18E-07 | HSPA55 | 0.000953832 | 0.47642297 | 0.5 | 0.947 | 1 |
| ATP1B1 | 6.98E-11 | -0.795334892 | 0.042 | 0.947 | 1.40E-07 | H1F0 | 0.001028312 | -0.326184396 | 0.25 | 0.316 | 1 |
| TENT5C | 7.68E-11 | 0.542214826 | 0.125 | 0.079 | 1.54E-07 | TYROBP1 | 0.001355784 | 0.408236091 | 0.167 | 0.342 | 1 |
| SLC25A391 | 1.11E-10 | 0.414027424 | 0.125 | 0.088 | 2.21E-07 | HSP90B14 | 0.001364682 | 0.373334254 | 0.167 | 0.991 | 1 |
| ETS2 | 1.16E-10 | -0.385078951 | 0.042 | 0.956 | 2.33E-07 | ZFP36L24 | 0.001418925 | 0.762223523 | 0.292 | 0.991 | 1 |
| KLRB14 | 1.42E-10 | 0.625622603 | 0.083 | 1 | 2.84E-07 | CD75 | 0.001418925 | 0.684789746 | 0.292 | 0.991 | 1 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| KLRD14 | 1.42E-10 | 0.613407164 | 0.083 | 1 | 2.84E-07 | FKBP22 | 0.001433638 | 0.274680217 | 0.125 | 0.807 | 1 |
| FCGR3A3 | 1.42E-10 | 0.437096776 | 0.083 | 1 | 2.84E-07 | TNS1 | 0.00188621 | 0.366845333 | 0.292 | 0.982 | 1 |
| CD300A | 1.42E-10 | 0.436064664 | 0.083 | 1 | 2.84E-07 | LTB4 | 0.00200083 | 0.467740504 | 0.25 | 0.921 | 1 |
| KLRF11 | 2.10E-10 | 0.275412611 | 0.083 | 0.991 | 4.20E-07 | CTSS1 | 0.002103273 | 0.294413551 | 0.125 | 0.798 | 1 |
| HERPUD13 | 2.25E-10 | 0.476022515 | 0.167 | 0.105 | 4.50E-07 | FAM110A | 0.002209236 | -0.670604066 | 0.375 | 0.991 | 1 |
| NUCB22 | 2.51E-10 | 0.259335923 | 0.167 | 0.096 | 5.02E-07 | CD272 | 0.002267626 | 0.584594759 | 0.125 | 0.798 | 1 |
| FAM30A1 | 2.74E-10 | -0.400392759 | 0.042 | 0.939 | 5.48E-07 | HNRNPA2B13 | 0.002480919 | 0.370194335 | 0.542 | 0.447 | 1 |
| MYOM22 | 3.10E-10 | 0.333433091 | 0.083 | 0.982 | 6.19E-07 | STXBP21 | 0.002567835 | -0.732518815 | 0.417 | 0.982 | 1 |
| PRF12 | 3.17E-10 | 0.642164262 | 0.083 | 0.991 | 6.35E-07 | AP001189.1 | 0.002628283 | 0.405656229 | 0.833 | 0.921 | 1 |
| HACD3 | 3.17E-10 | 0.434188614 | 0.083 | 0.991 | 6.35E-07 | PYGL1 | 0.002699126 | 0.296859524 | 0.208 | 0.342 | 1 |
| HOPX3 | 3.17E-10 | 0.260334122 | 0.083 | 0.991 | 6.35E-07 | ELOVL7 | 0.00360811 | -0.280859777 | 0.333 | 0.956 | 1 |
| GNLY6 | 3.71E-10 | 2.258277838 | 0.083 | 0.904 | 7.42E-07 | SH3BGRL2 | 0.00357396 | 0.360302342 | 0.583 | 0.421 | 1 |
| RPS27L1 | 3.97E-10 | 0.384544257 | 0.125 | 0.105 | 7.95E-07 | PNP1 | 0.003683981 | -0.39210761 | 0.292 | 0.333 | 1 |
| ME1S1 | 4.02E-10 | -0.566057704 | 0.083 | 0.965 | 8.04E-07 | PDGFA | 0.003683981 | -0.723044065 | 0.375 | 0.974 | 1 |
| LAPTM4B | 4.14E-10 | -0.419392463 | 0.083 | 0.974 | 8.27E-07 | VDAC32 | 0.00371124 | 0.299081673 | 0.625 | 0.43 | 1 |
| LTA4HI | 4.24E-10 | -0.327996423 | 0.083 | 0.982 | 8.48E-07 | CTSA1 | 0.003783076 | -0.610895042 | 0.917 | 0.982 | 1 |
| PAD14 | 4.32E-10 | 0.452638514 | 0.25 | 0.096 | 8.65E-07 | MT-ATP82 | 0.003918469 | 0.508278938 | 0.708 | 0.605 | 1 |
| HLA-DPB14 | 4.48E-10 | 0.553635665 | 0.167 | 0.105 | 8.97E-07 | PTMS1 | 0.003978081 | -0.274853137 | 0.042 | 0.325 | 1 |
| XCL23 | 4.55E-10 | 0.310099533 | 0.083 | 0.974 | 9.09E-07 | TUBB4B1 | 0.004507924 | 0.810611529 | 0.542 | 0.482 | 1 |
| CLIC32 | 4.67E-10 | 0.717012574 | 0.083 | 0.982 | 9.33E-07 | MINDY1 | 0.004807037 | -0.416762575 | 0.292 | 0.36 | 1 |
| SKA2 | 5.13E-10 | -0.26613208 | 0 | 0.877 | 1.03E-06 | FOS5 | 0.004884436 | -0.304639012 | 0.25 | 0.877 | 1 |
| CYB5D22 | 6.29E-10 | 0.347499067 | 0.083 | 0.982 | 1.26E-06 | HMGA11 | 0.005093338 | -1.162925235 | 0.042 | 0.325 | 1 |
| CD160 | 6.64E-10 | 0.326010335 | 0.083 | 0.965 | 1.33E-06 | LGALS121 | 0.005128595 | 0.41103683 | 0.333 | 0.965 | 1 |
| LYAR | 6.75E-10 | 0.45138584 | 0.083 | 0.982 | 1.35E-06 | PRKCD | 0.006090078 | 0.385813897 | 0.333 | 0.982 | 1 |
| LGMN | 8.65E-10 | -0.692381507 | 0.083 | 0.974 | 1.73E-06 | ITM2A | 0.006925783 | 0.407612749 | 0.208 | 0.395 | 1 |
| CACYBP1 | 8.87E-10 | -0.274999937 | 0.042 | 0.105 | 1.77E-06 | NPM12 | 0.007390668 | 0.594636993 | 0.333 | 0.991 | 1 |
| ADAMTS1 | 9.67E-10 | 0.281402457 | 0.083 | 0.956 | 1.93E-06 | LYN1 | 0.007523895 | -0.390829785 | 0.375 | 1 | 1 |
| DCAF12 | 1.04E-09 | 0.268873816 | 0.125 | 0.114 | 2.09E-06 | DMTN1 | 0.007934929 | 0.565072835 | 0.542 | 0.561 | 1 |
| PEA15 | 1.20E-09 | -0.617064715 | 0.083 | 0.105 | 2.41E-06 | EHD3 | 0.008001758 | -0.29916279 | 0.292 | 0.368 | 1 |
| VIM3 | 1.48E-09 | 0.368852523 | 0.333 | 0.123 | 2.97E-06 | BEND2 | 0.008136702 | 0.292306702 | 0.333 | 0.965 | 1 |
| GZMA4 | 1.79E-09 | 0.435212588 | 0.042 | 0.114 | 3.58E-06 | TMEM109 | 0.008272361 | 0.300889453 | 0.208 | 0.842 | 1 |
| EPSTI3 | 2.47E-09 | -0.407051868 | 0.083 | 0.114 | 4.94E-06 | SNCA | 0.008920415 | 0.334558497 | 0.667 | 0.509 | 1 |
| APOBEC3A1 | 4.57E-09 | 0.282827011 | 0.083 | 0.947 | 9.14E-06 | ZNF185 | 0.009052277 | -0.782264486 | 0.5 | 0.974 | 1 |
| MCM6 | 6.27E-09 | -0.312724547 | 0 | 0.123 | 1.25E-05 | FERMT31 | 0.009375594 | 0.569743082 | 0.792 | 0.825 | 1 |
| PSMB21 | 6.27E-09 | -0.340034058 | 0 | 0.123 | 1.25E-05 | NFE2 | 0.010790504 | 0.316330738 | 0.417 | 0.456 | 1 |
| SLC11A1 | 6.40E-09 | -0.4917044 | 0.042 | 0.904 | 1.28E-05 | IL327 | 0.011143455 | 1.340535639 | 0.333 | 0.991 | 1 |
| SELL3 | 6.68E-09 | 0.293681879 | 0.125 | 1 | 1.34E-05 | AP2S11 | 0.012326631 | 0.407532899 | 0.708 | 0.526 | 1 |
| CCR72 | 6.91E-09 | 0.282133912 | 0.125 | 1 | 1.38E-05 | CCT81 | 0.013843658 | 0.254017576 | 0.167 | 0.789 | 1 |
| MSRB3 | 7.83E-09 | -0.358016942 | 0.208 | 0.114 | 1.57E-05 | RGCC2 | 0.014810566 | 0.851183165 | 0.333 | 0.982 | 1 |
| SAMD32 | 7.90E-09 | 0.307177893 | 0.125 | 0.982 | 1.58E-05 | LMNA4 | 0.014855559 | 0.281861667 | 0.5 | 0.518 | 1 |
| PTGDR2 | 1.32E-08 | 0.396772855 | 0.125 | 0.974 | 2.63E-05 | SELP | 0.015261544 | 0.485994152 | 0.333 | 0.447 | 1 |
| PTGER2 | 1.37E-08 | 0.276412218 | 0.083 | 0.947 | 2.75E-05 | TNNC2 | 0.016739623 | -0.601880884 | 0.417 | 0.974 | 1 |
| IFI44L9 | 1.39E-08 | -0.299742046 | 0 | 0.132 | 2.78E-05 | PPBP4 | 0.017100933 | 0.381323876 | 1 | 0.991 | 1 |
| LEF12 | 1.43E-08 | 0.278384854 | 0.125 | 0.991 | 2.87E-05 | AL954642.1 | 0.019350547 | 0.790756881 | 0.25 | 0.439 | 1 |
| PBX1 | 1.50E-08 | 0.583263324 | 0.333 | 0.158 | 3.01E-05 | MYLK | 0.019946299 | 0.285981026 | 0.458 | 0.465 | 1 |
| DCTPP1 | 1.88E-08 | 0.259498975 | 0.125 | 0.982 | 3.75E-05 | MPP11 | 0.021111704 | 0.512519895 | 0.75 | 0.763 | 1 |
| H2AFV | 2.30E-08 | 0.487388292 | 0.208 | 0.167 | 4.59E-05 | ALOX12 | 0.023173863 | -0.790231939 | 0.542 | 0.965 | 1 |
| TNFRSF1B | 2.66E-08 | 0.326397783 | 0.125 | 0.982 | 5.32E-05 | RHOC2 | 0.025669681 | -0.564421794 | 0.125 | 0.386 | 1 |
| CCT6A | 3.67E-08 | -0.381423768 | 0.125 | 0.974 | 7.33E-05 | TIMP12 | 0.027077052 | -0.443852263 | 0.875 | 0.947 | 1 |
| C16orf74 | 4.09E-08 | 0.259310906 | 0.083 | 0.93 | 8.19E-05 | C2orfB8 | 0.03028389 | -0.455208822 | 0.542 | 0.982 | 1 |
| ANKRD281 | 4.47E-08 | 0.272904164 | 0.167 | 0.158 | 8.94E-05 | TMEM106C | 0.032004117 | 0.334221423 | 0.375 | 1 | 1 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| PDZK1IP1 | 4.99E-08 | 0.637785481 | 0.458 | 0.175 | 9.98E-05 | 2-Jun | 0.034323136 | 0.752701537 | 0.375 | 1 | 1 |
| PTAFR | 5.84E-08 | -0.427850505 | 0.125 | 0.956 | 0.000116763 | CORO1C | 0.037574199 | -0.342401044 | 0.458 | 0.982 | 1 |
| SYNGR2 | 5.90E-08 | 0.3268232 | 0.125 | 0.974 | 0.000118018 | SMOX | 0.03888335 | -0.903952319 | 0.5 | 0.851 | 1 |
| CHMP1B | 5.90E-08 | 0.320332058 | 0.125 | 0.974 | 0.000118018 | NEXN | 0.039802882 | -0.43139233v | 0.333 | 0.439 | 1 |
| CCT5I | 6.09E-08 | 0.261495896 | 0.125 | 0.974 | 0.000121791 | GLUL1 | 0.040939765 | -0.461066259 | 0.25 | 0.789 | 1 |
| SPDYC | 6.28E-08 | -0.734969882 | 0.125 | 0.956 | 0.000125681 | GSTP11 | 0.04103426 | 0.535400346 | 0.375 | 0.982 | 1 |
| LYST2 | 6.53E-08 | -0.3136121 | 0.167 | 0.158 | 0.000130635 | ILK2 | 0.041159102 | 0.350091552 | 0.792 | 0.64 | 1 |
| CTNNAL1 | 9.05E-08 | -0.797860221 | 0.042 | 0.149 | 0.000180994 | TAL1 | 0.041161414 | -0.971844888 | 0.833 | 1 | 1 |
| CRTAP2 | 1.04E-07 | -0.551369727 | 0.167 | 1 | 0.000208438 | HIST1H1C2 | 0.041285314 | 0.414339491 | 0.375 | 0.965 | 1 |
| PGAM1 | 1.13E-07 | 0.852384709 | 0.292 | 0.193 | 0.000225548 | LAT4 | 0.041639374 | -0.328047049 | 0.375 | 0.439 | 1 |
| MYC2 | 1.14E-07 | 0.40118891 | 0.125 | 0.965 | 0.000227072 | FTL | 0.041672956 | -0.411800478 | 0.542 | 0.991 | 1 |
| FDPS | 1.25E-07 | -0.32176407 | 0.125 | 0.956 | 0.00286477 | TNFSF13B | 0.04286477 | -0.331121581 | 1 | 1 | 1 |
| LGALS13 | 1.50E-07 | -0.495920817 | 0.125 | 0.167 | 0.000299343 | SLC25A371 | 0.043604336 | -0.344048828 | 0.083 | 0.395 | 1 |
| BANK11 | 1.81E-07 | 0.293038549 | 0.167 | 1 | 0.000361839 | ENDOD1 | 0.047810619 | -0.257090488 | 0.042 | 0.386 | 1 |
| PDIA4 | 1.84E-07 | 0.410442193 | 0.083 | 0.175 | 0.000367727 | GAPDH1 | 0.04891323 | -0.818487935 | 0.542 | 0.982 | 1 |
| S100A12 | 1.98E-07 | -0.386311513 | 0.083 | 0.886 | 0.000395545 | P2RX11 | 0.049618838 | 0.278104495 | 1 | 0.816 | 1 |
| ABLIM3 | 2.03E-07 | 0.587854929 | 0.458 | 0.202 | 0.000406178 | CAVIN2 | 0.056191264 | -0.308572965 | 0.292 | 0.43 | 1 |
| PKIG | 2.19E-07 | -0.273313574 | 0.167 | 0.974 | 0.00043743 | CENPU | 0.061018826 | 0.318733609 | 1 | 0.93 | 1 |
| MYEOV | 2.25E-07 | 0.284216994 | 0.125 | 0.904 | 0.000449111 | SNAP231 | 0.067389041 | -0.257276851 | 0 | 0.167 | 1 |
| CKLF | 2.27E-07 | 0.273829333 | 0.083 | 0.912 | 0.000454475 | ACTB4 | 0.067468883 | -0.706433218 | 0.708 | 0.825 | 1 |
| TCF73 | 2.76E-07 | 0.396734884 | 0.167 | 1 | 0.00055187 | SAT14 | 0.07092587 | 0.270469327 | 1 | 0.991 | 1 |
| CASP11 | 2.93E-07 | 0.378933487 | 0.167 | 1 | 0.000585885 | TFPI | 0.073598714 | 0.297296382 | 0.958 | 0.921 | 1 |
| PROS1 | 2.93E-07 | 0.638369434 | 0.458 | 0.211 | 0.000586019 | TRBV7-25 | 0.077453626 | -0.451521523 | 0.167 | 0.412 | 1 |
| GATA2 | 3.61E-07 | -0.414449794 | 0.167 | 0.965 | 0.000721508 | FRMD3 | 0.077659308 | -0.286356779 | 0 | 0.298 | 1 |
| DAAM11 | 3.74E-07 | -0.331527188 | 0.083 | 0.184 | 0.000747672 | GP9 | 0.091054837 | -0.902578334 | 0.25 | 0.456 | 1 |
| SOCS2 | 3.85E-07 | -0.282950037 | 0 | 0.149 | 0.000769648 | CD743 | 0.096693624 | -0.309226036 | 0.917 | 0.965 | 1 |
| IGFBP21 | 4.02E-07 | -0.652412715 | 0.125 | 0.167 | 0.000804892 | GRAP22 | 0.102539529 | 0.684590926 | 0.417 | 0.991 | 1 |
| LYZ3 | 4.54E-07 | 0.660987487 | 0.125 | 0.193 | 0.000908192 | RPLP01 | 0.108771936 | 0.299257202 | 0.875 | 0.728 | 1 |
| ANXA21 | 4.71E-07 | 0.640304628 | 0.167 | 0.991 | 0.000941242 | PPP1R14A | 0.111191146 | 0.984345266 | 0.417 | 1 | 1 |
| FCMR3 | 4.85E-07 | 0.378877373 | 0.167 | 0.991 | 0.000969296 | TMEM140 | 0.113587283 | -0.287565819 | 0.458 | 0.991 | 1 |
| CCT3 | 4.99E-07 | 0.368952276 | 0.167 | 0.991 | 0.000998155 | ITGB51 | 0.124108275 | 0.301231354 | 0.375 | 0.544 | 1 |
| FBL1 | 4.99E-07 | 0.312244789 | 0.167 | 0.991 | 0.000998155 | LYL11 | 0.128146343 | -0.357628113 | 0.458 | 0.956 | 1 |
| ATP5MC3 | 5.14E-07 | 0.37212833 | 0.125 | 0.202 | 0.001027842 | MPIG6B | 0.140338151 | -0.591524717 | 0.208 | 0.719 | 1 |
| AL157895.1 | 5.50E-07 | -0.288421453 | 0.167 | 0.965 | 0.001099141 | AC012507.4 | 0.145237779 | -0.261137255 | 0.958 | 0.956 | 1 |
| SMIM1 | 5.55E-07 | -0.539708471 | 0 | 0.158 | 0.00111 | TRAPPC3L | 0.153996731 | -0.39433463 | 0.042 | 0.377 | 1 |
| CORO1A2 | 6.62E-07 | 0.41350573 | 0.333 | 0.228 | 0.001323023 | CST74 | 0.168972719 | 0.856950221 | 0.417 | 0.64 | 1 |
| AC074327.1 | 7.16E-07 | -0.499799034 | 0.083 | 0.167 | 0.001432041 | 12-Sep | 0.187343612 | -1.160867359 | 0.167 | 0.439 | 1 |
| AC007952.42 | 8.66E-07 | 0.308548338 | 0.167 | 0.982 | 0.001732861 | CYTOR1 | 0.196660368 | 0.372416144 | 0.292 | 0.807 | 1 |
| MT1X1 | 9.00E-07 | -0.686274585 | 0.042 | 0.184 | 0.001799087 | RAB37 | 0.201127455 | -0.98812758 | 0.167 | 0.447 | 1 |
| PA2G42 | 1.01E-06 | 0.517822627 | 0.208 | 0.228 | 0.002010748 | PGRMC1 | 0.201245806 | -0.468389266 | 0.5 | 0.86 | 1 |
| PIM21 | 1.44E-06 | 0.250420873 | 0.125 | 0.211 | 0.002875903 | TSPAN13 | 0.208619684 | 0.318266704 | 0.708 | 0.658 | 1 |
| CD2 | 1.58E-06 | 0.367930803 | 0.167 | 0.211 | 0.003153618 | STAT16 | 0.208680102 | -0.444207072 | 0.167 | 0.675 | 1 |
| PRDX12 | 1.62E-06 | 0.266595923 | 0.167 | 0.974 | 0.003237166 | ARHGAP6 | 0.216880102 | 0.304181337 | 0.167 | 0.5 | 1 |
| FRMD4B | 1.67E-06 | -1.322815176 | 0.208 | 1 | 0.003346599 | GRHL1 | 0.228088413 | -0.579131463 | 0.583 | 0.877 | 1 |
| ZFP361 | 1.71E-06 | 0.276299743 | 0.167 | 0.965 | 0.003423886 | TMSB101 | 0.230654349 | 0.824032288 | 0.417 | 0.974 | 1 |
| AIF12 | 2.02E-06 | 0.346081868 | 0.167 | 0.965 | 0.00404822 | TUBA4A1 | 0.236838218 | 1.042447895 | 0.458 | 1 | 1 |
| ATP2B1-AS14 | 2.25E-06 | 0.318048495 | 0.125 | 0.921 | 0.004498448 | AP003068.2 | 0.243782467 | -0.349510261 | 0.917 | 0.807 | 1 |
| MYDGF1 | 2.82E-06 | 0.389576892 | 0.167 | 0.965 | 0.005640561 | STMN11 | 0.26956253 | -0.571386523 | 0.542 | 0.614 | 1 |
| HIST1H2AE | 2.85E-06 | -0.36189946 | 0.083 | 1 | 0.005693215 | GSN2 | 0.275798328 | 0.279704104 | 0.083 | 1 | 1 |
| CXCL16 | 2.91E-06 | -0.403702723 | 0.208 | 0.202 | 0.005826329 | AP003068.2 | 0.282012209 | -0.41247917 | 0.667 | 0.991 | 1 |
| CDK62 | 4.37E-06 | -0.273969277 | 0 | 1 | 0.008740153 | PRKAR2B | 0.282027593 | -0.276992617 | 0.708 | 1 | 1 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| PEAR1 | 4.43E-06 | -0.412709923 | 0.208 | 0.956 | 0.00855890 | H2AFZ1 | 0.286806464 | -0.38922078 | 0.375 | 0.579 | 1 |
| GATA1 | 5.17E-06 | -0.6155416 | 0.208 | 0.939 | 0.010342291 | CA2 | 0.306083013 | -0.49974771 | 0.375 | 0.553 | 1 |
| DECR1 | 5.29E-06 | 0.477726482 | 0.208 | 0.254 | 0.01057182 | GUCY1B1 | 0.322748519 | -0.579012601 | 0.625 | 0.982 | 1 |
| HSPA81 | 5.88E-06 | 0.613393931 | 0.208 | 1 | 0.011762741 | S100A61 | 0.337882708 | 0.656621038 | 0.375 | 0.86 | 1 |
| BMP6 | 5.91E-06 | -0.316303014 | 0.208 | 0.965 | 0.011820748 | ODC11 | 0.361342328 | -0.3084266 | 0.875 | 0.991 | 1 |
| PSME22 | 6.20E-06 | 0.339345426 | 0.208 | 1 | 0.01240534 | HMGN2 | 0.364000091 | 0.345450091 | 0.375 | 0.851 | 1 |
| TRBC22 | 6.72E-06 | 0.665228154 | 0.208 | 1 | 0.01343259 | MT-ATP6 | 0.376307788 | -0.774969576 | 1 | 1 | 1 |
| FHL2 | 6.78E-06 | -0.275418756 | 0.083 | 0.202 | 0.013562491 | RGS18 | 0.385455767 | 0.256992074 | 0.792 | 0.877 | 1 |
| MDK | 6.98E-06 | -0.408495383 | 0.042 | 0.211 | 0.013953513 | SUB12 | 0.391450623 | 0.373839886 | 0.458 | 0.965 | 1 |
| C1orf211 | 7.12E-06 | 0.30078683 | 0.125 | 0.895 | 0.014234049 | SPINT21 | 0.394571311 | -0.264527119 | 0.583 | 0.649 | 1 |
| AL138963.38 | 8.29E-06 | 0.437962672 | 0.208 | 0.991 | 0.016584982 | TPST21 | 0.426588386 | -0.269520749 | 0.542 | 0.605 | 1 |
| SAMD14 | 8.67E-06 | -0.747951861 | 0.125 | 0.202 | 0.017330238 | PDLIMI | 0.436563449 | -0.299506088 | 0.792 | 0.974 | 1 |
| IL7R6 | 8.74E-06 | 0.429812665 | 0.208 | 0.991 | 0.017477198 | SLC40A11 | 0.466920268 | -0.560968773 | 0.708 | 1 | 1 |
| FGFBP24 | 1.01E-05 | 0.392291413 | 0.125 | 0.886 | 0.020150947 | SMIM31 | 0.47034496 | -0.533034703 | 0.625 | 0.781 | 1 |
| NDUFAB12 | 1.05E-05 | 0.359056632 | 0.208 | 0.991 | 0.020975149 | AL731557.1 | 0.475560224 | -0.721550808 | 0.708 | 0.991 | 1 |
| SHMT2 | 1.08E-05 | 0.287455805 | 0.208 | 0.991 | 0.021526396 | CUX11 | 0.490815309 | -0.4964296 | 0.208 | 0.649 | 1 |
| PRDX22 | 1.13E-05 | 0.272566055 | 0.208 | 0.991 | 0.022670667 | CKB1 | 0.500618884 | -0.46766959 | 0 | 0.447 | 1 |
| TSPAN9 | 1.17E-05 | 0.30048198 | 0.292 | 0.272 | 0.02343862 | PKHD1L1 | 0.500778795 | -0.356961063 | 0.125 | 0.491 | 1 |
| NR4A23 | 1.71E-05 | 0.279722047 | 0.208 | 0.982 | 0.034159409 | MGLL | 0.520099577 | -0.669768773 | 0.792 | 1 | 1 |
| TRBC13 | 1.75E-05 | 0.518874221 | 0.208 | 0.982 | 0.035036948 | GABARAP | 0.572317399 | -0.372636834 | 0.583 | 0.64 | 1 |
| VWF | 2.12E-05 | 0.317817997 | 0.208 | 0.956 | 0.042332899 | MT-CYB | 0.576217543 | -0.41889758 | 1 | 1 | 1 |
| GPI1 | 2.80E-05 | -0.252712029 | 0.125 | 0.246 | 0.055931704 | GUCY1A1 | 0.586788825 | -0.322101152 | 0.167 | 0.605 | 1 |
| PGD1 | 3.17E-05 | 0.377573883 | 0.542 | 0.307 | 0.063473534 | CANX1 | 0.590789051 | -0.253776203 | 0.042 | 0.482 | 1 |
| HIST1H1E1 | 3.35E-05 | 0.251526438 | 0.208 | 0.965 | 0.067038253 | LINC00989 | 0.591597396 | 0.292562824 | 0.625 | 0.939 | 1 |
| YWHAQ3 | 3.93E-05 | 0.552218708 | 0.375 | 0.307 | 0.078564489 | LIPA1 | 0.599365236 | 0.619750483 | 0.583 | 0.982 | 1 |
| CTSW5 | 4.31E-05 | 0.449058585 | 0.292 | 0.281 | 0.08613531 | LGALS3 | 0.602609904 | -0.603462332 | 0.083 | 0.5 | 1 |
| TNFSF4 | 4.88E-05 | -0.437997514 | 0.25 | 0.965 | 0.097693328 | IFI63 | 0.650557976 | -1.296320548 | 0.125 | 0.482 | 1 |
| PLEK2 | 5.04E-05 | 0.754869835 | 0.583 | 0.412 | 0.10086127 | NDUFB62 | 0.650636423 | 0.288453332 | 0.167 | 0.632 | 1 |
| CTDSPL | 5.40E-05 | -0.287195784 | 0.25 | 0.965 | 0.108050272 | AC147651.1 | 0.6531125409 | -0.383914416 | 0.708 | 0.991 | 1 |
| IF27L1 | 5.61E-05 | -0.289665313 | 0.042 | 0.246 | 0.112279964 | LTBP1 | 0.657046283 | 0.291838817 | 0.542 | 0.939 | 1 |
| SLBP | 6.46E-05 | -0.331874981 | 0.25 | 0.965 | 0.129120383 | ABCC3 | 0.687912389 | -0.504476293 | 0.708 | 0.974 | 1 |
| CTTN | 7.17E-05 | 0.470508275 | 0.5 | 0.342 | 0.143345736 | RHOBTB1 | 0.701733744 | -0.899706683 | 0.125 | 0.509 | 1 |
| CD822 | 8.20E-05 | -0.533534086 | 0.292 | 0.991 | 0.163993325 | NT5C3A | 0.704494146 | -0.405997128 | 0.167 | 0.781 | 1 |
| PARD3 | 8.40E-05 | -0.502008647 | 0.208 | 0.904 | 0.167952552 | STOM | 0.708649572 | -0.613135051 | 0.5 | 0.658 | 1 |
| MEF2C1 | 8.67E-05 | 0.412231932 | 0.25 | 0.298 | 0.173494792 | ESAM | 0.717029108 | -0.354684608 | 0.708 | 0.605 | 1 |
| LCK2 | 9.19E-05 | 0.366678803 | 0.25 | 1 | 0.18372373 | ENO12 | 0.721268675 | -0.308379396 | 0.125 | 0.798 | 1 |
| TBXA2R | 9.51E-05 | -0.741031991 | 0.292 | 0.974 | 0.190248162 | EGFL7 | 0.725064672 | -0.8255766 | 0.583 | 0.588 | 1 |
| TRBV7-4 | 9.89E-05 | 0.418110592 | 0.25 | 0.289 | 0.197740863 | MAP3K7CL | 0.738203037 | -0.737250585 | 0.167 | 0.658 | 1 |
| PPIA1 | 0.000100117 | 0.478011043 | 0.25 | 0.123 | 0.200234905 | MIR4435-2HG1 | 0.750833404 | -0.291718813 | 0.833 | 0.982 | 1 |
| AP001189.3 | 0.000126894 | 0.600976049 | 0.625 | 0.404 | 0.253787899 | PTGS1 | 0.780970303 | -0.380617825 | 0.417 | 0.649 | 1 |
| GNG8 | 0.000132422 | -0.2795878 | 0.042 | 0.263 | 0.264843002 | IFI274 | 0.789066051 | -1.839934539 | 0 | 0.991 | 1 |
| NOSIP4 | 0.000137937 | 0.503214158 | 0.333 | 0.316 | 0.275875371 | SEPT111 | 0.824180438 | -0.847494014 | 0.208 | 0.518 | 1 |
| TUBB2A1 | 0.0001446085 | 0.662315812 | 0.708 | 0.447 | 0.292169546 | CLEC1B | 0.892703178 | -0.32471463 | 0.458 | 0.561 | 1 |
| GP6 | 0.000161873 | 0.462886284 | 0.417 | 0.342 | 0.323745681 | STX11 | 0.894945592 | 0.539705448 | 0.5 | 0.658 | 1 |
| MT-ND4L1 | 0.000197903 | -0.659443405 | 0.083 | 0.228 | 0.395806178 | DYNLL11 | 0.894949698 | -0.608350708 | 0.958 | 0.868 | 1 |
| RAB27B | 0.000210131 | -0.40258653 | 0.25 | 0.947 | 0.42026281 | SOD2 | 0.899399239 | -0.517229833 | 0.542 | 0.991 | 1 |
| E2F1 | 0.000220784 | | | | 0.441568851 | CST31 | 0.988795283 | -0.250209938 | 0.792 | 0.614 | 1 |
| ASAP1 | 0.000243188 | | | | 0.486376136 | | | | | 0.798 | |

Seurat Cluster 14

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| CENPK | 3.30E-11 | -0.335334987 | 0 | 1 | 6.59E-08 | TXN | 0.000589074 | -0.439952401 | 0 | 0.223 | 1 |
| RAN | 3.30E-11 | -0.388308181 | 0 | 1 | 6.59E-08 | CXCL83 | 0.000596703 | -1.069740771 | 0 | 0.241 | 1 |
| HNRNPF | 3.30E-11 | -0.427594735 | 0 | 1 | 6.59E-08 | IFITM23 | 0.000630966 | -0.318713763 | 0.118 | 0.259 | 1 |
| CD76 | 3.30E-11 | -0.546318533 | 0 | 1 | 6.59E-08 | IDH24 | 0.000679778 | 0.539984944 | 0.059 | 0.259 | 1 |
| SLC9A3R13 | 4.87E-11 | -0.336691867 | 0 | 0.991 | 9.74E-08 | NPC21 | 0.00070897 | 0.264091614 | 0.235 | 0.955 | 1 |
| CCT6A1 | 7.31E-11 | -0.266528847 | 0 | 0.991 | 1.46E-07 | GNAI2 | 0.000715242 | -0.292365925 | 0.059 | 0.259 | 1 |
| NOSIP5 | 7.31E-11 | -0.322053311 | 0 | 0.991 | 1.46E-07 | FKBP111 | 0.000729144 | -0.333834877 | 0 | 0.732 | 1 |
| GBP53 | 1.60E-10 | -0.262887845 | 0 | 0.982 | 3.20E-07 | H1F01 | 0.000734707 | -0.352411952 | 0 | 0.232 | 1 |
| PSMD81 | 1.60E-10 | -0.594820207 | 0 | 0.982 | 3.20E-07 | NCF11 | 0.000738592 | -0.571478547 | 0.294 | 0.964 | 1 |
| TUBB4B2 | 1.60E-10 | -0.848030097 | 0 | 0.982 | 3.20E-07 | NR4A24 | 0.000794413 | -0.48276205 | 0.176 | 0.884 | 1 |
| GRAP23 | 1.04E-09 | -0.507547594 | 0 | 0.946 | 2.07E-06 | SULF2 | 0.000815909 | 0.644493709 | 0.235 | 0.973 | 1 |
| PGAM11 | 3.19E-09 | -0.429156728 | 0 | 0.946 | 6.37E-06 | LILRB11 | 0.0008.36655 | 0.398219447 | 0.235 | 0.964 | 1 |
| C1orf1621 | 3.21E-09 | -0.538080124 | 0 | 1 | 6.42E-06 | PPIF | 0.000856019 | -1.131697938 | 0 | 0.188 | 1 |
| LTB5 | 4.69E-09 | -0.448367807 | 0.059 | 1 | 9.38E-06 | ANPEP | 0.000890805 | -0.720505804 | 0 | 0.214 | 1 |
| HLA-DQA21 | 4.89E-09 | 0.626015114 | 0.059 | 1 | 9.78E-06 | SYNGR21 | 0.000900504 | -0.596848791 | 0.176 | 0.884 | 1 |
| FCMR4 | 4.89E-09 | 0.534462276 | 0.059 | 1 | 9.78E-06 | BZW2 | 0.000906735 | -0.378056269 | 0 | 0.732 | 1 |
| NFE21 | 4.89E-09 | 0.4758734 | 0.059 | 1 | 9.78E-06 | CD141 | 0.000929651 | -0.342808457 | 0.059 | 0.241 | 1 |
| MRPS33 | 4.89E-09 | 0.365105614 | 0.059 | 1 | 9.78E-06 | Z93241.14 | 0.000991013 | 0.282322863 | 0.059 | 0.795 | 1 |
| PRMT12 | 4.89E-09 | 0.258713439 | 0.059 | 1 | 9.78E-06 | MAP3K7CL1 | 0.001015862 | 0.384725082 | 0.059 | 0.795 | 1 |
| CNN21 | 6.51E-09 | -0.556473474 | 0 | 0.938 | 1.30E-05 | CD823 | 0.00112319 | -1.00634194 | 0 | 0.241 | 1 |
| JPT11 | 7.12E-09 | -0.430323975 | 0 | 0.991 | 1.42E-05 | KCNK6 | 0.001264199 | 0.251805162 | 0.118 | 0.83 | 1 |
| PEA151 | 9.50E-09 | 0.341164213 | 0 | 0.991 | 1.90E-05 | SOD21 | 0.001288739 | -0.879291689 | 0.059 | 0.25 | 1 |
| IMPDH2 | 1.29E-08 | 0.424516864 | 0.059 | 0.973 | 2.58E-05 | FES1 | 0.001356456 | -0.476506639 | 0.059 | 0.259 | 1 |
| HIST1H1C3 | 1.29E-08 | 0.335171237 | 0.059 | 0.973 | 2.58E-05 | UBE2J12 | 0.001362578 | -0.262940859 | 0.059 | 0.268 | 1 |
| CD3D7 | 1.49E-08 | -0.346911539 | 0.059 | 0.982 | 2.98E-05 | TALDO1 | 0.001392977 | -0.907302804 | 0 | 0.259 | 1 |
| ZNF703 | 1.77E-08 | 0.451866896 | 0.059 | 0.964 | 3.54E-05 | LMNA5 | 0.001392977 | -1.461941848 | 0 | 0.259 | 1 |
| NREP | 1.77E-08 | 0.434964756 | 0.059 | 0.964 | 3.54E-05 | GD1632 | 0.001654301 | -1.029150187 | 0 | 0.223 | 1 |
| MRPS26 | 1.80E-08 | 0.704736364 | 0.059 | 0.973 | 3.60E-05 | PSME23 | 0.001656805 | 0.916756778 | 0.176 | 0.893 | 1 |
| AC064805.1 | 1.82E-08 | 0.610238159 | 0.059 | 0.982 | 3.65E-05 | BOP1 | 0.001703818 | -0.341362784 | 0 | 0.259 | 1 |
| MT-CO1 | 2.42E-08 | 0.649962437 | 0.059 | 0.955 | 4.84E-05 | SMIM25 | 0.001758216 | 0.797376202 | 0.235 | 0.946 | 1 |
| PDCD51 | 3.43E-08 | 0.759165685 | 1 | 1 | 6.86E-05 | HLA-DPA13 | 0.001912348 | 0.431463483 | 0.235 | 0.946 | 1 |
| RACGAP11 | 3.46E-08 | 0.471523986 | 0.059 | 0.973 | 6.92E-05 | CEBPD | 0.002038468 | -0.632802242 | 0.059 | 0.268 | 1 |
| PSMB22 | 3.57E-08 | 0.441014993 | 0.059 | 0.973 | 6.92E-05 | BID1 | 0.002086755 | -0.776115382 | 0 | 0.268 | 1 |
| CD1C | 4.48E-08 | -0.457677464 | 0 | 0.902 | 7.14E-05 | MAFF1 | 0.002086755 | -1.00138825 | 0 | 0.268 | 1 |
| LAT5 | 5.10E-08 | 0.52354735 | 0.059 | 0.938 | 8.96E-05 | PPBP5 | 0.00218518 | -0.839373645 | 0 | 0.116 | 1 |
| SLBP1 | 5.10E-08 | -0.387959426 | 0 | 0.911 | 0.000102071 | ISG153 | 0.002186491 | -0.474330773 | 0.059 | 0.768 | 1 |
| WDFY4 | 6.24E-08 | -0.599698477 | 0 | 0.911 | 0.000102071 | MT2A8 | 0.002216408 | -1.169375894 | 0.118 | 0.277 | 1 |
| ADSL | 9.87E-08 | 0.293195412 | 0.059 | 0.964 | 0.000124803 | AC020916.11 | 0.00244662 | -0.508856291 | 0 | 0.143 | 1 |
| GTSE1 | 1.10E-07 | -0.338815039 | 0 | 0.902 | 0.000197335 | ABCA1 | 0.002523386 | -0.634670366 | 0.235 | 0.259 | 1 |
| DHRS9 | 1.10E-07 | 0.26883799 | 0.059 | 0.911 | 0.00021923 | CPPED11 | 0.002705083 | 0.484944835 | 0.176 | 0.875 | 1 |
| BCL11A | 1.10E-07 | 0.26851582 | 0.059 | 0.911 | 0.00021923 | CCT21 | 0.002705083 | 0.4715541518 | 0.176 | 0.875 | 1 |
| IGHV4-4 | 1.15E-07 | 0.263263459 | 0.059 | 0.911 | 0.00021923 | ADA21 | 0.002966804 | 0.457664298 | 0.235 | 0.938 | 1 |
| BANF11 | 1.20E-07 | 0.441339193 | 0.059 | 0.929 | 0.000229832 | FGL2 | 0.002969937 | 0.569423435 | 0.294 | 1 | 1 |
| ILK3 | 1.20E-07 | 0.422046298 | 0.059 | 0.955 | 0.000240259 | MEF2C2 | 0.003243498 | 0.692317165 | 0.176 | 0.875 | 1 |
| NFKBID1 | 1.69E-07 | -0.326313291 | 0 | 0.946 | 0.00033797 | BHLHE402 | 0.003250798 | 0.499090642 | 0.294 | 1 | 1 |
| PPA1 | 1.70E-07 | -0.384337703 | 0 | 1 | 0.00033958 | SMIM14 | 0.003382489 | -0.442610943 | 0.059 | 0.295 | 1 |
| PHTF1 | 1.88E-07 | -0.405818108 | 0.118 | 0.893 | 0.000376345 | STX111 | 0.003688709 | 0.475262891 | 0.059 | 0.259 | 1 |
| STEAP4 | 1.88E-07 | -0.424103029 | 0 | 0.893 | 0.000376345 | CASP12 | 0.003703173 | -0.338034879 | 0.294 | 0.991 | 1 |
| MAL1 | 2.01E-07 | 0.379761559 | 0.059 | 0.902 | 0.000402555 | CPVL1 | 0.00415237 | 0.480020754 | 0.059 | 0.857 | 1 |
| CDKN1C1 | 2.17E-07 | 0.444341908 | 0.059 | 0.938 | 0.000434621 | MS4A7 | 0.004230012 | 0.328401498 | 0.176 | 0.92 | 1 |
| | 2.50E-07 | 0.303242835 | 0.059 | 0.884 | 0.000500622 | | 0.004334565 | 0.570489722 | 0.235 | | |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| FCER21 | 2.60E-07 | 0.526379844 | 0.059 | 0.884 | 0.00051968 | DUSP22 | 0.004502981 | -1.178063904 | 0 | 0.714 | 1 |
| CDK63 | 2.94E-07 | 0.400981283 | 0.059 | 0.938 | 0.000588766 | CYBB | 0.004948548 | -0.513168433 | 0.353 | 0.982 | 1 |
| PSMA41 | 3.32E-07 | 0.305068299 | 0.118 | 1 | 0.000664163 | PHACTR12 | 0.005843825 | -0.657699868 | 0.059 | 0.304 | 1 |
| CFD2 | 3.43E-07 | -0.363167415 | 0.059 | 0.938 | 0.000685964 | MTHFD21 | 0.00603334 | 0.371546777 | 0.118 | 0.795 | 1 |
| ELL23 | 3.54E-07 | -0.327150227 | 0 | 0.116 | 0.000708036 | EPST114 | 0.006487062 | -0.421728443 | 0 | 0.295 | 1 |
| ASGR21 | 3.54E-07 | -0.329371241 | 0 | 0.116 | 0.000708036 | HMGA12 | 0.006487062 | -0.488785135 | 0 | 0.295 | 1 |
| CCT82 | 3.57E-07 | 0.439131508 | 0.118 | 1 | 0.000714885 | IRAK3 | 0.006497246 | -0.293220229 | 0.059 | 0.312 | 1 |
| SNX10 | 3.57E-07 | 0.251025347 | 0.118 | 1 | 0.000714885 | TNF6 | 0.006776633 | -0.314355115 | 0 | 0.134 | 1 |
| MGST2 | 3.65E-07 | 0.267337806 | 0.059 | 0.893 | 0.00073027 | CDH23 | 0.006951187 | 0.763956969 | 0.294 | 0.991 | 1 |
| FBL2 | 3.71E-07 | 0.448144151 | 0.118 | 1 | 0.000741629 | PHF19 | 0.00786973 | -0.263492356 | 0 | 0.179 | 1 |
| CYB5D23 | 3.97E-07 | 0.341614143 | 0.059 | 0.938 | 0.000794478 | HRH2 | 0.008206616 | 0.289755393 | 0.294 | 0.955 | 1 |
| TUBA4A2 | 3.99E-07 | 0.417761749 | 0.118 | 1 | 0.000798042 | RNF1301 | 0.008337939 | -0.446995898 | 0.059 | 0.696 | 1 |
| RETN2 | 4.51E-07 | 0.485149667 | 0.118 | 0.991 | 0.000902864 | AC023157.3 | 0.008360944 | -0.290292369 | 0 | 0.42 | 1 |
| BATF3 | 4.54E-07 | 0.271833315 | 0.059 | 0.866 | 0.000907776 | P2RY131 | 0.009609932 | -0.416322084 | 0 | 0.438 | 1 |
| MT-CO2 | 4.55E-07 | 0.717253073 | 1 | 0.991 | 0.000909101 | COTL12 | 0.011125553 | 0.530556389 | 0.353 | 0.438 | 1 |
| C15orf39 | 4.62E-07 | 0.571244878 | 0.118 | 0.982 | 0.000923547 | IL1B1 | 0.011827522 | -1.655955644 | 0 | 0.214 | 1 |
| MT-CO3 | 5.45E-07 | 0.577882579 | 1 | 1 | 0.001090001 | NFKBIA3 | 0.012984574 | -0.910676451 | 0.118 | 0.75 | 1 |
| BST1 | 6.17E-07 | 0.293282337 | 0.118 | 0.991 | 0.001234088 | CTSA2 | 0.01301789 | -0.766510799 | 0 | 0.286 | 1 |
| RHOC3 | 6.57E-07 | 0.421332283 | 0.118 | 0.982 | 0.001314072 | FOSB4 | 0.01381208 | -0.320719533 | 0.353 | 0.973 | 1 |
| TOR3A1 | 6.57E-07 | -0.344670968 | 0 | 0.125 | 0.001314072 | TIMP13 | 0.014036851 | -0.430883899 | 0.118 | 0.348 | 1 |
| ANXA62 | 6.57E-07 | -0.579425813 | 0 | 0.875 | 0.001314072 | VNN3 | 0.014198758 | -0.327456877 | 0 | 0.375 | 1 |
| IL328 | 6.87E-07 | 0.548740224 | 0.118 | 0.991 | 0.001374729 | S100A62 | 0.014357759 | -0.551756913 | 0.353 | 0.911 | 1 |
| DNMT12 | 6.98E-07 | -0.405504195 | 0.059 | 0.911 | 0.001395694 | MT-ATP83 | 0.016453092 | 0.615230269 | 0.824 | 0.839 | 1 |
| FBP1 | 7.09E-07 | 0.304037465 | 0.059 | 0.929 | 0.001418836 | AHR1 | 0.01700331 | -0.321650196 | 0.118 | 0.357 | 1 |
| CIITA | 7.49E-07 | 0.268406842 | 0.118 | 0.982 | 0.001497208 | HSPA56 | 0.017953317 | -1.457722451 | 0 | 0.321 | 1 |
| XBP1 | 7.65E-07 | -0.565071223 | 0.118 | 0.973 | 0.00153075 | MAFB | 0.018353092 | -0.519379125 | 0.176 | 0.357 | 1 |
| SEC11C | 8.82E-07 | 0.568256899 | 0.059 | 0.884 | 0.001764407 | SOX43 | 0.018367944 | 0.584026983 | 0.235 | 0.875 | 1 |
| MIF2 | 9.82E-07 | 0.256520737 | 0.118 | 0.982 | 0.001963944 | HMGB11 | 0.018739329 | -0.354707179 | 0.353 | 0.911 | 1 |
| AC245014.32 | 9.82E-07 | -0.457230783 | 0.118 | 0.973 | 0.001963944 | IFI64 | 0.018967451 | -0.631255784 | 0.059 | 0.705 | 1 |
| NOP561 | 1.02E-06 | 0.343830137 | 0.118 | 0.982 | 0.002034737 | EREG2 | 0.020944082 | -1.388062796 | 0 | 0.312 | 1 |
| HIST1H1E2 | 1.13E-06 | -0.385022899 | 0.059 | 0.973 | 0.00226216 | GRN | 0.023084696 | -0.431212702 | 0.176 | 0.75 | 1 |
| GRASP3 | 1.20E-06 | -0.61306349 | 0 | 0.134 | 0.002405941 | TKT1 | 0.023746435 | -0.401290948 | 0.118 | 0.357 | 1 |
| PDE4B | 1.20E-06 | -0.811121899 | 0 | 0.866 | 0.002405941 | ICAM11 | 0.024571327 | -1.328675409 | 0 | 0.33 | 1 |
| TRBV181 | 1.33E-06 | 0.478843949 | 0.059 | 0.83 | 0.002657069 | CSF1R | 0.024691086 | 0.487944199 | 0.353 | 1 | 1 |
| TPPP3 | 1.38E-06 | 0.44526994 | 0.118 | 0.955 | 0.002768542 | DMXL21 | 0.024691086 | 0.439506802 | 0.353 | 0.446 | 1 |
| ABCC31 | 1.48E-06 | 0.595436137 | 0.118 | 0.955 | 0.002969097 | IFITM35 | 0.025526928 | -1.314872551 | 0.118 | 0.348 | 1 |
| ADM2 | 1.57E-06 | -0.633723343 | 0.118 | 0.116 | 0.003136683 | TNFAIP3 | 0.029028305 | 0.57340844 | 0.529 | 0.616 | 1 |
| UTY2 | 1.61E-06 | -0.581811312 | 0 | 0.134 | 0.00322241 | THBS1 | 0.032668257 | -0.705894865 | 0.059 | 0.357 | 1 |
| MARCKS1 | 1.61E-06 | -0.874661511 | 0 | 0.134 | 0.00322241 | SH3BGRL32 | 0.03278043 | -0.650286212 | 0.353 | 0.902 | 1 |
| STGLEC10 | 1.83E-06 | 0.26689331 | 0 | 0.964 | 0.00365721 | NCL2 | 0.03320688 | -0.87146298 | 0 | 0.339 | 1 |
| SEPT112 | 1.87E-06 | 0.676359176 | 0.118 | 0.955 | 0.003745516 | AC007952.43 | 0.038819487 | -0.299077354 | 0.118 | 0.732 | 1 |
| PSMA5 | 1.94E-06 | 0.659580969 | 0.118 | 0.955 | 0.003877283 | ANXA5 | 0.039111069 | -0.39110697 | 0.176 | 0.384 | 1 |
| SEC61B1 | 1.98E-06 | -0.522938972 | 0.118 | 0.955 | 0.003952232 | TMSB4X | 0.039627066 | -0.883674681 | 0.647 | 1 | 1 |
| NOLC1 | 2.17E-06 | -0.257801359 | 0 | 0.857 | 0.004345718 | PRKCD1 | 0.040865716 | 0.302384101 | 0.176 | 0.786 | 1 |
| IGLV2-231 | 2.23E-06 | 0.4552161 | 0.059 | 0.812 | 0.00445391 | TUBA1B2 | 0.041624718 | 1.015699716 | 0.353 | 0.991 | 1 |
| PRC1 | 2.82E-06 | -0.268229492 | 0 | 0.83 | 0.005635876 | MT-ND62 | 0.043101105 | 0.778805479 | 0.765 | 0.991 | 1 |
| UGCG | 2.88E-06 | 0.418865003 | 0.118 | 0.964 | 0.005759913 | PMAIP14 | 0.044318087 | -0.382496933 | 0 | 0.652 | 1 |
| FKBP23 | 2.88E-06 | 0.302400959 | 0.118 | 0.964 | 0.005759913 | S100A102 | 0.044318087 | -1.129778392 | 0.118 | 0.348 | 1 |
| EIF4A3 | 3.18E-06 | -0.293376851 | 0.059 | 0.902 | 0.006352566 | NEAT15 | 0.047599832 | 0.254093988 | 1 | 0.991 | 1 |
| LILRB41 | 4.73E-06 | 0.354268311 | 0.118 | 0.946 | 0.009464688 | GSN3 | 0.049006017 | 0.370352587 | 0.118 | 0.732 | 1 |
| THBD | 5.06E-06 | -0.731204566 | 0 | 0.143 | 0.01012526 | CTSL | 0.049103101 | -0.610077933 | 0 | 0.42 | 1 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| AC10359l.37 | 5.12E-06 | -0.52536135 | 0 | 0.152 | 0.010237209 | RXRA1 | 0.050693328 | 0.341736678 | 0.235 | 0.83 | 1 |
| TPI1 | 5.43E-06 | -0.463044253 | 0.059 | 0.893 | 0.010853923 | ACSL11 | 0.0509l012 | -1.251629361 | 0 | 0.348 | 1 |
| ANP32E1 | 5.45E-06 | 0.623058534 | 0.118 | 0.955 | 0.010893377 | HPRT11 | 0.051063662 | 0.373325926 | 0.059 | 0.661 | 1 |
| LSM4 | 6.14E-06 | 0.337298268 | 0 | 0.884 | 0.012279465 | NAAA3 | 0.051522705 | 0.543122026 | 0.235 | 0.446 | 1 |
| PRDX13 | 6.81E-06 | -0.364069934 | 0 | 0.839 | 0.001361386 | RASSF41 | 0.053263518 | 0.750640761 | 0.353 | 0.973 | 1 |
| GPR1831 | 6.81E-06 | -0.383808827 | 0 | 0.839 | 0.001361386 | MAP3K83 | 0.053977981 | -0.862536855 | 0.059 | 0.366 | 1 |
| CSTA1 | 6.81E-06 | -0.439976852 | 0 | 0.161 | 0.001361386 | IGSF61 | 0.054105488 | 0.827366066 | 0.294 | 0.902 | 1 |
| S100A121 | 6.81E-06 | -0.71787577 | 0 | 0.911 | 0.001361386 | TOB13 | 0.058415538 | -0.258644189 | 0 | 0.643 | 1 |
| NJNJ11 | 6.88E-06 | -0.562107018 | 0.118 | 0.911 | 0.013768875 | YWHAH | 0.058415538 | -0.48978562 | 0 | 0.357 | 1 |
| CD79B1 | 8.08E-06 | 0.322592219 | 0.118 | 0.946 | 0.016150144 | LAP3 | 0.059294954 | -0.250759172 | 0.059 | 0.67 | 1 |
| PILRA | 8.34E-06 | -0.480485867 | 0.176 | 0.982 | 0.01668383 | AHNAK4 | 0.059620244 | -0.574464547 | 0.588 | 1 | 1 |
| EMILIN21 | 9.55E-06 | -0.670903285 | 0.059 | 0.839 | 0.019104734 | MTRNR2L123 | 0.063511615 | 0.28750076 | 1 | 1 | 1 |
| CYC1 | 1.18E-05 | -0.285599671 | 0 | 0.17 | 0.023635926 | PLXNB21 | 0.074016077 | 0.538112341 | 0.353 | 0.938 | 1 |
| MIR181A1HG | 1.18E-05 | -0.578610125 | 0 | 0.17 | 0.023612572 | CALHM61 | 0.074906885 | 0.519416154 | 0.059 | 0.67 | 1 |
| MGLL1 | 1.43E-05 | -0.491986473 | 0 | 0.125 | 0.075184447 | F5 | 0.075184447 | -0.454527104 | 0.353 | 0.464 | 1 |
| ID11 | 1.43E-05 | -0.579925697 | 0 | 0.125 | 0.0286047 | CD68 | 0.080233589 | 0.313828807 | 0.118 | 0.705 | 1 |
| CHST15 | 1.49E-05 | 0.421054428 | 0.176 | 1 | 0.029801546 | JAML2 | 0.085975008 | 0.290796027 | 0.294 | 0.857 | 1 |
| LILRA51 | 1.52E-05 | -0.265865318 | 0.118 | 0.92 | 0.030455424 | CD834 | 0.091064677 | -0.417025425 | 0.118 | 0.696 | 1 |
| CREG1 | 1.53E-05 | -0.378826113 | 0 | 0.161 | 0.030506623 | IFNGR21 | 0.092289334 | -1.019160842 | 0.059 | 0.375 | 1 |
| CRTAP3 | 1.53E-05 | 0.370177955 | 0.176 | 0.991 | 0.030670335 | BCAT1 | 0.094682707 | 0.269751956 | 0.059 | 0.643 | 1 |
| ASGR1 | 1.59E-05 | 0.50346401 | 0.176 | 1 | 0.031745391 | PTGER21 | 0.097810947 | -0.806050695 | 0 | 0.625 | 1 |
| HLA-DQB12 | 1.74E-05 | 0.890639005 | 0.176 | 1 | 0.034889277 | HLA-DRA3 | 0.10243554 | 0.894248216 | 0.412 | 1 | 1 |
| CCT31 | 1.74E-05 | 0.777500832 | 0.176 | 1 | 0.034889277 | CD72I | 0.102701077 | -0.257170301 | 0 | 0.25 | 1 |
| PPT1 | 1.79E-05 | 0.425907919 | 0.176 | 0.991 | 0.035899622 | OASL4 | 0.1037l985 | -0.469691611 | 0 | 0.259 | 1 |
| MSLN1 | 1.80E-05 | 0.89174347 | 0.176 | 1 | 0.036001615 | ZNF385A | 0.108582061 | -0.554973259 | 0 | 0.321 | 1 |
| SLC7A71 | 1.81E-05 | -0.450422795 | 0 | 0.116 | 0.036123952 | PHLDA1 | 0.109679103 | -0.51338l551 | 0 | 0.589 | 1 |
| TXNDC111 | 2.02E-05 | -0.362921037 | 0 | 0.179 | 0.040406717 | SLC8A1 | 0.113000619 | 0.272626253 | 0.235 | 0.473 | 1 |
| MX14 | 2.02E-05 | -0.635962132 | 0 | 0.821 | 0.040406717 | FCER1G2 | 0.113100885 | 0.890393242 | 0.412 | 0.991 | 1 |
| ATP5F1A1 | 2.02E-05 | -0.670906126 | 0 | 0.179 | 0.040406717 | ANXA13 | 0.114592549 | -0.275094588 | 0.235 | 0.75 | 1 |
| GPBAR1 | 2.23E-05 | 0.826592242 | 0.176 | 0.991 | 0.044664374 | POU2F21 | 0.114693479 | 0.627106004 | 0.412 | 1 | 1 |
| EBNA1BP21 | 2.29E-05 | 0.450679675 | 0.059 | 0.866 | 0.045761563 | DDIT43 | 0.117666905 | -0.86385792 | 0.059 | 0.652 | 1 |
| CD931 | 2.31E-05 | 0.495097972 | 0.176 | 0.991 | 0.046199279 | CYP1B11 | 0.128160459 | -0.527402151 | 0 | 0.598 | 1 |
| FRMD4B1 | 2.44E-05 | 0.288437091 | 0.118 | 0.902 | 0.048782253 | PGRMC11 | 0.131701252 | -0.409455892 | 0 | 0.188 | 1 |
| CLU2 | 2.59E-05 | -0.705095964 | 0 | 0.17 | 0.051891976 | ACTB5 | 0.133487298 | -0.531220968 | 0.882 | 1 | 1 |
| HLA-DQA12 | 2.76E-05 | 0.613235006 | 0.176 | 0.982 | 0.055270705 | PSAP | 0.135280459 | 0.391032658 | 0.647 | 0.688 | 1 |
| LTBR | 3.03E-05 | 0.295989301 | 0.176 | 0.973 | 0.060595501 | ANKRD282 | 0.140471091 | -0.531412904 | 0.059 | 0.643 | 1 |
| CD79A2 | 3.21E-05 | 0.498311708 | 0.059 | 0.723 | 0.064172153 | TIPARP4 | 0.154084127 | -0.65877673 | 0.059 | 0.411 | 1 |
| MT1X2 | 3.31E-05 | -0.374345267 | 0 | 0.161 | 0.066159314 | FOS6 | 0.154473784 | -0.460524583 | 0.824 | 0.946 | 1 |
| MYOF | 3.32E-05 | 0.503016699 | 0.176 | 0.973 | 0.066405523 | HLA-DRB52 | 0.171152271 | 1.220309592 | 0.412 | 1 | 1 |
| CAPG1 | 3.54E-05 | 0.384706029 | 0.176 | 0.973 | 0.07078267 | ETS21 | 0.173103578 | -0.290028258 | 0.118 | 0.67 | 1 |
| SNRPD32 | 3.77E-05 | 0.460028143 | 0.176 | 0.982 | 0.075402932 | GLUL2 | 0.173166736 | -0.488228544 | 0.176 | 0.446 | 1 |
| HBEGF | 4.35E-05 | -0.615409l2v | 0 | 0.179 | 0.087088834 | KEF102 | 0.173958644 | -1.09078894 | 0 | 0.393 | 1 |
| GPBAR1 | 4.35E-05 | -0.446968149 | 0 | 0.661 | 0.094845454 | PGD2 | 0.184357395 | -0.664704083 | 0.118 | 0.429 | 1 |
| HERPUD14 | 5.56E-05 | -0.697696002 | 0.176 | 0.946 | 0.11128916 | NLRP31 | 0.196266569 | -0.397121047 | 0.235 | 0.732 | 1 |
| SRP9 | 5.68E-05 | -0.483927155 | 0 | 0.804 | 0.113648393 | TAGLN24 | 0.213626439 | -0.320182978 | 0.176 | 0.696 | 1 |
| ADA | 6.61E-05 | -0.460221622 | 0.059 | 0.848 | 0.132140458 | TCF7L2 | 0.226885085 | 0.507274676 | 0.353 | 0.875 | 1 |
| RHOB3 | 6.80E-05 | -0.260876514 | 0.059 | 0.848 | 0.136077706 | PLEC2 | 0.232285647 | -0.653022747 | 0.353 | 0.768 | 1 |
| CHMP1B2 | 7.05E-05 | -0.535849201 | 0 | 0.17 | 0.140969061 | ATF33 | 0.258846594 | -0.949805064 | 0.059 | 0.384 | 1 |
| ABRACL3 | 7.47E-05 | 0.365182787 | 0.176 | 0.964 | 0.14934467 | LYZ4 | 0.2697399 | -0.477862047 | 0.647 | 1 | 1 |
| CUX12 | 7.93E-05 | -0.270822549 | 0.235 | 1 | 0.158637967 | GAPDH2 | 0.281791263 | -0.863086102 | 0.235 | 0.661 | 1 |
| ODF3B1 | 8.89E-05 | -0.301104215 | 0.176 | 0.946 | 0.177773776 | HDAC1 | 0.286945073 | -0.294475632 | 0 | 0.393 | 1 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| PIK3AP11 | 9.34E-05 | -0.392353991 | 0 | 0.205 | 0.186804226 | SRPRB | 0.313967033 | 0.666377049 | 0.059 | 0.393 | 1 |
| CD1D | 9.86E-05 | -0.304905774 | 0.059 | 0.205 | 0.19719726 | HDAC9 | 0.323650002 | -0.31128032 | 0 | 0.25 | 1 |
| GADD45B3 | 9.95E-05 | -0.538865452 | 0.118 | 0.884 | 0.199018976 | MYADM3 | 0.337911712 | -0.799066655 | 0.176 | 0.643 | 1 |
| CLEC4E | 0.000109797 | -0.31849565 | 0 | 0.152 | 0.219594211 | SIGLEC11 | 0.341513589 | -1.099193395 | 0 | 0.152 | 1 |
| APOBEC3A2 | 0.000141259 | -0.846270401 | 0 | 0.161 | 0.282518782 | RBM47 | 0.341588865 | -0.466975188 | 0.176 | 0.661 | 1 |
| MTRNR2L81 | 0.000141334 | 0.618773174 | 0.471 | 0.312 | 0.282667843 | S100A44 | 0.341815067 | 0.50421806 | 0.471 | 0.929 | 1 |
| MT-CYB1 | 0.000141699 | 0.430252341 | 1 | 0.991 | 0.283397838 | ACTG13 | 0.345332985 | 0.457705244 | 0.412 | 0.884 | 1 |
| TTC381 | 0.000145389 | -0.310332809 | 0 | 0.554 | 0.290777965 | NR4A11 | 0.381905504 | 0.25811261 | 0.176 | 0.518 | 1 |
| SNRPG1 | 0.000151487 | -0.308444542 | 0 | 0.786 | 0.302974711 | P4HB | 0.393318681 | -0.632599006 | 0.118 | 0.473 | 1 |
| SPCS3 | 0.000151487 | -0.55191246 | 0 | 0.214 | 0.302974711 | AP2S12 | 0.406044533 | -0.674774373 | 0 | 0.5 | 1 |
| IRF7 | 0.000151487 | -0.727543214 | 0 | 0.214 | 0.302974711 | FPR2 | 0.409319111 | -0.359350105 | 0 | 0.152 | 1 |
| G0S22 | 0.000151487 | -1.008941457 | 0 | 0.214 | 0.302974711 | LILRA1 | 0.436917796 | -0.470651484 | 0.059 | 0.58 | 1 |
| PAK1 | 0.000152651 | -0.250237776 | 0.059 | 0.196 | 0.305301902 | CST32 | 0.445750396 | 0.27766785 | 0.529 | 0.982 | 1 |
| PLBD11 | 0.000164181 | -0.641225329 | 0.059 | 0.188 | 0.328361074 | FPR11 | 0.451217524 | 0.253285611 | 0.118 | 0.607 | 1 |
| RRBPI | 0.000175522 | 0.331002957 | 0.176 | 0.25 | 0.351044042 | RPS27L2 | 0.453802852 | 0.318648797 | 0 | 0.5 | 1 |
| CDA | 0.000188723 | 0.28841657 | 0.059 | 0.821 | 0.377445661 | BEX3 | 0.457383687 | -0.382502334 | 0.059 | 0.259 | 1 |
| CCR1 | 0.000190332 | 0.375938034 | 0.118 | 0.884 | 0.380664335 | TUBB2 | 0.470701438 | 0.417638492 | 0.118 | 0.473 | 1 |
| LIMS12 | 0.000190747 | -0.517442702 | 0.176 | 0.92 | 0.381493899 | TNFAIP35 | 0.492476252 | -1.300015885 | 0 | 0.58 | 1 |
| IFI275 | 0.000194389 | -1.144546213 | 0 | 0.116 | 0.388778018 | LRRC25 | 0.528343472 | 0.385208168 | 0.176 | 0.661 | 1 |
| METTL7A | 0.00019875 | 0.539360386 | 0.118 | 0.866 | 0.397500585 | LINC00937 | 0.565230918 | -0.539280383 | 0.118 | 0.473 | 1 |
| 3-Jun | 0.000202279 | -0.712648445 | 0.294 | 1 | 0.404558607 | SCIMP | 0.586704907 | 0.456250031 | 0.118 | 0.607 | 1 |
| IER32 | 0.00021791 | -0.585667811 | 0.059 | 0.223 | 0.435819772 | EGR14 | 0.593920722 | -0.530146026 | 0.059 | 0.571 | 1 |
| CD300E | 0.000218911 | -0.469866729 | 0.176 | 0.911 | 0.437822268 | ADGRE21 | 0.603665266 | -0.451384994 | 0.118 | 0.598 | 1 |
| KYNU | 0.00022884 | -0.286430656 | 0.059 | 0.223 | 0.457680861 | CLEC12A1 | 0.608631289 | 0.292551763 | 0 | 0.58 | 1 |
| HSP90B15 | 0.000242441 | -1.326777347 | 0 | 0.777 | 0.484882335 | SNX31 | 0.613129749 | -0.301944064 | 0.059 | 0.554 | 1 |
| HSPA82 | 0.000265429 | 0.354395825 | 0.235 | 1 | 0.530857537 | APLP2 | 0.613515425 | -0.326647813 | 0.235 | 0.554 | 1 |
| LGALS31 | 0.000279106 | -0.713536693 | 0.118 | 0.857 | 0.558211729 | MIR4435-2HG2 | 0.637825497 | -0.524230471 | 0 | 0.527 | 1 |
| EFHD23 | 0.000286069 | -0.717906586 | 0.059 | 0.232 | 0.572137032 | NKG75 | 0.638098586 | 0.929055735 | 0.118 | 0.607 | 1 |
| MT-ND4L2 | 0.000289913 | 0.705699511 | 1 | 1 | 0.579825815 | ZNF503 | 0.662491429 | -0.513530761 | 0 | 0.143 | 1 |
| AC015912.31 | 0.000294578 | -0.408440493 | 0.118 | 0.241 | 0.589156266 | PDLA61 | 0.680805543 | -0.328449086 | 0 | 0.464 | 1 |
| HLA-DMA2 | 0.000312037 | 0.54226303 | 0.235 | 1 | 0.624074281 | LILRB2 | 0.693990248 | 0.4578194409 | 0.529 | 1 | 1 |
| SGK13 | 0.000318558 | -0.284599815 | 0.059 | 0.241 | 0.637115821 | TMSB102 | 0.71469527 | -0.431654225 | 0.706 | 0.991 | 1 |
| SYK2 | 0.000329205 | -0.297873673 | 0.235 | 0.964 | 0.65840977 | CALM22 | 0.71969499 | -0.267626916 | 0.118 | 0.527 | 1 |
| SPN1 | 0.000347253 | 0.429997204 | 0.235 | 1 | 0.694506902 | ATP2B1-AS15 | 0.724820004 | -0.592354882 | 0 | 0.527 | 1 |
| CYP27A1 | 0.000380539 | -0.327487461 | 0 | 0.223 | 0.761077737 | JUND4 | 0.730185179 | -0.716221254 | 0.176 | 0.536 | 1 |
| DDX39A | 0.000382879 | -0.9315731361 | 0 | 0.232 | 0.765758092 | CSF3R1 | 0.735349322 | -1.077906245 | 0.059 | 0.545 | 1 |
| H1FX4 | 0.000382879 | -1.138857312 | 0 | 0.232 | 0.765758092 | LTA4H2 | 0.735489741 | -0.483758832 | 0.294 | 0.652 | 1 |
| MT-ATP61 | 0.000388818 | 0.491595107 | 1 | 0.973 | 0.777636438 | ALOX5AP2 | 0.751292741 | 0.390804942 | 0.294 | 0.643 | 1 |
| NAPSA | 0.000396505 | 0.917283601 | 1 | 1 | 0.793010394 | HLA-DRB16 | 0.815356786 | -0.331917103 | 0 | 0.518 | 1 |
| TNFSF102 | 0.000429113 | 1.092845545 | 0.235 | 1 | 0.858225618 | TNFAIP6 | 0.84813962 | 0.498289742 | 0.588 | 1 | 1 |
| MARCKSL11 | 0.000449594 | 0.559389233 | 0.059 | 0.25 | 0.899187899 | BRI3 | 0.879561074 | -0.610769177 | 0 | 0.152 | 1 |
| PSMB92 | 0.000452224 | 0.576492811 | 1 | 1 | 0.904448333 | LYST3 | 0.919472692 | -0.251899847 | 0.059 | 0.527 | 1 |
| ID22 | 0.000500187 | -0.457939407 | 0.118 | 0.25 | 1 | GNG11 | 0.925093412 | 0.882947826 | 0.412 | 0.821 | 1 |
| HLA-DPB15 | 0.000501972 | 0.809563219 | 0.235 | 0.991 | 1 | PLEK3 | 0.939249558 | -0.374149426 | 0 | 0.125 | 1 |
| ZFP36L25 | 0.000502684 | -0.334239961 | 0.294 | 1 | 1 | CTSS2 | 0.941663485 | -1.243496316 | 0.059 | 0.527 | 1 |
| FCGR3A4 | 0.000513358 | 0.653299638 | 0.235 | 0.982 | 1 | NAIP1 | 0.947268774 | 0.344664664 | 0.412 | 0.741 | 1 |
| CTSB | 0.000555879 | -0.250138394 | 0.176 | 0.259 | 1 | S100A92 | 0.952775539 | -0.358598001 | 0.176 | 0.58 | 1 |
| IFI44L10 | 0.000578028 | -0.921503854 | 0 | 0.205 | 1 | DDAH2 | 0.963890279 | -0.343740523 | 0.353 | 0.634 | 1 |
| TRIBI | 0.000582953 | -0.406133678 | 0.059 | 0.25 | 1 | | 1 | -0.369947637 | 0.059 | 0.482 | 1 |

Seurat Cluster 15

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| TTN | 5.66E-13 | -0.676592367 | 0.018 | 1 | 1.13E-09 | MARCKSL12 | 0.139630036 | -0.33543514 | 0.291 | 0.375 | 1 |
| TRIB11 | 3.22E-11 | -0.266780095 | 0.036 | 1 | 6.44E-08 | H2AFZ2 | 0.151704401 | -0.440772505 | 0.564 | 1 | 1 |
| CTSW6 | 4.77E-10 | 0.441284321 | 0.109 | 0 | 9.54E-07 | HSBP1 | 0.153355845 | 0.37225969 | 0.382 | 1 | 1 |
| CSF1R1 | 7.18E-10 | -0.275710806 | 0.055 | 1 | 1.44E-06 | GSN4 | 0.159351449 | 0.640997612 | 0.691 | 1 | 1 |
| FCN1 | 1.06E-09 | 0.418230023 | 0.055 | 1 | 2.12E-06 | DNASE1L3 | 0.168357647 | 0.378863025 | 0.782 | 1 | 1 |
| DUSP4 | 4.36E-09 | -0.385943107 | 0 | 0.125 | 8.72E-06 | AC245014.33 | 0.176764681 | -0.893197481 | 0.491 | 0.375 | 1 |
| RHOC4 | 6.72E-09 | 0.290583234 | 0.164 | 0 | 1.34E-05 | FABP5 | 0.177151643 | 0.283492759 | 0.4 | 1 | 1 |
| CCL55 | 1.62E-08 | 0.478753938 | 0.073 | 1 | 3.24E-05 | FKBP3 | 0.177237962 | 0.338443546 | 0.364 | 1 | 1 |
| P2RY11 | 2.40E-08 | -0.441916509 | 0.018 | 0.125 | 4.80E-05 | NUDT51 | 0.177237962 | 0.273864856 | 0.364 | 1 | 1 |
| IGKV3-151 | 9.15E-08 | 0.661739511 | 0.018 | 0.875 | 0.000183074 | RGS14 | 0.177841732 | -0.889303784 | 0.109 | 0.625 | 1 |
| IGLV1-441 | 9.15E-08 | 0.261396827 | 0.018 | 0.875 | 0.000183074 | CCT71 | 0.196056164 | -0.262438802 | 0.473 | 1 | 1 |
| ASAP11 | 9.39E-08 | -0.435210482 | 0.036 | 0.125 | 0.000187785 | SMPD3 | 0.19894094 | -0.285479666 | 0.455 | 1 | 1 |
| IL7R7 | 1.61E-07 | 0.340692871 | 0.091 | 1 | 0.000322215 | ADA22 | 0.201052984 | -0.310573812 | 0.8 | 1 | 1 |
| LGALS32 | 1.61E-07 | 0.258879524 | 0.055 | 1 | 0.000322215 | PYCARD2 | 0.210491091 | 0.361692952 | 0.982 | 1 | 1 |
| LINC01480 | 2.86E-07 | -0.399035929 | 0.055 | 0.125 | 0.000571725 | GZMB3 | 0.211699541 | -0.880579631 | 0.636 | 1 | 1 |
| SAE1 | 4.78E-07 | -0.404088738 | 0.109 | 1 | 0.000955031 | SMIM141 | 0.211903193 | 0.564210879 | 0.655 | 1 | 1 |
| KLRB15 | 1.14E-06 | 0.267954592 | 0.109 | 1 | 0.002289923 | SEC11C1 | 0.220768235 | -0.580382211 | 0.655 | 1 | 1 |
| GNLY7 | 1.52E-06 | 1.16720549 | 0.109 | 0.125 | 0.003045935 | HIST1H4C2 | 0.223377257 | -0.441478446 | 0.709 | 1 | 1 |
| HRH21 | 3.07E-06 | -0.345303394 | 0.109 | 0.125 | 0.006131546 | SNX32 | 0.22713783 | -0.299953761 | 0.927 | 1 | 1 |
| ATP2B1-AS16 | 3.22E-06 | 0.286941256 | 0.145 | 0.125 | 0.006441207 | MTRNR2L124 | 0.227193605 | 0.552314026 | 1 | 1 | 1 |
| CHST151 | 6.21E-06 | 0.358824111 | 0.127 | 1 | 0.012419072 | FRMD4B2 | 0.228449555 | 0.494841049 | 0.164 | 0 | 1 |
| ANXAI4 | 7.05E-06 | 0.368370189 | 0.182 | 0.125 | 0.014095917 | SAMHD11 | 0.243162677 | 0.259339047 | 0.873 | 1 | 1 |
| CD693 | 8.98E-06 | -0.279782698 | 0.145 | 0.125 | 0.017968056 | JCHAIN | 0.25192327 | -0.348726788 | 1 | 1 | 1 |
| NKG76 | 9.17E-06 | 0.992896296 | 0.2 | 0.125 | 0.018331146 | TNFSF13B1 | 0.260348604 | -0.385593414 | 0.455 | 0.75 | 1 |
| GNG111 | 1.02E-05 | -0.324205638 | 0.145 | 0.125 | 0.020362173 | DAAM12 | 0.266688718 | -0.443579192 | 0.491 | 1 | 1 |
| SLC29A1 | 1.09E-05 | 0.290210232 | 0.164 | 0.125 | 0.021872591 | PPT11 | 0.268805926 | 0.306196052 | 0.2 | 0.5 | 1 |
| GUCY1A11 | 1.39E-05 | -0.731173117 | 0.164 | 0.125 | 0.027860796 | ZFP36L26 | 0.276815822 | -0.443402216 | 0.782 | 1 | 1 |
| KYNU1 | 1.46E-05 | 0.354089312 | 0.2 | 0.125 | 0.029245929 | FAM129C | 0.287612654 | 0.344800353 | 0.909 | 1 | 1 |
| CTSD2 | 2.19E-05 | 0.251154551 | 0.236 | 0.125 | 0.043791188 | SNRPD33 | 0.289361525 | -0.316114039 | 0.636 | 1 | 1 |
| LYZ5 | 2.70E-05 | 1.302648328 | 0.145 | 1 | 0.05401179 | TCL1AI | 0.292876922 | 0.784755506 | 0.418 | 1 | 1 |
| AC004817.3 | 9.33E-05 | -0.435717917 | 0 | 0.25 | 0.186677226 | SSRP1 | 0.3031567 | 0.291307392 | 0.527 | 0.75 | 1 |
| ID12 | 9.33E-05 | -0.462502316 | 0 | 0.25 | 0.186677226 | JUND5 | 0.309205528 | -0.259325456 | 0.909 | 1 | 1 |
| MZT11 | 0.000120582 | -0.316967048 | 0.182 | 1 | 0.241164957 | CYB561A31 | 0.316619299 | -0.493208186 | 0.673 | 1 | 1 |
| AC020916.12 | 0.000177953 | -0.352420648 | 0.018 | 0.25 | 0.355905125 | DYNLL12 | 0.321123773 | 0.336598464 | 0.673 | 1 | 1 |
| CPVL2 | 0.000303947 | 0.31318898 | 0.182 | 1 | 0.607894724 | CD371 | 0.326758685 | 0.314196736 | 0.927 | 1 | 1 |
| IGFBP3 | 0.000303947 | 0.306625498 | 0.182 | 1 | 0.607894724 | ANXA22 | 0.331868496 | 0.330233892 | 0.4 | 1 | 1 |
| DDX39A1 | 0.000335208 | -0.362399531 | 0.291 | 1 | 1 | TALDO11 | 0.337114629 | -0.275821673 | 0.6 | 1 | 1 |
| ATF34 | 0.000634337 | -0.495880058 | 0.055 | 0.25 | 1 | RASD1 | 0.341963471 | -0.351805147 | 0.109 | 0.625 | 1 |
| MIR22HG2 | 0.000782452 | -0.419806523 | 0.073 | 0.25 | 1 | EIF4A31 | 0.342775955 | -0.409131458 | 0.545 | 0.75 | 1 |
| IL329 | 0.000829165 | 0.757377932 | 0.2 | 0.25 | 1 | CDK2AP2 | 0.346320967 | -0.471089505 | 0.8 | 1 | 1 |
| ANXA51 | 0.000829165 | 0.263589553 | 0.2 | 0.25 | 1 | CTSC3 | 0.347394824 | 0.280591248 | 0.891 | 1 | 1 |
| FH | 0.000829165 | 0.254782647 | 0.2 | 1 | 1 | PTMS2 | 0.358781529 | 0.653009755 | 0.6 | 1 | 1 |
| THBD1 | 0.000971409 | -0.410558156 | 0.073 | 0.25 | 1 | NCL3 | 0.367931997 | 0.252047421 | 0.8 | 0.75 | 1 |
| SWAP701 | 0.000971409 | -0.465494583 | 0.073 | 0.25 | 1 | IRF41 | 0.386035148 | -0.284153461 | 0.327 | 0.75 | 1 |
| TOX2 | 0.001024391 | -0.423067605 | 0.091 | 0.25 | 1 | H2AFY3 | 0.389015624 | 0.300152983 | 0.745 | 1 | 1 |
| AIF13 | 0.001028421 | 0.474522156 | 0.309 | 0.25 | 1 | HSP90AB12 | 0.402655289 | -0.254416371 | 0.855 | 0.875 | 1 |
| PLXNB22 | 0.001231265 | 0.424907409 | 0.364 | 0.25 | 1 | APP | 0.403124304 | 0.393782276 | 1 | 1 | 1 |
| ANXA63 | 0.001990661 | 0.334370128 | 0.382 | 0.25 | 1 | HSPA83 | 0.412278552 | 0.418386817 | 0.745 | 0.625 | 1 |
| COTL13 | 0.002014265 | 0.316884421 | 0.236 | 1 | 1 | TRAF4 | 0.421301887 | -0.495078843 | 0.673 | 0.75 | 1 |
| HIST1H2AC1 | 0.002023178 | 0.25689694 | 0.218 | 1 | 1 | VDAC33 | 0.425025826 | 0.449485113 | 0.455 | 1 | 1 |
| LMNB1 | 0.002153643 | -0.414773835 | 0.182 | 0.25 | 1 | NAGK1 | 0.425025826 | 0.388080064 | 0.455 | 1 | 1 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| SOD22 | 0.0031197 | -0.460084413 | 0.145 | 0.25 | 1 | SHTN11 | 0.431805652 | 0.635335291 | 0.418 | 1 | 1 |
| SERPINF2 | 0.003211372 | -0.278210952 | 0.255 | 1 | 1 | TMEM8B | 0.43432685 | 0.47825111 | 0.691 | 1 | 1 |
| CKS1B | 0.004482368 | 0.287110561 | 0.236 | 1 | 1 | GNAI21 | 0.455208471 | 0.325581611 | 0.618 | 1 | 1 |
| CD320 | 0.004494557 | 0.256205216 | 0.236 | 1 | 1 | TMEM1091 | 0.461699456 | 0.407664762 | 0.764 | 1 | 1 |
| MGST21 | 0.004894557 | 0.275699923 | 0.473 | 0.25 | 1 | PTGDS1 | 0.464933673 | 0.26935783 | 0.382 | 0.5 | 1 |
| MYADM4 | 0.007712209 | -0.409278819 | 0.382 | 1 | 1 | TXN1 | 0.476328477 | 0.394022366 | 0.945 | 1 | 1 |
| AL138963.39 | 0.00901262 | 1.28511508 | 0.545 | 0.375 | 1 | SNRPG2 | 0.482147933 | -0.422548514 | 0.636 | 1 | 1 |
| F13A1 | 0.009128522 | 0.341679481 | 0.255 | 1 | 1 | NBPF142 | 0.484589024 | -0.275641763 | 0.509 | 0.75 | 1 |
| CARD161 | 0.009128522 | 0.332505583 | 0.255 | 1 | 1 | FOSB5 | 0.484589024 | -0.301623903 | 0.509 | 0.75 | 1 |
| RNF144B | 0.009128522 | 0.286117099 | 0.255 | 1 | 1 | 4-Jun | 0.501852942 | -0.439680884 | 0.855 | 0.875 | 1 |
| S100A93 | 0.0100004291 | 0.832088857 | 0.073 | 0.75 | 1 | BCL11A1 | 0.502181748 | -0.30744154 | 0.909 | 1 | 1 |
| LDLRAD4 | 0.010252079 | -0.339381369 | 0.109 | 0.75 | 1 | HNRNPF1 | 0.523753642 | -0.320619802 | 0.491 | 1 | 1 |
| RPLP02 | 0.010789304 | -0.393554692 | 0.964 | 1 | 1 | ID23 | 0.534791823 | -0.272755396 | 0.164 | 0.625 | 1 |
| CPNE32 | 0.011591868 | -0.684445575 | 0.455 | 1 | 1 | STT3A | 0.535736085 | 0.352845132 | 0.473 | 1 | 1 |
| S100A111 | 0.016631312 | 0.605224359 | 0.764 | 1 | 1 | ABRACL4 | 0.539214157 | 0.275937713 | 0.709 | 1 | 1 |
| IFITM36 | 0.017263245 | 0.56285316 | 0.273 | 1 | 1 | FCGRT | 0.541474512 | 0.329695445 | 0.8 | 1 | 1 |
| SLIRP | 0.017263245 | 0.487237932 | 0.273 | 1 | 1 | CACYBP2 | 0.545294318 | 0.253769132 | 0.436 | 1 | 1 |
| LST1 | 0.017263245 | 0.417641423 | 0.273 | 1 | 1 | NCF12 | 0.55621769 | -0.271590685 | 0.909 | 1 | 1 |
| ESYT11 | 0.017263245 | 0.338060626 | 0.273 | 1 | 1 | S100A103 | 0.559197681 | 0.837185307 | 0.564 | 1 | 1 |
| FGD2 | 0.017263245 | 0.321965945 | 0.273 | 1 | 1 | TPM41 | 0.572300033 | -0.492548284 | 0.418 | 0.5 | 1 |
| PHACTR13 | 0.023563864 | -0.494820442 | 0.4 | 1 | 1 | CTSZ | 0.594290742 | 0.344045641 | 0.673 | 1 | 1 |
| ETFA1 | 0.025517225 | 0.274056618 | 0.291 | 0.375 | 1 | MYDGF2 | 0.594290742 | 0.288979606 | 0.673 | 1 | 1 |
| GPR1832 | 0.027251764 | -0.700847755 | 0.309 | 0.875 | 1 | HSP90B16 | 0.598611496 | -0.299095242 | 0.982 | 0.875 | 1 |
| TOR3A2 | 0.030282285 | 0.336070992 | 0.436 | 0.375 | 1 | FCER1A1 | 0.601451019 | 0.295523558 | 0.545 | 1 | 1 |
| NREP1 | 0.030573722 | 0.420571331 | 0.273 | 1 | 1 | ICAM12 | 0.6091409 | -0.274968293 | 0.127 | 0.5 | 1 |
| ATP1B3 | 0.030573722 | 0.324179942 | 0.291 | 1 | 1 | NDUFB32 | 0.613286368 | -0.470287425 | 0.509 | 1 | 1 |
| SIT11 | 0.030573722 | 0.266931676 | 0.291 | 1 | 1 | HIST1H1E3 | 0.622798314 | 0.385649577 | 0.655 | 1 | 1 |
| GNG7 | 0.032368171 | -0.407599986 | 0.509 | 1 | 1 | HLA-DQB13 | 0.625703599 | -0.451877394 | 0.745 | 1 | 1 |
| MS4A6A2 | 0.034093134 | 0.535328544 | 0.836 | 1 | 1 | LGALS14 | 0.636885202 | 0.356635202 | 0.636 | 1 | 1 |
| CANX2 | 0.037640439 | 0.264769716 | 0.818 | 0.625 | 1 | PIK3AP12 | 0.640377227 | -0.414009444 | 0.473 | 0.625 | 1 |
| AL355075.4 | 0.039654109 | -0.461657352 | 0.382 | 1 | 1 | C1orf1622 | 0.642168048 | 0.345715294 | 0.491 | 1 | 1 |
| FTL1 | 0.039974707 | -0.302838117 | 0.964 | 1 | 1 | MT-ATP84 | 0.65398206 | -0.263936564 | 0.691 | 1 | 1 |
| UBE2I3 | 0.043222919 | -0.527758736 | 0.764 | 1 | 1 | SPCS31 | 0.669096089 | -0.401132934 | 0.691 | 1 | 1 |
| NEAT16 | 0.043328173 | 0.390005977 | 0.309 | 0.375 | 1 | PPM1J | 0.669972481 | 0.406651601 | 0.455 | 1 | 1 |
| TSPO1 | 0.043509152 | -0.254314708 | 0.4 | 1 | 1 | PDE4B1 | 0.688583003 | -0.527027229 | 0.127 | 0.5 | 1 |
| HMGB12 | 0.046362257 | -0.475988458 | 0.964 | 1 | 1 | PLEK4 | 0.702503908 | -0.426919844 | 0.927 | 1 | 1 |
| HLA-DPB16 | 0.05180841 | -0.313885415 | 0 | 0.625 | 1 | AC007952.44 | 0.71697838 | -0.256479781 | 0.782 | 1 | 1 |
| IFITM24 | 0.049244861 | 0.25590367 | 1 | 0.375 | 1 | CYBB1 | 0.717673556 | -0.29193072 | 0.818 | 1 | 1 |
| CAT | 0.05062505 | -0.333256904 | 0.473 | 1 | 1 | SLC1A51 | 0.7277733 | 0.301961081 | 0.6 | 1 | 1 |
| NOP562 | 0.051070229 | 0.571172077 | 0.818 | 1 | 1 | CD362 | 0.7277733 | -0.287530274 | 0.6 | 1 | 1 |
| MGLL2 | 0.051070229 | 0.382623096 | 0.309 | 1 | 1 | NFKBIA4 | 0.746373366 | -0.56050937 | 0.6 | 0.625 | 1 |
| GRASP4 | 0.05180841 | -0.383684514 | 0.309 | 0.625 | 1 | TOB14 | 0.744257961 | -0.329822276 | 0.109 | 0.5 | 1 |
| IF1276 | 0.05180841 | -0.766854333 | 0 | 0.375 | 1 | PLSCR11 | 0.751765934 | -0.4125744 | 0.073 | 0.5 | 1 |
| SEMA7A | 0.057646784 | -0.323291719 | 0.036 | 0.375 | 1 | AREG4 | 0.751765934 | -0.47820343 | 0.073 | 0.5 | 1 |
| S100A85 | 0.059744014 | 1.08734103 | 0.091 | 0.375 | 1 | DAB21 | 0.758941504 | 0.54576957 | 0.582 | 1 | 1 |
| IGKC1 | 0.061721998 | -0.938393829 | 0.945 | 1 | 1 | TLN13 | 0.761991062 | 0.302092102 | 0.673 | 1 | 1 |
| TIPARP5 | 0.064491334 | -0.42860955 | 0.018 | 0.375 | 1 | SLC25A25 | 0.774735074 | -0.291411009 | 0.073 | 0.5 | 1 |
| TXNDC171 | 0.068829796 | 0.286228465 | 0.345 | 1 | 1 | NPC22 | 0.780489297 | -0.264441197 | 0.982 | 1 | 1 |
| AHCY | 0.070295132 | -0.288971223 | 0.382 | 1 | 1 | ALDH21 | 0.802678326 | 0.282331979 | 0.473 | 1 | 1 |
| PSMB81 | 0.074663748 | 0.38261612 | 0.691 | 0.5 | 1 | RANBP11 | 0.805531642 | 0.318691295 | 0.527 | 1 | 1 |
| RNASE61 | 0.077531102 | 0.480743845 | 0.927 | 1 | 1 | RGS23 | 0.831520303 | -0.943979867 | 0.109 | 0.5 | 1 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| EPRS3 | 0.080946967 | 0.513461895 | 0.327 | 1 | 1 | HLA-DQA13 | 0.841156097 | 0.287483941 | 0.6 | 1 | 1 |
| KCTD12 | 0.080946967 | 0.301660601 | 0.327 | 1 | 1 | S100A45 | 0.842281288 | 0.668418663 | 0.655 | 0.875 | 1 |
| EAF2 | 0.080946967 | 0.228721557 | 0.327 | 1 | 1 | SNRNP25 | 0.873446779 | 0.334566372 | 0.564 | 1 | 1 |
| SEPT113 | 0.080946967 | 0.258677079 | 0.327 | 1 | 1 | TUBB3 | 0.876637307 | -0.284104681 | 0.8 | 1 | 1 |
| CXCR3 | 0.08347614 | -0.591326295 | 0.564 | 1 | 1 | GRN1 | 0.876946185 | -0.63220745 | 0.927 | 1 | 1 |
| CALHM62 | 0.086125348 | -0.288623819 | 0.109 | 0.375 | 1 | NRP1 | 0.883803442 | 0.492057262 | 0.382 | 0.75 | 1 |
| CHMP1B3 | 0.088447407 | -0.522020479 | 0.164 | 0.375 | 1 | MIR181A1HG1 | 0.888341 | -0.434670165 | 0.055 | 0.5 | 1 |
| PPP1R14A1 | 0.091882873 | -0.378444281 | 0.236 | 0.375 | 1 | ISG154 | 0.888341 | -0.498627513 | 0.055 | 0.5 | 1 |
| SLC25A5 | 0.113573976 | -0.441129852 | 0.818 | 1 | 1 | PSMB23 | 0.889328904 | 0.360382744 | 0.527 | 1 | 1 |
| CCDC88A | 0.114047964 | -0.395151788 | 0.873 | 1 | 1 | CCT32 | 0.891525401 | 0.31944812 | 0.636 | 1 | 1 |
| ZFP362 | 0.117834285 | -0.298100776 | 0.782 | 1 | 1 | IF44L11 | 0.913041551 | -0.45095598 | 0.055 | 0.5 | 1 |
| S100A63 | 0.119013886 | -0.499623101 | 0.909 | 1 | 1 | PECAM12 | 0.939702413 | 0.568269286 | 0.491 | 1 | 1 |
| CSF2RA | 0.122373236 | 0.604315202 | 0.345 | 1 | 1 | CNN22 | 0.939702413 | 0.379545108 | 0.491 | 1 | 1 |
| CD77 | 0.122373236 | 0.514209079 | 0.345 | 1 | 1 | LDHA4 | 0.940519901 | 0.458451748 | 0.545 | 1 | 1 |
| JPT12 | 0.122373236 | 0.279046094 | 0.345 | 1 | 1 | CLEC4C | 0.942288169 | -0.571754631 | 0.818 | 1 | 1 |
| SEC61B2 | 0.124066412 | -0.303340383 | 0.964 | 1 | 1 | SPIB | 0.957657038 | 0.363858927 | 0.564 | 1 | 1 |
| PSME24 | 0.124942246 | 0.457820627 | 0.582 | 0.625 | 1 | PACSIN1 | 0.974893928 | 0.315176002 | 0.636 | 1 | 1 |
| SAT 15 | 0.138215388 | -0.368097077 | 0.764 | 1 | 1 | MEF2C3 | 0.991748398 | -0.275335051 | 0.818 | 1 | 1 |
| | | | | | | Seurat Cluster 16 | | | | | |
| IGHV1-21 | 1.22E-11 | -0.258236259 | 0 | 1 | 2.44E-08 | MRPS261 | 0.164650667 | 0.335453738 | 0.615 | 0.839 | 1 |
| TRBV7-26 | 4.09E-11 | -0.358926492 | 0 | 0.968 | 8.19E-08 | H2AFX | 0.169203786 | 0.381674566 | 0.577 | 0.742 | 1 |
| TRBV7-62 | 4.98E-10 | 0.590635161 | 0.038 | 1 | 9.95E-07 | EFHD24 | 0.170488912 | 0.362484236 | 0.769 | 0.839 | 1 |
| TRBV11-2 | 4.98E-10 | 0.564007032 | 0.038 | 1 | 9.95E-07 | GNGT2 | 0.181923681 | 0.2549917 | 0.231 | 0.774 | 1 |
| TRAV27 | 4.98E-10 | 0.264436483 | 0.038 | 1 | 9.95E-07 | CCL56 | 0.185380336 | 0.923673206 | 0.654 | 0.677 | 1 |
| IGHV3-212 | 1.24E-09 | -0.25023017 | 0 | 0.871 | 2.47E-06 | PCNA | 0.191025617 | 0.321846823 | 0.692 | 0.71 | 1 |
| TRBV4-13 | 4.31E-09 | 0.59772086 | 0.038 | 0.935 | 8.61E-06 | HMGN21 | 0.191630757 | 0.274257383 | 1 | 0.935 | 1 |
| LYZ6 | 1.17E-08 | -0.565904473 | 0 | 1 | 2.34E-05 | AOAH | 0.205772223 | 0.377329073 | 0.269 | 0.806 | 1 |
| TRAV12-3 | 1.29E-08 | 0.372142355 | 0.077 | 1 | 2.58E-05 | KIF4A | 0.208593592 | 0.257849164 | 0.308 | 0.516 | 1 |
| TRBV283 | 1.42E-08 | 0.324417765 | 0.077 | 1 | 2.84E-05 | AC10359138 | 0.212278119 | -0.38363794 | 0.038 | 0.419 | 1 |
| IGHV3-331 | 3.25E-08 | 3.050423266 | 0.038 | 0.871 | 6.50E-05 | HDAC11 | 0.21432376 | 0.270999767 | 0.885 | 0.935 | 1 |
| KLRC12 | 1.86E-07 | -0.441266855 | 0.115 | 1 | 0.000372237 | H2AFZ3 | 0.214353468 | 0.288066677 | 0.962 | 1 | 1 |
| VCAN | 2.15E-07 | 0.285718857 | 0.038 | 0.806 | 0.000430965 | IFNG1 | 0.218913969 | -0.317530681 | 0.154 | 0.452 | 1 |
| TRBV182 | 4.99E-07 | -0.256263492 | 0 | 0.129 | 0.000998162 | KIF23 | 0.220913791 | -0.260842328 | 0.154 | 0.419 | 1 |
| TRBV4-25 | 4.99E-07 | -0.561491068 | 0.038 | 0.871 | 0.000998162 | NEAT17 | 0.225995472 | -0.254992376 | 0.731 | 0.935 | 1 |
| TRBV5-12 | 6.10E-07 | -0.464869572 | 0.077 | 0.806 | 0.001220107 | KNL1 | 0.239097618 | -0.439816568 | 0.346 | 0.774 | 1 |
| TRAV1-21 | 1.31E-06 | -0.267764105 | 0 | 0.129 | 0.002619806 | ANXA15 | 0.245140443 | 0.290625185 | 0.769 | 0.903 | 1 |
| JCHAIN1 | 1.61E-06 | 2.355809145 | 0.115 | 0.935 | 0.003225014 | ASPM | 0.253295254 | -0.52869932 | 0.192 | 0.452 | 1 |
| ESPL1 | 2.22E-06 | -0.324352537 | 0.115 | 0.903 | 0.004447022 | SELENOS1 | 0.255850655 | 0.302085407 | 0.5 | 0.677 | 1 |
| IGKV1D-391 | 2.94E-06 | 2.403220376 | 0.038 | 0.71 | 0.005880412 | PNP2 | 0.25824136 | 0.371407253 | 0.731 | 1 | 1 |
| IGKV1-39 | 2.94E-06 | 0.444733973 | 0.038 | 0.71 | 0.005880412 | C1orf1623 | 0.261117592 | 0.49422001 | 0.423 | 1 | 1 |
| IGKC2 | 7.35E-06 | 1.481560861 | 0.154 | 0.968 | 0.014691672 | STOM1 | 0.270196738 | 0.335896625 | 0.538 | 0.742 | 1 |
| IGHA21 | 7.99E-06 | 0.376079796 | 0.115 | 0.871 | 0.015982294 | MIR4435-2HG3 | 0.270713352 | -0.453511854 | 0.577 | 0.839 | 1 |
| IGHV3-66 | 9.89E-06 | 0.737360307 | 0.038 | 0.806 | 0.019781129 | S100A86 | 0.282727734 | -0.544969642 | 0.077 | 0.452 | 1 |
| TKTL1 | 1.75E-05 | 0.279935946 | 0.077 | 0.871 | 0.035020088 | FTL2 | 0.293983669 | 0.29009594 | 1 | 0.968 | 1 |
| RAMP11 | 1.94E-05 | 0.275366573 | 0.154 | 0.935 | 0.038768845 | MT-CO11 | 0.301416343 | -0.421375125 | 1 | 1 | 1 |
| MS4A11 | 4.66E-05 | 0.528908857 | 0.077 | 0.871 | 0.093217383 | CENPE | 0.304268877 | -0.370684348 | 0.192 | 0.484 | 1 |
| EOMES 1 | 4.74E-05 | 0.375690971 | 0.192 | 1 | 0.094757437 | SRGN1 | 0.316654039 | 0.280196171 | 1 | 0.935 | 1 |
| IGHM | 5.07E-05 | 1.414049516 | 0.115 | 0.903 | 0.101357068 | TNFAIP36 | 0.318090797 | -0.789315689 | 0.154 | 0.613 | 1 |
| CTSZ1 | 7.13E-05 | 0.254208742 | 0.231 | 0.258 | 0.142657814 | CXXC51 | 0.320027865 | 0.50683091 | 0.423 | 1 | 1 |
| TRAV13-13 | 7.59E-05 | -0.423667024 | 0 | 0.194 | 0.151778687 | MATK1 | 0.320027865 | 0.400391129 | 0.423 | 0.645 | 1 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| RNASE62 | 0.000196858 | 0.250582695 | 0.192 | 0.968 | 0.393715882 | HIST1H2BC1 | 0.32404222 | -0.26497655 | 0.115 | 0.452 | 1 |
| AQP33 | 0.000274294 | -0.670198609 | 0.308 | 1 | 0.548587841 | MANF1 | 0.331446528 | 0.319697738 | 0.654 | 0.903 | 1 |
| MZB1 | 0.000400517 | 0.619676053 | 0.154 | 0.258 | 0.80103497 | TMEM106C1 | 0.340285463 | 0.386571899 | 0.808 | 0.903 | 1 |
| S100A94 | 0.000889925 | 0.546614984 | 0.115 | 0.839 | 1 | CTLA4 | 0.344589336 | -0.362269255 | 0.192 | 0.645 | 1 |
| CD79A3 | 0.001084906 | 0.94835654 | 0.231 | 0.968 | 1 | NCAPG | 0.344589336 | -0.465666552 | 0.192 | 0.484 | 1 |
| FADS2 | 0.001184023 | 0.311590474 | 0.077 | 0.935 | 1 | MTRNR2L82 | 0.346310848 | -0.256326741 | 0.231 | 0.645 | 1 |
| MYL9 | 0.002120992 | -0.273907739 | 0.269 | 0.29 | 1 | AC007952.45 | 0.347680215 | 0.25620428 | 0.654 | 0.935 | 1 |
| XCL24 | 0.002328144 | 0.47657363 | 0.077 | 1 | 1 | SDF2L1 | 0.34796238 | 0.332484831 | 0.692 | 0.806 | 1 |
| KIF20A | 0.003074373 | -0.276537036 | 0.038 | 0.161 | 1 | KLRF12 | 0.352513922 | 0.505547705 | 0.423 | 0.968 | 1 |
| GZMA5 | 0.003437668 | 0.904054941 | 0.769 | 0.742 | 1 | KLRD15 | 0.372611419 | 0.728838733 | 0.615 | 0.968 | 1 |
| PLEC3 | 0.003452067 | -0.380260259 | 0.385 | 1 | 1 | LGALS15 | 0.38255526 | 0.38523089 | 0.923 | 0.968 | 1 |
| IGHA11 | 0.003658678 | 0.495320423 | 0.115 | 0.742 | 1 | HJURP | 0.38883757 | -0.637198608 | 0.154 | 0.387 | 1 |
| HLA-DQA14 | 0.003842359 | 0.391016041 | 0.231 | 0.355 | 1 | MYOM23 | 0.396765869 | 1.183563105 | 0.462 | 1 | 1 |
| SYK3 | 0.003842359 | 0.336468784 | 0.231 | 0.935 | 1 | TOR3A3 | 0.396765869 | 0.293389859 | 0.462 | 0.71 | 1 |
| MELK | 0.004086586 | -0.310060258 | 0.192 | 0.839 | 1 | IFITM37 | 0.400261741 | 0.488595861 | 0.923 | 1 | 1 |
| TRBV7-94 | 0.004346862 | -0.277744582 | 0 | 0.29 | 1 | MT-ATP62 | 0.400269376 | -0.666521822 | 0.962 | 1 | 1 |
| CCNB1 | 0.005942162 | 0.35823123 | 0.269 | 0.387 | 1 | LAIR2 | 0.405008605 | 0.326117988 | 0.423 | 0.677 | 1 |
| KIR2DL12 | 0.006086462 | 0.342924693 | 0.192 | 0.839 | 1 | MMD1 | 0.416781668 | -0.282566909 | 0.038 | 0.452 | 1 |
| AHNAK5 | 0.00913179 | -0.643647964 | 0.692 | 1 | 1 | PPIB4 | 0.42773408 | 0.281053084 | 0.962 | 1 | 1 |
| CST75 | 0.009222396 | 0.904531476 | 0.885 | 0.806 | 1 | FGFBP25 | 0.432921523 | 0.859965334 | 0.423 | 0.935 | 1 |
| E2F7 | 0.009667507 | -0.294064856 | 0.038 | 0.258 | 1 | HOPX4 | 0.435897634 | 0.926625471 | 0.615 | 0.968 | 1 |
| TRGV93 | 0.011359428 | 0.369030155 | 0.308 | 1 | 1 | ALOX5AP3 | 0.435897634 | 0.357087052 | 0.615 | 0.871 | 1 |
| AKR1C3 | 0.012783742 | 0.358109936 | 0.308 | 0.968 | 1 | CENPF | 0.453589922 | -0.690807221 | 0.5 | 0.742 | 1 |
| PTGER42 | 0.013088323 | -0.337087665 | 0.231 | 0.355 | 1 | ID24 | 0.455057591 | 0.448770648 | 0.615 | 0.839 | 1 |
| TK1 | 0.015837567 | 0.519476711 | 0.769 | 0.677 | 1 | SELL4 | 0.455387866 | -0.312395389 | 0.654 | 0.839 | 1 |
| CD8A2 | 0.018045595 | 0.365608181 | 0.462 | 0.419 | 1 | IL3210 | 0.456119701 | 0.314887619 | 0.808 | 0.968 | 1 |
| CCL45 | 0.0205442 | 0.56839669 | 0.462 | 0.484 | 1 | SUB13 | 0.45626572 | 0.258995667 | 0.962 | 0.968 | 1 |
| HMGB21 | 0.022422598 | 0.458752739 | 0.923 | 1 | 1 | 5-Jun | 0.45626572 | -0.483531816 | 0.962 | 1 | 1 |
| HLA-DQA22 | 0.023501494 | 0.34079817 | 0.346 | 1 | 1 | TUBB4B3 | 0.473809936 | 0.289635734 | 0.538 | 0.71 | 1 |
| LMNA6 | 0.025347765 | -0.29400487 | 0.154 | 0.774 | 1 | UBE2S1 | 0.486372322 | -0.55843965 | 0.231 | 0.645 | 1 |
| ITM2C | 0.025372868 | 0.386138851 | 0.231 | 0.839 | 1 | CD744 | 0.495920183 | 0.577807575 | 1 | 1 | 1 |
| GZMH3 | 0.026458794 | 0.585728997 | 0.462 | 0.548 | 1 | TCF19 | 0.524369739 | 0.378507937 | 0.615 | 0.839 | 1 |
| PRF13 | 0.026461718 | 0.82554712 | 0.846 | 0.935 | 1 | MCM32 | 0.52669242 | 0.298435727 | 0.5 | 0.839 | 1 |
| NDUFB63 | 0.028654599 | 0.315516537 | 0.769 | 0.806 | 1 | MT-CO31 | 0.526826447 | -0.471773654 | 0.808 | 0.968 | 1 |
| HLA-DQB14 | 0.029757993 | 0.254586801 | 0.308 | 0.419 | 1 | PRC11 | 0.536024327 | -0.592227448 | 1 | 1 | 1 |
| CDC25B1 | 0.034775335 | -0.34529427 | 0.654 | 1 | 1 | MT-ATP85 | 0.537316413 | -0.650300353 | 0.154 | 0.613 | 1 |
| BLVRB1 | 0.035015491 | 0.367282129 | 0.308 | 0.935 | 1 | BHLHE403 | 0.548535536 | -0.368841089 | 0.885 | 0.935 | 1 |
| TTK | 0.035135993 | -0.342410076 | 0.077 | 0.355 | 1 | MT-CYB2 | 0.558687089 | -0.700590362 | 0.192 | 0.516 | 1 |
| LIMS13 | 0.037319734 | -0.27855088 | 0.577 | 1 | 1 | JUND6 | 0.562199048 | -0.420164721 | 0.269 | 0.645 | 1 |
| LINC024462 | 0.037515902 | 0.40166269 | 0.115 | 0.742 | 1 | HLA-DPB17 | 0.568475683 | 0.303515758 | 0.615 | 0.871 | 1 |
| GABARAP1 | 0.037991439 | 0.251446372 | 0.885 | 1 | 1 | HIST1H4C3 | 0.602565812 | 0.550427921 | 0.923 | 0.935 | 1 |
| CLIC33 | 0.038421647 | 0.909534267 | 0.346 | 1 | 1 | IL2RB2 | 0.624406065 | 0.693632382 | 0.654 | 0.871 | 1 |
| CTSD3 | 0.038860852 | -0.376932114 | 0.385 | 0.935 | 1 | TIPARP6 | 0.631055613 | -0.250671327 | 0.308 | 0.548 | 1 |
| TYMS | 0.041072018 | 0.500229138 | 0.923 | 0.839 | 1 | FCER1G3 | 0.635261245 | 0.831036782 | 0.577 | 0.968 | 1 |
| SNRPD34 | 0.047061065 | 0.299932966 | 0.885 | 0.903 | 1 | NCR31 | 0.644271257 | 0.424090862 | 0.385 | 0.806 | 1 |
| PLEK5 | 0.047725395 | 0.392872751 | 0.769 | 0.774 | 1 | TYROBP2 | 0.646413718 | 0.663276818 | 0.538 | 1 | 1 |
| LDHA5 | 0.053526548 | 0.287494938 | 0.923 | 0.935 | 1 | GZMB4 | 0.646413718 | 0.535785737 | 0.538 | 0.871 | 1 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| CD21 | 0.0546740 5 | -0.362654292 | 0.577 | 0.968 | 1 | FCGR3A5 | 0.668300549 | 1.19556891 | 0.462 | 0.968 | 1 |
| CD3G3 | 0.054877332 | -0.355186054 | 0.385 | 0.839 | 1 | UNG | 0.678826077 | 0.50495685 | 0.346 | 0.71 | 1 |
| CX3CR12 | 0.059100671 | 0.563799024 | 0.385 | 1 | 1 | IGFBP7 | 0.679510304 | 0.787799112 | 0.462 | 0.935 | 1 |
| SH2D1B | 0.059339417 | 0.384343845 | 0.346 | 0.935 | 1 | HLA-DRB17 | 0.681083415 | 0.551983814 | 0.5 | 0.774 | 1 |
| FKBP24 | 0.063998559 | 0.274877064 | 0.731 | 0.774 | 1 | HIST1H2AG1 | 0.713366657 | -0.30145927 | 0.269 | 0.581 | 1 |
| TMEM1092 | 0.064089185 | 0.275178238 | 0.769 | 0.677 | 1 | HIST1H2AL | 0.721576484 | -0.251352893 | 0.115 | 0.516 | 1 |
| TUBA1B3 | 0.066581765 | 0.474201461 | 1 | 0.968 | 1 | GPR1833 | 0.738585415 | -0.322123521 | 0.308 | 0.613 | 1 |
| MCM5 | 0.068835593 | 0.31491252 | 0.769 | 0.806 | 1 | TBX211 | 0.753306282 | 0.69260044 | 0.5 | 0.903 | 1 |
| NKG77 | 0.06894808 | 1.159265582 | 0.846 | 0.806 | 1 | MT-CO21 | 0.766923252 | -0.399494197 | 1 | 1 | 1 |
| DUSP23 | 0.070214866 | -0.303374796 | 0.346 | 0.452 | 1 | MTRNR2L125 | 0.779185919 | -0.259903385 | 1 | 1 | 1 |
| RHOC5 | 0.080885595 | 0.407129834 | 0.346 | 0.935 | 1 | KLRB16 | 0.790773856 | 0.309895608 | 0.577 | 0.548 | 1 |
| PDLIM11 | 0.08296182 | 0.44964975 | 0.308 | 0.516 | 1 | CKAP2L | 0.824390526 | -0.498756385 | 0.192 | 0.774 | 1 |
| CD300A1 | 0.083749562 | 0.547309536 | 0.346 | 0.968 | 1 | HLA-DRA4 | 0.827972514 | 0.748614304 | 0.538 | 1 | 1 |
| DUT1 | 0.085008892 | 0.354499369 | 0.962 | 0.806 | 1 | ZFP36L27 | 0.828756474 | -0.390078981 | 0.923 | 1 | 1 |
| GSTP12 | 0.087949809 | 0.295111777 | 0.962 | 0.968 | 1 | TOP2A | 0.852740068 | -0.473334915 | 0.462 | 0.645 | 1 |
| HIST1H1C4 | 0.09053224 | 0.458845947 | 0.692 | 0.742 | 1 | CCDC34 | 0.852957464 | 0.283647007 | 0.5 | 0.839 | 1 |
| HIST1H1D3 | 0.093629879 | -0.321743001 | 0.692 | 0.935 | 1 | HELLS | 0.853429534 | -0.250225499 | 0.615 | 0.774 | 1 |
| SLBP2 | 0.100432877 | 0.342181374 | 0.808 | 0.806 | 1 | TRBC14 | 0.853335655 | 0.511774184 | 0.654 | 0.968 | 1 |
| LAT21 | 0.103477404 | 0.292008672 | 1 | 1 | 1 | TTC382 | 0.865616375 | 0.467576008 | 0.5 | 1 | 1 |
| STMN12 | 0.107357968 | 0.371185769 | 0.385 | 0.871 | 1 | MT-ND4L3 | 0.866403877 | -0.472573676 | 1 | 1 | 1 |
| TRDC2 | 0.110528651 | 0.696298797 | 1 | 1 | 1 | SPN2 | 0.87904745 | -0.256537095 | 0.846 | 1 | 1 |
| HLA-DPA14 | 0.112851796 | 0.485009892 | 0.538 | 0.645 | 1 | HLA-DRB53 | 0.890469232 | 0.566117107 | 0.385 | 0.742 | 1 |
| ADGRG13 | 0.117125427 | 0.472277673 | 0.346 | 0.935 | 1 | ACOT7 | 0.90307009 | 0.263028689 | 0.346 | 0.71 | 1 |
| CTSW7 | 0.117759285 | 0.896633626 | 0.692 | 0.774 | 1 | UHRF1 | 0.941601456 | 0.400700152 | 0.385 | 0.742 | 1 |
| TPST22 | 0.12186964 | 0.336225886 | 0.769 | 1 | 1 | GZMM2 | 0.95516133 | 0.359927193 | 0.615 | 1 | 1 |
| CD633 | 0.125875636 | 0.437973944 | 0.808 | 0.935 | 1 | MT-ND63 | 0.955278355 | -0.484395557 | 0.885 | 0.968 | 1 |
| MCM71 | 0.133999126 | 0.361466268 | 0.808 | 0.903 | 1 | ZFP363 | 0.968020821 | -0.67758781 | 0.731 | 0.774 | 1 |
| CD78 | 0.142522301 | 0.548592581 | 0.808 | 1 | 1 | CDC45 | 0.993549526 | 0.273109438 | 0.423 | 0.774 | 1 |
| PGAM12 | 0.147041915 | 0.257799725 | 0.808 | 0.903 | 1 | ABI3 | 0.993595863 | 0.287454225 | 0.654 | 0.968 | 1 |
| PRDX23 | 0.15597863 | 0.265389468 | 0.769 | 0.806 | 1 | VIM4 | 0.993607913 | 0.252327073 | 0.885 | 1 | 1 |
| IFITM25 | 0.156186669 | 0.769681236 | 0.885 | 0.935 | 1 | SPON23 | 1 | 0.762496084 | 0.5 | 0.903 | 1 |
| ORC6 | 0.159081912 | -0.252908174 | 0.308 | 0.484 | 1 | | | | | | |
| | | | | | | Seurat Cluster 19 | | | | | |
| MYL91 | 1.69E-06 | -0.254144838 | 0 | 1 | 0.003370659 | LYN2 | 0.134288374 | 0.609367959 | 0.643 | 0.714 | 1 |
| SEL1L3 | 1.69E-06 | -0.267173242 | 0 | 1 | 0.003370659 | SCHIP1 | 0.141096551 | 0.283600716 | 0.357 | 1 | 1 |
| S100A2 | 1.69E-06 | -0.512961859 | 0 | 1 | 0.003370659 | PLCB2 | 0.141096551 | 0.278661461 | 0.357 | 1 | 1 |
| LGALS33 | 1.69E-06 | -0.573061522 | 0 | 1 | 0.003370659 | AC103591.39 | 0.144374344 | -0.956357797 | 0.143 | 0.357 | 1 |
| CTSH | 1 69E-06 | -0.653794066 | 0 | 1 | 0.003370659 | HIFX5 | 0.147243633 | 0.344225508 | 0.714 | 0.714 | 1 |
| CPVL3 | 2.81E-05 | -0.282310673 | 0.071 | 1 | 0.056142971 | MT-ATP63 | 0.147798384 | -0.279307125 | 1 | 1 | 1 |
| ANXA23 | 2.81E-05 | -0.459779732 | 0.071 | 1 | 0.056142971 | GNG112 | 0.154157616 | 0.451585012 | 0.357 | 1 | 1 |
| SRPRBI | 3.47E-05 | -0.398194206 | 0.071 | 1 | 0.069415904 | MZB11 | 0.154157616 | 0.362541097 | 0.357 | 1 | 1 |
| LGALS16 | 3.47E-05 | -0.814073792 | 0.071 | 1 | 0.069415904 | HIST1H2AE1 | 0.156250481 | -0.31844735 | 0.429 | 1 | 1 |
| IFI277 | 4.12E-05 | -0.987126238 | 0 | 0.929 | 0.082483993 | FAM19A2 | 0.157998655 | -0.429823522 | 0.143 | 0.714 | 1 |
| EPHB61 | 4.28E-05 | 0.667303671 | 0.143 | 0.071 | 0.085560473 | CNN23 | 0.161035909 | 0.319845932 | 0.857 | 1 | 1 |
| OASL5 | 4.28E-05 | -0.419598813 | 0.071 | 1 | 0.085634612 | ENO13 | 0.161093224 | 0.356644828 | 1 | 0.714 | 1 |
| ANXA2R1 | 5.07E-05 | 0.343429777 | 0.214 | 0.071 | 0.101383631 | ABRACL5 | 0.161093224 | 0.274964791 | 0.929 | 1 | 1 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| RAB311 | 5.25E-05 | 0.581014558 | 0.143 | 0.071 | 0.105063019 | PPIA2 | 0.161093224 | -0.297343071 | 0.929 | 1 | 1 |
| IGFBP41 | 5.27E-05 | 0.375365932 | 0.071 | 1 | 0.105406468 | NAAA4 | 0.168117689 | 0.40538126 | 0.357 | 1 | 1 |
| MT2A9 | 0.000251038 | -0.605576228 | 0.143 | 1 | 0.50207669 | STT3A1 | 0.168117689 | 0.334317162 | 0.357 | 1 | 1 |
| COTL14 | 0.000251038 | -0.675291667 | 0.143 | 1 | 0.50207669 | NINJ12 | 0.168117689 | 0.290414924 | 0.357 | 1 | 1 |
| GFI1B | 0.00032172 | 0.484455846 | 0.286 | 0.143 | 0.643440571 | ASAH1 | 0.171950221 | -0.288391024 | 0.5 | 1 | 1 |
| MTCH21 | 0.00036319 | -0.326777924 | 0.143 | 1 | 0.72637975 | APLP21 | 0.173199393 | -0.339302172 | 0.571 | 1 | 1 |
| MPL | 0.00038504 | 0.347401743 | 0.286 | 0.143 | 0.770080244 | SLC9A3R14 | 0.175035836 | 0.393113285 | 0.786 | 1 | 1 |
| DAB22 | 0.000435432 | -0.269877257 | 0.143 | 1 | 0.870864579 | Z93241.15 | 0.1830612 | 0.559698073 | 0.357 | 1 | 1 |
| BLVRB2 | 0.000435432 | -0.472351054 | 0.143 | 1 | 0.870864579 | SLA2 | 0.1830612 | 0.443846103 | 0.357 | 1 | 1 |
| TRO | 0.000447007 | -0.257868861 | 0.071 | 0.929 | 0.894014633 | FCMR5 | 0.1830612 | 0.402955739 | 0.357 | 1 | 1 |
| SID2 | 0.000535719 | 0.264117756 | 0.071 | 0.143 | 1 | TNFSF103 | 0.1830612 | 0.285850293 | 0.357 | 1 | 1 |
| IL3211 | 0.000640618 | 0.555801884 | 0.071 | 0.929 | 1 | HSPA57 | 0.188232486 | -0.459860382 | 0.571 | 0.5 | 1 |
| OTOF | 0.000642719 | -0.260573868 | 0 | 0.143 | 1 | TSC22D11 | 0.189754925 | 0.989075814 | 0.714 | 1 | 1 |
| RNASE11 | 0.000642719 | -0.26953436 | 0 | 0.143 | 1 | HSP90B17 | 0.190362031 | 0.361663115 | 0.929 | 0.786 | 1 |
| CD142 | 0.000642719 | -0.309033581 | 0 | 0.143 | 1 | NKG78 | 0.198850029 | 0.792282447 | 0.357 | 1 | 1 |
| CD1633 | 0.000642719 | -0.327365504 | 0 | 0.143 | 1 | HIST1H2AG2 | 0.198850029 | 0.586175577 | 0.357 | 1 | 1 |
| AL35075.41 | 0.000880429 | 0.325056405 | 0.143 | 1 | 1 | UBE2I14 | 0.205143317 | 0.284248466 | 0.643 | 0.571 | 1 |
| IGHG3 | 0.000880429 | 0.275363886 | 0.143 | 1 | 1 | NUCB23 | 0.205766039 | -0.26590686 | 0.714 | 0.857 | 1 |
| TNFRSF181 | 0.000880429 | 0.271840405 | 0.143 | 1 | 1 | VIM5 | 0.206387567 | -0.86620012 | 0.929 | 0.929 | 1 |
| HIP1 | 0.000880429 | 0.253041058 | 0.143 | 1 | 1 | HIST1H2BC2 | 0.218003216 | -1.549531525 | 0.429 | 1 | 1 |
| JPT13 | 0.000987487 | -0.260933456 | 0.214 | 0.214 | 1 | C1QBP1 | 0.223117388 | 0.264954035 | 0.786 | 0.786 | 1 |
| S100A112 | 0.001277533 | -0.897813222 | 0.286 | 1 | 1 | SLC43A3 | 0.230508223 | 0.292929174 | 0.286 | 0.5 | 1 |
| CD3021 | 0.001372338 | 0.456017367 | 0.357 | 0.214 | 1 | ATF35 | 0.2354807 | -0.2817296 | 0.071 | 0.643 | 1 |
| HOXA3 | 0.0014514 | 0.749643607 | 0.429 | 0.214 | 1 | LSM5 | 0.239068643 | -0.286880296 | 0.571 | 1 | 1 |
| ADAM281 | 0.001766383 | 0.602892909 | 0.286 | 0.286 | 1 | MDH11 | 0.24004049 | 0.26859409 | 0.643 | 0.714 | 1 |
| CFAP203 | 0.002422131 | 0.45487558 | 0.5 | 0.214 | 1 | CALM23 | 0.241207351 | 0.346580853 | 0.786 | 1 | 1 |
| S100A104 | 0.002827715 | 0.398988725 | 0.286 | 0.214 | 1 | ANXA64 | 0.241266841 | 0.270519668 | 0.857 | 1 | 1 |
| EMP1 | 0.002877715 | -0.86630313 | 0 | 0.214 | 1 | IGF2BP2 | 0.254751163 | 0.262559475 | 0.429 | 0.571 | 1 |
| PDLIMI2 | 0.00305359 | 0.311522463 | 0.214 | 0.214 | 1 | GUCY1B11 | 0.254751163 | 0.259217778 | 0.429 | 0.571 | 1 |
| FES2 | 0.00339421 | -0.433240309 | 0.071 | 0.857 | 1 | CCT83 | 0.259631841 | -0.346873367 | 0.714 | 1 | 1 |
| BRI31 | 0.003558089 | -0.28558026 | 0.214 | 1 | 1 | ERG | 0.272226448 | 0.439050291 | 0.357 | 0.571 | 1 |
| IFNG-AS11 | 0.003558089 | -0.432777595 | 0.214 | 1 | 1 | GSTM3 | 0.275927711 | -0.430449371 | 0.071 | 0.643 | 1 |
| PDE4B2 | 0.00474824 | 0.402903222 | 0.143 | 0.857 | 1 | DUSP12 | 0.28017858 | 0.382839632 | 0.857 | 0.857 | 1 |
| FADS21 | 0.005364156 | 0.607105425 | 0.071 | 0.857 | 1 | PECAM13 | 0.295600413 | 0.424488946 | 0.429 | 1 | 1 |
| RASSF6 | 0.005925403 | -0.256446812 | 0.143 | 0.214 | 1 | P2RX12 | 0.295600413 | 0.381518879 | 0.429 | 0.571 | 1 |
| CD363 | 0.006421939 | -0.287014882 | 0 | 0.214 | 1 | H1F02 | 0.300556676 | 0.356518605 | 0.714 | 0.714 | 1 |
| VCAN1 | 0.006421939 | -0.386569754 | 0 | 0.214 | 1 | CD745 | 0.30121901 | 0.308319856 | 1 | 1 | 1 |
| CTSD4 | 0.006421939 | -0.419607916 | 0 | 0.214 | 1 | STMN13 | 0.346163787 | -0.305827024 | 0.857 | 1 | 1 |
| S100A95 | 0.006421939 | -0.516922421 | 0 | 0.214 | 1 | TMSB4X1 | 0.34622979 | -0.300363818 | 1 | 1 | 1 |
| CPA3 | 0.006421939 | -1.652969722 | 0 | 0.214 | 1 | C1orf1624 | 0.355364071 | -0.36814301 | 0.214 | 0.429 | 1 |
| IFITM38 | 0.006424157 | -0.288661545 | 0.214 | 0.214 | 1 | HSH2D2 | 0.355364071 | -0.464526262 | 0.214 | 0.429 | 1 |
| S100A87 | 0.007189447 | -0.500841502 | 0.071 | 0.929 | 1 | YWHAQ4 | 0.370001489 | 0.323386518 | 0.786 | 0.857 | 1 |
| HIST1H3H | 0.007199654 | -1.665657176 | 0.214 | 0.214 | 1 | IFNGR22 | 0.375947495 | -0.357167139 | 0.143 | 0.429 | 1 |
| MARCKS2 | 0.008525574 | 0.350344561 | 0.214 | 0.214 | 1 | TAL11 | 0.396772748 | -0.283900757 | 0.071 | 0.429 | 1 |
| CLEC4A1 | 0.008525574 | 0.294932208 | 0.214 | 0.214 | 1 | PNP3 | 0.396772748 | -0.431092899 | 0.071 | 0.429 | 1 |
| | 0.008525574 | 0.280449815 | 0.214 | 1 | 1 | TRBV183 | 0.405362742 | 0.274956225 | 0.071 | 0.143 | 1 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| DCTPP11 | 0.009062202 | 0.270285442 | 0.286 | 0.286 | 1 | DDIT44 | 0.410577404 | 0.637607086 | 0.286 | 0.571 | 1 |
| SLBP3 | 0.009513442 | -0.367544975 | 0.357 | 1 | 1 | AC011139.1 | 0.410577404 | 0.556202844 | 0.286 | 0.571 | 1 |
| PPA11 | 0.018900002 | -0.555888043 | 0.429 | 1 | 1 | BTK1 | 0.415937626 | 0.474678287 | 0.429 | 1 | 1 |
| MMRN1 | 0.024720817 | 0.407998566 | 0.5 | 0.429 | 1 | 13-Sep | 0.415937626 | 0.37458482 | 0.429 | 1 | 1 |
| PROM1 | 0.030652334 | 0.446484722 | 0.429 | 0.429 | 1 | PADI41 | 0.415937626 | 0.275977543 | 0.429 | 1 | 1 |
| ATIC1 | 0.032396598 | 0.369149927 | 0.286 | 0.357 | 1 | SPI1 | 0.419111728 | -0.311627013 | 0.571 | 1 | 1 |
| CST33 | 0.033518456 | -0.716407954 | 0.357 | 0.857 | 1 | RPS27L3 | 0.420073329 | 0.293497513 | 0.643 | 0.786 | 1 |
| TUBA1C | 0.034423814 | -0.303878071 | 0.429 | 1 | 1 | HOPX5 | 0.420711809 | 0.41956662 | 0.714 | 0.786 | 1 |
| IFI65 | 0.034423814 | -0.375293699 | 0.429 | 0.929 | 1 | LIMS14 | 0.420711809 | 0.256157285 | 0.714 | 0.714 | 1 |
| CYB561A32 | 0.036397291 | 0.347125317 | 0.286 | 1 | 1 | LYZ7 | 0.424304199 | -1.255917934 | 0.071 | 0.429 | 1 |
| MT-CO22 | 0.036562191 | -0.291197148 | 1 | 1 | 1 | HLA-DQB15 | 0.447123038 | -0.321620335 | 0.643 | 1 | 1 |
| DST1 | 0.037608503 | -0.281063738 | 0.357 | 1 | 1 | AL138963.310 | 0.471205493 | 0.758338177 | 0.429 | 0.643 | 1 |
| NASP | 0.037608503 | -0.283374334 | 0.357 | 1 | 1 | IGHM1 | 0.475743303 | 0.50453617 | 0.714 | 1 | 1 |
| HIST1H1B | 0.040811551 | 0.367711647 | 0.286 | 1 | 1 | CORO1A3 | 0.476106202 | 0.455438926 | 0.786 | 1 | 1 |
| SNX101 | 0.040811551 | 0.357677799 | 0.286 | 1 | 1 | FTL3 | 0.476347722 | -0.315826391 | 1 | 1 | 1 |
| JAML3 | 0.040811551 | 0.325837359 | 0.286 | 1 | 1 | 6-Jun | 0.476347722 | -0.50068325 | 0.929 | 0.929 | 1 |
| ZFP36L28 | 0.040887229 | 0.613717798 | 1 | 1 | 1 | VSIR | 0.503205099 | 0.804732729 | 0.571 | 0.929 | 1 |
| TMSB103 | 0.040887229 | -0.301062388 | 1 | 1 | 1 | HADH | 0.504673198 | 0.256011534 | 0.714 | 1 | 1 |
| MT1X3 | 0.041557134 | -0.300774295 | 0 | 0.286 | 1 | FGR3 | 0.507368704 | -0.332456943 | 0 | 0.571 | 1 |
| CDKN1A1 | 0.041557134 | -0.308776124 | 0 | 0.286 | 1 | AREG5 | 0.507368704 | -0.532525932 | 0 | 0.429 | 1 |
| CNRIP1 | 0.041557134 | -0.315349406 | 0 | 0.286 | 1 | CXCL84 | 0.507368704 | -0.744494604 | 0 | 0.429 | 1 |
| TMEM1401 | 0.04195169 | -0.376731922 | 0.143 | 0.286 | 1 | RPS4Y12 | 0.507368704 | -0.877562846 | 0 | 0.429 | 1 |
| ALDH22 | 0.043165839 | 0.284101816 | 0.429 | 0.429 | 1 | ID13 | 0.525564369 | -0.653452195 | 0.286 | 0.643 | 1 |
| LAG32 | 0.044479234 | -0.271708492 | 0.071 | 0.286 | 1 | JCHAIN2 | 0.530299542 | 0.860157132 | 0.429 | 1 | 1 |
| PLEC4 | 0.044479234 | -0.440403062 | 0.071 | 0.286 | 1 | MEF2C4 | 0.531903964 | 0.358191583 | 0.5 | 1 | 1 |
| TYMP2 | 0.044479234 | -0.630358218 | 0.071 | 0.286 | 1 | LTB6 | 0.533096905 | 0.861006905 | 0.571 | 1 | 1 |
| PMAIP15 | 0.047071752 | -0.65394588 | 0.143 | 0.786 | 1 | ILK4 | 0.533096629 | 0.658908464 | 0.571 | 1 | 1 |
| H2AFZ4 | 0.047071785 | -0.514818979 | 0.357 | 0.857 | 1 | ADA1 | 0.533096629 | 0.421104984 | 0.571 | 1 | 1 |
| P4HB1 | 0.049077884 | -0.324552634 | 0.5 | 1 | 1 | SOD23 | 0.556686708 | -0.430396923 | 0.286 | 0.643 | 1 |
| NCL4 | 0.050814421 | 0.409570383 | 0.857 | 0.857 | 1 | GATA21 | 0.562752237 | 0.494910789 | 0.5 | 1 | 1 |
| GAPDH3 | 0.050846096 | -0.311154311 | 1 | 1 | 1 | PLSCR12 | 0.588681037 | -0.427001994 | 0.286 | 0.643 | 1 |
| CCR73 | 0.051009924 | 0.804429725 | 0.286 | 1 | 1 | PCDH9 | 0.594383555 | 0.457025301 | 0.5 | 1 | 1 |
| PRAM11 | 0.051009924 | 0.489204843 | 0.286 | 1 | 1 | FBL3 | 0.595455306 | 0.369055297 | 0.571 | 1 | 1 |
| HIST1H2BH | 0.051009924 | 0.43257587 | 0.286 | 1 | 1 | SPINK2 | 0.597222903 | 0.371803727 | 0.929 | 0.857 | 1 |
| ADGRE22 | 0.051009924 | 0.316456027 | 0.286 | 1 | 1 | RHOB4 | 0.649354859 | -0.251710734 | 0.143 | 1 | 1 |
| FHIT | 0.051009924 | 0.303698722 | 0.286 | 1 | 1 | LMNA7 | 0.655087947 | -0.624965452 | 0.286 | 0.5 | 1 |
| TSPO2 | 0.056508973 | -0.391792778 | 0.857 | 0.857 | 1 | LAT22 | 0.660019129 | 0.321989744 | 0.5 | 1 | 1 |
| MTRNR2L126 | 0.056542771 | 0.375801778 | 1 | 1 | 1 | HDAC12 | 0.660945142 | 0.57188722 | 0.571 | 1 | 1 |
| CANX3 | 0.062042098 | 0.338005276 | 0.643 | 0.5 | 1 | HLA-DPA15 | 0.662471852 | 0.284083421 | 1 | 1 | 1 |
| MT-ATP86 | 0.062617127 | -0.390859049 | 0.786 | 1 | 1 | PYCARD3 | 0.69573012 | 0.449289146 | 0.714 | 0.643 | 1 |
| SRP91 | 0.062760977 | 0.334983175 | 0.929 | 1 | 1 | ITM2C1 | 0.69573012 | 0.296852931 | 0.714 | 1 | 1 |
| STOML2 | 0.067399185 | -0.261470025 | 0.5 | 1 | 1 | SLC40A12 | 0.729139833 | 0.327904568 | 0.571 | 1 | 1 |
| HMGB13 | 0.069495981 | 0.528758979 | 0.857 | 0.929 | 1 | CSF3R2 | 0.759878472 | -0.467871439 | 0.286 | 0.5 | 1 |
| PIM22 | 0.074635322 | 0.31173082 | 0.5 | 0.5 | 1 | CD381 | 0.759878472 | -0.623193109 | 0.286 | 0.5 | 1 |
| CCT22 | 0.076088482 | 0.359840983 | 0.643 | 0.571 | 1 | XBP11 | 0.762535326 | -0.322327191 | 0.429 | 0.714 | 1 |
| S100A64 | 0.076088482 | -1.064602489 | 0.643 | 0.857 | 1 | CTSA3 | 0.764100389 | 0.395502337 | 0.571 | 1 | 1 |
| CALR3 | 0.076734683 | -0.434214691 | 0.786 | 1 | 1 | PRDX14 | 0.7650747 | 0.252790409 | 0.786 | 0.857 | 1 |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| FAM30A2 | 0.076896264 | 0.830253594 | 0.929 | 1 | 1 | S100A46 | 0.765199541 | −0.380360403 | 0.929 | 1 | 1 |
| AC074327.11 | 0.079463849 | 0.422236575 | 0.214 | 0 | 1 | SELENOP | 0.798977001 | 0.354982426 | 0.5 | 1 | 1 |
| HMGB22 | 0.091010505 | −0.270674878 | 0.5 | 0.5 | 1 | RAB13 | 0.798977001 | −0.309586514 | 0.5 | 0.714 | 1 |
| TLN14 | 0.093076078 | 0.461415352 | 0.714 | 0.571 | 1 | PARP11 | 0.799548623 | 0.305669161 | 0.571 | 1 | 1 |
| PLEK6 | 0.095064538 | −0.380293639 | 0.286 | 0.857 | 1 | CD34 | 0.800490588 | 0.366503195 | 0.929 | 1 | 1 |
| SOCS21 | 0.097195437 | −0.327240472 | 0.357 | 0.929 | 1 | HLA-DQA15 | 0.827504996 | −0.382268037 | 0.071 | 0.5 | 1 |
| NPR3 | 0.101918086 | 0.36448780l | 0.643 | 0.429 | 1 | EREG3 | 0.86697208 | −0.83839364 | 0.143 | 0.571 | 1 |
| AKR1C31 | 0.101918086 | 0.264780404 | 0.643 | 0.5 | 1 | CLEC11A | 0.868244854 | −0.250586144 | 0.214 | 0.571 | 1 |
| EGFL71 | 0.102860225 | 0.41728781 | 1 | 1 | 1 | MIDN2 | 0.868244854 | −0.395107728 | 0.214 | 0.571 | 1 |
| CTSC4 | 0.108772282 | 0.284051393 | 0.429 | 0.5 | 1 | TRBC23 | 0.871889566 | 0.271012159 | 0.643 | 1 | 1 |
| PTMS3 | 0.111195669 | −0.301613345 | 0.571 | 1 | 1 | PHGDH | 0.907843012 | 0.343064382 | 0.5 | 0.786 | 1 |
| SOX44 | 0.112922045 | 0.539184083 | 0.929 | 0.786 | 1 | ETS22 | 0.907843012 | 0.269918512 | 0.5 | 0.571 | 1 |
| AP000547.3 | 0.115204865 | 0.290536625 | 0.286 | 0.429 | 1 | CLIC2 | 0.942770462 | −0.267853447 | 0.143 | 0.571 | 1 |
| ISG155 | 0.115204865 | −0.336265828 | 0.286 | 0.857 | 1 | HNRNPAB | 0.943769917 | −0.35643729 | 0.286 | 0.571 | 1 |
| STXI12 | 0.115547329 | −0.588837302 | 0.071 | 0.714 | 1 | ZEB23 | 0.944410436 | −0.268362125 | 0.429 | 0.643 | 1 |
| CYTL1 | 0.119410955 | −0.276267369 | 0.429 | 1 | 1 | SLC2A5 | 0.944626811 | 1.03090784 | 0.5 | 1 | 1 |
| GPI2 | 0.120858647 | 0.351934536 | 0.5 | 0.571 | 1 | MCM33 | 0.944626811 | 0.311437035 | 0.5 | 0.929 | 1 |
| PA2G43 | 0.122715047 | 0.425394902 | 0.643 | 0.643 | 1 | ID25 | 0.981093239 | −0.275712733 | 0.214 | 0.571 | 1 |
| APP1 | 0.123464985 | −0.2622428 | 0.214 | 0.357 | 1 | PRDX3 | 0.981582738 | 0.263296693 | 0.571 | 1 | 1 |
| PSAP1 | 0.123743939 | −0.410516978 | 1 | 1 | 1 | HIST1H1C5 | 0.981661101 | −0.96675731 | 0.786 | 0.857 | 1 |
| TFPI1 | 0.128903239 | −0.360474802 | 0.357 | 0.857 | 1 | MAFF2 | 1 | −0.279027834 | 0 | 0.5 | 1 |
| CYTOR2 | 0.131669162 | −0.389914215 | 0.143 | 0.714 | 1 | ID32 | 1 | −0.542611753 | 0 | 0.5 | 1 |
| | | | | | | Seurat Cluster 20 | | | | | |
| IGKV3-112 | 3.76E−05 | 4.322754039 | 0.059 | 1 | 0.075167118 | FKBP112 | 0.281062269 | −0.256914371 | 0.941 | 1 | 1 |
| AC233755.1 | 3.76E−05 | 1.415528802 | 0.059 | 1 | 0.075167118 | GPRC5D | 0.299830535 | −0.274578734 | 0.235 | 0.444 | 1 |
| IGHV1-69D | 3.76E−05 | 0.575371914 | 0.059 | 1 | 0.075167118 | VIM6 | 0.30581671 | 0.471838557 | 1 | 1 | 1 |
| IGKV3-202 | 0.000159262 | 3.61524327 | 0.118 | 1 | 0.3185233 | HERPUD15 | 0.331975467 | 0.417124718 | 1 | 1 | 1 |
| IGHV4-41 | 0.000255895 | 2.712257204 | 0.118 | 1 | 0.511790624 | PSME25 | 0.331975467 | −0.251664212 | 1 | 1 | 1 |
| IGLV2-143 | 0.000283759 | −2.107895422 | 0.059 | 0.111 | 0.567518734 | CCND2 | 0.348028377 | −0.302048315 | 0.176 | 0.667 | 1 |
| IGLV1-442 | 0.000508063 | 5.616991676 | 0.118 | 1 | 1 | MT-CO23 | 0.388495557 | −0.556607236 | 1 | 1 | 1 |
| IGLV3-192 | 0.000508063 | 4.960587762 | 0.118 | 1 | 1 | IGHV3-301 | 0.401386415 | −0.582979 | 0.118 | 1 | 1 |
| IGHV3-213 | 0.000508063 | 3.713089989 | 0.118 | 1 | 1 | PDIA62 | 0.418830379 | −0.349324629 | 0.941 | 1 | 1 |
| IGHV4-591 | 0.000508063 | 3.708908917 | 0.118 | 1 | 1 | KLF103 | 0.446129377 | 0.280505986 | 0.588 | 0.667 | 1 |
| IGKV1-161 | 0.000508063 | 0.443911979 | 0.118 | 1 | 1 | S100A88 | 0.460367111 | 0.906854821 | 0.059 | 0.444 | 1 |
| IGHV1-181 | 0.000899551 | 0.389899551 | 0.118 | 1 | 1 | S100A96 | 0.460367111 | 0.630815602 | 0.0.59 | 0.444 | 1 |
| IGHV1-69 | 0.001539308 | 3.353625302 | 0.176 | 1 | 1 | IGLC31 | 0.460727916 | −1.181158695 | 0.294 | 0.444 | 1 |
| IGLV1-402 | 0.002778696 | 5.154557181 | 0.176 | 1 | 1 | CITED21 | 0.48201447 | 0.307642791 | 0.706 | 1 | 1 |
| IGHV4-61 | 0.004054211 | 3.313911209 | 0.176 | 1 | 1 | GNG71 | 0.483516178 | 0.266747543 | 0.941 | 1 | 1 |
| IGKV1D-392 | 0.004054211 | 2.333309769 | 0.176 | 1 | 1 | MT-ATP64 | 0.483516178 | −0.523994923 | 1 | 1 | 1 |
| IGKV1-391 | 0.004054211 | 0.801147793 | 0.176 | 1 | 1 | IGKV3D-11 | 0.49858218 | −1.289503394 | 0.059 | 0.667 | 1 |
| IGKV1-52 | 0.004873758 | 4.395678426 | 0.176 | 0.889 | 1 | IGHV1-461 | 0.49858218 | −2.354119502 | 0.059 | 0.444 | 1 |
| RPS4Y13 | 0.007679219 | 0.250535189 | 0 | 0.222 | 1 | IGLC31 | 0.501234611 | −0.336916698 | 0.353 | 0.444 | 1 |
| IGHV3-111 | 0.007679219 | −0.444783908 | 0 | 0.222 | 1 | CXCR31 | 0.517786205 | −0.435777016 | 1 | 1 | 1 |
| IGHV3-48 | 0.007679219 | −2.644967602 | 0 | 0.222 | 1 | MT-CO32 | 0.54942434 | 0.44414378 | 0.588 | 1 | 1 |
| IGHV3-742 | 0.007679219 | −3.430826267 | 0 | 0.222 | 1 | L1NC017811 | 0.553203752 | −0.295639362 | 0.882 | 0.444 | 1 |
| IGHV7-4-11 | 0.019296532 | 4.473170586 | 0.118 | 0.667 | 1 | HIST1H1C6 | 0.553271596 | −0.338290321 | 1 | 1 | 1 |
| | | | | | | PPIA3 | | | | | |

TABLE 14-continued

| | p_val | avg_logFC | pct.1 | pct.2 | p_val_adj | | p_val | avg_logFC | pct1 | pct.2 | p_val_adj |
|---|---|---|---|---|---|---|---|---|---|---|---|
| IGHV3-661 | 0.03092198 | -0.523447975 | 0.059 | 0.222 | 1 | POU2AF1 | 0.589908897 | -0.29313772 | 1 | 1 | 1 |
| IGHV3-532 | 0.03092198 | -0.913414836 | 0.059 | 0.222 | 1 | AQP34 | 0.589908897 | -0.3633566 | 1 | 1 | 1 |
| LYZ8 | 0.031302395 | 0.493757362 | 0.059 | 0.778 | 1 | IGLV3-11 | 0.604180307 | -0.845554259 | 0.235 | 0.667 | 1 |
| CD79B2 | 0.051942468 | -0.363211516 | 0.765 | 0.889 | 1 | AC10391.310 | 0.611605943 | -0.2855993 | 0 | 0.444 | 1 |
| GAS61 | 0.069035153 | -0.307573833 | 0.176 | 0.778 | 1 | PCNA1 | 0.611605943 | -0.333565639 | 0 | 0.556 | 1 |
| IGHV1-22 | 0.07857605 | 4.978001944 | 0.294 | 1 | 1 | AC233755.2 | 0.611605943 | -0.470231136 | 0 | 0.556 | 1 |
| ATF5 | 0.082169488 | -0.261547539 | 0.118 | 0.333 | 1 | IGLV6-571 | 0.613972356 | -0.251629987 | 0.353 | 1 | 1 |
| IGHV3-232 | 0.093289434 | 2.126326917 | 0.118 | 0.778 | 1 | S100A47 | 0.663299576 | 0.526141142 | 0.588 | 0.588 | 1 |
| STMN14 | 0.096005759 | -0.356143089 | 0.412 | 0.889 | 1 | IGLC21 | 0.697726504 | 0.570627454 | 0.412 | 0.667 | 1 |
| IGKV2D-28 | 0.096704291 | -0.6105871 | 0.059 | 0.333 | 1 | MYBL2 | 0.697726504 | -0.309941858 | 0.412 | 0.667 | 1 |
| SELL5 | 0.100541146 | -0.377481154 | 0.176 | 0.778 | 1 | FOS7 | 0.701857307 | 0.612560995 | 0.529 | 0.889 | 1 |
| IGHG2 | 0.106789025 | 1.197677694 | 0.235 | 0.889 | 1 | HIST1H2BC3 | 0.703246372 | 0.296691715 | 0.588 | 1 | 1 |
| IGLV3-251 | 0.112553406 | -1.482099693 | 0 | 0.333 | 1 | H1FX6 | 0.703246372 | -0.849716283 | 0.588 | 0.778 | 1 |
| IGHG31 | 0.166850198 | -0.956672116 | 0.235 | 0.778 | 1 | SAT16 | 0.705486892 | 0.314834564 | 0.765 | 1 | 1 |
| MT-ND64 | 0.177102816 | -0.312048394 | 0.765 | 1 | 1 | S100A105 | 0.705919354 | 0.261688343 | 0.882 | 1 | 1 |
| HIST1H2AH | 0.196383345 | -0.417543874 | 0.059 | 0.667 | 1 | LGALS17 | 0.705967288 | 0.557048053 | 0.588 | 1 | 1 |
| DUSP13 | 0.213541366 | 0.385345071 | 0.706 | 0.889 | 1 | MT-CO12 | 0.746406843 | -0.585005805 | 0.941 | 1 | 1 |
| IGLV1-41 | 0.214281133 | -0.782572693 | 0.059 | 0 | 1 | ITGB14 | 0.776631816 | 0.375636068 | 1 | 1 | 1 |
| MT-CYB3 | 0.215113564 | -0.631435363 | 1 | 1 | 1 | IGHV2-51 | 0.805619664 | -0.442577078 | 0.294 | 0.667 | 1 |
| IGHA22 | 0.228925515 | 1.500884815 | 0.529 | 1 | 1 | IGLV1-511 | 0.853573675 | 0.566802055 | 0.059 | 0.556 | 1 |
| MT-ND4L4 | 0.235729053 | -0.512461236 | 1 | 1 | 1 | HIST1H2BJ1 | 0.86033021 | -0.428579439 | 0.059 | 0.556 | 1 |
| CD694 | 0.239211561 | 0.280302781 | 0.353 | 0.556 | 1 | HIST1H1D4 | 0.869681266 | -0.392169685 | 0.176 | 0.556 | 1 |
| IGKV3-152 | 0.242450398 | 2.118605348 | 0.059 | 0.667 | 1 | MT-ATP87 | 0.871549652 | -0.52737163 | 0.529 | 0.667 | 1 |
| IGKC3 | 0.25078552 | -0.488575924 | 0.529 | 1 | 1 | IGKV4-12 | 0.906620299 | -3.77774944 | 1 | 1 | 1 |
| CD3201 | 0.253110985 | -0.371984606 | 0.588 | 0.889 | 1 | AC007952.46 | 0.914012868 | -0.387430355 | 0.176 | 0.556 | 1 |
| HIST1H4C4 | 0.257623318 | -0.811565514 | 0.882 | 1 | 1 | H2AFZ5 | 0.914159411 | -0.273825729 | 0.765 | 0.778 | 1 |
| IGHA12 | 0.257623318 | -0.950091683 | 0.882 | 1 | 1 | FAM30A3 | 0.954750547 | 0.424571103 | 0.941 | 1 | 1 |
| CD746 | 0.257704686 | 0.290920802 | 1 | 1 | 1 | HIST1H1E4 | 0.95701004 | -0.255961246 | 0.294 | 0.667 | 1 |
| ATP1B31 | 0.267132917 | -0.283617607 | 0.412 | 0.778 | 1 | CANX4 | 0.95701004 | -0.480207241 | 0.882 | 1 | 1 |
| IGHG4 | 0.273781033 | 0.471755028 | 0.235 | 0.778 | 1 | PRDM13 | 1 | -0.297844123 | 0.824 | 0.889 | 1 |
| RRBP11 | 0.279412359 | -0.253434169 | 0.706 | 0.889 | 1 | SHCBP1 | 1 | -0.424897669 | 0.176 | 0.556 | 1 |

TABLE 15

| | p_val | avg_logFC | pct.1 | pct.2 | p_val_adj | | p_val | avg_logFC | pct.1 | pct.2 | p_val_adj |
|---|---|---|---|---|---|---|---|---|---|---|---|
| | | | | | Seurat Cluster 0 | | | | | | |
| C1QC | 8.94E-122 | -0.418032 | 0.727 | 0.074 | 1.79E-118 | AC020916.1 | 2.35E-12 | -0.4577463 | 0.765 | 0.229 | 4.70E-09 |
| FCGR3A | 1.27E-77 | -0.2714226 | 0.734 | 0.125 | 2.54E-74 | MYL9 | 1.26E-10 | 0.25321932 | 0.406 | 0.009 | 2.51E-07 |
| C1QB | 4.17E-76 | -0.4575751 | 0.634 | 0.099 | 8.34E-73 | TAGLN2 | 1.74E-10 | 0.31865603 | 0.858 | 0.471 | 3.48E-07 |
| HLA-DMB | 1.17E-64 | -0.2540995 | 0.293 | 0.073 | 2.34E-61 | MX1 | 3.15E-10 | 0.27496279 | 0.444 | 0.078 | 6.31E-07 |
| C1QA | 4.62E-60 | -0.3073741 | 0.648 | 0.114 | 9.24E-57 | S100A12 | 9.34E-10 | 0.33584764 | 0.934 | 0.694 | 1.87E-06 |
| AC103591.3 | 9.75E-57 | 0.27191669 | 0.794 | 0.102 | 1.95E-53 | FABP5 | 1.02E-09 | -0.5984517 | 0.679 | 0.15 | 2.03E-06 |
| P2RY13 | 2.03E-54 | -0.3020527 | 0.809 | 0.121 | 4.05E-51 | MT-CYB | 4.29E-07 | -0.2507279 | 0.964 | 0.926 | 0.00085827 |
| SMIM25 | 3.98E-42 | -0.284764 | 0.361 | 0.156 | 7.96E-39 | CTSC | 4.51E-07 | -0.3015515 | 0.736 | 0.245 | 0.00090206 |
| CCL3L1 | 5.29E-39 | -0.4084756 | 0.953 | 0.3 | 1.06E-35 | ZFP36L2 | 1.39E-06 | -0.3042871 | 0.965 | 0.48 | 0.00278484 |
| MEF2C | 5.51E-38 | -0.3576721 | 0.927 | 0.281 | 1.10E-33 | H1FX | 5.03E-05 | -0.3026965 | 0.729 | 0.531 | 0.10055574 |
| RHOB | 1.43E-35 | -0.3692985 | 0.803 | 0.168 | 2.87E-32 | SGK1 | 6.11E-05 | -0.3052721 | 0.707 | 0.232 | 0.12218812 |
| HES4 | 7.75E-35 | -0.3715166 | 0.832 | 0.214 | 1.55E-31 | MT-ND6 | 0.00013471 | -0.3371457 | 0.681 | 0.203 | 0.26941857 |
| HIST1H1D | 1.58E-34 | -0.2501897 | 0.874 | 0.251 | 3.16E-31 | APOBEC3A | 0.03868626 | 0.2635256 | 0.537 | 0.152 | 1 |
| LIPA | 2.67E-31 | -0.2962896 | 0.386 | 0.129 | 5.34E-28 | LGALS2 | 0.05053918 | 0.2610873 | 0.514 | 0.093 | 1 |
| DUSP6 | 1.23E-23 | -0.3201799 | 0.891 | 0.301 | 2.47E-20 | ALOX5AP | 0.05582648 | -0.2932865 | 0.663 | 0.225 | 1 |
| NR4A2 | 2.61E-23 | -0.253004 | 0.94 | 0.352 | 5.22E-20 | C5AR1 | 0.0957702 | -0.2803736 | 0.636 | 0.29 | 1 |
| AREG | 2.96E-16 | -0.6046328 | 1 | 0.412 | 5.92E-13 | IFITM2 | 0.28960878 | -0.2799673 | 0.885 | 0.59 | 1 |
| XIST | 7.79E-14 | -0.3638533 | 0.809 | 0.27 | 1.56E-10 | ATP1B3 | 0.4636002 | -0.369094 | 0.636 | 0.214 | 1 |
| IL1B | 7.83E-14 | -0.3537619 | 0.789 | 0.253 | 1.57E-10 | G0S2 | 0.83057327 | 0.40249797 | 0.59 | 0.214 | 1 |
| LILRB2 | 1.03E-13 | -0.3652414 | 0.566 | 0.373 | 2.05E-10 | | | | | | |
| | | | | | Seurat Cluster 1 | | | | | | |
| XIST1 | 4.37E-64 | -0.4051312 | 0.778 | 0.09 | 8.74E-61 | CH25H | 4.63E-07 | -0.2925286 | 0.539 | 0.055 | 0.00092505 |
| KLRB1 | 9.33E-35 | -0.5097924 | 0.814 | 0.169 | 1.87E-31 | HMGB1 | 1.45E-06 | -0.2952237 | 0.858 | 0.717 | 0.00289796 |
| S100A8 | 3.24E-26 | -0.8871467 | 0.382 | 0.113 | 6.47E-23 | MT2A | 1.06E-05 | -0.4842262 | 0.736 | 0.256 | 0.02126962 |
| IFI44L | 9.16E-21 | 0.27191669 | 0.328 | 0.024 | 1.83E-17 | SEC61G | 4.88E-05 | -0.2650275 | 0.835 | 0.381 | 0.09765694 |
| RGCC | 6.41E-20 | -0.2916723 | 0.803 | 0.224 | 1.28E-16 | IFITM21 | 0.00027793 | -0.2506663 | 0.736 | 0.532 | 0.55586093 |
| PTGER4 | 9.65E-18 | -0.2660795 | 0.808 | 0.236 | 1.93E-14 | H1FX1 | 0.013338 | -0.5149901 | 0.827 | 0.411 | 1 |
| ANXA1 | 2.21E-16 | -0.3315336 | 0.924 | 0.359 | 4.42E-13 | AL138963.3 | 0.04360453 | 0.26896399 | 0.548 | 0.187 | 1 |
| RPL22L1 | 5.43E-13 | -0.2595398 | 0.565 | 0.367 | 1.09E-09 | TMEM156 | 0.04675996 | -0.3065187 | 0.553 | 0.162 | 1 |
| AREG1 | 1.97E-10 | -0.451984 | 0.827 | 0.314 | 3.95E-07 | CD3G | 0.20907097 | -0.284496 | 0.782 | 0.477 | 1 |
| S100A4 | 1.88E-09 | -0.4971855 | 0.915 | 0.738 | 3.77E-06 | PRDM1 | 0.40626428 | -0.286767 | 0.733 | 0.35 | 1 |
| DUSP2 | 1.27E-08 | -0.4782212 | 0.863 | 0.359 | 2.54E-05 | | | | | | |
| | | | | | Seurat Cluster 2 | | | | | | |
| TNFSF9 | 3.98E-132 | -0.2885356 | 0.909 | 0.074 | 7.96E-129 | SNRPF | 6.75E-18 | -0.2952663 | 0.43 | 0.162 | 1.35E-14 |
| AC020916.11 | 1.46E-86 | -0.2653655 | 0.892 | 0.102 | 2.93E-83 | HSH2D | 4.26E-16 | 0.28233956 | 0.413 | 0.12 | 8.52E-13 |
| IFI27 | 1.22E-78 | 0.30714095 | 0.164 | 0.01 | 2.44E-75 | CCL3 | 7.32E-15 | -0.4415959 | 0.797 | 0.236 | 1.46E-11 |
| IFIT44L1 | 1.16E-75 | 0.43451153 | 0.227 | 0.014 | 2.32E-72 | AC245014.3 | 5.55E-10 | -0.3733872 | 0.453 | 0.115 | 1.11E-06 |
| GZMK | 1.91E-59 | -0.444997 | 0.771 | 0.119 | 3.83E-56 | ISG15 | 1.74E-07 | 0.2538495 | 0.486 | 0.185 | 0.00034795 |
| XCL2 | 2.60E-57 | -0.3684424 | 0.838 | 0.116 | 5.19E-54 | GZMA | 5.41E-07 | 0.33219671 | 0.996 | 0.705 | 0.00108159 |
| XCL1 | 6.63E-51 | -0.6817768 | 0.858 | 0.152 | 1.33E-47 | IL7R | 6.21E-07 | -0.6216748 | 0.663 | 0.158 | 0.00124281 |
| CCL4L2 | 7.77E-50 | -0.621651 | 0.825 | 0.119 | 1.55E-46 | IFI6 | 7.08E-07 | 0.34798704 | 0.462 | 0.102 | 0.00141569 |
| TENT5C | 1.22E-43 | -0.2796355 | 0.899 | 0.213 | 2.44E-40 | MAP3K8 | 2.43E-06 | -0.2554628 | 0.803 | 0.322 | 0.00485576 |
| S100A8I | 1.74E-43 | -0.4546602 | 0.823 | 0.137 | 3.47E-40 | GADD45B | 4.79E-06 | -0.2970275 | 0.778 | 0.297 | 0.009583 |
| COTL1 | 9.23E-40 | -0.3194851 | 0.875 | 0.206 | 1.85E-36 | TUBB4B | 0.00012082 | -0.2568677 | 0.525 | 0.178 | 0.24163076 |
| ZBP1 | 4.75E-39 | 0.2576169 | 0.328 | 0.13 | 9.47E-36 | CCL4 | 0.002782 | -0.5518276 | 0.998 | 0.573 | 1 |

TABLE 15-continued

| | p_val | avg_logFC | pct.1 | pct.2 | p_val_adj | | p_val | avg_logFC | pct.1 | pct.2 | p_val_adj |
|---|---|---|---|---|---|---|---|---|---|---|---|
| TNF | 7.13E-27 | -0.3365811 | 0.631 | 0.056 | 1.43E-23 | HBA2 | 0.00415507 | 0.28270697 | 0.101 | 0.003 | 1 |
| CCL3L11 | 5.02E-22 | -0.2796582 | 0.695 | 0.073 | 1.00E-18 | HBB | 0.54290565 | 0.51817739 | 0.395 | 0.015 | 1 |
| LINC02446 | 1.30E-18 | -0.2692474 | 0.818 | 0.239 | 2.61E-15 | | | | | | |
| | | | | | | Seurat Cluster 3 | | | | | |
| TNFAIP6 | 3.18E-72 | -0.2725952 | 0.904 | 0.118 | 6.36E-69 | TMEM176A | 5.76E-06 | -0.2624806 | 0.64 | 0.451 | 1 |
| PPBP | 2.64E-33 | -0.4000851 | 0.321 | 0.087 | 5.28E-30 | IFITM3 | 0.00052193 | -0.2655815 | 0.959 | 0.847 | 1 |
| AC10591.31 | 5.67E-13 | -0.4560859 | 0.84 | 0.275 | 1.13E-09 | HLA-DRB5 | 0.02522165 | -0.2597936 | 0.901 | 0.651 | 1 |
| FCGR3A1 | 1.18E-07 | -0.2809197 | 0.664 | 0.172 | 0.00023584 | HLA-DPB1 | 0.2864815 | -0.2816441 | 0.95 | 0.638 | 1 |
| WARS | 4.12E-06 | -0.2640052 | 0.875 | 0.392 | 0.00823387 | CALHM6 | 0.80937266 | -0.2527273 | 0.904 | 0.564 | 1 |
| | | | | | | Seurat Cluster 4 | | | | | |
| GZMA1 | 1.22E-69 | -0.3152751 | 0.937 | 0.117 | 2.43E-66 | MT-CO3 | 0.00056722 | -0.2665439 | 1 | 0.997 | 1 |
| TRBV5-5 | 2.12E-66 | 0.25276451 | 0.124 | 0.003 | 4.23E-63 | HMGB11 | 0.00059017 | -0.2521351 | 0.98 | 0.878 | 1 |
| TRAV38-2DV8 | 3.97E-46 | -0.2571413 | 0.783 | 0.021 | 7.94E-43 | S100A6 | 0.00245604 | -0.3350419 | 0.982 | 0.948 | 1 |
| TRBV5-1 | 5.60E-12 | -0.2644149 | 0.396 | 0.091 | 1.12E-08 | ATP5MC3 | 0.00798083 | -0.2727064 | 0.735 | 0.509 | 1 |
| PRDX1 | 5.44E-10 | -0.3032759 | 0.939 | 0.374 | 1.09E-06 | ABRACL | 0.01109681 | -0.259011 | 0.952 | 0.491 | 1 |
| S100A11 | 1.36E-09 | -0.4318213 | 0.907 | 0.338 | 2.72E-06 | MT2A1 | 0.01461511 | -0.753668 | 0.763 | 0.491 | 1 |
| COTL11 | 1.98E-08 | -0.3421936 | 0.904 | 0.821 | 3.95E-05 | H1FX2 | 0.02179396 | -0.4455924 | 0.937 | 0.504 | 1 |
| TRAV12-2 | 3.67E-08 | -0.2569758 | 0.553 | 0.034 | 7.35E-05 | SH2D1A | 0.02220763 | -0.295314 | 0.533 | 0.156 | 1 |
| TRBV29-1 | 2.00E-06 | 0.27143995 | 0.384 | 0.01 | 0.00399593 | DUSP21 | 0.02591572 | -0.3152462 | 0.927 | 0.527 | 1 |
| ERH | 2.06E-06 | -0.2637981 | 0.583 | 0.366 | 0.00412451 | S100A82 | 0.03523702 | -0.5715622 | 0.508 | 0.104 | 1 |
| MIR4435-2HG | 1.72E-05 | -0.3248017 | 0.732 | 0.216 | 0.0348748 | TRBV7-9 | 0.04802129 | -0.3411901 | 0.48 | 0.06 | 1 |
| S100A41 | 3.93E-05 | -0.2778348 | 0.997 | 0.977 | 0.07851922 | HSPD1 | 0.12483761 | -0.2648372 | 0.902 | 0.483 | 1 |
| MT-CO1 | 4.07E-05 | -0.3471755 | 1 | 1 | 0.08148604 | KLRB11 | 0.22423523 | -0.3493222 | 0.775 | 0.481 | 1 |
| PFN1 | 0.0001659 | -0.2740778 | 0.997 | 0.987 | 0.33179006 | MT1X | 0.33604698 | -0.2871904 | 0.596 | 0.21 | 1 |
| PPIA | 0.0002323 | -0.2527187 | 0.97 | 0.932 | 0.46459488 | CORO1B | 0.34005355 | -0.2982902 | 0.808 | 0.522 | 1 |
| GAPDH | 0.00024996 | -0.3133406 | 0.99 | 0.935 | 0.4999218 | VDAC1 | 0.34523689 | -0.2632472 | 0.697 | 0.353 | 1 |
| IL32 | 0.00028043 | -0.3295136 | 1 | 0.971 | 0.56085457 | STMN1 | 0.46450804 | -0.2811464 | 0.578 | 0.114 | 1 |
| ACTB | 0.0002853 | -0.3069968 | 1 | 1 | 0.5706013 | TXN | 0.79397931 | -0.3021872 | 0.874 | 0.545 | 1 |
| TRBV10-3 | 0.00034026 | -0.3294473 | 0.437 | 0.021 | 0.68052584 | | | | | | |
| | | | | | | Seurat Cluster 5 | | | | | |
| IGLV2-8 | 1.54E-118 | -0.5271091 | 0.917 | 0.016 | 3.08E-115 | IGLV2-14 | 6.49E-11 | -0.5533299 | 0.68 | 0.075 | 1.30E-07 |
| IGLV6-57 | 1.38E-106 | -0.3837683 | 0.867 | 0.021 | 2.76E-103 | IGLV3-21 | 8.87E-11 | -0.2832448 | 0.38 | 0.033 | 1.77E-07 |
| IGKV2-29 | 1.77E-93 | -0.5655212 | 0.947 | 0.049 | 3.54E-90 | PNOC | 9.14E-11 | -0.2924034 | 0.73 | 0.138 | 1.83E-07 |
| MT2A2 | 3.77E-91 | -0.7272862 | 0.96 | 0.061 | 7.55E-88 | H1FX3 | 1.79E-09 | -0.4806624 | 0.923 | 0.354 | 3.58E-06 |
| IGLV1-40 | 6.71E-84 | -0.4087359 | 0.927 | 0.047 | 1.34E-80 | SOX4 | 2.40E-09 | 0.55149533 | 0.637 | 0.035 | 4.81E-06 |
| IGLV2-11 | 2.65E-81 | -0.3748275 | 0.87 | 0.035 | 5.30E-78 | S100A42 | 2.92E-09 | -0.5953525 | 0.927 | 0.354 | 5.85E-06 |
| CST3 | 1.52E-80 | -0.4171102 | 0.897 | 0.04 | 3.05E-77 | WDR74 | 4.34E-08 | -0.2994122 | 0.867 | 0.333 | 8.68E-05 |
| IGLV1-51 | 7.66E-66 | -0.6322691 | 0.853 | 0.04 | 1.53E-62 | SMIM14 | 1.61E-07 | -0.3576151 | 0.763 | 0.214 | 0.00032199 |
| IGHV3-49 | 3.26E-56 | 0.25218365 | 0.803 | 0.019 | 6.52E-53 | AC10591.32 | 2.84E-07 | -0.3160666 | 0.82 | 0.308 | 0.00056792 |
| IGKV1-9 | 3.39E-49 | -0.2916503 | 0.74 | 0.021 | 6.78E-46 | CD79B | 3.17E-07 | -0.2567043 | 0.983 | 0.453 | 0.00063481 |
| CNFN | 6.25E-49 | -0.3358497 | 0.93 | 0.143 | 1.25E-45 | AC020916.12 | 3.41E-07 | -0.2581518 | 0.65 | 0.075 | 0.00068213 |
| XIST2 | 5.05E-47 | -0.414309 | 0.997 | 0.207 | 1.01E-43 | PSMA3 | 1.03E-06 | 0.27568571 | 0.423 | 0.061 | 0.00206674 |
| IGHV1-3 | 8.89E-44 | -0.2768013 | 0.773 | 0.021 | 1.78E-40 | IGKV3-20 | 1.46E-06 | -0.8342068 | 0.647 | 0.08 | 0.00291414 |
| IF44L2 | 8.54E-42 | 0.4011261 | 0.22 | 0.021 | 1.71E-38 | FAM30A | 3.90E-06 | -0.3612965 | 0.757 | 0.23 | 0.00779826 |
| NCR3 | 7.83E-40 | -0.2547645 | 0.873 | 0.124 | 1.57E-36 | IGLV3-1 | 1.25E-05 | -0.6484364 | 0.617 | 0.049 | 0.02491545 |
| LINC01781 | 2.87E-37 | -0.4873064 | 0.957 | 0.209 | 5.74E-34 | MT-ND4L | 8.80E-05 | 0.25399291 | 1 | 0.93 | 0.17596217 |
| PPBP1 | 1.49E-34 | -0.4242453 | 0.663 | 0.028 | 2.97E-31 | S100A61 | 0.00034357 | -0.366883 | 0.877 | 0.406 | 0.68713307 |
| HSPD11 | 7.23E-29 | -0.2676769 | 0.907 | 0.204 | 1.45E-25 | IGKV3-11 | 0.00105717 | -0.3894642 | 0.603 | 0.068 | 1 |

TABLE 15-continued

| | p_val | avg_logFC | pct.1 | pct.2 | p_val_adj | | p_val | avg_logFC | pct.1 | pct.2 | p_val_adj |
|---|---|---|---|---|---|---|---|---|---|---|---|
| LGALS1 | 7.86E-28 | -0.3269437 | 0.84 | 0.146 | 1.57E-24 | HSPA5 | 0.00166982 | 0.36890767 | 0.72 | 0.296 | 1 |
| GZMB | 1.13E-27 | 0.48284145 | 0.283 | 0.002 | 2.25E-24 | TIMP1 | 0.0615803 | -0.2696278 | 0.44 | 0.047 | 1 |
| GADD45B1 | 4.92E-26 | 0.32849238 | 0.893 | 0.232 | 9.84E-23 | IGKV3-15 | 0.08817144 | -0.5925174 | 0.59 | 0.099 | 1 |
| HIST1H1D1 | 5.37E-23 | -0.2695228 | 0.9 | 0.228 | 1.07E-19 | AC233755.1 | 0.12564322 | -0.3402054 | 0.303 | 0.023 | 1 |
| GPR183 | 3.32E-18 | -0.2596122 | 0.877 | 0.239 | 6.63E-15 | HMGB2 | 0.22575392 | -0.3680774 | 0.65 | 0.204 | 1 |
| VDAC11 | 2.44E-14 | -0.259065 | 0.76 | 0.143 | 4.87E-11 | TMEM1561 | 0.32477835 | -0.3540786 | 0.713 | 0.298 | 1 |
| LINC01480 | 5.62E-14 | -0.3784361 | 0.74 | 0.124 | 1.12E-10 | IGHV4-39 | 0.42234406 | -0.3638993 | 0.497 | 0.035 | 1 |
| PA2G4 | 1.78E-13 | -0.3128779 | 0.82 | 0.218 | 3.56E-10 | IGKC | 0.4510412 | -0.3954849 | 0.667 | 0.317 | 1 |
| S100A10 | 3.70E-13 | -0.4859162 | 0.953 | 0.345 | 7.39E-10 | COTL12 | 0.48280412 | -0.344594 | 0.727 | 0.399 | 1 |
| S100A83 | 5.53E-13 | -1.1892745 | 0.403 | 0.131 | 1.11E-09 | IFITM22 | 0.54284166 | -0.3139542 | 0.767 | 0.383 | 1 |
| ID3 | 1.04E-11 | -0.3936996 | 0.71 | 0.106 | 2.07E-08 | PLPP5 | 0.8393866 | -0.33547 | 0.693 | 0.317 | 1 |
| HIST1H1E | 3.19E-11 | -0.366242 | 0.987 | 0.39 | 6.37E-08 | HIST1H4C | 0.89814909 | -0.2600485 | 0.677 | 0.298 | 1 |
| | | | | | | Seurat Cluster 6 | | | | | |
| TRBV6-2 | 3.49E-60 | 0.38040707 | 0.903 | 0.005 | 6.98E-57 | APOBEC3G | 3.77E-11 | -0.2591903 | 0.387 | 0.02 | 7.53E-08 |
| PRDX11 | 1.52E-57 | -0.257429 | 0.984 | 0.049 | 3.03E-54 | TRBV12-3 | 1.27E-10 | -0.253282 | 0.145 | 0.005 | 2.54E-07 |
| JAML | 3.09E-54 | -0.302276 | 0.962 | 0.039 | 6.17E-51 | PRF1 | 1.27E-10 | -0.3722485 | 0.661 | 0.049 | 2.55E-07 |
| YWHAQ | 6.78E-49 | 0.32556495 | 0.968 | 0.069 | 1.36E-45 | CTSW | 1.74E-10 | -0.6266122 | 0.355 | 0.093 | 3.48E-07 |
| CORO1B1 | 1.50E-47 | -0.3904933 | 0.957 | 0.078 | 3.00E-44 | SGK11 | 3.70E-10 | -0.2776648 | 0.36 | 0.103 | 7.41E-07 |
| IFNG | 3.50E-46 | -0.3849829 | 0.844 | 0.049 | 6.99E-43 | SRP9 | 8.39E-10 | -0.290805 | 0.36 | 0.088 | 1.68E-06 |
| ATP2B1-AS1 | 5.53E-46 | -0.3222308 | 0.973 | 0.083 | 1.11E-42 | IFNG-AS1 | 6.38E-10 | -0.2592611 | 0.661 | 0.029 | 1.28E-05 |
| JPT1 | 6.60E-46 | -0.3661186 | 0.962 | 0.074 | 1.32E-42 | MIF | 6.44E-09 | -0.3913002 | 0.78 | 0.157 | 1.29E-05 |
| GZMK1 | 1.19E-45 | -0.7365507 | 0.989 | 0.098 | 2.39E-42 | PRDM11 | 6.83E-09 | 0.2644473 | 0.919 | 0.348 | 1.37E-05 |
| CTSC1 | 8.58E-44 | -0.2578365 | 0.984 | 0.103 | 1.72E-40 | IDH2 | 3.16E-08 | 0.38140504 | 0.683 | 0.049 | 6.32E-05 |
| Z93241.1 | 9.45E-44 | -0.4950503 | 0.952 | 0.074 | 1.89E-40 | ENC1 | 3.49E-08 | -0.2847398 | 0.14 | 0.044 | 6.98E-05 |
| KLF10 | 1.38E-43 | -0.4236013 | 0.973 | 0.093 | 2.77E-40 | RRM1 | 3.83E-08 | 0.34130183 | 0.672 | 0.034 | 7.65E-05 |
| ADTRP | 4.67E-43 | -0.424142 | 0.124 | 0.034 | 9.34E-40 | TRBV20-1 | 6.84E-08 | -0.5602933 | 0.376 | 0.069 | 0.0001369 |
| EGR1 | 1.70E-40 | -0.5904567 | 0.952 | 0.088 | 3.40E-37 | HMGB12 | 1.52E-07 | -0.5019731 | 0.575 | 0.485 | 0.00030388 |
| ID1 | 2.69E-39 | -0.2838278 | 0.876 | 0.025 | 5.39E-36 | HIST1H2BC | 1.66E-07 | -0.3834393 | 0.237 | 0.034 | 0.00033275 |
| TUBA1B | 4.02E-39 | -0.4062606 | 1 | 0.137 | 8.04E-36 | CCL41 | 2.30E-07 | -0.9450276 | 0.441 | 0.078 | 0.00045997 |
| GZMA2 | 7.88E-39 | -0.7532343 | 0.93 | 0.093 | 1.58E-35 | KLRG1 | 3.01E-06 | -0.4544733 | 0.409 | 0.098 | 0.00602135 |
| NOLC1 | 2.77E-38 | -0.2777652 | 0.129 | 0.044 | 5.55E-35 | HNRNPF | 3.59E-06 | 0.28240024 | 0.645 | 0.029 | 0.00717831 |
| ATF5 | 1.00E-37 | 0.2640318 | 0.145 | 0.005 | 2.01E-34 | DUSP22 | 4.44E-06 | -0.5131936 | 0.978 | 0.402 | 0.00888219 |
| PDCD5 | 1.98E-37 | -0.4605915 | 0.882 | 0.078 | 3.96E-34 | CST7 | 5.64E-06 | -0.3643069 | 0.688 | 0.093 | 0.01127941 |
| LAT | 1.47E-36 | -0.3357465 | 0.989 | 0.142 | 2.94E-33 | CCL4L21 | 1.60E-05 | -0.2833039 | 0.188 | 0.015 | 0.03201661 |
| UBA5 | 2.84E-36 | 0.25565673 | 0.758 | 0.01 | 5.69E-33 | HLA-DRA | 1.92E-05 | -0.3720366 | 0.29 | 0.039 | 0.03844229 |
| SELL | 1.58E-34 | -0.2621794 | 0.957 | 0.127 | 3.16E-31 | CITED2 | 1.99E-05 | -0.4256218 | 0.694 | 0.113 | 0.03973177 |
| CYTOR | 5.43E-34 | -0.3132971 | 0.935 | 0.108 | 1.09E-30 | HSPE1 | 4.01E-05 | -0.3490033 | 0.419 | 0.083 | 0.08018681 |
| HIST1H4C1 | 1.08E-32 | -0.5880159 | 0.984 | 0.157 | 2.16E-29 | ANXA11 | 6.92E-05 | 0.28888216 | 0.651 | 0.069 | 0.13849447 |
| MIR4435-2HG1 | 6.60E-32 | -0.273476 | 0.726 | 0.039 | 1.32E-28 | LDHA | 9.15E-05 | -0.3318289 | 0.78 | 0.235 | 0.1829282 |
| CDC25B | 6.50E-31 | 0.30210775 | 0.892 | 0.083 | 1.30E-27 | TUFM | 0.00011023 | 0.27165287 | 0.984 | 0.554 | 0.22046147 |
| ATAD5 | 1.39E-30 | 0.279634336 | 0.145 | 0 | 2.78E-27 | FTH1 | 0.00011903 | 0.40356697 | 0.409 | 0.039 | 0.23805346 |
| CCND2 | 1.33E-29 | 0.279634336 | 0.903 | 0.108 | 2.67E-26 | NRIP1 | 0.00017523 | 0.27312205 | 0.328 | 0.01 | 0.35046335 |
| MX11 | 4.81E-29 | 0.52361839 | 0.188 | 0.015 | 9.63E-26 | PSMB9 | 0.00017676 | -0.5446004 | 0.446 | 0.118 | 0.35352323 |
| PSMA4 | 8.02E-29 | -0.2783888 | 0.866 | 0.069 | 1.60E-25 | GBP1 | 0.00023046 | -0.2863188 | 0.559 | 0.059 | 0.46092668 |
| EIF4A3 | 1.72E-28 | -0.280785 | 0.887 | 0.093 | 3.43E-25 | DTHD1 | 0.00028 1697 | -0.2834755 | 0.296 | 0.054 | 1 |
| PSMB2 | 5.72E-27 | 0.26750866 | 0.21 | 0.039 | 1.14E-23 | RAN | 0.00099982 | -0.2719777 | 0.473 | 0.152 | 1 |
| IFI61 | 1.20E-26 | 0.26134328 | 0.21 | 0.039 | 2.41E-23 | NCF1 | 0.00136081 | -0.3380007 | 0.435 | 0.054 | 1 |
| TGFBR3 | 2.71E-26 | -0.3212826 | 0.199 | 0.054 | 5.42E-23 | MIR22HG | 0.00147834 | -0.3083995 | 0.602 | 0.034 | 1 |
| TRAC | 7.15E-25 | 0.33856508 | 0.22 | 0.02 | 1.43E-21 | CD7 | 0.00163636 | 0.27306621 | 0.629 | 0.074 | 1 |
| HLA-DRB1 | 1.00E-24 | -0.4793362 | 0.903 | 0.132 | 2.00E-21 | NKG7 | 0.00173433 | -0.5447433 | 0.586 | 0.093 | 1 |

TABLE 15-continued

| | p_val | avg_logFC | pct.1 | pct.2 | p_val_adj | | p_val | avg_logFC | pct.1 | pct.2 | p_val_adj |
|---|---|---|---|---|---|---|---|---|---|---|---|
| LST1 | 2.28E-24 | -0.3077632 | 0.554 | 0.02 | 4.56E-21 | BCL2A1 | 0.00175957 | -0.3903807 | 0.613 | 0.049 | 1 |
| AC02916.13 | 2.97E-24 | -0.3046117 | 0.586 | 0.044 | 5.93E-21 | GALM | 0.00221424 | -0.3219767 | 0.43 | 0.044 | 1 |
| TSHZ2 | 5.72E-24 | 0.35753404 | 0.882 | 0.127 | 1.14E-20 | CALU | 0.00306953 | -0.3118233 | 0.435 | 0.044 | 1 |
| CCL5 | 6.46E-21 | -0.4264455 | 0.919 | 0.176 | 1.29E-17 | HSPA8 | 0.00424648 | -0.3369678 | 0.516 | 0.216 | 1 |
| S100A101 | 7.49E-21 | -0.4493582 | 0.946 | 0.201 | 1.50E-17 | TMSB4X | 0.00452586 | 0.32817996 | 0.989 | 0.569 | 1 |
| IFI44L3 | 7.99E-21 | 0.60827709 | 0.247 | 0.025 | 1.60E-17 | MAL | 0.01160955 | -0.2631215 | 0.457 | 0.059 | 1 |
| TNF1 | 4.25E-20 | -0.3627714 | 0.258 | 0.064 | 8.50E-17 | CD69 | 0.0249701 | -0.3681255 | 0.919 | 0.75 | 1 |
| HSH2D1 | 4.64E-20 | 0.25975144 | 0.253 | 0.025 | 9.27E-17 | TIMP11 | 0.04961663 | -0.2646063 | 0.527 | 0.049 | 1 |
| H2AFV | 3.50E-19 | 0.33963601 | 0.844 | 0.127 | 7.00E-16 | CRTAM | 0.05005667 | -0.3350929 | 0.183 | 0.034 | 1 |
| TOMM40 | 6.38E-19 | 0.38250689 | 0.226 | 0 | 1.28E-15 | NCL | 0.06078309 | -0.2758884 | 0.575 | 0.26 | 1 |
| MT2A3 | 1.93E-18 | -0.400958 | 0.812 | 0.088 | 3.85E-15 | ZFP36 | 0.06531404 | -0.2654109 | 0.989 | 0.608 | 1 |
| TRBC1 | 4.99E-18 | 0.30483404 | 0.274 | 0.049 | 9.97E-15 | TRBV9 | 0.06742527 | -0.2728394 | 0.296 | 0.015 | 1 |
| AC10591.33 | 1.09E-17 | -0.5608945 | 0.301 | 0.152 | 2.18E-14 | PFN11 | 0.09123936 | -0.3691796 | 0.737 | 0.289 | 1 |
| TRBV4-2 | 1.11E-17 | 0.40943188 | 0.581 | 0.01 | 2.21E-14 | HNRNPA2B1 | 0.09868096 | -0.2568407 | 0.774 | 0.569 | 1 |
| MARCKSL1 | 1.38E-17 | -0.2521551 | 0.489 | 0.029 | 2.76E-14 | AREG2 | 0.10891259 | -0.5844084 | 0.608 | 0.108 | 1 |
| C1QBP | 2.92E-17 | 0.31731432 | 0.753 | 0.034 | 5.84E-14 | ALG5 | 0.13222451 | 0.25118828 | 0.538 | 0.015 | 1 |
| MCM6 | 3.14E-17 | 0.37520131 | 0.737 | 0.01 | 6.28E-14 | SNRPG | 0.13703866 | -0.353354 | 0.608 | 0.113 | 1 |
| SNAP23 | 1.45E-16 | 0.25409026 | 0.263 | .001 | 2.90E-13 | MT-ND61 | 0.13711437 | -0.5033379 | 0.731 | 0.289 | 1 |
| ANXA2R | 2.28E-16 | -0.3976237 | 0.763 | 0.054 | 4.55E-13 | NR4A21 | 0.20335228 | -0.7508861 | 0.591 | 0.23 | 1 |
| GTF3C6 | 3.58E-16 | -0.3561281 | 0.742 | 0.044 | 7.16E-13 | CANX | 0.29290559 | -0.3457761 | 0.532 | 0.123 | 1 |
| MAP3K81 | 4.31E-16 | -0.2740125 | 0.296 | 0.074 | 8.61E-13 | MT-ATP8 | 0.32737376 | -0.4809918 | 1 | 0.681 | 1 |
| ITM2A | 5.46E-16 | 0.39827073 | 0.801 | 0.108 | 1.09E-12 | HSPAS1 | 0.36685604 | -0.4202657 | 0.694 | 0.397 | 1 |
| TRBV24-1 | 4.27E-15 | -0.2513829 | 0.269 | 0.015 | 8.53E-12 | HACD3 | 0.61063573 | 0.28996237 | 0.306 | 0.015 | 1 |
| MAFF | 7.51E-15 | -0.2514316 | 0.742 | 0.039 | 1.50E-11 | CORO1A | 0.62420497 | -0.3769576 | 0.581 | 0.176 | 1 |
| HIST1H1D2 | 3.87E-14 | -0.3904309 | 1 | 0.304 | 7.73E-11 | PASK | 0.66560219 | -0.3361597 | 0.5 | 0.039 | 1 |
| PPA1 | 9.45E-14 | 0.27084431 | 0.731 | 0.039 | 1.89E-10 | CD8A | 0.6707684 | -0.302769 | 0.548 | 0.078 | 1 |
| TRBV19 | 6.73E-13 | 0.27054273 | 0.688 | 0.015 | 1.35E-09 | TMPO | 0.74265862 | 0.64558196 | 0.511 | 0.044 | 1 |
| DNMT1 | 7.10E-13 | -0.281659 | 0.737 | 0.054 | 1.42E-09 | TUBA4A | 0.81939869 | -0.2837867 | 0.559 | 0.127 | 1 |
| IL7R1 | 8.45E-13 | 0.68510013 | 1 | 0.451 | 1.69E-09 | MIR181A1HG | 0.8980611 | -0.3804386 | 0.543 | 0.088 | 1 |
| ACAT2 | 1.54E-12 | -0.2798823 | 0.715 | 0.034 | 3.07E-09 | TIMM50 | 0.95098386 | 0.32435544 | 0.505 | 0.015 | 1 |
| RPN1 | 1.57E-12 | 0.32585792 | 0.753 | 0.083 | 3.14E-09 | | | | | | |

Seurat Cluster 7

| | p_val | avg_logFC | pct.1 | pct.2 | p_val_adj | | p_val | avg_logFC | pct.1 | pct.2 | p_val_adj |
|---|---|---|---|---|---|---|---|---|---|---|---|
| HLA-DQA1 | 1.98E-14 | -0.2689229 | 0.894 | 0.198 | 3.96E-11 | S100A84 | 0.00159655 | -0.4551409 | 0.451 | 0.104 | 1 |
| KLRB12 | 2.08E-12 | -0.3414921 | 0.331 | 0.129 | 4.15E-09 | PPBP2 | 0.01141139 | 0.3277552 | 0.57 | 0.03 | 1 |
| TRGV2 | 4.46E-11 | -0.2674919 | 0.894 | 0.233 | 8.91E-08 | GNIY | 0.0262912 | -0.4790033 | 0.782 | 0.317 | 1 |
| CCL4L22 | 2.25E-08 | -0.6311913 | 0.972 | 0.337 | 4.50E-05 | IL7R2 | 0.31402829 | -0.270252 | 0.81 | 0.436 | 1 |
| XCL11 | 6.21E-07 | 0.49983958 | 0.725 | 0.129 | 0.00124237 | CCL42 | 0.61699665 | -0.3361786 | 1 | 0.757 | 1 |
| ANXA2 | 3.39E-06 | 0.30753489 | 0.88 | 0.366 | 0.00678622 | GZMB1 | 0.67874492 | -0.4214924 | 0.704 | 0.312 | 1 |
| AL138963.31 | 1.07E-05 | 0.25375322 | 0.415 | 0.163 | 0.02139786 | GZMH | 0.8519085 | -0.299485 | 0.923 | 0.609 | 1 |
| TRBC11 | 0.00021725 | -0.2643921 | 0.521 | 0.337 | 0.43449351 | PLEK | 0.92333037 | -0.2793711 | 0.908 | 0.535 | 1 |

Seurat Cluster 8

| | p_val | avg_logFC | pct.1 | pct.2 | p_val_adj | | p_val | avg_logFC | pct.1 | pct.2 | p_val_adj |
|---|---|---|---|---|---|---|---|---|---|---|---|
| IL6 | 2.10E-37 | 0.30277417 | 0.898 | 0.011 | 4.19E-34 | CD163 | 0.00774364 | -0.3073751 | 0.943 | 0.414 | 1 |
| STAB1 | 2.08E-20 | 0.29974668 | 0.205 | 0.011 | 4.17E-17 | HSPE11 | 0.00981685 | -0.296381 | 0.932 | 0.391 | 1 |
| CD691 | 2.79E-15 | -0.2544464 | 0.875 | 0.126 | 5.57E-12 | ETS2 | 0.01647712 | -0.2835631 | 0.875 | 0.695 | 1 |
| AREG3 | 2.12E-10 | -0.266209 | 0.989 | 0.282 | 4.23E-07 | IGSF6 | 0.01846499 | 0.25678201 | 0.898 | 0.667 | 1 |
| CCL20 | 5.19E-08 | 0.28071251 | 0.455 | 0.011 | 0.00010373 | TIMP12 | 0.02488218 | -0.3533118 | 1 | 0.989 | 1 |
| HLA-DRB51 | 4.42E-05 | 0.35337295 | 0.909 | 0.552 | 0.08849479 | SULT1A1 | 0.02835858 | 0.28582177 | 0.727 | 0.293 | 1 |
| MT-ATP81 | 9.29E-05 | 0.26173942 | 1 | 0.534 | 0.18572283 | HPRT1 | 0.03507271 | -0.2665514 | 0.568 | 0.264 | 1 |
| XIST3 | 0.00013229 | -0.2871152 | 0.875 | 0.282 | 0.26457324 | S100A85 | 0.0370919 | -0.2778901 | 0.955 | 0.897 | 1 |

TABLE 15-continued

| | p_val | avg_logFC | pct.1 | pct.2 | p_val_adj | | p_val | avg_logFC | pct.1 | pct.2 | p_val_adj |
|---|---|---|---|---|---|---|---|---|---|---|---|
| FERMT3 | 0.00021202 | -0.2882889 | 0.545 | 0.385 | 0.4204426 | H1FX4 | 0.04507163 | -0.2726025 | 0.648 | 0.471 | 1 |
| HLA-DPB11 | 0.00022052 | 0.31532028 | 0.989 | 0.724 | 0.44104292 | RPS27L | 0.05451594 | -0.264178 | 0.966 | 0.799 | 1 |
| MT2A4 | 0.00023692 | -0.3626535 | 1 | 0.977 | 0.47384447 | MTRNR2L12 | 0.05760253 | 0.27674092 | 0.989 | 0.862 | 1 |
| RNF144B | 0.00037757 | 0.32282509 | 0.943 | 0.471 | 0.75513695 | SLC25A25 | 0.06546698 | -0.2972673 | 0.773 | 0.58 | 1 |
| CD74 | 0.00047452 | 0.34540536 | 0.989 | 0.983 | 0.94904371 | FBP1 | 0.09117027 | -0.247241 | 0.75 | 0.575 | 1 |
| CCT8 | 0.00052393 | -0.264117 | 0.545 | 0.379 | 1 | SSR4 | 0.09176755 | -0.2723833 | 0.886 | 0.69 | 1 |
| AL.138963.32 | 0.00055646 | 0.49230975 | 0.42 | 0.144 | 1 | JAML1 | 0.18387421 | 0.28284613 | 0.648 | 0.23 | 1 |
| C1QC1 | 0.00063378 | -0.3610573 | 0.977 | 0.425 | 1 | XRCC5 | 0.24623558 | -0.2532583 | 0.92 | 0.477 | 1 |
| GSTP1 | 0.00085525 | -0.2792257 | 0.977 | 0.948 | 1 | MT1E | 0.26387712 | -0.5262534 | 0.682 | 0.374 | 1 |
| HLA-DRA1 | 0.00093218 | 0.32400543 | 1 | 0.925 | 1 | IL1B1 | 0.30048307 | 0.4531563 | 0.545 | 0.305 | 1 |
| HLA-DPA1 | 0.00099922 | 0.26934468 | 1 | 0.856 | 1 | TMEM14C | 0.46712143 | -0.3096538 | 0.977 | 0.523 | 1 |
| MS4A6A | 0.00112279 | 0.30018772 | 0.818 | 0.397 | 1 | CXCL2 | 0.57455038 | 0.46700804 | 0.614 | 0.207 | 1 |
| BLVRB | 0.00117175 | -0.3982349 | 0.784 | 0.684 | 1 | CKLF | 0.63113489 | -0.2946861 | 0.795 | 0.385 | 1 |
| RANBP1 | 0.00135846 | -0.2927951 | 0.545 | 0.339 | 1 | HMGB21 | 0.76234978 | -0.3195183 | 1 | 0.598 | 1 |
| MT-ND4L1 | 0.00304515 | 0.2646899 | 0.989 | 0.943 | 1 | IFI271 | 0.82663273 | -0.750534 | 1 | 0.58 | 1 |
| NINJ1 | 0.00335703 | 0.26238871 | 0.875 | 0.603 | 1 | TMEM176B | 0.95836779 | 0.3137295 | 0.545 | 0.195 | 1 |
| | | | | | | Seurat Cluster 9 | | | | | |
| DUSP61 | 4.07E-40 | 0.38946463 | 0.99 | 0.009 | 8.14E-37 | GADD45B2 | 2.40E-06 | -0.3827233 | 1 | 0.333 | 0.00480711 |
| IGKV2-291 | 1.26E-38 | -0.7382866 | 1 | 0.026 | 2.52E-35 | KDELR2 | 2.78E-06 | -0.6429229 | 0.111 | 0.385 | 0.0055564 |
| SERPINA1 | 2.63E-38 | 0.49638507 | 0.96 | 0.009 | 5.26E-35 | PSMA5 | 2.94E-06 | -0.4940005 | 0.111 | 0.359 | 0.00587051 |
| IGKV3-30 | 3.79E-37 | -3.6754025 | 1 | 0.034 | 7.57E-34 | TXNDC5 | 3.06E-06 | -0.6186937 | 0.101 | 0.368 | 0.0061174 |
| IGHV3-15 | 2.96E-34 | 2.4454987 | 0.939 | 0.026 | 5.93E-31 | IGLL5 | 3.98E-06 | -0.9277609 | 0.111 | 0.368 | 0.00796711 |
| IGKV1-5 | 9.98E-34 | -3.8694949 | 0.98 | 0.043 | 2.00E-30 | CD79B1 | 4.17E-06 | -0.4328389 | 0.96 | 0.316 | 0.00833021 |
| HIST1H2AL | 3.26E-32 | -0.4951432 | 0.051 | 0.103 | 6.53E-29 | MAP3K82 | 4.28E-06 | -0.5284518 | 1 | 0.333 | 0.00855125 |
| IGHV4-59 | 5.46E-31 | -0.3722079 | 0.96 | 0.043 | 1.09E-27 | ERH1 | 4.64E-06 | -0.6255066 | 0.162 | 0.376 | 0.00928476 |
| IGHV1-2 | 1.89E-30 | -3.7205117 | 1 | 0.077 | 3.78E-27 | PDCD51 | 5.07E-06 | -0.5538399 | 1 | 0.333 | 0.01014819 |
| IGHV1-18 | 2.48E-30 | -3.2722683 | 0.99 | 0.068 | 4.97E-27 | FCRL5 | 5.24E-06 | -0.6681665 | 1 | 0.333 | 0.01047783 |
| IGLV3-25 | 5.38E-30 | -0.8156787 | 0.909 | 0.009 | 1.08E-26 | ATF3 | 6.38E-06 | -0.3178388 | 0.111 | 0.094 | 0.01275388 |
| NR4A22 | 2.66E-29 | 0.65880431 | 0.99 | 0.077 | 5.32E-26 | CD79A | 6.82E-06 | -0.8387733 | 0.101 | 0.342 | 0.0136411 |
| HIST1H2AG | 3.85E-29 | -0.3099789 | 0.99 | 0.077 | 7.70E-26 | CRELD2 | 7.07E-06 | -0.5165705 | 0.111 | 0.368 | 0.01414172 |
| HIST1H2BF | 5.37E-29 | -0.2855607 | 0.939 | 0.06 | 1.07E-25 | VDAC12 | 7.35E-06 | -0.5890851 | 1 | 0.333 | 0.01469541 |
| SLAMF7 | 1.94E-28 | -0.3485301 | 0.091 | 0.256 | 3.89E-25 | CTSH | 7.59E-06 | -0.4357339 | 0.091 | 0.342 | 0.01517539 |
| TUBB4B1 | 4.61E-28 | -0.6049028 | 0.101 | 0.222 | 9.23E-25 | RAN1 | 8.58E-06 | -0.6735402 | 1 | 0.333 | 0.017167 |
| IGHV3-74 | 4.85E-28 | -1.3458273 | 0.101 | 0.06 | 9.69E-25 | SRPRB | 9.66E-06 | -0.2634597 | 0.081 | 0.291 | 0.01932992 |
| DUT | 6.39E-28 | -0.4250906 | 0.101 | 0.222 | 1.28E-24 | ALG51 | 1.18E-05 | -0.4298781 | 0.111 | 0.342 | 0.02366861 |
| NASP | 1.18E-27 | -0.4095451 | 0.101 | 0.248 | 2.36E-24 | ITGB7 | 1.43E-05 | -0.3891957 | 0.939 | 0.299 | 0.02854968 |
| HBB1 | 2.23E-27 | 3.84888163 | 0.869 | 0 | 4.45E-24 | CDK6 | 1.69E-05 | -0.2845784 | 0.091 | 0.162 | 0.0337115 |
| CYC1 | 2.36E-27 | -0.2709477 | 0.101 | 0.248 | 4.73E-24 | AC103591.34 | 1.80E-05 | -0.7701895 | 0.97 | 0.325 | 0.0360127 |
| PSMA6 | 3.58E-27 | -0.409073 | 0.111 | 0.291 | 7.15E-24 | C1QBP1 | 2.36E-05 | -0.6608336 | 0.141 | 0.342 | 0.0472039 |
| SLC25A37 | 8.28E-27 | 0.3697303 | 0.111 | 0.043 | 1.66E-23 | HMGB22 | 2.43E-05 | -0.9862981 | 0.97 | 0.325 | 0.04863042 |
| UBE2S | 9.21E-27 | -0.2617257 | 0.111 | 0.137 | 1.84E-23 | ABRACL1 | 2.59E-05 | -0.3062599 | 0.101 | 0.222 | 0.05179796 |
| HIST1H2AM | 1.80E-26 | -0.2812148 | 0.97 | 0.094 | 3.60E-23 | NDUFB6 | 2.78E-05 | -0.5998884 | 0.111 | 0.342 | 0.05553386 |
| H1FX5 | 3.26E-26 | -0.889141 | 0.111 | 0.376 | 6.51E-23 | PPP1CA | 2.92E-05 | -0.4470778 | 0.99 | 0.342 | 0.05842885 |
| IGKV1-91 | 3.58E-26 | -3.2462389 | 0.889 | 0.051 | 7.15E-23 | PSMB8 | 3.31E-05 | -0.5037889 | 1 | 0.35 | 0.06617019 |
| NDUFAF3 | 4.52E-26 | -0.3362021 | 0.121 | 0.316 | 9.05E-23 | SRM | 3.57E-05 | -0.6863604 | 0.111 | 0.333 | 0.07145054 |
| TIMM10 | 4.77E-26 | -0.2924141 | 0.121 | 0.222 | 9.53E-23 | PRDX4 | 3.77E-05 | -0.587491 | 0.182 | 0.427 | 0.07532509 |
| CCT2 | 5.12E-26 | -0.2830642 | 0.121 | 0.265 | 1.02E-22 | RNASE6 | 4.45E-05 | -0.4083487 | 0.96 | 0.342 | 0.08897975 |
| SEC6IG1 | 5.44E-26 | -1.1712902 | 0.121 | 0.504 | 1.09E-22 | MT-ND62 | 4.63E-05 | -0.4793265 | 0.111 | 0.333 | 0.09256349 |
| SEC13 | 5.83E-26 | -0.5551329 | 0.121 | 0.342 | 1.17E-22 | IGLV2-141 | 6.06E-05 | 0.42452703 | 0.869 | 0.744 | 0.12119911 |
| TXNDC17 | 6.02E-26 | -0.5295495 | 0.121 | 0.316 | 1.20E-22 | | 6.81E-05 | -2.7676057 | 0.02 | 0.12 | 0.1362293 |

TABLE 15-continued

| | p_val | avg_logFC | pct.1 | pct.2 | p_val_adj | | p_val | avg_logFC | pct.1 | pct.2 | p_val_adj |
|---|---|---|---|---|---|---|---|---|---|---|---|
| HSPE12 | 7.77E-26 | -0.7111097 | 0.111 | 0.376 | 1.55E-22 | HMGN2 | 7.41E-05 | -0.693906 | 0.97 | 0.342 | 0.14828135 |
| LMAN1 | 8.11E-26 | -0.8873144 | 0.121 | 0.496 | 1.62E-22 | GZMA3 | 7.76E-05 | 0.3174195 | 0.333 | 0 | 0.15527027 |
| IGLV1-47 | 1.11E-25 | -3.9472752 | 0.121 | 0.085 | 2.21E-22 | TMED9 | 8.93E-05 | -0.622094 | 0.141 | 0.359 | 0.17855656 |
| ANXA6 | 1.36E-25 | -0.3305605 | 0.121 | 0.291 | 2.73E-22 | S100A9 | 0.00010479 | 1.07120168 | 0.374 | 0.085 | 0.2095757 |
| IGHV3-30 | 1.95E-25 | -1.2803405 | 0.939 | 0.06 | 3.91E-22 | PSMD8 | 0.00011213 | -0.457514 | 0.333 | 0.333 | 0.22425978 |
| CD27 | 2.57E-25 | -0.7144561 | 0.131 | 0.393 | 5.13E-22 | CISD2 | 0.00012164 | -0.3707113 | 0.081 | 0.265 | 0.24328716 |
| TNFAIP2 | 3.16E-25 | 0.3797071 | 0.869 | 0.017 | 6.31E-22 | MRPS34 | 0.0001256 | -0.6012301 | 1 | 0.359 | 0.25119573 |
| CALU1 | 4.87E-25 | -0.3305188 | 0.131 | 0.282 | 9.74E-22 | PPA11 | 0.00013441 | -0.5938299 | 0.98 | 0.35 | 0.26882853 |
| SPCS3 | 7.67E-25 | -0.9826974 | 0.131 | 0.521 | 1.53E-21 | JPT11 | 0.00027282 | -0.8099088 | 1 | 0.368 | 0.54564149 |
| SEL1L3 | 1.27E-24 | -0.4082922 | 0.131 | 0.274 | 2.53E-21 | CCDC50 | 0.00030244 | -0.3899451 | 0.081 | 0.239 | 0.60487316 |
| HNRNPAB | 1.42E-24 | -0.6212327 | 0.141 | 0.299 | 2.85E-21 | MANF | 0.00030353 | -0.6647253 | 1 | 0.376 | 0.60705789 |
| SNRPB | 1.46E-24 | -0.586357 | 0.141 | 0.077 | 2.92E-21 | CKAP4 | 0.00031197 | -0.3190364 | 0.111 | 0.256 | 0.62394078 |
| AREG4 | 1.83E-24 | -0.2616479 | 0.949 | 0.077 | 3.67E-21 | SLIRP | 0.00031576 | -0.3139901 | 0.121 | 0.274 | 0.6315209 |
| HIST1H4H | 3.41E-24 | -0.3678583 | 0.939 | 0.085 | 6.82E-21 | SSR1 | 0.00035405 | -0.7171501 | 1 | 0.376 | 0.70810373 |
| RPS27L1 | 4.31E-24 | -0.50526 | 0.141 | 0.385 | 8.61E-21 | PSMB91 | 0.0004716 | -0.4889073 | 1 | 0.376 | 0.9431922 |
| PPIB | 7.24E-24 | -1.2894891 | 0.162 | 0.607 | 1.45E-20 | FBL | 0.00052446 | -0.3852516 | 0.131 | 0.299 | 1 |
| IGKV2-24 | 7.88E-24 | -2.6800341 | 0.111 | 0.026 | 1.58E-20 | LDHA1 | 0.00054887 | -0.468074 | 1 | 0.385 | 1 |
| THBS1 | 8.40E-24 | 0.38572085 | 0.131 | 0.009 | 1.68E-20 | DNAJB11 | 0.00061588 | -0.4947687 | 1 | 0.385 | 1 |
| ENO1 | 1.05E-23 | -0.783744 | 0.152 | 0.333 | 2.10E-20 | HIST1H1D3 | 0.00064241 | -1.2669519 | 0.97 | 0.359 | 1 |
| EIF2S2 | 1.19E-23 | -0.3909396 | 0.141 | 0.359 | 2.37E-20 | PIM2 | 0.0006547 | -0.5327786 | 0.98 | 0.368 | 1 |
| HMGA1 | 1.19E-23 | -0.2895214 | 0.141 | 0.214 | 2.38E-20 | ANP32E | 0.00069234 | -0.5006892 | 0.111 | 0.274 | 1 |
| SNRPF1 | 1.25E-23 | -0.4062908 | 0.121 | 0.265 | 2.50E-20 | CCDC167 | 0.0007042 | -0.4497386 | 0.111 | 0.282 | 1 |
| CCL31 | 2.33E-23 | -0.4377228 | 0.939 | 0.077 | 4.67E-20 | STT3A | 0.00076545 | -0.402168 | 0.121 | 0.291 | 1 |
| FABP51 | 2.78E-23 | -0.7056422 | 0.111 | 0.316 | 5.57E-20 | IGHG1 | 0.00084479 | -2.3710382 | 1 | 0.385 | 1 |
| NCF11 | 2.93E-23 | -0.3469072 | 0.141 | 0.385 | 5.86E-20 | ADI1 | 0.00090025 | -0.2916205 | 0.091 | 0.239 | 1 |
| HELLS | 3.34E-23 | -0.4379044 | 0.101 | 0.188 | 6.69E-20 | ZBP11 | 0.00090058 | -0.9635653 | 1 | 0.385 | 1 |
| MTDH | 3.69E-23 | -0.847812 | 0.152 | 0.479 | 7.39E-20 | COPZ1 | 0.00100122 | -0.3579088 | 0.111 | 0.274 | 1 |
| H2AFV1 | 4.18E-23 | -0.430337 | 0.152 | 0.35 | 8.35E-20 | TUFM1 | 0.00106369 | -0.5557505 | 0.99 | 0.385 | 1 |
| ODC1 | 4.33E-23 | -0.2772737 | 0.101 | 0.231 | 8.67E-20 | SLC25A5 | 0.00113063 | -0.90329 | 0.273 | 0.402 | 1 |
| ATP5F1A | 5.22E-23 | -0.5879314 | 0.152 | 0.35 | 1.04E-19 | CHPF | 0.00113629 | -0.3819411 | 0.111 | 0.282 | 1 |
| SRP91 | 6.30E-23 | -0.2688641 | 0.152 | 0.256 | 1.26E-19 | WDR741 | 0.00113811 | -0.583136 | 0.818 | 0.248 | 1 |
| MRPL51 | 1.41E-22 | -0.2643112 | 1 | 0.333 | 2.81E-19 | RANBP11 | 0.00113909 | -0.406883 | 0.121 | 0.282 | 1 |
| HIST1H2AE | 2.26E-22 | -0.441285 | 0.172 | 0.137 | 4.53E-19 | GGH | 0.00116909 | -0.3119352 | 0.111 | 0.274 | 1 |
| HSPD12 | 2.64E-22 | -0.8143033 | 0.172 | 0.376 | 5.27E-19 | GNG7 | 0.00122767 | -0.3703843 | 0.111 | 0.265 | 1 |
| H2AFZ | 3.43E-22 | -0.8812882 | 0.172 | 0.376 | 6.85E-19 | C12orf75 | 0.00125975 | -0.4361564 | 0.101 | 0.248 | 1 |
| DERL1 | 4.02E-22 | -0.46137 | 0.172 | 0.368 | 8.05E-19 | SSR3 | 0.0012803 | -0.8628638 | 0.394 | 0.479 | 1 |
| HIST2H2AC | 5.65E-22 | -0.3381527 | 0.162 | 0.162 | 1.13E-18 | EZH2 | 0.0012882 | -0.3124614 | 0.525 | 0.171 | 1 |
| DUSP23 | 1.07E-21 | 0.33309404 | 0.96 | 0.111 | 2.15E-18 | CYTOR1 | 0.00129335 | -0.5184554 | 0.99 | 0.385 | 1 |
| IGHV6-1 | 2.40E-21 | -1.5242477 | 0.96 | 0.111 | 4.80E-18 | IFNG-AS11 | 0.00141869 | -0.3524095 | 0.061 | 0.128 | 1 |
| PRDX12 | 3.01E-21 | -0.5503308 | 0.182 | 0.393 | 6.03E-18 | UQCC2 | 0.00172114 | -0.2899953 | 0.131 | 0.282 | 1 |
| HYOU1 | 4.09E-21 | -0.2534948 | 0.111 | 0.274 | 8.17E-18 | LSM5 | 0.00178456 | -0.5147475 | 0.182 | 0.325 | 1 |
| CENPW | 4.22E-21 | -0.2783233 | 0.99 | 0.145 | 8.43E-18 | ANXA5 | 0.00191137 | -0.5278774 | 1 | 0.393 | 1 |
| ACTG1 | 9.49E-21 | -1.0778985 | 0.192 | 0.462 | 1.90E-17 | AQP3 | 0.00198596 | -0.6326021 | 0.919 | 0.368 | 1 |
| TP11 | 1.20E-20 | -0.8294714 | 0.121 | 0.402 | 2.41E-17 | UBA51 | 0.00201325 | -0.301757 | 0.121 | 0.274 | 1 |
| AL355075.4 | 2.14E-20 | -0.2975617 | 0.859 | 0.06 | 4.28E-17 | MYBL2 | 0.00227671 | -0.3253982 | 0.081 | 0.205 | 1 |
| HLA-DPA11 | 4.60E-20 | -0.4773734 | 0.192 | 0.308 | 9.20E-17 | IGLV1-511 | 0.00230298 | -2.6869771 | 0.313 | 0.077 | 1 |
| AIF1 | 7.69E-20 | 0.29430724 | 0.172 | 0.043 | 1.54E-16 | AC007569.1 | 0.00307095 | -0.445529 | 0.111 | 0.248 | 1 |
| IFITM23 | 1.03E-19 | 0.39644683 | 0.172 | 0.094 | 2.05E-16 | ABCB9 | 0.00308656 | -0.3275989 | 0.091 | 0.214 | 1 |
| IGLV3-11 | 1.41E-19 | -2.5788384 | 0.97 | 0.137 | 2.83E-16 | ETFA | 0.00309162 | -0.2769018 | 0.152 | 0.291 | 1 |
| SSR41 | 2.32E-19 | -1.3133065 | 0.273 | 0.59 | 4.64E-16 | CCT7 | 0.00339146 | -0.3064526 | 0.121 | 0.265 | 1 |
| IGHG2 | 4.94E-19 | -1.8896493 | 0.919 | 0.128 | 9.88E-16 | NDUFAB1 | 0.00356206 | -0.5567275 | 1 | 0.402 | 1 |

TABLE 15-continued

| | p_val | avg_logFC | pct.1 | pct.2 | p_val_adj | | p_val | avg_logFC | pct.1 | pct.2 | p_val_adj |
|---|---|---|---|---|---|---|---|---|---|---|---|
| SLC2A6 | 5.43E-19 | -0.2633224 | 0.869 | 0.06 | 1.09E-15 | MESD | 0.0037917 | -0.5781423 | 1 | 0.402 | 1 |
| FAM30A1 | 5.82E-19 | -0.3637615 | 0.939 | 0.145 | 1.16E-15 | GMPPB | 0.00391715 | -0.3271014 | 0.111 | 0.239 | 1 |
| HSPA8l | 2.91E-18 | -0.6259505 | 0.232 | 0.402 | 5.83E-15 | IGLV6-571 | 0.00399014 | -1.107723 | 0.364 | 0.145 | 1 |
| PTTG1 | 4.82E-18 | -0.4268688 | 0.111 | 0.222 | 9.63E-15 | CCT5 | 0.004353 | -0.2943125 | 0.101 | 0.231 | 1 |
| HIST1H2AH | 5.27E-18 | -0.264751 | 0.889 | 0.111 | 1.05E-14 | JCHAIN | 0.00450031 | -1.3180961 | 1 | 0.658 | 1 |
| CHEK1 | 5.37E-18 | -0.2543081 | 0.909 | 0.103 | 1.07E-14 | PA2G41 | 0.00472445 | -0.7480766 | 0.566 | 0.325 | 1 |
| HM13 | 6.22E-18 | -0.5845019 | 0.242 | 0.47 | 1.24E-14 | CCT81 | 0.00523212 | -0.5482899 | 0.879 | 0.368 | 1 |
| HIST1H2AC | 6.93E-18 | -0.3482049 | 0.869 | 0.077 | 1.39E-14 | NME1 | 0.00580413 | -0.3369928 | 0.091 | 0.205 | 1 |
| LYN | 7.06E-18 | -0.3188825 | 0.929 | 0.137 | 1.41E-14 | IGHV4-4 | 0.00696226 | -2.0861234 | 0.141 | 0.026 | 1 |
| ADA | 9.85E-18 | -0.2886064 | 0.97 | 0.162 | 1.97E-14 | SLC25A4 | 0.00795852 | -0.286086 | 0.111 | 0.231 | 1 |
| PLEK1 | 1.20E-17 | -0.3486778 | 0.96 | 0.145 | 2.41E-14 | PPBP3 | 0.00841894 | 0.29929251 | 0.212 | 0.06 | 1 |
| CDC25B1 | 1.32E-17 | -0.3155003 | 0.99 | 0.171 | 2.65E-14 | CISD1 | 0.00842355 | -0.344729 | 0.131 | 0.248 | 1 |
| MT2A5 | 1.77E-17 | -0.6046156 | 0.96 | 0.179 | 3.54E-14 | IGLVl-70 | 0.00886359 | -0.5099871 | 0.101 | 0.017 | 1 |
| CD741 | 5.19E-17 | -0.6353871 | 1 | 0.564 | 1.04E-13 | LINC014801 | 0.0089407 | -0.5342273 | 0.111 | 0.231 | 1 |
| DNMT11 | 5.72E-17 | -0.3793333 | 0.96 | 0.154 | 1.14E-13 | AL133467.1 | 0.00902724 | -0.3292482 | 0.111 | 0.231 | 1 |
| MCM7 | 6.81E-17 | -0.3093109 | 0.96 | 0.154 | 1.36E-13 | BIK | 0.01027684 | -0.4134852 | 0.111 | 0.222 | 1 |
| S100A102 | 7.94E-17 | -0.4500068 | 0.242 | 0.376 | 1.59E-13 | POU2AF1 | 0.01042562 | -0.5541131 | 0.99 | 0.41 | 1 |
| TUBA1B1 | 8.25E-17 | -0.8454725 | 0.232 | 0.291 | 1.65E-13 | RPA3 | 0.010721 | -0.472112 | 0.172 | 0.282 | 1 |
| SLC17A9 | 3.93E-16 | -0.3813903 | 0.97 | 0.171 | 7.87E-13 | EPRS | 0.01165286 | -0.451662 | 0.859 | 0.35 | 1 |
| SMC1A | 5.56E-16 | -0.2832156 | 0.98 | 0.179 | 1.11E-12 | IGLC2 | 0.01184923 | -3.0263463 | 0.99 | 0.402 | 1 |
| ADSL | 5.68E-16 | -0.2808575 | 0.96 | 0.162 | 1.14E-12 | TENT5C1 | 0.01232469 | -0.6146131 | 0.939 | 0.385 | 1 |
| IGHA2 | 6.87E-16 | -2.1464289 | 0.99 | 0.188 | 1.37E-12 | IGHV4-31 | 0.0143894 | -1.8043385 | 0.111 | 0.026 | 1 |
| CDKN2A | 7.83E-16 | -0.2801483 | 0.99 | 0.188 | 1.57E-12 | MZB1 | 0.0149205 | -1.415292 | 1 | 0.641 | 1 |
| COTL13 | 1.88E-15 | -0.2751913 | 0.263 | 0.35 | 3.75E-12 | HIST1H4C2 | 0.01724499 | -1.5669843 | 0.99 | 0.41 | 1 |
| SPI1 | 2.05E-15 | -0.397456 | 0.889 | 0.111 | 4.11E-12 | HLA-DRB11 | 0.0174398 | -0.2914814 | 0.596 | 0.359 | 1 |
| EEF1A1 | 2.33E-15 | -1.0374629 | 0.323 | 0.598 | 4.67E-12 | BOLA3 | 0.019132 | -0.2949101 | 0.111 | 0.214 | 1 |
| SOD2 | 3.02E-15 | -0.2617267 | 1 | 0.205 | 6.03E-12 | MX12 | 0.01947997 | -0.2991174 | 0.111 | 0.197 | 1 |
| TMED10 | 4.88E-15 | -0.7804075 | 0.283 | 0.453 | 9.76E-12 | HSP90B1 | 0.01951132 | -1.4210245 | 1 | 0.641 | 1 |
| PTCH2 | 8.17E-15 | -0.5217235 | 0.97 | 0.197 | 1.63E-11 | ZFP36L21 | 0.02105069 | -0.8698887 | 0.889 | 0.427 | 1 |
| SH2D2A | 1.27E-14 | 0.31215589 | 0.182 | 0 | 2.54E-11 | ENTPD1 | 0.02162662 | -0.3082493 | 0.141 | 0.222 | 1 |
| IGKV4-1 | 1.48E-14 | -1.150509 | 0.97 | 0.188 | 2.97E-11 | VBP1 | 0.02163753 | -0.2759591 | 0.101 | 0.188 | 1 |
| CKAP2 | 2.38E-14 | -0.2245001 | 0.99 | 0.205 | 4.76E-11 | IF162 | 0.02309894 | -0.3326277 | 0.141 | 0.222 | 1 |
| IGHG4 | 2.82E-14 | -2.8133584 | 1 | 0.214 | 5.64E-11 | PRDX3 | 0.02320692 | -0.4402978 | 0.152 | 0.248 | 1 |
| MYDGF | 3.71E-14 | -0.989508 | 0.97 | 0.513 | 7.41E-11 | ZFP36L21 | 0.02360738 | -0.3281463 | 0.889 | 0.359 | 1 |
| TUBB | 4.01E-14 | -0.5194892 | 0.354 | 0.496 | 8.02E-11 | HSPB11 | 0.02442831 | -0.3056549 | 0.141 | 0.205 | 1 |
| IGHG3 | 1.11E-13 | -2.0414883 | 0.212 | 0.231 | 2.23E-10 | IGKC1 | 0.02452833 | -1.8077876 | 0.98 | 0.419 | 1 |
| HIST1H1B | 1.45E-13 | -0.6299107 | 0.99 | 0.214 | 2.90E-10 | LDHB | 0.02524377 | -0.0864856 | 0.98 | 0.419 | 1 |
| VIM | 1.88E-13 | -0.3054562 | 0.293 | 0.462 | 3.76E-10 | IGHV3-491 | 0.02563883 | -2.1131153 | 0.101 | 0.026 | 1 |
| SEMA4A | 3.76E-13 | -0.454683 | 0.97 | 0.205 | 7.53E-10 | ATP5MC31 | 0.02965133 | -0.7946385 | 1 | 0.436 | 1 |
| ERLEC1 | 9.08E-13 | -0.6732961 | 0.384 | 0.496 | 1.82E-09 | MRPL3 | 0.02998673 | -0.268139 | 0.121 | 0.214 | 1 |
| MT-CO11 | 9.44E-13 | 0.84990083 | 1 | 0.991 | 1.89E-09 | IGLV1-44 | 0.03424788 | -3.8217387 | 0.111 | 0.034 | 1 |
| IGHM | 1.13E-12 | -4.3044719 | 1 | 0.231 | 2.25E-09 | ATP5MC1 | 0.04096109 | -0.6765414 | 1 | 0.436 | 1 |
| CPNE5 | 3.24E-12 | -0.409288 | 1 | 0.239 | 6.48E-09 | HMGB3 | 0.04097839 | -0.3232154 | 0.101 | 0.179 | 1 |
| MTRNR2L121 | 4.06E-12 | 0.97307593 | 0.949 | 0.949 | 8.11E-09 | TMEM106C | 0.04820506 | -0.3113654 | 0.111 | 0.188 | 1 |
| Z93241.11 | 4.33E-12 | -0.7222125 | 0.97 | 0.231 | 8.66E-09 | GSTP11 | 0.04910626 | -0.8509528 | 0.97 | 0.026 | 1 |
| CBWD1 | 5.50E-12 | -0.3253615 | 1 | 0.239 | 1.10E-08 | HSPA52 | 0.05294645 | -1.2443054 | 1 | 0.427 | 1 |
| SLC38A5 | 6.64E-12 | -0.3669197 | 0.949 | 0.205 | 1.33E-08 | PSAP | 0.05604852 | -0.4722358 | 1 | 0.624 | 1 |
| KLF101 | 1.28E-11 | -0.3313881 | 1 | 0.248 | 2.57E-08 | CORO1A1 | 0.05627203 | -0.370869 | 0.889 | 0.453 | 1 |
| LSM4 | 1.37E-11 | -0.305486 | 0.99 | 0.239 | 2.75E-08 | BRCA1 | 0.05785477 | -0.2675262 | 0.263 | 0.393 | 1 |
| SSRP1 | 1.46E-11 | -0.2553712 | 0.909 | 0.171 | 2.91E-08 | CDKN1A | 0.05945543 | -0.2719256 | 0.263 | 0.128 | 1 |
| MT-CO31 | 1.92E-11 | 0.77713021 | 1 | 1 | 3.83E-08 | IGKV3-201 | 0.07658367 | -4.5663441 | 0.111 | 0.043 | 1 |

TABLE 15-continued

| | p_val | avg_logFC | pct.1 | pct.2 | p_val_adj | | p_val | avg_logFC | pct.1 | pct.2 | p_val_adj |
|---|---|---|---|---|---|---|---|---|---|---|---|
| GPR35 | 2.17E-11 | 0.29390609 | 0.354 | 0 | 4.35E-08 | NT5C3A | 0.07724244 | -0.2703882 | 0.283 | 0.145 | 1 |
| CD320 | 4.84E-11 | -0.5348342 | 0.323 | 0.282 | 9.68E-08 | STMN11 | 0.08538464 | -0.502574 | 0.141 | 0.205 | 1 |
| RHOB1 | 5.46E-11 | -0.3878738 | 0.929 | 0.222 | 1.09E-07 | RRBP1 | 0.09703905 | -1.0588392 | 0.96 | 0.581 | 1 |
| COMTD1 | 5.93E-11 | -0.2931441 | 0.98 | 0.239 | 1.19E-07 | SNRPG1 | 0.10071662 | -0.6063611 | 0.859 | 0.376 | 1 |
| HSH2D2 | 8.06E-11 | -0.4895107 | 0.081 | 0.265 | 1.61E-07 | HIST1H1C | 0.10251137 | -1.0461507 | 0.929 | 0.41 | 1 |
| NAAA | 1.06E-10 | 0.25980137 | 0.798 | 0.077 | 2.11E-07 | TYMS | 0.10344072 | -0.2942594 | 0.081 | 0.12 | 1 |
| PFN12 | 1.07E-10 | -0.6432438 | 0.394 | 0.504 | 2.15E-07 | HNRNPA2B11 | 0.10374708 | -1.0215823 | 1 | 0.607 | 1 |
| IGLC3 | 1.28E-10 | -2.0333363 | 0.96 | 0.231 | 2.57E-07 | PRDM12 | 0.10944293 | -0.6655687 | 0.99 | 0.453 | 1 |
| LGALS11 | 1.65E-10 | -0.962953 | 0.394 | 0.419 | 3.29E-07 | DCTPP1 | 0.11318784 | -0.306574 | 0.111 | 0.171 | 1 |
| MT-CO2 | 1.77E-10 | 0.7363092 | 1 | 0.991 | 3.54E-07 | ZFP361 | 0.11692649 | -0.7929466 | 1 | 0.47 | 1 |
| UCHL5 | 2.02E-10 | -0.269873 | 0.99 | 0.256 | 4.04E-07 | RPN2 | 0.11713748 | -0.6124282 | 1 | 0.479 | 1 |
| FAM136A | 3.75E-10 | -0.4054947 | 1 | 0.265 | 7.49E-07 | SUB1 | 0.12418748 | -1.2333969 | 1 | 0.598 | 1 |
| ISOC2 | 4.68E-10 | -0.3457449 | 0.929 | 0.239 | 9.37E-07 | IGKV3-111 | 0.12481098 | -3.8692714 | 0.111 | 0.051 | 1 |
| MTHFD2 | 4.70E-10 | -0.4695994 | 0.111 | 0.282 | 9.40E-07 | IGHV3-64 | 0.14300378 | -0.3564697 | 0.111 | 0.051 | 1 |
| MT-CYB1 | 5.85E-10 | 0.67367859 | 1 | 0.957 | 1.17E-06 | DDOST | 0.14300378 | -1.9192223 | 1 | 0.51 | 1 |
| FTL | 6.27E-10 | -0.304806 | 0.354 | 0.547 | 1.25E-06 | IGHV3-7 | 0.14729777 | -0.5145741 | 0.424 | 0.402 | 1 |
| TUBA4A1 | 6.51E-10 | -0.2697733 | 0.97 | 0.248 | 1.30E-06 | TAGLN21 | 0.14897517 | -0.7413977 | 0.949 | 0.436 | 1 |
| NUCKS1 | 7.73E-10 | -0.3543527 | 0.97 | 0.248 | 1.55E-06 | ELL2 | 0.15163765 | -0.8386873 | 1 | 0.462 | 1 |
| FDPS | 1.21E-09 | -0.3206234 | 1 | 0.274 | 2.42E-06 | CAV1 | 0.15368374 | -0.2777391 | 0.091 | 0.128 | 1 |
| STOML2 | 1.32E-09 | -0.2964812 | 0.96 | 0.248 | 2.64E-06 | NDUFB3 | 0.16527044 | -0.3807758 | 0.384 | 0.35 | 1 |
| LRRC59 | 1.62E-09 | -0.424406 | 0.97 | 0.256 | 3.25E-06 | ACTB1 | 0.16758165 | -0.5863406 | 0.949 | 0.684 | 1 |
| SEC11C | 2.45E-09 | -0.9389347 | 0.121 | 0.521 | 4.90E-06 | PSME2 | 0.16831613 | -0.896928 | 1 | 0.47 | 1 |
| PRMT1 | 2.88E-09 | -0.313223 | 0.949 | 0.239 | 5.76E-06 | MEF2C1 | 0.20644547 | -0.839299 | 0.99 | 0.47 | 1 |
| HNRNPR | 4.09E-09 | -0.3392273 | 1 | 0.282 | 8.18E-06 | JUN | 0.20644547 | -1.435798 | 0.98 | 0.462 | 1 |
| PSMA41 | 5.08E-09 | -0.401895 | 1 | 0.282 | 1.02E-05 | CENPU | 0.21028893 | -0.3511415 | 0.343 | 0.171 | 1 |
| MT-ND4L2 | 5.63E-09 | 0.58236698 | 1 | 0.966 | 1.13E-05 | RPN11 | 0.24120328 | -0.9693639 | 1 | 0.47 | 1 |
| AC245014.31 | 6.25E-09 | 0.52199721 | 1 | 0.974 | 1.25E-05 | DERL3 | 0.24414883 | -0.8189151 | 1 | 0.479 | 1 |
| TLN1 | 9.29E-09 | -0.6909409 | 0.99 | 0.282 | 1.86E-05 | HSP90AB1 | 0.26875704 | -1.0747828 | 1 | 0.573 | 1 |
| PLPP51 | 1.01E-08 | 0.28708311 | 0.343 | 0.205 | 2.03E-05 | PD1A6 | 0.30855879 | -0.953821 | 1 | 0.487 | 1 |
| S100A86 | 1.07E-08 | -0.5219161 | 0.121 | 0.359 | 2.15E-05 | PPIA1 | 0.31383538 | -0.9059551 | 0.99 | 0.487 | 1 |
| PARP1 | 1.29E-08 | 0.52421969 | 0.303 | 0.103 | 2.58E-05 | COBLL1 | 0.3256574 | -0.4772664 | 0.354 | 0.316 | 1 |
| NUCB2 | 1.33E-08 | -0.4511627 | 0.98 | 0.274 | 2.66E-05 | RPLP0 | 0.33258952 | -0.9932215 | 1 | 0.59 | 1 |
| SNRPE | 1.36E-08 | -0.2912242 | 0.97 | 0.291 | 2.72E-05 | IGHV3-33 | 0.35724087 | -3.4233405 | 0.111 | 0.068 | 1 |
| MDH1 | 2.06E-08 | -0.4989883 | 0.121 | 0.308 | 4.13E-05 | SELENOS | 0.36281184 | -0.7456086 | 1 | 0.487 | 1 |
| TCF4 | 3.22E-08 | -0.3390821 | 0.98 | 0.282 | 6.43E-05 | HMGB13 | 0.36303874 | -0.6795949 | 0.97 | 0.59 | 1 |
| TMPO1 | 3.30E-08 | -0.3402248 | 0.98 | 0.282 | 6.60E-05 | TMEM208 | 0.37229288 | -0.4581888 | 0.404 | 0.342 | 1 |
| XIST4 | 3.39E-08 | -0.4929238 | 0.98 | 0.282 | 6.77E-05 | ITM2C | 0.42061494 | -0.8245716 | 1 | 0.504 | 1 |
| CD38 | 3.64E-08 | -0.9864471 | 1 | 0.291 | 7.28E-05 | HDLBP | 0.42257147 | -0.7182198 | 0.808 | 0.462 | 1 |
| EIF4A31 | 3.70E-08 | -0.8533388 | 0.141 | 0.487 | 7.40E-05 | MZT1 | 0.43430534 | -0.3163332 | 0.141 | 0.137 | 1 |
| PPM1G | 3.76E-08 | -0.5494371 | 0.97 | 0.274 | 7.53E-05 | CANXI | 0.45264409 | -0.4564405 | 0.899 | 0.444 | 1 |
| TDH21 | 3.80E-08 | -0.4629227 | 0.394 | 0.282 | 7.60E-05 | MIST1H3B | 0.47473679 | -0.3153834 | 0.081 | 0.103 | 1 |
| CACYBP | 4.69E-08 | -0.3374569 | 0.121 | 0.291 | 9.38E-05 | CALR | 0.48161159 | -0.8734727 | 0.869 | 0.419 | 1 |
| CCT6A | 4.81E-08 | -0.6224804 | 0.99 | 0.291 | 9.62E-05 | XBP1 | 0.50214421 | -0.855889 | 1 | 0.556 | 1 |
| OSTC | 4.88E-08 | -0.4039514 | 0.99 | 0.291 | 9.76E-05 | PRDX2 | 0.50456381 | -0.7685827 | 0.515 | 0.385 | 1 |
| TNFRSF17 | 5.72E-08 | -0.8181061 | 1 | 0.436 | 0.00011433 | PDIA4 | 0.51939137 | -0.7877606 | 1 | 0.504 | 1 |
| ANXA21 | 9.23E-08 | -0.7845634 | 0.111 | 0.427 | 0.0001847 | IGHV4-391 | 0.52016136 | -3.1111853 | 0.111 | 0.077 | 1 |
| SLC9A3R1 | 1.03E-07 | 0.27063027 | 0.96 | 0.282 | 0.00020527 | MRPL37 | 0.52038977 | -0.3352406 | 0.242 | 0.231 | 1 |
| MIR4435-2HG2 | 1.55E-07 | -0.3389629 | 0.131 | 0.222 | 0.0003105 | DYNLL1 | 0.54305824 | -0.5255634 | 0.414 | 0.333 | 1 |
| ATP5F1B | 1.64E-07 | -0.3143404 | 0.99 | 0.299 | 0.0003277 | NCL1 | 0.56917664 | -1.0940549 | 1 | 0.504 | 1 |
| | 1.84E-07 | -0.4634309 | 0.444 | 0.376 | 0.00036862 | NPM1 | 0.57498158 | -1.0247321 | 1 | 0.496 | 1 |
| CCT3 | 3.15E-07 | -0.4604766 | 0.111 | 0.299 | 0.0006298 | UBE2I1 | 0.59831679 | -0.4541937 | 0.98 | 0.521 | 1 |

TABLE 15-continued

| | p_val | avg_logFC | pct.1 | pct.2 | p_val_adj | | p_val | avg_logFC | pct.1 | pct.2 | p_val_adj |
|---|---|---|---|---|---|---|---|---|---|---|---|
| CDK2AP2 | 3.32E-07 | -0.3585834 | 0.919 | 0.265 | 0.00066405 | RPL22L11 | 0.60102363 | -0.9758808 | 1 | 0.504 | 1 |
| YIF1B | 3.45E-07 | -0.3652237 | 0.97 | 0.299 | 0.00069098 | AC007952.4 | 0.60729339 | -0.8670747 | 0.758 | 0.393 | 1 |
| ANKRD28 | 3.63E-07 | -0.4728037 | 0.444 | 0.35 | 0.0007266 | HIST1H2AJ | 0.62295563 | -0.2846638 | 0.111 | 0.12 | 1 |
| LYZ | 3.87E-07 | 0.75654781 | 0.707 | 0.034 | 0.00077475 | 1GLV2-111 | 0.62443032 | -3.7337892 | 0.101 | 0.103 | 1 |
| TOR3A | 4.78E-07 | -0.4470533 | 0.919 | 0.274 | 0.00095516 | IGHA1 | 0.66540383 | -2.6144627 | 0.99 | 0.504 | 1 |
| XRCC51 | 5.00E-07 | -0.3165916 | 0.98 | 0.308 | 0.00100085 | TPM4 | 0.73517288 | -0.4444188 | 0.475 | 0.316 | 1 |
| S100A62 | 5.72E-07 | -0.3116043 | 0.99 | 0.333 | 0.00114416 | FKBP11 | 0.7375871 | -0.8998795 | 1 | 0.521 | 1 |
| MLEC | 6.21E-07 | -0.305787 | 1 | 0.299 | 0.00124197 | TMEM14C1 | 0.75126637 | -0.3053482 | 0.253 | 0.222 | 1 |
| YWHAQ1 | 6.47E-07 | -0.4354146 | 0.97 | 0.316 | 0.00129456 | FKBP2 | 0.75981586 | -0.8817477 | 0.939 | 0.496 | 1 |
| CTSB | 8.10E-07 | 0.25200505 | 1 | 0.299 | 0.00162064 | SHMT2 | 0.81128686 | -0.3453338 | 0.354 | 0.282 | 1 |
| TPD52 | 8.20E-07 | -0.4112541 | 0.97 | 0.316 | 0.00163923 | ASPM | 0.82227797 | -0.3042192 | 0.131 | 0.128 | 1 |
| PDE4B | 8.75E-07 | -0.4155429 | 0.96 | 0.291 | 0.00174926 | HIST1H1E1 | 0.82748399 | -1.0123014 | 1 | 0.547 | 1 |
| CCND21 | 1.24E-06 | -0.5434871 | 1 | 0.325 | 0.00248925 | GAS6 | 0.83889314 | -0.2911648 | 0.354 | 0.282 | 1 |
| DECR1 | 1.26E-06 | -0.4039068 | 0.97 | 0.299 | 0.00252918 | GAPDH1 | 0.84467554 | -1.0338622 | 1 | 0.547 | 1 |
| LMAN2 | 1.57E-06 | -0.6410787 | 0.131 | 0.419 | 0.00313621 | MIF1 | 0.84792061 | -1.2078178 | 1 | 0.521 | 1 |
| PSMB21 | 1.63E-06 | -0.4082177 | 1 | 0.325 | 0.00325956 | P4HB | 0.87048649 | -0.7747141 | 0.97 | 0.53 | 1 |
| EAF2 | 1.69E-06 | -0.3907302 | 0.97 | 0.316 | 0.00337832 | SPCS2 | 0.87719036 | -0.9953429 | 0.97 | 0.496 | 1 |
| SNRPD3 | 1.82E-06 | -0.4898126 | 1 | 0.325 | 0.00364409 | SDF2L1 | 0.89129538 | -0.9247711 | 0.97 | 0.521 | 1 |
| S100A43 | 1.86E-06 | -0.3629322 | 1 | 0.35 | 0.00372577 | IGLV1-401 | 0.9371058 | -4.2499683 | 0.283 | 0.034 | 1 |
| | | | | | | Seurat Cluster 10 | | | | | |
| BUB1 | 1.62E-35 | -0.2797915 | 0.991 | 0.029 | 3.25E-32 | PDIA61 | 1.81E-06 | -0.3471375 | 0.745 | 0.087 | 0.00361777 |
| HERC5 | 1.59E-34 | -0.3408593 | 1 | 0.039 | 3.19E-31 | HBG2 | 2.36E-06 | 0.47772213 | 0.336 | 0.049 | 0.00472725 |
| SNRPG2 | 1.36E-32 | -0.318804 | 0.991 | 0.049 | 2.72E-29 | CDKN1A1 | 3.13E-06 | 0.31466069 | 0.982 | 0.437 | 0.00625066 |
| SEL1L31 | 5.46E-32 | -0.2259856 | 0.927 | 0.058 | 1.09E-28 | RAMP1 | 8.40E-06 | -0.2885911 | 0.355 | 0.068 | 0.01680942 |
| PSMA51 | 1.28E-31 | -0.3037761 | 1 | 0.058 | 2.56E-28 | HBA1 | 1.19E-05 | -1.0054395 | 0.345 | 0.049 | 0.02370242 |
| PRDX41 | 1.28E-31 | -0.3432647 | 0.991 | 0.058 | 2.56E-28 | SNCA | 2.17E-05 | 0.28805275 | 0.955 | 0.427 | 0.04339281 |
| HIST1H1D4 | 1.28E-31 | -0.4835561 | 1 | 0.058 | 2.56E-28 | LAT1 | 2.19E-05 | 0.27839337 | 0.9 | 0.369 | 0.0438648 |
| CENPU1 | 2.55E-30 | -0.3670706 | 1 | 0.068 | 5.11E-27 | NTSC3A1 | 3.11E-05 | 0.34262434 | 1 | 0.505 | 0.06213907 |
| PSMB5 | 3.00E-30 | -0.3065241 | 1 | 0.068 | 6.00E-27 | ETFA1 | 3.35E-05 | 0.31494581 | 1 | 0.466 | 0.06702377 |
| GNAI1 | 2.99E-29 | -0.2579841 | 0.927 | 0.049 | 5.99E-26 | NUDT1 | 3.39E-05 | -0.3731593 | 0.318 | 0.068 | 0.06778689 |
| H1ST1H3B1 | 3.48E-29 | -0.2947934 | 0.991 | 0.068 | 6.95E-26 | RHOC | 5.93E-05 | 0.50611667 | 0.818 | 0.262 | 0.1186482 |
| FKBP3 | 7.15E-29 | -0.3730331 | 1 | 0.078 | 1.43E-25 | RPN12 | 6.12E-05 | -0.4042341 | 0.727 | 0.107 | 0.12246924 |
| CAMK1 | 8.53E-29 | -0.2983522 | 0.945 | 0.058 | 1.71E-25 | ARHGAP6 | 6.38E-05 | 0.26756439 | 0.982 | 0.476 | 0.12765146 |
| RGCC1 | 6.99E-28 | -0.2715001 | 0.9 | 0.049 | 1.40E-24 | HSPE13 | 6.42E-05 | -0.3458659 | 0.264 | 0.049 | 0.12831944 |
| MRPS341 | 7.20E-28 | -0.3532805 | 0.991 | 0.078 | 1.44E-24 | GUCY1A1 | 7.48E-05 | 0.34974213 | 0.364 | 0.039 | 0.14961449 |
| ABRACL2 | 1.18E-27 | -0.2822631 | 1 | 0.068 | 2.35E-24 | MZT11 | 7.64E-05 | -0.2599589 | 0.636 | 0.204 | 0.15274328 |
| HIST1H1E2 | 1.55E-26 | -0.6925493 | 0.991 | 0.087 | 3.11E-23 | GTF3C61 | 7.85E-05 | 0.40822402 | 0.882 | 0.359 | 0.15693185 |
| FAM210B | 2.19E-26 | -0.6237103 | 1 | 0.097 | 4.38E-23 | MINDY1 | 8.17E-05 | 0.28633546 | 0.782 | 0.204 | 0.16339408 |
| CKLF1 | 4.40E-26 | -0.4869551 | 0.864 | 0.049 | 8.80E-23 | RPS27L2 | 9.15E-05 | -0.6159107 | 0.818 | 0.214 | 0.18293233 |
| ADH5 | 5.23E-26 | -0.5978122 | 0.809 | 0.029 | 1.05E-22 | CNN2 | 0.00016234 | -0.3433552 | 0.418 | 0.175 | 0.32468549 |
| AP005329.3 | 9.31E-26 | -0.2656241 | 0.973 | 0.078 | 1.86E-22 | MAP3K7CL | 0.00018882 | 0.27467461 | 1 | 0.476 | 0.37763737 |
| SPCS31 | 4.90E-25 | -0.4156374 | 1 | 0.107 | 9.79E-22 | H1ST1H4H1 | 0.0002095 | -0.6813678 | 0.736 | 0.136 | 0.41899267 |
| SOX41 | 2.15E-24 | -0.331246 | 0.827 | 0.049 | 4.31E-21 | CMTM5 | 0.00021589 | 0.55406331 | 1 | 0.825 | 0.43178703 |
| HPGD | 4.25E-24 | -0.3226998 | 1 | 0.117 | 8.49E-21 | MCM71 | 0.00033789 | -0.3195537 | 0.191 | 0.029 | 0.67578454 |
| CITED21 | 1.11E-23 | -0.2254738 | 0.8 | 0.039 | 2.23E-20 | SLIRP1 | 0.00041065 | -0.2704874 | 0.209 | 0.039 | 0.82129861 |
| LINC02284 | 3.32E-23 | -0.3057828 | 0.918 | 0.058 | 6.64E-20 | RGS18 | 0.00056527 | 0.37056488 | 1 | 0.854 | 1 |
| LGMN | 3.49E-23 | 0.32317015 | 0.118 | 0.049 | 6.99E-20 | SLC35B1 | 0.0006183 | -0.2501348 | 0.555 | 0.049 | 1 |
| HBA21 | 4.80E-23 | -1.5607626 | 0.718 | 0.019 | 9.60E-20 | TXNDC171 | 0.00081759 | -0.284855 | 0.7 | 0.107 | 1 |
| SCYGR4 | 5.95E-23 | -0.4354991 | 1 | 0.126 | 1.19E-19 | F13A1 | 0.00081812 | -0.7304843 | 0.809 | 0.68 | 1 |
| HLTF | 6.08E-23 | -0.3342621 | 1 | 0.126 | 1.22E-19 | RPLP01 | 0.00082471 | -0.9069182 | 0.709 | 0.117 | 1 |

TABLE 15-continued

| | p_val | avg_logFC | pct.1 | pct.2 | p_val_adj | | p_val | avg_logFC | pct.1 | pct.2 | p_val_adj |
|---|---|---|---|---|---|---|---|---|---|---|---|
| FKBP21 | 3.36E-22 | -0.3879057 | 0.882 | 0.078 | 6.72E-19 | SMIM3 | 0.00116364 | 0.50041406 | 0.855 | 0.456 | 1 |
| H1FX6 | 1.01E-21 | -0.5960441 | 1 | 0.136 | 2.02E-18 | FSTL1 | 0.00130146 | 0.56616819 | 0.655 | 0.058 | 1 |
| TESC | 1.33E-21 | -0.3783958 | 0.791 | 0.058 | 2.66E-18 | CA2 | 0.00148635 | 0.54962464 | 1 | 0.524 | 1 |
| CKS2 | 3.63E-21 | -0.2784784 | 0.755 | 0.049 | 7.25E-18 | HNRNPA2B12 | 0.00157316 | -0.4363674 | 0.527 | 0.34 | 1 |
| SMIM1 | 3.87E-21 | 0.35745313 | 1 | 0.155 | 7.74E-18 | ATP5MC11 | 0.00181872 | -0.2953137 | 0.182 | 0.039 | 1 |
| ERH2 | 4.96E-21 | -0.3233682 | 0.882 | 0.068 | 9.92E-18 | AL731557.1 | 0.00192875 | 0.66731183 | 0.955 | 0.476 | 1 |
| MDH11 | 9.94E-21 | -0.2737655 | 0.864 | 0.058 | 1.99E-17 | MIF2 | 0.00210174 | -0.6119289 | 0.727 | 0.155 | 1 |
| NCL2 | 4.11E-20 | -0.5533765 | 0.909 | 0.087 | 8.23E-17 | ACRBP | 0.00226084 | 0.34443016 | 1 | 0.699 | 1 |
| HDAC1 | 5.54E-20 | -0.3128595 | 0.927 | 0.087 | 1.11E-16 | TSPAN13 | 0.0024578 | 0.47668387 | 0.664 | 0.087 | 1 |
| HBB2 | 5.88E-19 | -1.0079565 | 1 | 0.058 | 1.18E-15 | TUBA1C | 0.00309568 | 0.37480297 | 1 | 0.544 | 1 |
| CHST8 | 1.34E-18 | 0.37919822 | 0.173 | 0.039 | 2.67E-15 | BCL2L1 | 0.00392692 | 0.38110013 | 0.682 | 0.126 | 1 |
| CAV2 | 1.65E-17 | -0.2661435 | 0.145 | 0.175 | 3.29E-14 | SNAP231 | 0.00440288 | 0.42085718 | 0.9 | 0.602 | 1 |
| ANXA3 | 2.09E-17 | -0.2688105 | 0.991 | 0.097 | 4.17E-14 | HSP90AB11 | 0.00546443 | -0.3655581 | 0.409 | 0.078 | 1 |
| CCT21 | 2.76E-17 | -0.5134395 | 0.909 | 0.097 | 5.52E-14 | RAN2 | 0.00563513 | -0.4355993 | 0.691 | 0.126 | 1 |
| SAMD14 | 4.19E-17 | 0.27701334 | 0.191 | 0.019 | 8.38E-14 | PLEK2 | 0.006395 | -0.6628342 | 0.927 | 0.398 | 1 |
| CPNE51 | 4.68E-17 | 0.50380221 | 0.2 | 0.194 | 9.35E-14 | PPIA2 | 0.00929064 | -0.3561187 | 0.882 | 0.369 | 1 |
| IGFBP2 | 7.06E-17 | -0.4590792 | 0.964 | 0.097 | 1.41E-13 | SMOX | 0.01018527 | 0.30537437 | 0.482 | 0.117 | 1 |
| HIST1H2AE1 | 2.60E-16 | -0.263868 | 0.964 | 0.068 | 5.20E-13 | GAS2L1 | 0.01090239 | 0.30895951 | 0.864 | 0.291 | 1 |
| CA1 | 3.12E-16 | -0.4389654 | 0.555 | 0.155 | 6.24E-13 | GP9 | 0.01266934 | 0.25412658 | 1 | 0.485 | 1 |
| ZNF778 | 3.30E-16 | -0.704542 | 1 | 0.019 | 6.60E-13 | EFHC2 | 0.01474886 | -0.4167103 | 1 | 0.893 | 1 |
| MTSS1 | 7.24E-16 | 0.28076466 | 0.2 | 0.049 | 1.45E-12 | CD742 | 0.0151317 | -0.3322745 | 0.655 | 0.097 | 1 |
| NDUFA8 | 1.78E-15 | -0.263868 | 0.964 | 0.165 | 3.56E-12 | COTL14 | 0.01513699 | 0.28101536 | 0.664 | 0.117 | 1 |
| S100A87 | 1.84E-15 | -0.8992143 | 0.209 | 0.097 | 3.67E-12 | LIMS1 | 0.01696448 | 0.30595125 | 0.973 | 0.718 | 1 |
| MOB1B | 2.19E-15 | -0.6437291 | 0.218 | 0.155 | 4.38E-12 | CLEC1B | 0.01729372 | 0.26354045 | 0.991 | 0.777 | 1 |
| PARD3 | 2.75E-15 | 0.47406488 | 0.964 | 0.049 | 5.50E-12 | ID2 | 0.01865018 | -0.4117448 | 1 | 0.709 | 1 |
| HIST1H2AG1 | 3.15E-15 | -0.2770482 | 0.218 | 0.107 | 6.29E-12 | PKHD1L1 | 0.02134879 | -0.361028 | 0.682 | 0.049 | 1 |
| MNDA | 1.02E-14 | -0.3209176 | 0.564 | 0.039 | 2.03E-11 | SLC25A371 | 0.02510596 | -0.7928906 | 0.436 | 0.146 | 1 |
| GP6 | 5.19E-14 | 0.3442576 | 0.955 | 0.204 | 1.04E-10 | MCEMP1 | 0.02532917 | -0.5106169 | 0.645 | 0.049 | 1 |
| GSTP12 | 6.29E-14 | -0.4989476 | 0.982 | 0.204 | 1.26E-10 | PRKAR2B | 0.02722451 | 0.5230364 | 1 | 0.097 | 1 |
| HMGN21 | 2.80E-13 | -0.7299748 | 0.245 | 0.097 | 5.59E-10 | ANKRD281 | 0.03221387 | -0.4355547 | 0.691 | 0.728 | 1 |
| TXN2 | 3.49E-13 | -0.3464176 | 0.955 | 0.194 | 6.98E-10 | YWHAH | 0.0338281 | 0.26655067 | 0.964 | 0.165 | 1 |
| MYCT1 | 8.83E-13 | -0.4064753 | 0.909 | 0.155 | 1.77E-09 | H2AFV2 | 0.04038168 | -0.4307762 | 0.645 | 0.806 | 1 |
| PRTFDC1 | 1.16E-12 | -0.4149414 | 0.9 | 0.146 | 2.31E-09 | MTRNR2L122 | 0.04854072 | -0.2998748 | 0.755 | 0.107 | 1 |
| ANK1 | 2.82E-12 | 0.26447774 | 0.245 | 0.039 | 5.65E-09 | SPARC | 0.05062706 | -0.3342517 | 0.955 | 0.563 | 1 |
| STMN12 | 2.94E-12 | -0.3379279 | 0.518 | 0.049 | 5.88E-09 | NME4 | 0.06373456 | 0.25490413 | 0.491 | 0.718 | 1 |
| GALM1 | 3.54E-12 | -0.3693489 | 0.818 | 0.068 | 7.08E-09 | ABCC3 | 0.06834343 | 0.33113949 | 0.709 | 0.165 | 1 |
| SMS | 6.82E-12 | -0.2954784 | 0.982 | 0.233 | 1.36E-08 | S100A63 | 0.07181734 | -1.0351499 | 0.545 | 0.262 | 1 |
| PSMA61 | 2.06E-11 | -0.5642046 | 0.873 | 0.136 | 4.12E-08 | S100A44 | 0.07375635 | -0.5628848 | 0.7 | 0.223 | 1 |
| GLUL | 1.21E-10 | 0.29738821 | 0.982 | 0.282 | 2.42E-07 | KLHDC8B | 0.07616635 | 0.42720233 | 0.645 | 0.204 | 1 |
| CTSW1 | 1.23E-10 | 0.37268978 | 0.273 | 0.087 | 2.47E-07 | CXCL16 | 0.09729291 | -0.291562 | 0.609 | 0.155 | 1 |
| MEIS1 | 2.04E-10 | -0.2819608 | 0.836 | 0.117 | 4.07E-07 | PSMB81 | 0.09857986 | -0.2509869 | 0.673 | 0.078 | 1 |
| BEND2 | 2.88E-10 | -0.3118855 | 0.8 | 0.078 | 5.76E-07 | TPST2 | 0.14519054 | 0.43960304 | 0.764 | 0.175 | 1 |
| ZFP36L22 | 3.21E-10 | -0.3167602 | 0.455 | 0.049 | 6.42E-07 | LDHB1 | 0.15741039 | -0.2808119 | 0.491 | 0.447 | 1 |
| SNRPE1 | 3.84E-10 | -0.3302044 | 1 | 0.039 | 7.67E-07 | EIF2S21 | 0.1606302 | -0.7095377 | 0.455 | 0.097 | 1 |
| 11-Sep | 4.37E-10 | 0.34430914 | 0.873 | 0.311 | 8.75E-07 | HIST1H3H | 0.16422559 | -0.5470152 | 0.645 | 0.117 | 1 |
| PPP1R14A | 5.93E-10 | 0.43489119 | 1 | 0.175 | 1.19E-06 | AL031005.1 | 0.20221168 | -0.5245346 | 0.582 | 0.398 | 1 |
| NPM11 | 1.73E-09 | -0.6181594 | 0.264 | 0.087 | 3.47E-06 | BLVRB1 | 0.2901196 | -0.3010729 | 0.573 | 0.058 | 1 |
| CALR1 | 1.98E-09 | -0.3436057 | 0.291 | 0.068 | 3.95E-06 | RHOBTB1 | 0.36251817 | 0.52455765 | 0.564 | 0.058 | 1 |
| COPS3 | 2.01E-09 | -0.4027681 | 0.773 | 0.078 | 4.02E-06 | ACTG11 | 0.37505842 | -0.4729819 | 0.891 | 0.621 | 1 |
| HSPA53 | 2.29E-09 | -0.5967027 | 0.655 | 0.087 | 4.59E-06 | F2R | 0.38338087 | -0.2685756 | 0.718 | 0.311 | 1 |
| SEC61G2 | 3.43E-09 | -1.034136 | 0.9 | 0.194 | 6.87E-06 | EIF2AK1 | 0.39845245 | -0.3210074 | 0.718 | 0.427 | 1 |

TABLE 15-continued

| | p_val | avg_logFC | pct.1 | pct.2 | p_val_adj | | p_val | avg_logFC | pct.1 | pct.2 | p_val_adj |
|---|---|---|---|---|---|---|---|---|---|---|---|
| S100A91 | 6.55E-09 | 0.5379231 | 0.3 | 0.087 | 1.31E-05 | IFI272 | 0.40033576 | 0.60596155 | 0.555 | 0.214 | 1 |
| SLC25A51 | 1.01E-08 | -0.4283975 | 0.836 | 0.146 | 2.03E-05 | KDELR21 | 0.40882726 | -0.2719311 | 0.509 | 0.068 | 1 |
| TNS1 | 1.10E-08 | -0.2730249 | 0.355 | 0.029 | 2.20E-05 | AC090409.1 | 0.41909304 | -0.2584666 | 0.7 | 0.282 | 1 |
| ZFP362 | 1.33E-08 | -0.4170748 | 0.282 | 0.058 | 2.65E-05 | CCT6A1 | 0.43072113 | 0.28719921 | 0.555 | 0.049 | 1 |
| CTTN | 1.33E-08 | 0.51924207 | 0.955 | 0.301 | 2.65E-05 | MYL91 | 0.43883644 | -0.2706375 | 0.918 | 0.709 | 1 |
| CCT82 | 2.35E-08 | -0.33749 | 0.755 | 0.058 | 4.70E-05 | CST71 | 0.46020167 | 0.57591189 | 0.982 | 0.039 | 1 |
| 1-Jun | 3.74E-08 | -0.503506 | 0.2 | 0.058 | 7.49E-05 | ACSM3 | 0.46900149 | -0.850655 | 0.282 | 0.039 | 1 |
| SUB11 | 4.83E-08 | 0.494673 | 0.873 | 0.194 | 9.66E-05 | TRAPPC3L | 0.47196458 | -0.4690318 | 0.627 | 0.165 | 1 |
| HBD | 6.72E-08 | 0.40998362 | 0.736 | 0.049 | 0.00013431 | FRMD3 | 0.63454438 | 0.44802919 | 0.682 | 0.301 | 1 |
| MTDH1 | 1.17E-07 | -0.3203323 | 0.791 | 0.117 | 0.00013949 | MMP1 | 0.63530949 | 0.39420247 | 0.491 | 0.029 | 1 |
| PA2G42 | 2.66E-07 | -0.303838 | 0.355 | 0.049 | 0.0005321 | PSMB22 | 0.65420187 | -0.3068711 | 0.527 | 0.087 | 1 |
| LXN | 3.43E-07 | -0.5014015 | 0.791 | 0.126 | 0.00068601 | IFITM31 | 0.77313389 | 0.54787437 | 0.891 | 0.777 | 1 |
| AATK | 4.64E-07 | -0.2907361 | 0.764 | 0.097 | 0.00092728 | GIPC3 | 0.81118407 | 0.2568133 | 0.5 | 0.019 | 1 |
| SLC40A1 | 5.65E-07 | 0.26171642 | 1 | 0.388 | 0.00112993 | FADS2 | 0.83948605 | -0.3175463 | 0.518 | 0.068 | 1 |
| PTCRA | 6.03E-07 | 0.49909694 | 0.982 | 0.447 | 0.0012065 | NINJ11 | 0.86842895 | -0.2691373 | 0.555 | 0.117 | 1 |
| EEF1A11 | 6.21E-07 | -0.3152576 | 1 | 0.35 | 0.00124106 | GATA2 | 0.90927441 | 0.32091024 | 0.518 | 0.029 | 1 |
| PPIB1 | 6.27E-07 | -0.6977537 | 0.855 | 0.194 | 0.00125359 | XK | 0.91841826 | -0.2540339 | 0.582 | 0.165 | 1 |
| WDR742 | 9.55E-07 | -0.2858942 | 0.282 | 0.019 | 0.00191004 | GGCT | 0.94567631 | -0.266574 | 0.518 | 0.039 | 1 |
| PLA2G12A | 1.20E-06 | 0.42926294 | 0.982 | 0.398 | 0.0024011 | MT-CO21 | 0.96184772 | 0.29819738 | 0.964 | 0.883 | 1 |
| ATP5MC32 | 1.28E-06 | -0.2790126 | 0.764 | 0.107 | 0.00255473 | | | | | | |
| | | | | | | Seurat Cluster 11 | | | | | |
| PTCH21 | 4.58E-30 | -0.3551208 | 1 | 0.037 | 9.16E-27 | LST11 | 8.57E-07 | -0.8810265 | 0.946 | 0.268 | 0.00171342 |
| IGKV1-51 | 9.97E-29 | -0.2631169 | 0.973 | 0.037 | 1.99E-25 | F13A11 | 9.33E-07 | -0.2752186 | 0.315 | 0.049 | 0.00186613 |
| TARS | 1.15E-26 | -0.3047019 | 0.973 | 0.049 | 2.30E-23 | DHFR | 1.48E-06 | 0.25499181 | 0.532 | 0 | 0.00296899 |
| PDCD52 | 5.37E-26 | -0.3057361 | 0.91 | 0.024 | 1.07E-22 | CLEC4A | 1.51E-06 | 0.25375903 | 0.486 | 0.024 | 0.00302616 |
| CCL4L23 | 6.81E-25 | -0.4482628 | 0.964 | 0.061 | 1.36E-21 | LILRB1 | 2.77E-06 | -0.6954236 | 0.396 | 0.256 | 0.00553257 |
| HSPB111 | 1.41E-24 | -0.273662 | 0.946 | 0.037 | 2.82E-21 | CSTA | 4.12E-06 | 0.57299012 | 0.703 | 0.024 | 0.00824087 |
| C1QC2 | 1.36E-23 | -0.2860715 | 0.892 | 0.049 | 2.71E-20 | HLA-DRB12 | 5.69E-06 | -0.3348262 | 0.991 | 0.341 | 0.01137413 |
| LDLRAD4 | 2.98E-23 | -0.3543152 | 0.964 | 0.061 | 5.96E-20 | IFI273 | 7.29E-06 | 0.3406102 | 0.676 | 0.012 | 0.01458428 |
| PDK4 | 6.84E-23 | -0.537797 | 1 | 0.098 | 1.37E-19 | JAML2 | 1.08E-05 | -0.7000362 | 0.405 | 0.232 | 0.02157994 |
| SPARC1 | 3.82E-22 | 0.29786374 | 0.108 | 0 | 7.64E-19 | HEY1 | 1.18E-05 | -0.2779801 | 0.27 | 0.024 | 0.02361687 |
| NDUFAB11 | 6.98E-22 | -0.4778656 | 0.865 | 0.049 | 1.40E-18 | HCK | 1.68E-05 | -0.3597829 | 0.369 | 0.134 | 0.03350738 |
| FKBP22 | 1.62E-21 | -0.3719795 | 0.946 | 0.085 | 3.24E-18 | MT2A6 | 1.68E-05 | -0.9713873 | 0.982 | 0.329 | 0.03367007 |
| COMTD11 | 1.76E-21 | -0.4185143 | 0.91 | 0.061 | 3.51E-18 | CD36 | 1.79E-05 | -0.3633443 | 0.378 | 0.159 | 0.03578283 |
| HLA-DQA11 | 3.41E-21 | -0.5082185 | 0.964 | 0.073 | 6.82E-18 | CKAP21 | 1.95E-05 | -0.672811 | 0.378 | 0.146 | 0.03906033 |
| HSPA1B | 2.34E-20 | -0.3076627 | 0.766 | 0.024 | 4.69E-17 | LGALS12 | 2.79E-05 | -0.322474 | 0.865 | 0.244 | 0.05574141 |
| GBP11 | 2.66E-20 | -0.2827568 | 0.946 | 0.073 | 5.32E-17 | GADD45B3 | 2.91E-05 | -0.3105573 | 0.901 | 0.28 | 0.0582235 |
| KPNA2 | 2.73E-20 | -0.3789009 | 0.946 | 0.073 | 5.46E-17 | CXCL21 | 3.90E-05 | -0.3252335 | 0.748 | 0.11 | 0.07808521 |
| LMNB1 | 2.73E-20 | -0.4275344 | 0.946 | 0.073 | 5.46E-17 | NUCB21 | 7.92E-05 | -0.2768375 | 0.667 | 0.037 | 0.1584854 |
| BANF1 | 2.81E-20 | -0.3618561 | 0.847 | 0.037 | 5.62E-17 | PTGS1 | 9.33E-05 | 0.32952845 | 0.189 | 0 | 0.18659184 |
| GLDN | 3.27E-20 | -0.3114011 | 0.748 | 0.024 | 6.53E-17 | TUBA1C1 | 0.000107 | 0.39605643 | 0.342 | 0.012 | 0.21400727 |
| ZNF503 | 5.03E-19 | 0.278329 | 0.883 | 0.037 | 1.01E-15 | MAP3K83 | 0.00012627 | 0.25797778 | 0.973 | 0.402 | 0.2525394 |
| CH25H1 | 5.58E-19 | 0.35247775 | 0.874 | 0.024 | 1.12E-15 | S100A45 | 0.00012763 | -0.3520595 | 1 | 0.402 | 0.25525285 |
| SEMA4A1 | 3.95E-18 | -0.387116 | 0.946 | 0.098 | 7.91E-15 | HMGB14 | 0.0001396 | 0.3071629 | 0.964 | 0.427 | 0.27920235 |
| START HERE | | | | | | | | | | | |
| FCGR3A2 | 5.00E-18 | -0.8533754 | 0.964 | 0.122 | 1.00E-14 | FTH11 | 0.00015929 | -0.3726079 | 0.946 | 0.927 | 0.31857612 |
| PSMB92 | 5.76E-18 | -0.4695057 | 0.946 | 0.098 | 1.15E-14 | IFI44L4 | 0.00017271 | 0.43619111 | 0.667 | 0.037 | 0.34542008 |
| TUBB2A | 6.65E-18 | -0.3957754 | 0.892 | 0.061 | 1.33E-14 | NUDT11 | 0.00017575 | -0.352187 | 0.658 | 0.049 | 0.35149967 |
| PTGER41 | 1.31E-17 | -0.4940826 | 0.162 | 0.073 | 2.61E-14 | WARS1 | 0.00017922 | -0.3177414 | 0.423 | 0.207 | 0.35843129 |

TABLE 15-continued

| | p_val | avg_logFC | pct.1 | pct.2 | p_val_adj | | p_val | avg_logFC | pct.1 | pct.2 | p_val_adj |
|---|---|---|---|---|---|---|---|---|---|---|---|
| CENPN | 1.74E-17 | -0.2504797 | 0.676 | 0.024 | 3.47E-14 | ACTN1 | 0.0002007 | 0.32923158 | 0.658 | 0.024 | 0.40139064 |
| PSMA42 | 1.94E-17 | -0.264961 | 0.937 | 0.098 | 3.87E-14 | ACTG12 | 0.00023909 | -0.3796666 | 0.432 | 0.232 | 0.4781892 |
| THBD | 1.69E-16 | 0.7871928 | 0.162 | 0 | 3.37E-13 | NCL3 | 0.00027528 | -0.3333016 | 0.414 | 0.171 | 0.55056832 |
| MGST1 | 2.56E-16 | 0.30406576 | 0.802 | 0.012 | 5.13E-13 | HDLBP1 | 0.00041519 | -0.3032385 | 0.378 | 0.061 | 0.8303898 |
| C1QA1 | 4.15E-16 | -0.7185597 | 0.82 | 0.098 | 8.30E-13 | PLAUR | 0.00054886 | -0.6971453 | 0.486 | 0.293 | 1 |
| TUFM2 | 7.72E-16 | -0.2954237 | 0.18 | 0.049 | 1.54E-12 | Z93241.12 | 0.00061013 | -0.521962 | 0.378 | 0.049 | 1 |
| PHTF1 | 1.22E-15 | -0.3164415 | 0.892 | 0.073 | 2.44E-12 | SIGLEC10 | 0.0007167 | -0.6228713 | 0.613 | 0.098 | 1 |
| IDH22 | 3.16E-15 | -0.3068202 | 0.18 | 0.024 | 6.33E-12 | AIF11 | 0.00073471 | -0.3937071 | 0.829 | 0.244 | 1 |
| RF10B2 | 5.95E-15 | -0.6661561 | 0.946 | 0.244 | 1.19E-11 | SLC25A372 | 0.00088971 | 0.26758494 | 0.793 | 0.244 | 1 |
| TFDP1 | 1.20E-14 | -0.3001096 | 0.829 | 0.024 | 2.39E-11 | SNRNP25 | 0.00131258 | -0.2839481 | 0.243 | 0.024 | 1 |
| HLA-DPA12 | 3.90E-14 | -0.6032556 | 0.973 | 0.171 | 7.80E-11 | THBS11 | 0.00181363 | 0.34003085 | 0.432 | 0.22 | 1 |
| S100A121 | 1.10E-13 | 0.35756376 | 0.937 | 0.159 | 2.21E-10 | KLF102 | 0.00197735 | -0.2624701 | 0.847 | 0.293 | 1 |
| SCGB3A1 | 1.20E-13 | -0.3443286 | 0.532 | 0.012 | 2.40E-10 | ANXA51 | 0.00208886 | 0.32522748 | 0.739 | 0.183 | 1 |
| MT1X1 | 1.40E-13 | 0.25836927 | 0.82 | 0.024 | 2.79E-10 | HIST1H2AC1 | 0.0020894 | -0.275304 | 0.631 | 0.085 | 1 |
| C5AR2 | 1.41E-13 | -0.5887204 | 0.883 | 0.098 | 2.81E-10 | C5AR11 | 0.00225692 | -0.2535083 | 0.739 | 0.171 | 1 |
| RGCC2 | 2.54E-13 | 0.25232899 | 0.982 | 0.207 | 5.09E-10 | PSAP1 | 0.00273404 | -0.5498077 | 0.604 | 0.463 | 1 |
| PSMA31 | 4.13E-13 | -0.4467314 | 0.919 | 0.134 | 8.25E-10 | CYTOR2 | 0.00389966 | 0.30186494 | 0.64 | 0.037 | 1 |
| MEF2C2 | 4.51E-13 | -0.4515198 | 1 | 0.207 | 9.01E-10 | SMIM251 | 0.00419161 | -0.4833369 | 0.432 | 0.122 | 1 |
| C1QB1 | 6.19E-13 | -0.9851519 | 0.694 | 0.085 | 1.24E-09 | ANPEP | 0.00494801 | 0.31483134 | 0.423 | 0.11 | 1 |
| TNFAIP61 | 7.07E-13 | -0.310417 | 0.865 | 0.085 | 1.41E-09 | DDAH2 | 0.00586898 | 0.34997611 | 0.396 | 0.024 | 1 |
| CXCL8 | 7.28E-13 | 0.53765491 | 0.91 | 0.146 | 1.46E-09 | CMC1 | 0.00673221 | 0.25747542 | 0.351 | 0 | 1 |
| TMED101 | 7.52E-13 | -0.2579218 | 0.856 | 0.085 | 1.50E-09 | LYN1 | 0.00715314 | -0.4806305 | 0.495 | 0.244 | 1 |
| HES41 | 1.73E-12 | -0.5553781 | 0.973 | 0.195 | 3.46E-09 | S100A88 | 0.0079833 | 0.3180911 | 0.991 | 0.695 | 1 |
| BZW2 | 1.81E-12 | 0.25177897 | 0.18 | 0.012 | 3.62E-09 | MS4A7 | 0.0118435 | -0.5483664 | 0.775 | 0.232 | 1 |
| HMOX1 | 3.22E-12 | -0.3973598 | 0.892 | 0.122 | 6.44E-09 | LILRA1 | 0.01228447 | 0.42603268 | 0.604 | 0.037 | 1 |
| HMGB23 | 5.74E-12 | -0.3615311 | 0.982 | 0.207 | 1.15E-08 | MT-ATP82 | 0.01510414 | -0.7503499 | 0.874 | 0.744 | 1 |
| CCL32 | 6.56E-12 | 0.31965903 | 0.838 | 0.073 | 1.31E-08 | PSMB82 | 0.0203424 | -0.4127196 | 0.658 | 0.098 | 1 |
| FPR1 | 7.40E-12 | -0.2989933 | 0.243 | 0.11 | 1.48E-08 | SERPINA11 | 0.02156413 | -0.2689575 | 0.495 | 0.207 | 1 |
| CENPF | 8.03E-12 | -0.4170142 | 0.568 | 0.024 | 1.61E-08 | HLA-DRA2 | 0.02294868 | -0.5460495 | 0.811 | 0.293 | 1 |
| CSF1R | 1.29E-11 | -0.899464 | 0.252 | 0.122 | 2.58E-08 | CCT22 | 0.02307292 | -0.358072 | 0.631 | 0.061 | 1 |
| EDN1 | 1.31E-11 | -0.273727 | 0.604 | 0.024 | 2.63E-08 | S100A92 | 0.02555654 | 0.46016333 | 0.766 | 0.402 | 1 |
| TRGC2 | 1.45E-11 | -0.3222723 | 0.495 | 0.024 | 2.91E-08 | MT-ND4L3 | 0.02863412 | -0.2672295 | 0.955 | 0.951 | 1 |
| SIGLEC1 | 2.95E-11 | 0.52038186 | 0.793 | 0.037 | 5.91E-08 | ISOC21 | 0.03098043 | -0.3329128 | 0.234 | 0.024 | 1 |
| CFD | 4.24E-11 | -0.3561847 | 0.91 | 0.159 | 8.49E-08 | TPI11 | 0.03755223 | -0.2804112 | 0.631 | 0.11 | 1 |
| TCF7L2 | 5.36E-11 | -0.6026776 | 0.27 | 0 | 1.07E-07 | TMEM2081 | 0.04421371 | 0.2506299 | 0.414 | 0.012 | 1 |
| TUBB1 | 6.75E-11 | 0.25736003 | 0.207 | 0.159 | 1.35E-07 | EIF4A32 | 0.04576569 | -0.3007271 | 0.45 | 0.073 | 1 |
| P4HB1 | 2.37E-10 | 0.25376428 | 0.261 | 0 | 4.74E-07 | PARVB | 0.04971927 | -0.3802888 | 0.441 | 0.049 | 1 |
| MZB11 | 2.92E-10 | -0.3093985 | 0.45 | 0.11 | 5.84E-07 | TRIB1 | 0.06095881 | 0.39145801 | 0.45 | 0.073 | 1 |
| CUX1 | 4.27E-10 | 0.57329890 | 0.838 | 0.024 | 8.55E-07 | MINDY11 | 0.06572884 | -0.2528577 | 0.523 | 0.037 | 1 |
| ATP5MC33 | 4.80E-10 | 0.26315466 | 0.252 | 0.024 | 9.60E-07 | NR4A1 | 0.06787713 | -0.6874037 | 0.73 | 0.22 | 1 |
| MYCBP | 4.96E-10 | -0.2592386 | 0.667 | 0.073 | 9.93E-07 | LDHA2 | 0.07589694 | -0.3975689 | 0.694 | 0.183 | 1 |
| SLC2A61 | 5.00E-10 | -0.3679306 | 0.865 | 0.134 | 1.00E-06 | BCL2A11 | 0.07949952 | -0.6125415 | 0.568 | 0.268 | 1 |
| CTSA | 6.18E-10 | 0.33452569 | 0.847 | 0.122 | 1.24E-06 | CLEC7A | 0.08567736 | -0.2990333 | 0.892 | 0.427 | 1 |
| ELL21 | 6.50E-10 | -0.3777304 | 0.856 | 0.122 | 1.30E-06 | HSH2D3 | 0.09152248 | 0.28830929 | 0.414 | 0.012 | 1 |
| GBP5 | 7.05E-10 | -0.3060093 | 0.261 | 0.049 | 1.41E-06 | CCL43 | 0.09676745 | -0.7206158 | 0.604 | 0.061 | 1 |
| RPS27L3 | 1.02E-09 | -0.4369935 | 0.27 | 0.073 | 2.05E-06 | GAPDH1 | 0.10171119 | -0.3134391 | 0.613 | 0.329 | 1 |
| TCF41 | 1.31E-09 | -0.5279305 | 0.829 | 0.098 | 2.62E-06 | HLA-DMA | 0.11505663 | -0.3612782 | 0.622 | 0.11 | 1 |
| CTSC2 | 1.59E-09 | -0.3486363 | 0.883 | 0.159 | 3.18E-06 | H2AFZ1 | 0.13554916 | -0.4864132 | 0.613 | 0.085 | 1 |
| SMC4 | 1.67E-09 | 0.38986459 | 0.225 | 0.012 | 3.35E-06 | HLA-DRB52 | 0.15419157 | -0.4756975 | 0.523 | 0.171 | 1 |
| CCT6A2 | 2.35E-09 | -0.4180778 | 0.261 | 0.049 | 4.71E-06 | EIF2S22 | 0.18933458 | -0.3151387 | 0.486 | 0.085 | 1 |
| NLRP3 | 3.74E-09 | 0.340988 | 0.982 | 0.293 | 7.49E-06 | IGSF61 | 0.21207728 | -0.3635945 | 0.613 | 0.11 | 1 |

TABLE 15-continued

| | p_val | avg_logFC | pct.1 | pct.2 | p_val_adj | | p_val | avg_logFC | pct.1 | pct.2 | p_val_adj |
|---|---|---|---|---|---|---|---|---|---|---|---|
| UBE2I1 | 5.15E-09 | -0.4682392 | 0.306 | 0.171 | 1.03E-05 | NCF12 | 0.2271152 | 0.34400101 | 0.73 | 0.354 | 1 |
| IFNGR2 | 5.16E-09 | 0.53865874 | 0.91 | 0.244 | 1.03E-05 | FTL1 | 0.25823653 | -0.4116565 | 0.829 | 0.585 | 1 |
| SNAP232 | 8.35E-09 | -0.3398092 | 0.793 | 0.073 | 1.67E-05 | SPI11 | 0.31815189 | -0.3733558 | 0.73 | 0.451 | 1 |
| ARL6IP1 | 1.14E-08 | -0.5513689 | 0.297 | 0.11 | 2.29E-05 | ATP5MC12 | 0.32678291 | -0.395329 | 0.495 | 0.073 | 1 |
| ATP5F1A1 | 1.42E-08 | 0.48663902 | 0.279 | 0.049 | 2.83E-05 | CDKN1C | 0.3442168 | -0.4025077 | 0.162 | 0.049 | 1 |
| EREG | 1.57E-08 | 0.35520477 | 0.919 | 0.244 | 3.14E-05 | CAPG | 0.35204589 | 0.25064265 | 0.459 | 0.024 | 1 |
| VMO1 | 2.27E-08 | -0.3265101 | 0.477 | 0.024 | 4.53E-05 | SLC31A2 | 0.35635701 | -0.4213209 | 0.523 | 0.122 | 1 |
| CORO1A2 | 2.36E-08 | -0.2724529 | 0.324 | 0.195 | 4.72E-05 | PPIA3 | 0.55137654 | -0.3014955 | 0.595 | 0.122 | 1 |
| GSTP13 | 2.58E-08 | 0.27705165 | 0.847 | 0.159 | 5.16E-05 | NDUFAF31 | 0.61319616 | 0.25825711 | 0.351 | 0.012 | 1 |
| RNF144B1 | 3.11E-08 | -0.391325 | 0.964 | 0.256 | 6.22E-05 | HLA-DPB12 | 0.67004622 | -0.5884151 | 0.604 | 0.146 | 1 |
| XIST5 | 5.80E-08 | -0.826041 | 1 | 0.293 | 0.00011609 | TIMP13 | 0.69080038 | -0.4363464 | 0.649 | 0.293 | 1 |
| XBP11 | 1.45E-07 | 0.52850089 | 0.748 | 0.049 | 0.00029029 | P2RY131 | 0.73253831 | -0.6427795 | 0.577 | 0.11 | 1 |
| CDKN1A2 | 1.45E-07 | 0.43646483 | 0.829 | 0.171 | 0.00029074 | FAM110A | 0.75163688 | -0.388404 | 0.505 | 0.061 | 1 |
| ATP1B31 | 2.05E-07 | -0.3058339 | 0.82 | 0.134 | 0.00040986 | ETS21 | 0.76165088 | -0.6038321 | 0.676 | 0.256 | 1 |
| FGL2 | 2.10E-07 | -0.4398959 | 0.82 | 0.159 | 0.0004204 | IFITM24 | 0.77379127 | -0.3201858 | 0.631 | 0.256 | 1 |
| FPR2 | 7.38E-07 | 0.35791011 | 0.532 | 0 | 0.00147521 | GRN | 0.95669214 | -0.2570653 | 0.649 | 0.256 | 1 |
| | | | | | | Seurat Cluster 12 | | | | | |
| JCHAIN1 | 1.34E-21 | -0.2591252 | 0.974 | 0.036 | 2.68E-18 | S100A46 | 0.01375439 | -0.3872949 | 1 | 0.881 | 1 |
| TRBV10-31 | 9.79E-18 | -0.5669549 | 0.842 | 0.036 | 1.96E-14 | HLA-DPB13 | 0.01548432 | 0.29650742 | 0.974 | 0.512 | 1 |
| TRBV12-31 | 5.49E-17 | -0.3062585 | 0.868 | 0.024 | 1.10E-13 | TRBV20-11 | 0.02299212 | -0.3996227 | 0.447 | 0.155 | 1 |
| TRBV30 | 1.98E-16 | -0.2882438 | 0.842 | 0.036 | 3.95E-13 | ORC6 | 0.02599466 | 0.27993355 | 0.737 | 0.238 | 1 |
| KLRC1 | 3.12E-15 | 0.28397624 | 0.947 | 0.083 | 6.23E-12 | GZMB2 | 0.02659635 | 0.82963519 | 0.684 | 0.143 | 1 |
| TRAV21 | 6.48E-13 | -0.3900092 | 0.842 | 0.036 | 1.30E-09 | ESCO2 | 0.03167654 | -0.3832587 | 0.632 | 0.262 | 1 |
| HJURP | 5.45E-12 | 1.03338088 | 0.895 | 0.155 | 1.09E-08 | ENO11 | 0.03287292 | 0.25563143 | 1 | 0.81 | 1 |
| LYZ1 | 2.60E-11 | 1.04020701 | 0.184 | 0.083 | 5.20E-08 | MAITK | 0.03426545 | 0.44405493 | 0.421 | 0.119 | 1 |
| TRAV12-3 | 2.95E-11 | -0.5189674 | 0.816 | 0.036 | 5.90E-08 | SPN | 0.03478566 | 0.37080241 | 0.947 | 0.512 | 1 |
| HIST1H2BM | 5.87E-11 | 0.35277438 | 0.737 | 0.012 | 1.17E-07 | TMPO2 | 0.0444888 | 0.31164545 | 0.947 | 0.679 | 1 |
| CPOX | 1.09E-09 | 0.37363608 | 0.237 | 0.06 | 2.17E-06 | TUBB4B2 | 0.04754575 | 0.41244281 | 0.895 | 0.536 | 1 |
| HIST1H3H1 | 1.22E-09 | 0.68887941 | 1 | 0.214 | 2.45E-06 | FBL1 | 0.0483891 | 0.26224037 | 0.947 | 0.607 | 1 |
| IGKC2 | 5.21E-08 | -1.8484113 | 0.526 | 0.06 | 0.00010415 | NASP1 | 0.04991798 | 0.25227563 | 0.947 | 0.667 | 1 |
| HIST1H3G | 5.95E-08 | 0.74164889 | 0.895 | 0.167 | 0.00011909 | IL321 | 0.06593109 | -0.2960783 | 1 | 0.869 | 1 |
| KIF2C | 1.02E-07 | 0.25012914 | 0.789 | 0.167 | 0.0002043 | HIST1H3C | 0.07798621 | 0.33694667 | 0.395 | 0.131 | 1 |
| CLIC3 | 1.75E-07 | 0.27673723 | 0.237 | 0.048 | 0.00035063 | CCL4L24 | 0.08342632 | -0.2762817 | 0.395 | 0.036 | 1 |
| S100A89 | 3.72E-07 | 0.65938727 | 0.947 | 0.214 | 0.00074336 | SAMD3 | 0.09199454 | -0.3277409 | 0.684 | 0.5 | 1 |
| PRC1 | 4.74E-07 | 0.5445247 | 0.868 | 0.167 | 0.00094765 | TUBB2 | 0.10226029 | 0.37146612 | 1 | 0.893 | 1 |
| TRBV28 | 5.22E-07 | -0.3008239 | 0.605 | 0.012 | 0.0010437 | DDX39A | 0.14323519 | 0.26664805 | 0.921 | 0.69 | 1 |
| PPBP4 | 2.03E-06 | 0.31058193 | 0.947 | 0.036 | 0.00406653 | TRBV5-6 | 0.15174856 | -0.2625709 | 0.105 | 0.036 | 1 |
| CENPE | 2.73E-06 | 0.30838119 | 1 | 0.31 | 0.00545981 | GZMA4 | 0.1709511 | -0.2529889 | 0.868 | 0.417 | 1 |
| ADGRG1 | 3.41E-06 | 0.32447679 | 0.263 | 0.024 | 0.00681977 | PRDX21 | 0.19523696 | -0.3818949 | 1 | 0.726 | 1 |
| HIST1H2BH | 4.99E-06 | 0.46573638 | 0.289 | 0.107 | 0.00998504 | TMEM1562 | 0.1993634 | -0.3148071 | 0.658 | 0.393 | 1 |
| DTHD11 | 5.67E-06 | 0.36626649 | 0.289 | 0.012 | 0.01133404 | CENPU2 | 0.20473817 | 0.2858951 | 1 | 0.631 | 1 |
| IFI274 | 2.92E-05 | -0.446519 | 0.868 | 0.19 | 0.05833763 | PMAIP1 | 0.21318229 | -0.3907488 | 0.737 | 0.583 | 1 |
| ENC11 | 3.82E-05 | 0.36198801 | 0.789 | 0.119 | 0.07649179 | CTSW2 | 0.21528652 | 0.41580641 | 0.5 | 0.226 | 1 |
| KIF18B | 5.28E-05 | 0.3559321 | 0.105 | 0 | 0.10554339 | FRMD4B | 0.22066787 | -0.2561892 | 0.526 | 0.179 | 1 |
| FANCI | 0.00010012 | 0.27099259 | 0.947 | 0.024314 | 0.20024314 | CENPF1 | 0.22505404 | 0.67955238 | 1 | 0.702 | 1 |
| HIST2H2BF | 0.0001366 | 0.30596706 | 0.763 | 0.107 | 0.27320328 | HSP90AB12 | 0.22693005 | 0.26539478 | 1 | 0.881 | 1 |
| EBP | 0.00019968 | 0.26774686 | 1 | 0.452 | 0.39936792 | AC245014.32 | 0.23260517 | 0.43879996 | 0.711 | 0.25 | 1 |
| NCAPG | 0.00027205 | 0.33264329 | 0.842 | 0.25 | 0.54409229 | H1FX7 | 0.24658873 | 0.35942404 | 0.947 | 0.607 | 1 |
| SGO2 | 0.00032447 | -0.2532543 | 0.895 | 0.238 | 0.64893822 | CD8A1 | 0.27910362 | 0.28100768 | 0.632 | 0.143 | 1 |
| KEFC1 | 0.00034123 | 0.55579328 | 0.789 | 0.19 | 0.68246971 | HIST1H1D5 | 0.31548173 | 0.54025406 | 1 | 0.869 | 1 |

TABLE 15-continued

| | p_val | avg_logFC | pct.1 | pct.2 | p_val_adj | | p_val | avg_logFC | pct.1 | pct.2 | p_val_adj |
|---|---|---|---|---|---|---|---|---|---|---|---|
| IGKV3D-11 | 0.00047998 | -0.3550433 | 0.184 | 0.012 | 0.95995558 | CD2 | 0.3391898 | 0.3689649 | 1 | 0.762 | 1 |
| IGHM1 | 0.00059978 | -1.5641324 | 0.342 | 0.06 | 1 | S100A111 | 0.35590344 | -0.2719143 | 0.974 | 0.738 | 1 |
| GNLY1 | 0.0006268 | 1.13068313 | 0.816 | 0.214 | 1 | UBE2S1 | 0.41642358 | 0.37027767 | 0.632 | 0.274 | 1 |
| GMNN | 0.00063222 | 0.29552768 | 0.868 | 0.333 | 1 | ZFP363 | 0.42533457 | 0.29311574 | 1 | 0.69 | 1 |
| CKAP2L | 0.00074042 | 0.3302547 | 0.737 | 0.179 | 1 | GRASP | 0.44416327 | 0.39281165 | 0.474 | 0.024 | 1 |
| AURKB | 0.00089349 | 0.30099819 | 0.711 | 0.143 | 1 | DUSP4 | 0.45493282 | 0.39144182 | 0.816 | 0.369 | 1 |
| MEF2C3 | 0.00091357 | -0.2861995 | 0.342 | 0.06 | 1 | IL7R3 | 0.45697144 | -0.5192762 | 1 | 0.548 | 1 |
| LEF1 | 0.00094246 | 0.26940307 | 0.895 | 0.25 | 1 | TYROBP | 0.46440174 | 0.25220871 | 0.579 | 0.083 | 1 |
| HIST2H2AC1 | 0.00162488 | -0.3190896 | 1 | 0.44 | 1 | LIMS13 | 0.57050344 | -0.3213486 | 0.947 | 0.595 | 1 |
| SHCBP1 | 0.00166899 | 0.3920258 | 0.868 | 0.298 | 1 | HIST1H3B2 | 0.69312567 | 0.30832638 | 0.579 | 0.321 | 1 |
| HACD31 | 0.0021307 | 0.32250909 | 0.921 | 0.345 | 1 | IGHG11 | 0.72377612 | -1.237727 | 0.184 | 0.024 | 1 |
| SPON2 | 0.00247189 | 0.32562339 | 0.763 | 0.179 | 1 | NUSAP1 | 0.73472112 | -0.2881507 | 0.842 | 0.571 | 1 |
| EZH21 | 0.00248565 | 0.41746588 | 1 | 0.56 | 1 | LTB | 0.73697278 | -0.6854475 | 0.816 | 0.5 | 1 |
| KPNA21 | 0.00413733 | 0.28208799 | 0.947 | 0.464 | 1 | NOSIP | 0.7913364 | -0.2587065 | 1 | 0.643 | 1 |
| HMGA11 | 0.00428758 | 0.393162 | 0.947 | 0.583 | 1 | TRBC2 | 0.79233934 | 0.33663103 | 0.947 | 0.75 | 1 |
| NCAPD2 | 0.0049988 | 0.56512663 | 0.895 | 0.369 | 1 | LGALS3 | 0.81011515 | -0.4145208 | 0.868 | 0.488 | 1 |
| CLSPN | 0.00790906 | 0.44151299 | 1 | 0.536 | 1 | WDR743 | 0.8353098 | 0.67275284 | 0.605 | 0.214 | 1 |
| TIMP14 | 0.00846918 | -0.3090333 | 1 | 0.393 | 1 | PRF11 | 0.85007378 | 0.44536386 | 0.579 | 0.226 | 1 |
| TUBA1B2 | 0.00927185 | 0.33969749 | 0.395 | 0.881 | 1 | CORO1B2 | 0.87806483 | -0.2987768 | 0.974 | 0.619 | 1 |
| SOX42 | 0.01025054 | -0.4089225 | 0.395 | 0.048 | 1 | GBP51 | 0.88571441 | -0.259333 | 0.842 | 0.512 | 1 |
| TUBA1C2 | 0.01261396 | 0.32707096 | 0.921 | 0.476 | 1 | | | | | | |
| | | | | | | Seurat Cluster 13 | | | | | |
| TRBV20-12 | 1.72E-17 | -0.467355 | 1 | 0.043 | 3.44E-14 | PA2G43 | 0.00254328 | -0.2792406 | 0.841 | 0.217 | 1 |
| SPARC2 | 2.92E-16 | -0.2761825 | 0.957 | 0.043 | 5.84E-13 | RGS1 | 0.00261465 | -0.5047021 | 1 | 0.348 | 1 |
| 2-Mar | 3.41E-16 | 0.3276497 | 0.957 | 0.022 | 6.82E-13 | SPOCK2 | 0.00342951 | 0.40777976 | 0.377 | 0.152 | 1 |
| TRBV24-11 | 5.98E-16 | -0.3843183 | 1 | 0.065 | 1.20E-12 | ANXA2R1 | 0.00404347 | -0.2833396 | 1 | 0.37 | 1 |
| FERMT31 | 9.80E-16 | 0.279046 | 0.971 | 0.043 | 1.96E-12 | VIM1 | 0.00425079 | -0.4480609 | 0.565 | 0.478 | 1 |
| IMPDH2 | 3.24E-15 | -0.3258046 | 0.957 | 0.043 | 6.49E-12 | SUPT16H | 0.00441114 | 0.58447662 | 0.348 | 0 | 1 |
| PSMD2 | 7.80E-15 | 0.31428736 | 0.957 | 0.043 | 1.56E-11 | CDK61 | 0.00441114 | 0.39272558 | 0.652 | 0 | 1 |
| TRBV7-2 | 1.03E-14 | -0.5483363 | 0.957 | 0.043 | 2.06E-11 | IRF4 | 0.00441114 | 0.32006123 | 0.348 | 0 | 1 |
| CH25H2 | 1.71E-14 | -0.3227537 | 1 | 0.087 | 3.42E-11 | IL7R4 | 0.00620731 | -0.736647 | 1 | 0.37 | 1 |
| NDUFB31 | 7.78E-14 | -0.2735146 | 0.957 | 0.065 | 1.56E-10 | SLC25A251 | 0.00694112 | 0.28869369 | 0.362 | 0.022 | 1 |
| KLRF1 | 1.89E-13 | -0.2519565 | 0.957 | 0.065 | 3.77E-10 | S100A64 | 0.00773252 | -0.3888272 | 0.986 | 0.848 | 1 |
| PLPP52 | 3.88E-13 | 0.26888955 | 0.928 | 0.043 | 7.77E-10 | ANXA12 | 0.00899385 | -0.2659068 | 0.928 | 0.348 | 1 |
| CKAP22 | 6.45E-13 | -0.2776531 | 0.971 | 0.087 | 1.29E-09 | LDLRAD41 | 0.00929212 | 0.30397495 | 0.333 | 0 | 1 |
| NUDT5 | 7.02E-13 | -0.3329624 | 0.971 | 0.043 | 1.40E-09 | GZMB3 | 0.00967775 | 0.40748502 | 0.406 | 0.152 | 1 |
| TNFSF91 | 7.49E-13 | -0.356651 | 0.986 | 0.109 | 1.50E-09 | TRBC12 | 0.01076052 | -0.3397845 | 0.986 | 0.391 | 1 |
| CKS21 | 3.40E-12 | -0.3445292 | 0.942 | 0.043 | 6.81E-09 | PRDM13 | 0.01112048 | 0.32937785 | 0.87 | 0.391 | 1 |
| HIST1H1B1 | 4.11E-12 | -0.463225 | 0.957 | 0.087 | 8.23E-09 | TMED91 | 0.0119801 | -0.3165477 | 0.696 | 0.087 | 1 |
| RHOC1 | 4.56E-12 | 0.28286425 | 0.13 | 0 | 9.11E-09 | 1F163 | 0.01344429 | 0.254203 | 0.391 | 0.065 | 1 |
| IL2RB | 4.56E-12 | 0.26507148 | 0.13 | 0 | 9.11E-09 | SSR11 | 0.01394838 | -0.2900597 | 0.725 | 0.13 | 1 |
| XCL21 | 5.11E-12 | 0.62800492 | 0.783 | 0.043 | 1.02E-08 | ATP2B1-AS11 | 0.01706984 | -0.3412995 | 0.406 | 0.087 | 1 |
| TRGV10 | 6.24E-12 | -0.2745488 | 1 | 0.13 | 1.25E-08 | MT-CO12 | 0.01741683 | 0.53130886 | 1 | 1 | 1 |
| MAP7D3 | 8.21E-12 | -0.4574568 | 0.928 | 0.065 | 1.64E-08 | PRF12 | 0.01810693 | 0.27462024 | 0.406 | 0.109 | 1 |
| CYC11 | 2.27E-11 | -0.3314269 | 0.942 | 0.087 | 4.55E-08 | HSH2D4 | 0.01865958 | 0.64958311 | 0.638 | 0.022 | 1 |
| GRASP1 | 2.41E-11 | 0.29154723 | 0.13 | 0 | 4.83E-08 | GZMM | 0.02049363 | 0.62828838 | 0.725 | 0.174 | 1 |
| SH2D2A1 | 4.64E-11 | -0.5106811 | 0.159 | 0.087 | 9.28E-08 | LGALS13 | 0.02145301 | -0.3005124 | 0.493 | 0.304 | 1 |
| MX13 | 1.22E-10 | 0.2842446 | 0.159 | 0.043 | 2.44E-07 | TUBB2A1 | 0.02146288 | -0.4792882 | 0.754 | 0.174 | 1 |
| TYROBP1 | 1.50E-10 | 0.62367336 | 0.826 | 0 | 2.99E-07 | HMGN22 | 0.02202867 | 0.29179875 | 0.884 | 0.413 | 1 |
| GNGT2 | 2.54E-10 | -0.3768316 | 0.899 | 0.065 | 5.08E-07 | MT-CYB2 | 0.02430012 | 0.42198576 | 0.986 | 0.87 | 1 |

TABLE 15-continued

| | p_val | avg_logFC | pct.1 | pct.2 | p_val_adj | | p_val | avg_logFC | pct.1 | pct.2 | p_val_adj |
|---|---|---|---|---|---|---|---|---|---|---|---|
| IFI27 | 4.44E-10 | 0.40102854 | 0.116 | 0 | 8.89E-07 | CCL5 | 0.02504079 | -0.2952357 | 0.971 | 0.978 | 1 |
| HES4 | 5.67E-10 | -0.5434755 | 0.986 | 0.152 | 1.13E-06 | ODC1 | 0.0254251 | -0.3960061 | 0.696 | 0.109 | 1 |
| WARS2 | 8.62E-10 | 0.46469185 | 0.159 | 0 | 1.72E-06 | TMEM156 | 0.04056868 | -0.3140624 | 0.435 | 0.109 | 1 |
| FBL2 | 9.34E-10 | -0.2661382 | 0.188 | 0.109 | 1.87E-06 | MRTO4 | 0.040587 | -0.2666017 | 0.638 | 0.043 | 1 |
| RGCC3 | 9.70E-10 | -0.3044748 | 1 | 0.174 | 1.94E-06 | TUBA4A2 | 0.04121567 | -0.340643 | 0.986 | 0.435 | 1 |
| IFI44L5 | 1.03E-09 | 0.51434831 | 0.174 | 0 | 2.06E-06 | RANBP12 | 0.0418357 | -0.4214773 | 0.754 | 0.196 | 1 |
| TMPO3 | 2.03E-09 | -0.385374 | 0.971 | 0.152 | 4.06E-06 | LIPA1 | 0.04206851 | 0.33357968 | 0.391 | 0 | 1 |
| TSC22D1 | 2.18E-09 | -0.3413878 | 0.855 | 0.065 | 4.37E-06 | ADH51 | 0.04234667 | 0.25479522 | 0.406 | 0.043 | 1 |
| UCHL51 | 2.42E-09 | 0.37372957 | 0.855 | 0.043 | 4.84E-06 | MT-CO32 | 0.04357682 | 0.34451241 | 1 | 0.935 | 1 |
| EIF1AY | 3.15E-09 | 0.3833832 | 0.768 | 0 | 6.30E-06 | TRAV8-2 | 0.04375346 | -0.4610519 | 0.667 | 0.087 | 1 |
| KIR3DL2 | 4.43E-09 | 0.47235556 | 0.188 | 0.022 | 8.85E-06 | TOR3A1 | 0.04600734 | -0.3676675 | 0.681 | 0.109 | 1 |
| SMC41 | 7.47E-09 | 0.26081905 | 0.884 | 0.087 | 1.49E-05 | COTL15 | 0.04647328 | -0.5297359 | 0.986 | 0.413 | 1 |
| TUBA1C3 | 1.06E-08 | -0.3043315 | 0.884 | 0.087 | 2.11E-05 | IL322 | 0.05755676 | -0.5648355 | 0.957 | 0.761 | 1 |
| RGS2 | 2.45E-08 | -0.3821122 | 0.899 | 0.109 | 4.89E-05 | ANXA22 | 0.05967307 | 0.64477642 | 0.623 | 0.043 | 1 |
| JPT12 | 1.10E-07 | -0.2740358 | 1 | 0.217 | 0.00022098 | ZBP12 | 0.0619347 | 0.54705635 | 0.449 | 0.196 | 1 |
| BCL2A12 | 1.11E-07 | -0.3892196 | 0.928 | 0.152 | 0.00022214 | HNRNPA2B13 | 0.06572804 | 0.46364717 | 0.942 | 0.565 | 1 |
| FXYD1 | 1.22E-07 | 0.40022113 | 0.217 | 0 | 0.00024449 | HSP90B11 | 0.06979534 | 0.29427622 | 1 | 0.522 | 1 |
| TRBV2 | 1.22E-07 | 0.31813722 | 0.217 | 0 | 0.00024449 | NME41 | 0.07415403 | -0.4640091 | 0.638 | 0.065 | 1 |
| APOBEC3G1 | 1.67E-07 | -0.4696739 | 0.841 | 0.087 | 0.00033461 | SMC1A1 | 0.07817025 | 0.31187814 | 0.594 | 0 | 1 |
| BOLA31 | 3.42E-07 | -0.4893744 | 0.913 | 0.152 | 0.00068447 | MT-CO22 | 0.08624435 | 0.35900867 | 0.522 | 0.957 | 1 |
| CD381 | 4.44E-07 | 0.75677207 | 0.232 | 0.022 | 0.00088837 | RHOB3 | 0.09592296 | -0.3366018 | 0.522 | 0.239 | 1 |
| DDX39A1 | 4.55E-07 | 0.52143679 | 0.232 | 0.043 | 0.00090992 | KLRB13 | 0.0980662 | -0.4976088 | 0.71 | 0.174 | 1 |
| MSC | 6.82E-07 | -0.4356458 | 0.841 | 0.087 | 0.00136356 | POLR2H | 0.10934105 | 0.51241084 | 0.609 | 0.043 | 1 |
| STOM | 1.03E-06 | 0.30232233 | 0.246 | 0.043 | 0.00206074 | HLA-DRB13 | 0.11737039 | -0.3161386 | 0.435 | 0.043 | 1 |
| DERL11 | 1.18E-06 | 0.47093396 | 0.841 | 0.109 | 0.00236782 | SNRPE2 | 0.11764135 | -0.7169332 | 0.667 | 0.435 | 1 |
| IFITM32 | 1.23E-06 | -0.4736747 | 0.29 | 0.217 | 0.00246321 | ZNF7781 | 0.12507184 | 0.34108404 | 0.594 | 0.022 | 1 |
| TCP1 | 1.32E-06 | 0.41480864 | 0.246 | 0.022 | 0.00263618 | SLAMF71 | 0.12515285 | -0.3568629 | 0.623 | 0.065 | 1 |
| STT3A1 | 2.06E-06 | 0.26684376 | 0.246 | 0 | 0.0041244 | MT-ATP61 | 0.12799593 | 0.321728140 | 0.594 | 0.022 | 1 |
| JAKMIP1 | 2.06E-06 | -0.4034204 | 0.261 | 0.087 | 0.00412699 | EZH22 | 0.13240862 | 0.32845657 | 0.957 | 0.804 | 1 |
| GBP12 | 2.16E-06 | -0.2586314 | 0.826 | 0.087 | 0.00431235 | PTGDR | 0.13623374 | 0.47687957 | 0.58 | 0 | 1 |
| BZW21 | 3.60E-06 | -0.2712632 | 0.783 | 0.043 | 0.00720506 | UBE2112 | 0.17459949 | -0.5443596 | 0.464 | 0.109 | 1 |
| CD8A2 | 4.96E-06 | -0.4376102 | 0.971 | 0.239 | 0.00992801 | IFNG1 | 0.18025204 | 0.46346057 | 0.609 | 0.065 | 1 |
| LYN2 | 6.35E-06 | 0.4058549 | 0.71 | 0.022 | 0.01269728 | ATF51 | 0.19172091 | -0.9967892 | 1 | 0.457 | 1 |
| CTSHI | 9.44E-06 | -0.2595183 | 0.551 | 0.043 | 0.01888256 | NINJ12 | 0.20333197 | -0.2768789 | 0.594 | 0.043 | 1 |
| TPM41 | 1.03E-05 | -0.3325093 | 0.275 | 0.022 | 0.02069268 | GAPDH3 | 0.21094194 | 0.25185776 | 0.435 | 0.022 | 1 |
| HIST1H1C1 | 1.61E-05 | -0.3563421 | 1 | 0.283 | 0.03221561 | MT-ND4L4 | 0.22062601 | -0.2967824 | 0.971 | 0.804 | 1 |
| LMNB11 | 2.35E-05 | -0.3170457 | 0.797 | 0.087 | 0.04695189 | LAT2 | 0.22935243 | 0.32800918 | 1 | 0.804 | 1 |
| HSPD13 | 2.49E-05 | -0.2909686 | 0.304 | 0.109 | 0.04982281 | HMGB24 | 0.2420034 | -0.4356953 | 0.536 | 0.196 | 1 |
| FKBP111 | 3.77E-05 | 0.25708728 | 0.304 | 0.13 | 0.07545221 | SUB12 | 0.27867654 | -0.3232429 | 0.754 | 0.283 | 1 |
| ENC12 | 3.85E-05 | 0.71170903 | 0.797 | 0.109 | 0.07709601 | ALOX5AP1 | 0.30131623 | -0.2988492 | 0.696 | 0.543 | 1 |
| PPM1G1 | 3.85E-05 | 0.35545081 | 0.29 | 0.043 | 0.07709601 | TXN3 | 0.30511727 | -0.6142615 | 0.609 | 0.087 | 1 |
| RPL22L12 | 4.12E-05 | 0.32626096 | 0.971 | 0.304 | 0.0824124 | HLA-DPB14 | 0.30884882 | -0.3632484 | 0.594 | 0.283 | 1 |
| PGAM11 | 4.61E-05 | -0.312177 | 0.319 | 0.13 | 0.09229534 | FCMR | 0.31827017 | -0.4142664 | 0.797 | 0.326 | 1 |
| MIR4435-2HG3 | 4.96E-05 | -0.3640884 | 0.957 | 0.261 | 0.09916874 | CD3D | 0.32583985 | 0.25353473 | 0.565 | 0.022 | 1 |
| LAG3 | 5.72E-05 | 0.26313114 | 0.304 | 0.087 | 0.11438226 | PSMD81 | 0.35975808 | -0.2888269 | 0.971 | 0.522 | 1 |
| AC007952.41 | 6.64E-05 | 0.35204856 | 0.304 | 0.087 | 0.13271004 | ATP5F1B1 | 0.36748658 | 0.30111774 | 0.536 | 0.174 | 1 |
| FXYD7 | 6.97E-05 | 0.26956368 | 0.145 | 0 | 0.13942052 | CALR2 | 0.40333066 | 0.3034754 | 0.507 | 0.13 | 1 |
| CNN21 | 7.12E-05 | -0.2708388 | 0.971 | 0.283 | 0.14248499 | CD692 | 0.43581404 | 0.63042503 | 0.522 | 0.152 | 1 |
| TRBV27 | 7.41E-05 | -0.5153262 | 0.652 | 0.065 | 0.14819956 | NCL4 | 0.45100187 | -0.3185062 | 1 | 0.935 | 1 |
| HSPE14 | 8.85E-05 | -0.3787454 | 0.971 | 0.283 | 0.1770308 | OASL | 0.48006616 | -0.3276545 | 0.739 | 0.5 | 1 |
| S100B | 0.00013002 | -0.2516382 | 0.754 | 0.065 | 0.26004266 | | | | 0.841 | 0.63 | |

TABLE 15-continued

| | p_val | avg_logFC | pct.1 | pct.2 | p_val_adj | | p_val | avg_logFC | pct.1 | pct.2 | p_val_adj |
|---|---|---|---|---|---|---|---|---|---|---|---|
| HIST1H2AC2 | 0.00013635 | −0.2506134 | 0.754 | 0.065 | 0.27270831 | HIST1H1D6 | 0.48334736 | −0.4160165 | 1 | 0.587 | 1 |
| H1FX8 | 0.00017485 | 0.28472606 | 0.986 | 0.348 | 0.34970777 | PRKDC | 0.51698573 | 0.25739045 | 0.493 | 0.065 | 1 |
| MAP3K84 | 0.00021029 | −0.4263827 | 0.391 | 0.283 | 0.42058392 | ALG52 | 0.56018809 | 0.28026269 | 0.464 | 0.022 | 1 |
| TXNDC172 | 0.00021439 | −0.3037187 | 0.333 | 0.109 | 0.42877237 | PSMB93 | 0.56865112 | −0.4125583 | 0.971 | 0.522 | 1 |
| SELL1 | 0.00028527 | 0.30263437 | 0.725 | 0.186 | 0.57054055 | CD3G1 | 0.58446733 | −0.4525622 | 1 | 0.543 | 1 |
| ERH3 | 0.00029495 | −0.4946978 | 0.841 | 0.174 | 0.58990356 | HERC51 | 0.58982399 | 0.30145289 | 0.609 | 0.326 | 1 |
| ITGB71 | 0.00037746 | 0.25609801 | 0.333 | 0.109 | 0.75492034 | PRDX22 | 0.59872382 | −0.6094427 | 0.638 | 0.174 | 1 |
| PSMA32 | 0.00048547 | 0.66321195 | 0.319 | 0.022 | 0.97093152 | CCND22 | 0.62368726 | 0.3356671 | 0.493 | 0.043 | 1 |
| ADGRG11 | 0.00058305 | 0.38027548 | 0.333 | 0.065 | 1 | ACTG13 | 0.62873018 | −0.2879598 | 1 | 0.652 | 1 |
| AC103591.35 | 0.00078714 | 0.65436651 | 0.725 | 0.065 | 1 | RPA1 | 0.68273279 | −0.3748583 | 1 | 0.043 | 1 |
| GATA3 | 0.00082224 | −0.2628553 | 0.362 | 0.13 | 1 | MIF3 | 0.68973279 | −0.4237355 | 0.478 | 0.652 | 1 |
| GIMAP4 | 0.0008397 | −0.4232869 | 0.783 | 0.13 | 1 | GSTP14 | 0.70807606 | −0.3371341 | 0.696 | 0.283 | 1 |
| FCGBP | 0.00091163 | 0.26778613 | 0.203 | 0 | 1 | S100A103 | 0.74847112 | −0.261245 | 0.971 | 0.674 | 1 |
| CHAF1A | 0.00098265 | 0.33749255 | 0.29 | 0 | 1 | TNFRSF18 | 0.76413638 | 0.29530947 | 0.449 | 0 | 1 |
| PTGDS | 0.00104625 | 0.58492764 | 0.652 | 0.022 | 1 | SNRPG3 | 0.78312773 | −0.5257245 | 0.652 | 0.217 | 1 |
| DNAJB111 | 0.00118964 | 0.41672976 | 0.333 | 0 | 1 | RPA31 | 0.78744306 | −0.332087 | 0.522 | 0.065 | 1 |
| LINC024461 | 0.00188567 | −0.6419685 | 1 | 0.348 | 1 | MT2A7 | 0.82137772 | −0.3443582 | 1 | 0.696 | 1 |
| CD71 | 0.00189606 | 0.29368865 | 0.754 | 0.13 | 1 | IER3 | 0.86164522 | 0.25102941 | 0.507 | 0.022 | 1 |
| MT1E1 | 0.0021685 | −0.3662904 | 0.783 | 0.152 | 1 | PPIA4 | 0.97027977 | −0.5354481 | 0.928 | 0.5 | 1 |
| | | | | | | Seurat Cluster 14 | | | | | |
| SMC1A2 | 3.48E-21 | −0.2739933 | 0 | 0.114 | 6.96E-18 | NUF2 | 0.0001268 | −0.5281519 | 1 | 0.286 | 0.25359171 |
| DUT1 | 3.48E-21 | −0.3214159 | 0 | 0.114 | 6.96E-18 | CCNB1 | 0.0001268 | −0.9224257 | 1 | 0.286 | 0.25359171 |
| CKLF2 | 1.83E-20 | −0.2731687 | 0 | 0.029 | 3.66E-17 | UBE2C | 0.0001268 | −1.039939 | 1 | 0.286 | 0.25359171 |
| EZH23 | 6.45E-19 | −0.451887 | 0 | 0.186 | 1.29E-15 | HIST1H4C3 | 0.00017718 | −1.7003534 | 1 | 0.457 | 0.35436969 |
| YWHAQ2 | 1.31E-18 | −0.2842215 | 0.027 | 0.157 | 2.61E-15 | EPB42 | 0.00019445 | −0.6062016 | 0.459 | 0.229 | 0.38889414 |
| CST31 | 1.25E-17 | −0.3499779 | 0.946 | 0.043 | 2.50E-14 | KIF2C1 | 0.00024521 | −0.6297123 | 0.811 | 0.114 | 0.49042465 |
| PIF1 | 6.30E-17 | −0.2784312 | 0.919 | 0.043 | 1.26E-13 | ELL22 | 0.0002786 | −0.4509137 | 0.784 | 0.143 | 0.55719537 |
| SNRPG4 | 1.45E-16 | −0.5906708 | 0.054 | 0.214 | 2.89E-13 | FBXO5 | 0.00028643 | −1.0762319 | 0.568 | 0.843 | 0.57285393 |
| H1ST1H2AL1 | 1.58E-16 | −0.2536272 | 1 | 0.071 | 3.16E-13 | PRDX23 | 0.0002886 | 0.4865947 | 1 | 1 | 0.57720508 |
| HIST1H4H2 | 1.58E-16 | −0.2602895 | 1 | 0.071 | 3.16E-13 | HBA11 | 0.00036389 | −0.5912806 | 1 | 0.3 | 0.72778816 |
| HIST1H2BC1 | 2.31E-15 | −0.3005863 | 1 | 0.086 | 4.63E-12 | ERH4 | 0.00036389 | −0.8614347 | 1 | 0.3 | 0.72778816 |
| NPC2 | 3.38E-15 | −0.2779325 | 1 | 0.071 | 6.76E-12 | DLGAP5 | 0.00036389 | −1.1992258 | 1 | 0.3 | 0.72778816 |
| GAPDH4 | 7.59E-15 | −0.6466456 | 0.081 | 0.243 | 1.52E-11 | TUBA1C4 | 0.00036389 | −1.0133885 | 0 | 0.286 | 0.74536654 |
| IFIT3 | 8.03E-15 | 0.46810611 | 0.108 | 0.014 | 1.61E-11 | TOP2A | 0.00037268 | −0.5173571 | 1 | 0.314 | 0.98427899 |
| CCT71 | 2.32E-14 | −0.3032969 | 1 | 0.1 | 4.64E-11 | TUBB2A2 | 0.00049214 | 0.41037301 | 0 | 1 | 1 |
| ARL6IP11 | 1.37E-13 | −0.8920501 | 0.108 | 0.286 | 2.74E-10 | HBA22 | 0.0005241 | −0.6554443 | 0.243 | 0.243 | 1 |
| AQP31 | 2.42E-13 | −0.266114 | 1 | 0.114 | 4.83E-10 | CENPW1 | 0.00056214 | −1.1490819 | 0.811 | 0.243 | 1 |
| ADI1 | 3.17E-13 | −0.2651118 | 1 | 0.114 | 6.34E-10 | HIST1H1B2 | 0.00053214 | −0.4935637 | 0.811 | 0.157 | 1 |
| ENDOD1 | 3.17E-13 | −0.2665534 | 1 | 0.114 | 6.34E-10 | NUCB22 | 0.00065811 | −0.5004049 | 0.514 | 0.543 | 1 |
| CRNDE | 3.17E-13 | −0.2959545 | 1 | 0.114 | 6.34E-10 | SELENBP1 | 0.00095668 | −0.701206 | 1 | 0.314 | 1 |
| HIST1H2AM1 | 3.17E-13 | −0.3072374 | 1 | 0.114 | 6.34E-10 | CDCA8 | 0.00096826 | −0.7499629 | 1 | 0.314 | 1 |
| TPI12 | 3.17E-13 | −0.3216596 | 1 | 0.114 | 6.34E-10 | TMPO4 | 0.00122954 | −0.6940749 | 0 | 0.243 | 1 |
| PSMA62 | 3.17E-13 | −0.3351501 | 1 | 0.114 | 6.34E-10 | TYMS1 | 0.00136954 | −0.5090044 | 1 | 0.529 | 1 |
| TMEM106C1 | 3.17E-13 | −0.3702539 | 1 | 0.114 | 6.34E-10 | MYL4 | 0.00143795 | −0.7319006 | 0.486 | 0.329 | 1 |
| CCT6A3 | 3.17E-13 | −0.3761748 | 1 | 0.114 | 6.34E-10 | JPT13 | 0.00149762 | −0.3390128 | 0.811 | 0.171 | 1 |
| MYBL21 | 3.17E-13 | −0.4149108 | 1 | 0.114 | 6.34E-10 | SPCS21 | 0.00149762 | −0.3896966 | 0.811 | 0.171 | 1 |
| HIST1H3G1 | 3.17E-13 | −0.4361595 | 1 | 0.114 | 6.34E-10 | DHFR1 | 0.00180993 | −0.7572006 | 1 | 0.229 | 1 |
| KIFC11 | 3.02E-12 | −0.2696488 | 1 | 0.129 | 6.03E-09 | CDK1 | 0.00253784 | −0.4022232 | 0.784 | 0.257 | 1 |
| H1ITF1 | 3.02E-12 | −0.3250716 | 1 | 0.129 | 6.03E-09 | PIP5K1B | 0.00253784 | −0.4022232 | 0 | 0.214 | 1 |
| AURKB1 | 3.02E-12 | −0.3568611 | 1 | 0.129 | 6.03E-09 | SPTB | 0.0026505 | −0.8803234 | 0 | 0.214 | 1 |

TABLE 15-continued

| | p_val | avg_logFC | pct.1 | pct.2 | p_val_adj | | p_val | avg_logFC | pct.1 | pct.2 | p_val_adj |
|---|---|---|---|---|---|---|---|---|---|---|---|
| ODC12 | 3.02E-12 | -0.3699485 | 1 | 0.129 | 6.03E-09 | USP1 | 0.00289891 | -0.3065165 | 0.486 | 0.129 | 1 |
| MCUR1 | 3.02E-12 | -0.3802549 | 1 | 0.129 | 6.03E-09 | YWHAH1 | 0.00297825 | -0.8243602 | 0.973 | 0.314 | 1 |
| TMED102 | 3.02E-12 | -0.3995326 | 1 | 0.129 | 6.03E-09 | RGCC4 | 0.0032361 | -0.3098573 | 1 | 0.357 | 1 |
| TLN11 | 3.02E-12 | -0.4075522 | 1 | 0.129 | 6.03E-09 | MAD2L1 | 0.00346566 | -0.2501735 | 0 | 0.143 | 1 |
| RPN13 | 3.02E-12 | -0.4465143 | 1 | 0.129 | 6.03E-09 | NCAPG1 | 0.0038625 | -0.491303 | 0 | 0.2 | 1 |
| NCL5 | 3.02E-12 | -0.4827787 | 1 | 0.129 | 6.03E-09 | PFN13 | 0.00420977 | -0.7563014 | 0.514 | 0.371 | 1 |
| MBOAT2 | 7.72E-12 | -0.6568771 | 0.135 | 0.343 | 1.54E-08 | NDUFAF32 | 0.0044221 | -0.3598326 | 0.946 | 0.314 | 1 |
| KCNH2 | 1.88E-11 | -0.3964246 | 1 | 0.143 | 3.76E-08 | FAM210B1 | 0.00488577 | -0.5095089 | 0.703 | 0.729 | 1 |
| ATP5F1A2 | 2.53E-11 | -0.2521249 | 1 | 0.143 | 5.05E-08 | SLC4A1 | 0.00507856 | -0.4306237 | 1 | 0.829 | 1 |
| CALR3 | 2.53E-11 | -0.2598044 | 1 | 0.143 | 5.05E-08 | DEPDC1 | 0.00560308 | -0.6469269 | 0 | 0.186 | 1 |
| MIR22HG1 | 2.53E-11 | -0.3904169 | 1 | 0.143 | 5.05E-08 | LMNA | 0.0061585 | -0.3388639 | 0.324 | 0.086 | 1 |
| NDUFAB12 | 2.53E-11 | -0.4406391 | 1 | 0.143 | 5.05E-08 | HEMGN | 0.00662176 | -1.0903288 | 0.865 | 0.671 | 1 |
| HIST2H2AC2 | 2.53E-11 | -0.4548799 | 1 | 0.143 | 5.05E-08 | HIST1H1E3 | 0.00769305 | -1.1545063 | 1 | 0.357 | 1 |
| KIF15 | 2.53E-11 | -0.4934527 | 1 | 0.143 | 5.05E-08 | CCNF | 0.00809396 | -0.4901527 | 0 | 0.171 | 1 |
| NFIX | 2.76E-11 | 0.61595116 | 1 | 0.157 | 5.53E-08 | KIF20A | 0.00809396 | -0.5637508 | 0 | 0.171 | 1 |
| SLC43A3 | 3.96E-11 | -0.4307219 | 0.811 | 0.086 | 7.93E-08 | SLIRP2 | 0.00878571 | -0.3792753 | 0.649 | 0.114 | 1 |
| TNS11 | 6.57E-11 | -0.4544621 | 0.162 | 0.271 | 1.31E-07 | NUCKS11 | 0.00997337 | -0.6430788 | 1 | 0.357 | 1 |
| SEC131 | 7.78E-11 | -0.3195198 | 0.919 | 0.086 | 1.56E-07 | ALAD | 0.01016902 | -0.4082313 | 1 | 0.371 | 1 |
| MTCH2 | 1.30E-10 | -0.4240509 | 0.919 | 0.129 | 2.60E-07 | ARHGAP11A | 0.01081222 | -0.3043979 | 0 | 0.129 | 1 |
| NEK2 | 1.87E-10 | -0.345921 | 1 | 0.157 | 3.75E-07 | CCDC34 | 0.01164816 | -0.3749101 | 0 | 0.157 | 1 |
| KNSTRN | 1.87E-10 | -0.372269 | 1 | 0.157 | 3.75E-07 | DIAPH3 | 0.01164816 | -0.3946882 | 0 | 0.157 | 1 |
| EPRS1 | 1.87E-10 | -0.3937859 | 1 | 0.157 | 3.75E-07 | CDCA2 | 0.01164816 | -0.6657215 | 0 | 0.157 | 1 |
| PP1B2 | 1.87E-10 | -0.4101705 | 1 | 0.157 | 3.75E-07 | MOB1B1 | 0.01188701 | -0.7840367 | 1 | 0.357 | 1 |
| EXOSC8 | 1.87E-10 | -0.4245108 | 1 | 0.157 | 3.75E-07 | TPX2 | 0.01188701 | -0.7863077 | 1 | 0.357 | 1 |
| SPINT2 | 1.87E-10 | -0.4471579 | 1 | 0.157 | 3.75E-07 | SMC42 | 0.01188701 | -1.092122 | 1 | 0.357 | 1 |
| VRK1 | 1.87E-10 | -0.5186414 | 1 | 0.157 | 3.75E-07 | MTRNR2L123 | 0.01319538 | 0.41049212 | 1 | 0.471 | 1 |
| MFSD2B | 2.56E-10 | -0.4240637 | 0.189 | 0.186 | 5.11E-07 | HBD1 | 0.01365836 | -0.379178 | 1 | 0.929 | 1 |
| MRPL13 | 2.93E-10 | -0.3431606 | 0.811 | 0.086 | 5.86E-07 | ASNS | 0.01474975 | -0.461399 | 0.324 | 0.1 | 1 |
| PCK2 | 3.16E-10 | -0.3711502 | 0.811 | 0.1 | 6.32E-07 | TUBG1 | 0.01492361 | -0.5371691 | 1 | 0.371 | 1 |
| TPM1 | 3.16E-10 | -0.3737463 | 0.811 | 0.1 | 6.32E-07 | NUSAP11 | 0.0154929 | -0.9774556 | 1 | 0.371 | 1 |
| RPA32 | 1.04E-09 | -0.5520486 | 1 | 0.171 | 2.07E-06 | OSBP2 | 0.01634604 | -0.6127294 | 1 | 0.386 | 1 |
| NDUFA81 | 1.24E-09 | -0.2813343 | 1 | 0.171 | 2.48E-06 | DEPDC1B | 0.01670835 | -0.262842 | 0 | 0.143 | 1 |
| PARVB1 | 1.24E-09 | -0.3245847 | 1 | 0.171 | 2.48E-06 | ATP5MC34 | 0.01894884 | -0.475581 | 0.757 | 0.171 | 1 |
| RACGAP1 | 1.24E-09 | -0.4207048 | 1 | 0.171 | 2.48E-06 | MINPP1 | 0.01932679 | -0.7715601 | 1 | 0.371 | 1 |
| KIF11 | 1.24E-09 | -0.4346909 | 1 | 0.171 | 2.48E-06 | RAN3 | 0.01932679 | -0.8644618 | 1 | 0.371 | 1 |
| KIF14 | 1.24E-09 | -0.4955334 | 1 | 0.171 | 2.48E-06 | ASPM1 | 0.02089675 | -1.2315346 | 0.189 | 0.343 | 1 |
| KIF4A | 1.24E-09 | -0.5024664 | 1 | 0.171 | 2.48E-06 | CKAP23 | 0.02153751 | -1.2984247 | 1 | 0.371 | 1 |
| SGO21 | 1.24E-09 | -0.553669 | 1 | 0.171 | 2.48E-06 | ANP32E1 | 0.02257421 | -0.4467957 | 1 | 0.4 | 1 |
| ANK11 | 1.37E-09 | -0.4232489 | 0.189 | 0.386 | 2.75E-06 | RHD | 0.02265644 | -0.4659385 | 1 | 0.386 | 1 |
| ATP1B32 | 1.83E-09 | -0.3122551 | 0.946 | 0.157 | 3.67E-06 | CDKN3 | 0.02265644 | -0.4685186 | 1 | 0.386 | 1 |
| UQCC21 | 2.19E-09 | -0.308871 | 0.811 | 0.114 | 4.37E-06 | SRP92 | 0.02280251 | -0.6330313 | 0.811 | 0.229 | 1 |
| SAT1 | 4.59E-09 | -0.2838853 | 1 | 0.186 | 9.18E-06 | CCT23 | 0.02280251 | -0.7597039 | 0.811 | 0.229 | 1 |
| PSMD82 | 5.00E-09 | -0.287605 | 1 | 0.186 | 1.00E-05 | CISD21 | 0.0234739 | -0.657262 | 1 | 0.386 | 1 |
| RRM2 | 7.33E-09 | -0.4205597 | 1 | 0.186 | 1.47E-05 | ACTB2 | 0.0238878 | -0.5638268 | 0.973 | 0.8 | 1 |
| HIST1H2AC3 | 7.33E-09 | -0.4733425 | 1 | 0.186 | 1.47E-05 | CCDC1671 | 0.02389343 | -0.3965784 | 0.432 | 0.157 | 1 |
| HIST1H3B3 | 7.33E-09 | -0.5358474 | 1 | 0.186 | 1.47E-05 | OIP5 | 0.0239031 | -0.2720251 | 0 | 0.129 | 1 |
| HIST1H1D7 | 7.33E-09 | -0.86063 | 1 | 0.129 | 1.47E-05 | TTK | 0.0239031 | -0.2852278 | 0 | 0.129 | 1 |
| LXN1 | 1.33E-08 | -0.303958 | 0.811 | 0.129 | 2.66E-05 | ANLN | 0.0239031 | -0.3507979 | 0 | 0.129 | 1 |
| MTDH2 | 1.61E-08 | -0.3052104 | 0.919 | 0.014 | 3.23E-05 | NCAPD21 | 0.0239031 | -0.3597381 | 0 | 0.129 | 1 |
| ISG151 | 1.87E-08 | 0.88761411 | 0.216 | 0.2 | 3.74E-05 | ESCO21 | 0.0239031 | -0.5192662 | 0 | 0.129 | 1 |
| TPST21 | 2.13E-08 | -0.3595109 | 1 | 0.2 | 4.26E-05 | BIRC5 | 0.02396521 | -0.6392697 | 1 | 0.371 | 1 |

TABLE 15-continued

| | p_val | avg_logFC | pct.1 | pct.2 | p_val_adj | | p_val | avg_logFC | pct.1 | pct.2 | p_val_adj |
|---|---|---|---|---|---|---|---|---|---|---|---|
| RAB13 | 2.61E-08 | -0.2811238 | 1 | 0.2 | 5.22E-05 | SOX6 | 0.02396521 | -0.7411873 | 1 | 0.371 | 1 |
| VBP1 | 3.91E-08 | -0.2919977 | 1 | 0.2 | 7.82E-05 | H1FX9 | 0.02396521 | -1.0705514 | 1 | 0.371 | 1 |
| SMC2 | 3.91E-08 | -0.3780042 | 1 | 0.2 | 7.82E-05 | PNP | 0.02784394 | -0.2716337 | 1 | 0.4 | 1 |
| MRPL51 | 3.91E-08 | -0.4026658 | 1 | 0.2 | 7.82E-05 | MPP1 | 0.02897277 | 0.27721513 | 1 | 0.529 | 1 |
| WDR34 | 3.91E-08 | -0.5557899 | 0.892 | 0.2 | 7.82E-05 | CPOX1 | 0.0331577 | -0.5620208 | 1 | 0.386 | 1 |
| HSPA54 | 4.32E-08 | -0.4397747 | 1 | 0.114 | 8.65E-05 | SKA1 | 0.03413111 | -0.2721191 | 0 | 0.114 | 1 |
| TFR2 | 7.14E-08 | -0.3684452 | 0.811 | 0.143 | 0.00014281 | SGO1 | 0.03680366 | -0.6729877 | 0.568 | 0.229 | 1 |
| H2AFX | 7.14E-08 | -0.4482733 | 0.811 | 0.143 | 0.00014281 | ALAS2 | 0.03803576 | 0.37982031 | 0.892 | 0.829 | 1 |
| DHRS13 | 8.09E-08 | -0.2513541 | 1 | 0.214 | 0.00016172 | MT-ND4L5 | 0.04145649 | -0.7500004 | 0.946 | 0.357 | 1 |
| LMAN21 | 9.27E-08 | -0.3227056 | 0.919 | 0.157 | 0.00018555 | HMGB15 | 0.0570008 | -1.3521647 | 1 | 0.629 | 1 |
| CENPA | 1.10E-07 | -0.2940807 | 1 | 0.214 | 0.00022065 | MT-CO13 | 0.05842766 | -1.0616305 | 1 | 0.671 | 1 |
| SLC40A11 | 1.10E-07 | -0.3667133 | 1 | 0.114 | 0.00022065 | SMIM11 | 0.06270263 | 0.4803907 | 1 | 0.743 | 1 |
| AL138963.33 | 1.15E-07 | -0.3096219 | 0.243 | 0.214 | 0.00022915 | UROD | 0.07196828 | -1.3506529 | 1 | 0.614 | 1 |
| ADD2 | 1.19E-07 | -0.5010798 | 1 | 0.214 | 0.00023836 | AC092490.1 | 0.08852017 | 0.32362122 | 0.432 | 0.057 | 1 |
| AC103876.1 | 1.39E-07 | -0.5237795 | 1 | 0.214 | 0.000278 | DYNLL11 | 0.09024368 | -0.3564808 | 0.892 | 0.371 | 1 |
| STMN13 | 1.89E-07 | -0.3834721 | 1 | 0.214 | 0.00037727 | GLRX5 | 0.09237145 | 0.31315124 | 1 | 0.543 | 1 |
| PRC11 | 1.89E-07 | -0.517519 | 1 | 0.214 | 0.00037727 | SNCA1 | 0.0941578 | -0.3837001 | 0.703 | 0.614 | 1 |
| HMMR | 1.89E-07 | -0.6289883 | 1 | 0.214 | 0.00037727 | EIF2AK11 | 0.09805381 | -0.6525012 | 0.703 | 0.514 | 1 |
| EIF2S23 | 1.89E-07 | -0.6395416 | 1 | 0.214 | 0.00037727 | SSRP11 | 0.1046219 | -0.3255691 | 0.297 | 0.129 | 1 |
| BUB11 | 1.89E-07 | -0.6709477 | 1 | 0.214 | 0.00037727 | NFE2 | 0.10557244 | -0.3707219 | 0.973 | 0.457 | 1 |
| CDCA5 | 2.88E-07 | -0.3096516 | 0.568 | 0.071 | 0.00057568 | TFRC | 0.10787207 | -1.4006475 | 1 | 0.614 | 1 |
| TARS1 | 3.42E-07 | -0.5455921 | 0.811 | 0.157 | 0.00068457 | MT-CYB3 | 0.10932107 | -0.6804226 | 1 | 0.414 | 1 |
| HJURP1 | 3.85E-07 | -0.3700774 | 1 | 0.229 | 0.0007703 | SDHC | 0.12402988 | -0.2599958 | 0.459 | 0.114 | 1 |
| ERFE | 5.36E-07 | -0.425861 | 1 | 0.229 | 0.0010717 | GATA1 | 0.13533817 | -0.8672695 | 1 | 0.414 | 1 |
| HMGB31 | 5.98E-07 | -0.4724308 | 1 | 0.229 | 0.00119538 | MKI67 | 0.13533817 | -1.4549101 | 1 | 0.414 | 1 |
| CKAP2L1 | 6.20E-07 | -0.4845513 | 1 | 0.229 | 0.00123959 | STOM1 | 0.14791642 | -0.5033793 | 1 | 0.443 | 1 |
| AURKA | 8.27E-07 | -0.4807387 | 1 | 0.229 | 0.00165458 | PPP1CA1 | 0.15405272 | -0.4918339 | 0.514 | 0.186 | 1 |
| CKS1B | 8.27E-07 | -0.494035 | 1 | 0.229 | 0.00165458 | GYPA | 0.1888089 | -0.4530284 | 1 | 0.657 | 1 |
| IDH23 | 8.27E-07 | -0.5349229 | 1 | 0.229 | 0.00165458 | UBAC1 | 0.20169176 | -0.9050015 | 0.919 | 0.386 | 1 |
| TSPAN131 | 8.27E-07 | -0.6664768 | 1 | 0.229 | 0.00165458 | RHCE | 0.20716265 | -0.6804226 | 0.595 | 0.286 | 1 |
| MDH12 | 1.35E-06 | -0.5104768 | 0.919 | 0.171 | 0.00269843 | PTTG11 | 0.20892166 | -0.66464 | 1 | 0.457 | 1 |
| IFI27L1 | 1.50E-06 | -0.3668718 | 0.568 | 0.086 | 0.00299088 | MT-CO33 | 0.21381881 | -1.1137733 | 1 | 0.457 | 1 |
| C2orf88 | 1.55E-06 | -0.3662545 | 1 | 0.243 | 0.00310598 | NT5C3A2 | 0.22144643 | -0.2784471 | 0.649 | 0.129 | 1 |
| UBE2S2 | 1.72E-06 | -0.5054985 | 1 | 0.243 | 0.00344831 | CENPE1 | 0.24910038 | -1.0497171 | 0.189 | 0.243 | 1 |
| VDAC3 | 1.85E-06 | -0.3436942 | 1 | 0.243 | 0.00369637 | CTSL | 0.2635969 | -0.6986547 | 1 | 0.443 | 1 |
| H2AFV3 | 2.35E-06 | -0.3404169 | 1 | 0.243 | 0.00470678 | CYTOR3 | 0.29427533 | -0.6357268 | 0.457 | 0.457 | 1 |
| LSM51 | 3.31E-06 | -0.374326 | 1 | 0.243 | 0.00662082 | TXN4 | 0.31640246 | -0.9083923 | 1 | 0.457 | 1 |
| NDUFB61 | 3.31E-06 | -0.4946171 | 1 | 0.243 | 0.00662082 | HMGB25 | 0.31939735 | -1.2326902 | 0.586 | 0.457 | 1 |
| HNRNPAB1 | 3.31E-06 | -0.5971524 | 1 | 0.243 | 0.00662082 | CAT | 0.33854587 | -0.7345225 | 1 | 0.571 | 1 |
| HIST1H2BJ | 3.31E-06 | -0.6066916 | 1 | 0.243 | 0.00662082 | KLF1 | 0.3507258 | -0.6775195 | 1 | 0.471 | 1 |
| KIF23 | 3.31E-06 | -0.6463377 | 1 | 0.229 | 0.00662082 | S100A810 | 0.35487144 | -0.4656771 | 0.514 | 0.6 | 1 |
| RPS27L4 | 5.37E-06 | -0.5058279 | 0.973 | 0.1 | 0.0107319 | HMBS | 0.35999335 | -0.8852276 | 1 | 0.457 | 1 |
| RAD51AP1 | 6.69E-06 | -0.4054511 | 0.568 | 0.257 | 0.01337504 | CKS22 | 0.36384823 | -1.3523532 | 1 | 0.129 | 1 |
| NSD2 | 6.78E-06 | -0.2509555 | 1 | 0.257 | 0.01355706 | MT-CO23 | 0.38685946 | -1.3217763 | 0.189 | 0.557 | 1 |
| PLK1 | 8.52E-06 | -0.6021944 | 1 | 0.171 | 0.01703092 | SLC25A52 | 0.4259687 | -0.5059969 | 0.676 | 0.2 | 1 |
| KPNA22 | 8.79E-06 | -0.6824398 | 0.757 | 0.171 | 0.017574 | CENPF2 | 0.45089626 | -1.2530936 | 1 | 0.457 | 1 |
| DDX39A2 | 9.96E-06 | -0.4684196 | 0.892 | 0.171 | 0.01991823 | RPLP02 | 0.49303224 | -1.039164 | 1 | 0.571 | 1 |
| BLVRB2 | 1.07E-05 | -0.974629 | 0.73 | 0.8 | 0.02134217 | MTHFD21 | 0.52205312 | -0.3695613 | 0.189 | 0.1 | 1 |
| CDC20 | 1.21E-05 | -0.9746252 | 1 | 0.257 | 0.02426179 | HSPA82 | 0.53721431 | -0.6707045 | 0.622 | 0.143 | 1 |
| CENPN1 | 1.23E-05 | -0.4335591 | 0.838 | 0.129 | 0.02462985 | IIMGN23 | 0.588911 | -0.5841268 | 1 | 0.557 | 1 |
| GSTM3 | 1.27E-05 | -0.2543482 | 0.811 | 0.1 | 0.02546953 | HNRNPA2B14 | 0.59086067 | -0.9467135 | 1 | 0.486 | 1 |

TABLE 15-continued

| | p_val | avg_logFC | pct.1 | pct.2 | p_val_adj | | p_val | avg_logFC | pct.1 | pct.2 | p_val_adj |
|---|---|---|---|---|---|---|---|---|---|---|---|
| MMD | 1.27E-05 | -0.3252786 | 0.811 | 0.1 | 0.02546953 | ORC61 | 0.62347727 | -0.2570803 | 0.189 | 0.129 | 1 |
| PDZK1IP1 | 1.74E-05 | 0.25421295 | 1 | 0.286 | 0.03482988 | H2AFZ2 | 0.62510685 | -1.3454218 | 1 | 0.529 | 1 |
| CCNB2 | 1.80E-05 | -0.5667492 | 0.351 | 0.3 | 0.03600908 | RAD51C | 0.67512375 | -0.2567513 | 0.162 | 0.114 | 1 |
| GLUL1 | 2.06E-05 | -0.2788304 | 0.324 | 0.357 | 0.04120169 | TUBB3 | 0.67904949 | -1.1493844 | 0.892 | 0.429 | 1 |
| MZT12 | 2.84E-05 | -0.4341001 | 1 | 0.271 | 0.05681765 | RFESD | 0.68177101 | -0.509845 | 1 | 0.5 | 1 |
| KNL1 | 2.84E-05 | -0.5544755 | 1 | 0.271 | 0.05681765 | H1F0 | 0.68753541 | -0.7562441 | 0.919 | 0.529 | 1 |
| MT-ATP62 | 3.11E-05 | -0.7456499 | 1 | 0.271 | 0.06225626 | PSMA43 | 0.72011893 | -0.2924224 | 0.568 | 0.086 | 1 |
| TMEM14C2 | 3.52E-05 | -0.3518678 | 1 | 0.286 | 0.07046108 | CACYBP1 | 0.72011893 | -0.342136 | 0.568 | 0.086 | 1 |
| BOLA32 | 3.73E-05 | -0.3719497 | 0.811 | 0.129 | 0.07468696 | SLC2A1 | 0.72707563 | -0.4385101 | 1 | 0.529 | 1 |
| CCNA2 | 3.77E-05 | -0.7429713 | 0.027 | 0.214 | 0.0753384 | CCT51 | 0.86708433 | -0.2528658 | 0.135 | 0.086 | 1 |
| SEC61G3 | 4.08E-05 | -0.3866594 | 1 | 0.271 | 0.08169659 | TROAP | 0.89492321 | -0.797596 | 0.811 | 0.386 | 1 |
| SKA2 | 4.08E-05 | -0.5843172 | 1 | 0.271 | 0.08169659 | TUBB4B3 | 0.90725278 | -1.0575696 | 1 | 0.514 | 1 |
| CENPU3 | 4.08E-05 | -0.7140362 | 1 | 0.271 | 0.08169659 | TUBA1B3 | 0.92309787 | -1.7073071 | 1 | 0.514 | 1 |
| HSP90B12 | 4.08E-05 | -0.7466039 | 1 | 0.271 | 0.08169659 | HIST1H1C2 | 0.93394242 | -1.1757887 | 1 | 0.557 | 1 |
| SUB13 | 4.08E-05 | -0.8673695 | 1 | 0.271 | 0.08169659 | ILK | 0.94019494 | -0.281563 | 0.135 | 0.114 | 1 |
| GTSE1 | 4.17E-05 | -0.5285396 | 0.027 | 0.2 | 0.08342787 | CD361 | 0.9495712 | -1.0419541 | 1 | 0.514 | 1 |
| PPIA5 | 4.83E-05 | -0.5465814 | 0.946 | 0.243 | 0.0966603 | RHAG | 0.9495712 | -1.2759532 | 1 | 0.514 | 1 |
| SLC1A5 | 5.03E-05 | -0.3366566 | 1 | 0.3 | 0.10066396 | FECH | 0.9549972 | -0.6929643 | 1 | 0.543 | 1 |
| BCL2L11 | 5.66E-05 | -0.3057117 | 0.351 | 0.429 | 0.11318011 | EEF1A12 | 0.95505321 | -0.4383434 | 1 | 0.557 | 1 |
| UBE2T | 6.55E-05 | -0.6800004 | 0.811 | 0.214 | 0.13105506 | NDC80 | 0.96258593 | -0.5650065 | 1 | 0.2 | 1 |
| MIR4435-2HG4 | 8.28E-05 | -0.6303697 | 1 | 0.286 | 0.16551052 | CENPK | 0.9639201 | -0.4357319 | 0.568 | 0.143 | 1 |
| HIST1H2AI | 9.02E-05 | -0.5118353 | 0.568 | 0.129 | 0.18042038 | | | | | | |
| | | | | | | Seurat Cluster 15 | | | | | |
| TUBA4A3 | 2.04E-13 | 0.45340115 | 1 | 0.037 | 4.07E-10 | FHL1 | 0.03608491 | 0.26970921 | 1 | 0.5 | 1 |
| CYB5D2 | 7.17E-11 | 0.32511598 | 1 | 0.074 | 1.43E-07 | UQCC22 | 0.038182 | -0.2570596 | 0.375 | 0.222 | 1 |
| CD14 | 1.30E-10 | 0.32080423 | 0.875 | 0.019 | 2.60E-07 | HIST1H2BC2 | 0.04163644 | 0.83579255 | 0.875 | 0.296 | 1 |
| SERPINA12 | 1.30E-10 | 0.27253435 | 0.875 | 0.019 | 2.60E-07 | MT2A8 | 0.04722879 | -0.3903837 | 0.938 | 0.37 | 1 |
| HIST1H2BF1 | 9.55E-10 | -0.2835226 | 0.938 | 0.074 | 1.91E-06 | ACTB3 | 0.04940264 | -0.3365382 | 1 | 0.963 | 1 |
| NCF13 | 7.00E-09 | 0.38882286 | 0.875 | 0.019 | 1.40E-05 | TXNDC173 | 0.04958088 | -0.4844268 | 0.938 | 0.333 | 1 |
| GP91 | 1.30E-08 | -0.2524205 | 0.125 | 0.167 | 2.61E-05 | MARCKSL11 | 0.05469975 | -0.2671624 | 0.5 | 0.352 | 1 |
| CXCL22 | 4.36E-08 | -0.6768673 | 0.125 | 0.019 | 8.72E-05 | NUCB23 | 0.05595017 | 0.27059532 | 0.938 | 0.667 | 1 |
| APOC1 | 5.40E-08 | -0.3007207 | 0.812 | 0.074 | 0.00010796 | DUSP62 | 0.0610003 | -0.8739441 | 1 | 0.389 | 1 |
| VCAN | 2.98E-07 | 0.50964884 | 0.188 | 0 | 0.00059594 | ANXA61 | 0.0681003 | 0.50140004 | 0.75 | 0.222 | 1 |
| ZNF385A | 5.15E-07 | 0.27443364 | 0.938 | 0.111 | 0.00012995 | CCT72 | 0.07018128 | -0.3627522 | 0.562 | 0.389 | 1 |
| C1QTNF4 | 6.43E-07 | -0.2609176 | 0.125 | 0.13 | 0.00128575 | PROM1 | 0.07056852 | -0.4281006 | 0.5 | 0.296 | 1 |
| CENPN2 | 7.00E-07 | 0.39167491 | 0.938 | 0.037 | 0.00140038 | CITED22 | 0.07458552 | -0.3274868 | 0.5 | 0.333 | 1 |
| EGR11 | 1.67E-06 | -0.5127263 | 1 | 0.167 | 0.00333399 | CCT24 | 0.07621889 | -0.299401 | 0.625 | 0.648 | 1 |
| IL1B2 | 3.01E-06 | 0.29845351 | 0.125 | 0.185 | 0.00602211 | CFH | 0.07841144 | -0.2687238 | 0.438 | 0.148 | 1 |
| IFIT1 | 3.82E-06 | 0.3903721 | 0.188 | 0.019 | 0.00764485 | TMSB4X1 | 0.07911823 | 0.51131426 | 1 | 0.889 | 1 |
| HLA-DMB1 | 4.14E-06 | -0.3780456 | 0.188 | 0.019 | 0.0082772 | CMBL | 0.08090351 | -0.2728147 | 0.438 | 0.315 | 1 |
| G0S21 | 4.43E-06 | 0.27859347 | 0.125 | 0 | 0.00886804 | SRM1 | 0.08924456 | -0.2542939 | 0.438 | 0.222 | 1 |
| S100A93 | 5.02E-06 | 1.46958292 | 0.875 | 0.093 | 0.01004876 | IFI64 | 0.10681803 | 0.28998956 | 0.812 | 0.37 | 1 |
| HIST1H2AI1 | 5.32E-06 | 0.28197803 | 0.188 | 0.056 | 0.01064478 | VDAC13 | 0.10737213 | -0.2722307 | 0.562 | 0.444 | 1 |
| CA11 | 6.97E-06 | -0.2788015 | 0.188 | 0.111 | 0.01393035 | LINC02573 | 0.11143319 | 0.26193837 | 1 | 0.5 | 1 |
| MAP1A | 7.69E-06 | 0.33660614 | 1 | 0.074 | 0.01537731 | TPM42 | 0.11143319 | -0.3309875 | 0.562 | 0.5 | 1 |
| IGHM2 | 1.10E-05 | 0.32939254 | 1 | 0.204 | 0.02204359 | SAT11 | 0.11300748 | 0.35138015 | 1 | 0.685 | 1 |
| AC123912.4 | 2.86E-05 | -0.3994571 | 0.188 | 0.111 | 0.05729527 | MT11X2 | 0.12142174 | -0.3254263 | 0.5 | 0.296 | 1 |
| FADS21 | 4.01E-05 | 0.28451666 | 0.875 | 0.185 | 0.08029934 | MEF2C4 | 0.12423277 | -0.295871 | 0.5 | 0.444 | 1 |
| NOLC11 | 4.10E-05 | -0.2575474 | 0.25 | 0.259 | 0.08205748 | MGLL | 0.13780046 | -0.2787165 | 0.5 | 0.278 | 1 |
| HSPA1B1 | 4.72E-05 | -0.318088 | 0.25 | 0.111 | 0.09435416 | TP113 | 0.14189045 | -0.4655602 | 0.875 | 0.722 | 1 |

TABLE 15-continued

| | p_val | avg_logFC | pct.1 | pct.2 | p_val_adj | | p_val | avg_logFC | pct.1 | pct.2 | p_val_adj |
|---|---|---|---|---|---|---|---|---|---|---|---|
| PTGS2 | 4.88E−05 | −0.4130744 | 0.875 | 0.167 | 0.09754115 | HSP90AB13 | 0.14385092 | −0.3378129 | 1 | 0.963 | 1 |
| TEX9 | 4.88E−05 | −0.2609783 | 0.25 | 0.074 | 0.09765942 | MIF4 | 0.15528543 | −0.3240243 | 0.875 | 0.833 | 1 |
| S100A811 | 6.11E−05 | −0.2940198 | 0.938 | 0.185 | 0.12212158 | CXCL81 | 0.1619702 | 0.46168351 | 0.438 | 0.13 | 1 |
| CDKN1A3 | 6.95E−05 | 0.29044426 | 0.25 | 0.037 | 0.13890579 | PA2G44 | 0.17123622 | −0.4055864 | 0.75 | 0.611 | 1 |
| OTOF | 0.00010164 | 0.28931885 | 0.188 | 0 | 0.20328928 | H1FX10 | 0.17259641 | −0.5285575 | 1 | 0.907 | 1 |
| CD362 | 0.00015661 | 0.26953304 | 0.25 | 0.111 | 0.31321236 | TAGLN22 | 0.18612584 | 0.30169741 | 1 | 0.889 | 1 |
| RBBP8 | 0.00020487 | 0.29231961 | 0.25 | 0.167 | 0.40973358 | GSTM1 | 0.19254973 | −0.621594 | 0.875 | 0.685 | 1 |
| CYC12 | 0.00028995 | 0.46081937 | 1 | 0.296 | 0.57989867 | S100A104 | 0.21353588 | 0.33948648 | 1 | 0.722 | 1 |
| NUDT12 | 0.00034003 | 0.44357489 | 1 | 0.315 | 0.68005317 | TSC22D11 | 0.21645301 | −0.4960325 | 0.812 | 0.315 | 1 |
| PCDH9 | 0.00062224 | 0.29315467 | 1 | 0.278 | | PHB | 0.217274 | −0.2823673 | 0.562 | 0.352 | 1 |
| RAB27B | 0.00081608 | −0.2749765 | 0.312 | 0.185 | 1 | VIM2 | 0.2262668 | 0.57989527 | 1 | 0.907 | 1 |
| EIF2AK12 | 0.00112376 | 0.33040662 | 1 | 0.333 | 1 | FTL2 | 0.22630743 | 0.26979808 | 1 | 0.926 | 1 |
| RFX2 | 0.00154298 | −0.3073826 | 0.312 | 0.074 | 1 | ID31 | 0.23055029 | 0.30524104 | 0.5 | 0.519 | 1 |
| MIR4435-2HG5 | 0.00166897 | 0.30900789 | 1 | 0.37 | 1 | HLA-DRA3 | 0.24805456 | −0.3185509 | 1 | 0.833 | 1 |
| SRP93 | 0.00177023 | 0.42189954 | 1 | 0.389 | 1 | MX14 | 0.25144418 | 0.47760792 | 0.625 | 0.111 | 1 |
| IFI44L6 | 0.00191187 | 0.33597986 | 0.875 | 0.204 | 1 | TYROBP2 | 0.25515581 | 0.66995625 | 0.438 | 0.037 | 1 |
| PPBP5 | 0.00196617 | −1.0289677 | 0.312 | 0.019 | 1 | HLA-DMA1 | 0.25813294 | 0.3652017 | 0.688 | 0.5 | 1 |
| HES1 | 0.00202851 | 0.39107421 | 0.312 | 0.037 | 1 | DUSP24 | 0.26743207 | −0.3811049 | 0.5 | 0.204 | 1 |
| LGALS31 | 0.00202851 | 0.26080213 | 0.312 | 0 | 1 | HSPA55 | 0.29620772 | −0.2900742 | 0.938 | 0.778 | 1 |
| IFI276 | 0.0021332 | 0.7035382 | 0.312 | 0.278 | 1 | TAF9 | 0.31284944 | −0.5350211 | 0.688 | 0.537 | 1 |
| NAAA1 | 0.00215479 | −0.3144594 | 0.312 | 0 | 1 | LYZ2 | 0.31290671 | 0.41406002 | 0.5 | 0.241 | 1 |
| HERC52 | 0.00215627 | 0.39689659 | 1 | 0.278 | 1 | HSPD14 | 0.31750569 | −0.4132167 | 0.875 | 0.611 | 1 |
| RGS21 | 0.00219265 | 0.69242414 | 0.312 | 0.037 | 1 | LMNA1 | 0.33486315 | 0.53977778 | 0.688 | 0.352 | 1 |
| MIR22HG2 | 0.00242314 | 0.61166832 | 0.312 | 0.056 | 1 | AC020916.14 | 0.35039545 | −0.4429139 | 0.875 | 0.407 | 1 |
| HIST1H1B3 | 0.00251203 | −0.3967203 | 0.312 | 0.111 | 1 | LIPA2 | 0.39704928 | 0.25612057 | 0.5 | 0.185 | 1 |
| LAG31 | 0.00271048 | −0.2634297 | 0.312 | 0.278 | 1 | HSPA83 | 0.42689004 | −0.2846473 | 1 | 0.537 | 1 |
| ATP2B1-AS12 | 0.00277946 | 0.7799813 | 0.938 | 0.111 | 1 | MAP7 | 0.43813205 | 0.31202248 | 0.5 | 0.278 | 1 |
| AC10359136 | 0.00292062 | 0.5126304 | 0.312 | 0.278 | 1 | CD34 | 0.44008008 | 0.3260082 | 0.75 | 0.407 | 1 |
| MPP11 | 0.00303965 | 0.29417776 | 1 | 0.204 | 1 | EREGI | 0.45043207 | 0.30641027 | 1 | 0.667 | 1 |
| PSMB51 | 0.00354354 | 0.25990969 | 0.938 | 0.389 | 1 | HNRNPR1 | 0.49805422 | −0.4406074 | 0.75 | 0.444 | 1 |
| ANGPT1 | 0.0037686 | −0.3778393 | 0.812 | 0.333 | 1 | LMAN22 | 0.51277636 | −0.3096104 | 0.812 | 0.333 | 1 |
| PGAM12 | 0.0045053 | −0.4235261 | 0.375 | 0.204 | 1 | ZFP364 | 0.52348839 | 0.61309229 | 1 | 0.778 | 1 |
| LMAN11 | 0.00525264 | 0.25955196 | 0.938 | 0.315 | 1 | DUT2 | 0.52807247 | −0.2523169 | 0.75 | 0.611 | 1 |
| HIST1H2AC4 | 0.005968 | −0.2724689 | 1 | 0.315 | 1 | AREG5 | 0.61812586 | −0.2931795 | 1 | 0.741 | 1 |
| HIST1H2BF1 | 0.00651577 | −0.4252633 | 0.375 | 0.204 | 1 | FBL3 | 0.62226237 | −0.3879438 | 0.875 | 0.407 | 1 |
| SLC1A51 | 0.00762091 | 0.57396632 | 0.312 | 0.185 | 1 | ID21 | 0.63094291 | 0.32551747 | 0.688 | 0.389 | 1 |
| DRAM1 | 0.00835203 | −0.3291673 | 0.375 | 0.185 | 1 | HIST1H4B | 0.65773403 | −0.2778506 | 0.188 | 0.074 | 1 |
| MEG3 | 0.00922637 | 0.3953671 | 0.312 | 0.056 | 1 | SOCS2 | 0.68720799 | −0.2808874 | 0.875 | 0.648 | 1 |
| FLT3 | 0.00986668 | −0.3166038 | 0.375 | 0.333 | 1 | TIPARP | 0.70121224 | 0.75846666 | 0.625 | 0.333 | 1 |
| PTMS | 0.01230791 | 0.32469792 | 1 | 0.463 | 1 | RPS27L5 | 0.72650702 | −0.3384807 | 1 | 0.556 | 1 |
| FABP52 | 0.01276755 | −0.3564047 | 1 | 0.333 | 1 | ATP8B4 | 0.72716507 | −0.300629 | 0.938 | 0.574 | 1 |
| SPRY1 | 0.01543006 | −0.4680374 | 0.938 | 0.278 | 1 | MGST11 | 0.78028789 | −0.3209752 | 0.812 | 0.389 | 1 |
| AL133415.1 | 0.01639913 | −0.5155579 | 1 | 0.333 | 1 | H2AFV4 | 0.8595871 | −0.2692908 | 0.938 | 0.63 | 1 |
| HDLBP2 | 0.01928929 | −0.3257739 | 0.438 | 0.352 | 1 | CD743 | 0.87221144 | 0.29508779 | 1 | 0.944 | 1 |
| PGRMC1 | 0.0197534 | −0.3830437 | 0.375 | 0.185 | 1 | ABRACL3 | 0.87728521 | 0.25818099 | 0.875 | 0.407 | 1 |
| CAVIN2 | 0.02088745 | −0.3802367 | 1 | 0.352 | 1 | RRM11 | 0.88339905 | −0.2705323 | 0.562 | 0.093 | 1 |
| SYTL4 | 0.02230098 | 0.48008749 | 0.375 | 0.111 | 1 | HIST1H1C3 | 0.89353767 | 0.45133661 | 0.812 | 0.685 | 1 |
| PSMD83 | 0.02251843 | 0.27405112 | 0.875 | 0.37 | 1 | GADD45B4 | 0.94145381 | 0.41673441 | 0.562 | 0.167 | 1 |
| MMRN1 | 0.0273007 | −0.3146859 | 1 | 0.37 | 1 | PHITF11 | 0.9433354 | 0.48282821 | 0.562 | 0.222 | 1 |
| NPDC1 | 0.02896641 | 0.35551594 | 1 | 0.463 | 1 | AVP | 0.97094136 | 0.78480572 | 0.688 | 0.444 | 1 |
| TPST22 | 0.03052346 | −0.3066846 | 0.875 | 0.259 | 1 | DNAJB112 | 0.98090433 | 0.28604595 | 0.562 | 0.204 | 1 |

TABLE 15-continued

| | p_val | avg_logFC | pct.1 | pct.2 | p_val_adj | | p_val | avg_logFC | pct.1 | pct.2 | p_val_adj |
|---|---|---|---|---|---|---|---|---|---|---|---|
| WDR744 | 0.03321187 | 0.26185102 | 1 | 0.426 | 1 | TUBA1B4 | 0.99428889 | -0.3310602 | 0.875 | 0.537 | 1 |
| CTSC3 | 0.03600456 | -0.3725367 | 0.5 | 0.463 | 1 | | | | | | |
| | | | | | | Seurat Cluster 16 | | | | | |
| CCL4L25 | 4.31E-05 | 0.27809491 | 1 | 0 | 0.08618494 | S100A812 | 0.46088275 | -1.2579575 | 1 | 0.875 | 1 |
| ID11 | 0.01749416 | -0.7221782 | 0.25 | 0.25 | 1 | 2-Jun | 0.49237309 | -0.2738521 | 0.8 | 1 | 1 |
| CXCL23 | 0.03793243 | 0.30658697 | 0.85 | 0.125 | 1 | RHOB4 | 0.52384388 | -0.2544874 | 0.9 | 0.375 | 1 |
| RAB32 | 0.03849419 | -0.3006524 | 1 | 0.25 | 1 | LILRA5 | 0.52441398 | -0.3338201 | 1 | 0.5 | 1 |
| RNASE1 | 0.04354407 | -0.4050504 | 1 | 0.25 | 1 | STXBP2 | 0.55812306 | -0.269371 | 1 | 0.5 | 1 |
| C1QA2 | 0.07790844 | -0.7343515 | 0.95 | 0.25 | 1 | CLEC10A | 0.55812306 | -0.3430085 | 0.75 | 0.5 | 1 |
| C1orf54 | 0.0860819 | 0.51156511 | 0.8 | 0.125 | 1 | CUX11 | 0.59234399 | -0.2623319 | 0.65 | 0.375 | 1 |
| CSTA1 | 0.12088485 | -0.3587833 | 1 | 1 | 1 | PDE4B1 | 0.59285235 | -0.250593 | 1 | 0.5 | 1 |
| CKS23 | 0.14412627 | 0.3080757 | 0.75 | 0.125 | 1 | ALOX5AP2 | 0.59315646 | -0.4515364 | 0.9 | 0.625 | 1 |
| S100A122 | 0.16190375 | -0.7581612 | 0.95 | 0.75 | 1 | LYN3 | 0.59335882 | -0.2506994 | 1 | 0.875 | 1 |
| BZW22 | 0.19408996 | -0.3276166 | 0.55 | 0.5 | 1 | HBEGF | 0.6653764 | -0.323356 | 1 | 0.625 | 1 |
| NAPSA | 0.19445686 | 0.35447386 | 0.95 | 0.625 | 1 | SPI12 | 0.66554847 | -0.2518831 | 1 | 1 | 1 |
| RGS22 | 0.2127858 | -0.2784071 | 0.75 | 0.875 | 1 | RAB131 | 0.70153394 | -0.2684394 | 0.7 | 0.25 | 1 |
| IFI277 | 0.22663786 | 1.01166818 | 0.35 | 0 | 1 | VDAC31 | 0.70251054 | -0.255832 | 1 | 0.5 | 1 |
| TNFRSF21 | 0.22663786 | 0.26556966 | 0.35 | 0.875 | 1 | TMED92 | 0.7027435 | -0.2803219 | 0.8 | 0.5 | 1 |
| NR4A23 | 0.23205307 | -0.2976619 | 0.8 | 0.875 | 1 | MPEG1 | 0.7027435 | -0.2625419 | 1 | 0.625 | 1 |
| DUT3 | 0.23205307 | -0.4796305 | 0.9 | 0.875 | 1 | CD693 | 0.7027435 | -0.2772111 | 1 | 0.625 | 1 |
| H1FX11 | 0.23205307 | -0.5074311 | 1 | 0.875 | 1 | PLEK3 | 0.70289851 | 0.26545775 | 0.95 | 0.875 | 1 |
| THBS12 | 0.25024608 | -0.8153411 | 0.85 | 0.25 | 1 | PHACTR1 | 0.70289851 | -0.3131011 | 0.85 | 0.875 | 1 |
| GSTM31 | 0.25122604 | -0.3199072 | 1 | 0.375 | 1 | EREG2 | 0.74084313 | -0.7154835 | 1 | 0.625 | 1 |
| GLUL2 | 0.25187746 | -0.3315137 | 0.55 | 0.5 | 1 | HIST1H1E4 | 0.74094574 | -0.2862263 | 0.9 | 0.75 | 1 |
| SNRPD31 | 0.25226758 | -0.4438311 | 0.8 | 0.625 | 1 | CD68 | 0.77941251 | -0.2509002 | 0.85 | 0.5 | 1 |
| SEC61G4 | 0.25246244 | -0.3520176 | 0.9 | 0.75 | 1 | F13A12 | 0.77941251 | -0.3693585 | 1 | 0.75 | 1 |
| RNASE61 | 0.25252737 | -0.3031768 | 1 | 0.875 | 1 | HIST1H1D8 | 0.81896393 | -0.455964 | 0.9 | 0.75 | 1 |
| EMP1 | 0.27291163 | -0.2764115 | 1 | 0.375 | 1 | AL133415.11 | 0.85764603 | 0.34676694 | 0.5 | 0.125 | 1 |
| C1QB2 | 0.27291163 | -0.7596166 | 1 | 0.375 | 1 | ICAM1 | 0.85764603 | 0.33552373 | 0.55 | 0.125 | 1 |
| MT1E2 | 0.29584391 | -0.2964601 | 1 | 0.375 | 1 | MRPL131 | 0.85805525 | -0.3446591 | 0.7 | 0.25 | 1 |
| CD83 | 0.34653655 | 0.6997948 | 0.95 | 0.625 | 1 | CTSB1 | 0.85853785 | -0.2519294 | 0.7 | 0.5 | 1 |
| LYZ3 | 0.34680064 | -0.2586785 | 1 | 1 | 1 | CISD22 | 0.85865295 | -0.250185 | 1 | 0.625 | 1 |
| HSPA56 | 0.37348825 | 0.55664891 | 1 | 0.875 | 1 | SRM2 | 0.89805205 | 0.31684602 | 0.5 | 0.125 | 1 |
| VCAN1 | 0.37348825 | -0.5642944 | 1 | 0.875 | 1 | MT2A9 | 0.89877692 | 0.32953822 | 1 | 0.625 | 1 |
| S100A94 | 0.37348825 | -0.7137846 | 0.95 | 0.875 | 1 | STOML21 | 0.89877692 | -0.2781341 | 1 | 0.625 | 1 |
| TMEM2082 | 0.42517904 | 0.27643455 | 0.4 | 0 | 1 | CYBB | 0.89877692 | -0.3196092 | 1 | 0.625 | 1 |
| CD1E | 0.43048809 | -0.3554831 | 1 | 0.75 | 1 | ANKRD282 | 0.89877692 | -0.4383737 | 0.95 | 0.625 | 1 |
| MTRNR2L124 | 0.43048809 | -0.4102794 | 1 | 0.75 | 1 | SOX43 | 0.93902786 | 0.61223372 | 0.65 | 0.375 | 1 |
| NDUFAF33 | 0.45872302 | 0.29741567 | 0.7 | 0.25 | 1 | TNF2 | 1 | 0.7194576 | 0.5 | 0 | 1 |
| CD141 | 0.45965174 | -0.5013689 | 0.95 | 0.375 | 1 | EIF4A33 | 1 | 0.36901005 | 0.5 | 0 | 1 |

SEQUENCE LISTING

SEQ ID NO:1 VL Protein Sequence; Signal Peptide at Amino Acids 1-19; CDRs Underlined
MKLPVRLLVLMFWIPASSSDIVMTQSPLSLPVTPG-
EPASISCRSSQRLLSSYGHTYLHWYLQKPGQ-
SPQLLIYEVSNRFSGVPDRFSGSGSGTDFTLKISRVE-
AEDVGVYYCSQSTHVPLTFGQGTKVEIK SEQ ID NO:2 VL Nucleotide Sequence SEQ ID NO:3 PRO #2 VII Protein Sequence; Signal Peptide at Amino Acids 1-19; CDRs Underlined
MEWSGVFIFLLSVTAGVHSEVQLVESGGGLVKPG-
GSLRLSCAASGYTFSNYWIGW VRQAPGKGLEWIG
DIYPGGNYIRNNEKFKDKTTLSADTSKNTAYLQMN-
SLKTEDT AVYYCGSSFGSNYVFAWFTYWGQGTLVT-
VSS SEQ ID NO:4 PRO #2 VII Nucleotide Sequence SEQ ID NO:5 PRO #1 VII Protein Sequence; Signal Peptide at Amino Acids 1-19;
CDRs Underlined
MEWSGVFIFLLSVTAGVHSQVQLVQSGPDVKKPG-
TSMKMSCKTSGYTFSNYWIG WVRQAPGQGLEWIG
DIYPGGNYIRNNEKFKDKTTLTADTSTSTAYMQLGS-
LRSED TAVYYCGSSFGSNYVFAWFTYWGQGTLV-
TVSS SEQ ID NO:6 PRO #1 VII Nucleotide Sequence SEQ ID NO:7 Heavy Chain Protein Sequence
EVQLVESGGG LVKPGGSLRL SCAASGYTFS NYWIGWVRQA PGKGLEWIGD IYPGG-
NYIRNNEKFKDKTTL SADTSKNTAY LQMNSLKTED TAVYYCGSSF GSNYVFAWFT YWGQGTLVTVSSAS-
TKGPSV FPLAPCSRST SESTAALGCL VKDYFPEPVT VSWNSGALTS GVHTFPAVLQSSGLYSLSSV
VTVPSSSLGT KTYTCNVDHK PSNTKVDKRV ESKY-
GPPCPS CPAPEFLGGPSVFLFPPKPK DTLMISRTPE VTCVVVDVSQ EDPEVQFNWY VDGVEVHNAK
TKPREEQFNS TYRVVSVLTV LHQDWLNGKE YKCKVSNKGL PSSIEKTISK AKGQPREPQV YTLPP-
SQEEMTKNQVSLTCL VKGFYPSDIA VEWESNGQPE NNYKTTPPVL DSDGSFFLYS RLTVDKSRWQEG-
NVFSCSVM HEALHNHYTQ KSLSLSLGK SEQ ID NO:8 Light Chain Protein Sequence
DIVMTQSPLS LPVTPGEPAS ISCRSSQRLL SSYGHTYLHW YLQKPGQSPQ LLI-
YEVSNRFSGVPDRFSGS GSGTDFTLKI SRVEAE-
DVGV YYCSQSTHVP LTFGQGTKVE IKRTVAAPSVFIFPPSDEQL KSGTASVVCL LNNFY-
PREAK VQWKVDNALQ SGNSQESVTE QDSKDSTYS-
LSSTLTLSKAD YEKHKVYACE VTHQGLSSPV TKSFNRGEC SEQ ID NO:9 LCDR1 Amino Acid Sequence
RSSQRLLSSYGHTYLH SEQ ID NO:10 LCDR2 Amino Acid Sequence
EVSNRFS SEQ ID NO:11 LCDR3 Amino Acid Sequence
SQSTHVPLT SEQ ID NO:12 HCDR1 Amino Acid Sequence
NYWIG SEQ ID NO:13 HCDR2 Amino Acid Sequence
DIYPGGNYIRNNEKFKD SEQ ID NO:14 HCDR3 Amino Acid Sequence
SFGSNYVFAWFTY SEQ ID NO:15 Homo sapiens CCR5, NCBI Reference Sequence: NP_000570.1
MDYQVSSPIYDINYYTSEPCQKINVKQIAARLLP-
PLYSLVFIFGFVGNMLVILILINC KRLKSMTDIYLLN-
LAISDLFFLLTVPFWAHYAAAQWDFGNTMCQLLTG-
LYFIGFFS GIFFIILLTIDRYLAVVHAVFALKARTVT-
FGVVTSVITWVVAVFASLPGIIFTRSQKE GLHYTCS-
SHFPYSQYQFWKNFQTLKIVILGLVLPLLVMVI-
CYSGILKTLLRCRNEKK RHRAVRLIFTIMIVYFL-
FWAPYNIVLLLNTFQEFFGLNNCSSSNRLDQA-
MQVTETLG MTHCCINPIIYAFVGEKFRNYLLVFFQK-
HIAKRFCKCCSIFQQEAPERASSVYTRST GEQEI-
SVGL

The invention claimed is:

1. A method for facilitating normalization of the CD4 T cell/CD8 T cell ratio in a subject infected with SARS-CoV-2, comprising administering a therapeutically effective amount of a CCR5 binding agent to the subject, wherein the CCR5 binding agent is anti-CCR5 antibody leronlimab or a binding fragment thereof and wherein the normal CD4 T cell/CD8 T cell ratio ranges from 0.9 to 1.9.

2. The method of claim 1, wherein the normal CD4 T cell/CD8 T cell ratio ranges is determined by using flow cytometry-based measurements of whole blood or peripheral blood mononuclear cells isolated from patient blood samples.

3. The method of claim 1, wherein facilitating normalization of the CD4 T cell/CD8 T cell ratio in a subject is observed by Day 14, Day 7, or Day 3 of treatment.

4. The method of claim 1, wherein the CCR5 binding agent comprises an antibody comprising:
 (a) a heavy chain variable region (VH) comprising a heavy chain complementary determining region 1 (HCDR1) of SEQ ID NO:12, a heavy chain complementary determining region 2 (HCDR2) of SEQ ID NO:13, and a heavy chain complementary determining region 3 (HCDR3) of SEQ ID NO:14; and
 (b) a light chain variable region (VL) comprising a light chain complementary determining region 1 (LCDR1) of SEQ ID NO:9, a light chain complementary determining region 2 (LCDR2) of SEQ ID NO:10, and a light chain complementary determining region 3 (LCDR3) of SEQ ID NO:11.

5. The method of claim 1, wherein leronlimab is administered subcutaneously.

6. The method of claim 1, wherein leronlimab is administered at a dose of about 700 mg.

7. The method of claim 6, wherein the dose is administered once a week for two weeks.

8. The method of claim 1, wherein the subject has mild, moderate, or severe COVID-19 or exhibits no symptoms associated with COVID-19.

9. The method of claim 1, wherein the subject exhibits one or more symptoms selected from dry cough, shortness of breath, rhinorrhea, fever, sore throat, headache, chills, malaise, diarrhea, loss of smell or taste, and muscle pain.

10. The method of claim 1, wherein the subject has cytokine release syndrome, acute respiratory distress syndrome (ARDS), hemophagocytic lymphohistiocytosis (HLH), or macrophage activation syndrome.

11. The method of claim 1, wherein the subject:
 exhibits severe respiratory symptoms and administration of the CCR5 binding agent reduces the severity or duration of the severe respiratory symptoms; or
 (ii) does not exhibit respiratory symptoms associated with COVID-19 or ARDS and administration of the CCR5 binding agent reduces the likelihood of the subject developing one or more of mild, moderate, or severe respiratory symptoms.

12. The method of claim 11, wherein severe respiratory symptoms comprise difficulty in breathing or shortness of breath at rest, severe pneumonia, a respiratory rate ≥30 breaths per minute, oxygen saturation (pulse oximetry) ≤93% on room air, partial pressure of oxygen/fraction of inspired oxygen (PaO2/FiO2) ≤300 mmHg (1 mmHg=0.133 kPa), evidence of rales/crackles, radiographic evidence of pulmonary infiltrates (chest x-ray, CT scan, etc.), or any combination thereof.

13. The method of claim 1, further comprising administering one or more additional therapeutic agents to the subject.

14. The method of claim 13, wherein the one or more additional therapeutic agents comprises an antiviral agent, a non-CCR5 immunomodulatory agent, a CCL5 binding agent, an immune checkpoint molecule inhibitor, or any combination thereof.

15. The method of claim 14, wherein the antiviral agent comprises seltamivir, zanamivir, laninamivir, laninamivir, peramivir, or remdesivir.

16. The method of claim 14, wherein the non-CCR5 immunomodulatory agent comprises baricitinib, ruxolitinib, tocilizumab, siltuximab, sarilumab, TZLS-501, anakinra, emapalumab, TJM2, hydroxychloroquine, gimsilumab, lenzilumab, fingolimod, or CD24-Fc.

17. The method of claim 14, wherein the immune checkpoint molecule inhibitor targets PD-1, PD-L1, PD-L2, CD80, CD86, B7-H3, B7-H4, HVEM, adenosine, GALS, VISTA, CEACAM-1, PVRL2, CTLA-4, BTLA, KIR, LAG3, TIM3, A2aR, CD244/2B4, CD160, TIGIT, LAIR-1, PVRIG/CD112R, arginase, or indoleamine 2,3-dioxygenase (IDO).

18. The method of claim 14, wherein the immune checkpoint molecule inhibitor comprises pidilizumab, nivolumab, pembrolizumab, durvalumab, atezolizumab, avelumab, ipilimumab, tremelimumab, abatacept, or belatacept.

19. A method for increasing CD8 T cell frequency in a subject infected with SARS-CoV-2, comprising administering to the subject a therapeutically effective amount of leronlimab or an antigen binding fragment thereof.

* * * * *

```
SEQUENCE LISTING

<160> NUMBER OF SEQ ID NOS: 15

<210> SEQ ID NO 1
<211> LENGTH: 131
<212> TYPE: PRT
<213> ORGANISM: Artificial Sequence
<220> FEATURE:
<223> OTHER INFORMATION: Humanized antidoby PRO140 VL
<220> FEATURE:
<221> NAME/KEY: sig_peptide
<222> LOCATION: 1...19
<223> OTHER INFORMATION: signal peptide at amino acids 1-19

<400> SEQUENCE: 1

Met Lys Leu Pro Val Arg Leu Leu Val Leu Met Phe Trp Ile Pro Ala
1               5                   10                  15

Ser Ser Ser Asp Ile Val Met Thr Gln Ser Pro Leu Ser Leu Pro Val
            20                  25                  30

Thr Pro Gly Glu Pro Ala Ser Ile Ser Cys Arg Ser Ser Gln Arg Leu
        35                  40                  45

Leu Ser Ser Tyr Gly His Thr Tyr Leu His Trp Tyr Leu Gln Lys Pro
    50                  55                  60

Gly Gln Ser Pro Gln Leu Leu Ile Tyr Glu Val Ser Asn Arg Phe Ser
65                  70                  75                  80
```

```
Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Ser Gln Ser Thr His Val Pro Leu Thr Phe Gly Gln Gly Thr Lys Val
        115                 120                 125

Glu Ile Lys
    130

<210> SEQ ID NO 2
<211> LENGTH: 429
<212> TYPE: DNA
<213> ORGANISM: Artificial Sequence
<220> FEATURE:
<223> OTHER INFORMATION: Humanized antibody PRO140 VL

<400> SEQUENCE: 2
tctagaccac catgaagttg cctgttaggc tgttggtgct gatgttctgg attcctgctt      60
ccagcagtga tattgtgatg acccaatctc cactctcccc gcctgtcact cctggagagc     120
cagcctccat ctcttgcaga tctagtcagc gccttctgag cagttatgga catacctatt     180
tacattggta cctacagaag ccaggccagt ctccacagct cctgatctac gaagtttcca     240
accgattttc tggggtccca gacaggttca gtggcagtgg gtcagggaca gatttcacac     300
ttaagatcag tagagtggag gctgaggatg tgggagttta ttactgctct caaagtacac     360
atgttcctct cacgttcgga caggggacca aggtggaaat aaaacgtaag tagtcttctc     420
aactctaga                                                             429

<210> SEQ ID NO 3
<211> LENGTH: 141
<212> TYPE: PRT
<213> ORGANISM: Artificial Sequence
<220> FEATURE:
<223> OTHER INFORMATION: Humanized antibody PRO140 #2 VH
<220> FEATURE:
<221> NAME/KEY: sig_peptide
<222> LOCATION: 1...19
<223> OTHER INFORMATION: signal peptide at amino acids 1-19

<400> SEQUENCE: 3

Met Glu Trp Ser Gly Val Phe Ile Phe Leu Leu Ser Val Thr Ala Gly
1               5                   10                  15

Val His Ser Glu Val Gln Leu Val Glu Ser Gly Gly Gly Leu Val Lys
            20                  25                  30

Pro Gly Gly Ser Leu Arg Leu Ser Cys Ala Ala Ser Gly Tyr Thr Phe
        35                  40                  45

Ser Asn Tyr Trp Ile Gly Trp Val Arg Gln Ala Pro Gly Lys Gly Leu
    50                  55                  60

Glu Trp Ile Gly Asp Ile Tyr Pro Gly Gly Asn Tyr Ile Arg Asn Asn
65                  70                  75                  80

Glu Lys Phe Lys Asp Lys Thr Thr Leu Ser Ala Asp Thr Ser Lys Asn
                85                  90                  95

Thr Ala Tyr Leu Gln Met Asn Ser Leu Lys Thr Glu Asp Thr Ala Val
            100                 105                 110

Tyr Tyr Cys Gly Ser Ser Phe Gly Ser Asn Tyr Val Phe Ala Trp Phe
        115                 120                 125

Thr Tyr Trp Gly Gln Gly Thr Leu Val Thr Val Ser Ser
        130                 135                 140
```

<210> SEQ ID NO 4
<211> LENGTH: 457
<212> TYPE: DNA
<213> ORGANISM: Artificial Sequence
<220> FEATURE:
<223> OTHER INFORMATION: Humanized antibody PRO#2 VH

<400> SEQUENCE: 4

```
acgcgtccac catggaatgg agcggagtct ttatctttct cctgtcagta actgcaggtg      60
tccactccga ggtgcagctg gtggagtctg gtggaggctt ggtaaagcct ggaggttccc     120
ttagactctc ctgtgcagcc tctggttaca ctttcagtaa ctattggatc ggatgggtcc     180
gccaggctcc aggcaaaggg ctggagtgga ttggcgatat ctaccctgga gggaactaca     240
tcaggaacaa tgagaagttc aaggacaaga ccacccctgtc agcagatact tccaagaaca     300
cagcctatct gcaaatgaac agcctgaaaa ccgaggacac agccgtgtat tactgtggaa     360
gcagcttcgg tagtaactac gtgttcgcct ggtttactta ctggggccaa gggactctgg     420
tcacagtctc ctcaggtgag tccttaaaac tctaga                               457
```

<210> SEQ ID NO 5
<211> LENGTH: 141
<212> TYPE: PRT
<213> ORGANISM: Artificial Sequence
<220> FEATURE:
<223> OTHER INFORMATION: Humanized antibody PRO140#1 VH
<220> FEATURE:
<221> NAME/KEY: sig_peptide
<222> LOCATION: 1...19
<223> OTHER INFORMATION: signal peptide at amino acids 1-19

<400> SEQUENCE: 5

```
Met Glu Trp Ser Gly Val Phe Ile Phe Leu Leu Ser Val Thr Ala Gly
1               5                   10                  15

Val His Ser Gln Val Gln Leu Val Gln Ser Gly Pro Asp Val Lys Lys
            20                  25                  30

Pro Gly Thr Ser Met Lys Met Ser Cys Lys Thr Ser Gly Tyr Thr Phe
        35                  40                  45

Ser Asn Tyr Trp Ile Gly Trp Val Arg Gln Ala Pro Gly Gln Gly Leu
    50                  55                  60

Glu Trp Ile Gly Asp Ile Tyr Pro Gly Gly Asn Tyr Ile Arg Asn Asn
65                  70                  75                  80

Glu Lys Phe Lys Asp Lys Thr Thr Leu Thr Ala Asp Thr Ser Thr Ser
                85                  90                  95

Thr Ala Tyr Met Gln Leu Gly Ser Leu Arg Ser Glu Asp Thr Ala Val
            100                 105                 110

Tyr Tyr Cys Gly Ser Ser Phe Gly Ser Asn Tyr Val Phe Ala Trp Phe
        115                 120                 125

Thr Tyr Trp Gly Gln Gly Thr Leu Val Thr Val Ser Ser
    130                 135                 140
```

<210> SEQ ID NO 6
<211> LENGTH: 457
<212> TYPE: DNA
<213> ORGANISM: Artificial Sequence
<220> FEATURE:
<223> OTHER INFORMATION: Humanized antibody PRO#1 VH

<400> SEQUENCE: 6

```
tctagaccac catggaatgg agcggggtct ttatctttct cctgtcagta actgcaggtg      60
```

```
tccactccca ggtccaactg gtgcagtctg gacctgatgt gaaaaagcct gggacttcaa    120
tgaagatgtc ctgcaagacg tctggataca ccttcagtaa ctattggatc ggatgggtta    180
ggcaggcgcc tggacaaggc cttgagtgga ttggagatat ttaccctgga gggaactata    240
tcaggaacaa tgagaagttc aaggacaaga ccacactgac ggcagacaca tcgaccagca    300
cggcctacat gcaacttggc agcctgagat ctgaagacac tgccgtctat tactgtggaa    360
gcagcttcgg tagtaactac gtgttcgcct ggtttactta ctggggccaa gggactctgg    420
tcacagtctc ctcaggtgag tccttaaaac ctctaga                             457
```

<210> SEQ ID NO 7  
<211> LENGTH: 449  
<212> TYPE: PRT  
<213> ORGANISM: Artificial Sequence  
<220> FEATURE:  
<223> OTHER INFORMATION: Humanized antibody heavy chain

<400> SEQUENCE: 7

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Ser Asn Tyr
            20                  25                  30

Trp Ile Gly Trp Val Arg Gln Ala Pro Gly Lys Gly Leu Glu Trp Ile
        35                  40                  45

Gly Asp Ile Tyr Pro Gly Gly Asn Tyr Ile Arg Asn Asn Glu Lys Phe
    50                  55                  60

Lys Asp Lys Thr Thr Leu Ser Ala Asp Thr Ser Lys Asn Thr Ala Tyr
65                  70                  75                  80

Leu Gln Met Asn Ser Leu Lys Thr Glu Asp Thr Ala Val Tyr Tyr Cys
                85                  90                  95

Gly Ser Ser Phe Gly Ser Asn Tyr Val Phe Ala Trp Phe Thr Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
```

```
                290                 295                 300
Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
                435                 440                 445

Lys

<210> SEQ ID NO 8
<211> LENGTH: 219
<212> TYPE: PRT
<213> ORGANISM: Artificial Sequence
<220> FEATURE:
<223> OTHER INFORMATION: Humanized antibody light chain

<400> SEQUENCE: 8

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Arg Leu Leu Ser Ser
                20                  25                  30

Tyr Gly His Thr Tyr Leu His Trp Tyr Leu Gln Lys Pro Gly Gln Ser
                35                  40                  45

Pro Gln Leu Leu Ile Tyr Glu Val Ser Asn Arg Phe Ser Gly Val Pro
                50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Leu Thr Phe Gly Gln Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
                130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205
```

```
Pro Val Thr Lys Ser Phe Asn Arg Gly Glu Cys
    210                 215

<210> SEQ ID NO 9
<211> LENGTH: 16
<212> TYPE: PRT
<213> ORGANISM: Artificial Sequence
<220> FEATURE:
<223> OTHER INFORMATION: Humanized antibody LCDR1

<400> SEQUENCE: 9

Arg Ser Ser Gln Arg Leu Leu Ser Ser Tyr Gly His Thr Tyr Leu His
1               5                   10                  15

<210> SEQ ID NO 10
<211> LENGTH: 7
<212> TYPE: PRT
<213> ORGANISM: Artificial Sequence
<220> FEATURE:
<223> OTHER INFORMATION: Humanized antibody LCDR2

<400> SEQUENCE: 10

Glu Val Ser Asn Arg Phe Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Humanized antibody LCDR3

<400> SEQUENCE: 11

Ser Gln Ser Thr His Val Pro Leu Thr
1               5

<210> SEQ ID NO 12
<211> LENGTH: 5
<212> TYPE: PRT
<213> ORGANISM: Artificial Sequence
<220> FEATURE:
<223> OTHER INFORMATION: Humanized antibody HCDR1

<400> SEQUENCE: 12

Asn Tyr Trp Ile Gly
1               5

<210> SEQ ID NO 13
<211> LENGTH: 17
<212> TYPE: PRT
<213> ORGANISM: Artificial Sequence
<220> FEATURE:
<223> OTHER INFORMATION: Humanized antibody HCDR2

<400> SEQUENCE: 13

Asp Ile Tyr Pro Gly Gly Asn Tyr Ile Arg Asn Asn Glu Lys Phe Lys
1               5                   10                  15

Asp

<210> SEQ ID NO 14
<211> LENGTH: 13
<212> TYPE: PRT
<213> ORGANISM: Artificial Sequence
<220> FEATURE:
<223> OTHER INFORMATION: Humanized antibody HCDR3
```

```
<400> SEQUENCE: 14

Ser Phe Gly Ser Asn Tyr Val Phe Ala Trp Phe Thr Tyr
1               5                   10

<210> SEQ ID NO 15
<211> LENGTH: 352
<212> TYPE: PRT
<213> ORGANISM: Homo sapiens
<220> FEATURE:
<223> OTHER INFORMATION: CCR5 NCBI Reference Sequence: NP_000570.1

<400> SEQUENCE: 15

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
        275                 280                 285

His Cys Cys Ile Asn Pro Ile Ile Tyr Ala Phe Val Gly Glu Lys Phe
    290                 295                 300

Arg Asn Tyr Leu Leu Val Phe Phe Gln Lys His Ile Ala Lys Arg Phe
305                 310                 315                 320
```

```
Cys Lys Cys Cys Ser Ile Phe Gln Gln Glu Ala Pro Glu Arg Ala Ser
            325                 330                 335

Ser Val Tyr Thr Arg Ser Thr Gly Glu Gln Glu Ile Ser Val Gly Leu
            340                 345                 350
```